United States Patent
Williams et al.

(10) Patent No.: US 7,671,094 B2
(45) Date of Patent: *Mar. 2, 2010

(54) BUPROPION HYDROBROMIDE AND THERAPEUTIC APPLICATIONS

(75) Inventors: Robert Parry Williams, Enniskerry (IE); Peter Harris Silverstone, Alberta (CA)

(73) Assignee: Biovail Laboratories International S.R.L., St. Michael (BB)

( * ) Notice: Subject to any disclaimer, the term of this patent is extended or adjusted under 35 U.S.C. 154(b) by 0 days.

This patent is subject to a terminal disclaimer.

(21) Appl. No.: 11/834,848

(22) Filed: Aug. 7, 2007

(65) Prior Publication Data
US 2008/0075774 A1     Mar. 27, 2008

Related U.S. Application Data

(63) Continuation-in-part of application No. 11/755,946, filed on May 31, 2007, now Pat. No. 7,553,992, and a continuation-in-part of application No. 11/751,768, filed on May 22, 2007, now Pat. No. 7,569,610, each which is a continuation of application No. 11/475,252, filed on Jun. 27, 2006, now Pat. No. 7,241,805.

(60) Provisional application No. 60/693,906, filed on Jun. 27, 2005.

(51) Int. Cl.
*A61K 31/135* (2006.01)
(52) U.S. Cl. ..................................... 514/649
(58) Field of Classification Search ............. None
See application file for complete search history.

(56) References Cited

U.S. PATENT DOCUMENTS

| 7,241,805 | B2 | 7/2007 | Oberegger et al. |
| 2007/0269516 | A1 | 11/2007 | Oberegger et al. |
| 2007/0276047 | A1 | 11/2007 | Oberegger et al. |
| 2007/0281012 | A1 | 12/2007 | Oberegger et al. |
| 2007/0293584 | A1 | 12/2007 | Oberegger et al. |
| 2008/0075774 | A1 | 3/2008 | Williams et al. |

FOREIGN PATENT DOCUMENTS

| WO | WO 2005/120523 A1 * | 12/2005 |
| WO | 2009/019294 | 2/2009 |
| WO | 2009/056550 | 5/2009 |

OTHER PUBLICATIONS

Berge et al, Journal of Pharmaceutical Sciences, Pharmaceutical Salts, 1977, 66(1), pp. 1-20.*
U.S. Appl. No. 11/930,644, filed Oct. 31, 2007, Oberegger, et al.
U.S. Appl. No. 11/774,109, filed Jul. 6, 2007, Oberegger, et al.
U.S. Appl. No. 11/766,239, filed Jun. 21, 2007, Oberegger, et al.
U.S. Appl. No. 11/766,213, filed Jun. 21, 2007, Oberegger, et al.
U.S. Appl. No. 11/762,820, filed Jun. 14, 2007, Oberegger, et al.
U.S. Appl. No. 11/762,343, filed Jun. 13, 2007, Oberegger, et al.
U.S. Appl. No. 11/762,840, filed Jun. 14, 2007, Oberegger, et al.
U.S. Appl. No. 11/759,413, filed Jun. 7, 2007, Oberegger, et al.
U.S. Appl. No. 11/755,946, filed May 31, 2007, Oberegger, et al.
U.S. Appl. No. 60/693,906, filed Jun. 27, 2005, Oberegger, et al.
U.S. Appl. No. 11/993,723, filed Dec. 21, 2007, Oberegger, et al.
U.S. Appl. No. 11/768,764, filed Jun. 26, 2007, Nighiem, et al.
U.S. Appl. No. 12/536,772, filed Aug. 6, 2009, Turchetta et al.

* cited by examiner

*Primary Examiner*—Paul A Zucker
(74) *Attorney, Agent, or Firm*—Oblon, Spivak, McClelland, Maier & Neustadt, L.L.P.

(57) ABSTRACT

Bupropion hydrobromide formulations as well as their use for the treatment of conditions is described.

16 Claims, 106 Drawing Sheets

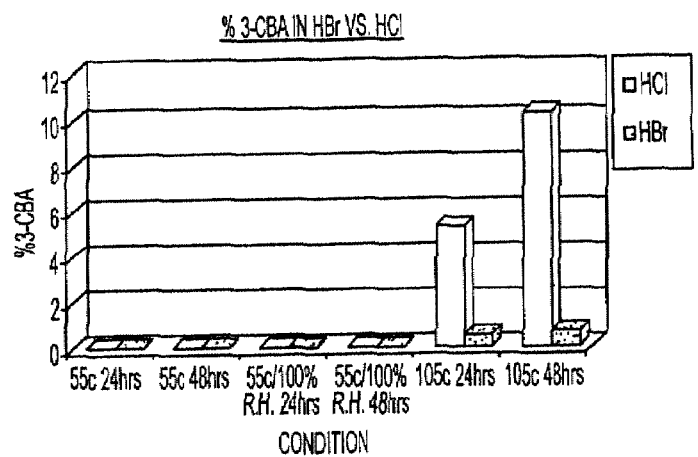
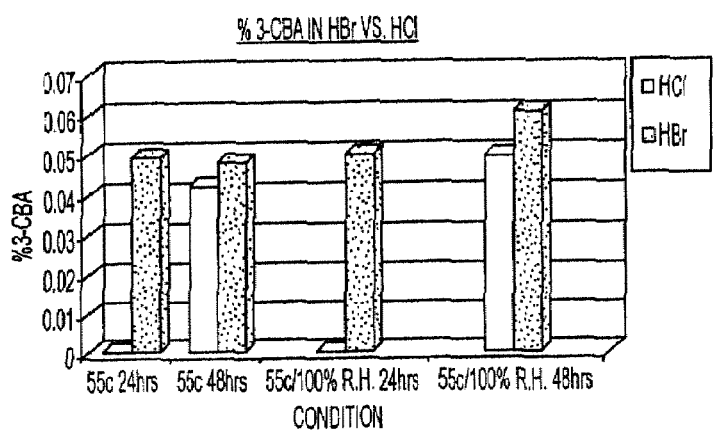
FIG. 49

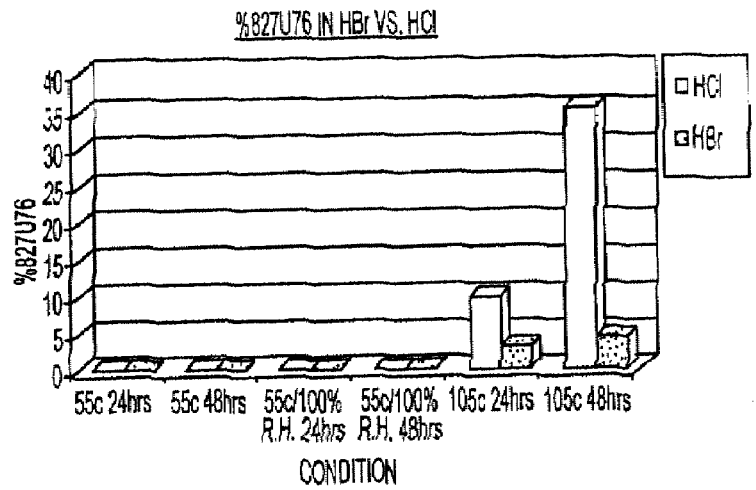
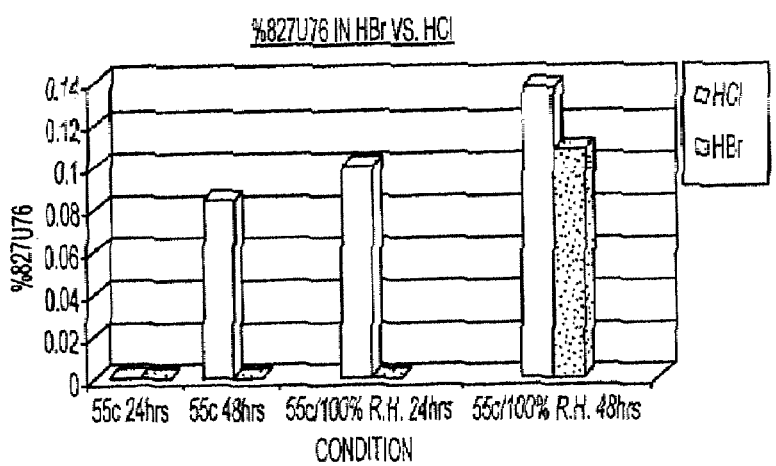
FIG. 52

PXRD of Bupropion Hydrobromide Polymorphic Form I

DSC of Bupropion Hydrobromide Polymorphic Form I

PXRD of Bupropion Hydrobromide Polymorphic Form II

DSC of Bupropion Hydrobromide Polymorphic Form II

PXRD of Bupropion Hydrobromide Polymorphic Form III

DSC of Bupropion Hydrobromide Polymorphic Form III

PXRD of Bupropion Hydrobromide Form I after 6 months in ICH Conditions (40°C, 75% R.H.)

PXRD of Bupropion Hydrobromide Polymorphic Form II after 1 month in ICH Conditions (40°C, 75% R.H.)

PXRD of Bupropion Hydrobromide Polymorphic Form III after 1 month in ICH Conditions (40°C, 75% R.H.)

| PROJECT: BUP 10121 | PROJECT: BUPROPION HBr XL TABLETS 348MG | | | | LOT NO.: BUP-HBr-XL-348-025-5 |
|---|---|---|---|---|---|
| ACTIVE DRUG MFG SITE: N/A | PRODUCT MFG SITE: N/A | PACKG. SITE: N/A | PACKG. DATE: N/A | | EXPIRY DATE: N/A |
| ACTIVE DRUG MFG DATE: N/A | PRODUCT MFG DATE: N/A | CONTAINER: BOTTLE | DESICCANT: N/A | | STABILITY STUDY #: STAB-05/064 |
| ACTIVE DRUG LOT#: N/A | PRODUCT BATCH SIZE: N/A | CLOSURE: N/A | COUNT: 90'S | | STABILITY PROGRAM: LONG TERM |
| ACTIVE DRUG EXPIRY DATE: N/A | PRODUCT DESCRIPTION: N/A | | | | STORAGE CONDITIONS: 25°C/60%RH |
| | | | | | SCHEDULE: INITIAL,3M,6M,9M,12M |

| TEST & METHODS | SPECIFICATIONS | INITIAL DATE: MAY 2005 | 3 MONTHS DATE: AUG 2005 | 6 MONTHS DATE: NOV 2005 | 9 MONTHS DATE: FEB 2006 | 12 MONTHS DATE: MAY 2006 |
|---|---|---|---|---|---|---|
| | LAB SAMPLE # | E05-71 | H05-35 | K05-51 | B06-51 | |
| DESCRIPTION | REPORT RESULTS | OFF-WHITE COLOUR, ROUND TABLETS | CONFORMS | CONFORMS | CONFORMS | |
| ASSAY (%) | REPORT RESULTS | 99.6 | 99.4 | 97.4 | 96.8 | |
| IMPURITIES (%) | | | | | | |
| 3-CBA | NMT 0.7% | 0.012 | 0.046 | 0.071 | 0.172 | |
| 852U77 | NMT 1.0% | 0.028 | 0.138 | 0.185 | 0.207 | |
| 20U78/DILUENT | NMT 0.3% | 0.034 | 0.051 | 0.040 | 0.046 | |
| 827U76 | NMT 0.4% | ND | 0.011 | 0.018 | 0.010 | |
| MAJOR UNKNOWN | REPORT RESULTS | 0.253 (RRT 0.14) | 0.186 (RRT 0.13) | 0.657 (RRT 0.09) | 0.177 (RRT 0.15) | |
| TOTAL UNKNOWN | REPORT RESULTS | 0.376 | 0.342 | 1.055 | 0.280 | |
| TOTAL IMPURITIES | REPORT RESULTS | 0.45 | 0.59 | 1.37 | 0.72 | |
| KF (%) | REPORT RESULTS | 0.62 | 0.85 | 0.42 | 0.49 | |
| DISSOLUTION* | | | | | | |
| 2H | NMT 20% | 14 - 19 (16) | 13 - 17 (15) | 12 - 17 (14) | 12 - 20 (16) | |
| 4H | 20 - 45% | 33 - 40 (36) | 30 - 35 (32) | 29 - 36 (32) | 29 - 40 (34) | |
| 8H | 65 - 85% | 64 - 72 (68) | 57 - 64 (61) | 54 - 63 (58) | 55 - 68 (61) | |
| 16H | NLT 80% | 92 - 101 (98) | 91 - 98 (94) | 89 - 97 (93) | 92 - 100 (96) | |

*TENTATIVE SPECIFICATION

FIG. 63

| PROJECT: BUP 10121 | | PROJECT: BUPROPION HBr EA TABLETS 300MG | | | | LOT NO.: BUP-HBr-EA-300-001-5 | |
|---|---|---|---|---|---|---|---|
| ACTIVE DRUG MFG SITE: | N/A | PRODUCT MFG SITE: | N/A | PACKG. SITE: | N/A | EXPIRY DATE: | N/A |
| ACTIVE DRUG MFG DATE: | N/A | PRODUCT MFG DATE: | APR 19/05 | CONTAINER: | BOTTLE | STABILITY STUDY # | STAB-05/072 |
| ACTIVE DRUG LOT #: | N/A | PRODUCT BATCH SIZE: | N/A | CLOSURE: | N/A | STABILITY PROGRAM: | ACCELERATED |
| ACTIVE DRUG EXPIRY DATE: | N/A | PRODUCT DESCRIPTION: | COATED TABLETS - 54MG WT GAIN | DESICCANT: | N/A | STORAGE CONDITIONS: | 40°C/75%RH |
| | | | | COUNT: | 90 COUNTS | SCHEDULE: INITIAL, 1M, 2M, 3M, 6M | |

| TEST & METHODS | SPECIFICATIONS | INITIAL | 1 MONTH | 2 MONTHS | 3 MONTHS | 6 MONTHS |
|---|---|---|---|---|---|---|
| | LAB SAMPLE # | DATE: JUN 13/05 | DATE: JUL 13/05 | DATE: AUG 13/05 | DATE: SEP 13/05 | DATE: DEC 13/05 |
| | | F05-5 | G05-10 | H05-24 | I05-13 | L05-23 |
| DESCRIPTION | REPORT RESULTS | CONFORMS | CONFORMS | CONFORMS | CONFORMS | CONFORMS |
| ASSAY (%) | REPORT RESULTS | 102.3 | 99.6 | 98.0 (*) | 101.8 | 101.0 |
| IMPURITIES (%) | | | | | | |
| 3-CBA | NMT 0.7% | 0.017 | 0.052 | 0.180 | 0.170 | 0.318 |
| 852U7 | NMT 1.0% | 0.023 | 0.221 | 0.438 | 0.256 | 0.221 |
| 20U78/DILUENT | NMT 0.3% | 0.044 | 0.036 | 0.032 | 0.057 | 0.059 |
| 827U76 | NMT 0.4% | 0.013 | 0.043 | 0.032 | 0.030 | 0.037 |
| MAJOR UNKNOWN | REPORT RESULTS | 0.623 (RRT 0.10) | 0.315 (RRT 0.10) | 0.205 (RRT 0.13) | 0.245 (RRT 0.14) | 0.651 (RRT 0.10) |
| TOTAL UNKNOWN | REPORT RESULTS | 1.054 | 0.675 | 0.381 | 0.421 | 1.125 |
| TOTAL IMPURITIES | REPORT RESULTS | 1.15 | 1.03 | 1.06 | 0.93 | 1.76 |
| KF (%) | REPORT RESULTS | 1.02 | 0.81 | 1.39 | 0.79 | 0.42 |
| DISSOLUTION* | | | | | | |
| 2H | NMT 20% | 13 - 15 (14) | 14 - 17 (16) | 15 - 17 (16) | 14 - 18 (16) | 12 - 13 (13) |
| 4H | 20 - 45% | 32 - 35 (33) | 33 - 37 (35) | 35 - 38 (36) | 33 - 38 (35) | 28 - 31 (30) |
| 8H | 65 - 85% | 64 - 69 (66) | 64 - 69 (67) | 65 - 71 (68) | 62 - 68 (65) | 55 - 59 (57) |
| 16H | NLT 80% | 96 - 101 (98) | 97 - 100 (98) | 97 - 102 (99) | 95 - 99 (97) | 90 - 92 (91) |

*TENTATIVE SPECIFICATION

FIG. 64-1

| PROJECT: BUP 10121 | PROJECT: BUPROPION HBr EA TABLETS 300MG | | | LOT NO.: BUP-HBr-EA-300-001-5 |
|---|---|---|---|---|
| | | | | EXPIRY DATE: N/A |
| ACTIVE DRUG MFG SITE: N/A | PRODUCT MFG SITE: N/A | PACKG. SITE: N/A | PACKG. DATE: N/A | STABILITY STUDY #: STAB-05/072 |
| ACTIVE DRUG MFG DATE: N/A | PRODUCT MFG DATE: APR 19/05 | CONTAINER: BOTTLE | DESICCANT: N/A | STABILITY PROGRAM: ACCELERATED |
| ACTIVE DRUG LOT #: N/A | PRODUCT BATCH SIZE: N/A | CLOSURE: N/A | COUNT: 90 COUNTS | STORAGE CONDITIONS: 40°C/75%RH |
| ACTIVE DRUG EXPIRY DATE: N/A | PRODUCT DESCRIPTION: | COATED TABLETS - 54MG WT GAIN | | SCHEDULE: INITIAL,1M,2M,3M,6M |
| | | APPROVED BY / DATE: | | |

FIG. 64-2

BUPROPION HBr XL 174MG CORE, LOT# BUP-HBr-XL-004-5 CORE

| TESTS | INITIAL | OPEN-CLOSED BOTTLE STABILITY (40C/75% RH) | | | |
|---|---|---|---|---|---|
| | | 10 DAYS-OPEN | 10 DAYS-CLOSED | 20 DAYS-OPEN | 20 DAYS-CLOSED |
| %ASSAY | 100.1 | 98.7 | 98.2 | 99.2 | 97.6 |
| %IMPURITIES | | | | | |
| 3-CBZ | 0.010 | 0.179 | 0.184 | 0.276 | 0.465 |
| 852U77 | 0.019 | 0.209 | 0.268 | 0.248 | 0.416 |
| 20U78/DILU | 0.054 | 0.055 | 0.060 | 0.058 | 0.063 |
| 827076 | 0.026 | 0.131 | 0.308 | 0.102 | 0.497 |
| TOTAL_UNKNOWN | 0.054 | 0.043 | 0.075 | 0.042 | 0.038 |
| TOTAL | 0.16 | 0.62 | 0.89 | 0.73 | 1.48 |

BUPROPION HBr XL 348MG CORE, LOT# BUP-HBr-XL-009-5 CORE

| TESTS | INITIAL | OPEN-CLOSED BOTTLE STABILITY (40C/75% RH) | | | |
|---|---|---|---|---|---|
| | | 10 DAYS-OPEN | 10 DAYS-CLOSED | 20 DAYS-OPEN | 20 DAYS-CLOSED |
| %ASSAY | 98.3 | 97.8 | 95.6 | 96.9 | 98.0 |
| %IMPURITIES | | | | | |
| 3-CBZ | 0.016 | 0.106 | 0.121 | 0.146 | 0.166 |
| 852U77 | 0.091 | 0.391 | 0.411 | 0.414 | 0.483 |
| 20U78/DILU | 0.054 | 0.051 | 0.055 | 0.056 | 0.055 |
| 827076 | 0.020 | 0.077 | 0.102 | 0.059 | 0.119 |
| TOTAL_UNKNOWN | 0.053 | 0.126 | 0.156 | 0.124 | 0.142 |
| TOTAL | 0.23ᴬ | 0.74 | 0.84 | 0.80 | 0.97 |

FIG. 65A

BUPROPION HCl XL 150MG CORE, LOT# 05E056

| TESTS | INITIAL | OPEN-CLOSED BOTTLE STABILITY (40C/75% RH) | | | | |
|---|---|---|---|---|---|---|
| | | 10 DAYS-OPEN | 10 DAYS-CLOSED | 20 DAYS-OPEN | 20 DAYS-CLOSED | 20 DAYS-CLOSED |
| %ASSAY | 97.5 | 98.4 | 97.5 | 98.1 | 97.6 | |
| %IMPURITIES | | | | | | |
| 3-CBZ | 0.006 | 0.079 | 0.052 | 0.185 | 0.238 | |
| 852U77 | 0.043 | 0.406 | 0.342 | 0.520 | 0.685 | |
| 20178/DILU | 0.014 | 0.046 | 0.046 | 0.059 | 0.052 | |
| 827U76 | 0.028 | 0.050 | 0.074 | 0.069 | 0.127 | |
| TOTAL UNKNOWN | 0.058 | 0.051 | 0.066 | 0.044 | 0.040 | |
| TOTAL | 0.18 | 0.63 | 0.58 | 0.88 | 1.14 | |

BUPROPION HCl XL 300MG CORE, LOT# 05D380

| TESTS | INITIAL | OPEN-CLOSED BOTTLE STABILITY (40C/75% RH) | | | | |
|---|---|---|---|---|---|---|
| | | 10 DAYS-OPEN | 10 DAYS-CLOSED | 20 DAYS-OPEN | 20 DAYS-CLOSED | 20 DAYS-CLOSED |
| %ASSAY | 99.2 | 99.1 | 98.4 | 96.8 | 97.1 | |
| %IMPURITIES | | | | | | |
| 3-CBZ | 0.006 | 0.100 | 0.015 | 0.245 | 0.171 | |
| 852U77 | 0.037 | 0.409 | 0.274 | 0.564 | 0.515 | |
| 20178/DILU | 0.044 | 0.045 | 0.046 | 0.051 | 0.050 | |
| 827U76 | 0.015 | 0.058 | 0.039 | 0.099 | 0.105 | |
| TOTAL UNKNOWN | 0.044 | 0.038 | 0.045 | 0.032 | 0.052 | |
| TOTAL | 0.15 | 0.65 | 0.42 | 0.99 | 0.90 | |

FIG. 65B

USP-3 DIFFERENT MEDIA (SGF pH 1.2, ACETATE BUFFER pH 4.5 & PHOSPHATE BUFFER pH 6.8)
BUPROPION HBr XL 348MG TABLETS (FINAL LOT# BUP-HBr-XL-012-5 (USP3)

| MEDIUM/TIME POINTS | | VESSEL-1 | VESSEL-2 | VESSEL-3 | VESSEL-4 | VESSEL-5 | VESSEL-6 | MEAN |
|---|---|---|---|---|---|---|---|---|
| SGF pH 1.2 | 2HRS | 9.0 | 8.3 | 8.9 | 11.6 | 8.8 | 8.6 | 9.2 |
| ACETATE BUFFER pH 4.5 | 2HRS | 15.8 | 15.0 | 19.3 | 18.5 | 17.5 | 18.2 | 17.4 |
| PHOSPHATE BUFFER SIF pH 6.8 | 2HRS | 26.8 | 25.4 | 24.9 | 33.3 | 27.7 | 24.2 | 27.1 |
| | 2HRS | 24.2 | 15.5 | 24.8 | 31.9 | 37.8 | 15.3 | 24.9 |
| | 2HRS | 22.5 | 19.5 | 16.6 | 1.4 | 2.4 | 25.8 | 14.7 |
| | 6HRS | 1.0 | 11.6 | 0.8 | 0.2 | 0.2 | 6.1 | 3.3 |
| TOTAL % RELEASED | | 99.3 | 95.3 | 95.3 | 96.9 | 94.4 | 98.2 | 96.6 |

WELLBUTRIN XL 300MG TABLETS (FINAL LOT# 05A116 (USP3)

| MEDIUM/TIME POINTS | | VESSEL-1 | VESSEL-2 | VESSEL-3 | VESSEL-4 | VESSEL-5 | VESSEL-6 | MEAN |
|---|---|---|---|---|---|---|---|---|
| SGF pH 1.2 | 2HRS | 3.1 | 2.7 | 2.1 | 1.8 | 2.8 | 2.6 | 2.5 |
| ACETATE BUFFER pH 4.5 | 2HRS | 53.0 | 38.8 | 32.6 | 10.7 | 20.1 | 38.8 | 32.3 |
| PHOSPHATE BUFFER SIF pH 6.8 | 2HRS | 30.8 | 36.4 | 37.0 | 47.8 | 46.1 | 33.5 | 38.6 |
| | 2HRS | 5.6 | 15.2 | 25.0 | 22.4 | 22.9 | 19.6 | 18.4 |
| | 2HRS | 2.2 | 3.1 | 1.6 | 13.7 | 2.8 | 0.8 | 4.0 |
| | 6HRS | 0.9 | 0.3 | 0.2 | 0.9 | 0.2 | 0.1 | 0.4 |
| TOTAL % RELEASED | | 95.7 | 96.3 | 98.4 | 97.3 | 94.8 | 95.2 | 96.3 |

FIG. 66A

BUPROPION HBr XL 340MG TABLETS (EC)-LOT # BUP-HBr-XL-012-5 (EC 32MG WG1) (USP3)

| MEDIUM/TIME POINTS | | VESSEL-1 | VESSEL-2 | VESSEL-3 | VESSEL-4 | VESSEL-5 | VESSEL-6 | MEAN |
|---|---|---|---|---|---|---|---|---|
| SGF pH 1.2 | 2HRS | 47.6 | 45.7 | 45.0 | 51.3 | 42.7 | 48.0 | 46.7 |
| ACETATE BUFFER pH 4.5 | 2HRS | 38.0 | 37.9 | 37.3 | 37.9 | 36.0 | 38.0 | 37.5 |
| PHOSPHATE BUFFER SIF pH 6.8 | 2HRS | 13.0 | 13.9 | 16.0 | 10.3 | 15.8 | 12.3 | 13.5 |
| | 2HRS | 1.9 | 2.1 | 3.1 | 0.9 | 3.5 | 1.5 | 2.2 |
| | 2HRS | 0.4 | 0.5 | 0.9 | 0.2 | 1.0 | 0.3 | 0.6 |
| | 6HRS | 0.2 | 0.2 | 0.4 | 0.1 | 0.4 | 0.1 | 0.2 |
| TOTAL % RELEASED | | 100.9 | 100.3 | 102.7 | 100.6 | 99.4 | 100.2 | 100.7 |

WELLBUTRIN XL 300MG TABLETS (EC)-LOT # 05DM47 (USP3)

| MEDIUM/TIME POINTS | | VESSEL-1 | VESSEL-2 | VESSEL-3 | VESSEL-4 | VESSEL-5 | VESSEL-6 | MEAN |
|---|---|---|---|---|---|---|---|---|
| SGF pH 1.2 | 2HRS | 63.1 | 61.5 | 58.9 | 58.2 | 57.9 | 60.8 | 60.1 |
| ACETATE BUFFER pH 4.5 | 2HRS | 32.9 | 35.4 | 36.6 | 38.2 | 37.2 | 35.3 | 35.9 |
| PHOSPHATE BUFFER SIF pH 6.8 | 2HRS | 0.6 | 0.9 | 1.0 | 1.0 | 1.1 | 0.9 | 0.9 |
| | 2HRS | 0.0 | 0.1 | 0.1 | 0.1 | 0.1 | 0.1 | 0.1 |
| | 2HRS | 0.0 | 0.0 | 0.0 | 0.0 | 0.0 | 0.0 | 0.0 |
| | 6HRS | 0.0 | 0.0 | 0.0 | 0.1 | 0.1 | 0.0 | 0.0 |
| TOTAL % RELEASED | | 96.7 | 97.9 | 96.6 | 97.6 | 96.3 | 97.1 | 97.0 |

FIG. 66B

Figure 75: Mean Plasma Bupropion Concentration-Time Plot for Study B06-756PK-10121 (3230)

Figure 76: Mean Plasma Hydroxybupropion Concentration-Time Plot for Study B06-756PK-10121 (3230)

Figure 77: Mean Plasma Bupropion Threoamino Alcohol Concentration-Time Plot for Study B06-756PK-10121 (3230)

Figure 78: Mean Plasma Bupropion Erythroamino Alcohol Concentration-Time Plot for Study B06-756PK-10121 (3230)

Figure 79: Mean Plasma Pharmacological Activity Weighted Composite (PAWC)-Time Plot for Study B06-756PK-10121 (3230)

Figure 80: Mean Plasma Bupropion Concentration-Time Plot for Study B06-755PK-10121 (3228)

Figure 81: Mean Plasma Bupropion Concentration-Time Plot for Study B06-755PK-10121 (3228) – Magnified Showing Only Datapoints From 0 – 36 Hours Figure 82: Mean Plasma Hydroxybupropion Concentration-Time Plot for Study B06-755PK-10121 (3228)

Figure 83: Mean Plasma Bupropion Threoamino Alcohol Concentration-Time Plot for Study B06-755PK-10121 (3228)

Figure 84: Mean Plasma Bupropion Erythroamino Alcohol Concentration-Time Plot for Study B06-755PK-10121 (3228)

Figure 85: Mean Plasma Pharmacological Activity Weighted Composite (PAWC)-Time Plot for Study B06-755PK-10121 (3228)

Figure 86: Mean Plasma Bupropion Concentration-Time Plot for Study B06-754PK-10121 (3229)

Figure 87: Mean Plasma Bupropion Concentration-Time Plot for Study B06-754PK-10121 (3229) – Magnified Showing Only Datapoints From 0 – 36 Hours Figure 88: Mean Plasma Hydroxybupropion Concentration-Time Plot for Study B06-754PK-10121 (3229)

Figure 89: Mean Plasma Bupropion Threoamino Alcohol Concentration-Time Plot for Study B06-754PK-10121 (3229)

Figure 90: Mean Plasma Bupropion Erythroamino Alcohol Concentration-Time Plot for Study B06-754PK-10121 (3229)

Figure 91: Mean Plasma Pharmacological Activity Weighted Composite (PAWC)-Time Plot for Study B06-754PK-10121 (3229)

Figure 92: Mean Plasma Bupropion Concentration-Time Plot For Study B06-802PK-10121 (AA40055)

Figure 93: Mean Plasma Hydroxybupropion Concentration-Time Plot For Study B06-802PK-10121 (AA40055)

Figure 94: Mean Plasma Bupropion Threoamino Alcohol Concentration-Time Plot For Study B06-802PK-10121 (AA40055)

Figure 95: Mean Plasma Bupropion Erythroamino Alcohol Concentration-Time Plot

Figure 96: Mean Plasma Pharmacological Activity Weighted Composite (PAWC)-Time Plot

BUPROPION HYDROBROMIDE AND THERAPEUTIC APPLICATIONS

RELATED APPLICATIONS

This application is a continuation-in-part of U.S. application Ser. No. 11/751,768, filed May 22, 2007, now U.S. Pat. No. 7,569,610; and a continuation-in-part of U.S. application Ser. No. 11/755,946 filed on May 31, 2007, now U.S. Pat. No. 7,553,992, both of which are continuations of U.S. application Ser. No. 11/475,252, filed Jun. 27, 2006, now U.S. Pat. No. 7,241,805; and claims priority to U.S. Provisional Application Ser. No. 60/693,906 filed Jun. 27, 2005. All of U.S. application Ser. No. 11/751,768, U.S. application Ser. No. 11/755,946, U.S. Pat. No. 7,241,805, and U.S. Provisional Application Ser. No. 60/693,906 are incorporated herein by reference.

FIELD OF THE INVENTION

The present invention relates to bupropion hydrobromide and bupropion hydrobromide formulations as well as their use for the treatment of conditions (e.g. major depressive disorder, bipolar depression mood disorder, other mood disorder, anxiety disorders, generalized anxiety disorder, panic disorder, post-traumatic stress disorder, nicotine addiction, obesity, attention-deficit hyperactivity disorder, restless legs syndrome, sexual dysfunction, and seasonal affective disorders)

BACKGROUND

Bupropion is known as an antidepressant of the aminoketone class, chemically unrelated to tricyclics, tetracyclics, selective serotonin re-uptake inhibitors (SSRIs), or other known antidepressant agents. The drug resembles a psychostimulant in terms of its neurochemical and behavioral profiles in-vivo, but it does not reliably produce stimulant-like effects in humans at clinically prescribed doses. Its structure closely resembles that of diethylpropion and it is related to phenylethylamines. It is designated as (±)-1-(3-chlorophenyl)-2-[(1,1-dimethylethyl)amino]-1-propanone hydrochloride and by its generic name amfebutamone hydrochloride. Bupropion hydrochloride is commercially available as an immediate release form (WELLBUTRIN®), a sustained release form (WELLBUTRIN® SR and ZYBAN®), and an extended release form ((WELLBUTRIN® XL). Both WELLBUTRIN® SR and ZYBAN® are chemically and pharmaceutically identical.

The neurochemical mechanism of the antidepressant effect of bupropion is not well known. Bupropion affects chemicals within the brain that nerves use to send messages to each other. These chemical messengers are called neurotransmitters. The neurotransmitters that are released by nerves are taken up again by the nerves that release them for reuse (this is referred to as reuptake). Many skilled artisans believe that depression is caused by an imbalance among the amounts of neurotransmitters that are released. Bupropion is a selective catecholamine (dopamine and norepinephrine) reuptake inhibitor, and works by inhibiting the reuptake of the neurotransmitters dopamine and norepinephrine, an action which results in more dopamine and norepinephrine made available to transmit messages to other nerves. It has a small effect, if any, on the serotonin reuptake mechanism. Accordingly, bupropion is unique in that its major effect is on dopamine, an effect which is not shared by the SSRIs, e.g. paroxetine (PAXIL®), fluoxetine (PROZAC®), sertraline (ZOLOFT®) or the tricyclic antidepressants or TCAs, e.g. amitriptyline (ELAVIL®), imipramine (TOFRANIL®), desipramine (NORPRAMIN®).

Bupropion can also be used to treat other conditions, non-limiting examples of which include nicotine addition (e.g. smoking cessation), weight gain (e.g. obesity), Parkinson's disease, and seasonal affective disorder.

WELLBUTRIN®, WELLBUTRIN® SR and WELLBUTRIN® XL are used clinically for the management of major depressive disorder, bipolar depression mood disorder, other mood disorder, anxiety disorders, generalized anxiety disorder, panic disorder, post-traumatic stress disorder, and seasonal affective disorders, and have been approved for use in the treatment of major depressive disorder. ZYBAN® has been approved as an aid to patients wanting to quit smoking. WELLBUTRIN®, the immediate release formulation of bupropion, is dosed three times a day, suitably with 6 or more hours in between doses. For patients requiring more than 300 mg bupropion a day, each dose is prescribed not to exceed 150 mg. This requires administration of the tablets at least 4 times a day with at least 4 hours in between doses. The immediate release formulation results in more than a 75% release of the bupropion into the dissolution media in 45 minutes. The sustained release products are dosed twice daily, and the extended release products are dosed once daily.

Certain advantages exist in using bupropion for the treatment of diseases and conditions. For example, bupropion does not inhibit monoamine oxidase, and does not significantly block the reuptake of serotonin, unlike other neuronal monoamine reuptake inhibitors. Administration of bupropion can thus avoid or lessen many adverse effects commonly associated with other antidepressants such as tricyclic agents and monoamine oxidase inhibitors.

One of the known major side effects of bupropion is the incidence of seizures (e.g. grand-mal epileptic seizures), which is known to be strongly associated with the dose strength of the bupropion. For example, with WELLBUTRIN® at the originally recommended dosage (400-600 mg) the incidence of seizures in those treated with the drug was found to be significantly greater than other antidepressants, and so in 1986 the drug was removed from the market. It was shown that the risk of seizures increased significantly between the 450 mg/day dosage and the 600 mg/day dosage. As a result, bupropion was re-introduced into the market in 1989 with the maximum dose of 450 mg/day. However, it has been documented that seizures occur in patients taking bupropion not only in overdose but also in doses considered to be therapeutic (i.e. 450 mg/day or less) [Pesola & Avasarala, Bupropion seizures proportion among new-onset generalized seizures and drug related seizures presenting to an emergency department, J. Emerg. Med. 2002, 22, 235-239.] The high concentrations of bupropion needed for efficacy (e.g. antidepressant efficacy) establish a high floor concentration, and thus sets the stage for a narrow therapeutic index, in light of its concentration-dependent risk of causing seizures. [Preskorn S., Bupropion: What Mechanism of Action? J. Practical Psychiatry and Behavioral Health, January 2000, 272-276.]

Bupropion is known to lower the seizure threshold, and has been cited as one of the leading causes of drug related seizures [third behind cocaine intoxication and benzodiazepine withdrawal seizures—Davidson J., Seizures and Bupropion: A Review, J. Clin. Psychiatry, 1989, 50, 256-61]. Bupropion alone or in combination with other medications, is known to induce seizures in some patients with no prior record of seizure activity. It is not uncommon for patients to receive treatment with other antidepressant and/or atypical antipsychotic medications in combination with bupropion. As such, there is a need to manage, reduce, or eliminate the incidences of seizures resulting from bupropion administration, whether administered alone or in combination with other medications prone to lower the seizure threshold. Bupropion has also been known to produce seizures in combination with non-prescription (recreational) drugs such as cocaine and alcohol.

The selection of a suitable salt for a drug candidate is recognized as an important step in the preclinical phase of drug development. Changing the salt form of a drug is a recognized means of modifying its chemical and biological properties without modifying its structure. The choice of a particular salt form can have a profound effect on the physicochemical properties of the drug (e.g. dissolution rate, solubility, stability, and hygroscopicity). Substitution of one salt form of a drug for another can alter therapeutic efficacy, safety and/or quality, which are critical for the optimal formulation of the dosage form and large-scale manufacturing. However, as yet there is no reliable way of predicting exactly what effect changing the salt form of an active drug will have on its biological activity. Furthermore, even after many salts of the same basic agent have been prepared, no efficient screening techniques exist to facilitate selection of the salt most likely to exhibit the desired pharmacokinetic, solubility, and formulation profiles. In short, there is no known reliable way of predicting the influence of a particular salt species on the behavior of the parent compound in dosage forms. [Berge et al., Pharmaceutical Salts, Journal Pharm. Sci., 1977, Vol. 66, No. 1; Verbeeck et al. Generic substitution: The use of medicinal products containing different salts and implications for safety and efficacy, EP Journal Pharm. Sci, 28, 2006, 1-6.] A decision to change the salt form at a later stage introduces the need to repeat toxicological, formulation and stability tests, with obvious implications for the overall development and production time for the new pharmaceutical product.

According to the CAS® ("Chemical Abstracts Registry") Database, as of the date of this application, the only other salts of bupropion that have been previously reported are the hydrochloride (HCl), (2Z)-2-butenedioate, (2E)-2-butenedioate, methane sulfonate, formic acid, 2-hydroxy-1,2,3-propanetricarboxylate, phosphate and trifluoromethanesulfonate salts. Sodium bromide and potassium bromide are salts that have been widely used as an anticonvulsant and a sedative in the late 19th and early 20th centuries. Its action is due to the bromide ion. As of the date of this application, bromide has not been approved by the US Food and Drug Administration (FDA) for use in humans to control seizures. However, in Germany it continues to be approved for use as an antiepileptic drug for humans, particularly children and adolescents (sold under the brand name DIBRO-BE MONO®). The indications include severe forms of generalized tonic-clonic seizures, early-childhood-related Grand-Mal-seizures, and also severe myoclonic seizures during childhood. One tablet contains a therapeutic dose of 850 mg of potassium bromide. Bromide was the first drug found to be effective for the treatment of epilepsy in humans. Bromide has also been used as a veterinary drug, e.g. as an antiepileptic medication for dogs and cats.

Recommended therapeutic dose levels of bromide for treating epilepsy have been reported. For adults, a reported usual dose ranges from 3-6 grams/day [Niedermeyer E., ed. Benzodiazepines and other antiepileptic drugs, In: The epilepsies: Diagnosis and management, Baltimore: Urban & Schwarzenberg, 1990, 311-2; Ryan and Baumann; Bromides in Epilepsy Treatment, Pediatr Neruol, 1999, 21; 523-528.]. For children under 6 years of age, dose levels of 600-1800 mg/day have been recommended in two to three doses. For children over 6 years of age, it has been recommended that 300 mg to 1 gram be given three times daily. [Dreifuss F. E. and Bertram D. H., Bromide therapy for intractable seizures, Epilepsia, 1986, 27; 593; Ryan and Baumann; Bromides in Epilepsy Treatment, Pediatr Neruol, 1999, 21; 523-528]. The ED50 (minimum effective dose required to produce a desired effect in 50% of test population) for sodium bromide against chemically-induced seizures (induced by pentylenetetrazole) in mice has been reported to be 910 mg/kg [J. S. Grewal et al., Journal of Pharmacology and Expt'l Therapeutics, 1954, Vol. 112, Issue 1, 109-115.]

Bromide was the principal anticonvulsant of choice until the introduction of Phenobarbital in 1912 and other safer anticonvulsants. It was subsequently discovered that the known therapeutic dose levels of bromide induced bromism and a number of other significant toxic effects. The known therapeutic index is very small for bromide. As with other anticonvulsants, sometimes even therapeutic doses give rise to intoxication. Often indistinguishable from 'expected' side-effects, these toxic effects can include: bromism (i.e. central nervous system reactions reaching from somnolence to coma, cachexia, exicosis, loss of reflexes or pathologic reflexes, clonic seizures, tremor, ataxia, loss of neural sensitivity, paresis, papillar edema of the eyes, abnormal speech, cerebral edema, frank delirium, aggressivity, psychoses); loss of appetite; nausea/emesis; lethargy; propensity to sleep during the daytime; depression; loss of concentration and memory; confusion; headache; and skin diseases such as acne-form dermatitis.

Bromide's precise mechanism of action is unknown. The pharmacological mechanism of bupropion-induced seizures and the usefulness of antiepileptic drugs (e.g. bromide) in treating such seizures have not been established. There is limited knowledge about the effectiveness of antiepileptic drugs in bupropion-induced seizures in mice [P. Tutka et al., Epilepsy Research 64, 2005, 13-22], and nothing is known about the effectiveness of bromide in controlling bupropion-induced seizures. While no formal studies have been carried out to determine the therapeutic dose ranges for the effectiveness of bromide against bupropion-induced seizures, the therapeutic dose ranges for the effectiveness of bromide against other known seizures are known. For example, the therapeutic dose level for bromide against pentylenetetrazole-induced seizures is known to be 910 mg/kg [M. S. Grewal et al., Journal of Pharmacology And Experimental Therapeutics, Vol. 112, Issue 1, 109-115, 1954]. For a number of other anti-epileptic drugs (e.g. clonazepam, vigabatrin, etosuximide, valproate), the therapeutic dose levels that are required for the treatment of bupropion-induced seizures are comparable to the dose levels that are required for the treatment of pentylenetetrazole-induced seizures in mice. [P. Tutka et al. Epilepsy Research 64 (2005) 13-22; J. J. Luszczki, 2005, 30, 958-973; J. A. Armijo et al. Pharmacological Res. 2005, 51, 489-496; K. K. Borowicz et al. Epilepsia, 2004, 45(10), 1176-1183; S. J. Czuczwar et al., Polish Journal of Pharmacology, 2003, 55, 363-370; P. Tutka et al., J. Neural Transmission, 2002, 109, 455-466; K. K. Borowicz et al. European Neuropsychopharmacology 2004, 14, 77-85; and K. K. Borowicz et al., Polish Journal of Pharmacology, 2004, 56, 187-193.]

There remains a need for a bupropion composition that can be used for the treatment and/or prevention of a condition (e.g. major depressive disorder and nicotine addiction) in subjects that can benefit from bupropion administration, and that can provide fewer incidences of and/or reduce the severity of seizures associated with the administration of bupropion, as compared to known bupropion compositions.

The development of a stable, once daily modified-release bupropion formulation comprising safe levels of the bupropion hydrobromide salt; that provides for the reduction of incidences and/or reduction of the severity of bupropion-induced seizures as compared to an otherwise similar or identical composition containing an equivalent molar amount of bupropion hydrochloride; would be an advance in the art.

DESCRIPTION

Certain embodiments of the present invention relate to a bupropion composition that comprises a safe and pharmaceutically effective amount of bupropion hydrobromide; wherein the composition unexpectedly provides for fewer incidences of seizures and/or less severe seizures associated with the administration of bupropion than an otherwise similar or identical composition containing an equivalent molar amount of bupropion hydrochloride.

Certain embodiments of the invention relate to a bupropion composition that comprises a safe and pharmaceutically effective amount of bupropion hydrobromide and at least one pharmaceutically acceptable excipient; wherein administration of an amount of the bupropion hydrobromide to a first rat unexpectedly results in less incidences of and/or reduces the severity of bupropion-induced seizures when compared to incidences of bupropion-induced seizures resulting from administration of an equivalent molar amount of bupropion hydrochloride to a second rat; and wherein the incidences of and/or severity of bupropion-induced seizures are measured by an electroencephalogram analysis using a hippocampally implanted depth electrode.

Certain embodiments of the present invention relate to a bupropion composition that comprises a safe and pharmaceutically effective amount of bupropion hydrobromide; wherein said composition unexpectedly provides for fewer incidences of seizures and/or less severe seizures associated with the administration of bupropion, and is more stable, than an otherwise similar or identical composition containing an equivalent molar amount of bupropion hydrochloride. In particular, such a bupropion hydrobromide composition is more stable than an otherwise similar or identical composition containing an equivalent molar amount of bupropion hydrochloride under certain storage conditions, (for example when stored for 3 months or 6 months at 40 degrees C. and 75% relative humidity) as evidenced by a reduced amount of at least one moiety (e.g. degradation product) that is characteristic of bupropion degradation and/or a reduced fluctuation or reduction in potency after being stored under accelerated storage conditions (for example after storage for 3 months or 6 months), and/or by a reduced fluctuation in the in-vitro dissolution profile in at least one dissolution medium over a 24 hour period.

Certain embodiments of the present invention relate to methods of reducing incidences of bupropion-induced seizures and/or reducing the severity of bupropion induced seizures comprising administering a safe and pharmaceutically effective amount of bupropion hydrobromide to a subject in need of bupropion administration, wherein said incidences of and/or severity of bupropion-induced seizures resulting from the administration of bupropion hydrobromide is less than the incidences of and/or severity of bupropion-induced seizures resulting from the administration of an equivalent molar amount of bupropion hydrochloride.

Certain embodiments of the present invention relate to methods of treating a condition comprising administering a safe and effective amount of bupropion hydrobromide to a subject in need of bupropion administration, wherein the bupropion hydrobromide provides for fewer incidences of bupropion-induced seizures than an equivalent molar amount of bupropion hydrochloride.

Certain embodiments of the present invention relate to methods of treating a condition comprising administering a safe and effective amount of bupropion hydrobromide to a subject in need of bupropion administration, wherein the bupropion hydrobromide provides for fewer incidences of bupropion-induced seizures and/or reduces the severity of such seizures than an equivalent molar amount of bupropion hydrochloride.

As shown herein below, it is demonstrated that bupropion hydrobromide has a lower propensity to induce seizures and/or reduce the severity of bupropion induced seizures when compared to bupropion hydrochloride. This allows one to reduce the incidences of such seizures, reduce the severity of the seizures, treat subjects who would otherwise not be candidates for bupropion therapy because of their risk for seizure induction, and/or to treat a subject with even higher doses of bupropion than would be possible and safe with bupropion hydrochloride.

Certain embodiments of the present invention relate to methods of treating a condition comprising administering a composition containing a safe and effective amount of bupropion hydrobromide to a subject in need of bupropion administration, wherein the bupropion hydrobromide provides for fewer incidences of bupropion-induced seizures than an equivalent molar amount of bupropion hydrochloride.

Certain embodiments of the present invention relate to a method of treating a subject at risk of bupropion-induced seizures in need of such treatment by administering a safe and effective amount of bupropion hydrobromide to the subject Certain embodiments of the present invention relate to the use of bupropion hydrobromide compositions to prepare a medicament for the treatment of one or more conditions that can benefit from the administration of bupropion, wherein the treatment allows for the reduction or avoidance of incidences of and/or the reduction of the severity of bupropion-induced seizures as compared to an otherwise identical or similar composition containing an equivalent molar amount of bupropion hydrochloride.

Certain embodiments of the present invention further contemplate a method of preparing a medicament for the treatment of a condition which can benefit from the administration of bupropion, comprising bringing an effective amount of bupropion hydrobromide into contact with one or more pharmaceutically acceptable excipients.

Certain embodiments relate to the use of bromide salts to reduce the incidences and/or severity of bupropion induced seizures, such as those seizures induced by the administration of bupropion hydrochloride.

Certain embodiments relate to compositions comprising a compound of formula I (bupropion hydrobromide):

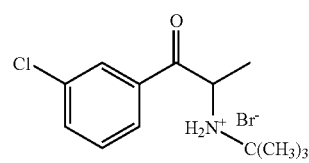

(I)

and pharmaceutically acceptable carriers, excipients and/or diluents; said composition having greater stability than a corresponding pharmaceutical composition comprising bupropion hydrochloride and pharmaceutically acceptable carriers, excipients and/or diluents; and providing a reduction or avoidance of incidences of and/or a reduction in the severity of bupropion-induced seizures.

In certain embodiments of the present invention, the bupropion salt can be in the form of its anhydrous, hydrated, and solvated forms, in the form of prodrugs, and in the individually optically active enantiomers of the bupropion salt, such as for example (+)-bupropion and (−)-bupropion. Suitable pharmaceutically acceptable salts of bupropion for use in the present invention are more stable than bupropion hydrochloride, and provide for the reduction or avoidance of incidences of seizures associated with the administration of bupropion. Suitable salts of bupropion also include for example, pharmaceutically acceptable acid addition salts. In certain embodiments, the acid addition salt of bupropion can be indirectly obtained by the separate addition of bupropion and an acid to the core formulation.

Certain embodiments of the present invention contemplate the use of bupropion hydrobromide to prepare a medicament to treat a condition which can benefit from administration of bupropion, wherein said medicament has greater stability than a corresponding medicament comprising bupropion hydrochloride, and provides for the reduction or avoidance of incidences of and/or the reduction in the severity of seizures associated with the administration of bupropion.

As discussed infra and generally known in the art, appropriate dissolution medium and appropriate conditions for assaying the dissolution characteristics of pharmaceutical dosage forms such as tablets are well known in the art and are contained in the United States Pharmacopoeia and its European or Japanese counterparts, and include by way of example dissolution in USP Type 1 apparatus (Rotating Basket Method) in 900 ml water; 0.1 N HCl; 0.1N HCl+0.1% Cetrimide; USP buffer pH 1.5; Acetate buffer pH 4.5; Phosphate Buffer pH 6.5; or Phosphate Buffer pH 7.4 at 75 RPM at 37 degrees C+/−0.5 degrees C. Additionally, other examples of appropriate dissolution media include USP-3 media and USP-3 dissolution conditions e.g, SGF pH 1.2; Acetate buffer pH 4.5 and Phosphate Buffer pH 6.8.

Certain embodiments of the present invention contemplate the use of bupropion hydrobromide to produce once-daily administrable tablets or other dosage forms that are bioequivalent to WELLBUTRIN™ or ZYBAN™/WELLBUTRIN™ SR tablets as defined by FDA criteria when administered once daily to a subject in need thereof. In particular at least one of the Tmax, Cmax, or AUC profile of certain embodiments of the present invention is within 80-125% of WELLBUTRIN™ and ZYBAN™/WELLBUTRIN™ when administered once daily to a subject in need thereof. In certain embodiments these formulations are also free of any significant food effect.

Certain embodiments of the present invention provide bupropion hydrobromide dosage forms (e.g. tablets) containing at least one coating (e.g. SMARTCOAT™ coating) which is resistant to dose dumping in high alcohol, (e.g., 40% ethanol), wherein the dosage forms allow for the reduction or avoidance of incidences of and/or the reduction in the severity of bupropion-induced seizures.

Certain embodiments of the present invention include both oral and non-oral bupropion hydrobromide containing medicaments. For example, the invention embraces compositions suitable for oral, topical, injectable, inhalation and other modes of administration.

Certain embodiments of the present invention include extended release formulations, delayed release formulations, and/or enhanced absorption formulations.

In a more particular implementation of certain embodiments of the invention, a bupropion medicament composition comprises (i) a core that includes bupropion hydrobromide, a binder and a lubricant; and (ii) a controlled release coat substantially surrounding said core; wherein said composition provides controlled release of said bupropion hydrobromide, and a reduction or avoidance of incidences of and/or a reduction in the severity of bupropion-induced seizures. Such compositions optionally can comprise one or more additional coatings surrounding the core and/or the controlled release coat such as a moisture barrier coat, enteric coat or a coating that affects the physical integrity and/or appearance of the composition. The binder can be selected from known pharmaceutical binders such as polyvinyl alcohol. The lubricant also can be selected from known pharmaceutical lubricants such as glyceryl behenate. The controlled release coat can include a water-insoluble polymer, a water-soluble polymer, and optionally a plasticizer. The water-insoluble polymer can be selected from a range of water insoluble polymers useful in extended release pharmaceutical compositions such as ethylcellulose. The water-soluble polymer can be selected from a variety of water-soluble polymers useful in extended release pharmaceutical compositions such as polyvinylpyrrolidone. The plasticizer if present can be selected from a range of known plasticizers such as mixtures of polyethylene glycol 4000 and dibutyl sebacate. Certain embodiments of these compositions include once-daily administrable compositions that are bioequivalent to WELLBUTRIN™ or ZYBAN™/WELLBUTRIN™ SR tablets when administered once-daily to a subject in need thereof. These compositions may or may not exhibit a food effect. Further, certain embodiments of these compositions can be resistant to dose dumping in the presence of high alcohol concentrations (e.g., 40% by weight of ethanol).

In another particular implementation of certain embodiments of the present invention, the bupropion composition comprises (i) a core that includes bupropion hydrobromide, a binder and a lubricant; and (ii) a controlled release coat substantially surrounding said core; wherein said controlled release coat includes an aqueous dispersion of a neutral ester copolymer without any functional groups, a polyglycol having a melting point greater than 55° C., and one or more pharmaceutically acceptable excipients, wherein said coat is coated onto said core and cured at a temperature at least equal to or greater than the melting point of the polyglycol. The composition provides controlled release of said bupropion hydrobromide, and a reduction or avoidance of incidences of bupropion-induced seizures. Optionally, this medicament can comprise one or more additional coatings surrounding the core and/or controlled release coating such as a moisture barrier coat, enteric coat, coat that precludes dose dumping in specific media such as alcohol, and/or a coating that affects the physical stability or integrity of the medicament and/or its physical appearance.

In a particular implementation of certain embodiments of the present invention, the bupropion composition comprises multiparticulates.

Certain embodiments of the present invention include controlled release matrix tablet formulations.

Certain embodiments of the present invention include a bupropion composition that comprises a second drug. The second drug (e.g. other anti-depressants, SSRI's, anti-anxiety agents, atypical antipsychotic drugs, medications that interact with serotonin neurotransmission, medications that interact with norepinephrine neurotransmission, medications that interact with dopamine neurotransmission) can be administered in combination with the subject bupropion hydrobromide salt. The second drug can elicit a synergistic benefit on bupropion efficacy as well as non-synergistic drug combinations. Non-limiting examples of the second drug include citalopram, escitalopram, venlafaxine, quetiapene, buspirone and mixtures thereof.

In accordance with one aspect of certain embodiments of the present invention, there is provided a controlled release composition comprising (i) a core comprising an effective amount of a bupropion hydrobromide, a binder, a lubricant; and (ii) a controlled release coat surrounding said core; and optionally (iii) a moisture barrier surrounding said controlled release coat or the core; and; wherein the composition exhibits a dissolution profile such that after 2 hours no more than about 20% of the bupropion hydrobromide content is released (e.g. in certain embodiments from about 2% to about 18%; from about 4% to about 8%; or about 5% of the bupropion hydrobromide content is released after 2 hours); after 4 hours from about 15% to about 45% of the bupropion hydrobromide content is released (e.g. in certain embodiments from about 21% to about 37%; from about 28% to about 34%, or about 32% of the bupropion hydrobromide content is released after 4 hours); after 8 hours from about 40% to about 90% of the bupropion hydrobromide content is released (e.g. in certain embodiments from about 60% to about 85%; from about 68% to about 74%; or about 74% of the bupropion hydrobromide content is released after 8 hours); and after 16 hours no less than about 80% of the bupropion hydrobromide content is released (e.g. in certain embodiments not less than about 93%; not less than about 96%; or not less than about 99% of the bupropion hydrobromide content is released after 16 hours) when using a USP apparatus design with a dissolution medium as found in the USP (e.g. USP Apparatus Type 1 at 75 rpm, 900 ml, 0.1N HCl, at 37° C.±0.5° C.); and wherein the bupropion hydrobromide composition is more stable than an otherwise similar or identical composition comprising the equivalent molar amount of bupropion hydrochloride when each are stored under accelerated storage conditions (e.g. stored for 3 months or 6 months at about 40 degrees C. and at about 75% relative humidity), and provides for the reduction or avoidance of incidences of and/or the reduction in the severity of bupropion-induced seizures.

In certain embodiments the composition exhibits a dissolution profile such that after 2 hours not more than about 40% of the bupropion hydrobromide is released (e.g., about 33%), after 4 hours from about 40% to about 75% of the bupropion hydrobromide is released (e.g. about 59%), after 8 hours not less than about 75% of the bupropion hydrobromide is released (e.g. about 91%), and after 16 hours not less than about 85% of the bupropion hydrobromide is released (e.g. about 97%), when using a USP apparatus design with a dissolution medium as found in the USP (e.g. USP Apparatus Type 1 at 75 rpm, 900 ml, 0.1N HCl, at 37° C.±0.5° C.).

Certain embodiments of the present invention include a bupropion composition that comprises from about 50 mg to about 1000 mg of bupropion hydrobromide, including 100, 150, 174, 200, 250, 300, 348, 350, 400, 450, 500, 510, 520, 530, 540, 550, 560, 570, 580, 590, 600, 650, 700, 750, 800, 850, 900, 950 and all values and ranges therebetween. For example, certain embodiments include a composition which comprises 174 mg, 348 mg or 522 mg of bupropion hydrobromide per unit dose.

In accordance with one aspect of certain embodiments of the present invention, there is provided an enhanced-absorption tablet comprising (i) a core comprising an effective amount of bupropion hydrobromide, a binder, a lubricant; and (ii) a controlled release coat surrounding said core; and wherein the enhanced absorption tablet exhibits a dissolution profile such that after 2 hours, no more than about 25% of the bupropion hydrobromide content is released (e.g. in certain embodiments from about 10% to about 20% of the bupropion hydrobromide content is released after 2 hours); after 4 hours from about 25% to about 55% of the bupropion hydrobromide content is released (e.g. in certain embodiments from about 30% to about 50% of the bupropion hydrobromide content is released after 4 hours); after 8 hours more than about 60% of the bupropion hydrobromide content is released (e.g. in certain embodiments from about 70% to about 90% of the bupropion hydrobromide content is released after 8 hours); and after 16 hours more than about 70% of the bupropion hydrobromide content is released (e.g. in certain embodiments more than about 80% of the bupropion hydrobromide content is released after 16 hours) when using a USP apparatus design with a dissolution medium as found in the USP (e.g. USP Apparatus Type 1 at 75 rpm, 900 ml, 0.1N HCl, at 37° C.±0.5° C.); and wherein the bupropion hydrobromide enhanced-absorption tablet is more stable than an otherwise similar or identical composition comprising the equivalent molar amount of bupropion hydrochloride when each are stored under accelerated storage conditions (e.g. stored for 3 months or 6 months at about 40 degrees C. and at about 75% relative humidity), and provides for the reduction or avoidance of incidences of and/or the reduction in the severity of bupropion-induced seizures.

In certain embodiments the bupropion hydrobromide composition can comprise a dissolution profile such that after 2 hours not more than about 40% of bupropion hydrobromide is released therefrom (e.g., about 33%); after 4 hours from about 40 to about 75% of bupropion hydrobromide is released therefrom (e.g., about 59%), after 8 hours not less than about 75% of bupropion hydrobromide is released therefrom (e.g., about 91%), and after 16 hours not less than about 85% of bupropion hydrobromide is released therefrom (e.g., about 97%) when using a USP apparatus design with a dissolution medium as found in the USP (e.g. USP Apparatus Type 1 at 75 rpm, 900 ml, 0.1N HCl, at 37° C.±0.5° C.).

As discussed infra, in-vitro dissolution of bupropion from controlled or extended release formulations according to certain embodiments of the invention can be determined by methods well known to those skilled in the pharmaceutical art. Suitable methods are contained in the United States Pharmacopoeia (USP) as well as European and Japanese counterparts of the USP and are exemplified infra. This includes by way of example effecting dissolution in a USP 1 apparatus (Rotating Type Basket Method) in 900 ml water, 0.1N HCl, 0.1N HCl+0.1% Cetrimide, USP Buffer pH 1.5, Acetate Buffer pH 6.5 or Phosphate Buffer pH 7.4 at 75 RPM at 37 degrees C+/−0.5 degrees C. or by effecting dissolution using a USP3 dissolution medium such as SGF having a pH 1.2; acetate buffer having a pH of 4.5 or phosphate buffer having a pH of 6.8.

BRIEF DESCRIPTION OF THE DRAWINGS

FIGS. 49A and 49B contain bar graphs showing the % of 3-CBA formed in forced degradation studies of bupropion hydrochloride (HCl) vs. bupropion HBr in the presence of excipients.

FIGS. 52A and 52B contain bar graphs showing the % of 827U76 formed in forced degradation studies of bupropion HCl vs. bupropion HBr in the presence of excipients.

FIG. 63 contains the results of stability studies for Bupropion HBr XL 174 mg core (Lot # Bup-HBr-XL-004-5 core; Bupropion HBr XL 348 mg core (Lot #Bup-HBr-XL-009-5 core; Bupropion HCl XL 150 mg core (Lot #05E056) and Bupropion HCl XL 300 mg core (Lot # 05D380) initially, after 10 days open and closed, and after 20 days open and closed. The % of impurities 3-CBZ, 852U77, 20U78dilu, 827U76 are shown therein.

FIG. 64 and FIGS. 65A and 65B respectively contain stability data for bupropion 348 mg HBr XL tablets (Lot #Bup-HBr-XL-348-025-5) and Bupropion HBr EA 300 mg tablets (Lot #Bup-HBr-EA-300-001-5 initially and after 3 months, 6 months, 9 months and 12 months under accelerated storage conditions (40 degrees C. and 75% relative humidity). The assay tested for amount of impurities 3-CBA, 852U77, 20U78/diluent, 827U76, and also compared the dissolution profiles and appearance thereof.

FIGS. 66A and 66B compare the dissolution profiles and in-vitro drug release of Bupropion HBr XL 348 mg tablets (final) Lot #Bup-HBr-XL-012-5, Wellbutrin XL 300 mg tablets final (Lot #05A116), Bupropion HBr XL 348 mg tablets EC1) Lot #Bup-HBr-XL-012-5 (EC 32 mg wg), and Wellbutrin XL 300 mg tablets (EC1) (Lot #05D047) in different USP-3 media (SGF pH 1.2, Acetate Buffer pH 4.5, and Phosphate Buffer pH 6.8 over a period of 16 hours.

DEFINITIONS

Figure 1:
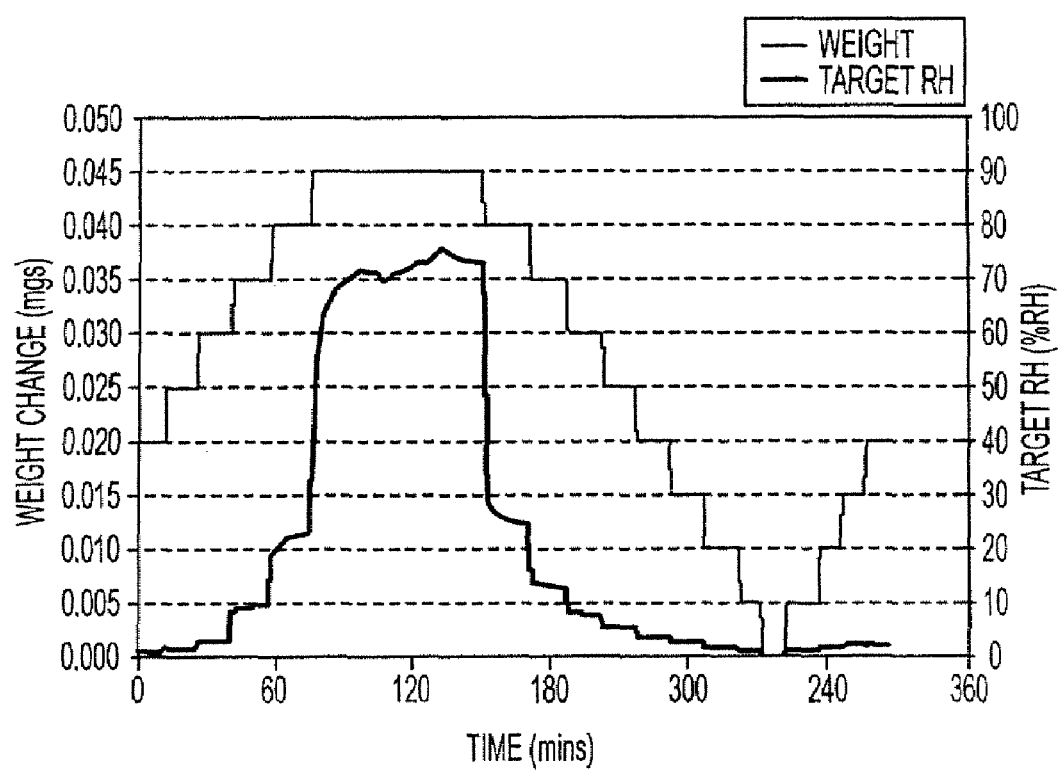
FIG. 1 shows a Dynamic Vapour Sorption ("DVS") profile for bupropion hydrobromide (HBr).

The following definitions are provided in order to more specifically describe the invention. Otherwise all terms are to be accorded their ordinary meaning as they would be construed by one of ordinary skill in the art, i.e. pharmaceutical drug formulations.

The term "seizure" as used herein, means a temporary abnormal electro-physiologic phenomena (e.g. involuntary electrical activity) of the brain, resulting in abnormal synchronization of electrical neuronal activity that can result in a wide variety of manifestations, non-limiting examples of which include tonic or clonic movements, convulsions, staring, tongue biting, urination, loss of consciousness, alteration in mental state, psychic symptoms such as déjà vu or jamais vu, and combinations thereof. Non-limiting examples of types of seizures include: (i) partial seizures (i.e. focal seizures) such as simple partial seizures, complex partial seizures (i.e. temporal lobe or psychomotor seizures) and partial seizures evolving to secondarily generalized seizures; (ii) generalized seizures such as absence seizures (i.e. petit-mal seizures), myoclonic seizures, clonic seizures, tonic seizures, tonic-clonic seizures (i.e. grand-mal seizures), and atonic seizures; and (iii) unclassified epileptic seizures.

The terms "bupropion-induced seizures" or "seizures associated with the administration of bupropion" as used herein are used interchangeably, and mean seizures that result from the administration of bupropion or a mixture of bupropion with one or more other drugs.

The term "incidences of bupropion-induced seizures" as used herein when referring to bupropion administration is defined to mean the number of bupropion-induced seizures as determined by behavioural observations of convulsions or other movements characteristic of a seizure; and/or as determined by electroencephalogram ("EEG") observations of electrical activity in the brain characteristic of a seizure using cortically mounted surface electrodes and/or hippocampally implanted depth electrodes.

The term "reducing incidences of bupropion-induced seizures", as used herein when referring to bupropion administration, is defined to mean that the administration of bupropion hydrobromide or compositions containing bupropion hydrobromide, results in fewer incidences of bupropion-induced seizures as compared to the administration of an equivalent molar amount of bupropion hydrochloride or otherwise identical composition containing an equivalent molar amount of bupropion hydrochloride, when exposed to identical conditions and after identical periods of time.

The terms "adverse effects associated with bupropion" or "side effects of bupropion" as used herein are used interchangeably, and mean the adverse drug reactions resulting from the administration of bupropion or a mixture of bupropion with one or more other drugs, non-limiting examples of which include seizures, nausea, vomiting, excitement, agitation, blurred or blurry vision, restlessness, postural tremors, hallucinations/confusional states with the potential for abuse, anxiety, insomnia, headaches and/or migraines, dry mouth, constipation, tremors, sleeping disturbances, dermatologic problems (e.g., rashes), neuropsychiatric signs and symptoms (e.g., delusions and paranoia), weight gain, and combinations thereof.

The term "depression" as used herein refers to any nervous system disorder and/or mental condition characterized by, but not limited to, the following symptoms: depressed mood, anhedonia, feelings of intense sadness and despair, mental slowing, loss of concentration, pessimistic worry, agitation, self-deprecation, disturbed sleep patterns (e.g. insomnia, loss of REM sleep, or hypersomnia), anorexia, changes in appetite and weight loss or weight gain, Psychomotor agitation, decreased energy, decreased libido, and changes in hormonal circadian rhythms, withdrawal, altered daily rhythms of mood, activity, temperature and neuroendocrine function, and combinations thereof. Non-limiting examples of "depression" include major depressive disorder, bipolar depressed mood disorder, adjustment mood disorder, and post-partum mood disorder.

The term "condition" as used herein when referring to the administration of bupropion, means a condition, disease or disorder which can be treated with bupropion. Non-limiting examples of which include depression, seasonal affective disorder, anxiety disorders, generalized anxiety disorder, social anxiety disorder, obsessive compulsive disorder, post traumatic stress disorder (PTSD), panic disorder, disorders requiring a stimulant effect, attention-deficit/hyperactivity disorder (ADHD), narcolepsy, hypersomnia, substance-abuse disorders, stimulant dependence, marijuana dependence, nicotine dependence, obesity, female and male sexual dysfunction (e.g. premature ejaculation), premenstrual syndrome, premenstrual dysphoric disorder, neuropathic pain, fibromyalgia, diabetic neuropathy, viral infection, sleep apnea, sleep disorders, migraines, Parkinson's disease, restless legs syndrome, and combinations thereof.

The terms "treatment", "treating" or "treat" as used herein when referring to a condition, and as understood in the art, are defined to mean an approach for obtaining beneficial or desired results, including clinical results. Beneficial or desired clinical results can include, but are not limited to, alleviation of one or more symptoms of the condition, diminishment of extent of disease or condition, stabilized (i.e. not worsening) state of disease or condition, preventing spread of disease, delay or slowing of disease progression, palliation of the disease state, and remission (whether partial or total), whether detectable or undetectable. "Treatment" can also mean prolonging survival of a subject as compared to the expected survival of the subject if not receiving treatment.

The terms "at risk," "patient at risk," and "a subject at risk of bupropion-induced seizures" refers to those subjects that either through existing illness, prior medical illness, past history of seizures, prior exposure, testing, dosing or other administration of bupropion hydrochloride are known to have a greater propensity to have bupropion induced seizures compared to a subject who does not exhibit seizures under the same or similar conditions and/or a subject who based on a clinical evaluation of the subject's health, other medications and/or treatments is expected to have a greater propensity to have bupropion induced seizure activity.

The term "palliating" as used herein when referring to a condition means that the extent and/or undesirable clinical manifestations of a condition or disease state are lessened and/or time course of the progression is slowed or lengthened, as compared to not treating the condition.

The terms "subject" or "patient" as used herein are used interchangeably and mean all members of the animal kingdom (e.g. humans).

The term "subject in need of" as used herein when referring to bupropion administration, means a subject having a condition that can be treated with bupropion.

The term "effective amount" or "pharmaceutically effective amount" as used herein are used interchangeably, and are defined to mean the amount or quantity of the active drug (e.g. bupropion hydrobromide) or polymorph or enantiomer thereof which is sufficient to elicit an appreciable biological response when administered to a patient. It will be appreciated that the precise therapeutic dose will depend on the age and condition of the patient and the nature of the condition to be treated and will be at the ultimate discretion of the attendant physician. The term "pharmaceutically acceptable" as used herein refers to compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

The terms "enhanced stability", "greater stability", "increased stability" or "more stable" as used herein when referring to bupropion hydrobromide, can be used interchangeably in this application, and are defined to mean that the bupropion hydrobromide or composition containing bupropion hydrobromide, shows less degradation as determined by the formation of less of at least one degradation product characteristic of bupropion degradation, than an equivalent molar amount of bupropion hydrochloride or an otherwise similar or identical composition containing an equivalent molar amount of bupropion hydrochloride, when exposed to similar or identical conditions. Non-limiting examples of conditions include accelerated storage conditions in open bottles or in closed bottles; and shelf-life storage conditions in open bottles or in closed bottles. Non-limiting examples of accelerated storage conditions include temperatures of 40 degrees C.; 55 degrees C.; 100 degrees C.; and 105 degrees C.; and relative humidities of 75% and 100%. A non-limiting example of a shelf-life storage condition includes a temperature of 25 degrees C. and a relative humidity of 60%. Non-limiting examples of storage times include 24 hours, 48 hours, 10 days, 13 days, 14 days, 20 days, 24 days, 1 month, 2 months, 3 months, 4 months, 5 months, 6 months, 9 months, 12 months and 18 months. In addition, enhanced stability can also mean that the composition containing bupropion hydrobromide exhibits less of a fluctuation (i.e. more consistent) or less of a reduction in potency as evidenced by less of a fluctuation in the in-vitro dissolution profile, as compared to an otherwise similar or identical composition containing an equivalent molar amount of bupropion hydrochloride, when exposed to like conditions.

The term "less degradation" as used herein when referring to bupropion hydrobromide or a composition containing bupropion hydrobromide, is defined to mean any measurable decrease in the amount of at least one bupropion degradation impurity characteristic of bupropion degradation, and/or any measurable difference in the retention of potency, relative to an equivalent molar amount of bupropion hydrochloride or an otherwise similar or identical composition containing an equivalent molar amount of bupropion hydrochloride, when exposed to similar or identical conditions. Non-limiting examples of conditions include accelerated storage conditions in open bottles or in closed bottles; and shelf-life storage conditions in open bottles or in closed bottles. Non-limiting examples of accelerated storage conditions include temperatures of 40 degrees C.; 55 degrees C.; 100 degrees C.; and 105 degrees C.; and relative humidity of 75% and 100%. A non-limiting example of a shelf-life storage condition includes a temperature of 25 degrees C. and a relative humidity of 60%. Non-limiting examples of storage times include 24 hours, 48 hours, 10 days, 13 days, 14 days, 20 days, 24 days, 1 month, 2 months, 3 months, 4 months, 5 months, 6 months, 9 months, 12 months and 18 months.

The terms "degradation product", "bupropion degradation product", "bupropion degradation impurity" or "impurity" as used herein when referring to the degradation of bupropion, are used interchangeably and are defined to include those listed on page 281 of the 26th edition of the USP and any other degradation product that may appear as peaks on a chromatogram during the assay that are characteristic of bupropion degradation.

The term "dissolution profile" or "release profile" as used herein are used interchangeably in this application, and are defined to mean a quality control test conducted according to instructions found in the United States Pharmacopoeia ("USP"), i.e. using a USP apparatus design with a dissolution medium as found in the USP. Dissolution tests in-vitro measure the rate and extent of dissolution of the active drug in an aqueous dissolution medium. The dissolution rate or in-vitro release rates of drug from the modified release dosage forms of the present invention can be measured using one of many USP apparatus designs and dissolution media; non-limiting examples of which include a USP Type 1 apparatus design or USP Type 2 apparatus design, with a dissolution medium selected from water; 0.1N HCl; 0.1N HCl with added Sodium Chloride (e.g. 15.7 g NaCl/Liter); 0.1N HCl with added 0.1% Cetrimide; USP Buffer pH 1.5; Acetate Buffer pH 4.5; Phosphate Buffer pH 6.5; Phosphate Buffer pH 6.8; and Phosphate Buffer pH 7.4.

The term "dose dumping" as used herein in respect of "alcohol induced dose dumping" is defined to mean the unintended premature release (in-vitro) of at least one drug from a modified release dosage form. The term "premature release" as used herein is defined to mean a release of at least one drug from a modified release dosage form in dissolution media containing alcohol (e.g. dissolution medium containing from about 5% to about 40% ethanol) wherein the rate of release is faster than the rate of release of the identical drug(s) from the identical modified release dosage form in the otherwise identical dissolution media not containing alcohol (e.g. dissolution medium containing about 100% 0.1 N HCl). A non-limiting example of an "alcohol induced dose dumping" is the premature release of bupropion from a modified release tablet over a period of about 2 hours when dissolution is tested in 900 ml of Alcohol USP comprising dissolution media using USP Apparatus Type 1 at 75 rpm at 37° C. In certain embodiments the term "Alcohol USP comprising dissolution media" means any dissolution media comprising from about 5% to about 40% (v/v) of Alcohol USP (e.g. 5% ethanol and 95% 0.1N HCl; 20% ethanol and 80% 0.1N HCl; and 40% ethanol and 60% 0.1N HCl).

The terms "resistant to alcohol", "resistant to ethanol", "resistant to dose dumping", "resistant to alcohol-induced dose dumping" and "resisting dose dumping" as used herein are used interchangeably, and are defined to mean the ability of the dosage form to modify release (in-vitro) of the at least one drug while in the presence of alcohol (e.g. from about 5% to about 40% ethanol), such that there is not a premature release of the at least one drug from the modified release dosage form. For example, in certain embodiments the rate of release of at least one drug from a modified release dosage form in dissolution media containing alcohol (e.g. dissolution medium containing from about 5% to about 40% ethanol) is slower than the rate of release of the identical drug(s) from the identical modified release dosage form in dissolution media not containing alcohol (e.g. dissolution medium containing about 100% 0.1 N HCl).

The terms "active", "active agent", "active pharmaceutical agent", "active drug" or "drug" as used herein are used interchangeably and are defined to mean any active pharmaceutical ingredient ("API"), including its pharmaceutically acceptable salts (non-limiting examples of which include the hydrochloride salts, the hydrobromide salts, the hydroiodide salts, and the saccharinate salts), as well as the anhydrous, hydrated, and solvated forms, polymorphs, prodrugs, and the individually optically active enantiomers of the API. The active drug includes the molecule or ion and the appended portions of the molecule that cause the drug to be an ester or salt of the molecule.

The term "other drug" or "second drug" as used herein means a drug other than bupropion, including but not limited to anti-depression agents, other neuropsychiatric drugs, atypical antipsychotics, drug that affects central or peripheral serotonin neurotransmission, drugs that affect central norepinephrine neurotransmission, drugs that affect central dopamine neurotransmission, vasodilators, anti-anxiety agents, appetite modulators, sleep modulating drugs, SSRIs, anti-viral agents, anti-pain agents, anti-migraine agents, anti-inflammatories (both steroidal and non-steroidal) serotonin receptor agonists, and more particularly can include citalopram, escitalopram, venlafaxine, clozapine, melperone, amperozide, iloperidone, risperidone, quetiapene, olanzapine, ziprasidone, aripiprazole, reboxetine, Viagra®, sertraline, paroxetine, fluoxetine, gabapentin, valproic acid, amitriptyline, lofepramine, fluvoxamine, imipramine, mirtazapine, nefazodone, nortriptyline, SAM-E, buspirone, combinations thereof, and their pharmaceutically acceptable salts (e.g. the hydrochloride salts, the hydrobromide salts, the hydroiodide salts, and the saccharinate salts), as well as the anhydrous, hydrated, and solvated forms, polymorphs, pro-drugs, and the individually optically active enantiomers of the other drug.

The term "moiety" as used herein is defined to mean the molecule or ion, excluding those appended portions of the molecule that cause the drug to be an ester or salt of the molecule, responsible for the physiological or pharmacological action of the drug substance.

The terms "formulation" or "composition" as used herein are used interchangeably and refer to the drug in combination with pharmaceutically acceptable carriers and additional inert ingredients. The formulation can be administrable by a variety of means.

The term "dosage form" as used herein is defined to mean a pharmaceutical preparation or system in which a dose of at least one active drug is included. For example, a dosage form can include at least one modified release dosage form, at least one osmotic dosage form, at least one erosion modified release dosage form, at least one dissolution modified release dosage form, at least one diffusion modified release dosage form, at least one modified release matrix core, at least one modified release matrix core coated with at least one modified release coat, at least one enteric coated dosage form, at least one dosage form surrounded by at least one osmotic subcoat, capsules, minitablets, caplets, uncoated microparticles, microparticles coated with at least one modified release coat, or any combination thereof.

The term "medicament" as used herein refers to oral and non-oral dosage forms, including but not limited to, all modified release dosage forms, osmosis controlled release systems, erosion controlled release systems, dissolution controlled release systems, diffusion controlled release systems, matrix tablets, enteric coated tablets, single and double coated tablets (including the extended release and enhanced absorption tablets as described herein), capsules, minitablets, caplets, coated beads, granules, spheroids, pellets, microparticles, suspensions, topicals such as transdermal and transmucosal compositions and delivery systems (containing or not containing matrices), injectables, and inhalable compositions.

"Modified release dosage forms" as used herein is defined (e.g. as by the United States Pharmacopoeia "USP") as those whose drug release characteristics of time course and/or location are chosen to accomplish therapeutic or convenience objectives not offered by conventional immediate release dosage forms. The rate of release of the active drug from a modified release dosage form is controlled by features of the dosage form and/or in combination with physiologic or environmental conditions rather than by physiologic or environmental conditions alone. The modified release dosage forms of certain embodiments can be contrasted with conventional immediate release dosage forms which typically produce large maximum/minimum plasma drug concentrations (Cmax/Cmin) due to rapid absorption of the drug into the body (i.e., in-vivo, relative to the drug's therapeutic index; i.e., the ratio of the maximum drug concentration needed to produce and maintain a desirable pharmacological response). In conventional immediate release dosage forms, the drug content is released into the gastrointestinal tract within a short period of time, and plasma drug levels peak shortly after dosing. The design of conventional immediate release dosage forms is generally based on getting the fastest possible rate of drug release, and therefore absorbed, often at the risk of creating undesirable dose related side effects. The modified release dosage forms of certain embodiments of the invention, on the other hand, improve the therapeutic value of the active drug by reducing the ratio of the maximum/minimum plasma drug concentration (Cmax/Cmin) while maintaining drug plasma levels within the therapeutic window. The modified release dosage forms of certain embodiments attempt to deliver therapeutically effective amounts of bupropion hydrobromide and mixtures of bupropion hydrobromide with at least one other drug as a once-daily dose so that the ratio Cmax/Cmin in the plasma at steady state is less than the therapeutic index, and to maintain drug levels at constant effective levels to provide a therapeutic benefit over a period of time (e.g. 24-hour period). The modified release dosage forms of certain embodiments of the invention, therefore, avoid large peak-to-trough fluctuations normally seen with conventional or immediate release dosage forms and can provide a substantially flat serum concentration curve throughout the therapeutic period. Modified-release dosage forms can be designed to provide a quick increase in the plasma concentration of the bupropion salt which remains substantially constant within the therapeutic range of bupropion salt for a period of time (e.g. 24-hour period). Alternatively, modified-release dosage forms can be designed to provide a quick increase in the plasma concentration of the drug, which although may not remain constant, declines at a rate such that the plasma concentration remains within the therapeutic range for a period of time (e.g. 24-hour period). The modified release dosage forms of certain embodiments of the invention can be constructed in many forms known to one of ordinary skill in the drug delivery arts and described in the prior art. The USP considers that the terms controlled release, prolonged release and sustained release are interchangeable. Accordingly, the terms "modified-release", controlled-release", "control-releasing", "rate-controlled release", "extended release", "prolonged-release", and "sustained-release" are used interchangeably herein. For the discussion herein, the definition of the term "modified-release" encompasses the scope of the definitions for the terms "extended release", "enhanced-absorption", "controlled release", "sustained release" and "delayed release". "Controlled release dosage forms", "control-releasing dosage forms", "rate-controlled release dosage forms", or dosage forms which exhibit a "controlled release" of the bupropion hydrobromide or mixtures of bupropion hydrobromide and a second drug, as used herein are used interchangeably in this application and are defined to mean dosage forms which release the bupropion hydrobromide in a controlled manner per unit time in-vivo. For example, controlled release dosage forms can be administered once daily, and release the bupropion hydrobromide at a controlled rate and provide plasma concentrations of the drug that remain controlled with time within the therapeutic range of bupropion over a 24-hour period. The rate of release of the bupropion hydrobromide from a controlled release dosage form is controlled by features of the dosage form and/or in combination with physiologic or environmental conditions rather than by physiologic or environmental conditions alone. The controlled release dosage forms of certain embodiments of the invention can be contrasted to immediate release dosage forms which typically produce large maximum/minimum plasma drug concentrations (Cmax/Cmin) due to rapid absorption of the drug into the body i.e., in-vivo, relative to the drug's therapeutic index i.e., the ratio of the maximum drug concentration needed to produce and maintain a desirable pharmacological response. In immediate release dosage forms, the drug content is released into the gastrointestinal tract within a short period of time, and plasma drug levels peak shortly after dosing. The design of immediate release dosage forms is generally based on getting the fastest possible rate of drug release, and therefore absorbed, often at the risk of creating undesirable dose related side effects. The controlled release dosage forms of certain embodiments of the invention, on the other hand, improve the therapeutic value of the active drug by reducing the ratio of the maximum/minimum plasma drug concentration (Cmax/Cmin) while maintaining drug plasma levels within the therapeutic window. The controlled release dosage forms of certain embodiments of the invention attempt to deliver therapeutically effective amounts of bupropion hydrobromide and/or mixtures of bupropion hydrobromide with at least one other drug as a dose administered at least once-daily so that the ratio Cmax/Cmin in the plasma at steady state is less than the therapeutic index, and to maintain drug levels at constant effective levels to provide therapeutic benefit over a period of time (e.g. a 24-hour period). The controlled release dosage forms of certain embodiments of the invention, therefore, avoid large peak-to-trough fluctuations normally seen with immediate release dosage forms and provide a substantially flat serum concentration curve throughout the therapeutic period. The controlled release dosage forms of certain embodiments of the invention can be constructed in many forms known to one of ordinary skill in the drug delivery arts and described in the prior art such as for example, osmotic dosage forms, multiparticulate dosage forms, and gastric retention dosage forms.

"Sustained-release dosage forms" or dosage forms which exhibit a "sustained-release" of bupropion hydrobromide or mixtures of bupropion hydrobromide and a second drug as used herein is defined to mean dosage forms administered at least once-daily that provide a release of bupropion hydrobromide sufficient to provide a therapeutic dose soon after administration, and then a gradual release over a period of time such that the sustained-release dosage form provides a therapeutic benefit over a period of time (e.g. a 12-hour or 24-hour period).

"Extended-release dosage forms" or dosage forms which exhibit an "extended release" of bupropion hydrobromide or mixtures of bupropion hydrobromide and a second drug as used herein is defined to mean dosage forms administered at least once-daily that release the bupropion hydrobromide slowly, so that plasma concentrations of the bupropion hydrobromide are maintained at a therapeutic level for an extended period of time such that the extended release dosage form provides therapeutic benefit over a period of time (e.g. 24-hour period).

"Delayed-release dosage forms" or dosage forms which exhibit a "delayed release" of bupropion hydrobromide or mixtures of bupropion hydrobromide and a second drug as used herein is defined to mean dosage forms administered at least once-daily that do not effectively release drug immediately following administration but at a later time. Delayed-release dosage forms provide a time delay prior to the commencement of drug-absorption. This time delay is referred to as "lag time" and should not be confused with "onset time" which represents latency, that is, the time required for the drug to reach minimum effective concentration.

"Enhanced absorption dosage forms" or dosage forms which exhibit an "enhanced absorption" of the active drug as used herein is defined to mean dosage forms that when exposed to like conditions, will show higher release and/or more absorption of the bupropion base as compared to other dosage forms with the same or higher amount of bupropion base. The same therapeutic effect can be achieved with less bupropion base in the enhanced absorption dosage form as compared to other dosage forms.

The term "microparticle", as used herein refers to a drug formulation in discrete particulate form, and is interchangeable with the terms "microspheres", "spherical particles", "microcapsules", "particles", "multiparticulates", "granules", "spheroids", beads" and "pellets".

The term "tablet" as used herein refers to a single dosage form, i.e. the single entity containing the active pharmaceutical agent that is administered to the subject. The term "tablet" also includes a tablet that may be the combination of one or more "minitablets".

The term "controlled release matrix" as used herein is defined to mean a dosage form in which the bupropion hydrobromide or mixtures of bupropion hydrobromide and a second drug, is dispersed within a matrix, which matrix can be either insoluble, soluble, or a combination thereof. Controlled release matrix dosage forms of the insoluble type are also referred to as "insoluble polymer matrices", "swellable matrices", or "lipid matrices" depending on the components that make up the matrix. Controlled release matrix dosage forms of the soluble type are also referred to as "hydrophilic colloid matrices", "erodible matrices", or "reservoir systems". Controlled release matrix dosage forms of the invention refer to dosage forms comprising an insoluble matrix, a soluble matrix or a combination of insoluble and soluble matrices in which the rate of release is slower than that of an uncoated non-matrix conventional or immediate release dosage forms or uncoated "normal release matrix" dosage forms. Controlled release matrix dosage forms can be coated with a "control-releasing coat" to further slow the release of the bupropion salt from the controlled release matrix dosage form. Such coated controlled release matrix dosage forms can exhibit "modified-release", controlled-release", "sustained-release", "extended-release", "prolonged-release", "delayed-release" or combinations thereof of the active drug.

The term "normal release matrix" as used herein is defined to mean dosage forms in which the bupropion hydrobromide or mixtures of bupropion hydrobromide and a second drug, is dispersed within a matrix, which matrix can be either insoluble, soluble, or combinations thereof but constructed such that the release of the active drug mimics the release rate of an uncoated non-matrix conventional or immediate release dosage form comprising the drug. The release rate from normal release matrix dosage forms can be slowed down or modified in conjunction with a controlled release coat.

The terms "osmotic dosage form", "osmotic delivery device", "modified release osmotic dosage form" or "controlled release osmotic dosage form" as used herein are used interchangeably in this application, and are defined to mean dosage forms which dispense the bupropion hydrobromide or mixture of bupropion hydrobromide and a second drug, all or in part as a result of the presence of an osmotic agent in the dosage form driving solvent (e.g. water, dissolution media, gastric fluid, intestinal fluid, or mixtures thereof) into the core of the dosage form, which subsequently facilitates the release of drug from the core.

The term "osmosis" as used herein refers to the flow of a solvent through a selectively-permeable membrane (e.g. controlled release coat) from a region of high solvent potential to a region of low solvent potential. The selectively-permeable membrane is permeable to the solvent, but not to the solute, resulting in a pressure gradient across the membrane. Non-limiting examples of selectively-permeable membranes include semipermeable membranes, and microporous, asymmetric membranes (which can be permeable, semipermeable, perforated, or unperforated) and can deliver the active drug(s) by osmotic pumping, diffusion or the combined mechanisms of diffusion and osmotic pumping. Thus, in principle, osmosis controlled release of the active drug(s) involves osmotic transport of an aqueous media into the osmotic dosage form followed by dissolution of the active drug(s) and the subsequent transport of the saturated solution of the active drug by osmotic pumping of the solution through at least one passageway in the selectively-permeable membrane and/or by diffusion through the selectively-permeable membrane.

The term "osmotic pressure gradient" as used herein is defined to mean the difference in hydrostatic pressure produced by a solution in a space divided by a selectively-permeable membrane due to a differential in the concentrations of solute.

The terms "osmotic agent", "osmagent", "osmotically effective solute", "osmotic enhancer" "osmotically effective compounds", "osmotic solutes", "osmopolymer" and "osmotic fluid imbibing agents" as used herein are used interchangeably, and define any material that is soluble (i.e. can be partially or totally solubilized) or swellable in a solvent (e.g. water) that enters the composition, and which exhibits an osmotic pressure gradient across the selectively-permeable membrane (e.g. controlled release coat), thus increasing the hydrostatic pressure inside the osmotic dosage form.

The terms "controlled release coat", "control releasing coat", "modified release coat" and "rate-controlling coat" as used herein are used interchangeably in this application, and are defined to mean a functional coat which comprises at least one modified release polymer. Non-limiting examples of modified release polymers include pH independent polymers, pH dependent polymers (such as for example enteric or reverse enteric types), soluble polymers, insoluble polymers, lipids, lipidic materials, and mixtures thereof. When applied onto a dosage form, the controlled release coat can modify (e.g. slow) the rate of release of the active drug. For example, the controlled release coat can be designed such that when the coat is applied onto a dosage form, the dosage form in conjunction with the controlled release coat, exhibits a "modified-release", "controlled-release", "sustained-release", "extended-release" and/or "delayed-release" profile. Combinations thereof are permissible. The controlled release coat can optionally comprise additional materials that can alter the functionality of the controlled release coat. The term "modified release" is interchangeable with the terms "controlled release", "control releasing" and "rate controlling". The term "coat" is interchangeable with the term "coating".

The terms "moisture barrier" and "moisture barrier coat" as used herein are used interchangeably and are defined to mean a coating which impedes or retards the absorption of moisture. It is known that bupropion salts are hygroscopic and, as such, are susceptible to decomposition over time under high humidity conditions. Other active drugs can also be susceptible to decomposition over time under high humidity conditions. The proportion of the components of the moisture barrier and the amount of the moisture barrier applied onto the controlled release coat is such that the moisture barrier does not fall within the USP definition and requirement for an enteric coat. Suitably, the moisture barrier is comprised of an enteric and/or acrylic polymer, suitably an acrylic polymer, optionally a plasticizer, and a permeation enhancer. The permeation enhancer is a hydrophilic substance, which allows water to enter without physical disruption of the coating. The moisture barrier can additionally contain other conventional inert excipients, which can improve processing of the extended-release formulation described herein.

The term "enteric coat" as used herein is defined to mean a coating or barrier applied to a dosage form that can control the location in the digestive system where the active drug(s) is absorbed. For example, an enteric coating can be used to: (i) protect the drug from the destructive action of the enzymes or low pH environment of the stomach; (ii) prevent nausea or bleeding associated with the irritation of the gastric mucosa by the drug; and/or (iii) deliver the drug in an undiluted form in the intestine. Based on these criteria, in certain embodiments, the enteric coated dosage form can be regarded as a type of delayed release dosage form. They differ from sustained release dosage forms in that with sustained release dosage forms, the drug release is extended over a period of time to maintain therapeutic blood levels and to decrease the incidence of side effects caused by a rapid release; whereas, with enteric coatings, the primary objective is to confine the release of the drug to a predetermined region of the gastrointestinal tract. Enteric coatings work by presenting a surface that is substantially stable at acidic pH, but breaks down at higher pH to allow release of the drug in the intestine.

The term "enteric polymer" as used herein is defined to mean a polymeric substance that when used in an enteric coat formulation, is substantially insoluble and/or substantially stable under acidic conditions exhibiting a pH of less than about 5 and which are substantially soluble or can decompose under conditions exhibiting a pH of about 5 or more. Non-limiting examples of such enteric polymers include carboxymethylethylcellulose, cellulose acetate phthalate, cellulose acetate succinate, methylcellulose phthalate, hydroxymethylethylcellulose phthalate, hydroxypropylmethylcellulose phthalate, hydroxypropylmethylcellulose acetate succinate, polyvinyl alcohol phthalate, polyvinyl butyrate phthalate, polyvinyl acetal phthalate, a copolymer of vinyl acetate/maleic anhydride, a copolymer of vinylbutylether/maleic anhydride, a copolymer of styrene/maleic acid monoester, a copolymer of methyl acrylate/methacrylic acid, a copolymer of styrene/acrylic acid, a copolymer of methyl acrylate/methacrylic acid/octyl acrylate, a copolymer of methacrylic acid/methyl methacrylate and mixtures thereof. Enteric polymers can be used individually or in combination with other hydrophobic or hydrophilic polymers in an enteric coat, a normal release matrix core, a controlled release matrix core, and/or in a controlled release coat. Enteric polymers can be combined with other pharmaceutically acceptable excipients to either facilitate processing of a coat comprising the enteric polymer or to alter the functionality of the coat.

The term "functional coat" as used herein is defined to mean a coating that affects the rate of release in-vitro or in-vivo of the active drug(s).

The term "non-functional coat" as used herein is defined to mean a coating that does not substantially affect the rate of release in-vitro or in-vivo of the active drug, but can enhance the chemical, biological, physical stability characteristics, or the physical appearance of the modified release dosage form.

The term "core" as used herein is defined to mean a solid vehicle in which at least one active drug is uniformly or non-uniformly dispersed. The core can be formed by methods and materials well known in the art, such as for example by compressing, fusing, or extruding the active drug together with at least one pharmaceutically acceptable excipient. The core can be manufactured into, for example, a homogenous or non-homogenous unitary core, a multiparticle, or a plurality of microparticles compressed into a unitary core. Non-limiting examples of cores include microparticle cores, matrix cores, and osmotic cores. The core(s) can be coated with at least one functional coat and/or non-functional coat.

The terms "modified release matrix core", "controlled release matrix core" or "matrix core" when referring to a controlled release matrix dosage form, as used herein are used interchangeably, and are defined to mean a core in which at least one active drug is dispersed within a matrix which controls or delays the release of the active drug over a 24-hour period so as to allow a composition comprising the modified release matrix core to be administered as a once-a-day composition. The release rate of the active drug from the modified release matrix core can be modified by the porosity and tortuosity of the matrix, (i.e. its pore structure). The addition of pore-forming hydrophilic salts, solutes, or wicking agents can influence the release rate, as can the manipulation of processing parameters. For example, the compression force used in the manufacture of the modified release matrix core can alter the porosity of the matrix core and hence the rate of release of the active drug. It will be understood by one of ordinary skill in the art of drug delivery that a more rigid matrix will be less porous and hence release the active drug more slowly compared to a less rigid modified release matrix core. The modified release matrix core can comprise insoluble or inert matrix dosage forms, swellable matrix dosage forms, swellable and erodable matrix dosage form, hydrophobic matrix dosage forms, hydrophilic matrix dosage forms, erodable matrix dosage forms, reservoir dosage forms, or any combination thereof. The modified release matrix core can comprise at least one insoluble matrix, at least one swellable matrix, at least one swellable and erodable matrix, at least one hydrophobic matrix, at least one hydrophilic matrix, at least one erodable matrix, or a combination thereof in which the rate of release is slower than that of uncoated immediate-release dosage forms. Modified release matrix cores can be coated with at least one controlled release coat to further slow the release of the active drug from the modified release matrix core. Such coated modified release matrix cores can exhibit modified-release, controlled-release, sustained-release, extended-release, prolonged-release, bi-phasic release, delayed-release or combinations thereof of the active drug. Modified release matrix cores can also be coated with a non-functional soluble coat.

The term "plasticizer" as used herein includes any compounds capable of plasticizing or softening a polymer or a binder used in the present invention. The use of plasticizers is optional, and can be included in the dosage form to modify the properties and characteristics of the polymers used in the coat(s) or core of the dosage form for convenient processing during manufacture of the coat(s) and/or the core of the dosage form. Once the coat(s) and/or core have been manufactured, certain plasticizers can function to increase the hydrophilicity of the coat(s) and/or the core of the dosage form in the environment of use. During manufacture of the coat(s) and/or core, the plasticizer can lower the melting temperature or glass transition temperature (softening point temperature) of the polymer or binder. Plasticizers can be included with a polymer and lower its glass transition temperature or softening point. Plasticizers also can reduce the viscosity of a polymer. Plasticizers can impart some particularly advantageous physical properties to the dosage forms of the invention.

The terms "pore former", "pore forming agent", and "pore forming additive" as used herein are used interchangeably in this application, and are defined to mean an excipient that can be added to a coating (e.g. the controlled release coat), wherein upon exposure to fluids in the environment of use, the pore former dissolves or leaches from the coating to form pores, channels or paths in the coating, that can fill with the environmental fluid and allow the fluid to enter the core and dissolve the active drug, and modify the release characteristics of the formulation. The pore formers can be inorganic or organic, and include materials that can be dissolved, extracted or leached from the coating in the environment of use.

The term "steady state" as used herein means that the blood plasma concentration curve for a given drug does not substantially fluctuate after repeated doses to dose of the formulation.

"AUC" as used herein means area under the plasma concentration-time curve, as calculated by the trapezoidal rule over a time interval (e.g. complete 24-hour interval); and signifies the extent of the absorption of a drug.

"Cmax" as used herein means the highest plasma concentration of the drug attained within the dosing interval (e.g., 24 hours).

"Cmin" as used herein means the minimum plasma concentration of the drug attained within the dosing interval (e.g. 24 hours).

"Cavg" as used herein means the plasma concentration of the drug within the dosing interval (e.g. 24-hours), and is calculated as AUC/dosing interval.

"Tmax" as used herein means the time period which elapses after administration of the dosage form at which the plasma concentration of the drug attains the highest plasma concentration of drug attained within the dosing interval (e.g. 24 hours).

The term "bioequivalence" as used herein is defined as there being about a 90% or greater probability that the bioavailability (AUC) of the active drug as determined by standard methods is from about 80% to about 125% of the second orally administrable dosage form comprising the same dose of the active drug and that there is about 90% or greater probability that the maximum blood plasma concentration (Cmax) of the active drug as measured by standard methods is from about 80% to about 125% of the second orally administrable dosage form. For example, the reader is referred to the final version of the guidance approved by the US Food and Drug Administration at the time of filing of this patent application i.e., the March 2003 Guidance for Industry Bioavailability and Bioequivalence Studies for Orally Administered Drug Products General Considerations, U.S. Department of Health and Human Services, Food and Drug Administration, Center for Drug Evaluation and Research (CDER), for a detailed discussion on bioequivalence.

The terms "a", "an" or "at least one" as used herein are used interchangeably in this application, and are defined to mean "one" or "one or more".

The numerical parameters set forth in the following specification and attached claims that are modified by the term "about", are approximations that can vary depending upon the technological properties of the particular case. For example, the term "about" can mean within an acceptable error range (e.g. standard deviations) for the particular value as determined by one of ordinary skill in the art, which will depend in part on how the value is measured or determined, e.g., the limitations of the measurement system. At the very least, and not as an attempt to limit the application of the doctrine of equivalents to the scope of the claims, each numerical parameter modified by the term "about" should at least be construed in light of the number of reported significant digits and by applying ordinary rounding techniques. The terms "about" and "approximately" as used herein are used interchangeably.

Other terms are defined as they appear in the following description and should be construed in the context with which they appear.

The present invention encompasses the bupropion hydrobromide salt and compositions containing safe and pharmaceutically effective levels of the bupropion hydrobromide salt, that can be used for the treatment of a condition in subjects that can benefit from bupropion administration, wherein the bupropion hydrobromide salt and compositions containing safe and pharmaceutically effective levels of the bupropion hydrobromide salt unexpectedly provide for the reduction of incidences of and/or the reduction in severity of bupropion-induced seizures, and are more stable, as compared with equivalent molar amounts of bupropion hydrochloride or otherwise similar or identical compositions containing equivalent molar amounts of bupropion hydrochloride.

Certain compositions containing bupropion hydrobromide contain from about 50 mg to about 1000 mg of bupropion hydrobromide. Certain other embodiments include more, e.g., from about 1200 to about 1500 mg, including all values therebetween. The range of bupropion hydrobromide of from about 50 to about 1000 mg includes, for example all values and ranges therebetween, for example, 100, 150, 174, 200, 250, 300, 348, 350, 400, 450, 500, 510, 520, 522, 530, 540, 550, 560, 570, 580, 590, 600, 650, 700, 750, 800, 850, 900, and 950 mg. For example, certain embodiments include a composition which comprises 174 mg, 348 mg or 522 mg of bupropion hydrobromide per unit dose.

Also, the present invention encompasses polymorphs thereof and specific purified enantiomeric forms thereof. The present invention also encompasses the use of such bupropion hydrobromide salt and compositions containing the bupropion hydrobromide salt for the treatment of one or more conditions in a subject suitable for treatment by bupropion or pharmaceutically acceptable salts thereof (e.g. depression, obesity, nicotine addiction, and other conditions treatable with bupropion such as are disclosed herein); wherein the incidences of and/or the severity of bupropion-induced seizures is reduced as compared with an equivalent molar amount of bupropion hydrochloride or an otherwise similar or identical composition containing an equivalent molar amount of bupropion hydrochloride.

The present invention encompasses any medicament containing a pharmaceutically effective amount of bupropion hydrobromide. This includes both oral and non-orally administrable medicaments such as topicals, injectables, aerosols and other inhalable medicaments. Particularly such medicament compositions include orally administrable modified release dosage forms containing bupropion hydrobromide. The dosages can be conveniently presented in unit dosage form and prepared by any of the methods well-known in the art of pharmacy. A "solid dosage form" as used herein, means a dosage form that is neither liquid nor gaseous. Dosage forms include solid dosage forms, such as tablets, powders, microparticles, capsules, suppositories, sachets, troches, patches and lozenges as well as liquid suspensions and elixirs. Capsule dosages contain the solid composition within a capsule that can be made of gelatin or other conventional encapsulating material.

The modified release dosage forms contemplated in the present invention can be multiparticulate or monolithic. For example, those skilled in the pharmaceutical art and the design of medicaments are aware of modified release matrices conventionally used in oral pharmaceutical compositions adopted for modified release and means for their preparation.

A modified release formulation containing bupropion hydrobromide according to the present invention can be coated with one or more functional or non-functional coatings. Non-limiting examples of functional coatings include controlled release polymeric coatings, moisture barrier coatings, enteric polymeric coatings, and the like. Non-functional coatings are coatings that do not substantially affect drug release, but which affect other properties; such as the enhancement of the chemical, biological or physical stability characteristics, or the enhancement of the physical appearance of the formulation.

In at least one embodiment of the present invention a bupropion hydrobromide composition comprises a controlled release polymeric coating that includes an acrylic polymer. Suitable acrylic polymers include but are not limited to acrylic acid and methacrylic acid copolymers, methyl methacrylate copolymers, ethoxyethyl methacrylates, cynaoethyl methacrylate, aminoalkyl methacrylate copolymer, poly (acrylic acid), poly(methacrylic acid), methacrylic acid alkylamine copolymer, poly(methyl methacrylate), poly(methacrylic acid) (anhydride), polyacrylamide, poly(methacrylic acid anhydride), glycidyl methacrylate copolymers and mixtures thereof.

In at least one embodiment polymerizable quaternary ammonium compounds are employed in the controlled release coat, of which non-limiting examples include quaternized aminoalkyl esters and aminoalkyl amides of acrylic acid and methacrylic acid, for example β-methacryl-oxyethyl-trimethyl-ammonium methosulfate, β-acryloxy-propyl-trimethyl-ammonium chloride, trimethylaminomethyl-methacrylamide methosulfate and mixtures thereof. The quaternary ammonium atom can also be part of a heterocycle, as in methacryloxyethylmethyl-morpholiniom chloride or the corresponding piperidinium salt, or it can be joined to an acrylic acid group or a methacrylic acid group by way of a group containing hetero atoms, such as a polyglycol ether group. Further suitable polymerizable quaternary ammonium compounds include quaternized vinyl-substituted nitrogen heterocycles such as methyl-vinyl pyridinium salts, vinyl esters of quaternized amino carboxylic acids, styryltrialkyl ammonium salts, and mixtures thereof. Other polymerizable quaternary ammonium compounds useful in the present invention include acryl- and methacryl-oxyethyltrimethyl-ammonium chloride and methosulfate, benzyldimethylammoniumethyl-methacrylate chloride, diethylmethylammoniumethyl-acrylate and -methacrylate methosulfate, N-trimethylammoniumpropylmethacrylamide chloride, N-trimethylammonium-2,2-dimethylpropyl-1-methacrylate chloride and mixtures thereof.

In at least one embodiment the acrylic polymer of the controlled release coat is comprised of one or more ammonio methacrylate copolymers. Ammonio methacrylate copolymers (such as those sold under the Trade Mark EUDRAGIT® RS and RL) are described in National Formulary (NF) XVII as fully polymerized copolymers of acrylic and methacrylic acid esters with a low content of quaternary ammonium groups. Two or more ammonio methacrylate copolymers having differing physical properties can be incorporated in the controlled release coat of certain embodiments. For example, it is known that by changing the molar ratio of the quaternary ammonium groups to the neutral (meth)acrylic esters, the permeability properties of the resultant coating can be modified.

In certain other embodiments of the present invention, the controlled release coat further includes a polymer whose permeability is pH dependent, such as anionic polymers synthesized from methacrylic acid and methacrylic acid methyl ester. Such polymers are commercially available, e.g., from Rohm Pharma GmbH under the tradename EUDRAGIT® L and EUDRAGIT® S. The ratio of free carboxyl groups to the esters is known to be 1:1 in EUDRAGIT® L and 1:2 in EUDRAGIT® S. EUDRAGIT® L is insoluble in acids and pure water, but becomes increasingly permeable above pH 5.0. EUDRAGIT® S is similar, except that it becomes increasingly permeable above pH 7. The hydrophobic acrylic polymer coatings can also include a polymer which is cationic in character based on dimethylaminoethyl methacrylate and neutral methacrylic acid esters (such as EUDRAGIT® E, commercially available from Rohm Pharma). The hydrophobic acrylic polymer coatings of certain embodiments of the present invention can further include a neutral copolymer based on poly (meth)acrylates, such as EUDRAGIT® NE (NE=neutral ester), commercially available from Rohm Pharma. EUDRAGIT® NE 30D lacquer films are insoluble in water and digestive fluids, but permeable and swellable.

In at least one other embodiment of the invention, the controlled release coat comprises a dispersion of poly (ethylacrylate, methyl methacrylate) 2:1 (KOLLICOAT® EMM 30 D, BASF).

In at least one other embodiment of the invention, the controlled release coat comprises a polyvinyl acetate stabilized with polyvinylpyrrolidone and sodium lauryl sulfate such as KOLLICOAT® SR30D (BASF). The dissolution profile can be altered by changing the relative amounts of different acrylic resin lacquers included in the coating. Also, by changing the molar ratio of polymerizable permeability-enhancing agent (e.g., the quaternary ammonium compounds) to the neutral (meth)acrylic esters, the permeability properties (and thus the dissolution profile) of the resultant coating can be modified.

In at least one embodiment of the invention the controlled release coat comprises ethylcellulose, which can be used as a dry polymer (such as ETHOCEL®, Dow Corning) solubilised in organic solvent prior to use, or as an aqueous dispersion. One suitable commercially-available aqueous dispersion of ethylcellulose is AQUACOAT® (FMC Corp., Philadelphia, Pa., U.S.A.). AQUACOAT® can be prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, the AQUACOAT® can be intimately mixed with a suitable plasticizer prior to use. Another suitable aqueous dispersion of ethylcellulose is commercially available as SURELEASE® (Colorcon, Inc., West Point, Pa., U.S.A.). This product can be prepared by incorporating plasticizer into the dispersion during the manufacturing process. A hot melt of a polymer, plasticizer (e.g. dibutyl sebacate), and stabilizer (e.g. oleic acid) is prepared as a homogeneous mixture, which is then diluted with an alkaline solution to obtain an aqueous dispersion which can be applied directly onto substrates.

Other examples of polymers that can be used in the controlled release coat include cellulose acetate phthalate, cellulose acetate trimaletate, hydroxy propyl methyl cellulose phthalate, polyvinyl acetate phthalate, polyvinyl alcohol phthalate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, ethyl cellulose, gelatin, starch, and cellulose based cross-linked polymers in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, pullulan, collagen, casein, agar, gum arabic, sodium carboxymethyl cellulose, (swellable hydrophilic polymers) poly(hydroxyalkyl methacrylate) (molecular weight from about 5 k to about 5000 k), polyvinylpyrrolidone (molecular weight from about 10 k to about 360 k), anionic and cationic hydrogels, zein, polyamides, polyvinyl alcohol having a low acetate residual, a swellable mixture of agar and carboxymethyl cellulose, copolymers of maleic anhydride and styrene, ethylene, propylene or isobutylene, pectin (molecular weight from about 30 k to about 300 k), polysaccharides such as agar, acacia, karaya, tragacanth, algins and guar, polyacrylamides, POLYOX® polyethylene oxides (molecular weight from about 100 k to about 5000 k), AQUAKEEP® acrylate polymers, diesters of polyglucan, crosslinked polyvinyl alcohol and poly N-vinyl-2-pyrrolidone, hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, methyl ethyl cellulose, ethylhydroxy ethylcellulose, cellulose acetate, cellulose butyrate, cellulose propionate, gelatin, starch, maltodextrin, pullulan, polyvinyl pyrrolidone, polyvinyl alcohol, polyvinyl acetate, glycerol fatty acid esters, polyacrylamide, polyacrylic acid, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures thereof.

In at least one embodiment of the invention the dosage forms are coated with polymers in order to facilitate mucoadhsion within the gastrointestinal tract. Non-limiting examples of polymers that can be used for mucoadhesion include carboxymethylcellulose, polyacrylic acid, CARBOPOL™, POLYCARBOPHIL™, gelatin, other natural or synthetic polymers, and mixtures thereof.

In at least one embodiment of the invention, the dosage form is an extended release tablet comprising: (i) a core that includes bupropion hydrobromide (e.g. from about 40% to about 99% by weight of tablet dry weight, including all values and ranges therebetween), a binder such as polyvinyl alcohol (e.g. from about 0.5% to about 25% by weight of tablet dry weight, including all values and ranges therebetween), and a lubricant such as glyceryl behenate (e.g. from about 0.1% to about 5% by weight of tablet dry weight, including all values and ranges therebetween); and (ii) a controlled release coat that includes a water-insoluble water-permeable film-forming polymer such as ethylcellulose (e.g. from about 1% to about 12% by weight of tablet dry weight, including all values and ranges therebetween), a water-soluble polymer such as polyvinylpyrrolidone (POVIDONE® USP), (e.g. from about 1.5% to about 10% by weight of tablet dry weight, including all values and ranges therebetween), optionally a plasticizer such as dibutyl sebacate, polyethylene glycol 4000 or a mixture thereof (e.g. from about 0.5% to about 4% by weight of tablet dry weight, including all values and ranges therebetween), and optionally a wax such as carnauba wax (e.g. from about 0.01% to about 0.05% by weight of tablet dry weight, including all values and ranges therebetween).

In at least one embodiment of the invention, the dosage form is a 174 mg extended release tablet comprising: (i) a core that includes bupropion hydrobromide (e.g. about 81% by weight of tablet dry weight), a binder such as polyvinyl alcohol (e.g. about 3% by weight of tablet dry weight), and a lubricant such as glyceryl behenate (e.g. about 3% by weight of tablet dry weight); and (ii) a controlled release coat that includes a water-insoluble water-permeable film-forming polymer such as ethylcellulose (e.g. about 7% by weight of tablet dry weight), a water-soluble polymer such as polyvinylpyrrolidone (POVIDONE® USP), (e.g. about 4% by weight of tablet dry weight), optionally a plasticizer such as dibutyl sebacate, polyethylene glycol 4000 or a mixture thereof (e.g. about 2% by weight of tablet dry weight), and optionally a wax such as carnauba wax (e.g. about 0.03% by weight of tablet dry weight).

In at least one embodiment of the invention, the dosage form is a 348 mg extended release tablet comprising: (i) a core that includes bupropion hydrobromide (e.g. about 87% by weight of tablet dry weight), a binder such as polyvinyl alcohol (e.g. about 3% by weight of tablet dry weight), and a lubricant such as glyceryl behenate (e.g. about 3% by weight of tablet dry weight); and (ii) a controlled release coat that includes a water-insoluble water-permeable film-forming polymer such as ethylcellulose (e.g. about 4% by weight of tablet dry weight), a water-soluble polymer such as polyvinylpyrrolidone (POVIDONE® USP), (e.g. about 2% by weight of tablet dry weight), optionally a plasticizer such as dibutyl sebacate, polyethylene glycol 4000 or a mixture thereof (e.g. about 1% by weight of tablet dry weight), and optionally a wax such as carnauba wax (e.g. about 0.01% by weight of tablet dry weight).

In at least one embodiment of the invention, the dosage form is a 522 mg XL tablet comprising: (i) a core that includes bupropion hydrobromide (e.g. about 85% by weight of tablet dry weight), a binder such as polyvinyl alcohol (e.g. about 3.5% by weight of tablet dry weight), and a lubricant such as glyceryl behenate (e.g. about 3.5% by weight of tablet dry weight); and (ii) a controlled release coat that includes a water-insoluble water-permeable film-forming polymer such as ethylcellulose (e.g. about 3% by weight of tablet dry weight), a water-soluble polymer such as polyvinylpyrrolidone (POVIDONE® USP), (e.g. about 3.5% by weight of tablet dry weight), optionally a plasticizer such as dibutyl sebacate, polyethylene glycol 4000 or a mixture thereof (e.g. about 1.5% by weight of tablet dry weight), and optionally a wax such as carnauba wax (e.g. about 0.01% by weight of tablet dry weight).

In addition to the modified release dosage forms described herein, other modified release technologies known to those skilled in the art can be used in order to achieve the modified release formulations of certain embodiments of the present invention. Such formulations can be manufactured as a modified release oral formulation, for example, in a suitable tablet or multiparticulate formulation known to those skilled in the art. In either case, the modified release dosage form can optionally include a controlled release carrier which is incorporated into a matrix along with the drug, or which is applied as a controlled release coating.

Tablets

In certain embodiments of the present invention, there is provided a modified-release tablet having a core comprising bupropion hydrobromide and conventional excipients, wherein the bupropion hydrobromide salt or the composition comprising the bupropion hydrobromide provides for the reduction of incidences of and/or severity of bupropion-induced seizures, and is more stable as compared with equivalent molar amounts of bupropion hydrochloride or otherwise similar or identical compositions containing equivalent molar amounts of bupropion hydrochloride. The core can be surrounded by a controlled release coat which can control the release of bupropion hydrobromide or mixture of bupropion hydrobromide with a second drug. In other embodiments, a moisture barrier can optionally be added to surround the controlled release coat. This moisture barrier is optional given the enhanced stability of bupropion hydrobromide relative to bupropion hydrochloride and by selection of an appropriate controlled release coating. If present, this moisture barrier can affect in-vitro drug release as well as precluding moisture from coming into contact with the bupropion hydrobromide salt. Optionally, this tablet can further comprise one or more additional functional or non-functional coatings surrounding the core, moisture barrier and/or controlled release coat.

Extended Release (XL) Tablets

In certain embodiments of the present invention, there is provided an extended-release (XL) tablet having a core comprising bupropion hydrobromide and conventional excipients, wherein the bupropion hydrobromide salt provides for the reduction of incidences of and/or severity of bupropion-induced seizures, and is more stable, as compared with equivalent molar amounts of bupropion hydrochloride. The core can be surrounded by a controlled release coat, which controls the release of the bupropion hydrobromide salt. The tablet optionally can comprise one or more additional functional or non-functional coats surrounding the core or controlled release coat. The extended-release tablet of certain embodiments has unexpected enhanced stability.

The XL Core

The core of the extended-release tablet comprises an effective amount of the bupropion hydrobromide salt, a binder, and a lubricant; and can contain other conventional inert excipients. The amount of the bupropion hydrobromide salt present in the XL core can vary in an amount from about 40% to about 99% by weight of the tablet dry weight, including all values and ranges therebetween. For example, in certain embodiments bupropion hydrobromide is present in an amount from about 70% to about 95% by weight of the tablet dry weight, including all values and ranges therebetween. For example, in certain embodiments, the core comprises bupropion hydrobromide in a proportion of about 40%, about 45%, about 50%, about 55%, about 60%, about 65%, about 70%, about 75%, about 80%, about 85%, about 90%, about 95% or about 99% of the core dry weight. In certain embodiments the tablet comprises an effective amount of bupropion hydrobromide and can have from about 50 to about 1000 mg of bupropion hydrobromide, including 100, 150, 200, 250, 300, 350, 400, 450, 500, 510, 520, 530, 540, 550, 560, 570, 580, 590, 600, 650, 700, 750, 800, 85, 900, 950 mg and all values and ranges therebetween. For example, certain embodiments include a composition which comprises 174 mg, 348 mg or 522 mg of bupropion hydrobromide per unit dose. For example, in certain embodiments, the tablet comprises about 174 mg of bupropion hydrobromide; in other embodiments the tablet comprises about 348 mg of bupropion hydrobromide; and in still other embodiments the tablet comprises about 522 mg of bupropion hydrobromide. In at least one embodiment of a 174 mg dose tablet, the bupropion hydrobromide is present at from about 75% to about 85% by weight of the tablet dry weight, including all values and ranges therebetween. In at least one embodiment of a 348 mg dose tablet, the amount of bupropion hydrobromide can be present at from about 80% to about 90% by weight of the tablet dry weight, including all values and ranges therebetween. In at least one embodiment of a 522 mg dose tablet, the bupropion hydrobromide is present at from about 75% to about 90% by weight of the tablet dry weight, including all values and ranges therebetween. In certain embodiments of the 174 mg, 348 mg and 522 mg dose bupropion hydrobromide extended-release tablets of the invention, the amount of bupropion hydrobromide is present in an amount of from about 85% to about 99% by weight of the dry core for each dose, including all values and ranges therebetween.

A binder (also sometimes called adhesive) can be added to a drug-filler mixture to increase the mechanical strength of the granules and tablets during formation. Binders can be added to the formulation in different ways: (1) as a dry powder, which is mixed with other ingredients before wet agglomeration, (2) as a solution, which is used as agglomeration liquid during wet agglomeration, and is referred to as a solution binder, and (3) as a dry powder, which is mixed with the other ingredients before compaction. In this form the binder is referred to as a dry binder. Solution binders are a common way of incorporating a binder into granules. In certain embodiments, the binder used in the XL tablets is in the form of a solution binder. Non-limiting examples of binders useful for the core include hydrogenated vegetable oil, castor oil, paraffin, higher aliphatic alcohols, higher aliphatic acids, long chain fatty acids, fatty acid esters, wax-like materials such as fatty alcohols, fatty acid esters, fatty acid glycerides, hydrogenated fats, hydrocarbons, normal waxes, stearic acid, stearyl alcohol, hydrophobic and hydrophilic polymers having hydrocarbon backbones, and mixtures thereof. Specific examples of water-soluble polymer binders include modified starch, gelatin, polyvinylpyrrolidone, cellulose derivatives (such as for example hydroxypropyl methylcellulose (HPMC) and hydroxypropyl cellulose (HPC)), polyvinyl alcohol and mixtures thereof. The amount of binder present can vary from about 0.5% to about 25% by weight of the tablet dry weight, including all values and ranges therebetween. For example, in certain embodiments the binder is present in an amount of from about 0.5% to about 15% by weight of the tablet dry weight; in other embodiments from about 1% to about 6% by weight of the tablet dry weight; and in still other embodiments at about 3% by weight of the tablet dry weight. For example, in certain embodiments of the 174 mg, 348 mg and 522 mg dose tablets, the binder is present in an amount of from about 1% to about 6% by weight of each dry core weight, and in other embodiments at about 3% by weight of each dry core weight. In at least one embodiment of the 522 mg dose tablet, the binder is present in an amount of about 4% by weight of dry core weight. In at least one embodiment of the invention the binder is polyvinyl alcohol.

Lubricants can be added to pharmaceutical formulations to decrease any friction that occurs between the solid and the die wall during tablet manufacturing. High friction during tabletting can cause a series of problems, including inadequate tablet quality (capping or even fragmentation of tablets during ejection, and vertical scratches on tablet edges) and may even stop production. Accordingly, lubricants are added to tablet formulations of certain embodiments of the XL tablet formulation described herein. Non-limiting examples of lubricants useful for the core include glyceryl behenate, stearic acid, hydrogenated vegetable oils (such as hydrogenated cottonseed oil (STERPTEX®), hydrogenated soybean oil (STEROTEX® HM) and hydrogenated soybean oil & castor wax (STERPTEX® K), stearyl alcohol, leucine, polyethylene glycol (MW 1450, suitably 4000, and higher), magnesium stearate, glyceryl monostearate, stearic acid, polyethylene glycol, ethylene oxide polymers (for example, available under the registered trademark CARBOWAX® from Union Carbide, Inc., Danbury, Conn.), sodium lauryl sulfate, magnesium lauryl sulfate, sodium oleate, sodium stearyl fumarate, DL-leucine, colloidal silica, mixtures thereof and others as known in the art. In at least one embodiment of the present invention, the lubricant is glyceryl behenate (for example, COMPRITOL® 888). The amount of lubricant present can vary from about 0.1% to about 6% by weight of the tablet dry weight, including all values and ranges therebetween. For example, in certain embodiments the amount of lubricant present is from about 2% to about 3% by weight of the tablet dry weight; and in other embodiments the amount of lubricant present is at about 3% by weight of the tablet dry weight. In certain embodiments of the 174 mg, 348 mg and 522 mg dose XL tablets of the invention, the lubricant is present in an amount of about 3% by weight of the tablet dry weight, or from about 1% to about 6% by weight of the dry core weight. For example, in certain embodiments the lubricant is present in an amount of about 3% by weight of the dry core weight for the 174 mg, 348 mg and 522 mg dose XL tablets. In at least one embodiment of the 522 mg dose tablet, the lubricant is present in an amount of about 4% by weight of dry core weight.

At this stage, the XL core formulation of certain embodiments of the present invention, is an uncoated immediate release formulation resulting in about 100% dissolution of the bupropion hydrobromide salt within about 1 hour. In at least one embodiment the XL core is a normal release matrix formulation. In certain embodiments the core comprises an effective pharmaceutical amount of bupropion hydrobromide, a binder (e.g. polyvinyl alcohol), and a lubricant (e.g. glyceryl behenate). Additional inert excipients consistent with the objects of the invention can also be added to the core formulation. The additional inert excipients can be added to facilitate the preparation and/or improve patient acceptability of the final extended-release dosage form as described herein. The additional inert excipients are well known to the skilled artisan and can be found in the relevant literature, for example in the Handbook of Pharmaceutical Excipients. Non-limiting examples of such excipients include spray dried lactose, sorbitol, mannitol, and any cellulose derivative.

In certain embodiments the core of the bupropion hydrobromide composition (e.g. core of an XL tablet) can be made according to any one of the methods described herein.

In at least one embodiment of the invention, the granules to be compressed to form the core of the bupropion hydrobromide XL tablet of the invention described herein, are manufactured by the wet granulation process. Wet granulation involves agitation of a powder (the active drug) by convention in the presence of a liquid (the solution binder) followed by drying. For forming the granules, which are to be eventually compressed into the tablet cores, the bupropion hydrobromide salt is first granulated, for example, with a solution binder, in a granulator, for example using a fluidized bed granulator (e.g. a fluidized bed granulator manufactured by Glatt (Germany) or Aeromatic (Switzerland)). The binder (e.g. polyvinyl alcohol) is first dissolved or dispersed in a suitable solvent (e.g. water). The solution binder is then top sprayed onto the drug in a granulator (e.g. a fluidized bed granulator). Alternatively, granulation can also be performed in a conventional or high shear mixer. If necessary, the additional inert excipients (e.g. a filler) can be mixed with the bupropion hydrobromide salt prior to the granulation step.

The granules formed are subsequently dried and then sieved prior to blending the granules with the lubricant. In certain embodiments, the dried granules are sieved through a 1.4 mm mesh screen. The sieved granules are then blended with the lubricant, and if necessary, any other additional inert excipients, which can improve processing of the extended-release tablets of the invention. Blending of the granules with the lubricant, and if necessary, any additional inert excipients, such as for example a glidant, can be performed in a V-blender or any other suitable blending apparatus. Glidants can improve the flowability of the powder. This for example, can be helpful during tablet production at high production speeds and during direct compaction. However, because the requirement for adequate flow is high, a glidant is often also added to a granulation before tabletting. The blended granules are subsequently pressed into tablets and are hereinafter referred to as tablet cores. Tablet cores can be obtained by the use of standard techniques and equipment well known to the skilled artisan. For example, the XL tablet cores can be obtained by a rotary press (also referred to as a multi-station press) fitted with suitable punches.

The granules can also be manufactured by using other processes known to the skilled artisan. Examples of other granule manufacturing processes include dry granulation (e.g. slugging, roller compaction), direct compression, extrusion, spheronization, melt granulation, and rotary granulation.

An example of the granulation process for the XL cores (60 kg batch) is as follows: A Fluid Bed Processor is used for granulation in order to agglomerate the particles of the materials to obtain a uniform particle size for the final blend. The granulating solution is prepared by dissolving the binder (e.g. polyvinyl alcohol) in hot purified water while mixing. The percent solids content can be adjusted to obtain a viscosity to control the build up (agglomeration size) of the material. A lower viscosity leads to smaller particles, and a higher viscosity leads to larger particles. In addition, the application rate (e.g. from about 150 gm/min to about 250 gm/min; or about 200 gm/min), position of Spray gun (e.g. center position) and nozzle size (e.g. from about 0.5 mm to about 2 mm; or about 1 mm) and atomization pressure (e.g. from 20 psi to about 40 psi; or about 30 psi) contribute further to control particle size. The active material is fluidized and heated (e.g. from about 35° C. to about 45° C.; or about 40° C.) prior to start of solution application. During the spray cycle, the bed temperature (e.g. from about 35° C. to about 45° C.; or about 40° C.) is kept at a constant temperature to avoid over-wetting. Once all the required binder solution is applied, the material is further dried to the targeted LOD value (i.e. loss on drying) (e.g. below about 1%) prior to unloading. The amount of binder (e.g. polyvinyl alcohol) is from about 2% to about 6%, and in some cases about 3%; and the solution concentration is from about 3% to about 7%, and in some cases about 4.5%. The time of agglomeration process for the 60 kg batch is from about 45 minutes to about 220 minutes, and in some cases about 150 minutes. Once the granulate is dry, material is passed through a 1.4 and 2.00 mm screen to remove any oversized particles. The oversize particles are passed through the mill to reduce oversize particles. Oversized particles are generally not present in an amount to exceed about 5% of total yield. The screened and milled materials are placed into a shell blender (e.g. V-Blender, Bin blender) and the lubricant (e.g. glyceryl behenate) is added. The lubricant is screened and added to the granules and blended at the predetermined number of revolutions or time (e.g. mix time of about 5 min to about 15 min, and in some cases about 10 min). The percent lubricant is from about 0.5% to about 4%, and in some cases about 2%. The level of lubrication is established for sufficient coverage of either larger or smaller particle size distribution. Additional characteristics include bulk density (e.g. from about 0.3 gm/ml to about 0.8 gm/ml, and in some cases about 0.5 gm/ml), and moisture content (e.g. not more than about 1%). Particle size and flow of final blend are factors in obtaining uniform fill of cavities on a rotary press. The flow and top rotation speed of the press are adjusted (dependant on the type/size of press) so as to not jeopardize the weight uniformity of individual tablets. The product blend is passed through a hopper into a feed frame to fill the die cavities passing under the feed frame. Weight adjustments are made to keep the weight within the specified range, and adjustments made to the pressure settings to obtain the required hardness. Some components monitored for the tablets are tablet thickness and friability (e.g. less than about 0.5%). Suitable thickness (related to overall surface area) and lower friability help reduce core damage and loss of active during coating. Tablet samples are removed at predetermined intervals to monitor specifications.

Coatings

The tablet cores can be coated for administration to a subject. In at least one embodiment of the invention, the tablet cores are coated with a controlled release coating ("XL Controlled Release Coat") that can provide an extended release of the bupropion hydrobromide salt or mixture of the bupropion hydrobromide salt and other drug. In at least one other embodiment, the tablet cores are coated with an aqueous controlled release coating that comprises an aqueous dispersion of a neutral ester copolymer without any functional groups ("AQ Controlled Release Coat").

In certain embodiments the tablet dosage form comprises an optional moisture barrier in addition to the controlled release coat. The controlled release coat and the moisture barrier can be applied in two stages. The controlled release coat can be applied directly onto the surface of the tablet cores and functions to control the release of the bupropion hydrobromide salt. The moisture barrier can be applied directly onto the surface of the controlled release coat to impede or retard the absorption of moisture.

Prophetic examples of controlled release coat formulations are provided below. It should be understood that the constituents and/or proportions of the constituents in these coatings as well as the amounts thereof can be varied in order to achieve formulations possessing different release characteristics. In all instances wherein prophetic examples are provided these compositions are intended to be exemplary and it should be understood that the specific procedures, constituents, amounts thereof and the like can be varied in order to obtain a composition possessing desired properties.

In at least one embodiment the controlled release coat is a coating formulation that provides a delayed release of the active drug(s) from the tablet core. In such embodiments the coating formulation to be applied to the core can comprise:

| | |
|---|---|
| EUDRAGIT ® L12.5 | about 50% by weight of coating suspension |
| Triethyl citrate | about 0.63% by weight of coating suspension |
| Talc | about 1.25% by weight of coating suspension |
| Isopropyl alcohol | about 48.12% by weight of coating suspension |
| Solids total = | about 8.1% |
| Polymer content of suspension = | about 6.3% |

In certain embodiments the controlled release coating of the bupropion hydrobromide dosage form (e.g. controlled release coat of an XL tablet) can be made according to any one of the methods described herein.

Preparation of the Controlled Release Coating Formulation of Such Embodiments (e.g. controlled release coat that can provide a delayed release of the active drug) can be as follows: Talc and triethyl citrate are homogenized in the solvent by means of a homogenizer for approximately 10 minutes. The suspension is poured directly into the EUDRAGIT® L12.5 dispersion and stirred gently to avoid sedimentation. The coating is sprayed onto tablets until approximately 5 mg/cm2 of EUDRAGIT® L has been applied to the tablet core.

In at least one embodiment the controlled release coat can provide a sustained release of the active drug from the tablet core. The coating formulation can comprise:

| | |
|---|---|
| EUDRAGIT ® RL 12.5 | about 10% by weight of coating suspension |
| EUDRAGIT ® RS 12.5 | about 30% by weight of coating suspension |
| Dibutyl sebacate | about 0.5% by weight of coating suspension |
| Talc | about 3.5 g by weight of coating suspension |
| Magnesium stearate | about 1% by weight of coating suspension |
| Acetone | about 27.5% by weight of coating suspension |
| Isopropyl alcohol | about 27.5% by weight of coating suspension |
| Solids total = | about 10% |
| Polymer content of suspension = | about 5% |

Preparation of the Controlled Release Coating Formulation of Such Embodiments (i.e. Controlled release coat that can provide a sustained release of the active drug) can be as follows: Dibutyl sebacate, talc and magnesium stearate are mixed and finely dispersed together with the diluents acetone and isopropyl alcohol. The suspension is then combined with the EUDRAGIT® polymer dispersions. The coating is sprayed onto the core until approximately 10 mg/cm2 of polymer has been applied to the core.

In at least one embodiment the controlled release coat is a polymer blend coating possessing pH dependent polymer (e.g. EUDRAGIT® L30D55) in combination with a sustained release polymer (e.g. AQUACOAT®). Such a coating formulation can comprise:

| | |
|---|---|
| AQUACOAT ® (ethylcellulose 30%) | about 21% by weight of coating suspension |
| EUDRAGIT ® L30 D 55 | about 21% by weight of coating suspension |
| Triethyl citrate | about 3% by weight of coating suspension |
| Water | about 55% by weight of coating suspension |
| Solids total = | about 15.6% |
| Polymer content of suspension = | about 12.6% |

Application of the polymer blend coating can be as follows: Coating applied to a 10 mg/cm2 application of polymer to the drug core.

In at least one embodiment the controlled release coat is a drug coating containing at least one other drug (e.g. Citalopram) on top of a core containing bupropion hydrobromide salt. The coating formulation can comprise:

| | |
|---|---|
| KOLLIDON ® VA64 (Vinylpyrrolidone-vinyl acetate copolymer) | about 2.5% by weight of drug coating suspension |
| KLUCEL ™ EF (Hydroxypropylcellulose) | about 2.5% by weight of drug coating suspension |

-continued

| | |
|---|---|
| Citalopram | about 2% by weight of drug coating suspension |
| Talc | about 3% by weight of drug coating suspension |
| 2-propanol | about 90% by weight of drug coating suspension |
| Solids total = | about 10% |
| Polymer content of suspension = | about 5% |

Application of the drug coating formulation can be as follows: Drug coating is sprayed onto tablets until the desired amount of other drug (e.g. Citalopram) is applied.

A top-coat can subsequently be applied as a cosmetic coating and also to prevent tablet sticking.

The top-coat formulation applied to the drug coated core can comprise:

| | |
|---|---|
| KOLLIDON ® VA64 (Vinylpyrrolidone-vinyl acetate copolymer) | about 2.5% by weight of top-coat suspension |
| KLUCEL ™ EF (Hydroxypropylcellulose) | about 2.5% by weight of top-coat suspension |
| Talc | about 2.5% by weight of top-coat suspension |
| Isopropyl alcohol | about 92.5% by weight of top-coat suspension |
| Solids total = | about 7.5% |
| Polymer content of suspension = | about 5% |

Application of the top-coating formulation can be as follows: Coating is applied to about a 2% weight gain (expressed as % of drug coated tablet core)

The Extended Release (XL) Controlled Release Coat

The XL controlled release coat is a semi-permeable coat comprising a water-insoluble, water-permeable film-forming polymer, a water-soluble polymer, and optionally a plasticizer.

Non-limiting examples of water-insoluble, water-permeable film-forming polymers useful for the XL controlled release coat of certain embodiments include cellulose ethers, cellulose esters, polyvinyl alcohol and mixtures thereof. In certain embodiments the water-insoluble, water-permeable film forming polymers can be the ethyl celluloses, and can be selected from the following non-limiting examples: ethyl cellulose grades PR100, PR45, PR20, PR10 and PR7 (ETHOCEL®, Dow), and any combination thereof. In at least one embodiment of the invention, ethyl cellulose grade PR 100 is the water-insoluble, water-permeable film-forming polymer. In certain embodiments the amount of the water-insoluble water-permeable film-forming polymer can vary from about 1% to about 12% by weight of the tablet dry weight, including all values and ranges therebetween. For example, in certain embodiments the amount of the water-insoluble water-permeable film-forming polymer is present in an amount from about 5% to about 10%, and in other embodiments from about 6% to about 8% by weight of the tablet dry weight. In certain embodiments of the 174 mg dose modified-release tablets of the invention, the amount of water-insoluble water permeable film-forming polymer is from about 3% to about 8% by weight of the tablet dry weight, and in other embodiments from about 6% to about 7% by weight of the tablet dry weight. With respect to the controlled release coat itself, the amount of water-insoluble water-permeable film-forming polymer in certain embodiments of the 174 mg dose tablet can be from about 35% to about 60% by weight of the controlled release coat dry weight, including all values and ranges therebetween; and in certain embodiments from about 40% to about 50% by weight of the controlled release coat dry weight. In certain embodiments of the 348 mg dose modified-release tablet of the invention, the amount of water-insoluble water-permeable film-forming polymer can be from about 2% to about 5% by weight of the tablet dry weight, and in other embodiments from about 3% to about 4% by weight of the tablet dry weight. With respect to the controlled release coat itself, the water-insoluble water-permeable film-forming polymer in certain embodiments of the 348 mg dose tablet is present in an amount of about 40% by weight of the controlled release coat dry weight. In certain embodiments of the 522 mg dose modified-release tablet of the invention, the amount of water-insoluble water-permeable film-forming polymer can be from about 0.5% to about 10% by weight of the tablet dry weight, and in other embodiments from about 1% to about 6% by weight of the tablet dry weight. With respect to the controlled release coat itself, the water-insoluble water-permeable film-forming polymer in certain embodiments of the 522 mg dose tablet is present in an amount of about 37% by weight of the controlled release coat dry weight.

Non-limiting examples of water-soluble polymers useful for the XL controlled release coat include polyvinylpyrrolidone, hydroxypropyl methylcellulose, hydroxypropyl cellulose and mixtures thereof. In at least one embodiment the water-soluble polymer is polyvinylpyrrolidone (POVIDONE® USP). The amount of water-soluble polymer can vary from about 1.5% to about 10% by weight of the tablet dry weight, including all values and ranges therebetween. For example, in certain embodiments the amount of water-soluble polymer is from about 3% to about 8%, and in other embodiments at about 4% by weight of the tablet dry weight. With respect to the controlled release coat itself, in certain embodiments the amount of water-soluble polymer present is from about 25% to about 55% by weight of the controlled release coat dry weight. For certain embodiments of the 174 mg dose of the extended release tablet of the invention, the amount of water-soluble polymer is from about 3% to about 5% by weight of the tablet dry weight, and from about 25% to about 50% by weight of the controlled release coat dry weight, including all values and ranges therebetween. For certain embodiments of the 348 mg dose of the extended release tablet of the invention, the amount of water-soluble polymer present is from about 2% to about 5% of the tablet dry weight and from about 40% to about 50% by weight of the controlled release coat dry weight, including all values and ranges therebetween. For certain embodiments of the 522 mg dose of the extended release tablet of the invention, the amount of water-soluble polymer present is from about 2% to about 5% of the tablet dry weight and from about 40% to about 50% by weight of the controlled release coat dry weight, including all values and ranges therebetween.

In certain embodiments, the XL controlled release coat further comprises a plasticizer. The use of plasticizers is optional, and they can be added to film coating formulations to modify the physical properties of a polymer to make it more usable during manufacturing. Plasticizers can be high boiling point organic solvents used to impart flexibility to otherwise hard or brittle polymeric materials. Plasticizers generally cause a reduction in the cohesive intermolecular forces along the polymer chains resulting in various changes in polymer properties including a reduction in tensile strength, and increase in elongation and a reduction in the glass transition or softening temperature of the polymer. The amount and choice of the plasticizer can affect the hardness of a tablet and can even affect its dissolution or disintegration characteristics, as well as its physical and chemical stability. Certain plasticizers can increase the elasticity and/or pliability of a coat, thereby decreasing the coat's brittleness. Once the dosage form is manufactured, certain plasticizers can function to increase the hydrophilicity of the coat(s) and/or the core of the dosage form in the environment of use (in-vitro or in-vivo). Non-limiting examples of plasticizers that can be used in the controlled release coat described herein include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropioin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, polyols (e.g. polyethylene glycol) of various molecular weights, and mixtures thereof. It is contemplated and within the scope of the invention, that a combination of plasticizers can be used in the present formulation. In at least one embodiment of the invention, the plastizer is polyethylene glycol 4000, dibutyl sebacate or a mixture thereof. The amount of plasticizer for the controlled release coat can vary in an amount of from about 0.5% to about 4% by weight of the tablet dry weight, including all values and ranges therebetween. For example, in certain embodiments the plasticizer is present in an amount of from about 2% to about 3% by weight of the tablet dry weight. For certain embodiments of the 174 mg dose extended-release tablet of the invention, the amount of plasticizer present in the controlled release coat is from about 1% to about 4% by weight of the tablet dry weight. For certain embodiments of the 348 mg dose extended release tablet of the invention, the amount of plasticizer present is from about 0.5% to about 4% by weight of the tablet dry weight. For certain embodiments of the 522 mg dose extended release tablet of the invention, the amount of plasticizer present is from about 0.5% to about 4% by weight of the tablet dry weight. In certain embodiments of the 174 mg, 348 mg and 522 mg dosage forms, the plasticizer is present in an amount of from about 6% to about 30% by weight of the controlled release coat dry weight, including all values and ranges therebetween. For example, in certain embodiments the plasticizer is present in an amount of about 12% by weight of the controlled release coat dry weight.

The ratio of water-insoluble water-permeable film forming polymer:plasticizer:water-soluble polymer for the XL controlled release coat of certain embodiments of the invention described herein can vary from about 3:1:4 to about 5:1:2, including all values and ranges therebetween. For example, in certain embodiments the ratio of water-insoluble water-permeable film forming polymer:plasticizer:water-soluble polymer for the XL controlled release coat is about 4:1:3. For certain other embodiments of the XL tablet the ratio of the water-insoluble water-permeable film-forming polymer:plasticizer:water-soluble polymer in the XL controlled release coat is from about 7:2:6 to about 19:5:18, including all values and ranges therebetween. In at least one embodiment the ratio of water-insoluble water-permeable film forming polymer:plasticizer:water-soluble polymer for the XL controlled release coat is about 13:4:12. In at least one embodiment of the 522 mg dosage form, the ratio of water-insoluble water-permeable film forming polymer:plasticizer:water-soluble polymer for the XL controlled release coat is about 13:6:16.

In certain embodiments the XL controlled release coat of the bupropion hydrobromide tablet can be made according to any one of the methods described herein.

Preparation and application of the XL controlled release coat can be as follows. The water-insoluble water-permeable film-forming polymer (e.g. ethylcellulose), and the plasticizer (e.g. polyethylene glycol 4000), are dissolved in an organic solvent (e.g. a mixture of ethyl alcohol). In the manufacture of embodiments that do not require a plasticizer, the water-insoluble water-permeable film-forming polymer can be dissolved in the organic solvent without the plasticizer. The water-soluble polymer (e.g. polyvinyl pyrrolidone) is next added until a homogenous mixture is achieved. The resulting controlled release coat solution is then sprayed onto the tablet cores using a tablet coater, fluidized bed apparatus or any other suitable coating apparatus known in the art until the desired weight gain is achieved. The tablet cores coated with the controlled release coat are subsequently dried. In the manufacture of embodiments that have a moisture barrier, the controlled release coat is dried before the moisture barrier is applied.

An example of the coating process for the XL controlled release coat is as follows: The XL controlled release coat solution is prepared by dissolving the water insoluble polymer (e.g. ethylcellulose) and water soluble polymer (e.g. polyvinylpyrrolidone) and an ethyl alcohol mixture while mixing and is followed with the addition of the plasticizer(s) (e.g. mixture of polyethylene glycol 4000 and dibutyl sebacate). Once completely dissolved, the solution is homogenized to obtain a uniform mixture of appropriate viscosity. This procedure helps obtain a complex mix of a water permeable film to control the release of the active drug. The composition of the solution can be formulated to contain various levels of the water insoluble polymer and water soluble polymer and a mix of the plasticizer(s). The release function is further controlled by the film thickness applied and measured as weight gain of solids in the coating required. Tablets are coated in a perforated coating pan with control of pan speed (e.g. from about 8 rpm to about 14 rpm, and in some cases about 12 rpm), spray rate (e.g. from about 150 gm/min to about 250 gm/min, and in some cases about 200 gm/min), atomization pressure (e.g. from about 15 psi to about 25 psi, and in some cases about 20 psi), supply volume (from about 800 to about 1000 cubic ft/min, and in some cases about 900 cubic ft/min), and air temperature (e.g. from about 50° C. to about 60° C., and in some cases about 55° C.), monitored through a bed temperature and/or outlet temperature of from about 38° C. to about 42° C., and in some cases about 40° C. On completion of the coating cycle, tablets are dried and unloaded into bulk containers. The printing process comprises the transfer of a print image from a print plate covered with edible black ink and transferred via a print roll or print pad onto the surface of the tablets. The printed tablets are transferred through a drying element prior to discharging into bulk containers. Samples for final testing are taken throughout the printing process.

The skilled artisan will appreciate that controlling the permeability can control the release of the bupropion hydrobromide salt and/or the amount of coating applied to the tablet cores. The permeability of the XL controlled release coat can be altered by varying the ratio of the water-insoluble, water-permeable film-forming polymer:plasticizer:water-soluble polymer and/or the quantity of coating applied to the tablet core. A more extended release can be obtained with a higher amount of water-insoluble, water-permeable film forming polymer. The addition of other excipients to the tablet core can also alter the permeability of the controlled release coat. For example, if it is desired that the tablet core further comprise an expanding agent, the amount of plasticizer in the controlled release coat could be increased to make the coat more pliable, as the pressure exerted on a less pliable coat by the expanding agent could rupture the coat. Further, the proportion of the water-insoluble water-permeable film forming polymer and water-soluble polymer can also be altered depending on whether a faster or slower dissolution and/or release profile is desired.

Depending on the dissolution or in-vivo release profile desired, the weight gained after coating the tablet core with the XL controlled release coat typically can vary from about 3% to about 30% of the weight of the dry tablet core. For a 174 mg dose extended release tablet according to certain embodiments, the weight gain can typically vary from about 10% to about 17% of the weight of the dry tablet core. For example in the 174 mg tablet of certain embodiments, the weight gain is about 14% of the weight of the dry tablet core. For the 348 mg dose extended release tablet of certain embodiments, the weight gain can vary from about 7% to about 10% of the weight of the dry tablet core. For example in the 348 mg tablet of certain embodiments, the weight gain is about 9% of the weight of the dry tablet core. For the 522 mg dose extended release tablet of certain embodiments, the weight gain can vary from about 5% to about 15% of the weight of the dry tablet core. For example in the 522 mg tablet of certain embodiments, the weight gain is about 8.5% of the weight of the dry tablet core.

AQ Controlled Release Coat

The AQ controlled release coat is a stable monolithic controlled release coating comprising an aqueous dispersion of a neutral ester copolymer without any functional groups, a poly glycol having a melting point greater than about 55° C., and one or more pharmaceutically acceptable excipients; wherein said coating composition is coated onto the dosage form and cured at a temperature at least equal to or greater than the melting point of the poly glycol. The coating formulation is quite versatile in that it can be used to coat a variety of drug cores and can be easily manipulated to obtain the desired drug release profile.

In certain other embodiments, the AQ controlled release coat comprises an aqueous dispersion of an ethylcellulose, a poly glycol having a melting point greater than about 55° C., and one or more pharmaceutically acceptable excipients; wherein said coating composition is coated onto the dosage form and cured at a temperature at least equal to or greater than the melting point of the poly glycol. Non limiting examples of aqueous dispersions of an ethylcellulose include SURELEASE® (Colorcon, Inc., West Point, Pa., U.S.A.), and AQUACOAT® (FMC Corp., Philadelphia, Pa., U.S.A.). Combinations are operable.

Non-limiting examples of neutral ester copolymers without any functional groups that can be used in the AQ controlled release coat include EUDRAGIT® NE30D, EUDRAGIT® NE40D (Röhm America LLC), and mixtures thereof. In at least one embodiment the polymer is EUDRAGIT® NE30D, which can be present in an amount of from about 1% to about 35% by weight of the controlled release coat, including all values and ranges therebetween, depending on the controlled release profile desired. Hydrophilic agents can also be included in the AQ controlled release coat to promote wetting of the coat when in contact with gastrointestinal fluids. Non-limiting examples of such hydrophilic agents include hydrophilic water soluble polymers such as hydroxypropyl methylcellulose (HPMC), hydroxypropyl cellulose (HPC) and combinations thereof. In at least one embodiment, HPMC is the hydrophilic water soluble polymer. If hydrophilic agents are to be included in the coat composition, the agents can be present in an amount from about 0.1% to about 10% by weight of the coating composition, including all values and ranges therebetween. For example, in certain embodiments the hydrophilic agents are present in an amount of from about 0.1% to about 5%, and in other embodiments from about 0.1% to about 3% by weight of the controlled release coat composition.

The AQ controlled release coat formulation also comprises a poly glycol with a melting point of greater than about 55° C. Non-limiting examples of the polyglycol include polyethylene glycol 6000, polyethylene glycol 8000, polyethylene glycol 10000, polyethylene glycol 20000, and mixtures thereof. In at least one embodiment, the poly glycol is polyethylene glycol 8000. The poly glycol can be present in an amount of from about 0.1% to about 5% by weight of the coat, including all values and ranges therebetween. Other examples of suitable polyglycol derivatives having a melting point of at least about 55° C. include, but are not limited to, Poloxamer 188, Poloxamer 338, Poloxamer 407, Polyethylene Oxides, Polyoxyethylene Alkyl Ethers, Polyoxyethylene Stearates and mixtures thereof.

In addition to the copolymers and the poly glycol, the AQ controlled release coat formulation comprises at least one pharmaceutically acceptable excipient. The excipients can include but are not limited to anti-tacking agents, emulsifying agents, antifoaming agents, flavourants, colourants, and mixtures thereof. It is known in the art that depending on the intended main function, excipients can affect the properties of the coat in a series of ways, and many substances used in coat formulations can thus be described as multifunctional. A skilled worker will know, based on his technical knowledge, which pharmaceutically acceptable excipients are suitable for the desired AQ controlled release coat composition.

The tackiness of polymeric films is a factor for the coating of solid dosage forms and for the subsequent curing step (post coating thermal treatment). During coating with either cellulosic or acrylic polymers, sometimes an unwanted agglomeration of several granules or beads can occur, for example at higher product processing temperatures. Accordingly, the addition of anti-tacking agents to coating formulations can be desirable in certain embodiments. The anti-tacking agents which can be used in certain embodiments include but are not limited to adipic acid, magnesium stearate, calcium stearate, zinc stearate, hydrogenated vegetable oils, sterotex, glyceryl monostearate, talc, sodium benzoate, sodium lauryl sulfate, magnesium lauryl sulfate, and mixtures thereof. In at least one embodiment, talc is the anti-tacking agent. Talc can also function as a wetting agent. Mixtures of the anti-tacking agents are operable. The amount of anti-tacking agent in the controlled release coat composition can range from about 1% to about 15% by weight of the controlled release coating dispersion, including all values and ranges therebetween. For example, in certain embodiments the anti-tacking agent is present in an amount of from about 1% to about 7% by weight of the controlled release coating dispersion.

Certain embodiments can include anti-foaming agents in the AQ controlled release coat composition. Non-limiting examples of useful anti-foaming agents include silicon oil, simethicone, and mixtures thereof. In at least one embodiment, simethicone is the anti-foaming agent used in the AQ controlled release coat composition. The anti-foaming agent can be present in an amount of up to about 0.5% by weight of the AQ controlled release coat composition. For example, in certain embodiment the anti-foaming agent is present in an amount of from about 0.1% to about 0.4% by weight of the AQ controlled release coat composition, including all values and ranges therebetween.

Certain embodiments can include emulsifying agents (also called emulsifiers or emulgents) in the AQ controlled release coat. Emulsifying agents can facilitate emulsification during manufacture of the AQ controlled release coat, and also provide emulsion stability during the shelf-life of the product. Non-limiting examples of emulsifying agents include naturally occurring materials and their semi synthetic derivatives, such as the polysaccharides, as well as glycerol esters, cellulose ethers, sorbitan esters and polysorbates. Mixtures are operable. In at least one embodiment the emulsifying agent is Polysorbate 80 (polyoxyethylene sorbitan mono-oleate) (TWEEN™ 80). The emulsifying agent can be present in an amount of up to about 0.5% by weight of the AQ controlled release coat composition. For example, in certain embodiments the emulsifying agent is present in an amount of from about 0.1% to about 0.3% by weight of the AQ controlled release coat composition, including all values and ranges therebetween.

Certain embodiments can include colorants in the film coat formula. Such colorants can be water-insoluble colors (pigments). Pigments have certain advantages over water-soluble colors in that they tend to be more chemically stable towards light, provide better opacity and covering power, and optimize the impermeability of a given film to water vapor. Non-limiting examples of suitable colorants include iron oxide pigments, titanium dioxide, and aluminum Lakes. Mixtures are operable. In at least one embodiment the pigment is titanium dioxide. The pigment or colorant can be present in an amount of from about 0.1% to about 10% by weight of the AQ controlled release coat composition, including all values and ranges therebetween. For example, in certain embodiments the pigment or colorant is present in an amount of from about 0.1% to about 5%, and in other embodiments from about 0.1% to about 2% by weight of the AQ controlled release coat composition.

In certain embodiments the AQ controlled release coat of the bupropion hydrobromide tablet can be made according to any one of the methods described herein.

The AQ controlled release coat can be applied onto a core comprising an effective amount of the bupropion hydrobromide salt by a process which involves the atomization (spraying) of the coating solution or suspension onto a bed of the tablet cores. Some examples of equipment suitable for film coating include: ACCELA COTA® (Manesty Machines, Liverpool, UK), HI-COATER® (Freund Company, Japan), DRIACOATER™ (Driam Metallprodukt GmbH, Germany), HTF/150 (GS, Italy), and IDA™ (Dumoulin, France). Examples of units that function on a fluidized-bed principle include: AEROMATIC™ (Fielder, Switzerland and UK) and GLATT™ AG (Switzerland). In at least one embodiment, the apparatus used for film coating is the ACCELA COTA®.

The coating fluid can be delivered to the coating apparatus from a peristaltic pump at the desired rate and sprayed onto the rotating or fluidizing tablet cores. The tablet cores are pre-warmed to about 30° C. During the coating process, the product temperature range is maintained at from about 25° C. to about 35° C. by adjusting the flow rate of the inlet and outlet air, temperature of the inlet air and spray rate. A single layer of coat is applied and once spraying is complete, the coated tablet cores are dried from about 30° C. to about 40° C. for a time period of from about 3 to about 5 minutes at a low pan speed and low air flow. The pan is readjusted to jog speed, and drying continues for a time period of from about 12 to about 15 minutes.

The coated tablet cores are placed onto a tray and cured (post coating thermal treatment) in an electrical or steam oven at a temperature above the temperature of the melting point of the polyethylene glycol or derivative thereof. In certain embodiments the curing temperature is greater than the melting point of the polyethylene glycol or derivative thereof. In certain embodiments the curing time is from about 2 to about 7 hours. The cured coated tablets are subsequently cooled to room temperature.

The AQ controlled release coat is quite versatile. The length and time for the delay can be controlled by rate of hydration and the thickness of the coat. The drug release rate subsequent to the delay can be determined by the thickness and permeability of the hydrated coat. Thus, it is possible to regulate the rate of hydration and permeability of the AQ controlled release coat so that the desired controlled-release drug profile can be achieved. There is no preferred coat thickness, as this will depend on the controlled release profile desired. Other parameters in combination with the thickness of the coat include varying the concentrations of some of the ingredients of the stable coat composition of the invention described and/or varying the curing temperature and length of curing the coated tablet cores. The skilled artisan will know which parameters or combination of parameters to change for a desired controlled release profile.

As will be seen from the non-limiting examples described herein, the coatings used in certain embodiments of the present invention are quite versatile. For example, the length and time for the lag time can be controlled by the rate of hydration and the thickness of the controlled release coat. Other parameters in combination with the thickness of the coatings include varying the concentrations of some of the ingredients of the coating compositions of certain embodiments described and/or varying the curing temperature and length of curing the coated tablet cores. The skilled artisan will know which parameters or combination of parameters to change for a desired controlled release profile.

The Moisture Barrier Coat

In certain embodiments, an optional moisture barrier is applied directly onto the controlled release coat. In other embodiments a moisture barrier coat is not included in the dosage form. In certain embodiments the moisture barrier comprises an enteric polymer (e.g. acrylic polymer), a permeation enhancer and optionally a plasticizer.

In certain embodiments, the enteric polymer is an acrylic polymer. For example, the acrylic polymer can be a methacrylic acid copolymer type C [poly(methacrylic acid, methyl methacrylate) 1:1] available commercially under the trade name EUDRAGIT® (e.g. EUDRAGIT® L 30 D-55). The methacrylic acid copolymer can be present in an amount, which can vary from about 1% to about 3% of the tablet dry weight and from about 55% to about 70% of the moisture barrier dry weight, including all values and ranges therebetween. For the 174 mg dose of the extended release tablet of certain embodiments of the present invention, the methacrylic acid copolymer can vary from about 2% to about 3% of the tablet dry weight. For example in the 174 mg tablet of certain embodiments, the amount of the methacrylic acid copolymer is present at about 2.5% of the tablet dry weight. With respect to the moisture barrier itself, the amount of the methacrylic acid copolymer in the 174 mg tablet can be present in an amount of from about 55% to about 70% by weight of the moisture barrier dry weight. For example, in the 174 mg tablet of certain embodiments the methacrylic acid copolymer is present in an amount of about 60% of the moisture barrier dry weight. For the 348 mg dose of the extended release tablet of certain embodiments, the amount of the methacrylic acid copolymer can vary from about 1.5% to about 3% of the tablet dry weight. For example, in the 348 mg tablet of certain embodiments, the amount of methacrylic acid copolymer is present at about 2% by weight of the tablet dry weight. With respect to the moisture barrier itself, the methacrylic acid copolymer in the 348 mg tablet typically will be present in an amount of from about 55% to about 70% of the moisture barrier dry weight. For example, in certain embodiments of the 348 mg tablet the methacrylic acid copolymer is present in an amount of about 60% of the moisture barrier dry weight. For the 522 mg dose of the extended release tablet of certain embodiments, the amount of the methacrylic acid copolymer can vary from about 0.5% to about 5% of the tablet dry weight. For example, in the 522 mg tablet of certain embodiments, the amount of methacrylic acid copolymer is present at about 2% by weight of the tablet dry weight. With respect to the moisture barrier itself, the methacrylic acid copolymer in the 522 mg tablet typically will be present in an amount of from about 40% to about 80% of the moisture barrier dry weight. For example, in certain embodiments of the 522 mg tablet the methacrylic acid copolymer is present in an amount of about 65% of the moisture barrier dry weight.

It is known in the art that methacrylic acid copolymers can become brittle, and that coatings that contain methacrylic acid copolymers could be made more elastic and pliable by the addition of a plasticizer. In certain embodiments the moisture barrier coat comprises a plasticizer. Non-limiting examples of plasticizers useful for the moisture barrier coat of certain embodiments include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropioin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, and mixtures thereof, polyols (e.g. polyethylene glycol) of various molecular weights, and mixtures thereof. In certain embodiments, the plasticizer in the moisture barrier coat comprises a combination of triethyl citrate and polyethylene glycol 4000 (e.g. CARBOWAX® 4000). In certain of these embodiments, the ratio of triethyl citrate to polyethylene glycol 4000 is about 1:2. The plasticizer can be present in the moisture barrier coat of certain embodiments in an amount which can vary from about 0.2% to about 0.5%, including all values and ranges therebetween. For example, in certain embodiments the plasticizer is present in the moisture barrier in an amount of from about 0.2% to about 0.4% of the tablet dry weight. The plasticizer can be present in an amount of about 0.35% of the tablet dry weight for a 174 mg tablet; in an amount of from about 0.2% to about 0.4% of the tablet dry weight for a 348 mg tablet; and in an amount of from about 0.05% to about 0.5% of the tablet dry weight for a 522 mg tablet. With respect to the moisture barrier itself, the plasticizer if present in certain embodiments can be present in an amount of from about 1% to about 30% by weight of the moisture barrier dry weight, including all values and ranges therebetween. For example, in certain embodiments the plasticizer is present in an amount of from about 10% to about 14% of the moisture barrier dry weight for the 174 mg, 348 mg and 522 mg dose extended release tablet of the present invention. It is well known in the art that depending on the intended main function, excipients to be used in tablets are subcategorized into different groups. However, one excipient can affect the properties of a drug or the tablet as a whole in a series of ways, and many substances used in tablet formulations can therefore be described as multifunctional. For example, the polyethylene glycol used in the plasticizer combination for the moisture barrier can serve not only to increase the hydrophilicity of the moisture barrier, but can also act as a glidant.

In certain embodiments the moisture barrier can further comprise a permeation enhancer that can increase its hydrophilicity, and can also act as a glidant. The permeation enhancer can be a hydrophilic substance and can be selected from the following non-limiting examples: hydrophilic polymers such as hydroxypropylmethylcellulose, cellulose ethers and protein-derived materials of these polymers, the cellulose ethers, such as hydroxyalkylcelluloses, carboxyalkylcelluloses, and mixtures thereof. Also, synthetic water-soluble polymers can be used, such as polyvinylpyrrolidone, cross-linked polyvinyl-pyrrolidone, polyethylene oxide, water-soluble polydextrose, saccharides and polysaccharides, such as pullulan, dextran, sucrose, glucose, lactose, fructose, mannitol, mannose, galactose, sorbitol and mixtures thereof. In at least one embodiment of the present invention, the hydrophilic polymer comprises hydroxypropyl-methylcellulose. Other non-limiting examples of permeation enhancers that can be used in the moisture barrier of certain embodiments include alkali metal salts such as aluminum oxidelithium carbonate, sodium chloride, sodium bromide, potassium chloride, potassium sulfate, potassium phosphate, sodium acetate, sodium citrate, and mixtures thereof. The permeation enhancers or pore-formers, can also be polymers which are soluble in the environment of use, such as CARBOWAX®, CARBOPOL®, and mixtures thereof. Non-limiting examples of pore formers include diols, polyols, polyhydric alcohols, polyalkylene glycols, polyglycols, poly(a-w)alkylenediols, and mixtures thereof. Other permeation enhancers which can be useful in the formulations of the present invention include starch, modified starch, and starch derivatives, gums, including but not limited to xanthan gum, alginic acid, other alginates, benitonite, veegum, agar, guar, locust bean gum, gum arabic, quince psyllium, flax seed, okra gum, arabinoglactin, pectin, tragacanth, scleroglucan, dextran, amylose, amylopectin, dextrin, cross-linked polyvinylpyrrolidone, ion-exchange resins, such as potassium polymethacrylate, carrageenan, kappa-carrageenan, lambda-carrageenan, gum karaya, biosynthetic gum, and mixtures thereof. Other permeation enhancers include materials useful for making microporous lamina in the environment of use, such as polycarbonates comprised of linear polyesters of carbonic acid in which carbonate groups reoccur in the polymer chain, microporous materials such as bisphenol, a microporous poly (vinylchloride), micro-porous polyamides, microporous modacrylic copolymers, microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid cross-linked poly(vinylpyrrolidone), silicon dioxide, colloidal silica, microcrystalline cellulose and any combination thereof. In at least one embodiment of the invention the permeation enhancer is silicon dioxide (e.g. SYLOID® 244FP). The amount of permeation enhancer can vary from about 0.5% to about 1% by weight of the tablet dry weight and from about 25% to about 30% by weight of the moisture barrier dry weight, including all values and ranges therebetween. For the 174 mg dose extended-release tablet of certain embodiments of the invention, the permeation enhancer can be present in an amount of about 0.5% to about 2% of the tablet dry weight, and from about 20% to about 40% by weight of the moisture barrier dry weight. For example, in certain embodiments of the 174 mg dose tablet, the permeation enhancer is present in an amount of from about 25% to about 30% by weight of the moisture barrier dry weight. For the 348 mg dose extended release tablet of the invention, the permeation enhancer can be present in an amount which can vary from about 0.5% to about 2% by weight of the tablet dry weight, and from about 20% to about 40% by weight of the moisture barrier dry weight. For example, in certain embodiments of the 348 mg dose tablet, the permeation enhancer is present in an amount of from about 25% to about 30% by weight of the moisture barrier dry weight. For the 522 mg dose extended release tablet of the invention, the permeation enhancer can be present in an amount which can vary from about 0.1% to about 2% by weight of the tablet dry weight, and from about 20% to about 40% by weight of the moisture barrier dry weight. For example, in certain embodiments of the 522 mg dose tablet, the permeation enhancer is present in an amount of from about 25% to about 30% by weight of the moisture barrier dry weight.

In at least one embodiment of the invention, the ratio of the methacrylic acid copolymer:plasticizer:permeation enhancer in the moisture barrier is about 13:2:5.

In certain embodiments the moisture barrier of the bupropion hydrobromide dosage form can be made according to any one of the methods described herein.

The preparation and application of the moisture barrier process can be as follows. The optional plasticizer (e.g. a combination of polyethylene glycol 4000 and triethyl citrate), can be first added to water and the mixture mixed to homogeneity. The methacrylic acid co-polymer (e.g. EUDRAGIT® L 30 D-55), is next sieved and added to the plasticizer mixture and mixed to homogeneity. In a separate container the permeation enhancer (e.g. silicon dioxide) is dissolved in water until a homogeneous mixture is achieved. The plasticizer and methacrylic acid copolymer mixture is then combined with the permeation enhancer solution and mixed to homogeneity. The resulting moisture barrier solution is then sprayed onto the tablet cores coated with the controlled release coat using a tablet coater, fluidized bed apparatus or any other suitable coating apparatus known in the art until the desired weight gain is achieved. The tablets coated with the moisture barrier are subsequently dried prior to packaging.

The moisture barrier is applied to the controlled release coated tablet cores such that the weight gain is not more than about 6% of the tablet dry weight for the 174 mg, 348 mg and 522 mg extended release tablets of certain embodiments of the present invention. In certain embodiments the weight gain is not more than about 3.5% of the tablet dry weight for the 174 mg, 348 mg and 522 mg extended release tablets. The amount of the moisture barrier applied typically does not significantly render the extended release tablet described herein more resistant to gastric fluid. However, in certain embodiments the moisture barrier can have an impact on the drug release characteristics.

The moisture barrier as used in certain embodiments, does not function as an enteric coat. Even though the methacrylic acid copolymer, EUDRAGIT® L 30 D-55, is referenced and is used in enteric coating formulations in the art, its functionality is formulation dependent and on the quantity of the material applied. As is known in the art, an enteric coating is applied where a drug may be destroyed or inactivated by gastric juice or where the drug may irritate the gastric mucosa. To meet the requirements for an enteric coat, the test as described in the USP (method A or B) stipulates that after 2 hours in acidic media (e.g. 0.1N HCl), no individual values of at least six experiments exceed about 10% of the active drug dissolved and not less than about 75% dissolved at about 45 minutes in pH about 6.8. The moisture barrier of certain embodiments does not meet this requirement for the following reasons even though the bupropion hydrobromide salt is not negatively affected in acidic media nor is it irritating the gastric mucosa: (1) to obtain enteric integrity with a film containing EUDRAGIT® L 30 D-55, a weight gain of from about 6% to about 8% based on the dry polymer per dosage unit is recommended. The amount of EUDRAGIT® L 30 D-55 solid applied onto the controlled release coated tablet cores is not more than about 6%, and in at least one embodiment, is not more than about 3%, (2) if enteric integrity would be required, the dissolution test for the finished product (i.e., the moisture barrier coated tablet cores) at the 2 hour time point would not stipulate a limit of no more than about 20%, and (3) analytical tests performed on these coatings indicate that the coatings do not meet all the test requirements as an enteric coated product as defined by USP test methods.

The XL tablet of certain embodiments of the invention provides an extended release of the bupropion hydrobromide salt. In at least one embodiment no pore forming agent is present in the XL coating formulation. An extended release bupropion hydrobromide formulation is provided in certain embodiments such that after about 2 hours, not more than about 20% of the bupropion hydrobromide content is released. For example, in certain embodiments, from about 2% to about 18%, from about 4% to about 8%, or about 5% of the bupropion hydrobromide content is released after about 2 hours. After about 4 hours, from about 15% to about 45% of the bupropion hydrobromide content is released. For example, in certain embodiments from about 21% to about 37%, from about 28% to about 34%, or about 32% of the bupropion hydrobromide content is released after about 4 hours. After about 8 hours, about 40% to about 90% of the bupropion hydrobromide content is released. For example, in certain embodiments from about 60% to about 85%, from about 68% to about 74%, or about 74% of the bupropion hydrobromide content is released after about 8 hours. After about 16 hours not less than about 80% of the bupropion hydrobromide content is released. For example, in certain embodiments not less than about 93%, not less than about 96%, or not less than about 99% of the bupropion hydrobromide content is released after about 16 hours.

Also, extended release tablets are provided in certain embodiments wherein after about 2 hours not more than about 40% (e.g., about 33%) of the bupropion hydrobromide is released; after about 4 hours from about 40 to about 75% of the bupropion hydrobromide is released (e.g., about 59%); after about 8 hours at least about 75% of the bupropion hydrobromide is released (e.g., about 91%); and after about 16 hours at least about 85% of the bupropion hydrobromide is released (e.g., about 97%). In all instances herein when actual or prophetic dissolution profiles are provided this means that the medicament possesses such a profile in at least one dissolution medium under prescribed conditions such as are identified herein and are well known to those skilled in the art. Such dissolution media, dissolution conditions and apparatus for use therein are disclosed in the United States Pharmacopoeia (USP) and European and Japanese counterparts thereof. Additionally, specific examples thereof are provided in this application.

Enhanced Absorption (EA) Tablets

In certain embodiments of the present invention, there is provided an enhanced absorption (EA) tablet having a core comprising a bupropion hydrobromide salt and conventional excipients, wherein the bupropion hydrobromide salt provides for the reduction of incidences of and/or severity of bupropion-induced seizures, and is more stable, as compared with equivalent molar amounts of bupropion hydrochloride. The core is surrounded by an EA coating, which controls the release of the bupropion hydrobromide salt. In certain embodiments, the EA coating consists of one coat. An advantage of the EA tablet includes the lower amount of drug required in the composition to be an effective amount, which in turn can lead to a reduction of side effects. The EA tablet optionally can comprise one or more additional functional or non-functional coats surrounding the core or EA coating.

The EA Core

The core of the EA tablet comprises an effective amount of a bupropion hydrobromide salt, a binder and a lubricant, and can contain other conventional inert excipients. The amount of the bupropion hydrobromide salt present in the EA core can vary from about 40% to about 99% by weight of the EA tablet dry weight, including all values and ranges therebetween. For example, in certain embodiments bupropion hydrobromide is present in an amount of from about 50% to about 95%, and in other embodiments in an amount of from about 70% to about 90% by weight of the EA tablet dry weight. The EA tablet comprises an effective amount of bupropion hydrobromide salt that can vary from about 50 mg to about 1000 mg, including 100, 150, 200, 250, 300, 350, 400, 450, 500, 510, 520, 530, 540, 550, 560, 570, 580, 590, 600, 650, 700, 750, 800, 85, 900, 950 mg and all values and ranges therebetween. For example, certain embodiments of the EA tablet can comprise about 150 mg, about 300 mg or about 450 mg of bupropion hydrobromide. For a 150 mg dose tablet the bupropion hydrobromide can be present in an amount of from about 76% to about 84% by weight of the tablet dry weight. For a 300 mg dose, the amount of bupropion hydrobromide can be present in an amount of from about 80% to about 83% by weight of the tablet dry weight. For a 450 mg dose, the amount of bupropion hydrobromide can be present in an amount of from about 75% to about 90% by weight of the tablet dry weight. For the 150 mg, 300 mg and 450 mg dose bupropion hydrobromide EA tablets of certain embodiments of the invention, the amount of bupropion hydrobromide can be present at about 94% by weight of the dry core for each dose.

A binder (also sometimes called adhesive) can be added to a drug-filler mixture to increase the mechanical strength of the granules and tablets during formation. Binders can be added to the formulation in different ways: (1) as a dry powder, which is mixed with other ingredients before wet agglomeration, (2) as a solution, which is used as agglomeration liquid during wet agglomeration, and is referred to as a solution binder, and (3) as a dry powder, which is mixed with the other ingredients before compaction, (referred to as a dry binder). Solution binders are a common way of incorporating a binder into granules. In certain embodiments, the binder used in the EA tablets is in the form of a solution binder. Non-limiting examples of binders include hydrogenated vegetable oil, castor oil, paraffin, higher aliphatic alcohols, higher aliphatic acids, long chain fatty acids, fatty acid esters, wax-like materials such as fatty alcohols, fatty acid esters, fatty acid glycerides, hydrogenated fats, hydrocarbons, normal waxes, stearic acid, stearyl alcohol, hydrophobic and hydrophilic polymers having hydrocarbon backbones, and mixtures thereof. Specific examples of water-soluble polymer binders include modified starch, gelatin, polyvinylpyrrolidone, cellulose derivatives (such as for example hydroxypropyl methylcellulose (HPMC) and hydroxypropyl cellulose (HPC)), polyvinyl alcohol and mixtures thereof. The amount of binder present can vary from about 0.5% to about 25% by weight of the EA tablet dry weight, including all values and ranges therebetween. For example, in certain embodiments of the invention, the amount of binder present varies from about 0.5% to about 15% by weight of the EA tablet dry weight; in other embodiments from about 1% to about 6% by weight of the EA tablet dry weight; and in still other embodiments about 3% by weight of the EA tablet dry weight. For the 150 mg, 300 mg and 450 mg dose EA tablets, the amount of binder can be present in an amount of from about 1% to about 6% by weight of each dry core weight. For example, in certain embodiments the amount of binder is present in an amount of about 3% by weight of each dry core weight. In certain embodiments of the 450 mg dosage form, the binder is present in an amount of about 4% by weight of dry core weight. In at least one embodiment of the invention the binder is polyvinyl alcohol.

Lubricants can be added to pharmaceutical formulations to decrease any friction that occurs between the solid and the die wall during tablet manufacturing. High friction during tabletting can cause a series of problems, including inadequate tablet quality (capping or even fragmentation of tablets during ejection, and vertical scratches on tablet edges) and may even stop production. Accordingly, lubricants can be added to certain tablet formulations of the present invention including the EA tablet formulation described herein. Non-limiting examples of lubricants useful for the EA core include glyceryl behenate, stearic acid, hydrogenated vegetable oils (such as hydrogenated cottonseed oil (STEROTEX®), hydrogenated soybean oil (STEROTEX® HM) and hydrogenated soybean oil & castor wax (STEROTEX® K), stearyl alcohol, leucine, polyethylene glycol (MW 1450, suitably 4000, and higher), magnesium stearate, glyceryl monostearate, stearic acid, polyethylene glycol, ethylene oxide polymers (for example, available under the registered trademark CARBOWAX® from Union Carbide, Inc., Danbury, Conn.), sodium lauryl sulfate, magnesium lauryl sulfate, sodium oleate, sodium stearyl fumarate, DL-leucine, colloidal silica, and mixtures thereof. In at least one embodiment of the invention, the lubricant is glyceryl behenate (e.g. COMPRITOL® 888). The amount of lubricant present can vary from about 0.1% to about 6% by weight of the tablet dry weight, including all values and ranges therebetween. For example, in certain embodiments the amount of lubricant present is about 3% by weight of the tablet dry weight. For certain embodiments of the 150 mg, 300 mg and 450 mg dose EA tablets of the invention the lubricant is present in an amount of about 3% by weight of the tablet dry weight and from about 1% to about 6% by weight of the dry core weight. For example, in certain embodiments the lubricant is present in an amount of about 3% by weight of the dry core weight for the 150 mg, 300 mg and 450 mg dose EA tablets. In certain embodiments of the 450 mg dosage form, the binder is present in an amount of about 4% by weight of dry core weight.

The uncoated EA core formulation of certain embodiments is an immediate release formulation resulting in approximately 100% dissolution of the bupropion hydrobromide salt within about 1 hour. In at least one embodiment the EA core is a normal release matrix formulation. In certain embodiments the EA core comprises an effective amount of bupropion hydrobromide, a binder (e.g. polyvinyl alcohol), and a lubricant (e.g. glyceryl behenate). However, if necessary, additional inert excipients consistent with the objects of the invention can be added to the core formulation. The additional inert excipients can be added to facilitate the preparation and/or improve patient acceptability of the final EA bupropion hydrobromide salt dosage form as described herein. The additional inert excipients are well known to the skilled artisan and can be found in the relevant literature, for example in the Handbook of Pharmaceutical Excipients. Non-limiting examples of such excipients include spray dried lactose, sorbitol, mannitol, and any cellulose derivative.

In certain embodiments the EA core of the bupropion hydrobromide tablet can be made according to any one of the methods described herein.

In certain embodiments, the granules to be compressed to form the core of the EA tablet are manufactured by the wet granulation process. Wet granulation involves agitation of a powder (the active drug) by convention in the presence of a liquid (the solution binder) followed by drying. For forming the granules, which are to be eventually compressed into the tablet cores, the bupropion hydrobromide salt is first granulated, for example with a solution binder, in a granulator, for example a fluidized bed granulator such as a fluidized bed granulator manufactured by GLATT™ (Germany) or AEROMATIC™ (Switzerland). The binder (e.g. polyvinyl alcohol) is first dissolved or dispersed in a suitable solvent (e.g. water). The solution binder is then top sprayed onto the drug in a granulator (e.g. a fluidized bed granulator). Alternatively, granulation can also be performed in a conventional or high shear mixer. If necessary, the additional inert excipients (e.g. a filler) can be mixed with the bupropion hydrobromide salt prior to the granulation step.

The granules formed are subsequently dried and then sieved prior to blending the granules with the lubricant. In certain embodiments the dried granules are sieved through a 1.4 mm mesh screen. The sieved granules are then blended with the lubricant, and if necessary, any other additional inert excipients, which can improve processing of the EA tablets. Blending of the granules with the lubricant, and if necessary, any additional inert excipients, such as for example a glidant, can be performed in a V-blender or any other suitable blending apparatus. Glidants can improve the flowability of the powder. This for example, can be helpful during tablet production at high production speeds and during direct compaction. However, because the requirement for adequate flow is high, a glidant is often also added to a granulation before tabletting. The blended granules are subsequently pressed into tablets and are hereinafter referred to as tablet cores. Tablet cores can be obtained by the use of standard techniques and equipment well known to the skilled artisan. In certain embodiments the tablet cores are obtained by a rotary press (also referred to as a multi-station press) fitted with suitable punches.

The granules can also be manufactured by using other processes known to the skilled artisan. Examples of other granule manufacturing processes include dry granulation (e.g. slugging, roller compaction), direct compression, extrusion, spheronization, melt granulation, and rotary granulation.

An example of the granulation process for the EA cores (60 kg batch) is as follows: A Fluid Bed Processor is used for granulation in order to agglomerate the particles of the materials to obtain a uniform particle size for the final blend. The granulating solution is prepared by dissolving the binder (e.g. polyvinyl alcohol) in hot purified water while mixing. The percent solids content can be adjusted to obtain a viscosity to control the build up (agglomeration size) of the material. A lower viscosity leads to smaller particles, and a higher viscosity leads to larger particles. In addition, the application rate (e.g. from about 150 gm/min to about 250 gm/min; or about 200 gm/min), position of Spray gun (e.g. center position) and nozzle size (e.g. from about 0.5 mm to about 2 mm; or about 1 mm) and atomization pressure (e.g. from about 20 psi to about 40 psi; or about 30 psi) contribute further to control particle size. The active material is fluidized and heated (e.g. from about 35° C. to about 45° C.; or about 40° C.) prior to start of solution application. During the spray cycle, the bed temperature (e.g. from about 35° C. to about 45° C.; or about 40° C.) is kept at a constant temperature to avoid over-wetting. Once all the required binder solution is applied, the material is further dried to the targeted LOD value (i.e. loss on drying) (e.g. below about 1%) prior to unloading. The amount of binder (e.g. polyvinyl alcohol) is from about 2% to about 6%, and in some cases about 3%; and the solution concentration is from about 3% to about 7%, and in some cases about 4.5%. The time of agglomeration process for the 60 kg batch is from about 45 minutes to about 220 minutes, and in some cases about 150 minutes. Once the granulate is dry, material is passed through a 1.4 and 2.00 mm screen to remove any oversized particles. The oversize particles are passed through the mill to reduce oversize particles. Oversized particles generally are present so as to not exceed about 5% of total yield. The screened and milled materials are placed into a shell blender (e.g. V-Blender, Bin blender) and the lubricant (e.g. glyceryl behenate) is added. The lubricant is screened and added to the granules and blended at the predetermined number of revolutions or time (e.g. mix time of about 5 min to about 15 min, and in some cases about 10 min). The percent lubricant is from about 0.5% to about 4%, and in some cases about 2%. The level of lubrication is established for sufficient coverage of either larger or smaller particle size distribution. Additional characteristics include bulk density (e.g. from about 0.3 gm/ml to about 0.8 gm/ml, and in some cases about 0.5 gm/ml), and moisture content (e.g. not more than about 1%). Particle size and flow of final blend are factors in obtaining uniform fill of cavities on a rotary press. The flow and top rotation speed of the press are adjusted (dependant on the type/size of press) so as to not jeopardize the weight uniformity of individual tablets. The product blend is passed through a hopper into a feed frame to fill the die cavities passing under the feed frame. Weight adjustments are made to keep the weight within the specified range, and adjustments made to the pressure settings to obtain the required hardness. Some components monitored for the tablets are tablet thickness and friability (e.g. less than about 0.5%). Suitable thickness (related to overall surface area) and lower friability help reduce core damage and loss of active during coating. Tablet samples are removed at predetermined intervals to monitor specifications.

The EA Tablet Coating

The EA tablet cores can be coated in one stage. The EA coating is applied directly onto the surface of the tablet cores and functions to control the release of the bupropion hydrobromide salt.

The EA coating is a semi-permeable coat comprising a water-insoluble, water-permeable film-forming polymer, a water-soluble polymer, and optionally a plasticizer.

Non-limiting examples of water-insoluble, water-permeable film-forming polymers useful for the EA coating include cellulose ethers, cellulose esters, polyvinyl alcohol and mixtures thereof, In certain embodiments, the water-insoluble, water-permeable film forming polymers are the ethyl celluloses, and can be selected from the following: ethyl cellulose grades PR100, PR45PR20, PR10 and PR7 (ETHOCEL®, Dow) and combinations thereof. In at least one embodiment ethyl cellulose grade PR 100 is the water-insoluble, water-permeable film-forming polymer. The amount of the water-insoluble water-permeable film-forming polymer can vary from about 1% to about 8% by weight of the tablet dry weight. For example, in certain embodiments the amount of the water-insoluble water-permeable film-forming polymer is from about 2% to about 6% by weight of the tablet dry weight. For certain embodiments of the 150 mg, 300 mg or 450 mg dose EA tablets of certain embodiments of the invention, the amount of water-insoluble water permeable film-forming polymer is from about 1% to about 15% by weight of the tablet dry weight. For example, in certain embodiments of the 150 mg dose EA tablets, the amount of the water-insoluble water-permeable film-forming polymer is present at about 10.5% by weight of the tablet dry weight. With respect to the EA coat itself, the amount of water-insoluble water-permeable film-forming polymer in certain embodiments of the 150 mg dose EA tablets is from about 35% to about 60% by weight of the EA coat dry weight. For example, in certain embodiments of the 150 mg dose EA tablet, the amount of water-insoluble water-permeable polymer is present at about 55% by weight of the EA coat dry weight. For certain embodiments of the 300 mg dose EA tablet of the invention, the amount of water-insoluble water-permeable film-forming polymer is from about 1% to about 8% by weight of the tablet dry weight. For example, in certain embodiments of the 300 mg dose EA tablet, the amount of water-insoluble water-permeable film forming polymer is present at about 6.3% by weight of the tablet dry weight. With respect to the EA coat itself, the water-insoluble water-permeable film-forming polymer in the 300 mg dose EA tablet can be present in an amount of about 55% by weight of the EA coat dry weight. For certain embodiments of the 450 mg dose EA tablet of the invention, the amount of water-insoluble water-permeable film-forming polymer is from about 0.5% to about 10% by weight of the tablet dry weight, and in other embodiments is from about 1% to about 6% by weight of the tablet dry weight. With respect to the EA coat itself, the water-insoluble water-permeable film-forming polymer in the 450 mg dose EA tablet can be present in an amount of about 37% by weight of the EA coat dry weight.

In certain embodiments, the EA coat further comprises a plasticizer. Non-limiting examples of plasticizers that can be used in the EA coat described herein include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropioin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, and mixtures thereof. Polyols (e.g. polyethylene glycol) of various molecular weights, and mixtures thereof can also be used. The amount of plasticizer for the EA coat can vary in an amount from about 0.5% to about 4% by weight of the tablet dry weight. In a further embodiment of the invention, when a mixture of two plasticizers is used, the ratio of the two plasticizers can range from about 5:95 to about 95:5. In at least one embodiment of the invention, the plasticizer is polyethylene glycol 4000, dibutyl sebacate, or a mixture thereof. The ratio of polyethylene glycol 4000:dibutyl sebacate can range from about 5:95 to about 95:5. For certain embodiments of the 150 mg dose EA tablet of the invention, the amount of plasticizer present in the EA coat is from about 0.5% to about 4% by weight of the tablet dry weight. For example, in certain embodiments of the 150 mg dose EA tablet, the amount of plasticizer is present at about 3.1% by weight of the tablet dry weight. For certain embodiments of the 300 mg dose EA tablet of the invention, the amount of plasticizer present is from about 0.5% to about 3% by weight of the tablet dry weight. For example, in certain embodiments of the 300 mg dose EA tablet, the amount of plasticizer is present at about 2.0% by weight of the tablet dry weight. For certain embodiments of the 450 mg dose EA tablet of the invention, the amount of plasticizer present is from about 0.5% to about 4% by weight of the tablet dry weight. For certain embodiments of the 150 mg, 300 mg and 450 mg dosage forms, the plasticizer is present in an amount of from about 6% to about 30% by weight of the EA coat dry weight. For example, in certain embodiments the amount of plasticizer is present at about 17% by weight of the EA coat dry weight Non-limiting examples of water-soluble polymers useful for the EA coat include polyvinylpyrrolidone, hydroxypropyl methylcellulose, hydroxypropyl cellulose and mixtures thereof. In at least one embodiment of the invention, the water-soluble polymer is polyvinylpyrrolidone (e.g. Povidone® USP) the amount of which can vary from about 1.5% to about 10% by weight of the tablet dry weight. With respect to the EA coat itself, the amount of water-soluble polymer present can vary from about 20% to about 50% by weight of the EA coat dry weight. For certain embodiments of the 150 mg dose of the EA tablet of the invention, the amount of water-soluble polymer present is from about 1.5% to about 10% by weight of the tablet dry weight or from about 20% to about 50% by weight of the EA coat dry weight. For example, in certain embodiments of the 150 mg dose EA tablet, the water-soluble polymer is present in an amount of about 28% by weight of the EA coat dry weight. For certain embodiments of the 300 mg dose of the EA tablet of the invention, the amount of water-soluble polymer present is from about 1.5% to about 10% of the tablet dry weight and from about 20% to about 50% by weight of the EA coat dry weight. For example, in certain embodiments of the 300 mg dose EA tablet, the water-soluble polymer is present in an amount of about 28% by weight of the EA coat dry weight. For certain embodiments of the 450 mg dose of the EA tablet of the invention, the amount of water-soluble polymer present is from about 2% to about 5% of the tablet dry weight and from about 40% to about 50% by weight of the EA coat dry weight.

The ratio of water-insoluble water-permeable film forming polymer:plasticizer:water-soluble polymer for the EA tablet coating typically will vary from about 3:1:4 to about 5:1:2. For example in certain embodiments the ratio of water-insoluble water-permeable film forming polymer:plasticizer:water-soluble polymer for the EA tablet coating is about 4:1:3. In at least one embodiment of the EA tablet coating, the ratio of the water-insoluble water-impermeable film-forming polymer:plasticizer:water-soluble polymer is from about 7:2:6 to about 19:5:18, and in another embodiment is about 13:4:12. In at least one embodiment of the 450 mg dosage form, the ratio of water-insoluble water-permeable film forming polymer:plasticizer:water-soluble polymer for the EA coating is about 13:6:16.

In certain embodiments the EA coat of the bupropion hydrobromide dosage form can be made according to any one of the methods described herein.

Preparation and application of the EA coat can be as follows. The water-insoluble water-permeable film-forming polymer, (e.g. ethylcellulose), and the plasticizer (e.g. polyethylene glycol 4000, dibutyl sebacate, or a mixture thereof), are dissolved in an organic solvent (e.g. ethyl alcohol). The water-soluble polymer (e.g. polyvinyl pyrrolidone) is next added until a homogenous mixture is achieved. The resulting coat solution is then sprayed onto the tablet cores using a tablet coater, fluidized bed apparatus or any other suitable coating apparatus known in the art until the desired weight gain is achieved. The tablet cores coated with the EA coat are subsequently dried before an optional moisture barrier is applied.

The skilled artisan will appreciate that controlling the permeability can control the release of the bupropion hydrobromide salt and/or the amount of coating applied to the tablet cores. The permeability of the EA coat can be altered by varying the ratio of the water-insoluble, water-permeable film-forming polymer:plasticizer:water-soluble polymer and/or the quantity of coating applied to the tablet core. A more extended release can be obtained with a higher amount of water-insoluble, water-permeable film forming polymer. The addition of other excipients to the tablet core can also alter the permeability of the EA coat. For example, if it is desired that the tablet core further comprise an expanding agent, the amount of plasticizer in the coat should be increased to make the coat more pliable as the pressure exerted on a less pliable coat by the expanding agent could rupture the coat. Further, the proportion of the water-insoluble water-permeable film forming polymer and water-soluble polymer may also have to be altered depending on whether a faster or slower dissolution and/or release profile is desired.

Depending on the dissolution or in-vivo release profile desired, the weight gained after coating the tablet core with the EA coat can vary from about 3% to about 30% of the weight of the dry tablet core. For certain embodiments of the 150 mg dose EA tablet of the invention the weight gain is from about 8% to about 20% of the weight of the dry tablet core. For example, in certain embodiments of the 150 mg dose EA tablet, the weight gain is about 14% of the weight of the dry tablet core. For certain embodiments of the 300 mg dose EA tablet of the invention the weight gain is from about 10% to about 15% of the weight of the dry tablet core. For example, in certain embodiments of the 300 mg dose EA tablet, the weight gain is about 13% of the weight of the dry tablet core. For certain embodiments of the 450 mg dose EA tablet of the invention the weight gain is from about 5% to about 15% of the weight of the dry tablet core. For example, in certain embodiments of the 450 mg dose EA tablet, the weight gain is about 8.5% of the weight of the dry tablet core.

The EA tablet provides an enhanced-absorption of the bupropion hydrobromide salt wherein typically no pore forming agent is present in the formulation. An enhanced absorption bupropion hydrobromide formulation is provided such that after about 2 hours, not more than about 25% of the bupropion hydrobromide content is released. For example, in certain embodiments from about 10% to about 20% of the bupropion hydrobromide content is released after about 2 hours. After about 4 hours, from about 25% to about 55% of the bupropion hydrobromide content is released. For example, in certain embodiments from about 30% to about 50% of the bupropion hydrobromide content is released after about 4 hours. After about 8 hours, more than about 60% of the bupropion hydrobromide content is released. For example, in certain embodiments from about 70% to about 90% of the bupropion hydrobromide content is released after about 8 hours. After about 16 hours more than about 70% of the bupropion hydrobromide content is released. For example, in certain embodiments more than about 80% of the bupropion hydrobromide content is released after about 16 hours.

In certain embodiments an enhanced absorption formulation is provided wherein not more than about 40% is released after about 2 hours; after about 4 hours from about 40% to about 75% is released; after about 8 hours at least about 75% is released; and after about 16 hours at least about 85% is released. For example, in at least one embodiment, the bupropion hydrobromide release profile is about 33% after about 2 hours; about 59% after about 4 hours; about 91% after about 8 hours; and about 97% after about 16 hours.

Controlled Release Matrix

In other embodiments of the present invention, a controlled release matrix is provided from which the kinetics of drug release from the matrix core are dependent at least in part upon the diffusion and/or erosion properties of excipients within the composition. In this embodiment controlled release matrices contain an effective amount of a bupropion hydrobromide salt and at least one pharmaceutically acceptable excipient. The amount of the bupropion hydrobromide salt present in the controlled release matrix can vary in an amount of from about 40% to about 90% by weight of the matrix tablet dry weight. For example, in certain embodiments bupropion hydrobromide is present in an amount from about 60% to about 80%, and in other embodiment at about 70% by weight of the matrix tablet dry weight. The controlled release matrix can be multiparticulate or uniparticulate, and can be coated with at least one functional or non-functional coating, or an immediate release coating containing another drug. Functional coatings include by way of example controlled release polymeric coatings, enteric polymeric coatings, and the like. Non-functional coatings are coatings that do not affect drug release but which affect other properties (e.g., they can enhance the chemical, biological, or the physical appearance of the controlled release formulation). Those skilled in the pharmaceutical art and the design of medicaments are well aware of controlled release matrices conventionally used in oral pharmaceutical compositions adopted for controlled release and means for their preparation.

Suitable excipient materials for use in such controlled release matrices include, by way of example, release-resistant or controlled release materials such as hydrophobic polymers, hydrophilic polymers, lipophilic materials and mixtures thereof. Non-limiting examples of hydrophobic, or lipophilic components include glyceryl monostearate, mixtures of glyceryl monostearate and glyceryl monopalmitate (MYVAPLEX™, Eastman Fine Chemical Company), glycerylmonooleate, a mixture of mono, di and tri-glycerides (ATMUL™ 84S), glycerylmonolaurate, paraffin, white wax, long chain carboxylic acids, long chain carboxylic acid esters, long chain carboxylic acid alcohols, and mixtures thereof. The long chain carboxylic acids can contain from about 6 to about 30 carbon atoms; in certain embodiments at least about 12 carbon atoms, and in other embodiments from about 12 to about 22 carbon atoms. In some embodiments this carbon chain is fully saturated and unbranched, while others contain one or more double bonds. In at least one embodiment the long chain carboxylic acids contain about 3-carbon rings or hydroxyl groups. Non-limiting examples of saturated straight chain acids include n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid, melissic acid and mixtures thereof. Also useful are unsaturated monoolefinic straight chain monocarboxylic acids. Non-limiting examples of these include oleic acid, gadoleic acid, erucic acid and mixtures thereof. Also useful are unsaturated (polyolefinic) straight chain monocaboxyic acids. Non-limiting examples of these include linoleic acid, linolenic acid, arachidonic acid, behenolic acid and mixtures thereof. Useful branched acids include, for example, diacetyl tartaric acid. Non-limiting examples of long chain carboxylic acid esters include glyceryl monostearates; glyceryl monopalmitates; mixtures of glyceryl monostearate and glyceryl monopalmitate (MYVAPLEX™ 600, Eastman Fine Chemical Company); glyceryl monolinoleate; glyceryl monooleate; mixtures of glyceryl monopalmitate, glyceryl monostearate glyceryl monooleate and glyceryl monolinoleate (MYVEROL™ 18-92, Eastman Fine Chemical Company); glyceryl monolinolenate; glyceryl monogadoleate; mixtures of glyceryl monopalmitate, glyceryl monostearate, glyceryl monooleate, glyceryl monolinoleate, glyceryl monolinolenate and glyceryl monogadoleate (MYVEROL™ 18-99, Eastman Fine Chemical Company); acetylated glycerides such as distilled acetylated monoglycerides (MYVACET™ 5-07, 7-07 and 9-45, Eastman Fine Chemical Company); mixtures of propylene glycol monoesters, distilled monoglycerides, sodium stearoyl lactylate and silicon dioxide (MYVATEX™ TL, Eastman Fine Chemical Company); mixtures of propylene glycol monoesters, distilled monoglycerides, sodium stearoyl lactylate and silicon dioxide (MYVATEX™ TL, Eastman Fine Chemical Company) d-alpha tocopherol polyethylene glycol 1000 succinate (Vitamin E TPGS, Eastman Chemical Company); mixtures of mono- and diglyceride esters such as ATMUL™ (Humko Chemical Division of Witco Chemical); calcium stearoyl lactylate; ethoxylated mono- and di-glycerides; lactated mono- and di-glycerides; lactylate carboxylic acid ester of glycerol and propylene glycol; lactylic esters of long chain carboxylic acids; polyglycerol esters of long chain carboxylic acids, propylene glycol mono- and di-esters of long chain carboxylic acids; sodium stearoyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; cetearyl octanoate; C10-C30 cholesterol/lavosterol esters; sucrose long chain carboxylic acid esters; and mixtures thereof.

The alcohols useful as excipient materials for controlled release matrices can include the hydroxyl forms of the carboxylic acids exemplified above and also cetearyl alcohol.

In addition, waxes can be useful alone or in combination with the materials listed above, as excipient materials for the controlled release matrix embodiments of the present invention. Non-limiting examples of these include white wax, paraffin, microcrystalline wax, carnauba wax, and mixtures thereof.

The lipophilic agent can be present in an amount of from about 5% to about 90% by weight of the controlled release matrix dosage form. For example, in certain embodiments the lipophilic agent is present in an amount of from about 10% to about 85%, and in other embodiments from about 30% to about 60% by weight of the controlled release matrix dosage form.

Non-limiting examples of hydrophilic polymers that can be used in certain embodiments of the controlled release matrix dosage form include hydroxypropylmethylcellulose (HPMC), hydroxypropylcellulose (HPC), hydroxyethylcellulose (HEC), carboxymethylcellulose (CMC) or other cellulose ethers, polyoxyethylene, alginic acid, acrylic acid derivatives such as polyacrylic acid, CARBOPOL™ (B.F. Goodrich, Cleveland, Ohio), polymethacrylate polymer such as EUDRAGIT® RL, RS, R, S, NE and E (Rhome Pharma, Darmstadt, Germany), acrylic acid polymer, methacrylic acid polymer, hydroyethyl methacrylic acid (HEMA) polymer, hydroxymethyl methacrylic acid (HMMA) polymer, polyvinyl alcohols and mixtures thereof.

The hydrophilic polymer can be present in an amount of from about 10% to about 90% by weight of the controlled release matrix dosage form. For example, in certain embodiments the hydrophilic polymer is present in an amount of from about 20% to about 75%, and in other embodiments from about 30% to about 60% by weight of the controlled release matrix dosage form.

In at least one embodiment, the controlled release matrix dosage form comprises hydroxypropylmethylcellulose (HPMC). HPMC is an anhydroglucose in which some of the hydroxyl groups are substituted with methyl groups to form methyl ether moieties, and others are substituted with hydroxypropyl groups or with methoxypropyl groups to form hydroxypropyl ether or methoxypropyl ether moieties. Non-limiting examples of hydroxypropyl methylcelluloses that are commercially available include METHOCEL® E (USP type 2910), METHOCEL® F (USP type 2906), METHOCEL® J (USP type 1828), METHOCEL® K (USP type 2201), and METHOCEL® 310 Series, products of The Dow Chemical Company, Midland, Mich., USA. The average degree of methoxyl substitution in these products can range from about 1.3 to about 1.9 (of the three positions on each unit of the cellulose polymer that are available for substitution) while the average degree of hydroxypropyl substitution per unit expressed in molar terms can range from about 0.13 to about 0.82. The dosage form can comprise the different HPMC grades having different viscosities. The size of a HPMC polymer is expressed not as molecular weight but instead in terms of its viscosity as about a 2% solution by weight in water. Different HPMC grades can be combined to achieve the desired viscosity characteristics. For example, the at least one pharmaceutically acceptable polymer can comprise two HPMC polymers such as for example METHOCEL® K3LV (which has a viscosity of about 3 cps) and METHOCEL® K100M CR (which has a viscosity of about 100,000 cps). In addition, the polymer can comprise two hydroxypropylcellulose forms such as KLUCEL® LF and KLUCEL® EF. In addition, the at least one polymer can comprise a mixture of a KLUCEL® and a METHOCEL®.

In at least one embodiment the controlled release matrix dosage form comprises a polyethylene oxide (PEO). PEO is a linear polymer of unsubstituted ethylene oxide. In certain embodiments poly(ethylene oxide) polymers having viscosity-average molecular weights of about 100,000 Daltons and higher are used. Non-limiting examples of poly(ethylene oxide)s that are commercially available include: POLYOX® NF, grade WSR Coagulant, molecular weight 5 million; POLYOX® grade WSR 301, molecular weight 4 million; POLYOX® grade WSR 303, molecular weight 7 million; POLYOX® grade WSR N-60K, molecular weight 2 million; and mixtures thereof. These particular polymers are products of Dow Chemical Company, Midland, Mich., USA. Other examples of polyethylene oxides exist and can likewise be used. The required molecular weight for the PEO can be obtained by mixing PEO of differing molecular weights that are available commercially.

In at least one embodiment of the controlled release matrix dosage form, PEO and HPMC are combined within the same controlled release matrix. In certain embodiments, the poly(ethylene oxide)s have molecular weights ranging from about 2,000,000 to about 10,000,000 Da. For example, in at least one embodiment the polyethylene oxides have molecular weights ranging from about 4,000,000 to about 7,000,000 Da. In certain embodiments the HPMC polymers have a viscosity within the range of about 4,000 centipoises to about 200,000 centipoises. For example, in at least one embodiment the HPMC polymers have a viscosity of from about 50,000 centipoises to about 200,000 centipoises, and in other embodiments from about 80,000 centipoises to about 120,000 centipoises. The relative amounts of PEO and HPMC within the controlled release matrix can vary within the scope of the invention. In at least one embodiment the PEO:HPMC weight ratio is from about 1:3 to about 3:1. For example, in certain embodiments the PEO:HPMC weight ratio is from about 1:2 to about 2:1. As for the total amount of polymer relative to the entire matrix, this can vary as well and can depend on the desired drug loading. In at least one embodiment the total amount of polymer in the matrix can constitute from about 15% to about 90% by weight of the matrix dosage form. For example, in certain embodiments the total amount of polymer in the matrix is from about 20% to about 75%, in other embodiments from about 30% to about 60%, and in still other embodiments from about 10% to about 20% by weight of the matrix dosage form.

In at least one embodiment of the invention the controlled release matrix dosage form comprises a hydrophobic polymer such as ethylcellulose. The viscosity of ethylcellulose can be selected in order to influence of rate the drug release. In certain embodiments the ethylcellulose has a viscosity from about 7 to about 100 cP (when measured as a 5% solution at 25° C. in an Ubbelohde viscometer, using a 80:20 toluene:ethanol solvent.) In certain embodiments the hydrophobic polymer can constitute from about 10% to about 90% by weight of the matrix dosage form. For example, in at least one embodiment the hydrophobic polymer constitutes from about 20% to about 75%, and in other embodiments from about 30% to about 60% by weight of the matrix dosage form.

In at least one embodiment of the invention the controlled release matrix dosage form comprises at least one binder. In certain embodiments the binder is water-insoluble. Examples of binders include hydrogenated vegetable oil, castor oil, paraffin, higher aliphatic alcohols, higher aliphatic acids, long chain fatty acids, fatty acid esters, wax-like materials such as fatty alcohols, fatty acid esters, fatty acid glycerides, hydrogenated fats, hydrocarbons, normal waxes, stearic acid, stearyl alcohol, hydrophobic and hydrophilic polymers having hydrocarbon backbones, and mixtures thereof. Non-limiting examples of water-soluble polymer binders include modified starch, gelatin, polyvinylpyrrolidone, cellulose derivatives (such as for example hydroxypropyl methylcellulose (HPMC) and hydroxypropyl cellulose (HPC)), polyvinyl alcohol and mixtures thereof. In at least one embodiment, the binder can be present in an amount of from about 0.1% to about 20% by weight of the matrix dosage form. For example, in certain embodiments the binder is present in an amount of from about 0.5% to about 15%, and in other embodiments from about 2% to about 10% by weight of the matrix dosage form.

In at least one embodiment of the invention the controlled release matrix dosage form comprises at least one lubricant. Non-limiting examples of lubricants include stearic acid, hydrogenated vegetable oils (such as hydrogenated cottonseed oil (Sterotex®), hydrogenated soybean oil (STEROTEX® HM) and hydrogenated soybean oil & castor wax (STEROTEX® K)) stearyl alcohol, leucine, polyethylene glycol (MW 1450, suitably 4000, and higher), magnesium stearate, glyceryl monostearate, stearic acid, glycerylbehenate, polyethylene glycol, ethylene oxide polymers (for example, available under the registered trademark CARBOWAX® from Union Carbide, Inc., Danbury, Conn.), sodium lauryl sulfate, magnesium lauryl sulfate, sodium oleate, sodium stearyl fumarate, DL-leucine, colloidal silica, and mixtures thereof. The lubricant can be present in an amount of from about 0 to about 4% by weight of the compressed uncoated matrix. For example, in certain embodiments the lubricant is present in an amount of from about 0% to about 2.5% by weight of the compressed, uncoated matrix.

In at least one embodiment of the invention the controlled release matrix dosage form comprises a plasticizer. Non-limiting examples of plasticizers include dibutyl sebacate, diethyl phthalate, triethyl citrate, tributyl citrate, triacetin, citric acid esters such as triethyl citrate NF XVI, tributyl citrate, dibutyl phthalate, 1,2-propylene glycol, polyethylene glycols, propylene glycol, diethyl phthalate, castor oil, acetylated monoglycerides, phthalate esters, and mixtures thereof. In at least one embodiment, the plasticizer can be present in an amount of from about 1% to about 70% by weight of the controlled release polymer in the matrix dosage form. For example, in certain embodiments the plasticizer is present in an amount of from about 5% to about 50%, and in other embodiments from about 10% to about 40% by weight of the controlled release polymer in the matrix dosage form.

In at least one embodiment of the invention the controlled release matrix dosage form comprises at least one diluent, non-limiting examples of which include dicalcium phosphate, calcium sulfate, lactose or sucrose or other disaccharides, cellulose, cellulose derivatives, kaolin, mannitol, dry starch, glucose or other monosaccharides, dextrin or other polysaccharides, sorbitol, inositol, sucralfate, calcium hydroxyl-apatite, calcium phosphates, fatty acid salts such as magnesium stearate, and mixtures thereof. In certain embodiments the diluent can be added in an amount so that the combination of the diluent and the active substance comprises up to about 60%, and in other embodiments up to about 50%, by weight of the composition.

In at least one embodiment of the invention the controlled release matrix dosage form comprises a solubilizer. The solubilizer can act to increase the instantaneous solubility of the bupropion salt. The solubilizer can be selected from hydrophilic surfactants or lipophilic surfactants or mixtures thereof. The surfactants can be anionic, nonionic, cationic, and zwitterionic surfactants. The hydrophilic non-ionic surfactants can be selected from the group comprised of, but not limited to: polyethylene glycol sorbitan fatty acid esters and hydrophilic transesterification products of a polyol with at least one member of the group from triglycerides, vegetable oils, and hydrogenated vegetable oils such as glycerol, ethylene glycol, polyethylene glycol, sorbitol, propylene glycol, pentaerythritol, or a saccharide, d-α-tocopheryl polyethylene glycol 1000 succinate. The ionic surfactants can be selected from the group comprised of, but not limited to: alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof. The lipophilic surfactants can be selected from the group comprised of, but not limited to: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group from glycerides, vegetable oils, hydrogenated vegetable oils, fatty acids and sterols; oil-soluble vitamins/vitamin derivatives; PEG sorbitan fatty acid esters, PEG glycerol fatty acid esters, polyglycerized fatty acid, polyoxyethylene-polyoxypropylene block copolymers, sorbitan fatty acid esters; and mixtures thereof. In at least one embodiment the solubilizer can be selected from: PEG-20-glyceryl stearate (CAPMUL® by Abitec), PEG-40 hydrogenated castor oil (CREMOPHOR RH 40® by BASF), PEG 6 corn oil (LABRAFIL® by Gattefosse), lauryl macrogol-32 glyceride (GELUCIRE44/14® by Gattefosse) stearoyl macrogol glyceride (GELUCIRE50/13® by Gattefosse), polyglyceryl-10 mono dioleate (CAPROL® PEG860 by Abitec), propylene glycol oleate (LUTROL® by BASF), Propylene glycol dioctanoate (CAPTEX® by Abitec), Propylene glycol caprylate/caprate (LABRAFAC® by Gattefosse), Glyceryl monooleate (PECEOL® by Gattefrosse), Glycerol monolinoleate (MAISINE® by Gattefosse), Glycerol monostearate (CAPMUL® by Abitec), PEG-20 sorbitan monolaurate (TWEEN20® by ICI), PEG-4 lauryl ether (BRIJ30® by ICI), Sucrose distearate (SUCROESTER7® by Gattefosse), Sucrose monopalmitate (SUCROESTER15® by Gattefosse), polyoxyethylene-polyoxypropylene block copolymer (LUTROL® series BASF), polyethylene glycol 660 hydroxystearate, (SOLUTOL® by BASF), Sodium lauryl sulfate, Sodium dodecyl sulphate, Dioctyl suphosuccinate, L-hydroxypropyl cellulose, hydroxyethylcellulose, hydroxylpropylcellulose, Propylene glycol alginate, sodium taurocholate, sodium glycocholate, sodium deoxycholate, betains, polyethylene glycol (CARBOWAX® by DOW), d-α-tocopheryl polyethylene glycol 1000 succinate, (Vitamin E TPGS® by Eastman), and mixtures thereof. In at least one other embodiment the solubilizer can be selected from PEG-40 hydrogenated castor oil (CREMOPHOR RH 40® by BASF), lauryl macrogol-32 glyceride (GELUCIRE44/14® by Gattefosse) stearoyl macrogol glyceride (GELUCIRE 50/13® by Gattefosse), PEG-20 sorbitan monolaurate (TWEEN 20® by ICI), PEG-4 lauryl ether (BRIJ30® by ICI), polyoxyethylene-polyoxypropylene block copolymer (LUTROL® series BASF), Sodium lauryl sulphate, Sodium dodecyl sulphate, polyethylene glycol (CARBOWAX® by DOW), and mixtures thereof.

In at least one embodiment of the invention the controlled release matrix dosage form comprises a swelling enhancer. Swelling enhancers are members of a category of excipients that swell rapidly to a large extent resulting in an increase in the size of the tablet. At lower concentrations, these excipients can be used as superdisintegrants; however at concentrations above 5% w/w these agents can function as swelling enhancers and help increase the size of the matrix dosage form. According to certain embodiments of the matrix dosage forms of the invention, examples of swelling enhancers include but are not limited to: low-substituted hydroxypropyl cellulose, microcrystalline cellulose, cross-linked sodium or calcium carboxymethyl cellulose, cellulose fiber, cross-linked polyvinyl pyrrolidone, cross-linked polyacrylic acid, cross-linked Amberlite resin, alginates, colloidal magnesium-aluminum silicate, corn starch granules, rice starch granules, potato starch granules, pregelatinised starch, sodium carboxymethyl starch and mixtures thereof. In at least one embodiment of the matrix dosage forms, the swelling enhancer is cross-linked polyvinyl pyrrolidone. The content of the swelling enhancer can be from about 5% to about 90% by weight of the matrix dosage form. For example, in certain embodiments the swelling enhancer is present in an amount of from about 10% to about 70%, and in other embodiments from about 15% to about 50% by weight of the matrix dosage form.

In at least one embodiment of the invention the controlled release matrix dosage form comprises additives for allowing water to penetrate into the core of the preparation (hereinafter referred to as "hydrophilic base"). In certain embodiments, the amount of water required to dissolve 1 g of the hydrophilic base is not more than about 5 ml, and in other embodiments is not more than about 4 ml at the temperature of about 20° C.±5° C. The higher the solubility of the hydrophilic base in water, the more effective is the base in allowing water into the core of the preparation. The hydrophilic base includes, inter alia, hydrophilic polymers such as polyethylene glycol (PEG); (e.g. PEG400, PEG1500, PEG4000, PEG6000 and PEG20000, produced by Nippon Oils and Fats Co.) and polyvinylpyrrolidone (PVP); (e.g. PVP K30, of BASF), sugar alcohols such as D-sorbitol, xylitol, or the like, sugars such as sucrose, anhydrous maltose, D-fructose, dextran (e.g. dextran 40), glucose or the like, surfactants such as polyoxyethylene-hydrogenated castor oil (HCO; e.g. CREMOPHOR™ RH40 produced by BASF, HCO-40 and HCO-60 produced by Nikko Chemicals Co.), polyoxyethylene-polyoxypropylene glycol (e.g. Pluronic F68 produced by Asahi Denka Kogyo K. K.), polyoxyethylene-sorbitan high molecular fatty acid ester (TWEEN™; e.g. TWEEN™ 80 produced by Kanto Kagaku K. K.), or the like; salts such as sodium chloride, magnesium chloride., or the like; organic acids such as citric acid, tartaric acid., or the like; amino acids such as glycine, β-alanine, lysine hydrochloride, or the like; and amino sugars such as meglumine. In at least one embodiment the hydrophilic base is PEG6000, PVP, D-sorbitol, or mixtures thereof.

In another embodiment of the invention the controlled release matrix dosage form comprises at least one disintegrant. Non-limiting examples of disintegrants for use in the matrix dosage form include croscarmellose sodium, crospovidone, alginic acid, sodium alginate, methacrylic acid DVB, cross-linked PVP, microcrystalline cellulose, polacrilin potassium, sodium starch glycolate, starch, pregelatinized starch and mixtures thereof. In at least one embodiment the disintegrant is selected from cross-linked polyvinylpyrrolidone (e.g. KOLLIDON® CL), cross-linked sodium carboxymethylcellulose (e.g. AC-DI-SOL™), starch or starch derivatives such as sodium starch glycolate (e.g. EXPLOTAB®), or combinations with starch (e.g. PRIMOJEL™), swellable ion-exchange resins, such as AMBERLITE™ IRP 88, formaldehyde-casein (e.g. ESMA SPRENG™), and mixtures thereof. In at least one embodiment the disintegrant is sodium starch glycolate. The disintegrant can be present in certain embodiments in an amount of from about 0% to about 20% of the total weight of the matrix.

The controlled release matrices of the present invention can further contain one or more pharmaceutically acceptable excipients such as granulating aids or agents, colorants, flavorants, pH adjusters, anti-adherents, glidants and like excipients conventionally used in pharmaceutical compositions.

In at least one embodiment of the invention comprising water swellable polymers formulated into the matrix, the release kinetics of the bupropion hydrobromide salt from the matrix are dependent upon the relative magnitude of the rate of polymer swelling at the moving rubbery/glassy front and the rate of polymer erosion at the swollen polymer/dissolution medium front. The release kinetics for the release of the bupropion hydrobromide salt from the matrix can be approximated by the following equation:

$$Mt/MT = kt^n$$

where t is time,

Mt is the amount of the pharmaceutical agent which has been released at time t,

MT is the total amount of the pharmaceutical agent contained in the matrix, k is a constant, and n is the release kinetics exponent This equation is valid so long as n remains nearly constant. When n is equal to one, the release of the pharmaceutical agent from the matrix has zero-order kinetics. The amount of pharmaceutical agent released is then directly proportional to the time.

Where the swelling process of the polymer chosen for the excipient is the primary process controlling the drug release (compared to erosion of the swollen polymer), non-zero order release kinetics can result. Generally, these release kinetics dictate a value of n approaching 0.5, leading to square-root Fickian-type release kinetics.

In at least one embodiment of the invention, polymers are selected for inclusion into the formulation to achieve zero order kinetics. The release kinetics of the matrix can also be dictated by the pharmaceutical agent itself. A drug which is highly soluble can tend to be released faster than drugs which have low solubility. Where a drug has high solubility, polymer swelling and erosion takes place rapidly to maintain zero order release kinetics. If the swelling and erosion take place too slowly, the swelling process of the polymer is the primary process controlling the drug release (since the drug will diffuse from the swollen polymer before the polymer erodes). In this situation, non-zero order release kinetics can result. As a result, the administration of a highly soluble pharmaceutical agent requires a relatively rapidly swelling and eroding excipient. To use such a material to produce a matrix which will last for 24 hours can require a large matrix. To overcome this difficulty, a doughnut-shaped matrix with a hole though the middle can be used with a less rapidly swelling and eroding polymer. With such a matrix, the surface area of the matrix increases as the matrix erodes. This exposes more polymer, resulting in more polymer swelling and erosion as the matrix shrinks in size. This type of matrix can also be used with very highly soluble pharmaceutical agents to maintain zero order release kinetics.

In at least one other embodiment of the invention, zero order drug release kinetics can be achieved by controlling the surface area of the matrix dosage form that is exposed to erosion. When water is allowed to diffuse into a polymer matrix composition zero order release is obtained when the release rate is governed or controlled by erosion of a constant surface area per time unit. In order to ensure that the erosion of the polymer matrix composition is the predominant release mechanism, it is helpful to provide a polymer matrix composition which has properties that ensures that the diffusion rate of water into the polymer matrix composition substantially corresponds to the dissolution rate of the polymer matrix composition into the aqueous medium. Thus, by adjusting the nature and amount of constituents in the polymer matrix composition a zero order release mechanism can be achieved. The compositions employed are coated in such a manner that at least one surface is exposed to the aqueous medium and this surface has a substantially constant or controlled surface area during erosion. In the present context controlled surface area relates to a predetermined surface area typically predicted from the shape of the coat of the unit dosage system. It may have a simple uniform cylindrical shape or the cylindrical form can have one or more tapered ends in order to decrease (or increase) the initial release period. Accordingly, these embodiments provide a method for controlling the release of a bupropion salt into an aqueous medium by erosion of at least one surface of a pharmaceutical composition comprising (i) a matrix composition comprising (a) a polymer or a mixture of polymers, (b) a bupropion hydrobromide salt and, optionally, (c) one or more pharmaceutically acceptable excipients, and (ii) a coating having at least one opening exposing at the one surface of said matrix, the coating comprising: (a) a first cellulose derivative which has thermoplastic properties and which is substantially insoluble in the aqueous medium in which the composition is to be used, and at least one of (b) a second cellulose derivative which is soluble or dispersible in water, (c) optionally a plasticizer, or (d) a filler, the method comprising adjusting the concentration and/or the nature of the ingredients making up the matrix composition in such a manner that the diffusion rate of the aqueous medium into the matrix composition corresponds to 100%±30% such as, for example 100%±25%, 100%±20%, 100%±15% or 100%±10%, or 100% of the dissolution rate of the matrix composition so as to obtain a zero order release of at least about 60% w/w such as, for example at least about 65% w/w, at least about 70% w/w, at least about 75% w/w, at least about 80% w/w, at least about 85% w/w, at least about 90% w/w, at least about 95% w/w or at least about 97% to about 98% w/w of the bupropion hydrobromide salt from the pharmaceutical composition when subject to an in-vitro dissolution test.

In at least one other embodiment of the invention, zero order drug release is approached through the use of: (a) a deposit-core comprising the bupropion hydrobromide salt and having defined geometric form, (b) a support-platform applied to said deposit-core, and is characterized in that the deposit-core contains, mixed with the bupropion hydrobromide salt, a polymeric material having a high degree of swelling on contact with water or aqueous liquids, a gellable polymeric material, said polymeric materials being replaceable by a single polymeric material having both swelling and gelling properties, and other adjuvants able to provide the mixture with suitable characteristics for its compression and for its intake of water, said support-platform comprising a polymeric material insoluble in aqueous liquids and partially coating said deposit-core.

These and further characteristics and advantages of the system according to certain embodiments of the matrix dosage form will be more apparent from the description of embodiments of the invention given hereinafter by way of non-limiting example. The deposit-core can generally be obtained by compressing the mixture containing the bupropion hydrobromide salt to a pressure of from about 1000 to about 4000 kg/cm2, to thus assume a defined geometric form. Polymeric materials having a high degree of swelling can generally be cross-linked insoluble polymers, whereas gellable polymeric materials are soluble, and can control the intake of water.

The coating platform comprises a polymeric material insoluble in water and optionally insoluble in biodegradable biological liquids, and able to maintain its impermeability characteristics at least until the complete transfer of the bupropion hydrobromide salt contained in the deposit-core. It is applied to a part of the external deposit-core surface chosen such as to suitably direct and quantitatively regulate the release of the bupropion hydrobromide salt. In this respect, as the support-platform is impermeable to water, the polymeric material of the deposit-core in certain embodiments can swell only in that portion of the deposit not coated with the platform.

The support-platform can be obtained by compressing prechosen polymeric materials onto the deposit-core, by immersing the deposit-core in a solution of said polymeric materials in normal organic solvents, or by spraying said solutions. Polymeric materials usable for preparing the support-platform can be chosen from the class comprising acrylates, celluloses and derivatives such as ethylcellulose, cellulose acetate-propionate, polyethylenes and methacrylates and copolymers of acrylic acid, polyvinylalcohols and mixtures thereof. This platform can have a thickness of from about 2 mm (for example, if applied by compression) to about 10 microns (for example, if applied by spraying or immersion), and comprises from about 10% to about 90% of the total surface of the system.

A factor in controlling the release of the bupropion hydrobromide salt is the intensity and duration of the swelling force developed by the swellable polymeric materials contained in the deposit-core on contact with aqueous fluids. In this respect, the energy for activating, executing and regulating the release of the bupropion hydrobromide salt can be determined by the swelling force developed in the deposit-core when this comes into contact with water or with biological liquids. Said force has an intensity and duration which can vary in relation to the type and quantity of the polymeric materials used in formulating the deposit, and it lies between limits having a maximum value which occurs in the case of a deposit mainly containing the swellable polymer, and a minimum value which occurs in the case of a deposit mainly containing the gellable polymer. Said swellable polymer can be present in an amount of from about 5% to about 80% by weight, and said gellable polymer present in an amount of from about 10% to about 90% by weight, with respect to the mixture forming the deposit-core.

A further control factor is the geometry of the support-platform, which limits the swelling of the deposit and directs the emission of material from it. Within the scope of these embodiments it is possible to conceive many systems for the controlled release of bupropion hydrobromide, which base their operation on the swelling force and differ from each other by the type of support-platform used.

In at least one other embodiment of the invention designed to achieve zero order release of the bupropion hydrobromide salt, the kinetics of drug release from a controlled release matrix is governed by a combination of different polymers with different swelling characteristics. More specifically, the bupropion hydrobromide salt is first granulated with or encapsulated in a less swellable polymer, such as a gum, to form a granule. This granule is disposed in a matrix of a more swellable, erodible polymer. The more swellable erodible polymer has a diffusion rate coefficient which is greater than the diffusion rate coefficient of the relatively less swellable polymer. Averaged over the entire period of drug release, the diffusion rate for the more swellable polymer is greater than the diffusion rate for the less swellable polymer. It is this general difference in rates of diffusion between the first and second polymers which controls the rate of drug release and allows the system to approach zero order drug delivery over the drug release period. In at least one embodiment, pectin and HPMC are present as the more swellable polymers in ratios of from about 2:7 to about 4:5, and gelatin is present as the less swellable polymer.

In at least one other embodiment of the invention there is provided a controlled release matrix composition comprising bupropion hydrobromide incorporated within a homogeneous matrix including effective amounts of at least two polymers having opposing wettability characteristics, wherein at least one polymer is selected which demonstrates a stronger tendency towards hydrophobicity and the other polymer(s) is selected which demonstrates a stronger tendency towards hydrophilicity. In at least one embodiment the polymer demonstrating a stronger tendency towards hydrophobicity is ethylcellulose (EC) whereas the polymer demonstrating a stronger tendency towards hydrophilicity is hydroxyethylcellulose (HEC) and/or hydroxypropyl methylcellulose (HPMC). The composition and device of the present invention can be provided as a matrix and can be optionally encased in a coating material which prevents the burst and/or food effect associated with orally ingested medicaments and imparts gastrointestinal "stealth" characteristics. In accordance with at least one embodiment is a method for preparing a device for the controlled release of the bupropion hydrobromide salt, the method comprising blending bupropion hydrobromide with from about 5% to about 25% by weight of hydrophilic polymer, and from about 1% to about 25% by weight of hydrophobic polymer, adding suitable pharmaceutical excipients, surface active agents and lubricants, granulating the mixture with solvents such as isopropyl alcohol, drying the granular mixture, milling the dried mixture, adding from about 5% to about 70% by weight of ethylcellulose, adding a lubricant and optionally a glidant and compressing the granules into matrices. The matrices are optionally encased in a gastrointestinal encasement or a pharmaceutically acceptable film coat.

In another embodiment of the present invention, a swellable matrix dosage form is provided in which the bupropion hydrobromide salt is dispersed in a polymeric matrix that is water-swellable rather than merely hydrophilic, that has an erosion rate that is substantially slower than its swelling rate, and that releases the bupropion hydrobromide salt primarily by diffusion. The rate of diffusion of the bupropion hydrobromide salt out of the swellable matrix can be slowed by increasing the drug particle size, by the choice of polymer used in the matrix, and/or by the choice of molecular weight of the polymer. The swellable matrix is comprised of a relatively high molecular weight polymer that swells upon ingestion. In at least one embodiment the swellable matrix swells upon ingestion to a size that is at least twice its unswelled volume, and that promotes gastric retention during the fed mode. Upon swelling, the swellable matrix can also convert over a prolonged period of time from a glassy polymer to a polymer that is rubbery in consistency, or from a crystalline polymer to a rubbery one. The penetrating fluid then causes release of the bupropion hydrobromide salt in a gradual and prolonged manner by the process of solution diffusion, i.e., dissolution of the bupropion hydrobromide salt in the penetrating fluid and diffusion of the dissolved bupropion hydrobromide salt back out of the swellable matrix. The swellable matrix itself is solid prior to administration and, once administered, remains undissolved in (i.e., is not eroded by) the gastric fluid for a period of time sufficient to permit the majority of the bupropion hydrobromide salt to be released by the solution diffusion process during the fed mode. The rate-limiting factor in the release of the bupropion hydrobromide salt from the swellable matrix is therefore controlled diffusion of the bupropion hydrobromide salt from the swellable matrix rather than erosion, dissolving or chemical decomposition of the swellable matrix.

As such, the swelling of the polymeric matrix can achieve at least the following objectives: (i) renders the matrix sufficiently large to cause retention in the stomach during the fed mode; (ii) localizes the release of the drug to the stomach and small intestine so that the drug will have its full effect without colonic degradation, inactivation, or loss of bioavailability; (iii) retards the rate of diffusion of the drug long enough to provide multi-hour, controlled delivery of the drug into the stomach.

The bupropion hydrobromide salt in the swellable matrix can be present in an effective amount of from about 0.1% to about 99% by weight of the matrix. For example, in certain embodiments bupropion hydrobromide is present in the swellable matrix in an amount of from about 0.1% to about 90%, in other embodiments from about 5% to about 90%, in still other embodiments from about 10% to about 80%, and in even still other embodiments from about 25% to about 80% by weight of the swellable matrix.

The water-swellable polymer forming the swellable matrix in accordance with these embodiments of the present invention can be any polymer that is non-toxic, that swells in a dimensionally unrestricted manner upon imbibition of water, and that provides for a modified release of the bupropion hydrobromide salt. Non-limiting examples of polymers suitable for use in the swellable matrix include cellulose polymers and their derivatives, such as for example, hydroxyethylcellulose, hydroxypropylcellulose, carboxymethylcellulose, and microcrystalline cellulose, polysaccharides and their derivatives, polyalkylene oxides, polyethylene glycols, chitosan, poly(vinyl alcohol), xanthan gum, maleic anhydride copolymers, poly(vinyl pyrrolidone), starch and starch-based polymers, poly (2-ethyl-2-oxazoline), poly(ethyleneimine), polyurethane hydrogels, and crosslinked polyacrylic acids and their derivatives, and mixtures thereof. Further examples include copolymers of the polymers listed in the preceding sentence, including block copolymers and grafted polymers. Specific examples of copolymers include PLURONIC® and TECTONIC®, which are polyethylene oxide-polypropylene oxide block copolymers available from BASF Corporation, Chemicals Div., Wyandotte, Mich., USA.

The terms "cellulose" and "cellulosic", as used within this section regarding the swellable matrix embodiments of the present invention, can denote a linear polymer of anhydroglucose. Non-limiting examples of cellulosic polymers include alkyl-substituted cellulosic polymers that ultimately dissolve in the gastrointestinal (GI) tract in a predictably delayed manner. In certain embodiments the alkyl-substituted cellulose derivatives are those substituted with alkyl groups of 1 to 3 carbon atoms each. Non-limiting examples include methylcellulose, hydroxymethyl-cellulose, hydroxyethylcellulose, hydroxypropylcellulose, hydroxypropylmethylcellulose, carboxymethylcellulose, and mixtures thereof. In terms of their viscosities, one class of alkyl-substituted celluloses includes those whose viscosity is within the range of about 100 to about 110,000 centipoises as a 2% aqueous solution at 20° C. Another class includes those whose viscosity is within the range of about 1,000 to about 4,000 centipoises as a 1% aqueous solution at 20° C. In certain embodiments the alkyl-substituted celluloses are hydroxyethylcellulose and hydroxypropylmethylcellulose. In at least one embodiment the hydroxyethylcellulose is NATRASOL® 250HX NF (National Formulary), available from Aqualon Company, Wilmington, Del., USA.

Polyalkylene oxides that can be used in certain embodiments of the swellable matrices include those having the properties described above for alkyl-substituted cellulose polymers. In at least one embodiment the polyalkylene oxide is poly(ethylene oxide), which term is used herein to denote a linear polymer of unsubstituted ethylene oxide. In at least one embodiment the poly(ethylene oxide) polymers have molecular weights of about 4,000,000 and higher. For example, in certain embodiment the poly(ethylene oxide) polymers have molecular weights within the range of about 4,500,000 to about 10,000,000, and in other embodiments have molecular weights within the range of about 5,000,000 to about 8,000,000. In certain embodiments the poly(ethylene oxide)s are those with a weight-average molecular weight within the range of about $1\times10^5$ to about $1\times10^7$, and in other embodiments within the range of about $9\times10^5$ to about $8\times10^6$. Poly(ethylene oxide)s are often characterized by their viscosity in solution. For example, in certain embodiments the poly(ethylene oxide)s have a viscosity range of about 50 to about 2,000,000 centipoises for a 2% aqueous solution at 20° C. In at least one embodiment the poly(ethylene oxide) is one or more of POLYOX® NF, grade WSR Coagulant, molecular weight 5 million, and grade WSR 303, molecular weight 7 million, both products of Union Carbide Chemicals and Plastics Company Inc. of Danbury, Conn., USA. Mixtures thereof are operable.

Polysaccharide gums, both natural and modified (semi-synthetic) can be used in the swellable matrix embodiments of the present invention. Non-limiting examples include dextran, xanthan gum, gellan gum, welan gum, rhamsan gum, and mixtures thereof. In at least one embodiment the polysaccharide gum is xanthan gum.

Crosslinked polyacrylic acids that can be used in the swellable matrices of the present invention include those whose properties are the same as those described above for alkyl-substituted cellulose and polyalkylene oxide polymers. In certain embodiments the crosslinked polyacrylic acids are those with a viscosity ranging from about 4,000 to about 40,000 centipoises for a 1% aqueous solution at 25° C. Non-limiting examples of suitable crosslinked polyacrylic acids include CARBOPOL® NF grades 971P, 974P and 934P (BF-Goodrich Co., Specialty Polymers and Chemicals Div., Cleveland, Ohio, USA). Further examples of suitable crosslinked polyacrylic acids include polymers known as WATER LOCK®, which are starch/acrylates/acrylamide copolymers available from Grain Processing Corporation, Muscatine, Iowa, USA.

The hydrophilicity and water swellability of these polymers can cause the drug-containing swellable matrices to swell in size in the gastric cavity due to ingress of water in order to achieve a size that can be retained in the stomach when introduced during the fed mode. These qualities also cause the swellable matrices to become slippery, which provides resistance to peristalsis and further promotes their retention in the stomach. The release rate of drug from the swellable matrix is primarily dependent upon the rate of water imbibition and the rate at which the drug dissolves and diffuses from the swollen polymer, which in turn is related to the drug concentration in the swellable matrix. Also, because these polymers dissolve very slowly in gastric fluid, the swellable matrix maintains its physical integrity over at least a substantial period of time, for example in many cases at least about 90% and in certain embodiments over about 100% of the dosing period. The particles will then slowly dissolve or decompose. Complete dissolution or decomposition may not occur until about 24 hours or more after the intended dosing period ceases, although in most cases, complete dissolution or decomposition will occur within about 10 to about 24 hours after the dosing period.

The amount of polymer relative to the drug can vary, depending on the drug release rate desired and on the polymer, its molecular weight, and excipients that may be present in the formulation. The amount of polymer will typically be sufficient to retain at least about 40% of the drug within the swellable matrix about one hour after ingestion (or immersion in the gastric fluid). In certain embodiments, the amount of polymer is such that at least about 50% of the drug remains in the matrix about one hour after ingestion; in other embodiments at least about 60%, and in still other embodiments at least about 80% of the drug remains in the swellable matrix about one hour after ingestion. In certain embodiments the drug will be substantially all released from the swellable matrix within about 10 hours; and in other embodiments within about 8 hours, after ingestion, and the polymeric matrix will remain substantially intact until all of the drug is released. In other embodiments the amount of polymer will be such that after about 2 hours no more than about 40% is released; after about 4 hours from about 40% to about 75% is released; after about 8 hours at least about 75% is released, and after about 16 hours at least about 85% is released. The term "substantially intact" is used herein to denote a polymeric matrix in which the polymer portion substantially retains its size and shape without deterioration due to becoming solubilized in the gastric fluid or due to breakage into fragments or small particles.

In other exemplary embodiments the swellable matrix after about 2 hours will release no more than about 40% of the bupropion hydrobromide, after about 4 hours from about 40% to about 75%, after about 8 hours at least about 75%, and after about 16 hours at least about 85% of the bupropion hydrobromide.

The water-swellable polymers of the swellable matrices can be used individually or in combination. Certain combinations will often provide a more controlled release of the drug than their components when used individually. Examples include cellulose-based polymers combined with gums, such as hydroxyethyl cellulose or hydroxypropyl cellulose combined with xanthan gum. Another example is poly(ethylene oxide) combined with xanthan gum.

The benefits of certain embodiments of this invention can be achieved over a wide range of drug loadings and polymer levels, with the weight ratio of drug to polymer ranging in general from about 0.01:99.99 to about 80:20, including all values and ranges therebetween. For example, in certain embodiments the drug loadings (expressed in terms of the weight percent of drug relative to total of drug and polymer) are within the range of about 15% to about 80%; in other embodiments within the range of about 30% to about 80%; and in still other embodiments within the range of about 30% to about 70%. In at least one embodiment the drug loading is within the range of about 0.01% to about 80%, and in at least one other embodiment from about 15% to about 80%. In at least one embodiment the weight ratio of bupropion hydrobromide to polymer in the swellable matrix is from about 15:85 to about 80:20.

The formulations of the swellable matrices of the present invention can assume the form of microparticles, tablets, or microparticles retained in capsules. In at least one embodiment the formulation comprises microparticles consolidated into a packed mass for ingestion, even though the packed mass will separate into individual particles after ingestion. Conventional methods can be used for consolidating the microparticles in this manner. For example, the microparticles can be placed in gelatin capsules known in the art as "hard-filled" capsules and "soft-elastic" capsules. The compositions of these capsules and procedures for filling them are known among those skilled in drug formulations and manufacture. The encapsulating material should be highly soluble so that the particles are freed and rapidly dispersed in the stomach after the capsule is ingested.

In certain embodiments of the swellable matrices of the present invention, the formulation contains an additional amount of bupropion hydrobromide salt or other drug applied as a quickly dissolving coating on the outside of the microparticle or tablet. This coating is referred to as a "loading dose" and it is included for immediate release into the recipient's bloodstream upon ingestion of the formulation without first undergoing the diffusion process that the remainder of the drug in the formulation must pass before it is released. The "loading dose" can be high enough to quickly raise the blood concentration of the drug but not high enough to produce the transient overdosing that is characteristic of immediate release dosage forms that are not formulated in accordance with this invention.

In at least one embodiment of the swellable matrices of the present invention, the dosage form is a size 0 gelatin capsule containing either two or three pellets of drug-impregnated polymer. For two-pellet capsules, the pellets are cylindrically shaped, about 6.6 mm or about 6.7 mm in diameter (or more generally, from about 6.5 mm to about 7 mm in diameter) and about 9.5 mm or about 10.25 mm in length (or more generally, from about 9 mm to about 12 mm in length). For three-pellet capsules, the pellets are again cylindrically shaped, about 6.6 mm in diameter and about 7 mm in length. For a size 00 gelatin capsule with two pellets, the pellets are cylindrical, about 7.5 mm in diameter and about 11.25 mm in length. For a size 00 gelatin capsule with three pellets, the pellets are cylindrical, about 7.5 mm in diameter and about 7.5 mm in length. In at least one other embodiment, the dosage form is a single, elongated tablet, with dimensions of about 18 mm to about 22 mm in length, from about 6.5 mm to about 10 mm in width, and from about 5 mm to about 7.5 mm in height. In at least one other embodiment, the dosage form is a single, elongated tablet, with dimensions of from about 18 mm to about 22 mm in length, from about 6.5 mm to about 7.8 mm in width, and from about 6.2 mm to about 7.5 mm in height. In at least one embodiment the dimensions are about 20 mm in length, about 6.7 mm in width, and about 6.4 mm in height. These are merely examples; the shapes and sizes can be varied considerably.

In certain embodiments the bupropion hydrobromide-containing matrix can be made according to any one of the methods described herein.

The particulate drug/polymer mixture or drug-impregnated swellable polymer matrix of certain embodiments can be prepared by various conventional mixing, comminution and fabrication techniques readily apparent to those skilled in the chemistry of drug formulations. Examples of such techniques include: (1) Direct compression, using appropriate punches and dies, such as those available from Elizabeth Carbide Die Company, Inc., McKeesport, Pa., USA; the punches and dies are fitted to a suitable rotary tableting press, such as the Elizabeth-Hata single-sided Hata Auto Press machine, with either 15, 18 or 22 stations, and available from Elizabeth-Hata International, Inc., North Huntington, Pa., USA; (2) Injection or compression molding using suitable molds fitted to a compression unit, such as those available from Cincinnati Milacron, Plastics Machinery Division, Batavia, Ohio, USA.; (3) Granulation followed by compression; and (4) Extrusion in the form of a paste, into a mold or to an extrudate to be cut into lengths.

In regards to the swellable matrices of certain embodiments of the present invention, when microparticles are made by direct compression, the addition of lubricants can be helpful and, in certain embodiments, helpful to promote powder flow and to prevent capping of the microparticle (breaking off of a portion of the particle) when the pressure is relieved. Non-limiting examples of suitable lubricants include magnesium stearate (in a concentration of from about 0.25% to about 3% by weight, and in certain embodiments less than about 1% by weight, in the powder mix), and hydrogenated vegetable oil (in certain embodiments hydrogenated and refined triglycerides of stearic and palmitic acids at from about 1% to about 5% by weight, for example in at least one embodiment at about 2% by weight). Additional excipients can be added to enhance powder flowability and reduce adherence.

Certain embodiments of the swellable matrices of the present invention can find utility when administered to a subject who is in the digestive state (also referred to as the postprandial or "fed" mode). The postprandial mode is distinguishable from the interdigestive (or "fasting") mode by their distinct patterns of gastroduodenal motor activity, which determine the gastric retention or gastric transit time of the stomach contents.

The controlled release matrices of certain embodiments of the present invention can be manufactured by methods known in the art. An example of a method of manufacturing controlled release matrices is melt-extrusion of a mixture containing the bupropion salt, hydrophobic polymer(s), hydrophilic polymer(s), and optionally a binder, plasticizer, and other excipient(s) as described above. Other examples of methods of manufacturing controlled release matrices include wet granulation, dry granulation (e.g. slugging, roller compaction), direct compression, melt granulation, and rotary granulation.

Additionally, controlled release particles which can be compressed or placed in capsules can be produced by combining the bupropion hydrobromide salt and a hydrophobic fusible component and/or a diluent, optionally with a release modifying agent including a water soluble fusible material or a particulate soluble or insoluble organic or inorganic material. Examples of potential hydrophobic fusible components include hydrophobic materials such as natural or synthetic waxes or oils (e.g., hydrogenated vegetable oil, hydrogenated castor oil, microcrystalline wax, Beeswax, carnauba wax and glyceyl monostearate). In at least one embodiment the hydrophobic fusible component has a melting point from about 35° C. to about 140° C. Examples of release modifying agents include polyethylene glycol and particulate materials such as dicalcium phosphate and lactose.

In certain embodiments, controlled release matrices can be produced by mechanically working a mixture of bupropion hydrobromide salt, a hydrophobic fusible component, and optionally a release component including a water soluble fusible material or a particulate soluble or insoluble organic or inorganic material under mixing conditions that yield aglomerates, breaking down the agglomerates to produce controlled release seeds having desired release properties; and optionally adding more carrier or diluent and repeating the mixing steps until controlled release seeds having desired release properties are obtained. These particles also can be size separated (e.g. by sieving and encapsulated in capsules or compressed into a matrix).

The amount of the hydrophobic fusible material used in the foregoing methods can range from about 10% to about 90% by weight. Mixers useful in such methods are known and include conventional high-speed mixers with stainless steel interiors. For example, a mixture can be processed until a bed temperature of about 40° C. or higher is realized, and the mixture achieves a cohesive granular texture comprising desired particle sizes.

As noted if the mixture contains agglomerates, they can be broken down using conventional methods to produce a mixture of powder and particles of the desired size which, can be size-separated using a sieve, screen or mesh of the appropriate size. This material can be returned to a high-speed mixer and further processed as desired until the hydrophobic fusible materials begin to soften/melt, and optionally additional hydrophobic material can be added and mixing continued until particles having a desired size range are obtained. Still further, particles containing bupropion hydrobromide salt can be produced by melt processing as known in the art and combined into capsules or compressed into matrices.

These particles can be combined with one or more excipients such as diluents, lubricants, binding agents, flow aids, disentegrating agents, surface acting agents, water soluble materials, colorants, and the like.

In addition, the controlled release matrices can optionally be coated with one or more functional or non-functional coatings using well-known coating methods. Examples of coatings can include the XL controlled release coat and the EA matrix coating described herein, which can further control the release of the bupropion hydrobromide salt and/or other drug.

In at least one embodiment, the controlled release matrices can each be coated with at least one taste-masking coating. The taste-masking coating can mask the taste of the bupropion hydrobromide salt in the matrices. In at least one embodiment the taste-masking coating formulations contain polymeric ingredients. It is contemplated that other excipients consistent with the objects of the present invention can also be used in the taste-masking coating.

In at least one embodiment of the matrix dosage form, the taste-masking coating comprises a polymer such as ethylcellulose, which can be used as a dry polymer (such as ETHOCEL®, Dow Corning) solubilised in organic solvent prior to use, or as an aqueous dispersion. One commercially-available aqueous dispersion of ethylcellulose is AQUACOAT® (FMC Corp., Philadelphia, Pa., U.S.A.). AQUACOAT® can be prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, the Aquacoat is intimately mixed with a suitable plasticizer prior to use. Another aqueous dispersion of ethylcellulose is commercially available as SURELEASE® (Colorcon, Inc., West Point, Pa., U.S.A.). This product can be prepared by incorporating plasticizer into the dispersion during the manufacturing process. A hot melt of a polymer, plasticizer (e.g. dibutyl sebacate), and stabilizer (e.g. oleic acid) is prepared as a homogeneous mixture, which is then diluted with an alkaline solution to obtain an aqueous dispersion which can be applied directly onto substrates.

In other embodiments of the matrix dosage form, polymethacrylate acrylic polymers can be employed as taste masking polymers. In at least one embodiment, the taste masking coating is an acrylic resin lacquer used in the form of an aqueous dispersion, such as that which is commercially available from Rohm Pharma under the tradename EUDRAGIT® or from BASF under the tradename KOLLICOAT®. In further embodiments, the acrylic coating comprises a mixture of two acrylic resin lacquers commercially available from Rohm Pharma under the tradenames EUDRAGIT® RL and EUDRAGIT® RS, respectively. EUDRAGIT® RL and EUDRAGIT® RS are copolymers of acrylic and methacrylic esters with a low content of quaternary ammonium groups, the molar ratio of ammonium groups to the remaining neutral (meth)acrylic esters being 1:20 in EUDRAGIT® RL and 1:40 in EUDRAGIT® RS. The mean molecular weight is 150,000. The code designations RL (high permeability) and RS (low permeability) refer to the permeability properties of these agents. EUDRAGIT® RL/RS mixtures are insoluble in water and in digestive fluids. However, coatings formed from the same are swellable and permeable in aqueous solutions and digestive fluids. EUDRAGIT® RL/RS dispersions or solutions of the certain embodiments can be mixed together in any desired ratio in order to ultimately obtain a taste masking coating having a desirable drug dissolution profile. Controlled release formulations of certain embodiments can be obtained, for example, from a retardant coating derived from 100% EUDRAGIT® RL; 50% EUDRAGIT® RL with 50% EUDRAGIT® RS; and 10% EUDRAGIT® RL with 90% EUDRAGIT® RS.

In other embodiments of the matrix dosage form, the taste masking polymer can be an acrylic polymer which is cationic in character based on dimethylaminoethyl methacrylate and neutral methacrylic acid esters (such as EUDRAGIT® E, commercially available from Rohm Pharma). The hydrophobic acrylic polymer coatings of the present invention can further include a neutral copolymer based on poly (meth) acrylates, such as EUDRAGIT® NE (NE=neutral ester), commercially available from Rohm Pharma. EUDRAGIT® NE 30D lacquer films are insoluble in water and digestive fluids, but permeable and swellable.

In other embodiments of the matrix dosage form, the taste masking polymer is a dispersion of poly (ethylacrylate, methyl methacrylate) 2:1 (KOLLICOAT® EMM 30 D, BASF).

In other embodiments of the matrix dosage form, the taste masking polymer can be a polyvinyl acetate stabilized with polyvinylpyrrolidone and sodium lauryl sulfate such as KOLLICOAT® SR30D (BASF).

Other taste masking polymers that can be used in the matrix dosage forms include hydroxypropylcellulose (HPC); hydroxypropylmethylcellulose (HPMC); hydroxyethylcellulose; gelatin; gelatin/acacia; gelatin/acacia/vinvylmethylether maleic anhydride; gelatin/acacia/ethylenemaleic anhydride; carboxymethyl cellulose; polyvinvylalcohol; nitrocellulose; polyvinylalcohol-polyethylene glycol graftcopolymers; shellac; wax and mixtures thereof.

The taste-masking coatings can be applied to the matrices from one or more organic or aqueous solvent solutions or suspensions. In at least one embodiment of the matrix dosage forms the organic solvents that can be used to apply the taste-masking coatings include one or more of acetone, lower alcohols such as ethanol, isopropanol and alcohol/water mixtures, chlorinated hydrocarbons, and the like. Devices used to coat the matrices of certain embodiments with a taste-masking coating include those conventionally used in pharmaceutical processing, such as fluidized bed coating devices. The controlled release coatings applied to the matrices can contain ingredients other than the cellulosic polymers. One or more colorants, flavorants, sweeteners, can also be used in the taste-masking coating.

In some embodiments of the matrix dosage forms, a pore former can be included into the taste masking coat in order to influence the rate of release of bupropion hydrobromide from the matrix. In other embodiments, a pore former is not included in the taste masking coat. The pore formers can be inorganic or organic, and may be particulate in nature and include materials that can be dissolved, extracted or leached from the coating in the environment of use. Upon exposure to fluids in the environment of use, the pore-formers can for example be dissolved, and channels and pores are formed that fill with the environmental fluid.

For example, the pore-formers of certain embodiments of the matrix dosage forms can comprise one or more watersoluble hydrophilic polymers in order to modify the release characteristics of the formulation. Examples of suitable hydrophilic polymers that can be used as pore-formers include hydroxypropylmethylcellulose, cellulose ethers and protein-derived materials of these polymers, the cellulose ethers, such as hydroxyalkylcelluloses, carboxyalkylcelluloses and mixtures thereof. Also, synthetic water-soluble polymers can be used, examples of which include polyvinylpyrrolidone, cross-linked polyvinyl-pyrrolidone, polyethylene oxide, water-soluble polydextrose, saccharides and polysaccharides, such as pullulan, dextran, sucrose, glucose, fructose, mannitol, lactose, mannose, galactose, sorbitol and mixtures thereof. In at least one embodiment, the hydrophilic polymer comprises hydroxypropyl-methylcellulose.

Other non-limiting examples of pore-formers that can be used in the taste masking coat include alkali metal salts such as lithium carbonate, sodium chloride, sodium bromide, potassium chloride, potassium sulfate, potassium phosphate, sodium acetate, sodium citrate and mixtures thereof. The pore-forming solids can also be polymers which are soluble in the environment of use, such as CARBOWAX™ and CARBOPOL™. In addition, the pore-formers embrace diols, polyols, polyhydric alcohols, polyalkylene glycols, polyglycols, poly(a-w)alkylenediols and mixtures thereof. Other pore-formers which can be useful in the formulations of certain embodiments of the present invention include starch, modified starch, and starch derivatives, gums, including but not limited to xanthan gum, alginic acid, other alginates, benitoniite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan, kappa-carrageenan, lambda-carrageenan, gum karaya, biosynthetic gum, and mixtures thereof. Other poreformers include materials useful for making microporous lamina in the environment of use, such as polycarbonates comprised of linear polyesters of carbonic acid in which carbonate groups reoccur in the polymer chain, microporous materials such as bisphenol, a microporous poly(vinylchloride), micro-porous polyamides, microporous modacrylic copolymers, microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous hiomopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid cross-linked poly(vinylpyrrolidone), and mixtures thereof. In general, the amount of pore-former included in the taste masking coatings of certain embodiments of the matrix dosage forms can be from about 0.1% to about 80%, by weight, relative to the combined weight of polymer and pore-former. The percentage of pore former as it relates to the dry weight of the taste-masking polymer, can have an influence on the drug release properties of the coated matrix. In at least one embodiment that uses water soluble pore formers such as hydroxypropylmethylcellulose, a taste masking polymer: pore former dry weight ratio of from about 10:1 to about 1:1 can be present. In certain embodiments the taste masking polymer: pore former dry weight ratio is from about 8:1 to about 1.5:1; and in other embodiments from about 6:1 to about 2:1. In at least one embodiment using EUDRAGIT® NE30D as the taste masking polymer and a hydroxypropylmethylcellulose (approx 5 cps viscosity (in a 2% aqueous solution)) such as METHOCEL® E5, PHARMACOAT® 606G as the water soluble pore former, a taste masking polymer: pore former dry weight ratio of about 2:1 is present.

Colorants that can be used in the taste-masking coating of certain embodiments of the matrix dosage forms include food, drug and cosmetic colors (FD&C), drug and cosmetic colors (D&C) or external drug and cosmetic colors (Ext. D&C). These colors are dyes, lakes, and certain natural and derived colorants. Useful lakes include dyes absorbed on aluminum hydroxide or other suitable carriers.

Flavorants that can be used in the taste-masking coating of certain embodiments of the matrix dosage forms include natural and synthetic flavoring liquids. An illustrative list of such flavorants includes volatile oils, synthetic flavor oils, flavoring aromatics, oils, liquids, oleoresins and extracts derived from plants, leaves, flowers, fruits, stems and combinations thereof. A non-limiting representative list of these includes citric oils, such as lemon, orange, grape, lime and grapefruit, and fruit essences, including apple, pear, peach, grape, strawberry, raspberry, cherry, plum, pineapple, apricot, or other fruit flavors. Other useful flavorants include aldehydes and esters, such as benzaldehyde (cherry, almond); citral, i.e., alpha-citral (lemon, lime); neral, i.e., beta-citral (lemon, lime); decanal (orange, lemon); aldehyde C-8 (citrus fruits); aldehyde C-9 (citrus fruits); aldehyde C-12 (citrus fruits); tolyl aldehyde (cherry, almond); 2,6-dimethyloctanal (green fruit); 2-dodenal (citrus mandarin); and mixtures thereof.

Sweeteners that can be used in the taste-masking coating of certain embodiments of the matrix dosage forms include glucose (corn syrup), dextrose, invert sugar, fructose, and mixtures thereof (when not used as a carrier); saccharin and its various salts, such as sodium salt; dipeptide sweeteners such as aspartame; dihydrochalcone compounds, glycyrrhizin; Steva Rebaudiana (Stevioside); chloro derivatives or sucrose such as sucralose; and sugar alcohols such as sorbitol, mannitol, xylitol, and the like. Also contemplated are hydrogenated starch hydrolysates and the synthetic sweeteners such as 3,6-dihydro-6-methyl-1-1-1,2,3-oxathiazin-4-1-2,2-dioxide, particularly the potassium salt (acesulfame-K), and sodium and calcium salts thereof. The sweeteners can be used alone or in any combination thereof.

The matrix taste masking coat can also include one or more pharmaceutically acceptable excipients such as lubricants, emulsifiers, anti-foaming agents, plasticizers, solvents and the like.

Lubricants can be included to help reduce friction of coated matrices during manufacturing. The lubricants that can be used in the taste masking coat of certain embodiments of the present invention include but are not limited to adipic acid, magnesium stearate, calcium stearate, zinc stearate, calcium silicate, magnesium silicate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil, waxy fatty acid esters such as glyceryl behenate, (i.e. COMPRITOL™), STEAR-O-WET™, MYVATEX™ TL and mixtures thereof. In at least one embodiment, the lubricant is selected from magnesium stearate, talc and a mixture thereof. The lubricant can be present in an amount of from about 1% to about 100% by weight of the polymer dry weight in the taste masking coat. For example, in certain embodiments wherein the taste masking polymer is EUDRAGIT® NE30D or EUDRAGIT® NE40D (Rohm America LLC) together with a hydrophilic pore former, the lubricant is present in an amount of from about 1% to about 30% by weight of the polymer dry weight; in other embodiments from about 2% to about 20%; and in still other embodiments at about 10% by weight of the matrix taste masking coat dry weight. In another embodiment where the taste masking polymer is ethylcellulose (ETHOCEL™ PR100, PR45, PR20, PR10 or PR7 polymer, or a mixture thereof), the lubricant can be present in an amount of from about 10% to about 100% by weight of the matrix taste-masking coat dry weight; in another embodiment from about 20% to about 80%; and in still another embodiments at about 50% by weight of the matrix taste masking coat dry weight. In other embodiments, the taste masking coat does not include a pore former.

Emulsifying agent(s) (also called emulsifiers or emulgents) can be included in the matrix taste masking coat to facilitate actual emulsification during manufacture of the coat, and also to ensure emulsion stability during the shelf-life of the product. Emulsifying agents useful for the matrix taste masking coat composition of certain embodiments include, but are not limited to naturally occurring materials and their semi synthetic derivatives, such as the polysaccharides, as well as glycerol esters, cellulose ethers, sorbitan esters (e.g. sorbitan monooleate or SPAN™ 80), and polysorbates (e.g. TWEEN™ 80). Combinations of emulsifying agents are operable. In at least one embodiment, the emulsifying agent is TWEEN™ 80. The emulsifying agent(s) can be present in an amount of from about 0.01% to about 5% by weight of the matrix taste masking polymer dry weight. For example, in certain embodiments the emulsifying agent is present in an amount of from about 0.05% to about 3%; in other embodiments from about 0.08% to about 1.5%, and in still other embodiments at about 0.1% by weight of the matrix taste masking polymer dry weight.

Anti-foaming agent(s) can be included in the matrix taste masking coat to reduce frothing or foaming during manufacture of the coat. Anti-foaming agents useful for the coat composition include, but are not limited to simethicone, polyglycol, silicon oil, and mixtures thereof. In at least one embodiment the anti-foaming agent is Simethicone C. The anti-foaming agent can be present in an amount of from about 0.1% to about 10% of the matrix taste masking coat weight. For example, in certain embodiments the anti-foaming agent is present in an amount of from about 0.2% to about 5%; in other embodiments from about 0.3% to about 1%, and in still other embodiments at about 0.6% by weight of the matrix taste masking polymer dry weight.

Plasticizer(s) can be included in the matrix taste masking coat to provide increased flexibility and durability during manufacturing. Plasticizers that can be used in the matrix taste masking coat of certain embodiments include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropioin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, and mixtures thereof. The plasticizer can be present in an amount of from about 1% to about 80% of the taste masking polymer dry weight. For example, in certain embodiments the plasticizer is present in an amount of from about 5% to about 50%, in other embodiments from about 10% to about 40%, and in still other embodiments at about 20% of the taste masking polymer dry weight.

In some embodiments mixtures of plasticizers are provided, e.g., a mixture of PEG 4000 and Dibutyl Sebacate (DBS). For example, in a 174 mg bupropion hydrobromide tablet, PEG4000 is present in an amount of 1.6% by weight of the total formulation and DBS is present in an amount of 0.8% by weight of the total formulation, in a 348 mg bupropion hydrobromide tablet, PEG4000 is present in an amount of 0.9% by weight of the total formulation and DBS is present in an amount of 0.4% by weight of the total formulation, and in a 522 mg bupropion hydrobromide tablet, PEG4000 is present in an amount of 0.9% by weight of the total formulation and DBS is present in an amount of 0.4% by weight of the total formulation, The taste-masking coating can be present in an amount of from about 1% to about 90% by weight of the matrix, depending upon the choice of polymer, the ratio of polymer:pore former, and the total surface area of the matrix formulation. Since a certain thickness of taste masking coating has to be achieved in order to achieve effective taste masking, the amount of taste masking polymer coating used during manufacture is related to the total surface area of the batch of uncoated matrices that requires a coating. For example, the taste masking polymer surface area coverage can range from about 0.5 mg/cm2 to about 20 mg/cm2. For example, in certain embodiments the surface area coverage of the taste masking polymer is from about 0.6 mg/cm2 to about 10 mg/cm2, and in other embodiments is from about 1 mg/cm2 to about 5 mg/cm2. In at least one embodiment of the invention, EUDRAGIT® E is employed as the taste masking polymer at a surface area coverage of about 4 mg/cm2.

In the absence of an accurate determination of total surface area of a matrix, the amount of taste masking polymer to be applied can be expressed as a percentage of the uncoated matrix. For example, in certain embodiments the taste-masking coating is present in an amount of from about 5% to about 60%; in other embodiments from about 10% to about 40%; and in still other embodiments from about 15% to about 35% by weight of the matrix. In at least one embodiment the taste-masking coating is present in an amount of about 30% by weight of the matrix.

Prophetic examples of matrix tablet formulations are described below. It should be understood that these examples are intended to be exemplary and that the specific constituents, amounts thereof, and formulation methods may be varied therefrom in order to achieve different release characteristics:

In at least one embodiment, the controlled matrices comprise:

| | |
|---|---|
| Bupropion HBr | about 30.0% by weight of the matrix |
| Hydroxypropylmethylcellulose E50 | about 10.0% by weight of the matrix |
| Hydroxypropylmethylcellulose K15M | about 30.0% by weight of the matrix |
| Calcium phosphate dehydrate | about 9.5% by weight of the matrix |
| ATMUL ™ 84S (mono/di/tri glycerides) | about 20.0% by weight of the matrix |
| Magnesium stearate | about 0.5% by weight of the matrix |

Preparation of the Matrix Formulation can be as Follows: Combine the Drug, a Portion of Each HPMC, calcium phosphate and Atmul 84S in a planetary mixer and dry mix for 15 minutes. Add a solution of the remainder of the HPMC in water to the mixer while mixing, until a wet mass is obtained. Pass the wet material through a screen to make the resultant granules of uniform size (to achieve uniform drying) and dry in an oven at about 40° C. for about 24 hours. Mill the dried granules through a Fitzpatrick Mill, knives forward, and collect the material in a mixer. Add the magnesium stearate and mix for about 5 minutes. The resultant mixture is tabletted on a suitable tablet press.

In at least one embodiment, the controlled release matrices comprise a deposit-core and support-platform. Preparation of the deposit-core can be as follows: Deposit-cores can be prepared using the following materials in the stated quantities:

| | |
|---|---|
| Bupropion HBr | about 45.0 g |
| hydroxypropylmethylcellulose (METHOCEL ® K 100M-Colorcon) | about 35.0 g |
| mannitol | about 10.0 g |
| ethylcellulose (high viscosity-BDH) | about 3.75 g |
| 3.75 g magnesium stearate | about 1.0 g |
| 5:1 ethanol-chloroform mixture | about 75.0 ml |

The bupropion hydrobromide is mixed intimately with the mannitol and hydroxypropylmethylcellulose in a suitable mixer. The solution of ethylcellulose in ethanol-chloroform is prepared separately, and is used for wetting the previously obtained powder mixture. The resultant homogeneous mass is forced through an 800 micron screen and then dried to obtain a granulate which is passed through a 420 micron screen. The homogeneous granulate obtained is mixed with the magnesium stearate and then compressed using concave punches of diameter 7 mm (radius of curvature 9 mm) using a pressure of about 3000 kg/cm2 to obtain cylindrical deposit-cores with convex bases.

Application of the support-platform can be as follows: The support-platform can be applied by coating one or both the convex bases of the deposit-core with a solution of about 15 g low-permeability acrylic-methacrylic copolymer (EUDRAGIT® RS Rohm Pharma) in methylene chloride of a quantity to make up to 100 ml. Thereafter about 0.3 ml of said solution is applied to each base to be covered, taking care to protect the lateral core surface. The system is then dried with tepid air. The quantity of polymeric material deposited is sufficient to keep the structure intact during transfer.

In at least one embodiment, the matrix formulation is a polyethylene oxide (PEO) based tablet matrix formulation comprising:

| | |
|---|---|
| Bupropion Hydrobromide | about 50% |
| PEO WSR Coagulant (polyethylene oxide) | about 15% |
| METHOCEL ® K100M (hydroxypropylmethyl cellulose) | about 15% |
| Avicel PH101 (microcrystalline cellulose) | about 19% |
| Magnesium Stearate | about 1% |

Preparation of the PEO Based Tablet Matrix Formulation can be as Follows: Excipients dry blended in an appropriate mixer and compressed into tablets using conventional apparatus.

Multiparticulates

In certain embodiments of the present invention, a multiparticulate system is provided which contains multiple microparticles each containing an effective amount of bupropion hydrobromide and at least one pharmaceutically acceptable excipient. The multiparticulates can be contained within a capsule, or can be compressed into a matrix or tablet, that upon ingestion dissolves into multiple units (e.g. pellets), wherein the sub-units or pellets possess the desired controlled release properties of the dosage form. The multiparticulates or the multiple unit dosage forms can be surrounded by one or more coatings. Examples of such coatings include polymeric controlled release coatings, delayed release coatings, enteric coatings, immediate release coatings, taste-masking coatings, extended release coatings, and non-functional coatings.

The bupropion hydrobromide salt in the microparticles of certain embodiments can be present in an effective amount of from about 0.1% to about 99% by weight of the microparticles. For example, in certain embodiments bupropion hydrobromide is present in the microparticles in an amount of from about 0.1% to about 90%, in other embodiments from about 5% to about 90%, in still other embodiments from about 10% to about 80%, and in even still other embodiments from about 25% to about 80% by weight of the microparticle. In certain embodiments wherein the microparticles are manufactured using a spheronization process, the bupropion hydrobromide can be present in the microparticles in an amount of from about 0.1% to about 60%; in other such embodiments from about 5% to about 50%; and in still other such embodiments from about 10% to about 40% by weight of the microparticle. In at least one embodiment wherein the microparticles are manufactured using a spheronization process, the bupropion hydrobromide is present in the microparticle in an amount of about 30% by weight of the microparticle.

In addition to the bupropion hydrobromide salt, the microparticles of the present invention also include at least one pharmaceutically acceptable excipient. Excipients can be added to facilitate in the preparation, patient acceptability and functioning of the dosage form as a drug delivery system. Examples of possible excipients include spheronization aids, solubility enhancers, disintegrating agents, diluents, lubricants, binders, fillers, glidants, suspending agents, emulsifying agents, anti-foaming agents, flavoring agents, coloring agents, chemical stabilizers, pH modifiers, and mixtures thereof. Depending on the intended main function, excipients to be used in formulating compositions are subcategorized into different groups. However, one excipient can affect the properties of a composition in a series of ways, and many excipients used in compositions can thus be described as being multifunctional.

The microparticles of certain embodiments of the present invention can be manufactured using standard techniques known to one of skill in the art. In certain embodiments the microparticles can be made according to any one of the methods described herein. Useful microparticles include drug-layered microparticles and drug-containing microparticles.

Drug-Containing Microparticles

Microparticles containing drug in the core can be prepared by a number of different procedures. For example: In a spray drying process, an aqueous solution of core material and hot solution of polymer is atomized into hot air, the water then evaporates, and the dry solid is separated in the form of pellets, for example by air suspension. A spray-drying process can produce hollow pellets when the liquid evaporates at a rate that is faster than the diffusion of the dissolved substances back into the droplet interior, or if due to capillary action the dissolved substance migrates out with the liquid to the droplet surface, leaving behind a void. Another example is a spray congealing process, where a slurry of drug material that is insoluble in a molten mass is spray congealed to obtain discrete particles of the insoluble materials coated with the congealed substance. A further example is a fluidized bed based granulation/pelletization process, where a dry drug is suspended in a stream of hot air to form a constantly agitated fluidized bed. An amount of binder or granulating liquid is then introduced in a finely dispersed form to cause pelletization.

The drug-containing microparticles of certain embodiments of the present invention can also be made by, for example, a spheronization process. One method of manufacturing the drug-containing microparticles is the applicant's proprietary CEFORM™ (Centrifugally Extruded & Formed Microspheres/Microparticles) technology, which is the simultaneous use of flash heat and centrifugal force, using proprietary designed equipment, to convert dry powder systems into microparticles of uniform size and shape. The production of microparticles containing an active drug using this CEFORM™ technology is known. This patent deals with the use of LIQUIFLASH® processing to spheronize compositions containing one or more active drugs to form LIQUIFLASH® microparticles.

With the CEFORM™ technology, the processing of the drug-containing microparticles of the present invention is carried out in a continuous fashion, whereby a pre-blend of drug and excipients is fed into a spinning "microsphere head", also termed as a "spheronizing head". The microsphere head, which is a multi-aperture production unit, spins on its axis and is heated by electrical power. The drug and excipient(s) pre-blend is fed into the center of the head with an automated feeder. The material moves, via centrifugal force, to the outer rim where the heaters, located in the rim of the head, heat the material. Microparticles are formed when the molten material exits the head, which are then cooled by convection as they fall to the bottom of the microparticle chamber. The product is then collected and stored in suitable product containers. Careful selection of the types and levels of excipient(s) control microparticle properties such as sphericity, surface morphology, and dissolution rate. One advantage of such a process is that the microparticles are produced and collected from a dry feedstock without the use of any solvents.

There are at least two approaches that can be used to produce drug-containing microparticles using the CEFORM process: (i) the encapsulation approach and (ii) the co-melt approach. In the encapsulation approach, the process is conducted below the melting point of the drug. Therefore, the excipients are designed to melt and entrain the drug particles on passing through the apertures to form microparticles. The resulting microparticles contain the drug, in its native state, essentially enveloped by or as an intimate matrix with the resolidified excipients. In the co-melt approach, the process is conducted above the melting point of the drug. In this case, the drug and the excipients melt or become fluid simultaneously upon exposure to the heat. The molten mixture exits the head and forms microparticles, which cool as they fall to the bottom of the collection bin where they are collected.

In at least one embodiment the microparticles are manufactured using the encapsulation approach. In the encapsulation approach the excipient(s) which are chosen have a lower melting point than the drug with which they will be combined. Therefore the spheronizing process can be performed at lower temperatures, than the melting point of the drug. As a result, this can reduce the risk of polymeric interconversion, which can occur when using processing temperatures close to the melting point.

In a prophetic example of certain embodiments of the present invention, the manufacturing process for the microparticles can hypothetically be as follows: Spheronization aid is screened through a 425 micron (µm) screen. In at least one embodiment, the spheronization aid is distilled glyceryl monostearate (i.e. DMG-03VF). About 50% of the spheronization aid is added to a bowl in a high shear mixer. In at least one embodiment, the bowl is a 6 liter bowl and the high shear mixer is a Diosna P1-6 high speed mixer granulator. The active drug is then added to the bowl of the mixer, and then the remainder of the spheronization aid is added. The material is then blended in the mixer for a time from about 1 minute to about 30 minutes; in certain embodiments from about 3 minutes to about 10 minutes; and in at least one embodiment at about 6 minutes. The mixer motor speed is from about 50 rpm to about 2000 rpm; in certain embodiments from about 200 rpm to about 500 rpm; and in at least one embodiment at about 300 rpm. The chopper motor speed is from about 50 rpm to about 2000 rpm; in certain embodiments from about 200 rpm to about 500 rpm; and in at least one embodiment at about 400 rpm. The blended material is then spheronized in a CEFORM™ spheronizing head. The spheronizing head speed is from about 5 Hz to about 60 Hz; in certain embodiments from about 10 Hz to about 30 Hz; and in at least one embodiment at about 15 Hz. In at least one embodiment the CEFORM™ spheronizing head is a 5 inch head. The spheronizing head temperature is maintained at a temperature from about 70° C. to about 130° C.; in certain embodiments from about 90° C. to about 110° C.; and in at least one embodiment at about 100° C. The microparticles obtained from the spinning process are then screened through a screen that is from about 150 µm to about 800 µm.

For microparticles manufactured using a spheronization process such as the CEFORM™ process, the microparticles include, in addition to the bupropion hydrobromide salt, at least one spheronization aid. Spheronization aids can assist the drug-containing mix to form robust durable spherical particles. Some examples of materials useful as spheronization aids include, but are not limited to glyceryl monostearate, glyceryl behenate, glyceryl dibehenate, glyceryl palmitostearate, hydrogenated oils such as hydrogenated castor oil marketed under the name CUTINA™ HR, fatty acid salts such as magnesium or calcium stearate, polyols such as mannitol, sorbitol, xylitol, stearic acid, palmitic acid, sodium lauryl sulfate, polyoxyethylene ethers, esterified polyoxyethylenes such as PEG-32 distearate, PEG-150 distearate, cetostearyl alcohol, waxes (e.g. carnauba wax, white wax, paraffin wax) and wax-like materials. Certain thermo-plastic or thermo-softening polymers can also function as spheronization aids. Some non-limiting examples of such thermo-plastic or thermo-softening polymers include Povidone, cellulose ethers and polyvinylalcohols. Combinations of spheronization aids can be used. In at least one embodiment, the spheronization aid is glyceryl monostearate (i.e. DMG-03VF). The spheronization aid can be present in an amount of from about 0.1% to about 99% by weight of the microparticle. For example, in certain embodiments the spheronization aid is present in an amount of from about 5% to about 90%; in other embodiments from about 10% to about 80%; in still other embodiments from about 20% to about 70%; and in even still other embodiments from about 30% to about 60% by weight of the microparticle. In at least one embodiment the spheronization aid is present in an amount of about 50% by weight of the microparticle. In at least one other embodiment, the microparticles include about 50% (w/w) of bupropion hydrobromide and about 50% (w/w) of the spheronization aid.

In certain embodiments, each microparticle can also include at least one solubility enhancer. Solubility enhancers can be surfactants. Certain embodiments of the invention include a solubility enhancer that is a hydrophilic surfactant. Hydrophilic surfactants can be used to provide any of several advantageous characteristics to the compositions, including: increased solubility of the bupropion hydrobromide salt in the microparticle; improved dissolution of the bupropion hydrobromide salt; improved solubilization of the bupropion hydrobromide salt upon dissolution; enhanced absorption and/or bioavailability of the bupropion hydrobromide salt. The hydrophilic surfactant can be a single hydrophilic surfactant or a mixture of hydrophilic surfactants, and can be ionic or non-ionic.

Likewise, various other embodiments of the invention include a lipophilic component, which can be a lipophilic surfactant, including a mixture of lipophilic surfactants, a triglyceride, or a mixture thereof. The lipophilic surfactant can provide any of the advantageous characteristics listed above for hydrophilic surfactants, as well as further enhancing the function of the surfactants. These various embodiments are described in more detail below.

As is well known in the art, the terms "hydrophilic" and "lipophilic" are relative terms. To function as a surfactant, a compound includes polar or charged hydrophilic moieties as well as non-polar hydrophobic (lipophilic) moieties; i.e., a surfactant compound is amphiphilic. An empirical parameter commonly used to characterize the relative hydrophilicity and lipophilicity of non-ionic amphiphilic compounds is the hydrophilic-lipophilic balance (the "HLB" value). Surfactants with lower HLB values are more lipophilic, and have greater solubility in oils, whereas surfactants with higher HLB values are more hydrophilic, and have greater solubility in aqueous solutions.

Using HLB values as a rough guide, hydrophilic surfactants can generally be considered to be those compounds having an HLB value greater than about 10, as well as anionic, cationic, or zwitterionic compounds for which the HLB scale is not generally applicable. Similarly, lipophilic surfactants can be compounds having an HLB value less than about 10.

It should be appreciated that the HLB value of a surfactant is merely a rough guide generally used to enable formulation of industrial, pharmaceutical and cosmetic emulsions. For many surfactants, including several polyethoxylated surfactants, it has been reported that HLB values can differ by as much as about 8 HLB units, depending upon the empirical method chosen to determine the HLB value (Schott, J. Pharm. Sciences, 79(1), 87-88 (1990)). Likewise, for certain polypropylene oxide containing block copolymers (poloxamers, available commercially as PLURONIC® surfactants, BASF Corp.), the HLB values may not accurately reflect the true physical chemical nature of the compounds. Finally, commercial surfactant products are generally not pure compounds, but are often complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected even for a single commercial surfactant product. Keeping these inherent difficulties in mind, and using HLB values as a guide, one skilled in the art can readily identify surfactants having suitable hydrophilicity or lipophilicity for use in the present invention, as described herein.

Solubility enhancers can be any surfactant suitable for use in pharmaceutical compositions. Suitable surfactants can be anionic, cationic, zwitterionic or non-ionic. Such surfactants can be grouped into the following general chemical classes detailed in Tables 81-98 herein. The HLB values given in Tables 81-98 below generally represent the HLB value as reported by the manufacturer of the corresponding commercial product. In cases where more than one commercial product is listed, the HLB value in the Tables is the value as reported for one of the commercial products, a rough average of the reported values, or a value that, in the judgment of the present inventors, is more reliable.

It should be emphasized that the invention is not limited to the surfactants in Tables 81-98, which show representative, but not exclusive, lists of available surfactants. In addition, refined, distilled or fractionated surfactants, purified fractions thereof, or re-esterified fractions, are also within the scope of the invention, although not specifically listed in the Tables.

Although polyethylene glycol (PEG) itself does not function as a surfactant, a variety of PEG-fatty acid esters have useful surfactant properties. Examples of polyethoxylated fatty acid monoester surfactants commercially available are shown in Table 81.

Polyethylene glycol (PEG) fatty acid diesters are also suitable for use as surfactants in the compositions of the present invention. Representative PEG-fatty acid diesters are shown in Table 82.

In general, mixtures of surfactants are also useful in the present invention, including mixtures of two or more commercial surfactant products. Several PEG-fatty acid esters are marketed commercially as mixtures or mono- and diesters. Representative surfactant mixtures are shown in Table 83.

Suitable PEG glycerol fatty acid esters are shown in Table 84.

A large number of surfactants of different degrees of lipophilicity or hydrophilicity can be prepared by reaction of alcohols or polyalcohols with a variety of natural and/or hydrogenated oils. In certain embodiments, the oils used are castor oil or hydrogenated castor oil or an edible vegetable oil such as corn oil, olive oil, peanut oil, palm kernel oil, apricot kernel oil, or almond oil. Examples of alcohols include glycerol, propylene glycol, ethylene glycol, polyethylene glycol, sorbitol, and pentaerythritol. Representative surfactants of this class suitable for use in the present invention are shown in Table 85.

Polyglycerol esters of fatty acids are also suitable surfactants for the present invention. Examples of suitable polyglyceryl esters are shown in Table 86.

Esters of propylene glycol and fatty acids are suitable surfactants for use in the present invention. Examples of surfactants of this class are given in Table 87.

In general, mixtures of surfactants are also suitable for use in the present invention. In particular, mixtures of propylene glycol fatty acid esters and glycerol fatty acid esters are suitable and are commercially available. Examples of these surfactants are shown in Table 88.

Another class of surfactants is the class of mono- and diglycerides. These surfactants are generally lipophilic. Examples of these surfactants are given in Table 89.

Sterols and derivatives of sterols are suitable surfactants for use in the present invention. These surfactants can be hydrophilic or lipophilic. Examples of surfactants of this class are shown in Table 90.

A variety of PEG-sorbitan fatty acid esters are available and are suitable for use as surfactants in the present invention. In general, these surfactants are hydrophilic, although several lipophilic surfactants of this class can be used. Examples of these surfactants are shown in Table 91.

Ethers of polyethylene glycol and alkyl alcohols are suitable surfactants for use in the present invention. Examples of these surfactants are shown in Table 92.

Esters of sugars are suitable surfactants for use in the present invention. Examples of such surfactants are shown in Table 93.

Several hydrophilic PEG-alkyl phenol surfactants are available, and are suitable for use in the present invention. Examples of these surfactants are shown in Table 94.

The POE-POP block copolymers are a unique class of polymeric surfactants. The unique structure of the surfactants, with hydrophilic POE and lipophilic POP moieties in well-defined ratios and positions, provides a wide variety of surfactants suitable for use in the present invention. These surfactants are available under various trade names, including SYNPERONIC™ PE series (ICI); PLURONIC® series (BASF), EMKALYX™, LUTROL™ (BASF), SUPRONIC™ MONOLAN™, PLURACARE™, and PLURODAC™. The generic term for these polymers is "poloxamer" (CAS 9003-11-6). These polymers have the formula:

where "a" and "b" denote the number of polyoxyethylene and polyoxypropylene units, respectively. Examples of suitable surfactants of this class are shown in Table 95.

Sorbitan esters of fatty acids are suitable surfactants for use in the present invention. Examples of these surfactants are shown in Table 96.

Esters of lower alcohols (C2 to C4) and fatty acids (C8 to C18) are suitable surfactants for use in the present invention. Examples of these surfactants are shown in Table 97.

Ionic surfactants, including cationic, anionic and zwitterionic surfactants, are suitable hydrophilic surfactants for use in the present invention. In certain embodiments, the surfactant is an anionic surfactant such as a fatty acid salt, a bile salt, or a combination thereof. In other embodiments the surfactant is a cationic surfactant such as a carnitine. Examples of ionic surfactants include sodium oleate, sodium lauryl sulfate, sodium lauryl sarcosinate, sodium dioctyl sulfosuccinate, sodium cholate, sodium taurocholate; lauroyl carnitine; palmitoyl carnitine; and myristoyl carnitine. Examples of such surfactants are shown in Table 98.

Ionizable surfactants, when present in their unionized (neutral, non-salt) form, are lipophilic surfactants suitable for use in the compositions of the present invention. Particular examples of such surfactants include free fatty acids, particularly C6-C22 fatty acids, and bile acids. More specifically, suitable unionized ionizable surfactants include the free fatty acid and bile acid forms of any of the fatty acid salts and bile salts shown in Table 98.

Derivatives of oil-soluble vitamins, such as vitamins A, D, E, K, etc., are also useful surfactants for the compositions of the present invention. An example of such a derivative is tocopheryl PEG-1000 succinate (TPGS, available from Eastman).

In certain embodiments, surfactants or mixtures of surfactants that solidify at ambient room temperature are used. In other embodiments, surfactants or mixtures of surfactants that solidify at ambient room temperature in combination with particular lipophilic components, such as triglycerides, or with addition of appropriate additives, such as viscosity modifiers, binders, thickeners, and the like, are used.

Examples of non-ionic hydrophilic surfactants include alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols with fatty acids, glycerides, vegetable oils, hydrogenated vegetable oils, and sterols; sugar esters, sugar ethers; sucroglycerides; polyethoxylated fat-soluble vitamins or derivatives; and mixtures thereof.

In certain embodiments, the non-ionic hydrophilic surfactant is selected from the group comprising polyoxyethylene alkylethers; polyethylene glycol fatty acids esters; polyethylene glycol glycerol fatty acid esters; polyoxyethylene sorbitan fatty acid esters; polyoxyethylene-polyoxypropylene block copolymers; polyglyceryl fatty acid esters; polyoxyethylene glycerides; polyoxyethylene vegetable oils; polyoxyethylene hydrogenated vegetable oils, and mixtures thereof. The glyceride can be a monoglyceride, diglyceride, triglyceride, or a mixture thereof.

In certain other embodiments, the surfactants used are non-ionic hydrophilic surfactants that are reaction mixtures of polyols and fatty acids, glycerides, vegetable oils, hydrogenated vegetable oils or sterols. These reaction mixtures are largely composed of the transesterification products of the reaction, along with often complex mixtures of other reaction products. The polyol can be glycerol, ethylene glycol, polyethylene glycol, sorbitol, propylene glycol, pentaerythritol, a saccharide, or a mixture thereof.

The hydrophilic surfactant can also be, or include as a component, an ionic surfactant. Examples of ionic surfactants include alkyl ammonium salts; bile acids and salts, analogues, and derivatives thereof; fusidic acid and derivatives thereof; fatty acid derivatives of amino acids, oligopeptides, and polypeptides; glyceride derivatives of amino acids, oligopeptides, and polypeptides; acyl lactylates; mono-, diacetylated tartaric acid esters of mono-, diglycerides; succinylated monoglycerides; citric acid esters of mono-, diglycerides; alginate salts; propylene glycol alginate; lecithins and hydrogenated lecithins; lysolecithin and hydrogenated lysolecithins; lysophospholipids and derivatives thereof; phospholipids and derivatives thereof; salts of alkylsulfates; salts of fatty acids; sodium docusate; carnitines; and mixtures thereof.

In certain embodiments the ionic surfactants include bile acids and salts, analogues, and derivatives thereof; lecithins, lysolecithin, phospholipids, lysophospholipids and derivatives thereof; salts of alkylsulfates; salts of fatty acids; sodium docusate; acyl lactylates; mono-, diacetylated tartaric acid esters of mono-, diglycerides; succinylated monoglycerides; citric acid esters of mono-diglycerides; carnitines; and mixtures thereof.

Examples of ionic surfactants include lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, chenodeoxycholate, glycodeoxycholate, glycochenodeoxycholate, taurochenodeoxycholate, ursodeoxycholate, tauroursodeoxycholate, glycoursodeoxycholate, cholylsarcosine, N-methyl taurocholate, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

In certain embodiments, ionic surfactants used include lecithin, lysolecithin, phosphatidylcholine, phosphatidylethanolamine, phosphatidylglycerol, lysophosphatidylcholine, PEG-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholate, taurocholate, glycocholate, deoxycholate, taurodeoxycholate, glycodeoxycholate, cholylsarcosine, caproate, caprylate, caprate, laurate, oleate, lauryl sulfate, docusate, and salts and mixtures thereof. In at least one embodiment, the ionic surfactant is selected from lecithin, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, taurocholate, caprylate, caprate, oleate, lauryl sulfate, docusate, and salts and mixtures thereof.

Examples of lipophilic surfactants include alcohols; polyoxyethylene alkylethers; fatty acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid derivatives of mono/diglycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; polyoxyethylene hydrogenated vegetable oils; and mixtures thereof.

As with the hydrophilic surfactants, lipophilic surfactants can be reaction mixtures of polyols and fatty acids, glycerides, vegetable oils, hydrogenated vegetable oils, and sterols.

In certain embodiments, the lipophilic surfactants include one or more selected from the group comprising fatty acids; lower alcohol fatty acid esters; polyethylene glycol glycerol fatty acid esters; polypropylene glycol fatty acid esters; polyoxyethylene glycerides; glycerol fatty acid esters; acetylated glycerol fatty acid esters; lactic acid derivatives of mono/diglycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; and reaction mixtures of polyols and fatty acids, glycerides, vegetable oils, hydrogenated vegetable oils, sterols, and mixtures thereof.

In certain other embodiments, the lipophilic surfactants include one or more selected from the group comprising lower alcohol fatty acids esters; polypropylene glycol fatty acid esters; propylene glycol fatty acid esters; glycerol fatty acid esters; acetylated glycerol fatty acid esters; lactic acid derivatives of mono/diglycerides; sorbitan fatty acid esters; polyoxyethylene vegetable oils; and mixtures thereof. Among the glycerol fatty acid esters, the esters can be mono- or diglycerides, or mixtures of mono- and diglycerides, where the fatty acid moiety is a C6 to C22 fatty acid.

Other embodiments include lipophilic surfactants which are the reaction mixture of polyols and fatty acids, glycerides, vegetable oils, hydrogenated vegetable oils, and sterols. Examples of polyols are polyethylene glycol, sorbitol, propylene glycol, pentaerythritol, and mixtures thereof.

Combinations of solubility enhancers (i.e. surfactants) can be used. Examples of macrogol fatty acid esters useful as solubility enhancers include GELUCIRE® 50/13 and GELUCIRE® 44/14. In at least one embodiment the solubility enhancer is GELUCIRE® 50/13. The solubility enhancer can be present in an amount of from about 0.1% to about 70% by weight of the microparticle. For example, in certain embodiments, the solubility enhancer is present in an amount of from about 1% to about 50%; in other embodiments from about 10% to about 30%; in still other embodiments from about 15% to about 25% by weight of the microparticle. In at least one embodiment the solubility enhancer is present in an amount of about 20% by weight of the microparticle.

It is contemplated that in some embodiments, one or more other pharmaceutically acceptable excipients consistent with the objects of the present invention can be used in the microparticles, such as a lubricant, a binder, a pH modifier, a filler and/or a glidant.

The process for manufacturing the drug-containing microparticles of certain embodiments of the present invention by spheronization are not limited to the CEFORM™ technology, and any other technology resulting in the formation of the microparticles consistent with the objects of the present invention can also be used. For example, microparticles of certain embodiments of the invention can also be manufactured by extrusion/spheronization, granulation or pelletization.

Extrusion/spheronization is a multi-step process used to make uniformly sized spherical particles. The technique offers the ability to incorporate high levels of active ingredients without producing excessively large particles. The main steps in the process are:

Dry-mixing of ingredients to achieve a homogenous powder dispersion;

Wet massing using for example a high-shear wet granulator to form rod shaped particles of uniform diameter;

Extrusion to form rod-shaped particles of uniform diameter;

Spheronization to round off the rods into spherical particles;

Screening to achieve the desired narrow particle size distribution.

The mixing vessel used for dry-mixing can be of any size and shape compatible with the size of the formulation to be produced. For example, commercially available mixing devices such as planetary mixers, high shear mixers, or twin cone blenders can be used. If relatively small quantities of formulation are to be prepared, a simple mortar and pestle can be sufficient to mix the ingredients. The type of mixing vessel would be apparent to one skilled in the pharmaceutical art. The moistened mass formed by wet-massing in conventional granulation equipment is extruded through a perforated mesh in order to produce cylindrical filaments. The port of the meshes can determine the diameter of the filaments. A port ranging from about 0.2 mm to about 3 mm can be used in this process. In at least one embodiment utilizing this process, the port ranges from about 0.4 mm to about 2 mm. The extrusion can be carried out using screw, double screw, "sieve and basket" kind, "roll extruder", "ram extruder" extruders or any other pharmaceutically acceptable means to produce cylindrical filaments. In certain embodiments utilizing this extrusion/spheronization process, a double screw coaxial extruder is used. The spheronization device comprises a hollow cylinder with a horizontal rotating plate. The filaments are broken in short segments which are transformed in spherical or quasi-spherical particles on the upper surface of the rotating plate at a velocity ranging from about 200 rpm to about 2,000 rpm. The particles can be dried in any pharmaceutically acceptable way, such as for example by air drying in a static condition. The particles are used as they are or they are coated to obtain granules to use in tablets, capsules, packets or other pharmaceutical formulations.

A prophetic example of an extrusion/spheronization formulation comprising bupropion hydrobromide can be as follows: In this example, the bupropion hydrobromide can be present in an amount of from about 1% to about 80% w/w. In certain embodiments within this example, the bupropion hydrobromide is present in an amount of from about 1% to about 50% w/w; in other embodiments from about 10% to about 30%; and in still other embodiments about 10% w/w. In this example, the filler can be present in an amount of from about 0% to about 80% w/w. In certain embodiments of this example, the filler is present in an amount of from about 10% to about 60%; and in other embodiments at about 40% w/w. In this example, the microcrystalline cellulose can be present in an amount of from about 10% to about 90% w/w. In certain embodiments of this example, the microcrystalline cellulose is present in an amount of from about 10% to about 70%; and in other embodiments from about 20% to about 50% w/w. In this example, the binder can be present in an amount of from about 0% to about 10% w/w. In certain embodiments of this example, the binder is present in an amount of from about 1% to about 8%; and in other embodiments from about 2% to about 4% w/w. In this example, water can be present in an amount of from about 10% to about 80% w/w. In certain embodiments of this example, water is present in an amount of from about 15% to about 70%; and in other embodiments from about 20% to about 50% w/w. Suitable fillers that can be used in this example include but are not limited to calcium phosphate dibasic, tricalcium phosphate, calcium carbonate, starch (such as corn, maize, potato and rice starches), modified starches (such as carboxymethyl starch, etc.), microcrystalline cellulose, sucrose, dextrose, maltodextrins, lactose, and fructose. Suitable lubricants that can be used in this example include but are not limited to metal stearates (such as calcium, magnesium on zinc stearates), stearic acid, hydrogenated vegetable oils, talc, starch, light mineral oil, sodium benzoate, sodium chloride, sodium lauryl sulfate, magnesium lauryl sulfate, sodium stearyl fumarate, glyceryl behenate and polyethylene glycol (such as CARBOWAX™ 4000 and 6000). Suitable antiadherents in this example include but are not limited to colloidal silicon dioxide. Suitable binders in this example include but are not limited to ethyl cellulose, a polymethacrylate polymer, polyvinylalcohol, polyvinyl pyrrolidone, polyvinylpyrrolidone-vinylacetate copolymer (e.g. KOLLIDON® VA64) hydroxyethylcellulose, low molecular weight hydroxypropylmethylcellulose (e.g. viscosity of about 1-50 cps at about 20° C.; about 2-12 cps at about 20° C.; or about 4-6 cps at about 20° C.), hydroxypropylcellulose polymethacrylates, and mixtures thereof.

The drug-containing microparticles formed by extrusion/spheronization in this prophetic example can be produced using cross-linked amphiphilic polymers by the following steps: (a) the mixing of one or more cross-linked amphiphilic polymers with bupropion hydrobromide and optionally other pharmaceutical excipients in order to obtain a uniform mixture in the form of dry powder to which a suitable amount of liquid is added to obtain a pasty consistency; (b) the extrusion of the mixture obtained from step (a) through a perforated mesh in order to obtain cylindrical filaments having desired length and diameter; (c) the spheronization of the filaments in order to obtain a product in the form of spherical multiparticulates; (d) the drying of the product; and (e) the optional depositing of a drug on the surface of the microparticles. "Cross-linked amphiphilic polymer" refers in this example to polymers showing characteristics of swellability in the whole pH range of aqueous solutions and also in solvents or solvent mixtures having different polarity characteristics. The polymers can be cross-linked either physically through the interpenetration of the macromolecular meshes, or chemically, thus showing points of link among the macromolecular chains. Non-limiting examples of such polymers include cross-linked polyvinyl pyrrolidone, sodium carboxymethylcellulose, sodium glycolate starch and dextrans. Optional excipients include dispersing, emulsifying, wetting agents and coloring agents. The expression "uniform mixture" in this example means that the components of the mixture are uniformly dispersed in the formulation by a mixing process which assures the uniform distribution of each component. A reasonable mixing time can range from about 1 to about 60 minutes using one of the mixing equipments conventionally used for the dry mixing of the powders (e.g. "V", fixed body, rotating body, sigma mixers). The term "liquid" in this example means any liquid substance or mix (solution or emulsion) of liquids of normal pharmaceutical use able to moisten the powder mix, as for example water, aqueous solutions having different pH, organic solvents of normal pharmaceutical use (e.g. alcohols, chlorinated solvents), and oils. Among the oils and surfactants which can be used in this example are: natural oils, either saturated or unsaturated (olive, peanut, soybean, corn, coconut, palm, sesame and similar oils); semisynthetic and synthetic mono-, di- and triglycerides containing saturated and/or unsaturated fatty acids and their polyhydroxyethylated derivatives (caprico-caprilic triglycerides [MYGLIOL™, CAPTEX™, LABRAFAC™, LIPO™], saturated or unsaturated polyhydroxylated triglycerides of various kind [LABRAFIL™, LABRAFAC™Hydro, GELUCIRE™]); liquid waxes (isopropyl myristate, isopropyl-caprinate, -caprylate, -laurate, -palmitate, -stearate); fatty acids esters (ethyl oleate, oleyl oleate); silicone oils; polyethylene glycols (PEG 200, PEG 400, PEG 600, PEG 1000, and so on); polyglycolic glycerides (for example LABRASOL™); polyglycols (propylene glycol, tetraglycol, and ethoxydiglycol (TRANSCUTOL™), sorbitan-esters of fatty acids (for example SPAN®, ARLACEL®, BRIJ®), polyoxyethylenesorbitan esters of fatty acids (for example TWEEN®, CAPMUL®, LIPOSORB®), polypropylene oxide-polyethylene oxide (Poloxamer) copolymers, polyethylene glycol esters (PEG)-glycerol (LABRASOL®, LABRAFIL®), PEG esters and long chain aliphatic acids or alcohols (for example CREMOPHOR®), polyglycerid esters (PLUROL®), saccharide, fatty acid esters (sucro-esters), and mixtures thereof. Moreover, anionic surfactants (for example sodium lauryl sulfate, sodium stearate, sodium oleate) or cationic surfactants (for example tricetol), can be used as well as lecithins, phospholipids and their semi-synthetic or synthetic derivatives. Also bupropion hydrobromide and/or excipients can be dissolved, dispersed and/or emulsified in such liquids.

In a particular embodiment formed by an extrusion/spheronization process from the prophetic example described above, the moistening liquid comprises an oil/surfactant system wherein the bupropion hydrobromide optionally emulsified with an aqueous phase is dissolved or dispersed. The amount of liquid with respect to the solid used in the preparation of the mixture can range from about 1% to about 80% by weight. As a prophetic example of this embodiment, a mixture of bupropion hydrobromide and KOLLIDON™ CL in a ratio equal to about 1:3 by weight is co-milled obtaining the mixture in the form of powder having about 100% of granulometry lower than about 50 microns. The mixture is moistened using a liquid demineralized water containing KOLLIDON™ 25 (polyvinyl pyrrolidone, BASF) in a solution 3% w/w. The extrusion is carried out forcing the moistened mass through a threader having diameter of the holes equal to about 1 mm. The operative parameters in this prophetic example can be as follows: powder flow rate: about 4.5 kg/h; liquid flow rate: about 4.1 kg/h; torsional stress: about 27%; head temperature: about 46° C.; and screw rotation velocity: about 140 rpm. The extrusion filaments are then processed in a spheronizer adjusted at a velocity equal to about 1,000 rpm for about 2 minutes. The obtained microparticles are then dried in a fluid bed for about 2 hours to a maximum temperature equal to about 59° C. At the end of the drying the product is discharged and is mechanically screened separating the fraction ranging from about 0.7 mm to about 1.2 mm.

Another prophetic example of a drug-containing microparticle embodiment of the invention formed by an extrusion/spheronization process, uses a charged resin, the steps of which can comprise: (a) adding the charged resin, bupropion hydrobromide and other excipients, to a mixing vessel; (b) mixing the ingredients to obtain a uniform mixture; (c) adding a granulating solution—a liquid capable of wetting the dry mixture. Liquids resulting in conversion of the dry powder mixture into a wet granulation that supports subsequent extrusion and spheronization (marumerization) are included. Typically, water or aqueous solutions are employed. Alcohols, typically ethanol or isopropanol, can be included with the granulating water to enhance the workability of the granulation. In another embodiment of this invention, one or more of the components of the formulation is first dissolved in water and this solution is used to produce the wet granulation. An active ingredient or an excipient which is present at very low concentration can initially be dissolved or suspended in the granulating solvent to assure more uniform distribution throughout the formulation. (d) granulating the mixture until a uniform granulation results; (e) extruding the wet granulation through a screen to produce strands of granulation; (f) spheronizing the strands of granulation to produce spherical multiparticulates; and (g) collecting and drying the spherical multiparticulates. By "charged resin" is meant in this example to mean a polymer with ionizable functional groups that becomes useful in the embodiment of this invention. This broadly encompasses any polymer that upon ionization, is capable of producing cationic or anionic polymeric chains and which support spheronization. Typically from about 10% to about 70% by weight of the spherical multiparticulate is charged resin. Non limiting examples of these charged resins include sodium polystyrene sulfonate which is sold under the trade name AMBERLITE IRP-69™ by Rohm and Haas, Co., Philadelphia, Pa.; the chloride salt of cholestyramine resin USP, sold as AMBERLITE IRP-276™ by Rohm and Haas, Co., Philadelphia, Pa.; the acid form of methacrylic acid-divinyl benzene, sold as AMBERLITE IRP-64™ by Rohm and Haas Co., Philadelphia, Pa.; carboxypolymethylenes sold under the trade names CARBOPOL™ 974P and CARBOPOL™ 934P by B.F. Goodrich, Inc., Brecksville, Ohio, and sodium polyacrylate, sold under the trade name AQUA-KEEP™ J-550 by Seitetsu Kagaku, Japan. In order for the resin to maintain the desired degree of ionization, agents which produce an acidic or basic environment during granulation and spheronization can be included within the formulation. Among the groups of compounds that can exert this effect are acids, bases, and the salts of acids and bases such as adipic acid, citric acid, fumaric acid, tartaric acid, succinic acid, sodium carbonate, sodium bicarbonate, sodium citrate, sodium acetate, sodium phosphates, potassium phosphates, ammonium phosphate, magnesium oxide, magnesium hydroxide, sodium tartrate, and tromethamine. Certain compounds can be added to the granulation to provide the proper degree of hydration of the charged resin, medicament and excipients. These hydrating agents include sugars such as lactose, sucrose, mannitol, sorbitol, pentaerythritol, glucose and dextrose. Polymers such as polyethylene glycol as well as surfactants and other organic and inorganic salts can also be used to modulate polymer hydration.

In another prophetic example, multiparticulates containing bupropion hydrobromide can be obtained as follows:

| Component | Percent w/w |
| --- | --- |
| Bupropion HBr | about 8.7 |
| Disodium Phosphate | about 7.0 |
| Monosodium phosphate | about 1.7 |
| Sodium dodecyl sulfate | about 21.7 |
| Sodium Chloride | about 17.4 |
| Povidone 29-32K | about 8.7 |
| AMBERLITE IRP-69 | about 34.8 |
| Butylated Hydroxyanisol | about 0.0002 |

In this prophetic example, approximately 5.75 kg of the above formulation is mixed in a planetary mixer for about 15 minutes. The butylated hydroxyanisol is dissolved in about 60 cc of ethanol and water is added to bring the final solution to a volume of about 133 cc. This solution is added to the planetary mixer over about a two (2) minute period. The mixer is then granulated with seven aliquots of about 250 cc of water added over about a fifteen minute period. The granulation thus formed is extruded through a 1.0 mm screen and aliquots spheronized by marumerization at approximately 1200 rpm for approximately 10 minutes each. The spherical multiparticulates formed are then dried at about 50° C. for about 24 hours.

Another embodiment of this invention involves the production of drug containing microparticles in the form of 'pearls'. Pearls can be manufactured by mixing bupropion hydrobromide with one or more pharmaceutical excipients in molten form; the melt is forced to pass through a nozzle which is subjected to a vibration; the pearls formed are allowed to fall in a tower countercurrentwise to a gas; and the solid pearls are collected in the bottom of the tower. In this example, the quantity of bupropion hydrobromide can vary from about 5% to about 95% by weight; and in certain embodiments from about 40% to about 60% by weight. The additives which enable the crystallization of the supercooled product to be induced in this example can be chosen from the following: fatty alcohols such as: cetyl alcohol, stearyl alcohol, fatty acids such as: stearic acid, palmitic acid, glycerol esters such as: glycerol palmitostearate, the glycerol stearate marketed under the mark PRECIROL™, the glycerol behenate marketed under the mark COMPRITOL™, hydrogenated oils such as: hydrogenated castor oil marketed under the mark CUTINA™ HR, fatty acid salts such as: magnesium or calcium stearate, polyols such as: mannitol, sorbitol, xylitol, waxes such as: white wax, carnauba wax, paraffin wax, polyoxyethylene glycols of high molecular weight, and esterified polyoxyethylenes such as: PEG-32 distearate, and PEG-150 distearate. To these crystallization additives it can be desirable in this example to add polymers which are soluble or dispersible in the melt, and which provide a controlled and adjustable dissolution of the pearls when they are used, examples of which include: cellulose derivatives (hydroxypropyl cellulose, hydroxypropyl methyl cellulose, hydroxyethyl cellulose, ethyl cellulose, carboxymethyl cellulose), acrylic resins (marketed under the mark EUDRAGIT®), polyvinyl acetates (marketed under the mark RHODOPAS®), polyalkylene (ethylene propylene), polylactic, maleic anhydride and silicone resins. In addition, inorganic additives can be added to accelerate the solidification of the active substances, examples of which include: silicas, inorganic oxides such as titanium or iron oxide, phosphates, carbonates, clays, and talc. In addition, a surface-active agent can be added to improve the dispersion of the active substance in the crystallization additive, examples of which include: sorbitol esters, the polyoxyethylene polysorbates marketed under the mark TWEEN®, and glycols such as glycerine or propylene glycol. The process for the preparation of pearls comprise preparing a melt of the bupropion hydrobromide with one or more excipients. This melt can be prepared by separately melting the various constituents and then mixing them or by melting the mixture of the constituents, possible insoluble compounds being added at the end of the melting so as to obtain a homogeneous mass. The nature of the constituents of the melt is chosen by the person skilled in the art, which is considered as a function of the compatibility of the constituents, the viscosity of the mixture of constituents, the nozzle diameter, the hydrophilicity of the active substance, the surface tension of the active substance, the particle size of the insoluble additives, the flow rate of the nozzle, the temperature of the tower, its height and, above all, the size of the desired pearls, the proportion of bupropion hydrobromide to be included therein and the desired release time of the active substance.

Alternative procedures other than extrusion or spheronization for manufacturing drug-containing microparticles can include wet granulation, solvent granulation and melt granulation. All of these techniques involve the addition of an inactive binder to aggregate smaller particles into larger granules. For example, wet granulation and solvent granulation involve the addition of a liquid binder which aggregates the active materials and excipients into granules. After granulation, the liquid can be removed by a separate drying step. Melt granulation is similar to wet granulation, but uses a low melting point solid material as a binder. The solid binder in melt granulation is melted and acts as a liquid binder thereby aggregating the powdered active material and excipients into granules. The binder thereby, can be incorporated into the granules when the granules cool.

Certain embodiments of the present invention include microparticles manufactured by a process for producing granules by rotomelt granulation that comprises mixing bupropion hydrobromide and a powdered excipient material that has a higher melting point than bupropion hydrobromide in a zone wherein both powdered materials are maintained in a fluidized state by a rising stream of gas in an apparatus having a rapidly rotating horizontal-disk located within a vertical vessel having a bottom surface; wherein said rapidly rotating disk is located on the bottom surface of the vertical vessel wherein said gas is at a temperature sufficient to cause the bupropion hydrobromide to at least partially melt thereby causing said powdered materials to aggregate and form granules. Other embodiments of the present invention include microparticles manufactured by a process for producing granules by rotomelt granulation comprising mixing powdered binder material and bupropion hydrobromide wherein the bupropion hydrobromide has a higher melting point than the powdered binder material in a zone wherein both powdered materials are maintained in a fluidized state by a rising stream of gas in an apparatus having a rapidly rotating horizontal-disk located within a vertical vessel having a bottom surface; and wherein said rapidly rotating disk is located on the bottom surface of the vertical vessel wherein said gas is at a temperature sufficient to cause the powdered binder material to at least partially melt thereby causing said powdered materials to aggregate and form granules.

In rotomelt granulation, one of the feed powders must have a lower melting point than the other powder in order to serve as a binder. The feed powders are introduced into a vertical vessel with rotatable horizontal-disk located in the bottom of the vessel. The powder is maintained in fluidized state by at least one stream of filtered air being circulated from the bottom of the vertical vessel through one or more inlets. The rotatable horizontal disk is then rotated while the air supplied to fluidize the powder is maintained at a temperature sufficient to soften or melt the lower melting point powder. The temperature to which the binder must be heated to soften can be empirically determined by observing the formation of granules at various temperatures for various binders. It is presently believed that temperatures from about 3° C. to about 5° C. below the melting point or melting range provides sufficient softening to result in granule formation. The lower melting point powder then acts as a binding agent to promote the aggregation of powder particles into granules. Suitable powders for use in rotomelt granulation have a diameter size in the range of from about 5 microns to about 150 microns; and in certain embodiments have a diameter size in the range of about 35 microns to about 80 microns. The temperature which the components will be exposed to depends on the binder employed to aggregate the powders. Generally, the melting point of the binder is above about 30° C.; and in certain embodiments is below about 100° C.

The powders used in these microparticles manufactured by rotomelt granulation can be formed into granules by at least two alternative granulation mechanisms. The first mechanism for granule formation utilizes a larger particulate binder and a smaller particulate powder. The temperature during the rotomelt granulation is then elevated only to the point where the external surface of the binder particles become tacky. As the second powdered material of a smaller size is contacted with the tacky surface it forms a microlayer on the surface of the binder particle. This granulation mechanism results in granules which have size distribution similar to the original binder particles employed. Alternatively, the rotomelt granulation can be conducted at a temperature at which the binder acts as a cement bridging the gaps between the unmelted particles (this is referred to as agglomeration). This mechanism results in the formation of granules where the components are intermingled. For each binder used the mechanism can be controlled primarily by the temperature at which the rotomelt granulation is performed. Those skilled in the art will appreciate that the granules formed can be observed by electron microscopy to determine the type of granulation process occurring. If one particular type of granule is desired, the process conditions or starting materials can be varied to produce the desired granules.

In at least one embodiment of the present invention, bupropion hydrobromide is melted to act as a binding agent in the rotomelt granulation process. Examples of suitable excipients include those selected from the following: fillers, lubricants, glidants and antiadherents. Suitable fillers include but are not limited to calcium phosphate dibasic, tricalcium phosphate, calcium carbonate, starch (such as corn, maize, potato and rice starches), modified starches (such as carboxymethyl starch, etc.), microcrystalline cellulose, sucrose, dextrose, maltodextrins, lactose, and fructose. The amount of binder added to aggregate the particles into granules can be in the range of from about 10% w/w to about 80% w/w; and in certain embodiments is in the range of from about 30% w/w to about 70% w/w of the powdered materials in the rotomelt granulation. The remaining weight percentage to provide a total of about 100% w/w can be one or more suitable powdered pharmaceutical actives. Optionally the rotomelt granulation can also contain from about 0% to about 60% w/w of one or more powdered excipients wherein the total weight of all the powdered materials equals about 100% w/w. The binder used in these embodiment of the invention can be a pharmaceutically acceptable dry powder having a particle size in the range of from about 5 µm to about 150 µm; and in certain embodiments in the range of from about 35 µm to about 80 µm. Suitable binders for rotomelt granulation are low melting point powdered binders, examples of which include: polyethylene glycol 4000, polyethylene glycol 6000, stearic acid, and low melting point waxes. Suitable low melting point waxes include but are not limited to glyceryl monostearate, hydrogenated tallow, myristyl alcohol, myristic acid, stearyl alcohol, substituted monoglycerides, substituted diglycerides, substituted triglycerides, white beeswax, carnauba wax, castor wax, japan wax, acetylate monoglycerides and combinations thereof. The binders can have a melting point of from about 30° C. to about 100° C.; and in certain embodiments from about 40° C. to about 85° C.

As a prophetic example of these embodiments that are manufactured by a rotomelt granulation process, about 320 g of bupropion hydrobromide and about 80 g PEG 8000 is dry blended and poured into a Glatt 1.1 chamber set-up as a rotary granulator with a longitudinal plate. Inlet air temperature is set to about 60° C. and the product chamber heated to approximately 50° C. The blend is fluidized at approximately 120 m3/hr and the frictional plate set to about 900 rpm. The product chamber temperature is raised to about 60° C. and then gradually reduced to about 20° C. over a period of approximately 20 minutes, during which spheronization is achieved.

Other embodiments of the invention involve the formation of a microparticle that has a core which includes bupropion hydrobromide and a compound which is sweet in taste and which has a negative heat of solution. Examples of compounds falling into this category include mannitol and sorbitol. Sugars or artificial sweeteners to which, for example, menthol have been added can also work as well. A binder and/or other excipient can also be disposed within the core. The amount of sweetening compound used can depend on a number of factors including the size of the resulting microparticles, the size or volume of the resulting tablet, the sturdiness of the microparticle-coated microparticulant, the speed at which the tablet will disintegrate in the mouth, the degree of sweetness imparted by the particular sweetener used, either in the microparticle or in the tablet, or both, the amount of drug used, and the like. For example, particularly rugged microparticles can be less likely to break during chewing and/or compression. Therefore, the amount of material provided to protect against the release of objectionably flavored material can be lessened. In other cases a greater relative amount of sweetening compound can be used. Generally, the amount of sweetening material used will range from greater than zero to about 80% of the weight of the resulting microparticles. The sweetener and bupropion hydrobromide can be combined in any number of known ways, such as for example by wet granulation, dry granulation, agglomeration, or spray coating. For example, the sweetener can be used as an adsorbent for the active agent. Alternatively, particles of each can also be simply mixed together. One or more binders, or other adjuvants can also be used in the formulation of a tablet as well. Binders in these embodiments include, for example: starch (for example, in an amount of from about 5% to about 10% as an aqueous paste); pregelatinized starch (for example, in an amount of about 5% to about 10% added dry to powder); gelatin (for example, in an amount of from about 2% to about 10% as an aqueous solution, or about 2% in starch paste); polyvinylpyrrolidone (for example, in an amount of from about 2% to about 20% in an aqueous or alcoholic solution); methylcellulose (for example, in an amount of from about 2% to about 10% as an aqueous solution); sodium carboxy methylcellulose (for example, in an amount of from about 2% to about 10% as an aqueous solution); ethylcellulose (for example, in an amount of from about 5% to about 10% as an alcohol or hydroalcoholic solution); polyacrylamides (Polymer JR) (for example, in an amount of from about 2% to about 8% as an aqueous solution); polyvinyloxoazolidone (Devlex) (for example, in an amount of from about 5% to about 10% as an aqueous or hydroalcoholic solution); and polyvinyl alcohols (for example, in an amount of from about 5% to about 20% in aqueous solutions). Other adjuvants can also be used in forming the core of the microparticles of the present embodiments of the invention, non-limiting examples of which include: calcium sulfate NF, Dibasic Calcium phosphate NF, Tribasic calcium sulfate NF, starch, calcium carbonate, microcrystalline cellulose, modified starches, lactose, sucrose and the like, STA-RX™, AVICEL™, SOLKA-FLOC™ BW40, alginic acid, EXPLOTAB™, AUTOTAB™, guar gum, kaolin VECGUM™, and bentonite. These adjuvants can be used in up to about 20% w/w; and in certain embodiments are present in an amount of from about 3% to about 5% w/w.

As a prophetic example of these embodiments that have a core comprising bupropion hydrobromide and a compound which is sweet in taste, bupropion hydrobromide can be granulated using the following procedure: Polyvinylpyrrolidone K-30 USP (about 240.0 gm) is dissolved into distilled water (about 1,890.0 gm) with agitation. Mannitol powder USP (about 11,160 gm) and bupropion hydrobromide (about 600.0 gm) are placed in a Zanchetta 50-liter granulator/processor. After an initial two-minute dry mix of the powders with the chopper on and the propeller adjusted to about 200 rpm, the polyvinylpyrrolidone K-30 solution is slowly sprayed into the mixing powder bed using an air-driven spray system. The total time of granulation including the time of solution addition is approximately eight minutes. The granulation end-point is determined visually and by the consistency of the resulting material. The material is then discharged onto trays and dried at about 80° C. utilizing supplied dry air for a period of about six hours to a moisture content of not more than about 0.08 percent. The dried material is then passed through a hammermill (knives forward) equipped with a U.S. #40 (420 micron) screen.

Other embodiments of this invention involve the combined granulation and coating of bupropion hydrobromide into microparticles in which the drug is at least partly located within the microparticle core but capable of immediate release. To do this, the bupropion hydrobromide and a granular disintegrant are first dry-mixed; the powder obtained is then granulated, in the presence of a mixture of excipients comprising at least one binder capable of binding the particles together to give grains; the grains thus formed are then coated by spraying with a suspension comprising at least one coating agent and a membrane disintegrant; and then the coated granules obtained are dried. The distinction between the actual granulation and coating steps is relatively theoretical, insofar as, even though the primary function of the binder used in the granulation step is to bind together the particles, it nevertheless already partially coats the grains formed. Similarly, even though the primary function of the coating agent used in the actual coating step is to complete the final coating of each of the grains, it may, however, arbitrarily bind other coated grains by a mechanism of granular agglomeration. The binder and the coating agent are chosen from the group comprising cellulose polymers and acrylic polymers. However, even though the binder and the coating agent are chosen from the same group of compounds, they nevertheless differ from each other in their function as previously mentioned. Among the cellulose polymers that can be advantageously chosen are ethylcellulose, hydroxypropylcellulose (HPC), carboxymethylcellulose (CMC) and hydroxypropylmethylcellulose (HPMC), or mixtures thereof. Among the acrylic polymers that can be advantageously chosen are the ammonio-methacrylate copolymer (EUDRAGIT® RL or RS), the polyacrylate (EUDRAGIT® NE) and the methacrylic acid copolymer (EUDRAGIT® L or S), EUDRAGIT® being a registered trademark of Rohm. In at least one embodiment, the binder is of the same nature as the coating agent. To further accelerate the release of the bupropion hydrobromide, the coating suspension also comprises a permeabilizer which, on account of its intrinsic solubility properties, causes perforation of the membrane coating, thus allowing the bupropion hydrobromide to be released. Non-limiting examples of permeabilizers include povidone and its derivatives, polyethylene glycol, silica, polyols and low-viscosity cellulose polymers. Polymers of the type such as hypromellose, whose viscosity is equal to about 6 centipoises, are used, for example, as low-viscosity cellulose polymer. In at least one embodiment, the dry-mixing of initial powder and the granulation, coating and drying steps are performed in a fluidized bed. In this case, the initial powder mixture is first fluidized before being granulated by spraying said powder with the excipient mixture comprising at least the binder, the grains obtained then being coated by spraying with the coating suspension, the coated granules formed finally being dried in the fluidized bed. In at least one embodiment, the mixture of excipients used during the granulation step and the coating suspension used during the coating step form a single mixture. In this case, the granulation step can be distinguished from the spraying step by varying different parameters, such as the rate of spraying of the mixture and the atomization pressure of said mixture. Thus, only some of the mixture of excipients is used during the granulation step, while the other portion can be used during the coating step. Thus, the rate of spraying of the coating suspension is higher during the granulation step than during the coating step, whereas the atomization pressure of the coating suspension is lower during the granulation step than during the coating step. In practice, at the laboratory scale in a fluidized-bed device, for example of the type such as Glatt GPCG1, during the granulation step, the rate of spraying of the coating suspension is from about 10 grams/minute to about 25 grams/minute, and the atomization pressure is from about 1 bar to about 1.8 bar. During the coating step, the rate of spraying of the coating suspension is from about 5 grams/minute to about 15 grams/minute, while the atomization pressure is from about 1.5 bar to about 2.5 bar. In at least one embodiment, from about 10% to about 20% of the mixture of excipients is sprayed during the granulation step, the remainder being sprayed during the coating step.

As a prophetic example of these embodiments that involve the combined granulation and coating of bupropion hydrobromide into microparticles in which the drug is at least partly located within the microparticle core but capable of immediate release, the microparticles can be manufactured according to the following process: A granulation solution is first prepared by dissolving about 48 g of ethylcellulose in about 273 g of ethyl alcohol. A coating suspension is then prepared by mixing about 97 g of ethylcellulose, about 28.5 g of polyethylene glycol 6000, about 26 g of sodium croscarmellose, about 10 g of precipitated silica and about 27.5 g of aspartam in about 1900 g of ethyl alcohol, until a homogeneous suspension is obtained. The powder mixture consisting of about 700 grams of bupropion hydrobromide and about 35 grams of Acdisol is then fluidized. The granulation is then started by spraying the granulation solution for about 15 to about 20 minutes at a spraying rate of about 25 grams/minute and a suspension atomization pressure of about 0.8 bar. The actual coating is then performed by spraying the coating suspension for about 1 hour 30 minutes at a spraying rate of about 15 to about 20 grams/minute and a suspension spraying pressure of about 1.5 bar.

Other embodiments of the invention involve coating the bupropion hydrobromide material, thereby forming a drug-containing microparticle. One such process for achieving this involves:

Blending and fluidizing a powder mix of active principle and an adjuvant in order to obtain individual grains, Separately liquefying under warm conditions a lipid matrix agent comprising either an ester of behenic acid and alcohol or an ester of palmitic/stearic acid and alcohol, Coating the fluidized powder mix under warm conditions by spraying the lipid matrix agent over the individual grains, Lowering the temperature of the combined product in order to allow the lipid matrix agent to solidify.

This process does not require an evaporation phase or a drying phase, since it does not require a wet-route or solvent-route granulation step, thus making it possible to be freed from any risk due to the presence of toxic residues in the final product. Furthermore, it is not necessary to carry out the quantitative determination of the traces of solvents, an analysis that can be very expensive. According to the process of this embodiment of the invention, the spraying conditions and thus the coating characteristics can be modified, in order to vary the release profile of bupropion hydrobromide, by varying several parameters, the adjustment characteristics of which remain simple. Thus, the spraying air pressure can be increased in order to promote the formation of a homogeneous film of lipid matrix agent around the grains. Advantageously, the rate of spraying of the lipid matrix agent can simultaneously be decreased. In this case, the bupropion hydrobromide release profile, that is to say a percentage of dissolution as a function of the time, is obtained which can be low, corresponding to a slow release of the drug. Conversely, the spraying air pressure can be decreased in order to promote the agglomeration of the grains with one another. Advantageously, the rate of spraying of the lipid matrix agent can simultaneously be increased. In this case, a release profile of the grains obtained can be obtained which is high, corresponding to a rapid release of bupropion hydrobromide. In practice and according to the mass of powder employed, the value of the rate of spraying of the lipid matrix agent can be from two to four times higher when it is desired to promote the agglomeration of the grains with one another than when it is desired to promote the formation of a homogeneous film around the grains. On the other hand, the value of the spraying air pressure can be from one to two times lower when it is desired to promote the agglomeration of the grains with one another than when it is desired to promote the formation of a homogeneous film around the grains. According to the process for manufacturing these embodiments, it is possible, after having determined a given drug release profile, to vary the values of spraying air pressure and of spraying rate throughout the coating stage, making it possible to promote the formation of a homogeneous film around the grains or to promote the agglomeration of the grains. Once the sequence of the duration of the spraying air pressure and of the spraying rate has been determined, the coating operation can be carried out continuously and automatically. According to another characteristic of the process of manufacturing these embodiments, the temperature of the mixture of liquefied matrix agent and of spraying air is greater by about 35° C. to about 60° C. than the melting temperature of the lipid matrix agent. Likewise, the temperature of the fluidization air and that of the powder is approximately equal to the melting temperature of the lipid matrix agent, plus or minus about 10° C. Furthermore, in order to obtain a mixture of individual grains, an air-operated fluidized bed device or a turbine device can be used. Furthermore, the lipid matrix agent can be sprayed by the air spray technique, that is to say liquid spraying under pressure in the presence of compressed air. According to at least one embodiment, use is made of a powder comprising the drug and the adjuvant. In other words, after mixing and fluidizing the combined constituents of the powder, the lipid matrix agent is sprayed over the individual grains obtained. In order to avoid adhesion of the coated grains obtained, whether in the case where all the grains are treated or whether in the case where only a portion of the grains is treated, a stage of lubrication of the grains is inserted between the coating stage and the stage of putting into a pharmaceutical form. Furthermore, in order to obtain greater stability of the pharmaceutical composition, that is to say in order to minimize modifications relating to the release of the bupropion hydrobromide over time, the granules or tablets obtained in certain embodiments of this example can be subjected to a maturing stage in an oven, for at least about 8 hours, at a temperature of from about 45° C. to about 60° C.; and in certain embodiments at about 55° C.

As a prophetic example of these drug-containing microparticle embodiments that are formed by coating the bupropion hydrobromide material, the drug-containing microparticles can be manufactured according to the following process: A mixture of powder is prepared comprising: bupropion hydrobromide; dicalcium phosphate dehydrate; and polyvinylpyrrolidone. Batches of granules are prepared by a process comprising the following stages: the mixture of powder obtained is sieved; the said powder is mixed, heating while by means of an air-operated fluidized bed, in order to obtain individual grains; the lipid matrix agent (glyceryl behenate, sold under the trade name COMPRITOL® 880 ATO) is liquefied separately at about 120° C.; the lipid matrix agent is sprayed over the heated powder mixture, and, finally, the temperature is lowered in order to allow the lipid matrix agent to solidify. These stages are carried out while varying various parameters, either in order to promote the formation of a homogeneous film around the grains or in order to promote the agglomeration of the grains, in accordance with the following table:

| Parameters | Batch 1 | Batch 2 | Batch 3 | Batch 4 |
|---|---|---|---|---|
| % by weight of lipid matrix agent (COMPRITOL ® 888 ATO) | 5 | 4 | 4 | 5 |
| Fluidization air flow rate (m3/h) | 80 | 110 | 80 | 80 |
| Agglomeration | | | | |
| Atomization air pressure (bar) | 2 | | 1.5 | 1.5 |
| Temperature of the powder bed (° C.) | 70 | | 70 | 74 |
| Spraying rate for COMPRITOL ® (g/min) | 42 | | 40 | 40 |
| Coating | | | | |
| Atomization air pressure (bar) | 2.5 | 3.5 | 2 | 2 |
| Temperature of the powder bed (° C.) | 70 | 66 | 71 | 70 |
| Spraying rate for COMPRITOL ® (g/min) | 41 | 20 | 40 | 40 |

Another embodiment of the invention for coating the bupropion hydrobromide material, thereby forming a drug-containing microparticle, involves the formation of coated microcrystals that can subsequently be incorporated into a tablet. Through selection of the appropriate polymer the microcrystals can possess diversified features such as gastroresistance and controlled release due to the fact that the said coated or non-coated microcrystals and microgranules preserve, after having been shaped in the form of a multiparticulate tablet, their initial properties amongst which are included masking of taste, gastroresistance and controlled release of the bupropion hydrobromide. In certain embodiments of this example, the following non-limiting list of polymers can be selected for coating of the bupropion hydrobromide in conventional fluidized based coating equipment: ethylcellulose (EC); hydroxypropylcellulose (HPC); hydroxypropylmethylcellulose (HPMC); gelatin; gelatin/acacia; gelatin/acacia/vinvylmethylether maleic anhydride; gelatin/acacia/ethylenemaleic anhydride; carboxymethyl cellulose; polyvinvylalcohol; cellulose acetate phthalate; nitrocellulose; shellac; wax; polymethacrylate polymers such as EUDRAGIT® RS; EUDRAGIT® RL or combinations of both, EUDRAGIT® E and EUDRAGIT® NE30D; KOLLICOAT™ SR30D; and mixtures thereof.

Drug-Layered Microparticles

The drug-layered microparticles of certain embodiments can be made by coating an inert particle or core, such as a non-pareil sphere (e.g. sugar sphere), with the bupropion hydrobromide salt and a polymeric binder. In certain embodiments of the drug-layered microparticles, the inert cores include water-insoluble materials such as cellulose spheres or silicon dioxide. In other embodiments, the inert cores include water-soluble materials such as starch, salt or sugar spheres. The inert cores can have a diameter ranging from about 100 microns to about 2000 microns. For example, in certain embodiments the diameter of the inert cores range from about 150 microns to about 1500 microns. In at least one embodiment, the inert cores are sugar spheres NF, containing not less than about 62.5% and not more than about 91.5% of sucrose. In at least one embodiment the inert cores have substantially consistent bulk density, low friability, and low dust generation properties. In at least one embodiment, the inert cores are coated with an osmotic sub-coat comprising an osmotic agent and a polymeric binding agent. Further, the inert cores can initially be coated with a seal-coat to provide a more consistent core surface and to minimize any osmotic effects. The seal-coat layer can be applied to the core prior to the application of the drug, polymeric binder, and any polymeric film layers. In at least one embodiment, the seal-coat layer does not substantially modify the release of the bupropion hydrobromide salt. Examples of suitable sealants that can be used in the seal-coat include permeable or soluble agents such as hydroxypropyl methylcellulose, hydroxypropyl cellulose, ethylcellulose, a polymethacrylate polymer, hydroxypropyl ethylcellulose, xanthan gum, and mixtures thereof. In at least one embodiment the sealant used in the seal-coat is hydroxypropyl methylcellulose. Other agents can be added to improve the processability of the sealant. Examples of such agents include talc, colloidal silica, polyvinyl alcohol, titanium dioxide, micronised silica, fumed silica, glycerol monostearate, magnesium trisilicate, magnesium stearate, and mixtures thereof. The seal-coat layer can be applied from solution (e.g. aqueous) or suspension using a fluidised bed coater (e.g. Wurster coating), or in a pan coating system. Examples of such seal-coats coatings are commercially available such as those sold under the trademarks OPADRY® White Y-1-7000 and OPADRY® OY/B/28920 White, each of which is available from Colorcon Limited, England.

The binding agent of these drug-layered embodiments is used to adhere the bupropion hydrobromide salt layer to the inert core or seal-coat of the core. In certain embodiments, the binding agent is water soluble, possesses sufficiently high adhesivity in order to adhere the bupropion hydrobromide salt layer to the inert core, and possesses an appropriate viscosity to provide substantial adhesion between the inert core and the bupropion hydrobromide salt. In other embodiments the binding agent is water-insoluble. In at least one embodiment the binding agent is ethyl cellulose, a polymethacrylate polymer, polyvinylalcohol, polyvinyl pyrrolidone, polyvinylpyrrolidone-vinylacetate copolymer (such as KOLLIDON® VA64), hydroxyethylcellulose, low molecular weight hydroxypropylmethylcellulose (e.g. viscosity of about 1-50 cps at about 20° C.; about 2-12 cps at about 20° C.; or about 4-6 cps at about 20° C.), hydroxypropylcellulose polymethacrylates, or mixtures thereof. For example, in certain embodiments the composition of the binder for bupropion hydrobromide is from about 1% to about 25% w/w; in other embodiments from about 2% to about 10% w/w; and in still other embodiments from about 3% to about 5% w/w, expressed as a percentage of the total weight of the core.

Solvents can be used to apply the bupropion hydrobromide salt to the inert core, examples of which include lower alcohols such as ethanol, isopropanol and alcohol/water mixtures, acetone and chlorinated hydrocarbons.

The drug-layered microparticles can be prepared by forming a suspension or solution of the binder and the bupropion hydrobromide salt and then layering the suspension or solution on to the inert or sub-coated core using any of the layering techniques known in the art, such as fluidized bed coating or pan coating. This can be affected in a single coating or the process can be carried out in multiple layers, optionally with intervening drying/evaporation steps. This process can be conducted so as to produce microparticles containing a desired amount of bupropion hydrobromide salt and achieve the desired dosage and release thereof upon in-vivo administration.

In certain embodiments, the drug-layered microparticles can be manufactured using for example, the procedure in the following hypothetical experiment: Bupropion hydrobromide (about 2.8 kg) and hydroxypropyl methylcellulose (METHOCEL® E5) (about 0.40 kg) is dissolved in a mixture of water and isopropyl alcohol. The active drug solution can then be sprayed onto sugar spheres 30/35 (about 1.06 kg) in a fluidized bed processor with a Wurster insert. The active core microparticles can then be dried in a fluidized bed processor until the loss on drying is below about 1%. The bupropion microparticles can then be passed through a 16 mesh screen and a 30 mesh screen and microparticles can be collected that are smaller than 16 mesh and larger than 30 mesh.

Microparticle Taste-Masking Coatings

The microparticles of the present invention can each be coated with at least one taste-masking coating. The taste-masking coating can mask the taste of the active drug in the microparticles. In at least one embodiment the taste-masking coating formulations contain polymeric ingredients. It is contemplated that other excipients consistent with the objects of the present invention can also be used in the taste-masking coating.

In at least one embodiment, the taste-masking coating comprises a polymer such as ethylcellulose, which can be used as a dry polymer (such as ETHOCEL®, Dow Corning) solubilised in organic solvent prior to use, or as an aqueous dispersion. One commercially-available aqueous dispersion of ethylcellulose is AQUACOAT® (FMC Corp., Philadelphia, Pa., U.S.A.). AQUACOAT® can be prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, the AQUACOAT® is intimately mixed with a suitable plasticizer prior to use. Another aqueous dispersion of ethylcellulose is commercially available as SURELEASE® (Colorcon, Inc., West Point, Pa., U.S.A.). This product can be prepared by incorporating plasticizer into the dispersion during the manufacturing process. A hot melt of a polymer, plasticizer (e.g. dibutyl sebacate), and stabilizer (e.g. oleic acid) is prepared as a homogeneous mixture, which is then diluted with an alkaline solution to obtain an aqueous dispersion which can be applied directly onto substrates.

In other embodiments, polymethacrylate acrylic polymers can be employed as taste masking polymers. In at least one embodiment, the taste masking coating is an acrylic resin lacquer used in the form of an aqueous dispersion, such as that which is commercially available from Rohm Pharma under the tradename EUDRAGIT® or from BASF under the tradename KOLLICOAT®. In further embodiments, the acrylic coating comprises a mixture of two acrylic resin lacquers commercially available from Rohm Pharma under the tradenames EUDRAGIT® RL and EUDRAGIT® RS, respectively.

EUDRAGIT® RL and EUDRAGIT® RS are copolymers of acrylic and methacrylic esters with a low content of quaternary ammonium groups, the molar ratio of ammonium groups to the remaining neutral (meth)acrylic esters being 1:20 in EUDRAGIT® RL and 1:40 in EUDRAGIT® RS. The mean molecular weight is 150,000. The code designations RL (high permeability) and RS (low permeability) refer to the permeability properties of these agents. EUDRAGIT® RL/RS mixtures are insoluble in water and in digestive fluids. However, coatings formed from the same are swellable and permeable in aqueous solutions and digestive fluids. EUDRAGIT® RL/RS dispersions or solutions of certain embodiments can be mixed together in any desired ratio in order to ultimately obtain a taste masking coating having a desirable drug dissolution profile. In certain embodiments formulations can be obtained, for example, from a coating derived from 100% EUDRAGIT® RL; 50% EUDRAGIT® RL with 50% EUDRAGIT® RS; and 10% EUDRAGIT® RL with 90% EUDRAGIT® RS.

In other embodiments, the taste masking polymer can be an acrylic polymer which is cationic in character based on dimethylaminoethyl methacrylate and neutral methacrylic acid esters (such as EUDRAGIT® E, commercially available from Rohm Pharma). The hydrophobic acrylic polymer coatings of the present invention can further include a neutral copolymer based on poly (meth)acrylates, such as EUDRAGIT® NE (NE=neutral ester), commercially available from Rohm Pharma. EUDRAGIT® NE 30D lacquer films are insoluble in water and digestive fluids, but permeable and swellable.

In other embodiments, the taste masking polymer is a dispersion of poly (ethylacrylate, methyl methacrylate) 2:1 (KOLLICOAT® EMM 30 D, BASF).

In other embodiments, the taste masking polymer can be a polyvinyl acetate stabilized with polyvinylpyrrolidone and sodium lauryl sulfate such as KOLLICOAT® SR30D (BASF).

Other taste masking polymers include hydroxypropylcellulose (HPC); hydroxypropylmethylcellulose (HPMC); hydroxyethylcellulose; gelatin; gelatin/acacia; gelatin/acacia/vinvylmethylether maleic anhydride; gelatin/acacia/ethylenemaleic anhydride; carboxymethyl cellulose; polyvinvylalcohol; nitrocellulose; polyvinylalcohol-polyethylene glycol graft-copolymers; shellac; wax and mixtures thereof.

The taste-masking coatings can be applied to the microparticles from one or more organic or aqueous solvent solutions or suspensions. In at least one embodiment the organic solvents that can be used to apply the taste-masking coatings include one or more of acetone, lower alcohols such as ethanol, isopropanol and alcohol/water mixtures, chlorinated hydrocarbons, and the like. Devices used to coat the microparticles of the invention with a taste-masking coating include those conventionally used in pharmaceutical processing, such as fluidized bed coating devices. The coatings applied to the microparticles can contain ingredients other than the functional polymers. One or more colorants, flavorants, sweeteners, can also be used in the taste-masking coating.

In some embodiments a pore former can be included into the taste masking coat in order to influence the rate of release of bupropion hydrobromide from the microparticle. In other embodiments, a pore former is not included in the taste masking coat. The pore formers can be inorganic or organic, and include materials such as particulate materials that can be dissolved, extracted or leached from the coating in the environment of use. Upon exposure to fluids in the environment of use, the pore-formers can for example be dissolved, and channels and pores are formed that fill with the environmental fluid.

For example, the pore-formers of certain embodiments can comprise one or more water-soluble hydrophilic polymers in order to modify the release characteristics of the formulation. Examples of suitable hydrophilic polymers used as pore-formers include hydroxypropylmethylcellulose, cellulose ethers and protein-derived materials of these polymers, the cellulose ethers, such as hydroxyalkylcelluloses and carboxyalkylcelluloses. Also, synthetic water-soluble polymers can be used, examples of which include polyvinylpyrrolidone, cross-linked polyvinyl-pyrrolidone, polyethylene oxide, water-soluble polydextrose, saccharides and polysaccharides, such as pullulan, dextran, sucrose, glucose, fructose, mannitol, lactose, mannose, galactose, sorbitol and mixtures thereof. In at least one embodiment, the hydrophilic polymer comprises hydroxypropyl-methylcellulose.

Other non-limiting examples of pore-formers that can be used in certain embodiments containing a taste masking coat include alkali metal salts such as lithium carbonate, sodium chloride, sodium bromide, potassium chloride, potassium sulfate, potassium phosphate, sodium acetate, sodium citrate and mixtures thereof. The pore-forming solids can also be polymers which are soluble in the environment of use, such as CARBOWAX™, and CARBOPOL™. In addition, the pore-formers embrace diols, polyols, polyhydric alcohols, polyalkylene glycols, polyglycols, poly(a-w)alkylenediols and mixtures thereof. Other pore-formers which can be useful in the formulations of certain embodiments of the present invention include starch, modified starch, and starch derivatives, gums, including but not limited to xanthan gum, alginic acid, other alginates, benitoniite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan, kappa-carrageenan, lambdacarrageenan, gum karaya, biosynthetic gum, and mixtures thereof. Other pore-formers include materials useful for making microporous lamina in the environment of use, such as polycarbonates comprised of linear polyesters of carbonic acid in which carbonate groups reoccur in the polymer chain, microporous materials such as bisphenol, a microporous poly (vinylchloride), micro-porous polyamides, microporous modacrylic copolymers, microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous hiomopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid crosslinked poly(vinylpyrrolidone), and mixtures thereof.

In general, the amount of pore-former included in the taste masking coatings of certain embodiments of the present invention can be from about 0.1% to about 80%, by weight, relative to the combined weight of polymer and pore-former. The percentage of pore former as it relates to the dry weight of the taste-masking polymer, can have an influence on the drug release properties of the coated microparticle. In at least one embodiment that uses water soluble pore formers such as hydroxypropylmethylcellulose, a taste masking polymer: pore former dry weight ratio of from about 10:1 to about 1:1 can be present. In certain embodiments the taste masking polymer: pore former dry weight ratio is from about 8:1 to about 1.5:1; and in other embodiments from about 6:1 to about 2:1. In at least one embodiment using EUDRAGIT® NE30D as the taste masking polymer and a hydroxypropylmethylcellulose (approx 5 cps viscosity (in a 2% aqueous solution)) such as METHOCEL® E5, Pharmacoat 606G as the water soluble pore former, a taste masking polymer: pore former dry weight ratio of about 2:1 is present.

Colorants that can be used in the taste-masking coating include food, drug and cosmetic colors (FD&C), drug and cosmetic colors (D&C) or external drug and cosmetic colors (Ext. D&C). These colors are dyes, lakes, and certain natural and derived colorants. Useful lakes include dyes absorbed on aluminum hydroxide or other suitable carriers.

Flavorants that can be used in the taste-masking coating include natural and synthetic flavoring liquids. An illustrative list of such flavorants includes volatile oils, synthetic flavor oils, flavoring aromatics, oils, liquids, oleoresins and extracts derived from plants, leaves, flowers, fruits, stems and combinations thereof. A non-limiting representative list of these includes citric oils, such as lemon, orange, grape, lime and grapefruit, and fruit essences, including apple, pear, peach, grape, strawberry, raspberry, cherry, plum, pineapple, apricot, or other fruit flavors. Other useful flavorants include aldehydes and esters, such as benzaldehyde (cherry, almond); citral, i.e., alpha-citral (lemon, lime); neral, i.e., beta-citral (lemon, lime); decanal (orange, lemon); aldehyde C-8 (citrus fruits); aldehyde C-9 (citrus fruits); aldehyde C-12 (citrus fruits); tolyl aldehyde (cherry, almond); 2,6-dimethyloctanal (green fruit); 2-dodenal (citrus mandarin); and mixtures thereof.

Sweeteners that can be used in the taste-masking coating include glucose (corn syrup), dextrose, invert sugar, fructose, and mixtures thereof (when not used as a carrier); saccharin and its various salts, such as sodium salt; dipeptide sweeteners such as aspartame; dihydrochalcone compounds, glycyrrhizin; Steva Rebaudiana (Stevioside); chloro derivatives or sucrose such as sucralose; and sugar alcohols such as sorbitol, mannitol, xylitol, and the like. Also contemplated are hydrogenated starch hydrolysates and the synthetic sweeteners such as 3,6-dihydro-6-methyl-1-1-1,2,3-oxathiazin-4-1-2,2-dioxide, particularly the potassium salt (acesulfame-K), and sodium and calcium salts thereof. The sweeteners can be used alone or in any combination thereof.

The microparticle taste masking coat can also include one or more pharmaceutically acceptable excipients such as lubricants, emulsifiers, anti-foaming agents, plasticizers, solvents and the like.

Lubricants can be included to help reduce friction of coated microparticles during manufacturing. The lubricants that can be used in the taste masking coat of the present invention include but are not limited to adipic acid, magnesium stearate, calcium stearate, zinc stearate, calcium silicate, magnesium silicate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil, waxy fatty acid esters such as glyceryl behenate, (i.e. COMPRITOL™), STEAR-O-WET™, MYVATEX™ TL and mixtures thereof. In at least one embodiment, the lubricant is selected from magnesium stearate, talc and a mixture thereof. Combinations of these lubricants are operable. The lubricant can each be present in an amount of from about 1% to about 100% by weight of the polymer dry weight in the taste masking coat. For example, in certain embodiments wherein the taste masking polymer is EUDRAGIT® NE30D or EUDRAGIT® NE40D (Rohm America LLC) together with a hydrophilic pore former, the lubricant is present in an amount of from about 1% to about 30% by weight of the polymer dry weight; in other embodiments from about 2% to about 20%; and in still other embodiments at about 10% by weight of the microparticle taste masking coat dry weight. In another embodiment where the taste masking polymer is ethylcellulose (ETHOCEL™ PR100, PR45, PR20, PR10 or PR7 polymer, or a mixture thereof), the lubricant can be present in an amount of from about 10% to about 100% by weight of the microparticle taste masking coat dry weight; in another embodiment from about 20% to about 80%; and in still another embodiments at about 50% by weight of the microparticle taste masking coat dry weight. In other embodiments, the taste masking coat does not include a pore former.

Emulsifying agent(s) (also called emulsifiers or emulgents) can be included in the microparticle taste masking coat to facilitate actual emulsification during manufacture of the coat, and also to ensure emulsion stability during the shelf-life of the product. Emulsifying agents useful for the microparticle taste masking coat composition of certain embodiments include, but are not limited to naturally occurring materials and their semi synthetic derivatives, such as the polysaccharides, as well as glycerol esters, cellulose ethers, sorbitan esters (e.g. sorbitan monooleate or SPAN™ 80), and polysorbates (e.g. TWEEN™ 80).

Combinations of emulsifying agents are operable. In at least one embodiment, the emulsifying agent is TWEEN™ 80. The emulsifying agent(s) can be present in an amount of from about 0.01% to about 5% by weight of the microparticle taste masking polymer dry weight. For example, in certain embodiments the emulsifying agent is present in an amount of from about 0.05% to about 3%; in other embodiments from about 0.08% to about 1.5%, and in still other embodiments at about 0.1% by weight of the microparticle taste masking polymer dry weight.

Anti-foaming agent(s) can be included in the microparticle taste masking coat to reduce frothing or foaming during manufacture of the coat. Anti-foaming agents useful for the coat composition include, but are not liminted to simethicone, polyglycol, silicon oil, and mixtures thereof. In at least one embodiment the anti-foaming agent is Simethicone C. The anti-foaming agent can be present in an amount of from about 0.1% to about 10% of the microparticle taste masking coat weight. For example, in certain embodiments the anti-foaming agent is present in an amount of from about 0.2% to about 5%; in other embodiments from about 0.3% to about 1%, and in still other embodiments at about 0.6% by weight of the microparticle taste masking polymer dry weight.

Plasticizer(s) can be included in the microparticle taste masking coat to provide increased flexibility and durability during manufacturing. Plasticizers that can be used in the microparticle taste masking coat of certain embodiments include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropioin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, and mixtures thereof. The plasticizer can be present in an amount of from about 1% to about 80% of the taste masking polymer dry weight. For example, in certain embodiments the plasticizer is present in an amount of from about 5% to about 50%, in other embodiments from about 10% to about 40%, and in still other embodiments at about 20% of the taste masking polymer dry weight.

The taste-masking coating can be present in an amount of from about 1% to about 90% by weight of the microparticle, depending upon the choice of polymer, the ratio of polymer: pore former, and the total surface area of the microparticle formulation. Since a certain thickness of taste masking coating has to be achieved in order to achieve effective taste masking, the amount of taste masking polymer coating used during manufacture is related to the total surface area of the batch of uncoated microparticles that requires a coating. The taste masking polymer surface area coverage can range from about 0.5 mg/cm2 to about 20 mg/cm2. For example, in certain embodiments the surface area coverage of the taste masking polymer is from about 0.6 mg/cm2 to about 10 mg/cm2, and in other embodiments is from about 1 mg/cm2 to about 5 mg/cm2. In at least one embodiment of the invention, EUDRAGIT® E is employed as the taste masking polymer at a surface area coverage of about 4 mg/cm2. One approach in estimating the total surface area of a multiparticulate batch is the permeability method according to Blaine (ASTM Des. C 205-55), which is based upon the mathematical model of laminar flow through capillaries arranged in parallel.

In the absence of an accurate determination of total surface area of a microparticle, the amount of taste masking polymer to be applied can be expressed as a percentage of the uncoated microparticle. For example, in certain embodiments the taste-masking coating is present in an amount of from about 5% to about 60%; in other embodiments from about 10% to about 40%; and in still other embodiments from about 15% to about 35% by weight of the microparticle. In at least one embodiment the taste-masking coating is present in an amount of about 30% by weight of the microparticle.

In certain embodiments, the diameter of the microparticles (with or without the taste-masking coating) range from about 50 µm to about 800 µm. For example, in certain embodiments the diameter of the microparticles range from about 100 µm to about 600 µm, and in other embodiments from about 150 µm to about 450 µm.

Microparticle Controlled Release Coat

The microparticles of the present invention can each be coated with at least one controlled release coat. As used herein, the term "microparticle controlled release coat" refers to the controlled release coat that substantially surrounds each microparticle. The microparticle controlled release coat is designed to achieve a controlled release of the bupropion hydrobromide salt from the microparticle. For example, the microparticle controlled release coat can be an enteric coat with low solubility at a gastric pH to reduce or minimize the drug release in the lumen of the stomach, whilst possessing pH dependent solubility to facilitate drug release in the duodenum. In another embodiment, the controlled release coat can be a delayed release coating that provides a delayed release of the bupropion hydrobromide salt with a predetermined lagtime that is independent of, or alternatively dependent on, the pH of the dissolution medium. For example, by increasing the thickness of the microparticle controlled release coat using a pH independent diffusion polymer, lagtimes of about 1 hour, about 2 hours, about 3 hours, about 4 hours, about 5 hours, about 6 hours, about 7 hours, about 8 hours, about 9 hours, about 10 hours, about 11 hours, or about 12 hours can be achieved. Alternatively, controlled release polymers can be selected that become soluble above a certain pH. Drug release from such a system is reduced or minimized until the certain pH for the polymer of choice is exceeded. With either approach, following the predetermined lag, drug is released, for example within about 1 hour for an immediate release pulse, or alternatively over a prolonged period of time, for example from about 3 to about 24 hours. In other embodiments, the microparticle controlled release coat can provide a diffusion barrier that is independent of pH, thus facilitating a sustained release profile, with substantially full release of the bupropion hydrobromide salt occurring in from about 3 to about 24 hours following administration. In at least one embodiment, the microparticle controlled release coat provides a delayed and sustained release of the bupropion hydrobromide salt from the microparticle with substantially full release in about 24 hours following administration.

In certain embodiments, the microparticle controlled release coat can provide substantially full release of the bupropion hydrobromide salt from the microparticle without requiring the use of any pore formers. Unnecessary pore formers that are not required in the microparticle controlled release coat include hydrophilic polymers such as hydroxypropyl methylcellulose. The microparticle controlled release coat includes at least one polymer in an amount sufficient to achieve a controlled release of the bupropion hydrobromide salt. In at least one embodiment of the invention the controlled release polymer is an acrylic polymer. Suitable acrylic polymers include but are not limited to acrylic acid and methacrylic acid copolymers, methyl methacrylate copolymers, ethoxyethyl methacrylates, cynaoethyl methacrylate, aminoalkyl methacrylate copolymer, poly(acrylic acid), poly(methacrylic acid, methacrylic acid alkylamine copolymer, poly(methyl methacrylate), poly(methacrylic acid) (anhydride), glycidyl methacrylate copolymers, and mixtures thereof.

In at least one embodiment the controlled release coat comprises polymerizable quaternary ammonium compounds, of which non-limiting examples include quaternized aminoalkyl esters and aminoalkyl amides of acrylic acid and methacrylic acid, for example β-methacryl-oxyethyl-trimethyl-ammonium methosulfate, β-acryloxy-propyl-trimethyl-ammonium chloride, trimethylaminomethyl-methacrylamide methosulfate and mixtures thereof. The quaternary ammonium atom can also be part of a heterocycle, as in methacryloxyethylmethyl-morpholiniom chloride or the corresponding piperidinium salt, or it can be joined to an acrylic acid group or a methacrylic acid group by way of a group containing hetero atoms, such as a polyglycol ether group. Further suitable polymerizable quaternary ammonium compounds include quaternized vinyl-substituted nitrogen heterocycles such as methyl-vinyl pyridinium salts, vinyl esters of quaternized amino carboxylic acids, and styryltrialkyl ammonium salts. Other polymerizable quaternary ammonium compounds useful in the present invention include acryl- and methacryl-oxyethyltrimethyl-ammonium chloride and methosulfate, benzyldimethylammoniumethyl-methacrylate chloride, diethylmethylammoniumethyl-acrylate and -methacrylate methosulfate, N-trimethylammoniumpropylmethacrylamide chloride, N-trimethylammonium-2, 2-dimethylpropyl-1-methacrylate chloride and mixtures thereof.

In at least one embodiment, the polymer of the controlled release coat is an acrylic polymer comprised of one or more ammonio methacrylate copolymers. Ammonio methacrylate copolymers (such as those sold under the trademark EUDRAGIT® RS and RL) are described in NF XVII as fully polymerized copolymers of acrylic and methacrylic acid esters with a low content of quaternary ammonium groups. In order to obtain a desirable dissolution profile for a given therapeutically active agent such as bupropion hydrobromide, it may be helpful in some embodiments to incorporate two or more ammonio methacrylate copolymers having differing physical properties. For example, it is known that by changing the molar ratio of the quaternary ammonium groups to the neutral (meth)acrylic esters, the permeability properties of the resultant controlled release coat can be modified.

In other embodiments of the present invention, the acrylic polymer coating further includes a polymer whose permeability is pH dependent, such as anionic polymers synthesized from methacrylic acid and methacrylic acid methyl ester. Such polymers are commercially available, e.g., from Rohm Pharma GmbH under the tradename EUDRAGIT® L and EUDRAGIT® S, and the ratio of free carboxyl groups to the esters is said to be 1:1 in EUDRAGIT® L and 1:2 in EUDRAGIT® S. EUDRAGIT® L is insoluble in acids and pure water, but becomes increasingly permeable above pH 5.0. EUDRAGIT® S is similar, except that it becomes increasingly permeable above pH 7. The hydrophobic acrylic polymer coatings can also include a polymer which is cationic in character based on dimethylaminoethyl methacrylate and neutral methacrylic acid esters (such as EUDRAGIT® E, commercially available from Rohm Pharma). The hydrophobic acrylic polymer coatings of certain embodiments can further include a neutral copolymer based on poly (meth) acrylates, such as EUDRAGIT® NE (NE=neutral ester), commercially available from Rohm Pharma. EUDRAGIT® NE 30D lacquer films are insoluble in water and digestive fluids, but permeable and swellable.

In other embodiments of the invention the controlled release polymer is a dispersion of poly (ethylacrylate, methyl methacrylate) 2:1 (KOLLICOAT® EMM 30 D, BASF). In other embodiments the controlled release polymer can be a polyvinyl acetate stabilized with polyvinylpyrrolidone and sodium lauryl sulfate such as KOLLICOAT® SR30D (BASF). The dissolution profile can be altered by changing the relative amounts of different acrylic resin lacquers included in the coating. Also, by changing the molar ratio of polymerizable permeability-enhancing agent (e.g., the quaternary ammonium compounds) in certain embodiments to the neutral (meth)acrylic esters, the permeability properties (and thus the dissolution profile) of the resultant coating can be modified.

In at least one embodiment the controlled release polymer is ethylcellulose, which can be used as a dry polymer (such as ETHOCEL®, Dow Corning) solubilised in organic solvent prior to use, or as an aqueous dispersion. One commercially available aqueous dispersion of ethylcellulose is AQUACOAT® (FMC Corp., Philadelphia, Pa., U.S.A.). AQUACOAT® can be prepared by dissolving the ethylcellulose in a water-immiscible organic solvent and then emulsifying the same in water in the presence of a surfactant and a stabilizer. After homogenization to generate submicron droplets, the organic solvent is evaporated under vacuum to form a pseudolatex. The plasticizer is not incorporated in the pseudolatex during the manufacturing phase. Thus, prior to using the same as a coating, the AQUACOAT® is intimately mixed with a suitable plasticizer prior to use. Another aqueous dispersion of ethylcellulose is commercially available as SURELEASE® (Colorcon, Inc., West Point, Pa., U.S.A.). This product can be prepared by incorporating a plasticizer into the dispersion during the manufacturing process. A hot melt of a polymer, plasticizer (e.g. dibutyl sebacate), and stabilizer (e.g. oleic acid) is prepared as a homogeneous mixture, which is then diluted with an alkaline solution to obtain an aqueous dispersion which can be applied directly onto substrates.

Other examples of polymers that can be used in the microparticle controlled release coat include cellulose acetate phthalate, cellulose acetate trimaletate, hydroxy propyl methylcellulose phthalate, polyvinyl acetate phthalate, polyvinyl alcohol phthalate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, ethyl cellulose, gelatin, starch, and cellulose based cross-linked polymers in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, pullulan, collagen, casein, agar, gum arabic, sodium carboxymethyl cellulose, (swellable hydrophilic polymers) poly(hydroxyalkyl methacrylate) (molecular weight from about 5 k to about 5000 k), polyvinylpyrrolidone (molecular weight from about 10 k to about 360 k), anionic and cationic hydrogels, zein, polyamides, polyvinyl alcohol having a low acetate residual, a swellable mixture of agar and carboxymethyl cellulose, copolymers of maleic anhydride and styrene, ethylene, propylene or isobutylene, pectin (molecular weight from about 30 k to about 300 k), polysaccharides such as agar, acacia, karaya, tragacanth, algins and guar, polyacrylamides, POLYOX® polyethylene oxides (molecular weight from about 100 k to about 5000 k), AQUAKEEP® acrylate polymers, diesters of polyglucan, crosslinked polyvinyl alcohol and poly N-vinyl-2-pyrrolidone, hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, methyl ethyl cellulose, ethylhydroxy ethylcellulose, cellulose acetate, cellulose butyrate, cellulose propionate, gelatin, starch, maltodextrin, pullulan, polyvinyl pyrrolidone, polyvinyl alcohol, polyvinyl acetate, glycerol fatty acid esters, polyacrylamide, polyacrylic acid, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof.

In at least one embodiment the controlled release coat of the microparticles comprises polymers that can facilitate mucoadhesion within the gastrointestinal tract. Non-limiting examples of polymers that can be used for mucoadhesion include carboxymethylcellulose, polyacrylic acid, CARBOPOL™, POLYCARBOPHIL™, gelatin and other natural or synthetic polymers.

In at least one embodiment the microparticles are coated with a controlled release coat comprised of:

at least one film-forming polymer which is insoluble in the liquids of the digestive tract, present in an amount of from about 50% to about 90% (e.g. from about 50% to about 80%) by weight of dry matter of the controlled release coat composition, and including at least one non-hydrosoluble cellulose derivate, (e.g. ethylcellulose, cellulose acetate, or mixtures thereof);

at least one nitrogen-containing polymer, present in an amount of from about 2% to about 25% (e.g. from about 5% to about 15%) by weight of dry matter of the controlled release coat composition, and including at least one polyacrylamide, poly-N-vinylaride, poly-N-vinyl-lactame, polyvinylpyrrolidone, or mixtures thereof;

optionally a plasticizer present in an amount of from about 2% to about 20% (e.g. from about 4% to about 15%) by weight of dry matter of the controlled release coat composition, and including at least one of the following compounds: glycerol esters, phtalates, citrates, sebacates, cetylalcohol esters, castor oil, cutin, or mixtures thereof;

at least one surface-active and/or lubricating agent, present in an amount of from about 2% to about 20% (e.g. from about 4% to about 15%) by weight of dry matter of the controlled release coat composition, and chosen from anionic surfactants such as the alkali metal and alkakine-earth metal salts of fatty acids, (e.g. stearic acid, oleic acid, and mixtures thereof), and/or from nonionic surfactants such as polyoxyethylenated esters of sorbitan, polyoxyethylenated esters of sorbitan, polyoxyethylenated derivatives of castor oil, and/or from lubricants such as stearates (e.g. calcium, magnesium, aluminium, zinc stearate and mixtures thereof), stearylfumarates (e.g. sodium stearylfumarate, glyceryl behenate and mixtures thereof); and mixtures thereof;

wherein the coated microparticles are designed so as to be able to remain in the small intestine for a period of at least about 5 hours; in certain embodiments at least about 7 hours; and in certain other embodiments for a period of from about 8 hours to about 24 hours; so as to allow absorption of the bupropion hydrobromide during at least part of its time in the small intestine.

In a prophetic example of this embodiment of the invention, the microparticles are coated in a fluidized bead coater with the following coating solution:

| Ethylcellulose | about 44.7 g |
| PVP | about 4.8 g |
| Castor oil | about 4.8 g |
| Magnesium Stearate | about 6.1 g |
| Acetone | about 479 g |
| Isopranol | about 53 g |

In other embodiments of the present invention, the release of the bupropion hydrobromide from a controlled release formulation can be further influenced, i.e., adjusted to a desired rate, by the addition of one or more pore-formers to the controlled release coat, where the pore-formers can be inorganic or organic, and can include materials that can be dissolved, extracted or leached from the controlled release coat in the environment of use. Upon exposure to fluids in the environment of use, the pore-formers are, for example, dissolved, and channels and pores are formed that fill with the environmental fluid. For example, the pore-formers can include one or more water-soluble hydrophilic polymers in order to modify the release characteristics of the formulation. Non-limiting examples of suitable hydrophilic polymers include hydroxypropylmethylcellulose, cellulose ethers and protein-derived materials of these polymers, the cellulose ethers, (e.g. hydroxyalkylcelluloses and carboxyalkylcelluloses), and mixtures thereof. Also, synthetic water-soluble polymers can be used, such as polyvinylpyrrolidone, cross-linked polyvinyl-pyrrolidone, polyethylene oxide, water-soluble polydextrose, saccharides and polysaccharides, such as pullulan, dextran, sucrose, glucose, fructose, mannitol, lactose, mannose, galactose, sorbitol, and mixtures thereof. In at least one embodiment the hydrophilic polymer(s) include hydroxypropyl-methylcellulose. Other examples of pore-formers include alkali metal salts such as lithium carbonate, sodium chloride, sodium bromide, potassium chloride, potassium sulfate, potassium phosphate, sodium acetate, sodium citrate, and mixtures thereof. The pore-forming solids can also be polymers which are soluble in the environment of use, such as CARBOWAX®, CARBOPOL®, and the like. The possible pore-formers embrace diols, polyols, polyhydric alcohols, polyalkylene glycols, polyglycols, poly(a-w) alkylenediols, and mixtures thereof. Other pore-formers which can be useful in the formulations of the present invention include starch, modified starch, and starch derivatives, gums, including but not limited to xanthan gum, alginic acid, other alginates, benitoniite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, such as potassium polymethacrylate, carrageenan, kappa-carrageenan, lambda-carrageenan, gum karaya, biosynthetic gum, and mixtures thereof. Other pore-formers include materials useful for making microporous lamina in the environment of use, such as polycarbonates comprised of linear polyesters of carbonic acid in which carbonate groups reoccur in the polymer chain, microporous materials such as bisphenol, a microporous poly(vinylchloride), micro-porous polyamides, microporous modacrylic copolymers, microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous hiomopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid cross-linked poly(vinylpyrrolidone), and mixtures thereof.

In other embodiments a surfactant or an effervescent base can be included in the controlled release coat, which can reduce and in certain embodiments overcome surface tension effects. In addition, the controlled release coat of certain embodiments can include one or more osmagents (i.e., which can osmotically deliver the active agent from the device by providing an osmotic pressure gradient against the external fluid), swelling agents (i.e., which can include, but are not limited to hydrophilic pharmaceutically acceptable compounds with various swelling rates in water), or other pharmaceutically acceptable agents (i.e., provided in an amount sufficient to facilitate the entry of the environmental fluid without causing the disruption of the impermeable coating).

The surfactants that can be used in the controlled release coat of certain embodiments can be anionic, cationic, nonionic, or amphoteric. Non-limiting examples of such surfactants include sodium lauryl sulfate, sodium dodecyl sulfate, sorbitan esters, polysorbates, pluronics, potassium laurate, and mixtures thereof. Non-limiting examples of effervescent bases that can be used in the controlled release coat of certain embodiments include sodium glycine carbonate, sodium carbonate, potassium carbonate, sodium bicarbonate, potassium bicarbonate, calcium bicarbonate, and mixtures thereof. Non-limiting examples of osmagents that can be used in the controlled release coat of certain embodiments include sodium chloride, calcium chloride, calcium lactate, sodium sulfate, lactose, glucose, sucrose, mannitol, urea, other organic and inorganic compounds known in the art, and mixtures thereof. The swelling agent can include, but is not limited to at least one pharmaceutically acceptable hydrophilic compound, having a swelling rate or swelling amount in water at about 25° C. that is: greater than or equal to at least about 10% by weight (wt/wt), greater than or equal to at least about 15% by weight (wt/wt), or greater than or equal to at least about 20% by weight (wt/wt). Non-limiting examples of swelling agents that can be used in the controlled release coat of certain embodiments of the present invention include crosslinked polyvinylpyrrolidones (e.g. polyplasdone, crospovidone and mixtures thereof), crosslinked carboxyalkylcelluloses, crosslinked carboxymethylcellulose (e.g. crosslinked sodium croscarmellose), hydrophilic polymers of high molar mass (i.e., which can be, but are not limited to being greater than or equal to 100,000 Daltons) which can include, but are not limited to: polyvinylpyrrolidone(s), polyalkylene oxides (e.g. polyethylene oxide, polypropylene oxide, and mixtures thereof), hydroxyalkylcelluloses (e.g. hydroxypropylcellulose, hydroxypropylmethylcellulose and mixtures thereof), carboxyalkylcellulose (e.g. carboxymethylcellulose), modified starch (e.g. sodium glycolate), starch or natural starch (e.g. corn, wheat, rice, potato and mixtures thereof), cellulose (i.e. which can be, but is not limited to being in powder form or microcrystalline form), sodium alginate, potassium polacriline, and corresponding blends or mixtures thereof. In other embodiments, non-limiting examples of the swelling agent include the following sub-set of compounds: crosslinked polyvinylpyrrolidone (e.g. polyplasdone, crospovidone or mixtures thereof), crosslinked carboxyalkylcelluloses (e.g. crosslinked carboxymethylcelluloses such as crosslinked sodium croscarmellose), and mixtures thereof. In other embodiments, the swelling agent can be a nitrogen containing polymer, non-limiting examples of which can include polyvinylpyrrolidone, crosslinked polyvinylpyrrolidone and mixtures thereof. The concentration of the swelling agent in the controlled release coat of certain embodiments of the present invention can be from about 3% to about 40% by weight of the microparticle. For example, in certain embodiments the concentration of the swelling agent in the controlled release coat is from about 4% to about 30%, and in other embodiments from about 5% to about 25% by weight of the microparticle.

In certain embodiments one or more pharmaceutically acceptable excipients consistent with the objects of the present invention can be used in the controlled release coat, such as a lubricant, an emulsifying agent, an anti-foaming agent, and/or a plasticizer.

Lubricants can be included in the controlled release coat to help reduce friction of coated microparticles during manufacturing. The lubricants that can be used in the controlled release coat of certain embodiments of the present invention include but are not limited to adipic acid, magnesium stearate, calcium stearate, zinc stearate, calcium silicate, magnesium silicate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil, waxy fatty acid esters such as glyceryl behenate, (e.g. COMPRITOL™), STEAR-O-WET™ and MYVATEX™ TL. In at least one embodiment, the lubricant is selected from magnesium stearate, talc and mixtures thereof. Combinations of these lubricants are operable. The lubricant can each be present in an amount of from about 1% to about 100% by weight of the controlled release coat dry weight. For example, in certain embodiments wherein the controlled release polymer is EUDRAGIT® NE30D or EUDRAGIT® NE40D (Rohm America LLC) together with a hydrophilic pore former, the lubricant is present in an amount of from about 1% to about 30% by weight of the controlled release coat dry weight; in other embodiments from about 2% to about 20%; and in still other embodiments at about 10% by weight of the microparticle controlled release coat dry weight. In another embodiments where the controlled release polymer is ethylcellulose (ETHOCEL™ PR100, PR45, PR20, PR10 or PR7 polymer, or a mixture thereof), the lubricant can be present in an amount of from about 10% to about 100% by weight of the microparticle control-releasing coat dry weight; in another embodiment from about 20% to about 80%; and in still another embodiments at about 50% by weight of the microparticle control-releasing coat dry weight.

Emulsifying agent(s) (also called emulsifiers or emulgents) can be included in the microparticle controlled release coat to facilitate actual emulsification during manufacture of the coat, and also to ensure emulsion stability during the shelf-life of the product. Emulsifying agents useful for the microparticle control-releasing coat composition include, but are not limited to naturally occurring materials and their semi synthetic derivatives, such as the polysaccharides, as well as glycerol esters, cellulose ethers, sorbitan esters (e.g. sorbitan monooleate or SPAN™ 80), and polysorbates (e.g. TWEEN™ 80). Combinations of emulsifying agents are operable. In at least one embodiment, the emulsifying agent is TWEEN™ 80. The emulsifying agent(s) can be present in an amount of from about 0.01% to about 5% by weight of the microparticle controlled release coat dry weight. For example, in certain embodiments the emulsifying agent is present in an amount of from about 0.05% to about 3%; in other embodiments from about 0.08% to about 1.5%, and in still other embodiments at about 0.1% by weight of the microparticle controlled release coat dry weight.

Anti-foaming agent(s) can be included in the microparticle controlled release coat to reduce frothing or foaming during manufacture of the coat. Anti-foaming agents useful for the coat composition include, but are not limited to simethicone, polyglycol and silicon oil. In at least one embodiment the anti-foaming agent is Simethicone C. The anti-foaming agent can be present in an amount of from about 0.1% to about 10% of the microparticle controlled release coat weight. For example, in certain embodiments the anti-foaming agent is present in an amount of from about 0.2% to about 5%; in other embodiments from about 0.3% to about 1%, and in still other embodiments at about 0.6% by weight of the microparticle controlled release coat dry weight.

Plasticizer(s) can be included in the microparticle controlled release coat to modify the properties and characteristics of the polymers used in the coat for convenient processing during manufacturing (e.g. provide increased flexibility and durability during manufacturing). As used herein, the term "plasticizer" includes any compounds capable of plasticizing or softening a polymer or binder used in the present invention.

Once the coat has been manufactured, certain plasticizers can function to increase the hydrophilicity of the coat in the environment of use. During manufacture of the coat, the plasticizer can lower the melting temperature or glass transition temperature (softening point temperature) of the polymer or binder. The addition of a plasticizer, such as low molecular weight PEG, generally broadens the average molecular weight of a polymer in which they are included thereby lowering its glass transition temperature or softening point. Plasticizers can also generally reduce the viscosity of a polymer. Non-limiting examples of plasticisers that can be used in the microparticle controlled release coat include acetylated monoglycerides; acetyltributyl citrate, butyl phthalyl butyl glycolate; dibutyl tartrate; diethyl phthalate; dimethyl phthalate; ethyl phthalyl ethyl glycolate; glycerin; propylene glycol; triacetin; tripropioin; diacetin; dibutyl phthalate; acetyl monoglyceride; acetyltriethyl citrate, polyethylene glycols; castor oil; rape seed oil, olive oil, sesame oil, triethyl citrate; polyhydric alcohols, glycerol, glycerin sorbitol, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidized tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, diethyloxalate, diethylmalate, diethylfumerate, dibutylsuccinate, diethylmalonate, dibutylphthalate, dibutylsebacate, glyceroltributyrate, and mixtures thereof. The plasticizer can be present in an amount of from about 1% to about 80% of the controlled release coat dry weight. For example, in certain embodiments the plasticizer is present in an amount of from about 5% to about 50%, in other embodiments from about 10% to about 40%, and in still other embodiments at about 20% of the controlled release coat dry weight.

The controlled release coat can be present in an amount of from about 1% to about 100% by weight of the microparticle, depending upon the choice of polymer, the ratio of polymer: pore former, and the total surface area of the microparticle formulation. Since a certain thickness of controlled release coating has to be achieved in order to achieve the desired dissolution profile, the amount of polymer coating required during manufacture is related to the total surface area of the batch of uncoated microparticles that requires a coating. The controlled release polymer surface area coverage can range from about 0.5 mg/cm$^2$ to about 30 mg/cm$^2$. For example in certain embodiments the surface area coverage of the controlled release polymer is from about 0.6 mg/cm$^2$ to about 20 mg/cm$^2$, and in other embodiments from about 1 mg/cm$^2$ to about 5 mg/cm$^2$. In at least one embodiment of the invention, EUDRAGIT® NE30D is used as the controlled release polymer at a surface area coverage of about 10 mg/cm$^2$. One approach to estimate the total surface area of a multiparticulate batch is the permeability method according to Blaine (ASTM Des. C 205-55), which is based upon the mathematical model of laminar flow through capillaries arranged in parallel. In the absence of an accurate determination of total surface area of a microparticle, the amount of controlled release polymer to be applied can be expressed as a percentage of the uncoated microparticle.

The controlled release polymer can be present in an amount of from about 1% to about 99% by weight of the coated microparticle, depending on the controlled release profile desired. For example, in certain embodiments the polymer is present in an amount of from about 5% to about 80%, and in other embodiments from about 10% to about 50% by weight of the coated microparticle. In at least one embodiment wherein the controlled release polymer is EUDRAGIT® NE30D, EUDRAGIT® NE40D (Rohm America LLC), KOLLICOAT® SR 30D, or a mixture thereof, the polymer is present in an amount of from about 1% to about 50%; in other embodiments from about 5% to about 30%; and in still other embodiments is about 15% by weight of the coated microparticle. In at least one embodiment wherein the controlled release polymer is ethylcellulose, the polymer is present in an amount of from about 1% to about 99% by weight of the coated microparticle; in other embodiments from about 5% to about 50%; and in still other embodiments at about 20% by weight of the coated microparticle. In at least one embodiment wherein the controlled release polymer is ETHOCEL™, an ethyl cellulose grade PR100, PR45, PR20, PR10, PR7 polymer, or a mixture thereof, the polymer is present in an amount of from about 5% to about 30% by weight of the coated microparticle; in other embodiments from about 10% to about 25%; and in still other embodiments at about 20% by weight of the coated microparticle.

In certain embodiments, the diameter of the microparticles (with or without the controlled release coat) can range from about 50 μm to about 800 μm. For example, in certain embodiments the diameter of the microparticles range from about 100 μm to about 600 μm, and in other embodiments from about 150 μm to about 450 μm.

It is contemplated that in alternative embodiments, other excipients consistent with the objects of the present invention can also be used in the microparticle controlled release coat.

In at least one embodiment, the microparticle controlled release coat includes about 96% EUDRAGIT® NE30D, about 1.9% Magnesium stearate, about 1.9% Talc, about 0.04% TWEEN® 80, and about 0.19% Simethicone C, when expressed as percentage by weight of the dry controlled release coat composition. In another embodiment, the microparticle controlled release coat includes about 68% ethylcellulose, about 17% glyceryl monostearate and about 15% acetyl tributylcitrate when expressed as percentage by weight of the dry controlled release coat composition.

In certain embodiments the microparticle controlled release coat can be made according to any one of the methods described herein.

The manufacturing process for the microparticle controlled release coat can be as follows. Water is split into two portions of about 15% and about 85%. The anti-foaming agent and the emulsifying agent are then added to the 15% water portion, and mixed at about 300 rpm to form portion A. In at least one embodiment, the anti-foaming agent is Simethicone C, and the emulsifying agent is TWEEM™ 80. A first lubricant is then added to the 85% water portion and mixed at about 9500 rpm to form portion B. In at least one embodiment, the first lubricant is talc. Then portion A is mixed with portion B, a second lubricant is slowly added, and mixed at about 700 rpm overnight. In at least one embodiment, the second lubricant is magnesium stearate. Finally, an aqueous dispersion of a neutral ester copolymer is added and mixed for about 30 minutes at about 500 rpm. In at least one embodiment, the aqueous dispersion of a neutral ester copolymer is EUDRAGIT® NE30D. The resultant controlled release coat solution can then be used to coat the microparticles to about a 35% weight gain with the following parameters: An inlet temperature of from about 10° C. to about 60° C., in certain embodiments from about 20° C. to about 40° C., and in at least one embodiment from about 25° C. to about 35° C.; an outlet temperature of from about 10° C. to about 60° C., in certain embodiments from about 20° C. to about 40° C., and in at least one embodiment from about 25°

C. to about 35° C.; a product temperature of from about 10° C. to about 60° C., in certain embodiments from about 15° C. to about 35° C., and in at least one embodiment from about 22° C. to about 27° C.; an air flow of from about 10 cm/h to about 180 c.m/h, in certain embodiments from about 40 c.m/h to about 120 c.m/h, and in at least one embodiment from about 60 c.m/h to about 80 c.m/h; and an atomizing pressure of from about 0.5 bar to about 4.5 bar, in certain embodiments from about 1 bar to about 3 bar, and in at least one embodiment at about 2 bar. The resultant controlled release coated microparticles can then be discharged from the coating chamber and oven cured with the following parameters: A curing temperature of from about 20° C. to about 65° C., in certain embodiments from about 30° C. to about 55° C., and in at least one embodiment at about 40° C.; and a curing time of from about 2 hours to about 120 hours, in certain embodiments from about 10 hours to about 40 hours, and in at least one embodiment at about 24 hours. Any other technology resulting in the formulation of the microparticle controlled release coat consistent with the objects of the invention can also be used.

Microparticle Dosage Forms

Highly useful dosage forms result when microparticles made from compositions containing a bupropion hydrobromide salt, spheronization aids, and other excipient(s) are coated with controlled release polymer(s). The controlled release coated microparticles can then be combined with an excipient mass and/or other pharmaceutical excipients, and compressed into tablets. Conventional tablets can be manufactured by compressing the coated microparticles with suitable excipients using known compression techniques. The dissolution profile of the controlled release coated multiparticles is not substantially affected by the compression of the microparticles into a tablet. The resultant dosage forms enjoy the processing ease associated with the use of excipient masses and the release properties associated with controlled release coated microparticles. Alternatively, the coated microparticles can be filled into capsules.

The forms of administration according to the invention are suitable for oral administration. In certain embodiments the forms of administration are tablets and capsules. However, the composition of the invention can also take the form of pellets, beads or microtablets, which can then be packaged into capsules or compressed into a unitary solid dosage form. Other solid oral dosage forms as disclosed herein can be prepared by the skilled artisan, despite the fact that such other solid oral dosage forms may be more difficult to commercially manufacture.

The present invention also contemplates combinations of differently coated microparticles into a dosage form to provide a variety of different release profiles. For example, in certain embodiments, microparticles with a delayed release profile can be combined with other microparticles having a sustained release profile to provide a multiple component controlled release bupropion formulation. In addition, other embodiments can include one or more further components of immediate release bupropion. The immediate release bupropion component can take the form of uncoated bupropion microparticles or powders; bupropion microparticles coated with a highly soluble immediate release coating, such as an OPADRY® type coating, as are known to those skilled in the art, or a combination of any of the foregoing. The multiple components can then be blended together in the desired ratio and placed in a capsule, or formed into a tablet. Examples of multiple component controlled release bupropion formulations are described in U.S. Pat. No. 6,905,708.

Dose Sipping Technology

The present invention also contemplates an oral delivery system for delivering microparticles containing bupropion hydrobromide in admixture with a fluid. For example, an oral delivery system is provided which comprises a hollow drug formulation chamber. In at least one embodiment, the chamber has a first end and a second end and contains a formulation in the form of microparticles. The drug formulation comprises bupropion hydrobromide. The system further comprises a fluid passing drug formulation retainer in the first end of the chamber. The retainer prevents release of the microparticles from the first end while permitting fluid entry into the chamber. In other embodiments, the microparticles contained within the chamber comprise bupropion hydrobromide and at least one other drug.

Certain embodiments of the present invention further provide a method for orally delivering microparticles containing bupropion hydrobromide formulation in admixture with a fluid. The method involves inserting microparticles of bupropion hydrobromide formulation into a hollow drug delivery chamber of a drug delivery device. The chamber has a first end and a second end. The first end of the chamber has a fluid passing drug formulation retainer. The drug delivery device has a first and second end. The first end of the drug delivering device is inserted into a fluid and the second end is inserted into the mouth of a patient. The patient then applies suction to the second end of the device to cause delivery of the fluid and microparticles of bupropion hydrobromide formulation into the patient's mouth.

The term "drug formulation retainer" as used herein, refers to a valve, plug or restriction, or the like that prevents passage of the drug formulation from the device. By "fluid passing drug formulation retainer" is intended a valve, plug or restriction or the like that allows for passage of fluids but does not allow for passage of other ingredients such as the drug formulation that is contained in the delivery device.

The dispensing device of this embodiment of the invention finds use where it is inconvenient or unsafe to use solid oral dosage forms such as capsules or tablets. The devices can be particularly useful in geriatric or pediatric patient populations but they can also be useful for those who have difficulty swallowing capsules or tablets. A single delivery device or several devices can be administered to a patient during a therapeutic program.

Generally the device is in prepared form prior to placement in a fluid. In at least one embodiment the dispensing device comprises a hollow drug formulation chamber with a first end and a second end. Contained within the chamber are drug formulation and fluid passing drug formulation retainers. The fluid passing drug formulation retainer comprises a restriction and a one-way plug. The diameter of the opening is smaller than the plug. In at least one embodiment the restriction is made by crimping an end of the chamber. The second end of the chamber has a drug formulation retainer for preventing release of the plug. In at least one embodiment the retainer is prepared by crimping the end of the chamber. Microparticles of bupropion hydrobromide are then placed in the chamber. An end-cap is placed over the second end of the chamber prior to use to prevent release of the drug formulation. In prepared form, the plug substantially seals the first end of the chamber, thereby preventing loss of the drug formulation from the first end.

The device can be formed from any suitable material that is physically and/or chemically compatible with both the active drug and the liquid diluent to be mixed therein. In certain embodiments, representative materials for forming devices including the drug formulation chamber, the elongated tubular member, the end caps and tabs, include, without limitation, paper, plastic such as propylene/styrene copolymers, polyproylene, high density polyethylene, low density polyethylene and the like. The devices can have an inner diameter of from about 3 mm to about 8 mm and a wall thickness of from about 0.1 mm to about 0.4 mm. The devices can be from about 10 cm to about 30 cm in length.

The fluid passing drug formulation retainer permits the free flow of liquid medium but prohibits passage of the drug formulation from the device prior to delivery. Where the retainer comprises a one-way plug or valve, the plug or valve will seal the straw at atmospheric pressure. When suction is applied, fluid will be drawn around the plug and into the drug formulation chamber. Further, the plug has a density of less than one so that it will ascend to the top as the drug formulation is delivered into the oral cavity. When suction is no longer applied, the plug will remain in the highest position it reached during sipping. The plug can be prepared from closed cell polyethylene foam such as ETHAFOAM®. Other forms of one way plugs can be a balloon of elastomeric material, a one-way mechanical ball valve and the like.

Examples of fluid that can be used for suspending the drug formulation by sipping through the drug formulation chamber include any palatable liquid such as water, juice, milk, soda, coffee, tea etc. Care must be taken to ensure compatibility of the fluid with the drug formulation.

In at least one embodiment, a dose sipping delivery device according to the present invention can be prepared as follows. Jumbo size straws with an inside diameter of about 0.21 inches and a length of about 8 inches are heat sealed at one end. The seal is partially cut off so that the "one-way" plug cannot escape. The partially sealed end is enclosed by half of a size 1 hard gelatin capsule. Microparticles are then placed inside the open end of the straw. A "one-way" plug made of closed cell polyethylene foam, MICROFOAM® (DuPont) is trimmed to snugly fit inside the straw. The plug is then placed inside the straw, on top of the microparticles. During operation, the plug end of the straw is placed into a glass of water and the protective gelatin capsule on the top of the straw is removed. By slowly applying suction through the partially sealed end of the straw, the microparticles are sucked into the mouth and easily swallowed.

Osmotic Dosage Forms

Osmotic dosage forms, osmotic delivery devices, modified release osmotic dosage forms, or osmosis-controlled extended-release systems are terms used interchangeably herein and are defined to mean dosage forms which forcibly dispense the bupropion hydrobromide salt by pressure created by osmosis or by osmosis and diffusion of fluid into a material which expands and forces the bupropion hydrobromide salt to be dispensed from the osmotic dosage form. Osmosis can be defined as the flow of solvent from a compartment with a low concentration of solute to a compartment with a high concentration of solute. The two compartments are separated by a membrane, wall, or coat, which allows flow of solvent (a liquid, aqueous media, or biological fluids) but not the solute. Examples of such membranes can for example be, a semipermeable membrane, microporous, asymmetric membrane, which asymmetric membrane can be permeable, semipermeable, perforated, or unperforated and can deliver the bupropion hydrobromide salt by osmotic pumping, diffusion or the combined mechanisms of diffusion and osmotic pumping. Thus, in principle, osmosis controlled release of the bupropion hydrobromide salt involves osmotic transport of an aqueous media into the osmotic dosage form followed by dissolution of the bupropion hydrobromide salt and the subsequent transport of the saturated solution of the bupropion hydrobromide salt by osmotic pumping of the solution through at least one passageway in the semipermeable membrane or by a combination of osmosis and diffusion through the semipermeable membrane.

It is well known to one of ordinary skill in the art that the desired in-vitro release rate and the in-vivo pharmacokinetic parameters can be influenced by several factors, such as for example, the amount of the bupropion hydrobromide salt used to form the core, the amount of pharmaceutically acceptable excipient used to form the core, the type of pharmaceutically acceptable excipient used to form the core, the amount or type of any other materials used to form the core such as, for example, osmagents (the term osmagent, osmotically effective solutes, osmotically effective compound and osmotic agents are used interchangeably herein) osmopolymers, and any combination thereof. The release profile can also be influenced by the material used to form the semipermeable membrane covering the core or by the material used to form any coating, such as a controlled release coating (e.g. a delayed release coat) on the semipermeable membrane. With these factors in mind, an osmotic device can therefore be designed to exhibit an in-vitro release rate such that in certain embodiments, after about 2 hours from about 0 to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released, when measured for example by using a USP Type 1 apparatus (Rotating Basket Method) in 900 ml water, 0.1N HCl, 0.1N HCl+0.1% Cetrimide, USP Buffer pH 1.5, Acetate Buffer pH 4.5, Phosphate Buffer, pH 6.5 or Phosphate Buffer pH 7.4 at 75 rpm at 37° C.±0.5° C. Alternatively dissolution may be effected in USP-3 media such as SGF pH 1.2, Acetate Buffer at pH 4.5 or phosphate buffer at pH 6.8.

Osmotic devices also may be designed to achieve an in-vitro release of no more than about 40% after about 2 hours, from about 40% to about 75% release after about 4 hours, at least about 75% after about 8 hours, and at least about 85% after about 16 hours when assayed using a dissolution medium such as identified above or known in the art.

In certain embodiments of the present invention, an osmotic dosage form is provided having a core comprising the bupropion hydrobromide salt and one or more excipients. In at least one embodiment the osmotic dosage form comprises an osmagent. The osmotic delivery system for example, can be in the form of a tablet or capsule containing microparticles.

In certain embodiments, the core of the osmotic dosage form comprises a water swellable polymer, non-limiting examples of which include hydroxypropyl cellulose, alkylcellulose, hydroxyalkylcellulose, polyalkylene oxide, polyethylene oxide, and mixtures thereof. A binder can be included in the core of certain embodiments of the osmotic dosage form to increase the core's mechanical strength. Non-limiting examples of binders include polyvinyl pyrollidine, carboxyvinyl polymer, methylcellulose, hydroxyethylcellulose, hydroxypropylcellulose, hydroxypropylmethylcellulose, a low molecular weight polyethylene oxide polymer, hydroxypropylmethylcellulose, dextrin, maltodextrin, gelatin, polyvinyl alcohol, xanthan gum, carbomers, caragheen, starch derivatives, and mixtures thereof. Lubricants can be included in certain embodiments of the osmotic dosage form to provide decreased friction between the solid and die wall during tablet manufacturing. Non-limiting examples of lubricants include stearic acid, magnesium stearate, glyceryl behenate, talc, mineral oil, sodium stearyl fumarate, hydrogenated vegetable oil, sodium benzoate, calcium stearate, and mixtures thereof. In other embodiments, additional inert excipients consistent with the objects of the invention can also be included in the core of the osmotic dosage form to facilitate the preparation and/or improve patient acceptability of the final osmotic dosage form as described herein. Suitable inert excipients are well known to the skilled artisan and can be found in the relevant literature, for example in the Handbook of Pharmaceutical Excipients (Rowe et. al., 4th Ed., Pharmaceutical Press, 2003).

In at least one embodiment, a modified release osmotic dosage form comprises bupropion hydrobromide in a therapeutically effective amount, which releases the bupropion hydrobromide by forcibly dispensing the bupropion hydrobromide from a core via a semipermeable membrane by diffusion and/or at least one passageway in the membrane by osmotic pumping (i) all or in part by pressure created in the core by osmosis i.e., positive hydrostatic pressure of a liquid, solvent, biological fluid or aqueous media and/or all or in part by the expansion of a swellable material which forces the bupropion hydrobromide to be dispensed from the core of the dosage form, and (ii) is formulated such that the dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released.

In at least one embodiment, the modified release dosage form comprises an osmotic delivery device comprising a homogenous solid core comprising substantially the bupropion hydrobromide salt present in a therapeutically effective amount with at least one pharmaceutically acceptable excipient, said core surrounded by a semipermeable membrane which permits entry of an aqueous liquid into the core and delivery of the bupropion hydrobromide salt from the core to the exterior of the dosage form through at least one passageway or by a combination of osmosis and diffusion such that the dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release rate of the bupropion hydrobromide salt is such that after about 2 hours no more than about 40% is released, after about 4 hours from about 40% to about 75% is released, after about 8 hours at least about 75% is released, and after about 16 hours at least about 85% is released.

In at least one embodiment, the modified release dosage form comprises a multiparticulate dosage form, each microparticle comprising an osmotic delivery device, each microparticle comprising a homogenous solid core comprising substantially the bupropion hydrobromide salt with at least one pharmaceutically acceptable excipient, said core of each microparticle surrounded by a semipermeable membrane which permits entry of an aqueous liquid into the core and delivery of the bupropion hydrobromide salt from the core to the exterior of the dosage form through a plurality of pores formed in the semipermeable membrane by inclusion of a pore forming agent in the membrane or by a combination of osmosis and diffusion so as to allow communication of the core with the outside of the device for delivery of the bupropion hydrobromide salt and is formulated such that the dosage form comprises a therapeutically effective amount of the bupropion hydrobromide salt and exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release rate of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment, the modified release dosage form comprises a multiparticulate dosage form, each microparticle comprising an osmotic delivery device, each microparticle comprising a homogenous solid core comprising substantially the bupropion hydrobromide salt in admixture with at least one pharmaceutically acceptable excipient, an osmagent and/or an osmopolymer, said core of each microparticle surrounded by a semipermeable membrane which permits entry of an aqueous liquid into the core and delivery of the bupropion hydrobromide salt from the core to the exterior of the dosage form through a plurality of pores formed in the semipermeable membrane by inclusion of a pore forming agent in the membrane or by a combination of osmosis and by diffusion so as to allow communication of the core with the outside of the device for delivery of the bupropion hydrobromide salt and is formulated such that the dosage form comprises a therapeutically effective amount of the bupropion hydrobromide salt and exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release rate of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment, the modified release dosage form comprises a multiparticulate dosage form, each microparticle comprising a homogenous solid core comprising substantially the bupropion hydrobromide salt with at least one pharmaceutically acceptable excipient in admixture with an osmagent, and/or an osmopolymer, and/or an absorption enhancer, said microparticles compressed into a tablet together with at least one pharmaceutically acceptable excipient, said tablet surrounded by a semipermeable membrane which permits entry of an aqueous liquid into the core and delivery of the bupropion hydrobromide salt from the tablet interior to the exterior of the dosage form through at least one passageway in the semipermeable membrane and/or by diffusion through the semipermeable membrane so as to allow communication of the tablet interior with the exterior of the tablet for delivery of the bupropion hydrobromide salt and is formulated such that the dosage form comprises a therapeutically effective amount of the bupropion hydrobromide salt and exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released, and after about 16 hours at least about 85% is released.

In at least one embodiment, the modified release dosage form comprises a multiparticulate dosage form, each microparticle comprising a sugar sphere or nonpareil bead coated with at least one layer comprising substantially the bupropion hydrobromide salt with at least one pharmaceutically acceptable excipient, said at least one layer surrounded by a semipermeable membrane which permits entry of an aqueous liquid into the layer and delivery of the bupropion hydrobromide salt from the layer to the exterior of the dosage form through a plurality of pores formed in the semipermeable membrane by inclusion of a pore forming agent in the membrane and/or by diffusion so as to allow communication of the core with the outside of the device for delivery of the bupropion hydrobromide salt and is formulated such that the dosage form comprises a therapeutically effective amount of the bupropion hydrobromide salt and exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment, the modified release dosage form comprises a multiparticulate dosage form, each microparticle comprising a sugar sphere or nonpareil bead coated with at least one layer comprising substantially the bupropion hydrobromide salt in admixture with at least one pharmaceutically acceptable excipient, an osmagent and/or an osmopolymer, said at least one layer surrounded by a semipermeable membrane which permits entry of an aqueous liquid into the layer and delivery of the bupropion hydrobromide salt from the layer to the exterior of the dosage form through a plurality of pores formed in the semipermeable membrane by inclusion of a pore forming agent in the membrane and/or by diffusion so as to allow communication of the core with the outside of the device for delivery of the bupropion hydrobromide salt and is formulated such that the dosage form comprises a therapeutically effective amount of the bupropion hydrobromide salt and exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment, the modified release dosage form comprises a modified release osmotic dosage form comprising a homogenous core comprising a therapeutically effective amount of the bupropion hydrobromide salt in admixture with an osmagent, and/or an osmopolymer, and/or and absorption enhancer, said core surrounded by a nontoxic wall, membrane or coat, such as for example a semipermeable membrane which permits entry of an aqueous liquid into the core and delivery of the bupropion hydrobromide salt from the core to the exterior of the dosage form through at least one passageway in the semipermeable membrane and/or by diffusion through the membrane so as to allow communication of the core with the outside of the dosage form for delivery of the bupropion hydrobromide salt and is formulated such that the dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment the modified release dosage form comprises an osmotic delivery device comprising the bupropion hydrobromide salt present in a therapeutically effective amount in a layered, contacting arrangement with a swellable material composition to yield a solid core with two or more layers, which core is surrounded by a nontoxic wall, membrane or coat, such as for example a semipermeable membrane which permits entry of an aqueous liquid into the core and delivery of the bupropion hydrobromide salt from the core to the exterior of the dosage form through at least one passageway in the semipermeable membrane or by osmosis and diffusion through the membrane so as to allow communication of the core with the outside of the dosage form for delivery of the bupropion hydrobromide salt and is formulated such that the dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours about 40% to about 75% is released, after about 8 hours at least about 75% is released and after about 16 hours at least about 85% is released.

In at least one embodiment, the modified release dosage form comprises an osmotic delivery device comprising a core and a membrane surrounding said core, said core comprising a therapeutically effective amount of the bupropion hydrobromide salt, and optionally at least one means for forcibly dispensing the bupropion hydrobromide salt from the device, said membrane comprising at least one means for the exit of the bupropion hydrobromide salt from the device, said device formulated such that when the device is in an aqueous medium, the bupropion hydrobromide salt, and optionally the at least one means for forcibly dispensing the bupropion hydrobromide salt from the device and the at least one means for the exit of the bupropion hydrobromide salt from the device cooperatively function to exhibit an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment, the modified release dosage form comprises an osmotic delivery device comprising a core and a membrane surrounding said core, said core comprising a therapeutically effective amount of the bupropion hydrobromide salt, at least one means for increasing the hydrostatic pressure inside the membrane and optionally at least one means for forcibly dispensing the bupropion hydrobromide salt from the device, said membrane comprising at least one means for the exit of the bupropion hydrobromide salt from the device, said device formulated such that when the device is in an aqueous medium, the at least one means for increasing the hydrostatic pressure inside the membrane, and optionally the at least one means for forcibly dispensing the bupropion hydrobromide salt from the device and the at least one means for the exit of the bupropion hydrobromide salt cooperatively function to exhibit an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment the invention is directed to once-a-day bupropion hydrobromide sustained release formulations that are bioequivalent according to FDA guidelines to WELLBUTRIN™ ER or ZYBAN™/WELLBUTRIN™ SR when administered once-daily to a subject in need thereof and wherein the bupropion hydrobromide salt contained is more stable than an equivalent molar amount of the bupropion hydrochloride salt contained in WELLBUTRIN™ ER or ZYBAN™ when exposed to like conditions, for example when stored for 10 days, 13 days, 14 days, 20 days, 24 days, 1 month, 2 months, 3 months, 4 months, 5 months, 6 months, or more under accelerated storage conditions (e.g. 40 degrees C., 75% relative humidity). In at least one embodiment the invention encompasses 174 mg, 348 mg and 522 mg bupropion hydrobromide formulations that are bioequivalent to bupropion hydrochloride formulations.

In at least one embodiment the invention is directed to topical formulations containing bupropion hydrobromide that can be administered topically, e.g., transmucosally or transdermally. Particularly, the invention embraces topically administrable gels and patch type delivery devices which can comprise another active agent such as nicotine.

In at least one embodiment the invention is directed to inhalable pulmonary deliverable compositions containing bupropion hydrobromide that can be administered via pulmonary delivery to a subject in need thereof. These compositions can be produced according to the aerosol technology as known in the art.

In at least one embodiment the invention is directed to injectable compositions comprising an effective amount of bupropion hydrobromide and a pharmaceutically acceptable carrier or excipient.

In at least one embodiment, the invention is directed to a method of treating a condition comprising administering any one of the above described osmotic dosage forms to a patient in need of such administration once-daily.

The invention, in at least one embodiment, is directed to a method for administering a bupropion hydrobromide salt to the gastrointestinal tract of a human for the treatment or management of a condition, wherein the method comprises: (a) admitting orally into the human a modified release dosage form comprising a bupropion hydrobromide salt, the modified release dosage form comprising an osmotic dosage form; and (b) administering the bupropion hydrobromide salt from the osmotic dosage form in a therapeutically responsive dose to produce the treatment or management of the condition such that the osmotic dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

The invention, in at least one embodiment, is directed to a method for administering a bupropion hydrobromide salt to the gastrointestinal tract of a human for the treatment or management of a condition, wherein the method comprises: (a) admitting orally into the human a modified release dosage form comprising a core and a membrane surrounding said core, said core comprising the bupropion hydrobromide salt and optionally a means for forcibly dispensing the bupropion hydrobromide salt from the device, said membrane comprising at least one means for the exit of the bupropion hydrobromide salt from the dosage form, and (b) administering the bupropion hydrobromide salt from the dosage form which is formulated such that when the dosage form is in an aqueous medium, the bupropion hydrobromide salt and optionally the means for forcibly dispensing the bupropion hydrobromide salt and the at least one means for the exit of the bupropion hydrobromide salt cooperatively function to exhibit an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

The invention, in at least one embodiment, is directed to a method for administering a bupropion hydrobromide salt to the gastrointestinal tract of a human for the treatment or management of a condition, wherein the method comprises: (a) admitting orally into the human a modified release dosage form comprising a core and a membrane surrounding said core, said core comprising the bupropion hydrobromide salt, a means for increasing the hydrostatic pressure within the core and optionally a means for forcibly dispensing the bupropion hydrobromide salt from the device, said membrane comprising at least one means for the exit of the bupropion hydrobromide salt from the dosage form, and (b) administering the bupropion hydrobromide salt from the dosage form which is formulated such that when the dosage form is in an aqueous medium, the bupropion hydrobromide salt, the means for increasing the hydrostatic pressure within the core and optionally the means for forcibly dispensing the bupropion hydrobromide salt and the at least one means for the exit of the bupropion hydrobromide salt cooperatively function to exhibit an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one other embodiment, the osmotic dosage form further comprises an immediate release coat for the immediate release of the bupropion hydrobromide salt from the immediate release coat. In embodiments comprising the immediate release coat, the osmotic dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one other embodiment, the osmotic dosage forms further comprise an inert water-soluble coat covering the semipermeable membrane or coat. This inert water-soluble coat can be impermeable in a first external fluid, while being soluble in a second external fluid. In embodiments comprising the inert water-soluble coat, the osmotic dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one other embodiment, the osmotic dosage forms further comprise an osmotic subcoat. In certain embodiments comprising the osmotic subcoat, the osmotic dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one other embodiment, the osmotic dosage forms further comprise a controlled release coat. The controlled release coat of the osmotic dosage form can, for example, control, extend, and/or delay the release of the bupropion hydrobromide salt. In certain embodiments comprising the controlled release coat, the osmotic dosage form exhibits an in-vitro release rate such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In at least one such embodiment the in-vitro release profile of the bupropion hydrobromide salt is such that after about 2 hours no more than about 40% is released, after about 4 hours from about 40% to about 75% is released, after about 8 hours at least about 75% is released and after about 16 hours at least about 85% is released.

In at least one embodiment, the controlled release coat of the osmotic dosage form comprises a material that is soluble or erodible in intestinal juices, substantially pH neutral or basic fluids of fluids having a pH higher than gastric fluid, but for the most part insoluble in gastric juices or acidic fluids.

In at least one embodiment, the controlled release coat of the osmotic dosage form comprises at least one water-insoluble water-permeable film-forming polymer and at least one water-soluble polymer.

In at least one embodiment, the controlled release coat of the osmotic dosage form comprises at least one water-insoluble water-permeable film-forming polymer and at least one water-soluble polymer and optionally at least one plasticizer.

In at least one embodiment, the controlled release coat of the osmotic dosage form comprises at least one water-insoluble water-permeable film-forming polymer, at least one water-soluble polymer and at least one means for the exit of the bupropion hydrobromide salt from the core of the osmotic dosage form.

In at least one embodiment, the controlled release coat of the osmotic dosage form comprises at least one water-insoluble water-permeable film-forming polymer, at least one water-soluble polymer and at least one passageway.

In at least one embodiment, the controlled release coat of the osmotic dosage form comprises at least one water-insoluble water-permeable film-forming polymer, at least one water-soluble polymer and at least one plasticizer.

In at least one embodiment, the controlled release coat of the osmotic dosage form comprises at least one water-insoluble water-permeable film-forming polymer, at least one water-soluble polymer, optionally at least one plasticizer, and at least one means for the exit of the bupropion hydrobromide salt from the core of the osmotic dosage form.

In at least one embodiment, the controlled release coat of the osmotic dosage form comprises at least one water-insoluble water-permeable film-forming polymer, at least one water-soluble polymer, optionally at least one plasticizer, and at least one passageway.

In at least one embodiment, the controlled release coat of the osmotic dosage form comprises an aqueous dispersion of a neutral ester copolymer without any functional groups; a poly glycol having a melting point greater than about 55° C., one or more pharmaceutically acceptable excipients, and optionally at least one means for the exit of the bupropion hydrobromide salt form the core of the osmotic dosage form. This controlled release coat is cured at a temperature at least equal to or greater than the melting point of the polyglycol.

In at least one other embodiment, the controlled release coat of the osmotic dosage form comprises at least one enteric polymer.

In certain embodiments the membrane or wall is permeable to the passage of aqueous media but not to the passage of the bupropion hydrobromide salt present in the core. The membrane can be, for example, a semipermeable membrane or an asymmetric membrane, which can be permeable, semipermeable, perforated, or unperforated and can deliver the bupropion hydrobromide salt by osmotic pumping, or the combined mechanisms of diffusion and osmotic pumping. The structural integrity of such membranes preferably remain substantially intact during the period of delivery of the bupropion hydrobromide salt. By "substantially intact" it is meant that the semipermeable property of the membrane is not compromised during the period of delivery of the bupropion hydrobromide salt.

The semipermeable membrane of the osmotic dosage form of certain embodiments comprises at least one pharmaceutically acceptable excipient, at least one polymer, wax, or combination thereof, although appropriately treated inorganic materials such as ceramics, metals or glasses can be used. When the semipermeable membrane comprises at least one polymer, the molecular weight of the at least one polymer or combination of polymers are preferably such that the polymer or combination of polymers is solid at the temperature of use i.e., both in-vitro and in-vivo.

In certain embodiments, the at least one polymer included in the semipermeable membrane of the osmotic dosage form can be a cellulose ester, such as for example, cellulose acetate, cellulose acetate acetoacetate, cellulose acetate benzoate, cellulose acetate butylsulfonate, cellulose acetate butyrate, cellulose acetate butyrate sulfate, cellulose acetate butyrate valerate. cellulose acetate caprate, cellulose acetate caproate, cellulose acetate caprylate, cellulose acetate carboxymethoxypropionate, cellulose acetate chloroacetate, cellulose acetate dimethaminoacetate, cellulose acetate dimethylaminoacetate, cellulose acetate dimethylsulfamate, cellulose acetate dipalmitate, cellulose acetate dipropylsulfamate, cellulose acetate ethoxyacetate, cellulose acetate ethyl carbamate, cellulose acetate ethyl carbonate, cellulose acetate ethyl oxalate. cellulose acetate furoate, cellulose acetate heptanoate, cellulose acetate heptylate, cellulose acetate isobutyrate, cellulose acetate laurate, cellulose acetate methacrylate, cellulose acetate methoxyacetate, cellulose acetate methylcarbamate, cellulose acetate methylsulfonate, cellulose acetate myristate, cellulose acetate octanoate, cellulose acetate palmitate, cellulose acetate phthalate, cellulose acetate propionate, cellulose acetate propionate sulfate, cellulose acetate propionate valerate, cellulose acetate p-toluene sulfonate, cellulose acetate succinate, cellulose acetate sulfate, cellulose acetate trimellitate, cellulose acetate tripropionate, cellulose acetate valerate, cellulose benzoate, cellulose butyrate napthylate, cellulose butyrate, cellulose chlorobenzoate, cellulose cyanoacetates, cellulose dicaprylate, cellulose dioctanoate, cellulose dipentanate, cellulose dipentanlate, cellulose formate, cellulose methacrylates, cellulose methoxybenzoate, cellulose nitrate, cellulose nitrobenzoate, cellulose phosphate (sodium salt), cellulose phosphinates, cellulose phosphites, cellulose phosphonates, cellulose propionate, cellulose propionate crotonate, cellulose propionate isobutyrate, cellulose propionate succinate, cellulose stearate, cellulose sulfate (sodium salt), cellulose triacetate, cellulose tricaprylate, cellulose triformate, cellulose triheptanoate, cellulose triheptylate, cellulose trilaurate, cellulose trimyristate, cellulose trinitrate, cellulose trioctanoate, cellulose tripalmitate, cellulose tripropionate, cellulose trisuccinate, cellulose trivalerate, cellulose valerate palmitate; a cellulose ether, such as for example, 2-cyanoethyl cellulose, 2-hydroxybutyl methyl cellulose, 2-hydroxyethyl cellulose, 2-hydroxyethyl ethyl cellulose, 2-hydroxyethyl methyl cellulose, 2-hydroxypropyl cellulose, 2-hydroxypropyl methyl cellulose, dimethoxyethyl cellulose acetate, ethyl 2-hydroxylethyl cellulose, ethyl cellulose, ethyl cellulose sulfate, ethylcellulose dimethylsulfamate, methyl cellulose, methyl cellulose acetate, methylcyanoethyl cellulose, sodium carboxymethyl 2-hydroxyethyl cellulose, sodium carboxymethyl cellulose; a polysulfone, such as for example, polyethersulfones; a polycarbonate; a polyurethane; a polyvinyl acetate; a polyvinyl alcohol; a polyester; a polyalkene such as polyethylene, ethylene vinyl alcohol copolymer, polypropylene, poly(1,2-dimethyl-1-butenylene), poly(1-bromo-1-butenylene), poly(1, butene), poly(1-chloro-1-butenylene), poly(1-decyl-1-butenylene), poly(1-hexane), poly(1-isopropyl-1-butenylene), poly(1-pentene), poly(3-vinylpyrene), poly(4-methoxyl 1-butenylene), poly(ethylene-co-methyl styrene), poly vinyl-chloride, poly(ethylene-co-tetrafluoroethylene), poly(ethylene-terephthalate), poly(dodecafluorobutoxylethylene), poly(hexafluoroprolylene), poly(hexyloxyethylene), poly(isobutene), poly(isobutene-co-isoprene), poly(isoprene), poly-butadiene, poly[(pentafluoroethyl)ethylene], poly[2-ethylhexyloxy)ethylene], poly(butylethylene), poly(tertbutyl ethylene), poly(cylclohexylethylene), poly[(cyclohexylmethyl)ethylene], poly(cyclopentylethylene), poly(decylethylene), poly-(dodecy-lethylene), poly (neopentyl ethylene), poly(propyl ethylene); a polystyrene, such as for example, poly(2,4-dimethyl styrene), poly(3-methyl styrene), poly(4-methoxystyrene), poly(4-methoxystyrene-stat-styrene), poly(4-methyl styrene), poly(isopentyl styrene), poly(isopropyl styrene), polyvinyl esters or polyvinyl ethers, such as form example, poly(benzoylethylene), poly(butoxyethylene), poly(chloroprene), poly(cyclohexloxyethylene), poly(decyloxyethylene), poly(dichloroethylene), poly(difluoroethylene), poly(vinyl acetate), poly(vinyltrimethyl)styrene); a polysiloxane, such as for example, poly (dimethylsiloxane); a polyacrylic acid derivative, such as for example, polyacrylates, polymethyl methacrylate, poly (acrylic acid) higher alkyl esters, poly(ethylmethacrylate), poly(hexadecyl methacrylate-co-methylmethacrylate), poly-(methylacrylate-co-styrene), poly(n-butyl methacrylate), poly(n-butyl-acrylate), poly (cyclododecyl acrylate), poly (benzyl acrylate), poly(butylacrylate), poly(secbutylacrylate), poly(hexyl acrylate), poly(octyl acrylate), poly(decyl acrylate), poly(dodecyl acrylate), poly(2-methyl butyl acrylate), poly(adamantyl methacrylate), poly(benzyl methacrylate), poly(butyl methacrylate), poly(2-ethylhexyl methacrylate), poly(octyl methacrylate), acrylic resins; a polyamide, such as for example, poly(iminoadipoyliminododecamethylene), poly(iminoadipoyliminohexamethylene), polyethers, such as for example, poly(octyloxyethylene), poly(oxyphenylethylene), poly(oxypropylene), poly(pentyloxyethylene), poly(phenoxy styrene), poly(secbutroxylethylene), poly(tertbutoxyethylene); and combinations thereof.

In at least one embodiment, the at least one wax included in the semipermeable membrane of the osmotic dosage form can be, for example, insect and animal waxes, such as for example, chinese insect wax, beeswax, spermaceti, fats and wool wax; vegetable waxes, such as for example, bamboo leaf wax, candelilla wax, carnauba wax, Japan wax, ouricury wax, Jojoba wax, bayberry wax, Douglas-Fir wax, cotton wax, cranberry wax, cape berry wax, rice-bran wax, castor wax, indian corn wax, hydrogenated vegetable oils (e.g., castor, palm, cottonseed, soybean), sorghum grain wax, Spanish moss wax, sugarcane wax, caranda wax, bleached wax, Esparto wax, flax wax, Madagascar wax, orange peel wax, shellac wax, sisal hemp wax and rice wax; mineral waxes, such as for example, Montan wax, peat waxes, petroleum wax, petroleum ceresin, ozokerite wax, microcrystalline wax and paraffins; synthetic waxes, such as for example, polyethylene wax, Fischer-Tropsch wax, chemically modified hydrocarbon waxes, cetyl esters wax; and combinations thereof.

In at least one embodiment, the semipermeable membrane of the osmotic dosage form can comprise a combination of at least one polymer, wax, or combinations thereof and optionally at least one excipient.

In embodiments where the bupropion hydrobromide salt is released through the membrane or wall in a controlled manner by the combined mechanisms of diffusion and osmotic pumping, the membrane or wall can comprise at least one of the above described polymers and/or waxes or a combination of polymers, such as for example, cellulose esters, copolymers of methacrylate salts and optionally a plasticizer.

The poly(methacrylate) copolymer salts used in the manufacturing of the membrane for the osmotic dosage form can be, for example, insoluble in water and in digestive fluids, but are permeable to different degrees. Examples of such copolymers are poly(ammonium methacrylate) copolymer RL (EUDRAGIT® RL), poly(ammonium methacrylate) copolymer (type A-USP/NF), poly(aminoalkyl methacrylate) copolymer RL-JSP I), and (ethyl acrylate)-(methyl methacrylate)-[(trimethylammonium)-ethylmethacrylate] (1:2:0.2) copolymer, MW 150,000. Other examples of such copolymers include those available from Rohm Pharma, Weiterstadt, such as for example, EUDRAGIT® RS100: solid polymer, EUDRAGIT® RL 12.5:12.5% solution in solvent, EUDRAGIT® RL 30 D: 30% aqueous dispersion, and other equivalent products. The following poly (ammonium methacrylate) copolymers can also be used: ammonium methacrylate copolymer RS (EUDRAGIT®RS), poly(ammonium methacrylate) copolymer (type B-USP/NF), poly(aminoalkyl methacrylate) copolymer (RSL-JSP I), (ethyl acrylate)-(methyl methacrylate)-[(trimethylammonium)-ethyl methacrylate] (1:2:0.1) copolymer, PM 150,000. Specific polymers include (Rohm Pharma, Weiterstadt): EUDRAGIT® RS 100: solid polymer, EUDRAGIT® RS 12.5:12.5% solution in solvent, EUDRAGIT® RS 30 D: 30% aqueous dispersion and other equivalent products. RL is readily water permeable while EUDRAGIT® RS is hardly water permeable. By employing mixtures of both EUDRAGIT® RL and EUDRAGIT®RS, membranes having the desired degree of permeability to achieve the in-vitro dissolution rates and in-vivo pharmacokinetic parameters can be prepared.

The use of plasticizers is optional but can be included in the osmotic dosage forms of certain embodiments to modify the properties and characteristics of the polymers used in the coats or core of the osmotic dosage forms for convenient processing during manufacture of the coats and/or the core of the osmotic dosage forms if necessary. As used herein, the term "plasticizer" includes any compounds capable of plasticizing or softening a polymer or binder used in invention. Once the coat or membrane has been manufactured, certain plasticizers can function to increase the hydrophilicity of the coat(s) and/or the core of the osmotic dosage form in the environment of use. During manufacture of the coat, the plasticizer lowers the melting temperature or glass transition temperature (softening point temperature) of the polymer or binder. Plasticizers, such as low molecular weight PEG, can be included with a polymer and lower its glass transition temperature or softening point. Plasticizers also can reduce the viscosity of a polymer. The plasticizer can impart some particularly advantageous physical properties to the osmotic device of the invention.

Plasticizers useful in the osmotic dosage form of certain embodiments of the invention can include, for example, low molecular weight polymers, oligomers, copolymers, oils, small organic molecules, low molecular weight polyols having aliphatic hydroxyls, ester-type plasticizers, glycol ethers, poly(propylene glycol), multi-block polymers, single block polymers, low molecular weight poly(ethylene glycol), citrate ester-type plasticizers, triacetin, propylene glycol, glycerin, ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate, allyl glycolate and mixtures thereof. All such plasticizers are commercially available from sources such as Aldrich or Sigma Chemical Co. It is also contemplated and within the scope of the invention, that a combination of plasticizers can be used in the present formulation. The PEG based plasticizers are available commercially or can be made by a variety of methods, such as disclosed in Poly(ethylene glycol) Chemistry: Biotechnical and Biomedical Applications (J. M. Harris, Ed.; Plenum Press, NY). Once the osmotic dosage form is manufactured, certain plasticizers can function to increase the hydrophilicity of the coat(s) and/or the core of the osmotic dosage form in the environment of use may it be in-vitro or in-vivo. Accordingly, certain plasticizers can function as flux enhancers.

The ratio of cellulose esters:copolymers of methacrylate salts:plasticizer of the osmotic dosage forms can be, for example, about 1% to about 99% of the cellulose ester by weight: about 0.5% to about 84% of the copolymers of methacrylate salt by weight: about 0.5% to about 15% of the plasticizer by weight. The total weight percent of all components comprising the wall is 100%.

Aside from the semipermeable membranes of the osmotic dosage form described above, asymmetric membranes can also be used to surround the core of an osmotic dosage form for the controlled release of the bupropion hydrobromide salt to provide the in-vitro release rates described above and the therapeutically beneficial in-vivo pharmacokinetic parameters for the treatment or management of a condition. Such asymmetric membranes can be permeable, semipermeable, perforated, or unperforated and can deliver the bupropion hydrobromide salt by osmotic pumping, diffusion or the combined mechanisms of diffusion and osmotic pumping. The manufacture and use thereof of asymmetric membranes for the controlled-release of an active drug through one or more asymmetric membranes by osmosis or by a combination of diffusion osmotic pumping is known.

In certain embodiments of the osmotic dosage form, the semipermeable membrane can further comprise a flux enhancing, or channeling agent. "Flux enhancing agents" or "channeling agents" are any materials which function to increase the volume of fluid imbibed into the core to enable the osmotic dosage form to dispense substantially all of the bupropion hydrobromide salt through at least one passageway in the semipermeable membrane by osmosis or by osmosis and by diffusion through the semipermeable membrane. The flux enhancing agent dissolves to form paths in the semipermeable membrane for the fluid to enter the core and dissolve the bupropion hydrobromide salt in the core together with the osmagent, if one is present, but does not allow exit of the bupropion hydrobromide salt. The flux enhancing agent can be any water soluble material or an enteric material which allows an increase in the volume of liquid imbibed into the core but does not allow for the exit of the bupropion hydrobromide salt. Such materials can be, for example, sodium chloride, potassium chloride, sucrose, sorbitol, mannitol, polyethylene glycol, propylene glycol, hydroxypropyl cellulose, hydroxypropyl methylcellulose, hydroxypropyl methylcellulose phthalate, cellulose acetate phthalate, polyvinyl alcohols, methacrylic copolymers, and combinations thereof. Some plasticizers can also function as flux enhancers by increasing the hydrophilicity of the semipermeable membrane and/or the core of the osmotic dosage form. Flux enhancers or channeling agents can also function as a means for the exit of the bupropion hydrobromide salt from the core if the flux enhancing or channeling agent is used in a sufficient amount.

The expression "passageway" as used herein comprises means and methods suitable for the metered release of the bupropion hydrobromide salt from the core of the osmotic dosage form. The means for the exit of the bupropion hydrobromide salt comprises at least one passageway, including orifice, bore, aperture, pore, porous element, hollow fiber, capillary tube, porous overlay, or porous element that provides for the osmotic controlled release of the bupropion hydrobromide salt. The means for the exit can be linear or tortuous. The means for the exit includes a weakened area of the semipermeable membrane or a material that erodes or is leached from the wall in a fluid environment of use to produce at least one dimensioned passageway. The means for the exit of the bupropion hydrobromide salt can comprise any leachable material, which when leaches out of the semipermeable membrane forms a passageway suitable for the exit of the bupropion hydrobromide salt from the core of the osmotic dosage form. Such leachable materials can comprise, for example, a leachable poly(glycolic) acid or poly(lactic) acid polymer in the semipermeable membrane, a gelatinous filament, poly(vinyl alcohol), leachable polysaccharides, salts, oxides, sorbitol, sucrose or mixtures thereof. The means for exit can also comprise a flux enhancer or channeling agent if present in a sufficient amount. The means for the exit possesses controlled-release dimensions, such as round, triangular, square and elliptical, for the metered release of the bupropion hydrobromide salt from the dosage form. The dimensions of the means of the exit for the bupropion hydrobromide salt is sized such so as to allow the bupropion hydrobromide salt to pass through the means for the exit. The dosage form can be constructed with one or more means for the exit in spaced apart relationship on a single surface or on more than one surface of the wall.

The expression "fluid environment" denotes an aqueous or biological fluid as in a human patient, including the gastrointestinal tract. The means for the exit can be preformed for example by mechanical means after the semipermeable membrane is applied to the core of the osmotic dosage form, such as for example by mechanical perforation, laser perforation, or by using a properly sized projection on the interior of a tablet punch to form the means for the exit of the bupropion hydrobromide salt, such as for example a cylindrical or frustoconical pin which is integral with the inside surface of the upper punch of a punch used to form the osmotic dosage form. Alternatively, the means for the exit of the bupropion hydrobromide salt can be formed by incorporating a leachable material or pore forming agent into the semipermeable composition before the semipermeable membrane is applied to the core of the osmotic dosage form. The means for the exit of the bupropion hydrobromide salt can comprise a combination of the different exit means described above. The osmotic dosage form can comprise more than one means for the exit of the bupropion hydrobromide salt including two, three, four, five, six seven, eight, nine ten or more exit means and can be formed in any place of the osmotic dosage form. The various positions of the means for the exit are disclosed. The type, number, and dimension(s) of the means for the exit of the bupropion hydrobromide salt is such that the dosage form exhibits the desired in-vitro release rates described herein and can be determined by routine experimentation by those skilled in the pharmaceutical delivery arts. The means for the exit and equipment for forming the means for the exit are known.

The osmotic device can further comprise a controlled release coat surrounding the semipermeable membrane comprising an enteric or delayed release coat that is soluble or erodible in intestinal juices, substantially pH neutral or basic fluids of fluids having a pH higher than gastric fluid, but for the most part insoluble in gastric juices or acidic fluids. A wide variety of other polymeric materials are known to possess these various solubility properties. Such other polymeric materials include, for example, cellulose acetate phthalate (CAP), cellulose acetate trimelletate (CAT), poly(vinyl acetate) phthalate (PVAP), hydroxypropyl methylcellulose phthalate (HP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, EUDRAGIT® L-30-D (MA-EA, 1:1), EUDRAGIT® L-100-55 (MA-EA, 1:1), hyciroxypropyl methylcellulose acetate succinate (HPM-CAS), COATERIC® (PVAP), AQUATERIC® (CAP), AQUACOAT® (HPMCAS) and combinations thereof. The enteric coat can also comprise dissolution aids, stability modifiers, and bioabsorption enhancers.

In at least one embodiment the controlled release coat of certain osmotic dosage forms include materials such as hydroxypropylcellulose, microcrystalline cellulose (MCC, AVICEL™ from FMC Corp.), poly (ethylene-vinyl acetate) (60:40) copolymer (EVAC from Aldrich Chemical Co.), 2-hydroxyethylmethacrylate (HEMA), MMA, terpolymers of HEMA: MMA:MA synthesized in the presence of N,N'-bis(methacryloyloxyethyloxycarbonylamino)-azobenzene, azopolymers, enteric coated timed release system (TIME CLOCK® from Pharmaceutical Profiles, Ltd., UK), calcium pectinate, and mixtures thereof.

Polymers that can be used in the controlled release coat of osmotic dosage forms of certain embodiments can be, for example, enteric materials that resist the action of gastric fluid avoiding permeation through the semipermeable wall while one or more of the materials in the core of the dosage form are solubilized in the intestinal tract thereby allowing delivery of the bupropion hydrobromide salt in the core by osmotic pumping in the osmotic dosage form to begin. A material that adapts to this kind of requirement can be, for example, a poly(vinylpyrrolidone)-vinyl acetate copolymer, such as the material supplied by BASF under its KOLLIDON® VA64 trademark, mixed with magnesium stearate and other similar excipients. The coat can also comprise povidone, which is supplied by BASF under its KOLLIDON® K 30 trademark, and hydroxypropyl methylcellulose, which is supplied by Dow under its METHOCEL® E-15 trademark. The materials can be prepared in solutions having different concentrations of polymer according to the desired solution viscosity. For example, a 10% P/V aqueous solution of KOLLIDON® K 30 has a viscosity of about 5.5 to about 8.5 cps at 20° C., and a 2% P/V aqueous solution of METHOCEL® E-15 has a viscosity of about 13 to about 18 cps at 20° C.

The controlled release coat of osmotic dosage forms of certain embodiments can comprise one or more materials that do not dissolve, disintegrate, or change their structural integrity in the stomach and during the period of time that the tablet resides in the stomach, such as for example a member chosen from the group (a) keratin, keratin saridarac-tolu, salol (phenyl salicylate), salol beta-naphthylbenzoate and acetotannin, salol with balsam of Peru, salol with tolu, salol with gum mastic, salol and stearic acid, and salol and shellac; (b) a member chosen from the group of formalized protein, formalized gelatin, and formalized cross-linked gelatin and exchange resins; (c) a member chosen from the group of myristic acid-hydrogenated castor oil-cholesterol, stearic acid-mutton tallow, stearic acid-balsam of tolu, and stearic acid-castor oil; (d) a member chosen from the group of shellac, ammoniated shellac, ammoniated shellac-salol, shellac-wool fat, shellac-acetyl alcohol, shellac-stearic acid-balsam of tolu, and shellac n-butyl stearate; (e) a member chosen from the group of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethyl-methacrylate-butylmethacrylate-methylmethacrylate copolymer of about 150,000 molecular weight, methacrylic acid-methylmethacrylate 50:50 copolymer of about 135,000 molecular weight, methacrylic acid-methylmethacrylate-30:70-copolymer of about 135,000 mol. wt., methacrylic acid-dimethylaminoethyl-methacrylate-ethylacrylate of about 750,000 mol. wt., methacrylic acid-methylmethacrylate-ethylacrylate of about 1,000,000 mol. wt., and ethylacrylate-methylmethacrylate-ethylacrylate of about 550,000 mol. wt; and, (g) an enteric composition chosen from the group of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from about 1 to about 7 straight and branched alkyl groups, aryl phthalates, and other materials known to one or ordinary skill in the art. Combinations thereof are operable.

Accordingly, in at least one other embodiment, the controlled release coat of osmotic dosage forms of certain embodiments comprises a water-insoluble water-permeable film-forming polymer, water-soluble polymer, and optionally a plasticizer and/or a pore-forming agent. The water-insoluble, water-permeable film-forming polymers useful for the manufacture of the controlled release coat can be cellulose ethers, such as for example, ethyl celluloses chosen from the group of ethyl cellulose grade PR100, ethyl cellulose grade PR20, cellulose esters, polyvinyl alcohol, and any combination thereof. The water-soluble polymers useful for the controlled release coat can be, for example, polyvinylpyrrolidone, hydroxypropyl methylcellulose, hydroxypropyl cellulose, and any combination thereof.

The skilled artisan will appreciate that that the desired in-vitro release rates described herein for the bupropion hydrobromide salt can be achieved by controlling the permeability and/or the amount of coating applied to the core of the osmotic dosage form. The permeability of the controlled release coat, can be altered by varying the ratio of the water-insoluble, water-permeable film-forming polymer:water-soluble polymer:optionally the plasticizer and/or the quantity of coating applied to the core of the osmotic dosage form. A more extended release is generally obtained with a higher amount of water-insoluble, water-permeable film forming polymer. The addition of other excipients to the core of the osmotic dosage form can also alter the permeability of the controlled release coat. For example, if the core of the osmotic dosage form comprises a swellable polymer, the amount of plasticizer in the controlled release coat can be increased to make the coat more pliable as the pressure exerted on a less pliable coat by the swellable polymer could rupture the coat. Further, the proportion of the water-insoluble water-permeable film forming polymer and water-soluble polymer can also be altered depending on whether a faster or slower in-vitro dissolution is desired.

In at least one other embodiment, the controlled release coat of the osmotic dosage form comprises an aqueous dispersion of a neutral ester copolymer without any functional groups; a poly glycol having a melting point greater than about 55° C., and one or more pharmaceutically acceptable excipients and cured at a temperature at least equal to or greater than the melting point of the poly glycol. The manufacture and use of such coating formulations are known. In brief, examples of neutral ester copolymers without any functional groups comprising the coat can be EUDRAGIT® NE30D, EUDRAGIT® NE40D (Röhm America LLC), or mixtures thereof. This coat can comprise hydrophilic agents to promote wetting of the coat when in contact with gastrointestinal fluids. Such hydrophilic agents include, for example, hydrophilic water-soluble polymers such as hydroxypropyl methylcellulose (HPMC), hydroxypropyl cellulose (HPC) and combinations thereof. The poly glycol can be, for example, chosen from the group of polyethylene glycol 6000, polyethylene glycol 8000, polyethylene glycol 10000, polyethylene glycol 20000, Poloxamer 188, Poloxamer 338, Poloxamer 407, Polyethylene Oxides, Polyoxyethylene Alkyl Ethers, and Polyoxyethylene Stearates, and combinations thereof. This controlled release coat of the osmotic dosage form can further comprise a pore-forming agent. In at least one embodiment the pore former is sufficiently insoluble in the aqueous dispersion, and is sufficiently soluble in the environment of use. Methods for producing such coats are known.

The controlled release coat of certain embodiments of the osmotic dosage form of certain embodiments of the present invention includes at least one polymer in an amount sufficient to achieve a controlled release of the bupropion hydrobromide salt. Examples of polymers that can be used in the controlled release coat of these embodiments include cellulose acetate phthalate, cellulose acetate trimaletate, hydroxy propyl methyl cellulose phthalate, polyvinyl acetate phthalate, ammonio methacrylate copolymers such as those sold under the trademark EUDRAGIT® RS and RL, poly acrylic acid and poly acrylate and methacrylate copolymers such as those sold under the trademark EUDRAGIT® S and L, polyvinyl acetaldiethylamino acetate, hydroxypropyl methylcellulose acetate succinate, shellac; hydrogels and gel-forming materials, such as carboxyvinyl polymers, sodium alginate, sodium carmellose, calcium carmellose, sodium carboxymethyl starch, poly vinyl alcohol, hydroxyethyl cellulose, methyl cellulose, gelatin, starch, and cellulose based crosslinked polymers in which the degree of crosslinking is low so as to facilitate adsorption of water and expansion of the polymer matrix, hydroxypropyl cellulose, hydroxypropyl methylcellulose, polyvinylpyrrolidone, crosslinked starch, microcrystalline cellulose, chitin, aminoacryl-methacrylate copolymer (EUDRAGIT® RS-PM, Rohm & Haas), pullulan, collagen, casein, agar, gum arabic, sodium carboxymethyl cellulose, (swellable hydrophilic polymers) poly(hydroxyalkyl methacrylate) (molecular weight from about 5K to about 5000K), polyvinylpyrrolidone (molecular weight from about 10K to about 360K), anionic and cationic hydrogels, polyvinyl alcohol having a low acetate residual, a swellable mixture of agar and carboxymethyl cellulose, copolymers of maleic anhydride and styrene, ethylene, propylene or isobutylene, pectin (molecular weight from about 30K to about 300K), polysaccharides such as agar, acacia, karaya, tragacanth, algins and guar, polyacrylamides, POLYOX® polyethylene oxides (molecular weight from about 100K to about 5000K), AQUAKEEP® acrylate polymers, diesters of polyglucan, crosslinked polyvinyl alcohol and poly N-vinyl-2-pyrrolidone, sodium starch glycolate (e.g. EXPLOTAB®; Edward Mandell C. Ltd.); hydrophilic polymers such as polysaccharides, methyl cellulose, sodium or calcium carboxymethyl cellulose, hydroxypropyl methyl cellulose, hydroxypropyl cellulose, hydroxyethyl cellulose, nitro cellulose, carboxymethyl cellulose, cellulose ethers, polyethylene oxides (e.g. POLYOX, Union Carbide), methyl ethyl cellulose, ethylhydroxy ethylcellulose, cellulose acetate, cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid, copolymers of methacrylic acid or methacrylic acid (e.g. EUDRAGIT®, Rohm and Haas), other acrylic acid derivatives, sorbitan esters, natural gums, lecithins, pectin, alginates, ammonia alginate, sodium, calcium, potassium alginates, propylene glycol alginate, agar, and gums such as arabic, karaya, locust bean, tragacanth, carrageens, guar, xanthan, scleroglucan and mixtures and blends thereof. In at least one embodiment of the osmotic dosage form of the present invention, the polymer is an acrylate dispersion such as EUDRAGIT® NE30D, EUDRAGIT® NE40D (Rohm America LLC), KOLLICOAT® SR 30D, SURELEASE®, or a mixture thereof. The polymer can be present in an amount of from about 20% to about 90% by weight of the controlled release coat, depending on the controlled release profile desired. For example, in certain embodiments of the osmotic dosage form, the polymer is present in an amount of from about 50% to about 95%, in other embodiments from about 60% to about 90%, and in still other embodiments about 75% of the controlled release coat weight.

The controlled release coat of certain embodiments of the osmotic dosage form of the present invention can also include one or more pharmaceutically acceptable excipients such as lubricants, emulsifiers, anti-foaming agents, plasticisers, solvents and the like.

Lubricants can be included in the controlled release coat of certain embodiments of the osmotic dosage form of the present invention to help reduce friction of coated microparticles during manufacturing. The lubricants that can be used in the controlled release coat include but are not limited to adipic acid, magnesium stearate, calcium stearate, zinc stearate, calcium silicate, magnesium silicate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil, waxy fatty acid esters such as glyceryl behenate, (i.e. COMPRITOL™), STEAR-O-WET™ and MYVATEX™ TL. Combinations of these lubricants are operable. In at least one embodiment, the lubricant is selected from magnesium stearate, talc and a mixture thereof. The lubricant(s) can each be present in an amount of from about 0.1% to about 80% of the controlled release coat weight. For example, in certain embodiments the lubricant is present in an amount of from about 0.5% to about 20%, in other embodiments from about 0.8% to about 10%, and in still other embodiments about 1.5% of the controlled release coat weight. Emulsifying agent(s) (also called emulsifiers or emulgents) can be included in the controlled release coat of the osmotic dosage forms of certain embodiments of the present invention to facilitate actual emulsification during manufacture of the coat, and also to increase or ensure emulsion stability during the shelf-life of the product. Emulsifying agents useful for the controlled release coat composition of the osmotic dosage form include, but are not limited to naturally occurring materials and their semi synthetic derivatives, such as the polysaccharides, as well as glycerol esters, cellulose ethers, sorbitan esters (e.g. sorbitan monooleate or SPAN™ 80), and polysorbates (e.g. TWEEN™ 80). Combinations of emulsifying agents are operable. The emulsifying agent(s) can be present in an amount of from about 0.01% to about 0.25% of the controlled release coat weight. For example, in certain embodiments the emulsifying agent is present in an amount of from about 0.01% to about 0.15%, in other embodiments from about 0.01% to about 0.07%, and in still other embodiments about 0.03% of the controlled release coat weight.

Anti-foaming agent(s) can be included in the controlled release coat of the osmotic dosage form of certain embodiments of the present invention to reduce frothing or foaming during manufacture of the coat. Anti-foaming agents useful for the controlled release coat composition of the osmotic dosage form include, but are not limited to simethicone, polyglycol, silicon oil and mixtures thereof. In at least one embodiment the anti-foaming agent is Simethicone C. The anti-foaming agent can be present in an amount of from about 0.01% to about 10% of the controlled release coat weight. For example, in certain embodiments the anti-foaming agent is present in an amount of from about 0.05% to about 1%, in other embodiments from about 0.1% to about 0.3%, and in still other embodiments about 0.15% of the controlled release coat weight.

It is contemplated that in certain embodiments, other excipients consistent with the objects of the present invention can also be used in the controlled release coat of the osmotic dosage form.

In at least one embodiment, the controlled release coat of the osmotic dosage form includes about 75% EUDRAGIT® NE30D, about 1.5% Magnesium stearate, about 1.5% Talc, about 0.03% TWEEN™ 80, about 0.15% Simethicone C, and about 21.82% water, by weight of the controlled release coat composition.

The osmotic dosage form of certain embodiments can be made according to any one of the methods described herein. In a prophetic example of certain embodiments of osmotic dosage forms of the present invention, the manufacturing process for the controlled release coat of the osmotic dosage form can hypothetically be as follows: Water is split into two portions of about 15% and about 85%. The anti-foaming agent and the emulsifying agent are then added to the 15% water portion, and mixed at about 300 rpm to form portion A. In at least one embodiment, the anti-foaming agent is Simethicone C, and the emulsifying agent is TWEEN™ 80. A first lubricant is then added to the 85% water portion and mixed at about 9500 rpm to form portion B. In at least one embodiment, the first lubricant is talc. Then portion A is mixed with portion B, a second lubricant is slowly added, and mixed at about 700 rpm overnight. In at least one embodiment, the second lubricant is magnesium stearate. Finally, an aqueous dispersion of a neutral ester copolymer is added and mixed for about 30 minutes at about 500 rpm. In at least one embodiment, the aqueous dispersion of a neutral ester copolymer is EUDRAGIT® NE30D. The resultant coat solution can then be used to coat the osmotic subcoated microparticles to about a 35% weight gain with the following parameters: An inlet temperature of from about 10° C. to about 60° C., in certain embodiments from about 20° C. to about 40° C., and in at least one embodiment from about 25° C. to about 35° C.; an outlet temperature of from about 10° C. to about 60° C., in certain embodiments from about 20° C. to about 40° C., and in at least one embodiment from about 25° C. to about 35° C.; a product temperature of from about 10° C. to about 60° C., in certain embodiments from about 15° C. to about 35° C., and in at least one embodiment from about 22° C. to about 27° C.; an air flow of from about 10 cm/h to about 180 cm/h, in certain embodiments from about 40 cm/h to about 120 cm/h, and in at least one embodiment from about 60 cm/h to about 80 cm/h; and an atomizing pressure of from about 0.5 bar to about 4.5 bar, in certain embodiments from about 1 bar to about 3 bar, and in at least one embodiment at about 2 bar. The resultant coated microparticles can then be discharged from the coating chamber and overcured with the following parameters: A curing temperature of from about 20° C. to about 65° C., in certain embodiments from about 30° C. to about 55° C., and in at least one embodiment at about 40° C.; and a curing time of from about 2 hours to about 120 hours, in certain embodiments from about 10 hours to about 40 hours, and in at least one embodiment at about 24 hours. Any other technology resulting in the coating formulation of the controlled release coat of the osmotic dosage form that is consistent with the objects of the invention can also be used.

In at least one other embodiment, the osmotic dosage forms comprise a water-soluble or rapidly dissolving coat between the semipermeable membrane and the controlled release coat. The rapidly dissolving coat can be soluble in the buccal cavity and/or upper GI tract, such as the stomach, duodenum, jejunum or upper small intestines. Materials suitable for the manufacture of the water-soluble coat are known. In certain embodiments, the rapidly dissolving coat can be soluble in saliva, gastric juices, or acidic fluids. Materials which are suitable for making the water soluble coat or layer can comprise, for example, water soluble polysaccharide gums such as carrageenan, fucoidan, gum ghatti, tragacanth, arabinogalactan, pectin, and xanthan; water-soluble salts of polysaccharide gums such as sodium alginate, sodium tragacanthin, and sodium gum ghattate; water-soluble hydroxyalkylcellulose wherein the alkyl member is straight or branched of 1 to 7 carbons such as, for example, hydroxymethylcellulose, hydroxyethylcellulose, and hydroxypropylcellulose; synthetic water-soluble cellulose-based lamina formers such as, for example, methyl cellulose and its hydroxyalkyl methylcellulose cellulose derivatives such as a member chosen from the group of hydroxyethyl methylcellulose, hydroxypropyl methyl cellulose, and hydroxybutyl methylcellulose; croscarmellose sodium; other cellulose polymers such as sodium carboxymethylcellulose; and mixtures thereof. Other lamina forming materials that can be used for this purpose include, for example, poly(vinylpyrrolidone), polyvinylalcohol, polyethylene oxide, a blend of gelatin and polyvinyl-pyrrolidone, gelatin, glucose, saccharides, povidone, copovidone, poly (vinylpyrrolidone)-poly(vinyl acetate) copolymer and mixtures thereof. The water soluble coating can comprise other pharmaceutical excipients that in certain embodiments can alter the way in which the water soluble coating behaves. The artisan of ordinary skill will recognize that the above-noted materials include film-forming polymers. The inert water-soluble coat covering the semipermeable wall and blocking the passageway of osmotic dosage forms of the present invention, is made of synthetic or natural material which, through selective dissolution or erosion can allow the passageway to be unblocked thus allowing the process of osmotic delivery to start. This water-soluble coat can be impermeable to a first external fluid, while being soluble in a second external fluid. This property can help to achieve a controlled and selective release of the bupropion hydrobromide salt from the osmotic dosage form so as to achieve the desired in-vitro release rates.

In embodiments where the core of the osmotic dosage form does not comprise an osmagent, the osmotic dosage forms can comprise an osmotic subcoat, which can surround the core of the osmotic dosage form. The osmotic subcoat comprises at least one osmotic agent and at least one hydrophilic polymer. The osmotic subcoat of these embodiments provides for the substantial separation of the bupropion hydrobromide salt from the osmotic agent into substantially separate compartments/layers. This separation can potentially increase the stability of the bupropion hydrobromide salt by reducing possible unfavorable interactions between the bupropion hydrobromide salt and the osmagent, and/or between the bupropion hydrobromide salt and the components of the controlled release coat. For example, the osmagent can be hygroscopic in nature, and can attract water that can lead to the degradation of the bupropion hydrobromide salt. Since the osmotic agent of these embodiments can be substantially separated from the bupropion hydrobromide salt, the bupropion hydrobromide salt can be less prone to degradation from the water drawn in by the osmagent. The controlled release coat comprises at least one controlled release polymer and optionally a plasticizer. The coated cores of the osmotic dosage form can be filled into capsules, or alternatively can be compressed into tablets using suitable excipients. In these embodiments the osmotic dosage form can utilize both diffusion and osmosis to control drug release, and can be incorporated into sustained release and/or delayed release dosage forms. In addition, in certain embodiments the osmotic pressure gradient and rate of release of the bupropion hydrobromide salt can be controlled by varying the level of the osmotic agent and/or the level of the hydrophilic polymer in the osmotic subcoat, without the need for a seal coat around the osmotic subcoat.

The hydrophilic polymer used in an osmotic subcoat of certain embodiments of the present invention functions as a carrier for the osmotic agent. In certain embodiments the hydrophilic polymer in the osmotic subcoat does not substantially affect the drug release. In at least one embodiment, the hydrophilic polymer used in the osmotic subcoat does not act as a diffusion barrier to the release of the bupropion hydrobromide salt. In at least one embodiment the release profile of the osmotic agent is substantially the same as the release profile of the bupropion hydrobromide salt. Such hydrophilic polymers useful in an osmotic subcoat of certain embodiments of the present invention include by way of example, polyvinyl pyrrolidone, hydroxyethyl cellulose, hydroxypropyl cellulose, low molecular weight hydroxypropyl methylcellulose (HPMC), polymethacrylate, ethyl cellulose, and mixtures thereof. In at least one embodiment, the hydrophilic polymer of the osmotic subcoat is a low molecular weight and a low viscosity hydrophilic polymer. A wide variety of low molecular weight and low viscosity hydrophilic polymers can be used in the osmotic subcoat. Examples of HPMC polymers that can be used in the osmotic subcoat include PHARMACOAT® 606, PHARMACOAT® 606G, PHARMACOAT® 603, METHOCEL® E3, METHOCEL® E5, METHOCEL® E6, and mixtures thereof. The hydrophilic polymer of the osmotic subcoat can be present in an amount of from about 1% to about 30% by weight of the osmotic subcoat composition. For example, in certain embodiments the hydrophilic polymer is present in an amount of from about 1% to about 20%, in other embodiments from about 3% to about 10%, and in still other embodiments about 7% by weight of the osmotic subcoat composition.

In at least one embodiment, the osmotic subcoat comprises about 7% PHARMACOAT® 606, about 1% sodium chloride, and about 92% water, by weight of the osmotic subcoat composition.

One method for producing the osmotic subcoat can be as follows. The at least one osmotic agent, for example sodium chloride, is dissolved in water. The solution of osmotic agent and water is then heated to about 60° C. The hydrophilic polymer is then added gradually to the solution. A magnetic stirrer can be used to aid in the mixing of the hydrophilic polymer to the solution of osmotic agent and water. The resultant osmotic subcoating solution can then be used to coat the core of the osmotic dosage form in a fluidized bed granulator, such as a granulator manufactured by Glatt (Germany) or Aeromatic (Switzerland) to the desired weight gain. An inlet temperature of from about 10° C. to about 70° C., in certain embodiments from about 30° C. to about 55° C., and in at least one embodiment from about 40° C. to about 45° C.; an outlet temperature of from about 110° C. to about 70° C., in certain embodiments from about 20° C. to about 45° C., and in at least one embodiment from about 30° C. to about 35° C.; a product temperature of from about 10° C. to about 70° C., in certain embodiments from about 20° C. to about 45° C., and in at least one embodiment from about 30° C. to about 35° C.; an air flow of from about 10 cm/h to about 180 cm/h; in certain embodiments from about 40 cm/h to about 120 cm/h; and in at least one embodiment from about 60 cm/h to about 80 cm/h; an atomizing pressure of from about 0.5 bar to about 4.5 bar, in certain embodiments from about 1 bar to about 3 bar, and in at least one embodiment at about 2 bar; a curing temperature of from about 10° C. to about 70° C., in certain embodiments from about 20° C. to about 50° C., and in at least one embodiment from about 30° C. to about 40° C.; and a curing time of from about 5 minutes to about 720 minutes; in certain embodiments from about 10 minutes to about 120 minutes, and in at least one embodiment at about 30 minutes. Any other technology resulting in the coating formulation of the osmotic subcoat consistent with the objects of the invention can also be used.

The ratio of the components in the core, semipermeable membrane and/or water-soluble membrane and/or at least one controlled release coat and/or osmotic subcoat as well as the amount of the various membranes or coats applied can be varied to control delivery of the bupropion hydrobromide salt either predominantly by diffusion across the surface of the semipermeable membrane to predominantly by osmotic pumping through the at least one passageway in the semipermeable membrane, and combinations thereof such that the dosage form can exhibit a modified-release, controlled-release, sustained-release, extended-release, prolonged-release, bi-phasic release, delayed-release profile or a combination of release profiles whereby the in-vitro release rates of the bupropion hydrobromide salt is such that after about 2 hours from about 0% to about 20% by weight of the bupropion hydrobromide salt is released, after about 4 hours from about 15% to about 45% by weight of the bupropion hydrobromide salt is released, after about 8 hours, from about 40% to about 90% by weight of the bupropion hydrobromide salt is released, and after about 16 hours, more than about 80% by weight of the bupropion hydrobromide salt is released. In embodiments where the mode of exit of the bupropion hydrobromide salt comprises a plurality of pores, the amount of pore forming agent employed to achieve the desired in-vitro dissolution rates can be readily determined by those skilled in the drug delivery art.

In at least one embodiment of the osmotic dosage form, the core comprises bupropion hydrobromide in an amount of from about 40% to about 99% of the core dry weight. For example in certain embodiments the core comprises bupropion hydrobromide in an amount of about 40%, about 45%, about 50%, about 55%, about 60%, about 65%, about 70%, about 75%, about 80%, about 85%, about 90%, about 95% or about 99% of the core dry weight.

In certain embodiments, the core of the osmotic dosage form comprises at least one means for increasing the hydrostatic pressure inside the membrane or coat. The membrane or coat can be a semipermeable membrane, a controlled release coat, a water-soluble coat, an osmotic subcoat, or any combination thereof. The core of the osmotic dosage form has an effective osmotic pressure greater than that of the surrounding fluid in the environment of use so that there is a net driving force for water to enter the core. The at least one means for increasing the hydrostatic pressure inside the membrane or coat can be any material that increases the osmotic pressure of the core of the osmotic dosage form. The at least one means for increasing the hydrostatic pressure inside the membrane or coat can be, for example, the bupropion hydrobromide salt, an osmagent, any material which can interact with water and/or an aqueous biological fluid, swell and retain water within their structure, such as for example an osmopolymer, and any combination thereof. The osmagent can be soluble or swellable. Examples of osmotically effective solutes are inorganic and organic salts and sugars. The bupropion hydrobromide salt can itself be an osmagent or can be combined with one or more other osmagents, such as for example, magnesium sulfate, magnesium chloride, sodium chloride, lithium chloride, potassium sulfate, sodium carbonate, sodium sulfite, lithium sulfate, potassium chloride, calcium carbonate, sodium sulfate, calcium sulfate, potassium acid phosphate, calcium lactate, d-mannitol, urea, inositol, magnesium succinate, tartaric acid, water soluble acids, alcohols, surfactants, and carbohydrates such as raffinose, sucrose, glucose, lactose, fructose, algin, sodium alginate, potassium alginate, carrageenan, fucoridan, furcellaran, laminaran, hypnea, gum arabic, gum ghatti, gum karaya, locust bean gum, pectin, starch and mixtures thereof. In certain embodiments the core comprises osmagent in an amount of about 15%, about 20%, about 25%, about 30%, about 35%, about 40%, about 45%, about 50%, about 55%, about 60%, about 65%, about 70%, about 75%, about 80%, about 85%, about 90%, or about 95% of the core dry weight.

The osmagent useful in certain embodiments of the present invention can be any agent that can generate an osmotic pressure gradient for the transport of water from the external environment of use into the osmotic dosage form. Osmagents are also known as osmotically effective compounds, osmotic solutes, and osmotic fluid imbibing agents. Osmagents useful in certain embodiments of the present invention are soluble in aqueous and biological fluids, such as ionizing compounds, inherently polar compounds, inorganic acids, organic acids, bases and salts. In at least one embodiment the osmagent is a solid and dissolves to form a solution with fluids imbibed into the osmotic dosage form. A wide variety of osagents can be used to provide the osmotic pressure gradient used to drive the bupropion hydrobromide salt from the core of the osmotic dosage form. Examples of inorganic salts useful as osmagents include lithium chloride, lithium sulfate, lithium phosphate, magnesium chloride, magnesium sulfate, potassium chloride, potassium sulfate, potassium phosphate, potassium acid phosphate, sodium chloride, sodium sulfate, sodium phosphate, sodium sulfite, sodium nitrate, sodium nitrite, and mixtures thereof. Examples of salts of organic acids useful as osagents include sodium citrate, potassium acid tartrate, potassium bitartrate, sodium bitartrate, and mixtures thereof. Examples of ionizable solid acids useful as osmagents include tartaric, citric, maleic, malic, fumaric, tartronic, itaconic, adipic, succinic, mesaconic acid, and mixtures thereof. Examples of other compounds useful as osmagents include potassium carbonate, sodium carbonate, ammonium carbonate, calcium lactate, mannitol, urea, inositol, magnesium succinate, sorbitol, and carbohydrates such as raffinose, sucrose, glucose, lactose, lactose monohydrate, a blend of fructose glucose and mixtures thereof. In at least one embodiment the osmagent is selected from sodium chloride, sodium bromide, sodium bisulfate, potassium acid tartrate, citric acid, mannitol, sucrose and mixtures thereof. Combinations of these osmagents is permissible. The osmagent can be present in an amount of from about 0.1% to about 50% of the dosage form weight. For example, in certain embodiments the osmagent is present in an amount of from about 1% to about 40%, and in other embodiments from about 1% to about 20% of the dosage form weight.

In certain embodiments, the at least one means for increasing the hydrostatic pressure can comprise, in addition to an osmagent, any material which can interact with water and/or an aqueous biological fluid, swell and retain water within their structure. In certain embodiments where the at least one means for increasing the hydrostatic pressure is an osmopolymer, which can be slightly cross-linked or uncross-linked. The uncross-linked polymers to be used as osmopolymers, when in contact with water and/or aqueous biological fluid, preferably do not dissolve in water, hence maintaining their physical integrity. Such polymers can be, for example, chosen from the group of polyacrylic acid derivatives (e.g., polyacrylates, poly-methyl methacrylate, poly(acrylic acid) higher alkyl esters, poly(ethylmethacrylate), poly(hexadecyl methacrylate-co-methylmethacrylate), poly(methylacrylate-co-styrene), poly(n-butyl methacrylate), poly(n-butyl-acrylate), poly(cyclododecyl acrylate), poly(benzyl acrylate), poly(butylacrylate), poly(secbutylacrylate), poly(hexyl acrylate), poly(octyl acrylate), poly(decyl acrylate), poly(dodecyl acrylate), poly(2-methyl butyl acrylate), poly(adamantyl methacrylate), poly(benzyl methacrylate), poly(butyl methacrylate), poly(2-ethylhexyl methacrylate), poly(octyl methacrylate), acrylic resins), polyacrylamides, poly(hydroxy ethyl methacrylate), poly(vinyl alcohol), poly(ethylene oxide), poly N-vinyl-2-pyrrolidone, naturally occurring resins such as polysaccharides (e.g., dextrans, water-soluble gums, starches, chemically modified starches), cellulose derivatives (e.g., cellulose esters, cellulose ethers, chemically modified cellulose, microcrystalline cellulose, sodium carboxymethylcellulose and methylcellulose), starches, CARBOPOL™, acidic carboxy polymer, CYANAMER™, polyacrylamides, cross-linked water-swellable indene-maleic anhydride polymers, GOOD-RITE™, polyacrylic acid, polyethyleneoxide, starch graft copolymers, AQUA-KEEPS™, acrylate polymer, diester cross-linked polyglucan, and any combination thereof.

In certain embodiments, the core of the osmotic dosage form further comprises a means for forcibly dispensing the bupropion hydrobromide salt from the core to the exterior of the dosage form. The at least one means for forcibly dispensing the bupropion hydrobromide salt can be any material which can swell in water and/or aqueous biological fluid and retain a significant fraction of water within its structure, and will not dissolve in water and/or aqueous biological fluid, a means for generating a gas, an osmotically effective solute or any combination thereof which can optionally be surrounded by a membrane or coat depending on the particular means used. The membrane or coat can be, for example, a membrane or coat that is essentially impermeable to the passage of the bupropion hydrobromide salt, gas and compounds, and is permeable to the passage of water and/or aqueous biological fluids. Such a coat or membrane comprises, for example, a semipermeable membrane, microporous membrane, asymmetric membrane, which asymmetric membrane can be permeable, semipermeable, perforated, or unperforated. In at least one embodiment, the at least one means for forcibly dispensing the bupropion hydrobromide salt from the core of the osmotic dosage form comprises a means for generating gas, which means for generating gas is surrounded by, for example, a semipermeable membrane. In operation, when the gas generating means imbibes water and/or aqueous biological fluids, the means for generating gas reacts and generates gas, thereby enlarging and expanding the at least one means for forcibly dispensing the bupropion hydrobromide salt unidirectionally or multidirectionally. The means for generating a gas comprises any compound or compounds, which can produce effervescence, such as for example, at least one solid acid compound and at least one solid basic compound, which in the presence of a fluid can react to form a gas, such as for example, carbon dioxide. Examples of acid compounds include, organic acids such as malic, fumaric, tartaric, itaconic, maleic, citric, adipic, succinic and mesaconic, and inorganic acids such as sulfamic or phosphoric, also acid salts such as monosodium citrate, potassium acid tartrate and potassium bitartrate. The basic compounds include, for example, metal carbonates and bicarbonates salts, such as alkali metal carbonates and bicarbonates. The acid and base materials can be used in any convenient proportion from about 1 to about 200 parts of the at least one acid compound to the at least one basic compound or from about 1 to about 200 parts of the at least one basic compound to the at least one acid compound. The means for generating gas is known.

In at least one embodiment, the at least one means for forcibly dispensing the bupropion hydrobromide salt form the core of the osmotic dosage form comprises any material which can swell in water and/or aqueous biological fluid and retain a significant fraction of water within its structure, and will not dissolve in water and/or aqueous biological fluid, such as for example, a hydrogel. Hydrogels include, for example, lightly cross-linked hydrophilic polymers, which swell in the presence of fluid to a high degree without dissolution, usually exhibiting a 5-fold to a 50-fold volume increase. Non-limiting examples of hydrogels include poly(hydroxyalkyl methacrylates), poly(acrylamide), poly(methacrylamide), poly(N-vinyl-2-pyrrolidone), anionic and cationic hydrogels, polyelectrolyte complexes, a water-insoluble, water-swellable copolymer produced by forming a dispersion of finely divided copolymers of maleic anhydride with styrene, ethylene, propylene butylene or isobutylene cross-linked with from about 0.001 to about 0.5 moles of a polyunsaturated cross-linking agent per mole of maleic anhydride in a copolymer, water-swellable polymers or N-vinyl lactams, semi-solid cross-linked poly(vinyl pyrrolidone), diester cross-linked polyglucan hydrogels, anionic hydrogels of heterocyclic N-vinyl monomers, ionogenic hydrophilic gels, and mixtures thereof. Some of the osmopolymers and hydrogels are interchangeable. Such means can optionally be covered by a membrane or coat impermeable to the passage of the bupropion hydrobromide salt, and compounds, and is permeable to the passage of water and/or aqueous biological fluids. Such a coat or membrane comprises, for example, a semipermeable membrane, microporous membrane, asymmetric membrane, which asymmetric membrane can be permeable, semipermeable, perforated, or unperforated.

In at least one other embodiment, the at least one means for forcibly dispensing the bupropion hydrobromide salt from the core of the osmotic dosage form comprises at least one osmotically effective solute surrounded by a membrane or coat impermeable to the passage of the bupropion hydrobromide salt, and compounds, and is permeable to the passage of water and/or aqueous biological fluids such that the osmotically effective solute exhibits an osmotic pressure gradient across a membrane or coat. Such coat or membrane comprises, for example, a semipermeable membrane, microporous membrane, asymmetric membrane, which asymmetric membrane can be permeable, semipermeable, perforated, or unperforated. The osmotically effective solutes include, for example, the osmagents described above.

In embodiments of the osmotic dosage form where the means for forcibly dispensing the bupropion hydrobromide salt is surrounded by a membrane or coat, at least one plasticizer can be added to the membrane composition to impart flexibility and stretchability to the membrane or coat. In embodiments where the means for forcibly dispensing the bupropion hydrobromide salt comprises a means for generating a gas, the membrane or coat preferably is stretchable so as to prevent rupturing of the membrane or coat during the period of delivery of the bupropion hydrobromide salt. Methods of manufacturing such a membrane or coat is known. Plasticizers, which can be used in these embodiments include, for example, cyclic and acyclic plasticizers, phthalates, phosphates, citrates, adipates, tartrates, sebacates, succinates, glycolates, glycerolates, benzoates, myristates, sulfonamides halogenated phenyls, poly(alkylene glycols), poly(alkylenediols), polyesters of alkylene glycols, dialkyl phthalates, dicycloalkyl phthalates, diaryl phthalates and mixed alkyl-aryl phthalates, such as for example, dimethyl phthalate, dipropyl phthalate, di(2-ethylhexyl)phthalate, diisopropyl phthalate, diamyl phthalate and dicapryl phthalate; alkyl and aryl phosphates, such as for example, tributyl phosphate, trioctyl phosphate, tricresyl phosphate, trioctyl phosphate, tricresyl phosphate and triphenyl phosphate; alkyl citrate and citrates esters such as tributyl citrate, triethyl citrate, and acetyl triethyl citrate; alkyl adipates, such as for example, dioctyl adipate, diethyl adipate and di(2-methoxyethyl)adipate; dialkyl tartrates, such as for example, diethyl tartrates and dibutyl tartrate; alkyl sebacates, such as for example, diethyl sebacate, dipropyl sebacate and dinonyl sebacate; alkyl succinates, such as for example, diethyl succinate and dibutyl succinate; alkyl glycolates, alkyl glycerolates, glycol esters and glycerol esters, such as for example, glycerol diacetate, glycerol triacetate, glycerol monolactate diacetate, methyl phthalyl ethyl glycolate, butyl phthalyl butyl glycolate, ethylene glycol diacetate, ethylene glycol dibutyrate, triethylene glycol diacetate, triethylene glycol dibutyrate, triethylene glycol dipropionate and mixtures thereof. Other plasticizers include camphor, N-ethyl (o- and p-toulene) sulfonamide, chlorinated biphenyl, benzophenone, N-cyclohexyl-p-toluene sulfonamide, substituted epoxides and mixtures thereof.

The at least one means for forcibly dispensing the bupropion hydrobromide salt from the core of certain embodiments of the osmotic dosage form can be located such that it is approximately centrally located within the core of the osmotic dosage form and is surrounded by a layer comprising the bupropion hydrobromide salt. Alternatively, the core of the osmotic dosage form comprises at least two layers in which the first layer comprises the bupropion salt, osmagent and/or osmopolymer and optionally at least one pharmaceutically acceptable excipient adjacent to a second layer comprising the means for forcibly dispensing the bupropion hydrobromide salt. Alternatively, the core of the osmotic dosage form comprises a multilayered structure in which the layer comprising the bupropion hydrobromide salt is sandwiched between two layers of the means for forcibly dispensing the bupropion hydrobromide salt from the osmotic dosage form.

Combinations

The present invention also contemplates combinations of the bupropion hydrobromide salt with at least one other drug. For example, a composition is provided which comprises a first component of bupropion hydrobromide, and a second component of at least one other drug, wherein the two components are each present in an amount effective in the treatment of a condition. The present invention further provides a method for treating a condition, comprising administering to a patient an effective amount of a first component of bupropion hydrobromide in combination with an effective amount of at least one other drug. The skilled artisan will know or can determine by known methods which drug combinations are acceptable. Types of drugs that can be selected as the second drug include by way of example other depressants, anti-anxiety agents, steroidal and non-steroidal inflammatories, SSRIs, serotonin receptor agonists, anti-migraine agents, anti-pain agents, anti-emetics, drugs for treating abuse such as nicotine, appetite modulators, anti-virals, vasodilators, and anti-pain agents. For example, the other drug can be an antidepressant selected from: monoamine oxidase (MAO) inhibitor, tricyclic antidepressant, serotonin reuptake inhibitor, selective norepinephrine reuptake inhibitors (SNRIs), aminoketones, serotonin antagonists, dopamine reuptake inhibitors, dual reuptake inhibitors, norepinephrine enhancers, serotonin activity enhancers, dopamine activity enhancers, and combinations thereof. Examples of other drugs that can be combined with bupropion hydrobromide include citalopram, escitalopram, venlafaxine, clozapine, melperone, amperozide, iloperidone, risperidone, quetiapene, olanzapine, ziprasidone, aripiprazole, reboxetine, VIAGRA®, sertraline, paroxetine, fluoxetine, gabapentin, valproic acid, amitriptyline, lofepramine, fluvoxamine, imipramine, mirtazapine, nefazodone, nortriptyline, SAM-E, buspirone, and combinations thereof. In at least one embodiment, a combination of bupropion hydrobromide and citalopram is provided. In at least one other embodiment, a combination of bupropion hydrobromide and escitalopram is provided. In at least one other embodiment a combination of bupropion hydrobromide and venlafaxine is provided. In at least one other embodiment a combination of bupropion hydrobromide and quetiapene is provided.

In certain embodiments combination products can be made by providing an overcoat that contains at least one other drug. For example, certain embodiments can include a core that comprises bupropion hydrobromide, wherein the core is substantially surrounded by a controlled release coat, which in turn is substantially surrounded by an overcoat that contains at least one other drug. In certain embodiments the overcoat provides an immediate release of the other drug. In addition to the other drug, the overcoat can include at least one low viscosity hydrophilic polymer. The low-viscosity polymer provides for the immediate release of the other drug from the overcoat. In at least one embodiment, the low-viscosity polymer used in the overcoat is hydroxypropyl methylcellulose (HPMC). The overcoat can also include a lubricant such as talc. For example, such embodiments can provide an immediate release of at least one other drug from the overcoat in a first phase of drug release, and then a subsequent controlled release of the bupropion hydrobromide from the controlled release coated core in a second phase of drug release.

In addition, combinations of microparticles of the invention each with a different functional coating can be combined together in a dosage form. For example, by combining a first group of uncoated, taste-masked or enteric coated microparticles with a second group of delayed or sustained release coated microparticles, a pulsatile drug release profile or chronotherapeutic profile can be achieved. (e.g. see U.S. Pat. No. 5,260,068, U.S. Pat. No. 6,270,805, U.S. Pat. No. 6,926,909, US2002/0098232, US2004/0197405, U.S. Pat. No. 6,635,284, or U.S. Pat. No. 6,228,398).

In other embodiments, the combination can comprise at least 2 different microparticles. For example, the combination can include one group of microparticles that provide for a controlled release of bupropion hydrobromide, and a second group of microparticles that provide for an immediate release of the other drug. The microparticles can be combined in a capsule formulation.

While only specific combinations of the various features and components of the present invention have been discussed herein, it will be apparent to those of skill in the art that desired subsets of the disclosed features and components and/or alternative combinations of these features and components can be utilized as desired.

As will be seen from the non-limiting examples described below, the coatings of the invention are quite versatile. For example, the length and time for the lagtime can be controlled by the rate of hydration and the thickness of the controlled release coat. It is possible to regulate the rate of hydration and permeability of the controlled release coat so that the desired controlled release profile can be achieved. There is no general preferred controlled release coat thickness, as this will depend on the controlled release profile desired. Other parameters in combination with the thickness of the controlled release coat include varying the concentrations of one or more of the ingredients of the controlled release coat composition, varying the curing temperature and length of time for curing the coated tablet microparticles, and in certain embodiments, varying the level of osmotic agent. The skilled artisan will know which parameters or combination of parameters to change for a desired controlled release profile.

Stability Studies

The enhanced stability of the bupropion hydrobromide salt and compositions containing the bupropion hydrobromide salt, in particular when compared to the bupropion hydrochloride salt and compositions containing the bupropion hydrochloride salt respectively, is evident from degradation studies performed on the active pharmaceutical ingredient (API), alone, in the presence of excipients and in the form of tablets (e.g. extended release tablets). The results are described in greater detail in the examples below.

A comparison of the stability of several bupropion salts, including the hydrobromide, hydrochloride, maleate, tosylate, fumarate, succinate, tartrate and citrate salts, was performed by placing these salts in both open and closed vials in a stability chamber kept at about 40 degrees C. and about 75% relative humidity for various periods of time (e.g. 10 days, 13 days, 14 days, 20 days, 24 days, or 32 days). The stability of the salts was evaluated based on the formation of the main degradation products (see below) as determined by HPLC analysis and the % potency (or assay) of the API, after specific time periods in the stability chamber. The effect of the addition of solvents, such as water, ethanol and isopropyl alcohol, was also studied.

The results unexpectedly show that after various periods of time the hydrobromide salt of bupropion, on average, showed the least amount of degradation products, particularly when compared to the hydrochloride salt. Accordingly the bupropion hydrobromide salt showed greater stability than the hydrochloride salt Further stability tests were performed by directly comparing bupropion hydrobromide and bupropion hydrochloride salts in forced degradation studies. These studies were performed in closed bottles in a stability chamber kept at about 40 degrees C. and about 75% relative humidity. At specified times, the material in the bottles was analyzed for the presence of degradation products and % potency (% assay). It was unexpectedly found that the amount of impurities was generally lower and the % potency was generally higher for the bupropion hydrobromide salt when compared to the bupropion hydrochloride salt.

Forced degradation studies were also performed on bupropion hydrobromide and bupropion hydrochloride API's in the presence of standard excipients used in pharmaceutical formulations. The amount of the main degradation products was observed at about 24 and about 48 hours after treatment at about 55° C., at about 55° C. and 100% relative humidity, and at about 105° C. Once again, it was unexpectedly found that the bupropion hydrobromide salt showed the lowest amount of degradation (as determined by the formation of bupropion degradation impurities) under these conditions.

The stability of the tablet formulations of bupropion hydrobromide and bupropion hydrochloride salts was also compared. With both salts, a single coated tablet having a controlled release coat (e.g. ETHOCEL® or "EC" coat), as well as a double-coated tablet (with a controlled release coat and a moisture barrier coat) were evaluated. The tablets were placed individually on an open dish, and exposed to the accelerated conditions of about 40° C. and about 75% relative humidity in a stability chamber. After 13 days and 20 days, the samples were assayed and impurity analysis was performed.

For the single coated bupropion hydrochloride tablets, the main degradation impurities 3-CBZ and 852U77 were about 0.12% and about 0.38% respectively, whereas, for the bupropion hydrobromide tablets, these values were about 0.07% and about 0.49% respectively. The other degradation impurities and the total unknowns were very similar for both products; however, the assay value for the hydrobromide product was higher than the hydrochloride. The difference in the assay and the impurity levels were more significant in the double coated tablets products. For the same period of the study the assay of the bupropion hydrochloride was lower (about 95.5% compared to about 98.6% for bupropion hydrobromide) and the level of the degradation and total unknowns were higher (3-CBZ: about 0.28%; 852U77: about 1.23%; 827U76: about 0.10%; and total about 1.73%) than the bupropion hydrobromide (3-CBZ: about 0.12%, 852U77: about 0.41%, 827U76: about 0.05%; and total about 0.75%).

The stability studies performed herein have demonstrated the unexpected enhanced stability of bupropion hydrobromide, in particular when compared to bupropion hydrochloride. This enhanced stability is seen with the API form alone, the API form plus excipients, and the extended release and enhanced absorption tablets. The enhanced stability of pharmaceutical formulations comprising bupropion hydrobromide will provide enhanced shelf life and an ability to withstand storage at higher temperatures and humidity levels when compared with bupropion hydrochloride formulations.

Polymorphic Forms

It is well known that organic molecules can crystallize into solid forms. Moreover the same organic compound may assume different crystalline arrangements in solid form, depending on the conditions under which the crystal product is formed. This phenomenon is commonly known as polymorphism. A study was undertaken to explore the polymorphic forms of bupropion hydrobromide. The crystal forms of the products obtained in this study were determined by powder X-ray diffraction (PXRD). A RIGAKU miniflex instrument (Radiation Cu Kα, generator 30 KV, filter Ni) was used to obtain the PXRD data.

Figure 54:
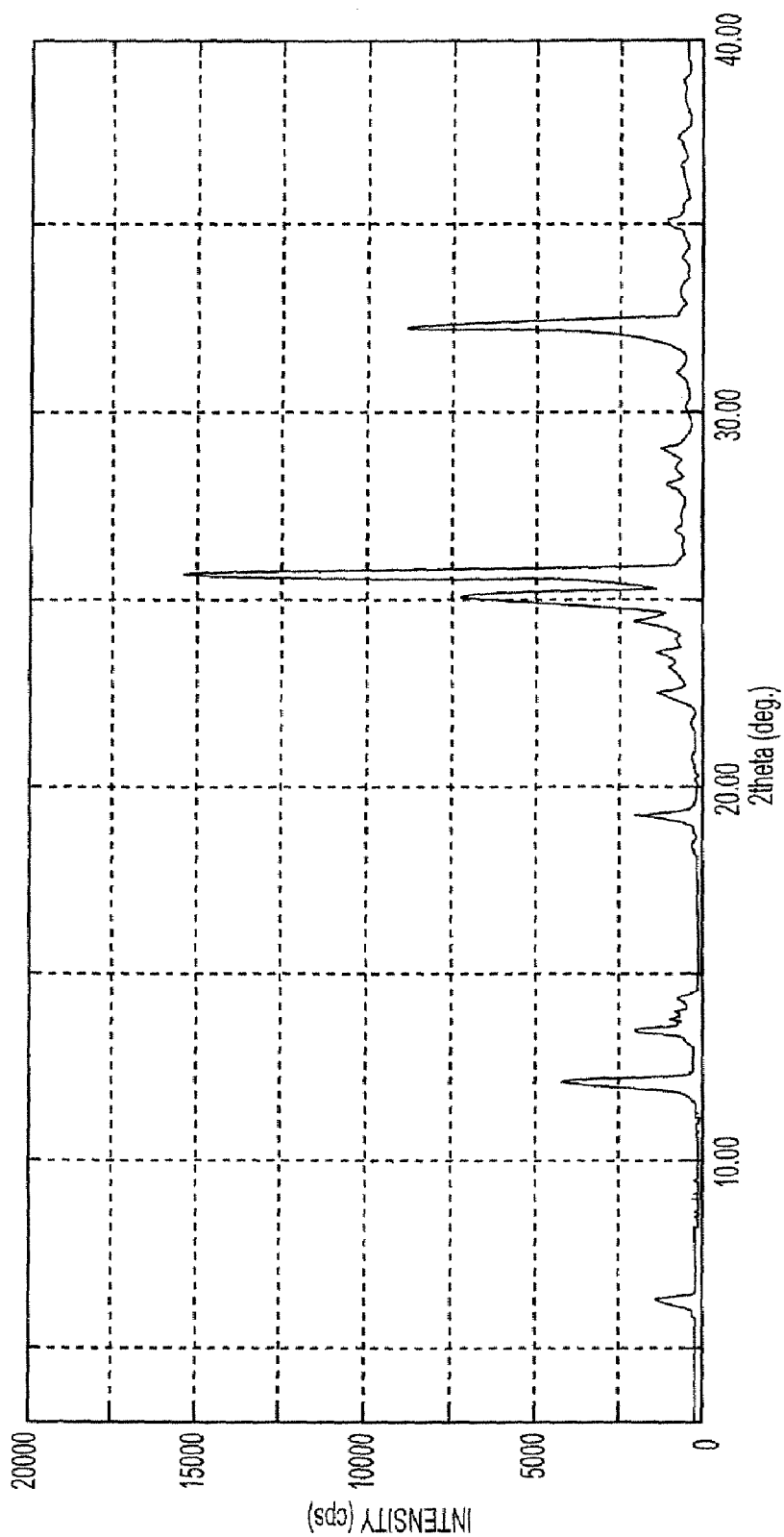
FIG. 54 is a graph showing the relative powder X-ray diffraction (PXRD) for bupropion hydrobromide polymorphic form I.
Figure 55:
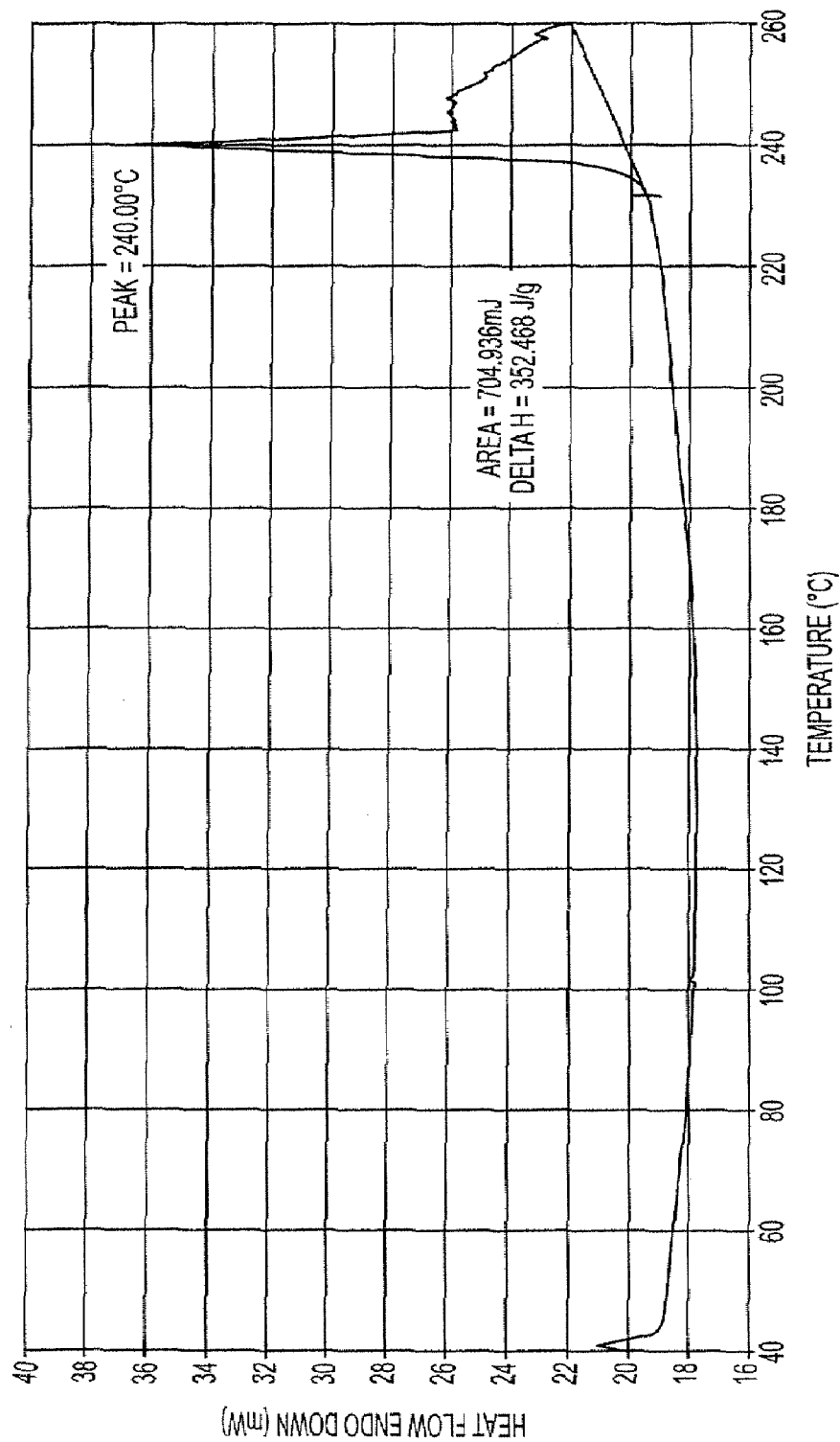
FIG. 55 is a graph showing the differential scanning calorimetry (DSC) profile of bupropion hydrobromide polymorphic form I.

A standard procedure was established to generate bupropion hydrobromide, this standard procedure produces a first polymorphic form which has been termed polymorphic form I. The relative PXRD for form I is shown in FIG. 54 and the differential scanning calorimetry (DSC) profile is shown in FIG. 55.

Figure 56:
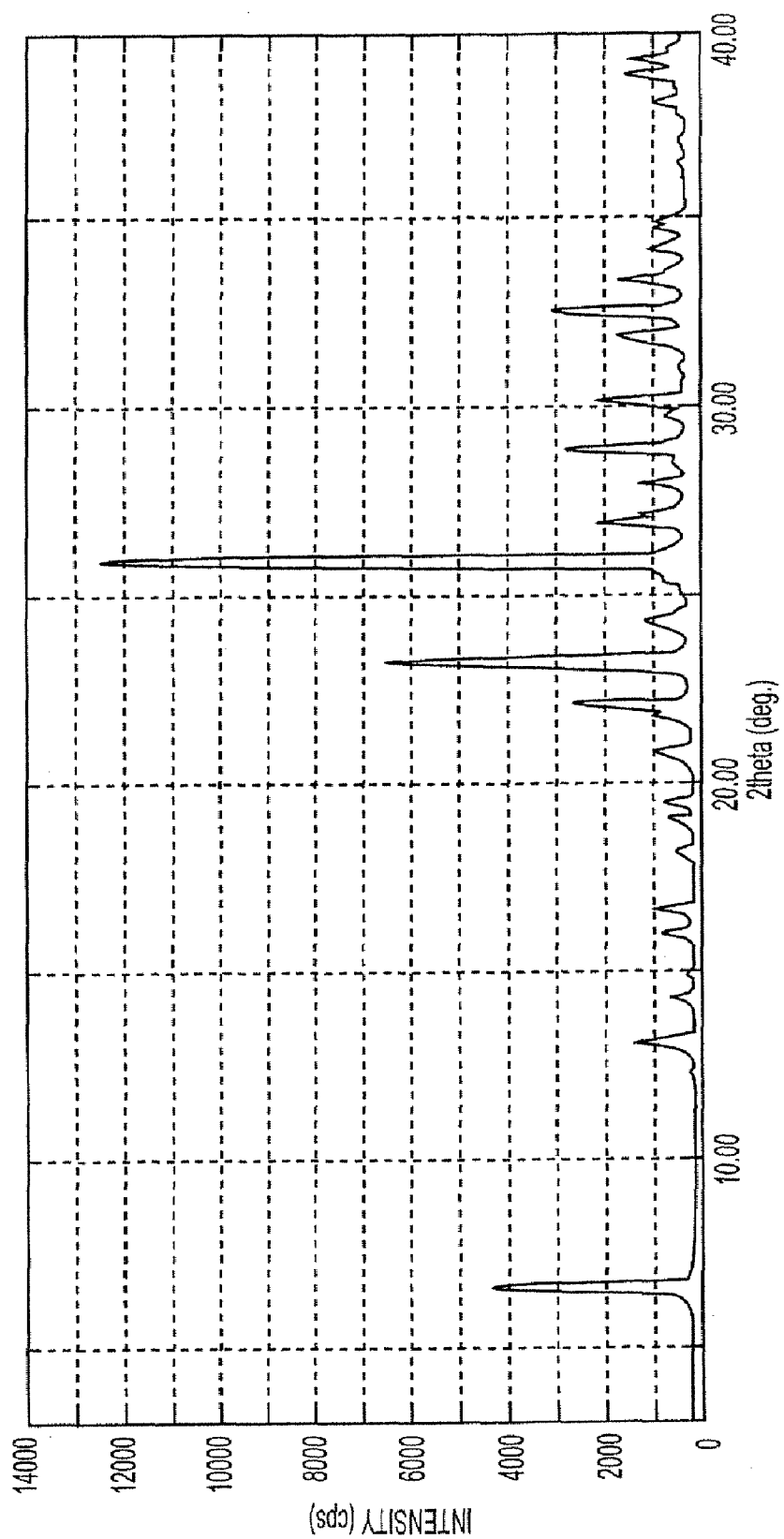
FIG. 56 is a graph showing the relative PXRD for bupropion hydrobromide polymorphic form II.
Figure 57:
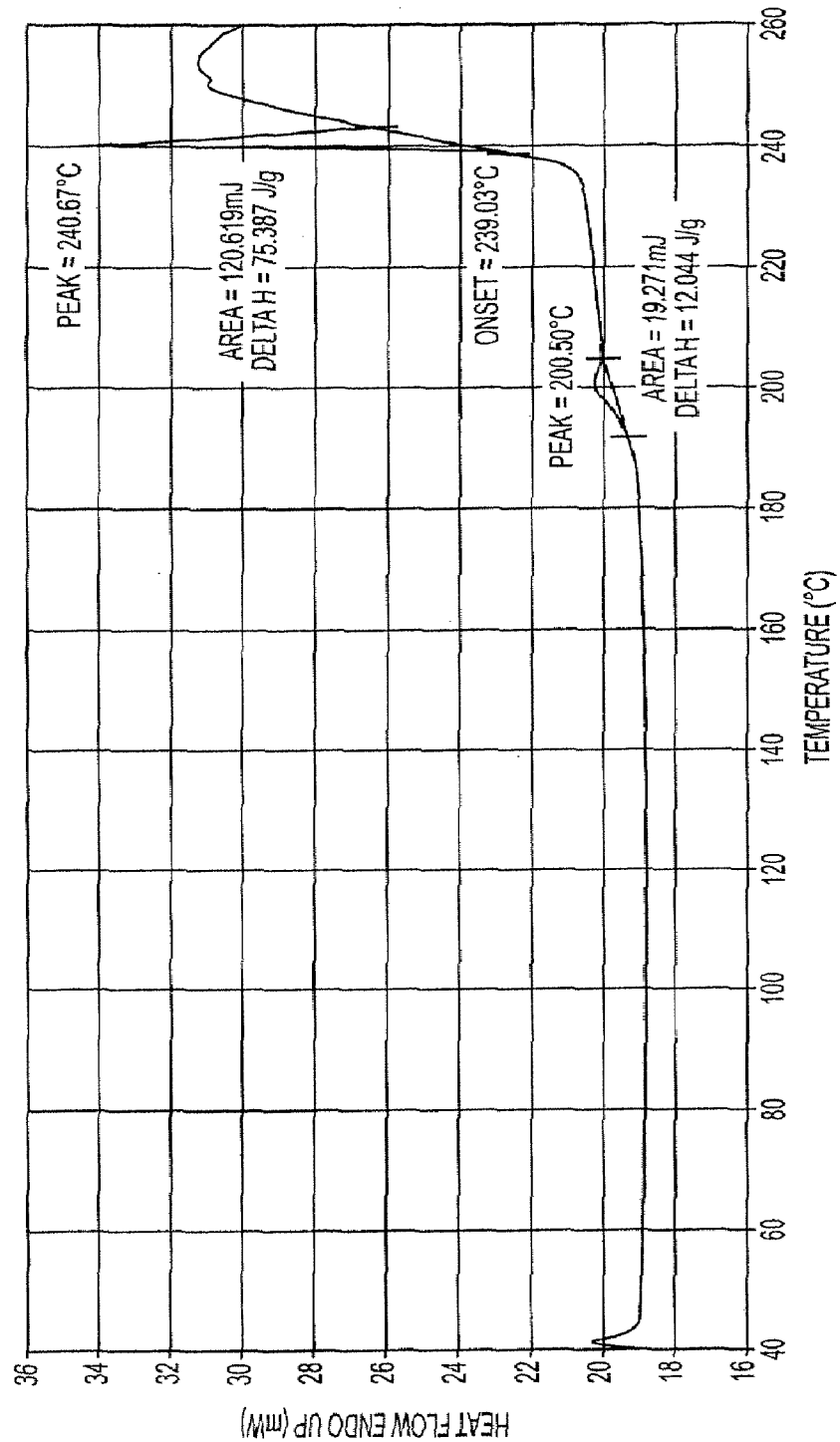
FIG. 57 is a graph showing the DSC profile of bupropion hydrobromide polymorphic form II.
Figure 58:
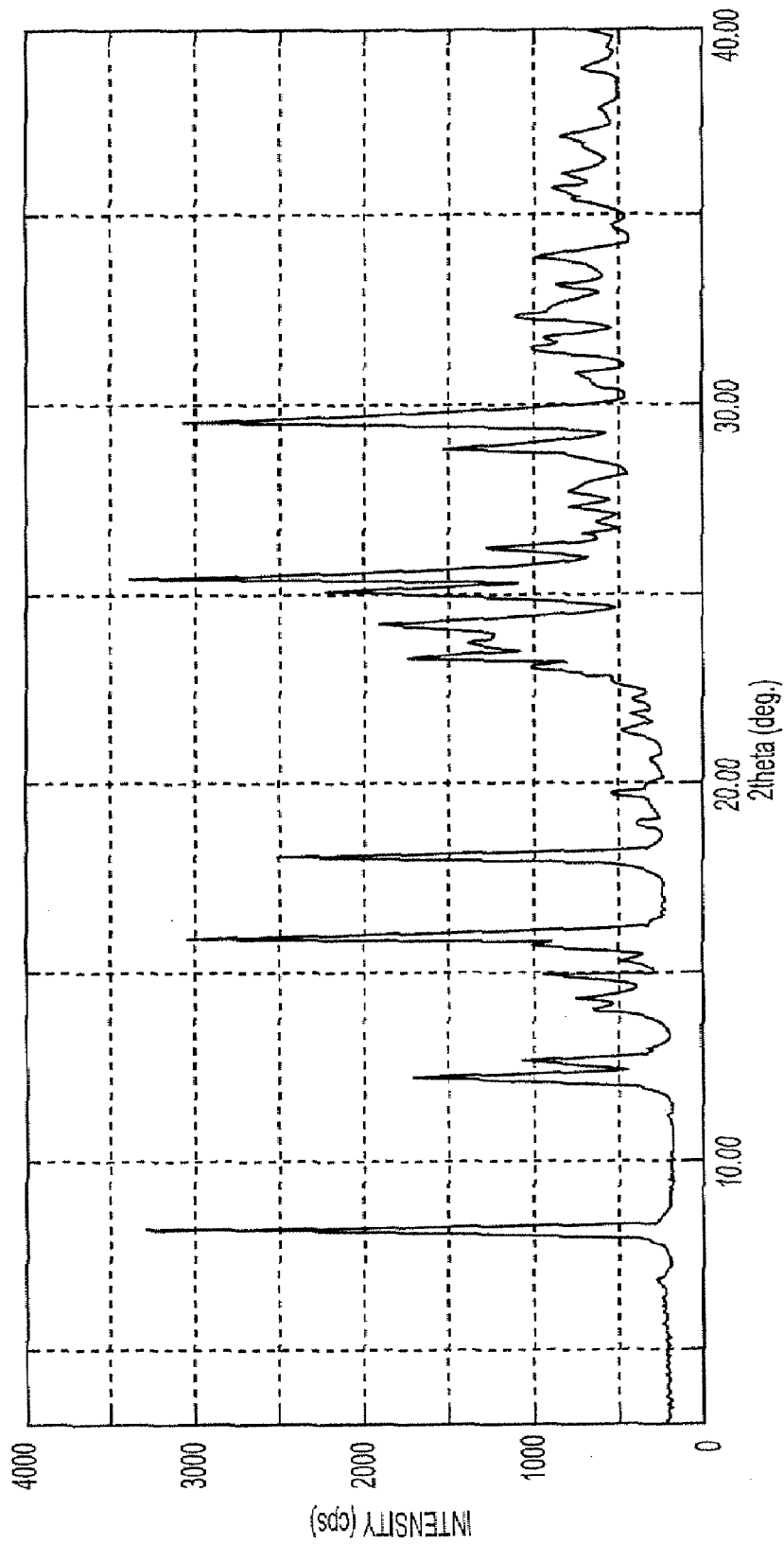
FIG. 58 is a graph showing the relative PXRD for bupropion hydrobromide polymorphic form III.
Figure 59:
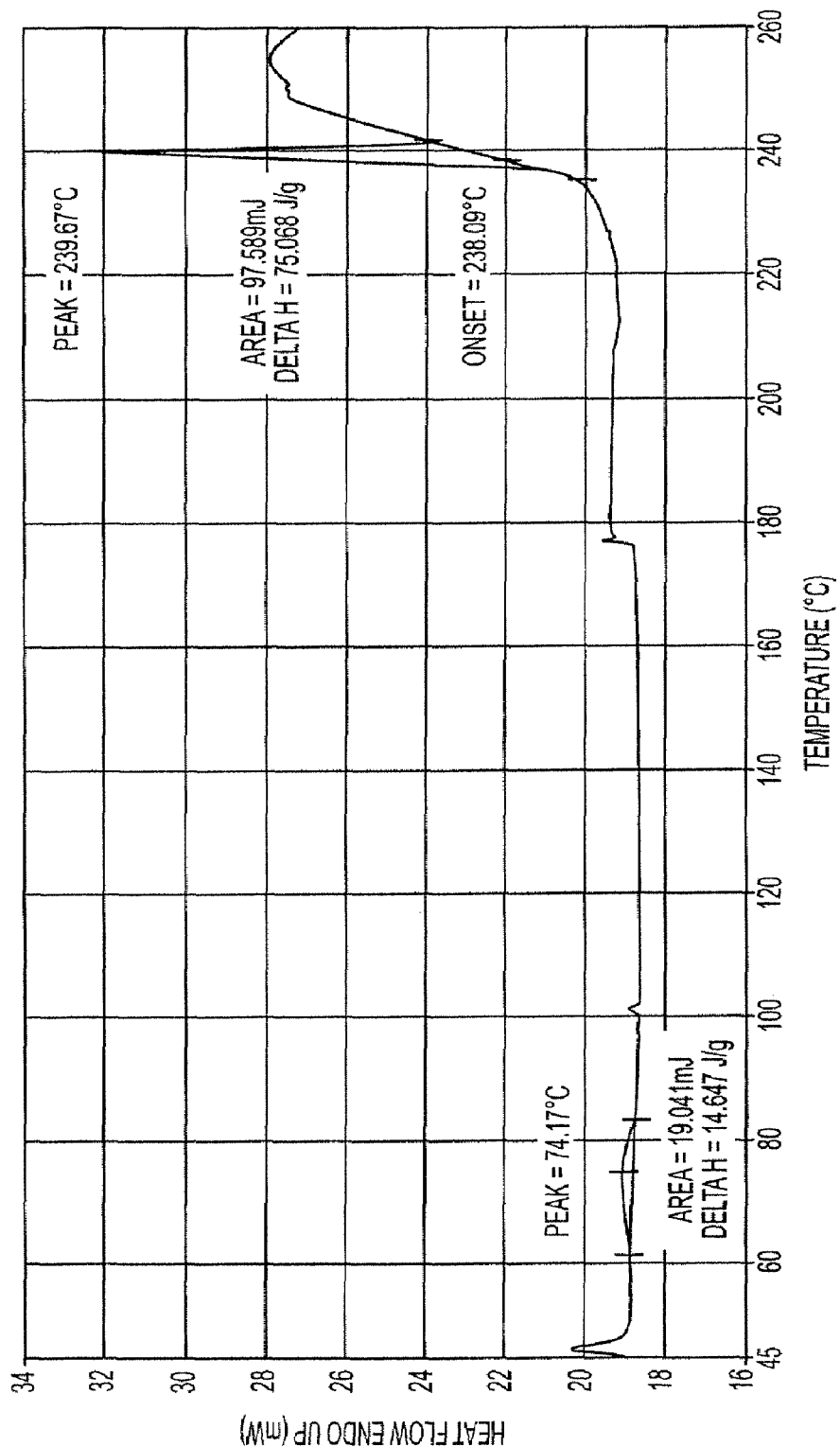
FIG. 59 is a graph showing the DSC profile of bupropion hydrobromide polymorphic form III.

Bupropion hydrobromide of form I has been used as the starting material in experiments to identify other polymorphic forms. Two additional polymorphic forms were identified and have been named form II and form III. FIGS. 56 and 57 show the PXRD data and DSC profile respectively of polymorphic form II. FIGS. 58 and 59 shown the PXRD data and DSC profile respectively of form III.

Polymorphic form II was obtained by recrystallization of form 1 from solvents or mixtures of solvents such as acetone-water, methanol, dichloromethane, toluene-methanol and dimethylcarbonate-methanol. Polymorphic form III was obtained by recrystallization of polymorphic form I in methanol. Table 80 provides a list of recrystallization conditions and the polymorphic form obtained under each set of conditions.

The three polymorphic forms were subjected to stability testing. Samples of the polymorphic forms were subjected to ICH conditions (40° C., 75% R.H.) and PXRD data was obtained at 3 months and 6 months. All of the samples had the same PXRD profile indicating that this polymorphic form is stable at these conditions and is not changing or degrading. Samples of the polymorphic forms II and III were tested after 1 month under the same accelerated stability conditions. Polymorphic form II showed no change in the PXRD profile at that time while the PXRD profile of form III showed conversion to form II. This data suggests that polymorphic forms I and II are quite stable while polymorphic form III is not as stable as forms I and II under the test conditions.

Bupropion-Induced Seizures

EEG studies, using implanted electrodes to detect electroencephalographic activity in conscious rats, analyzed the effects of equimolar doses of bupropion hydrochloride and bupropion hydrobromide on central nervous system activity after intraperitoneal administration. The results (described in greater detail below) show that bupropion hydrobromide has a lower potency for inducing convulsions as well as reducing the severity of convulsive seizures compared with bupropion hydrochloride. In contrast to bupropion hydrochloride, the bupropion hydrobromide salt form induced fewer convulsions in fewer animals. In still further comparisons, the severity of seizures observed with bupropion hydrobromide were surprisingly observed to be significantly less than the severity of seizures in animals administered bupropion hydrochloride.

The maximum dose of bupropion hydrobromide administered in the studies on rats was 100 mg/kg, and in the studies on mice was 150 mg/kg. The dose of 150 mg/kg equates to about 37.5 mg/kg of bromide or about 48.3 mg/kg of sodium bromide. These therapeutic levels of bromide in which incidences of and/or severity of bupropion-induced seizures are reduced, are surprisingly lower than what one would have expected from the known pharmacological data studying the minimum dosages of bromide needed for any observable therapeutic benefit. As noted earlier, the level of bromide required to treat pentylenetetrazole-induced seizures in mice is known to be 910 mg/kg [M. S. Grewal et al., Journal of Pharmacology And Experimental Therapeutics, Vol. 112, Issue 1, 109-115, 1954].

Certain embodiments of the present invention relate to bupropion compositions that comprise safe and pharmaceutically effective amounts of bupropion hydrobromide; wherein said compositions unexpectedly provide for fewer incidences of seizures and/or less severe seizures associated with the administration of bupropion hydrobromide than an otherwise similar or identical composition containing an equivalent molar amount of bupropion hydrochloride.

ADDITIONAL EMBODIMENTS

Further embodiments of the invention described herein and enabled by the present description include the following:

Certain embodiments include bupropion hydrobromide and 3'-chloro-2-bromo-propiophenone. 3'-chloro-2-bromo-propiophenone is an impurity associated with the preparation of bupropion hydrobromide. In certain embodiments, 3'-chloro-2-bromo-propiophenone is present in an amount that is non-genotoxic; or in an amount that would result in a daily exposure of not more than ("NMT") about 1.5 µg/day in the drug product. Certain embodiments contain less than about 1.5 µg of 3'-chloro-2-bromo-propiophenone. For example in certain embodiments the 3'-chloro-2-bromo-propiophenone impurity is present in an amount of less than about 1.5 µg, 1.4 µg, 1.3 µg, 1.2 µg, 1.1 µg, 1.0 kg, 0.9 µg, 0.8 µg, 0.7 µg, 0.6 µg, 0.5 µg, 0.4 µg, 0.3 µg, 0.2 µg, 0.1 µg, 0.09 µg, 0.08 µg, 0.07 µg, 0.06 µg, 0.05 µg, 0.04 µg, 0.03 µg, 0.02 µg, or 0.1 µg, including all values and subranges therebetween. In at least one embodiment the 3'-chloro-2-bromo-propiophenone impurity is present in undetectable amounts wherein the limit of detection is 1.0 µg, or 1 ppm.

In certain embodiments the 3-chlorobenzoic acid degradation product is limited in the drug product to about 0.7% or less. In at least one embodiment the 3-chlorobenzoic acid degradation product is limited in the composition to about 0.5% or less. In at least one further embodiment the 3-chlorobenzoic acid degradation product is limited in the composition to about 0.3% or less.

In certain embodiments the moisture content in the drug product is limited to not more than about 2.0%. In certain embodiments the moisture content is limited to not more than about 2.0% after a storage time of about 1 minute when stored in a closed container using a Karl Fischer apparatus and UPS Method 1. For example in certain embodiments the moisture content after a storage time of about 1 minute when stored in a closed container using a Karl Fischer apparatus, and USP Method 1, is less than about 2.0%, 1.9%, 1.8%, 1.7%, 1.6%, 1.5% 1.4%, 1.3%, 1.2%, 1.1%, 1.0%, 0.9%, 0.8%, 0.7%, 0.6%, 0.5%, 0.4%, 0.3%, 0.2%, or 0.1%, including all values and subranges therebetween.

In another embodiment there is a tablet comprising (i) a core and (ii) a controlled release coat, said core comprising:

(a) bupropion HBr;

(b) binder (e.g. polyvinyl alcohol); and (c) lubricant (e.g. glyceryl behenate—i.e. Compritol® 888);

said controlled release coat (e.g., "SMARTCOAT") comprising:

(d) water-insoluble water-permeable film-forming polymer (e.g. ethyl cellulose grade PR 100);

(e) plasticizer (e.g. polyethylene glycol 4000, dibutyl sebacate, or a mixture thereof);

(f) water-soluble polymer (e.g. polyvinylpyrrolidone—i.e. Povidone® USP);

wherein in the controlled release coat the ratio of (d):(e):(f)=from about 3:1:4 to about 5:1:2; or from about 7:2:6 to about 19:5:18; or about 13:4:12; or about 13:6:16;

the tablet optionally further comprising a moisture barrier coat;

said optional moisture barrier coat comprising:

(g) enteric polymer (e.g. an acrylic polymer such as methacrylic acid copolymer type C—i.e. Eudragit® L30 D-55);

(h) permeation enhancer (e.g. silicon dioxide—i.e. Syloid® 244FP); and (i) plasticizer (optional)—(e.g. mixture of triethyl citrate and polyethylene glycol 4000—i.e. Carbowax® 4000).

In another embodiment there is a once-daily modified release pharmaceutical composition comprising 522 mg of bupropion hydrobromide, said composition providing an in-vivo plasma profile selected from:

Mean Tmax of from about 2 hours to about 7 hours;

Mean Cmax of from about 113 ng/ml to about 239 ng/ml;

Mean Cmin of from about 18 ng/ml to about 44 ng/ml; and

Mean AUC0-t of from about 1236 ng-hr/ml to about 2224 ng-hr/ml.

In another embodiment there is a once-daily modified release pharmaceutical composition comprising 348 mg of bupropion hydrobromide, said composition providing an in-vivo plasma profile selected from:

Mean Tmax of from about 2 hours to about 7 hours;

Mean Cmax of from about 96 ng/ml to about 172 ng/ml;

Mean Cmin of from about 17 ng/ml to about 36 ng/ml; and

Mean AUC0-t of from about 1063 ng-hr/ml to about 1755 ng-hr/ml.

In another embodiment there is a once-daily modified release pharmaceutical composition comprising bupropion hydrobromide, said composition providing a mean Tmax of from about 2 hours to about 7 hours.

In another embodiment there is a once-daily modified release pharmaceutical composition comprising bupropion hydrobromide, said composition providing a mean Tmax that is substantially equivalent to that of a once-daily modified release pharmaceutical composition comprising bupropion hydrochloride.

In another embodiment there is a once-daily modified release pharmaceutical composition comprising bupropion hydrobromide, said composition providing a mean Tmax that is from about 80% to about 125% of that of a once-daily modified release pharmaceutical composition comprising bupropion hydrochloride.

In another embodiment there is a once-daily modified release pharmaceutical composition comprising bupropion hydrobromide, said composition providing a mean Cmax that is substantially equivalent to that of a once-daily modified release pharmaceutical composition comprising bupropion hydrochloride.

In another embodiment there is a once-daily modified release pharmaceutical composition comprising bupropion hydrobromide, said composition providing a mean Cmax that is from about 80% to about 125% of that of a once-daily modified release pharmaceutical composition comprising bupropion hydrochloride.

In another embodiment there is a once-daily modified release pharmaceutical composition comprising bupropion hydrobromide, said composition providing a mean Cmin that is substantially equivalent to that of a once-daily modified release pharmaceutical composition comprising bupropion hydrochloride.

In another embodiment there is a once-daily modified release pharmaceutical composition comprising bupropion hydrobromide, said composition providing a mean Cmin that is from about 80% to about 125% of that of a once-daily modified release pharmaceutical composition comprising bupropion hydrochloride.

In another embodiment there is a once-daily modified release pharmaceutical composition comprising bupropion hydrobromide, said composition providing a mean AUC0-t that is substantially equivalent to that of a once-daily modified release pharmaceutical composition comprising bupropion hydrochloride.

In another embodiment there is a once-daily modified release pharmaceutical composition comprising bupropion hydrobromide, said composition providing a mean AUC0-t that is from about 80% to about 125% of that of a once-daily modified release pharmaceutical composition comprising bupropion hydrochloride.

In another embodiment there is a modified release pharmaceutical composition comprising:

a core comprising a therapeutically effective amount of bupropion hydrobromide; and a controlled release polymeric coat comprising a water-insoluble polymer and a water-soluble polymer;

wherein said coat surrounds at least a part of said core; and wherein the amount of bupropion hydrobromide released at a time point from about 0 hours to about 16 hours, in the presence of at least 5% ethanol, using USP Apparatus I at 75 rpm and 37±0.5° C., is less than the amount of bupropion hydrobromide released at the same time point in 0.1 N HCl using USP Apparatus I at 75 rpm and 37±0.5° C.

In another embodiment there is a modified release pharmaceutical composition comprising:

a core comprising a therapeutically effective amount of bupropion hydrobromide; and a controlled release polymeric coat comprising a water-insoluble polymer and a water-soluble polymer;

wherein said coat surrounds at least a part of said core; and wherein the amount of bupropion hydrobromide released at a time point from about 0 hours to about 16 hours, in the presence of at least 5% ethanol, using USP Apparatus I at 75 rpm and 37±0.5° C., is less than about 125% of the amount of bupropion hydrobromide released at the same time point in 0.1 N HCl using USP Apparatus I at 75 rpm and 37±0.5° C.

In another embodiment there is a modified release pharmaceutical composition comprising:

a core comprising a therapeutically effective amount of bupropion hydrobromide; and a controlled release polymeric coat comprising a water-insoluble polymer and a water-soluble polymer;

wherein said coat at least partially surrounds said core; and wherein dose dumping does not occur in the presence of 0.1 N HCl with 40% EtOH.

In another embodiment there is a method of reducing dose dumping comprising administering to a subject a modified release pharmaceutical composition comprising:

a core comprising a therapeutically effective amount of bupropion hydrobromide; and a controlled release polymeric coat comprising a water-insoluble polymer and a water-soluble polymer;

wherein said coat at least partially surrounds said core.

In another embodiment there is a pharmaceutical composition comprising 522 mg of bupropion hydrobromide, said composition providing an in-vivo plasma profile selected from:

Mean Tmax of from about 2 hours to about 7 hours;

Mean Cmax of from about 115 ng/ml to about 235 ng/ml;

Mean Cmin of from about 20 ng/ml to about 40 ng/ml; and

Mean AUC0-24 hr of from about 1240 ng-hr/ml to about 2220 ng-hr/ml.

In another embodiment there is a pharmaceutical composition comprising 522 mg of bupropion hydrobromide, said composition providing an in-vivo plasma profile selected from:

Mean Tmax of about 4 hours;

Mean Cmax of less than about 200 ng/ml; and

Mean AUC0-24 hr of more than about 2000 ng-hr/ml.

In another embodiment there is a once-daily modified release pharmaceutical composition comprising bupropion hydrobromide, said composition providing a mean Tmax that is substantially equivalent to that of the same once-daily modified release pharmaceutical composition comprising bupropion hydrochloride instead of bupropion hydrobromide.

In another embodiment there is a once-daily modified release pharmaceutical composition comprising bupropion hydrobromide, said composition providing a mean Tmax that is from about 80% to about 125% of that of the same once-daily modified release pharmaceutical composition comprising bupropion hydrochloride instead of bupropion hydrobromide.

In another embodiment there is a modified release tablet comprising (i) a core comprising (a) a therapeutically effective amount of bupropion hydrobromide;

(b) a binder; and (c) a lubricant; and (ii) a control-releasing polymeric coat at least partially surrounding said core;

wherein said modified release tablet provides for the controlled release of said bupropion hydrobromide from said modified release tablet over a period of about 24 hours; and wherein said modified release tablet has improved stability when compared to an otherwise similar or identical modified release tablet comprising an equivalent molar amount of bupropion hydrochloride instead of bupropion hydrobromide, when each are stored for at least about 12 months at about 25° C. and at about 60% relative humidity.

In another embodiment there is a modified release bupropion hydrobromide tablet suitable for oral administration comprising (i) a core comprising (a) a therapeutically effective amount of bupropion hydrobromide;

(b) a binder; and (c) a lubricant;

(ii) a controlled release polymeric coat which at least partially surrounds said core; and (iii) a degradation product chosen from 3-chlorobenzoic acid, 827U76, 20U78, 852U77, and mixtures thereof;

wherein said modified release bupropion hydrobromide tablet contains less of said degradation product as compared to an otherwise similar or identical modified release tablet containing an equivalent molar amount of bupropion hydrochloride instead of bupropion hydrobromide;

when the modified release bupropion hydrobromide tablet and the otherwise similar or identical modified release tablet containing bupropion hydrochloride are each are stored for at least about 12 months at 25° C. and 60% relative humidity after tablet formulation.

In another embodiment there is a modified release tablet comprising:

a therapeutically effective amount of bupropion hydrobromide;

wherein at about 12 months after formulation of said modified release tablet, at about 37±0.5° C., from about 0% to 40% of said bupropion hydrobromide is released after 2 hours; from about 40% to about 75% of said bupropion hydrobromide is released after 4 hours; not less than about 75% of said bupropion hydrobromide is released after 8 hours; and not less than about 85% of said bupropion hydrobromide is released after 16 hours, in 900 ml of 0.1 N HCl using USP Type 1 apparatus with a rotational speed of 75 rpm.

In another embodiment there is a modified release pharmaceutical composition comprising:

(i) a core comprising a therapeutically effective amount of bupropion hydrobromide; and (ii) a controlled release polymeric coat comprising a water-insoluble polymer and a water-soluble polymer;

wherein said coat at least partially surrounds said core; and wherein said composition is resistant to alcohol-induced dose dumping.

In another embodiment there is a modified release pharmaceutical composition comprising:

(i) a core comprising a therapeutically effective amount of bupropion hydrobromide; and (ii) a controlled release polymeric coat comprising a water-insoluble polymer and a water-soluble polymer;

wherein said coat at least partially surrounds said core; and wherein the rate of release of bupropion hydrobromide in dissolution media containing alcohol is slower than the rate of release of bupropion hydrobromide in dissolution media not containing alcohol.

In another embodiment there is a modified release pharmaceutical composition comprising:

(i) a core comprising a therapeutically effective amount of bupropion hydrobromide; and (ii) a controlled release polymeric coat comprising a water-insoluble polymer and a water-soluble polymer;

wherein said coat at least partially surrounds said core; and wherein the amount of bupropion hydrobromide released at a time point from about 0 hours to about 16 hours, in dissolution media comprising about 40% EtOH and 60% 0.1N HCl, using USP Apparatus Type 1 at 75 rpm, is not more than the amount of bupropion hydrobromide released at the same time point in dissolution media comprising about 100% 0.1N HCl using USP Apparatus Type 1 at 75 rpm.

In another embodiment there is a modified release pharmaceutical composition comprising:

(i) a core comprising a therapeutically effective amount of bupropion hydrobromide; and (ii) a controlled release polymeric coat comprising a water-insoluble polymer and a water-soluble polymer;

wherein said coat at least partially surrounds said core; and wherein the amount of bupropion hydrobromide released at a time point from about 0 minutes to about 120 minutes, in dissolution media comprising about 40% EtOH and 60% 0.1N HCl, using USP Apparatus Type 1 at 75 rpm, is not more than the amount of bupropion hydrobromide released at the same time point in dissolution media comprising about 100% 0.1N HCl using USP Apparatus Type 1 at 75 rpm.

In another embodiment there is a method of resisting alcohol-induced dose dumping of bupropion hydrobromide comprising administering to a subject a modified release pharmaceutical composition, said composition comprising:

(i) a core comprising a therapeutically effective amount of bupropion hydrobromide; and (ii) a controlled release polymeric coat comprising a water-insoluble polymer and a water-soluble polymer;

wherein said coat at least partially surrounds said core.

In another embodiment there is a method of treating a subject at risk of alcohol-induced dose dumping of bupropion hydrobromide and in need of bupropion treatment, the method comprising administering to a subject a modified release pharmaceutical composition, said composition comprising:

(i) a core comprising a therapeutically effective amount of bupropion hydrobromide; and (ii) a controlled release polymeric coat comprising a water-insoluble polymer and a water-soluble polymer;

wherein said coat at least partially surrounds said core.

In another embodiment there is a composition comprising bupropion hydrobromide and 3'-chloro-2-bromo-propiophenone.

In another embodiment there is a composition comprising bupropion hydrobromide and less than about 1.5 µg of 3'-chloro-2-bromo-propiophenone.

In another embodiment there is a composition comprising bupropion hydrobromide and less than about 1.0 µg of 3'-chloro-2-bromo-propiophenone.

In another embodiment there is a modified release composition comprising bupropion hydrobromide wherein the moisture content is not more than about 2.0% in said composition after a storage time of about 1 minute, when stored in a closed container using a Karl Fischer apparatus, USP Method 1.

In another embodiment there is a composition comprising bupropion hydrobromide and at least one pharmaceutically acceptable excipient, wherein the amount of bupropion hydrobromide is chosen from 174 mg, 348 mg and 522 mg.

In another embodiment there is a modified release tablet comprising bupropion hydrobromide and at least one pharmaceutically acceptable excipient, wherein the amount of bupropion hydrobromide is chosen from 174 mg, 348 mg and 522 mg.

In another embodiment there is a modified release tablet comprising bupropion hydrobromide and at least one pharmaceutically acceptable excipient, wherein the amount of bupropion hydrobromide is chosen from 174 mg, 348 mg and 522 mg; and wherein the bupropion hydrobromide is contained within a core of the tablet further comprising a controlled release coating over the core.

In another embodiment there is a composition comprising at least bupropion hydrobromide in the concentration specified in one of A, B, and C in the following Table admixed with one or more additional components listed in A, B and C in the following Table:

| Component | A | B | C |
|---|---|---|---|
| Bupropion Hydrobromide | 174 mg | 348 mg | 522 mg |
| Polyvinyl Alcohol | 5.8 mg | 11.6 mg | 22.5 mg |
| Glyceryl Behenate | 5.8 mg | 11.6 mg | 22.5 mg |
| Target Core Tablet Weight (mg) | 185.6 mg | 371.2 mg | 567 mg |
| Ethylcellulose 100, NF | 15.4 mg | 16.4 mg | 18.13 mg |
| Povidone (K-90) | 9.5 mg | 10.2 mg | 21.87 mg |
| Polyethylene Glycol, 4000 | 3.4 mg | 3.7 mg | 5.33 mg |
| Dibutyl Sebacate (DBS) | 1.7 mg | 1.8 mg | 2.67 mg |
| Target Coating Weight Gain (mg) | +30 mg | +32 mg | +48 mg |
| Carnauba Wax | Trace Amount | Trace Amount | N/A |
| Denatured Ethyl Alcohol, 200 proof | Evaporated Off | Evaporated Off | Evaporated Off |
| Ethyl Alcohol, 190 proof | Evaporated Off | Evaporated Off | Evaporated Off |
| Purified Water | Evaporated Off | Evaporated Off | Evaporated Off |
| Opacode R Black Ink | Trace Amount | Trace Amount | Trace Amount |
| Isopropyl Alcohol, 99% | None | None | None |
| Final Printed Tablet Weight (mg) | 216 mg | 403 mg | 615 mg |

In another embodiment there is a composition comprising at least about 522 mg of bupropion hydrobromide and at least one pharmaceutically acceptable excipient. In other aspects of this embodiment the composition is in tablet form. In other aspects of this embodiment the composition is a modified release formulation. In other aspects of this embodiment the composition is in tablet form and the bupropion hydrobromide is contained within a core of the tablet further comprising a coating over the core. In other aspects of this embodiment the coating is a controlled release coating.

In another embodiment there is a composition comprising bupropion hydrobromide and at least one pharmaceutically acceptable excipient;

wherein administration of an amount of the bupropion hydrobromide to a first rat results in less incidences of and/or less severe bupropion-induced seizures when compared to incidences of and/or severity of bupropion-induced seizures resulting from administration of an equivalent molar amount of bupropion hydrochloride to a second rat; and wherein the incidences of and/or severity of bupropion-induced seizures are measured by an electroencephalogram analysis using a hippocampally implanted depth electrode.

In another embodiment there is a modified release tablet comprising bupropion hydrobromide and at least one pharmaceutically acceptable excipient;

wherein administration of an amount of the bupropion hydrobromide to a first rat results in less incidences of and/or severity of bupropion-induced seizures when compared to incidences of and/or severity of bupropion-induced seizures resulting from administration of an equivalent molar amount of bupropion hydrochloride to a second rat; and wherein the incidences of and/or severity of bupropion-induced seizures are measured by an electroencephalogram analysis using a hippocampally implanted depth electrode.

In another embodiment there is a composition comprising bupropion hydrobromide and at least one pharmaceutically acceptable excipient;

wherein administration of about 100 mg/kg of the bupropion hydrobromide to a first rat results in less incidences of and/or severity of bupropion-induced seizures when compared to incidences of and/or severity of bupropion-induced seizures resulting from administration of an equivalent molar amount of bupropion hydrochloride to a second rat; and wherein the incidences of and/or severity of bupropion-induced seizures are measured by an electroencephalogram analysis using a hippocampally implanted depth electrode.

In another embodiment there is a method of treating a subject at risk of bupropion-induced seizures in need of bupropion treatment, the method comprising:

administering a composition comprising bupropion hydrobromide to said subject in an amount sufficient to treat said subject.

In another embodiment there is a method of treating a subject at risk of bupropion-induced seizures in need of bupropion treatment, the method comprising:

administering a composition comprising bupropion hydrobromide to said subject in an amount sufficient to treat said subject; wherein the composition comprises an amount of bupropion hydrobromide chosen from 174 mg, 348 mg and 522 mg.

In another embodiment there is a method of treating a subject at risk of bupropion-induced seizures in need of bupropion treatment, the method comprising:

administering a composition comprising bupropion hydrobromide to said subject in an amount sufficient to treat said subject; wherein the composition comprises an amount of bupropion hydrobromide chosen from 174 mg, 348 mg and 522 mg; wherein the composition is in a modified release tablet form; wherein the tablet comprises a controlled release coating; and wherein the administering comprises oral administration.

In another embodiment there is a method of reducing incidences of bupropion-induced seizures comprising: administering a pharmaceutically effective amount of bupropion hydrobromide to a subject in need of bupropion administration;

wherein the incidences of and/or severity of bupropion-induced seizures resulting from the administration of bupropion hydrobromide is less than incidences of and/or severity of bupropion-induced seizures resulting from administration of an equivalent molar amount of bupropion hydrochloride.

In another embodiment there is a method of reducing incidences of and/or severity of bupropion-induced seizures comprising:

administering a pharmaceutically effective amount of bupropion hydrobromide to a subject in need of bupropion administration;

wherein administration of about 100 mg/kg of the bupropion hydrobromide to a first rat results in less incidences of and/or severity of bupropion-induced seizures when compared to incidences of and/or severity of bupropion-induced seizures resulting from administration of an equivalent molar amount of bupropion hydrochloride to a second rat; and wherein the incidences of and/or severity of bupropion-induced seizures in the first and second rats are measured by an electroencephalogram analysis using a hippocampally implanted depth electrode.

In other embodiments of assessing the incidences of and/or severity of bupropion induced seizures, a phenotypic assessment of the subject is assessed. For example, a mild seizure can be characterized by a little jerking of the head, a moderate seizure can be characterized by some jerking of the head, and severe seizures can be characterized by strong jerking of the head.

In another embodiment there is a method of reducing the incidences and/or the severity of bupropion induced seizures by coadministration of a bromide salt with a bupropion salt, wherein the bromide salt is administered in an amount of less than about 3.5 mg/kg. In other aspects of this embodiment, the bromide salt is administered in amounts of from about 1.0 to about 3.5 mg/kg, inclusive of 1.5, 1.75, 2.0, 2.5, 2.67, 2.9, 3.0 and 3.1 and all values and ranges therebetween. In other aspects of this embodiment, the bromide salt is a sodium bromide salt. In other aspects of this embodiment, the bupropion salt is a hydrochloride salt.

In at least one embodiment there is a composition comprising bupropion hydrobromide and at least one pharmaceutically acceptable excipient; wherein administration of an amount (e.g. about 100 mg/kg) of a bupropion hydrobromide to a first rat results in less incidences of and/or severity of bupropion-induced seizures when compared to incidences of and/or severity of bupropion-induced seizures resulting from administration of an equivalent molar amount of bupropion hydrochloride to a second rat; wherein the bupropion hydrobromide that is administered to the first rat is from a source other than the composition (i.e. the bupropion hydrobromide that is administered to the first rat is not extracted from the composition); wherein the bupropion hydrobromide that is administered to the first rat can be the same form as the bupropion hydrobromide that is in the composition; and wherein the incidences of and/or severity of bupropion-induced seizures are measured by an electroencephalogram analysis using a hippocampally implanted depth electrode.

Tables 99-104 contain exemplary 348 mg and 174 mg bupropion hydrobromide XL tablets according to certain embodiments of the invention. Table 105 contains stability data for at least one embodiment of bupropion hydrobromide formulations under accelerated conditions for different batches over different time periods.

The examples below are non-limiting and are representative of various aspects of certain embodiments of the present invention.

EXAMPLES

Example 1

Preparation of Bupropion HBr Salt

Bupropion HBr salt was prepared according to the method shown in Scheme 1:

Scheme 1

Bromination Reaction

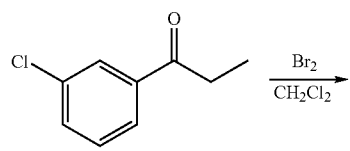

3'-chloro-propiophenone
MW = 168.62

-continued

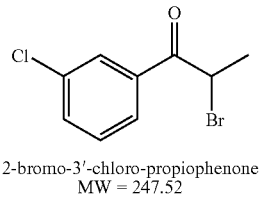

2-bromo-3'-chloro-propiophenone
MW = 247.52

Amination Reaction

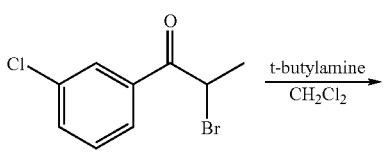

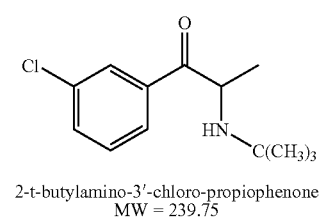

2-t-butylamino-3'-chloro-propiophenone
MW = 239.75

Work Up/Precipitation/Drying 1) work up, toluene
2) precipitation: IPA, HBr gas
3) drying Bupropion•HBr Intermediate Finishing Step

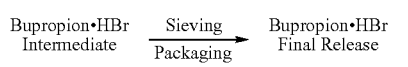

(a) Bromination and Condensation Reactions

3-Chloro-propiophenone starting material was brominated in methylene chloride by dropping bromine under controlled conditions. On reaction completion the mother liquor was worked up and then the second reaction was executed by transferring the bromoderivative solution onto the tert-butylamine. The second substitution reaction (the tert-butylamine amino-group substitutes the bromine atom) forms the final bupropion molecule. After work up of the mother liquor, a bupropion toluene solution was obtained. The solvent was evaporated and bupropion was dissolved in isopropanol. From the isopropanol solution, the hydrobromide was precipitated with hydrogen bromide gas. On precipitation completion, the product was centrifuged, washed with isopropanol and dried under vacuum. On dryer discharge approval it was discharged in Kraft drums within double polyethylene bags.

In the last finishing step, the above intermediate was sieved to obtain the Final Release which was packed in Kraft drums within double polyethylene bags.

Elemental analysis of the bupropion HBr was carried out using a Fisons Elemental Analyser EA 1108. The results were consistent with the molecular formula of bupropion HBr.

Example 2

Physiochemical Characterization of Bupropion Salts

The following bupropion salts were characterized against the HCl salt:

| Product ID | Lot# | Quantity | Potency (HPLC) determined by R&D |
|---|---|---|---|
| Bupropion maleate | 030/018 | 100 g | 99.7 |
| Bupropion tosylate | 030/011/A | 50 g | 97.4% |
| Bupropion Fumarate | 031/1 | 10 g | 89.8% |
| Bupropion HBr | 031/2 | 10 g | 99.7% |
| Bupropion succinate | 031/3 | 10 g | 97.6% |
| Bupropion tartrate acid | 031/5 | 10 g | 84.9% |
| Bupropion tartrate neutral | 031/5B | 10 g | 51.7%* |
| Bupropion citrate | 031/8 | 10 g | 85.0% |

*uncorrected for potency

Thermal Analysis (DSC) Samples:

2-5 mg of each salt was placed in an aluminium pan and covered with its lid. DSC was run for each sample at the rate of 10 degrees C./min (for HBr salt, different rates were used to investigate for polymorphs) from 30 degrees C. to 400 degrees C. TGA was also used for each of the HBr, HCl, maleate and tosylate salts.

Results and Discussion:

Physicochemical Data:

The eight salts were first evaluated by HPLC, KF, pH and DSC for purity, water content, aqueous pH and possible polymorphs. As shown in the Table 1, only the maleate, tosylate, HBr and succinate salts were sufficiently pure, the assay of others ranged from 51.7% to 89.8%.

The salts were analyzed by DSC (at 10° C./min from 30° C. up to 400° C.) and the pH (aq. 0.5%), and the moisture content by KF were also measured. The TGA was performed on the HCl, maleate, tosylate and HBr salts.

Maleate: DSC showed a melting endothermic peak at the onset temperature 199.1° C. and a smaller sharp peak at 205° C. The moisture content was 0.10% and the pH of the aqueous solution of 0.5% was 4.29.

By re-crystallization in isopropyl alcohol (IPA)/EtOAc, the smaller peak almost disappeared. The TGA showed that this product was thermally stable to at least 150° C. as 1.3% weight lost at temperatures from room temperature to 100° C. was observed. Like Bupropion HCl, no glass transition was observed when a heat-cool-heat experiment was done by TA instrument.

Fumarate: DSC showed multiple endothermic peaks at different onset temperatures (172.3, 182.3, 202 and 217° C.). The moisture content was 0.09% and the pH of the aqueous solution of 0.5% was 3.84.

Tosylate: DSC showed a melting endothermic peak at the onset temperature 150° C., a smaller peak at 90° C. and multiple peaks at higher temperature (>200° C., probably decomposition). The peak at 90° C. was probably due to the solvent isopropyl acetate. The moisture content was 1.71% and the pH of the aqueous solution of 0.5% was 5.56.

By re-crystallization in acetonitrile/hexane or acetonitrile/EtOAc, the small peak at 90° C. disappeared, the moisture content dropped to 0.23%, and the pH changed to 5.88. After two months, the re-crystallized sample was retested for moisture content and found to be 0.18%. Therefore, there was a difference between the original and the re-crystallized salt in terms of purity and moisture content (originally thought to be hydrated and/or hygroscopic).

The TGA showed that this product was not thermally stable as 1.3% weight lost was observed at temperatures from room temperature to 100° C. Also the sample gave a residue of 10.3% at 400° C. as compared to minimal residues for bupropion HCl and maleate. The Heat-Cool-Heat experiment was done by TA instrument showed a glass transition (Tg) at 45° C. The Tg indicates that the morphology is amorphous rather than crystalline.

HBr: DSC showed melting endothermic peak at temperature 224° C., with a shoulder peak. The sample was run at different temperature rates, 1, 10, 15 & 20° C./min to seek for possible polymorphs. No significant differences were observed for the endothermic peak shape at different temperature rates. By-crystallization of the HBr salt in different solvents or by internal synthesis starting from 3-chloropropiophenone, no improvements in the shape of the endothermic peak melting at ~224° C. was observed (i.e., still the same shoulder at 10° C. or higher rates). A Heat-Cool-Heat experiment was done by TA instrument showed a glass transition (Tg) at 23° C.

The moisture content was 0.00% and the pH of the aqueous solution of 0.5% was 5.92. Other salts: The DSC results of other salts show multiple melting endothermic peaks. The pH, and the water content of all of the salts are shown in Table 2.

A comparison of the solubility & other physical properties of bupropion HBr vs. bupropion HCl is presented in Table 3.

Figure 2:
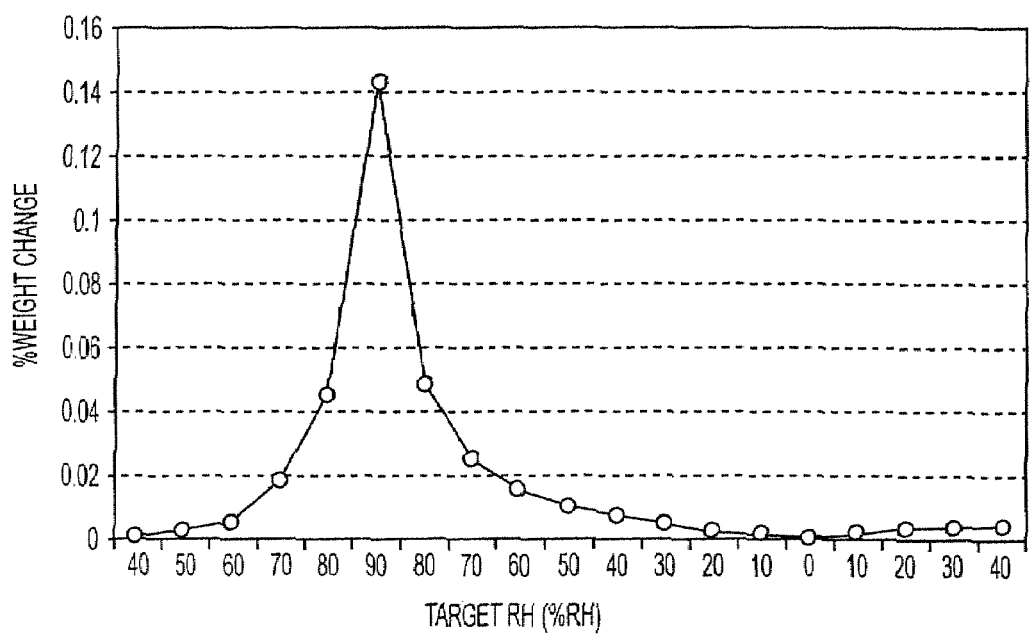
FIG. 2 shows DVS isotherm data for bupropion HBr.

Hygroscopicity of Bupropion HBr:

The Dynamic Vapour Sorption (DVS) analysis of bupropion HBr suggests that the sample is a crystalline anhydrate and has very little water uptake capacity (i.e. non-hygroscopic). The sample of bupropion HBr shows no significant water uptake over the range 0% RH-90% RH. The maximum water uptake was measured at 0.14% weight at 90% RH. A DVS profile for bupropion HBr is shown in FIG. 1 and DVS isotherm data for bupropion HBr is shown in FIG. 2.

Example 3

Forced Degradation Stability Study

The samples of each salt and the spiked salts with the bupropion HCl XL were prepared under the conditions mentioned in Table 4. The samples were placed in the stability chamber at 40 degrees C./75% RH, pulled out at 10, 20 and 32 days and analyzed by HPLC for assay and impurities. The stability of the bupropion salts were evaluated based on the formation of the main degradation product 3-chlorobenzoic acid (3-CBZ) and the intermediate degradation products diketone 827U76 and the ketohydroxyl derivatives (20U78 and 852U77) (Scheme 2). The 3-chlorobenzoic acid is formed as a result of the oxidation/hydrolysis of the parent compound bupropion salts.

Scheme 2

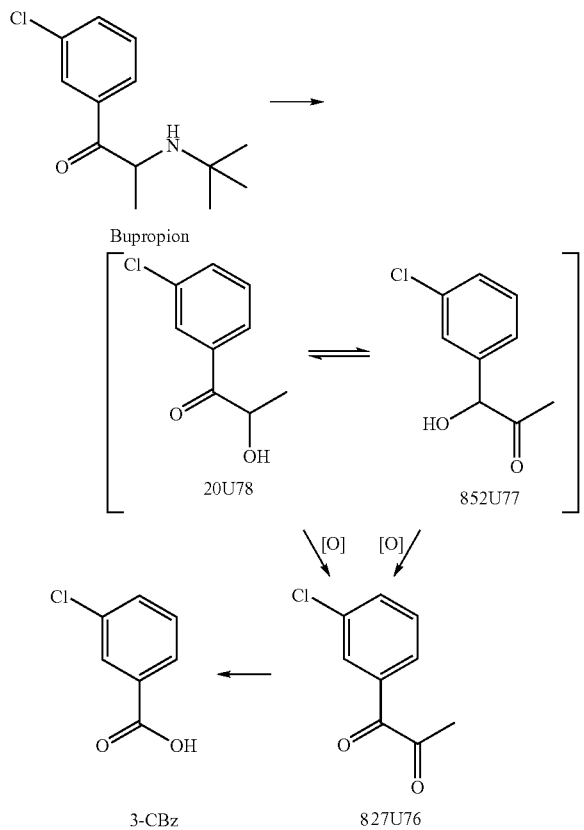

As mentioned above, the stability samples were prepared in 2 mL vials and used directly for assay and bupropion degradation impurity analysis by HPLC without further sample preparations to minimize errors.

The 10 days forced degradation studies on these salts showed that the succinate, tartrate and citrate (with or without mixing with excipients in closed vials) were not stable under the conditions mentioned in Table 4. The assay substantially dropped down, the level of known and unknown impurities increased and the colors of these salts changed from the original white powders to yellow semi liquid products. Therefore, further study on these salts was not continued.

Figure 4:
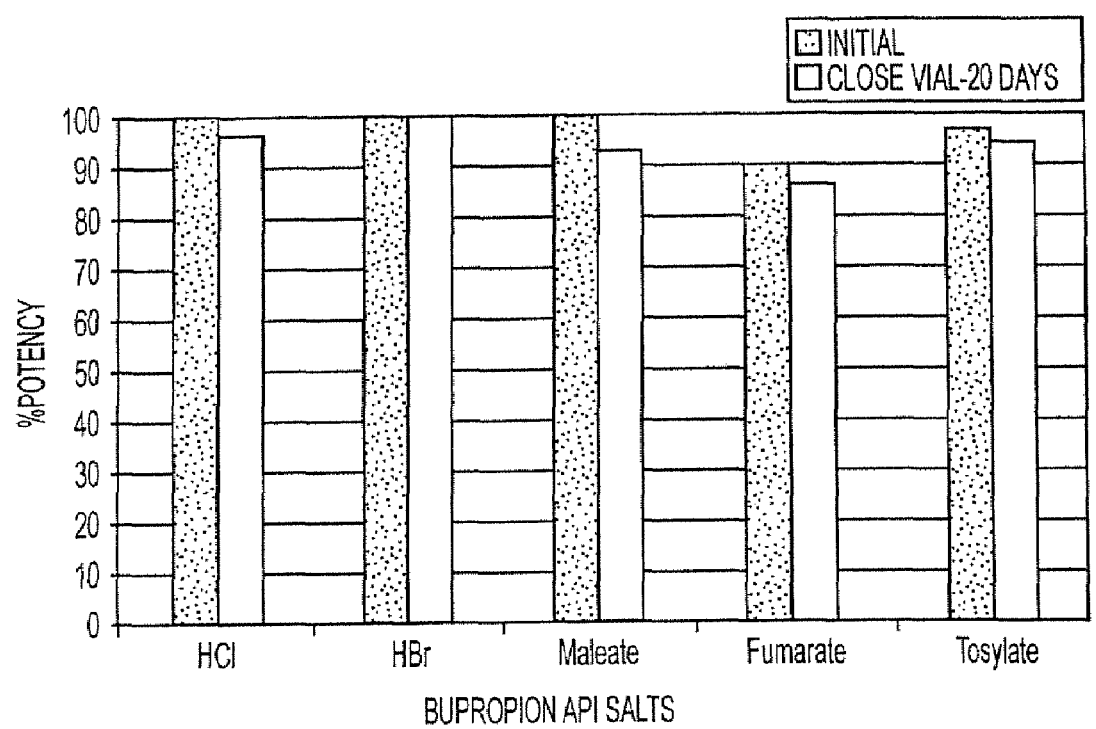
FIG. 4 is a bar graph showing the potency of the bupropion salts mixed with excipients after storage in closed vials over 20 days at 40 degrees C./75% RH compared to their initial potency.
Figure 5:
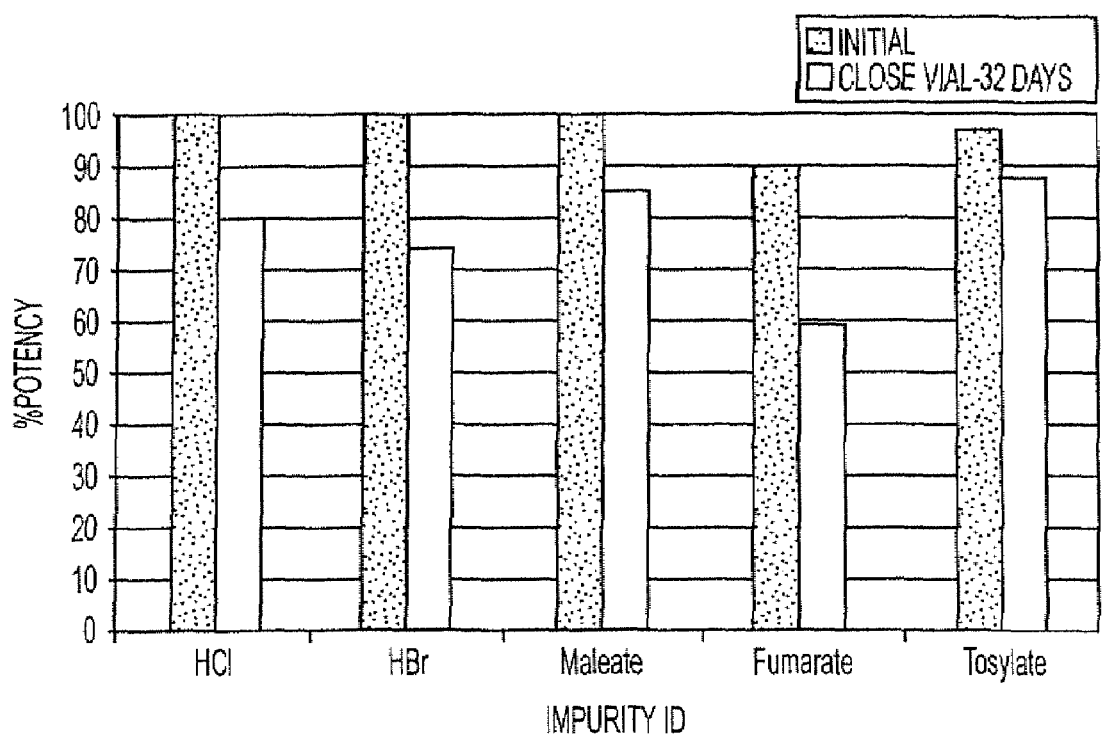
FIG. 5 is a bar graph showing the potency of the bupropion salts mixed with excipients and water after storage in closed vials over 32 days at 40 degrees C. compared to their initial potency.
Figure 6:
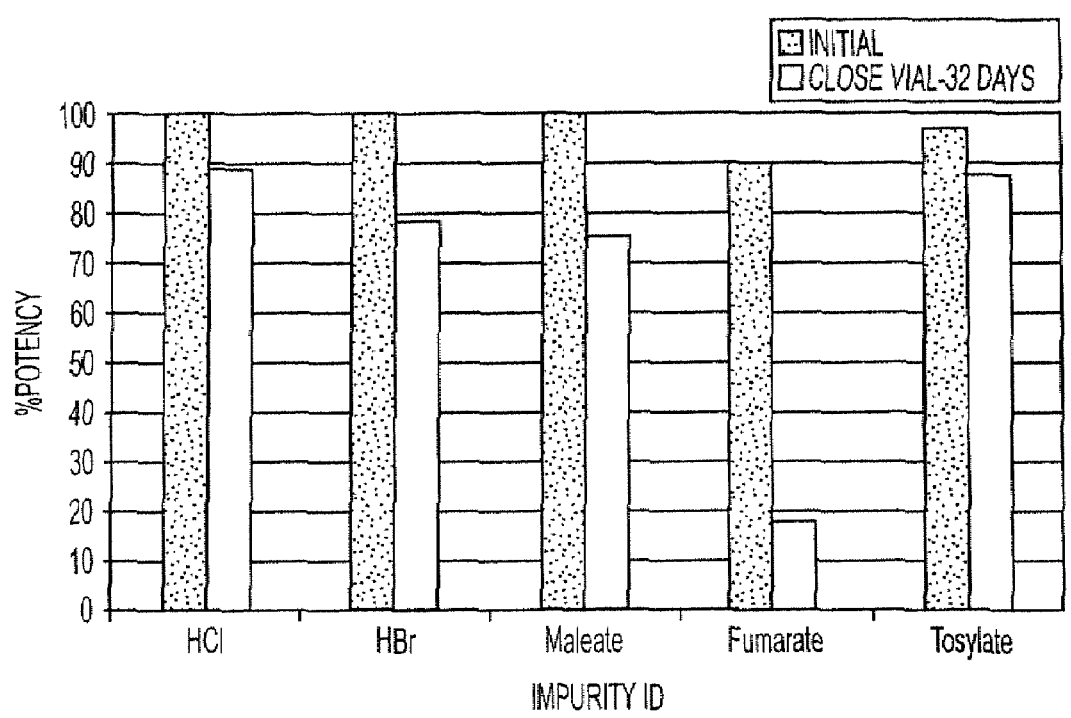
FIG. 6 is a bar graph showing the potency of the bupropion salts mixed with excipients, water, isopropyl alcohol and ethanol after storage in closed vials over 32 days at 40 degrees C. compared to their initial potency.
Figure 7:
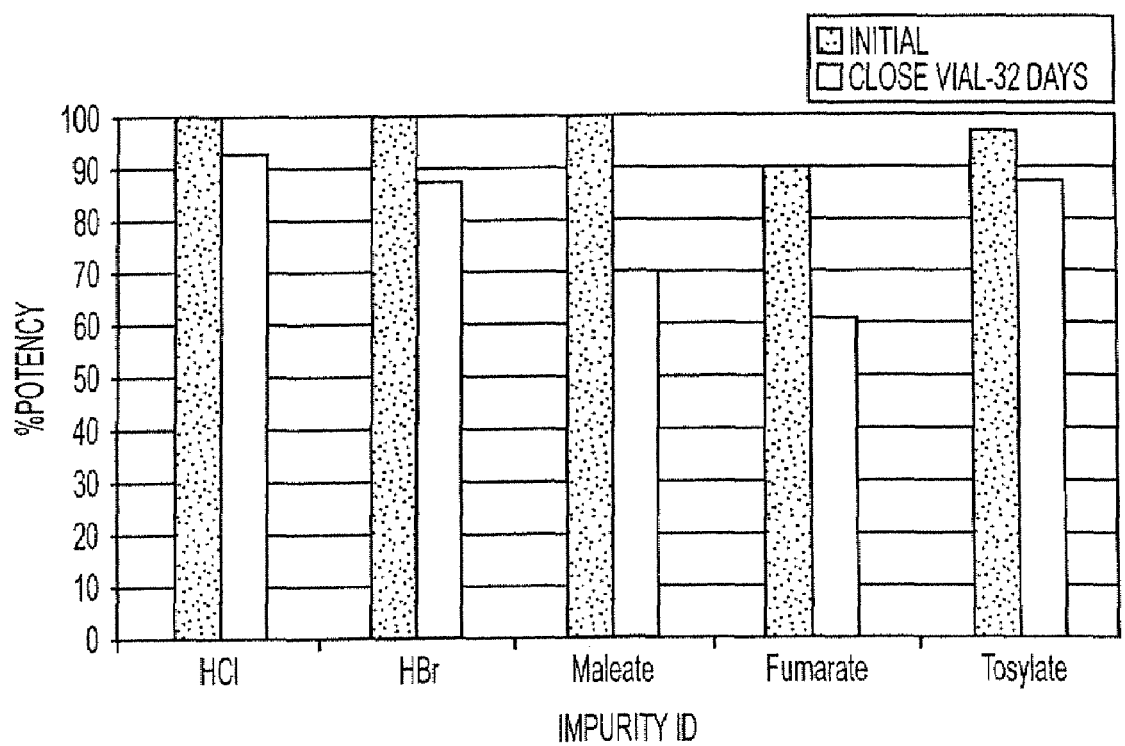
FIG. 7 is a bar graph showing the potency of the bupropion salts mixed with excipients, isopropyl alcohol and ethanol after storage in closed vials over 32 days at 40 degrees C. compared to their initial potency.
Figure 8:
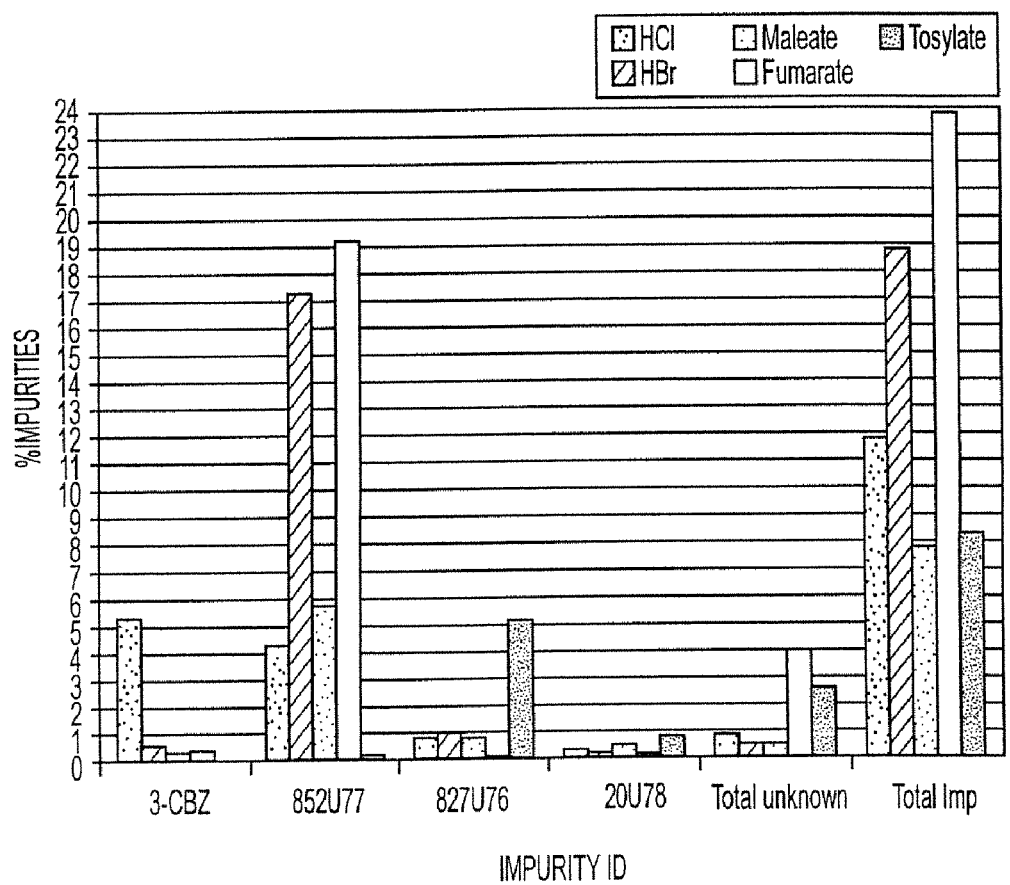
FIG. 8 is a bar graph showing the % impurities for the bupropion salts mixed with excipients and treated for 32 days in closed vials and spiked with water.
Figure 9:
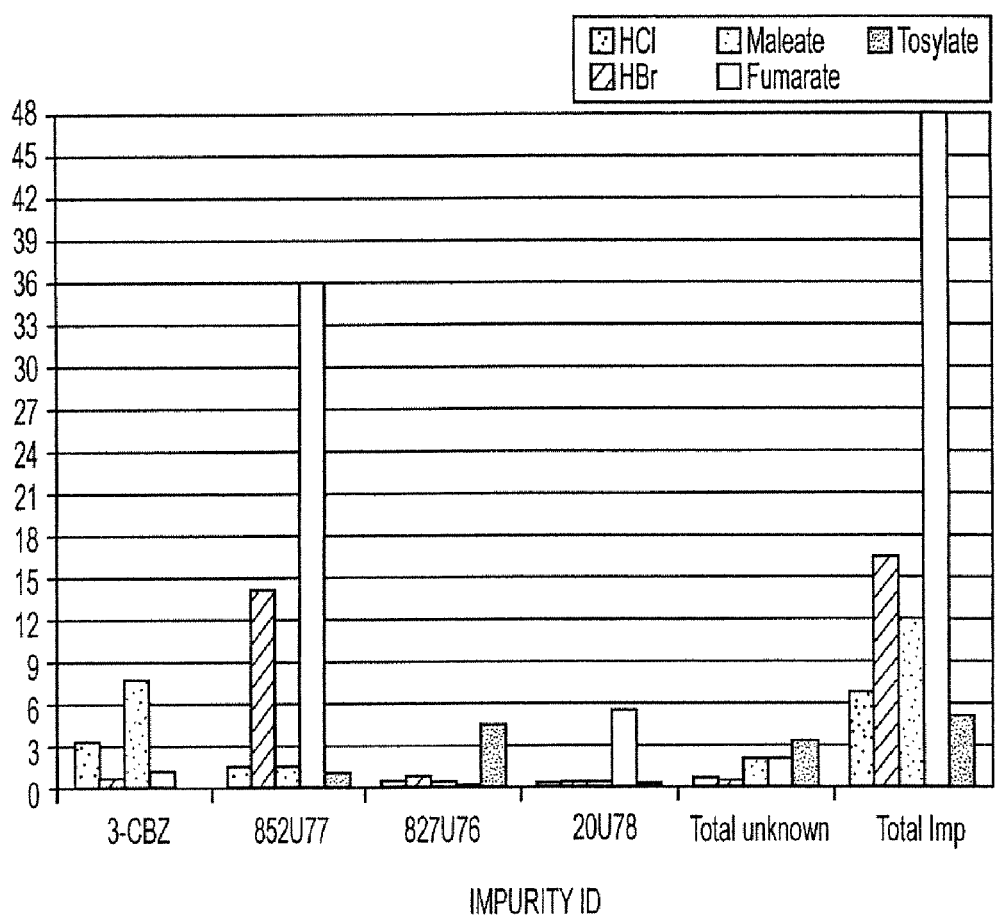
FIG. 9 is a bar graph showing the % impurities for the bupropion salts mixed with excipients and treated for 32 days in closed vials and spiked with water, isopropyl alcohol (IPA) and ethanol (EtOH).
Figure 10:
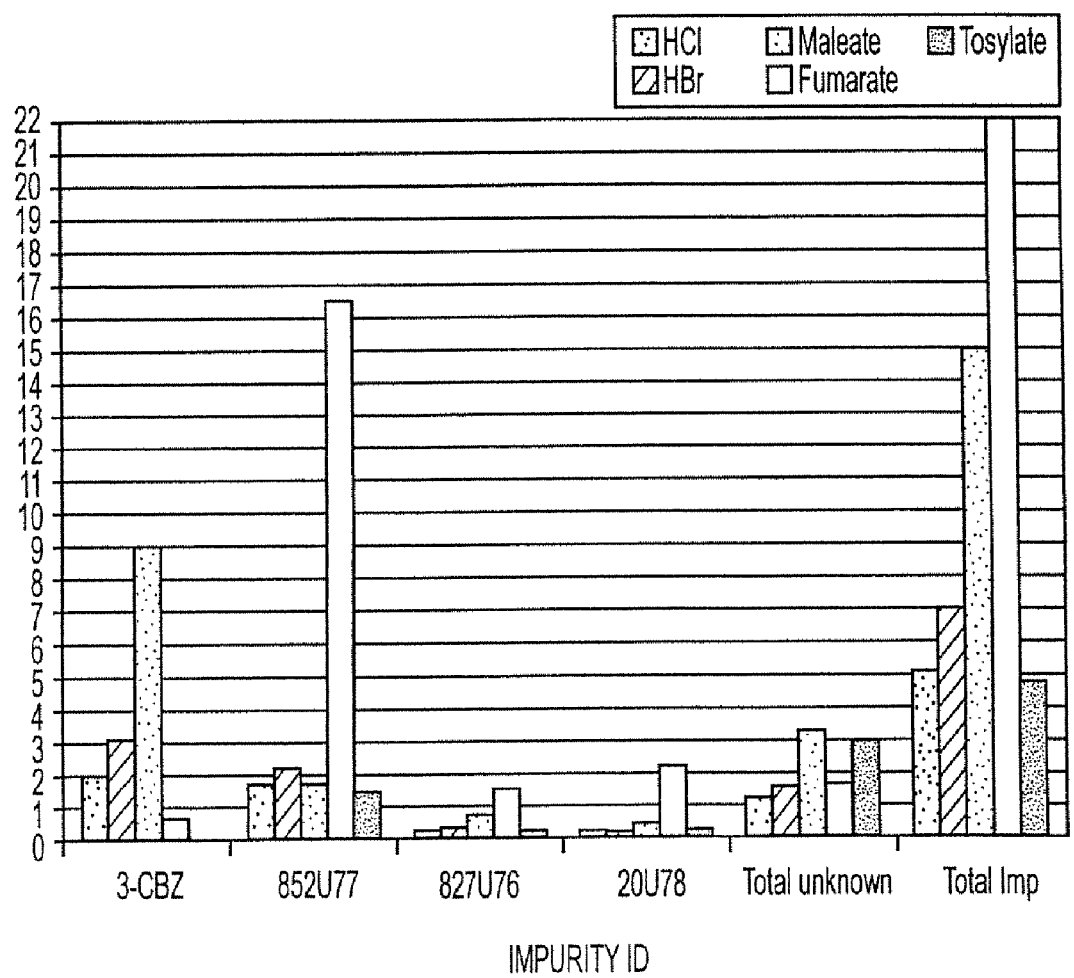
FIG. 10 is a bar graph showing the % impurities for the bupropion salts mixed with excipients and treated for 32 days in closed vials and spiked with isopropyl alcohol (IPA) and ethanol (EtOH).

The 10, 20 and 32 days stability time points for the maleate, tosylate, HBr, and fumarate salts were continued in parallel to Bupropion HCl. The results are shown in FIGS. 3-10. The assay and bupropion degradation impurity results for 20-days in closed vials for these five salts were compared for salt plus excipients and are presented FIGS. 3 and 4. FIGS. 5-7 show the results for the drug salts (DS) kept for 32 days in closed vials and spiked with water, water-isopropyl alcohol (IPA)-ethanol (EtOH) and IPA-EtOH.

Figure 3:
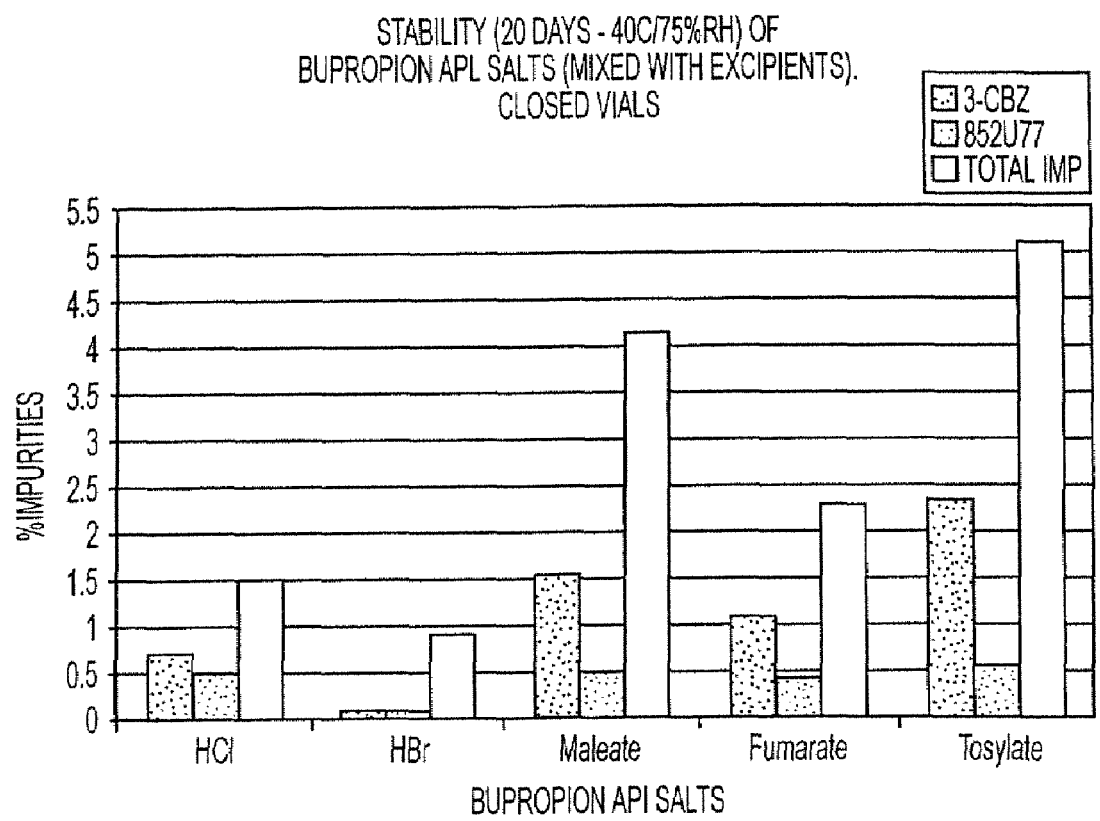
FIG. 3 is a bar graph showing the results of stability testing on the bupropion salts mixed with excipients in closed vials over 20 days at 40 degrees C./75% relative humidity (RH).

In the closed vial assays, it is of note that the bupropion degradation impurities (3-CBZ, 852U77 & total) in the HBr salt were the lowest compared to all of the other salts including HCl (see FIG. 3). The levels of 852U77 in the other salts were comparable with HCl, however, the levels of 3-CBZ and, in particular levels of the total bupropion degradation impurities were more with the other salts than HCl. In the assay results (% potency), the tosylate and the HCl salts had similar potency after the 20 days in a closed vial (FIG. 4). In the assay study, the order of stability for the bupropion salts was as follows:

HBr>HCl≈tosylate>fumarate>maleate).

The stability of the salts was then evaluated under more aggressive conditions. The drug salts (DS) and excipients were spiked with water, water plus EtOH and IPA and EtOH and IPA. As can be seen from the results shown in FIGS. 5-7, the order of stability (assay) of the salts can be summarized as follows:

| | |
|---|---|
| Stability with water: | tosylate > maleate > HCl > HBr > fumarate. |
| Stability with IPA & EtOH: | HCl > HBr > tosylate > maleate > fumarate |

Tosylate and maleate salts were more stable than other salts when exposed directly to water, and less stable when exposed to the organic solvents IPA & EtOH.

The HCl and HBr salts were more stable than other salts when exposed directly to IPA & EtOH and less stable with water. The fumarate salt was neither stable in water nor in the organic solvents IPA & EtOH.

The level of the impurities (known, unknown & total) varied in each of the salts under the conditions of this experiment. The content of each of the major bupropion degradation impurities (3CBZ & 52U77) and the total impurities was as follows (FIGS. 8-10):

| | |
|---|---|
| In water, 3-CBZ: | HCl > HBr ≈ maleate ≈ fumarate |
| 852U77: | fumarate > HBr > maleate > HCl |
| Total imp. | fumarate > HBr > HCl > tosylate > maleate |
| In IPA/EtOH: 3-CBZ: | maleate > HBr > HCl > Fumarate |
| 852U77: | fumarate > HBr ≈ HCl ≈ maleate ≈ tosylate |
| Total imp. | fumarate > maleate > HBr > HCl > tosylate |

Based on the forced degradation stability studies conducted on the above bupropion salts, the stability of oxalate, citrate, succinate and tartarate were shown to be very poor for the DS and the spiked DS (20 days: discoloration, Low assay & high level of degradation impurities). The HBr, tosylate, maleate and to some extent fumarate salts are good candidates for further studies. Among the latter salts, HBr was the best candidate due to its superior stability in a closed container, lowest water content, non-hygroscopic and its easy preparation.

The tosylate salt also showed good stability, although it was not as pure as the HBr, HCl or maleate. The tosylate salt, however, does not have an acceptable toxicity profile.

It also was found that the presence of the organic solvents ethanol and isopropyl alcohol have significant impact on the stability of these salts.

Example 4

Comparative Forced Degradation Studies of Bupropion HCl and Bupropion HBr API Salts The stability of bupropion HCl and bupropion HBr API salts were further evaluated under the accelerated conditions of 40° C./75% RH in a stability chamber. The samples were exposed to the above conditions in a closed bottle for few days, and then subjected to HPLC analysis.

The amount of the main degradation products present after treatment were compared with those amounts that were present initially.

Accurately quantities of each API were weighed individually in 50-mL amber glass bottles as shown in the Table 5. The bottles were closed and placed in the stability chamber at 40° C./75% RH. The samples were analyzed after 14 and 24 days (study-1) and 10 days (study II), in a quantitative manner by direct treatment of the whole content of the bottle as per the HPLC standard test method (P05.901.10).

As shown in the Table 6, the resulting degradation products in both bupropion HCl and bupropion HBr were either similar or better for the HBr salt.

The above study was repeated on two batches of each of the APIs for 10 days. As shown in table 7, the level of bupropion degradation impurities in the case of bupropion HBr salt was lower than bupropion HCl, also the assay value for the latter was lower than that for the HBr salt.

Example 5

Bupropion HBr Extended Release (XL) Tablets

The aim of this example was to describe the development of bupropion HBr XL (174 and 348 mg). Granulation, tabletting and coating procedures are all described thoroughly in this example. In-vitro testing was conducted on the cores, the ethylcellulose coated cores and the final coated tablets in order to determine which formulation gave the desired results.

From their structural formulae, it is observable that the difference between bupropion HCl and bupropion HBr is the salt. This, of course, results in a different molecular weight. However, these differences were taken into account in the present study, and modifications were made in order to obtain in-vitro correlation results to the bupropion HCl using dissolution studies.

It was previously observed that when 150 mg of bupropion HCl was tested for its release of bupropion, the base value that was released was 130 mg. However, when 150 mg of bupropion HBr was tested, the base value released was only 112 mg. Thus, the amount of bupropion HBr had to be increased in order to increase the base value from 112 mg to 130 mg, which was the target. Studies showed that 174 mg of bupropion HBr gave a base value release of 130 mg and is therefore why 174 mg was used as opposed to 150 mg bupropion HBr.

Bupropion HBr XL—Granulation Process

Figure 11:
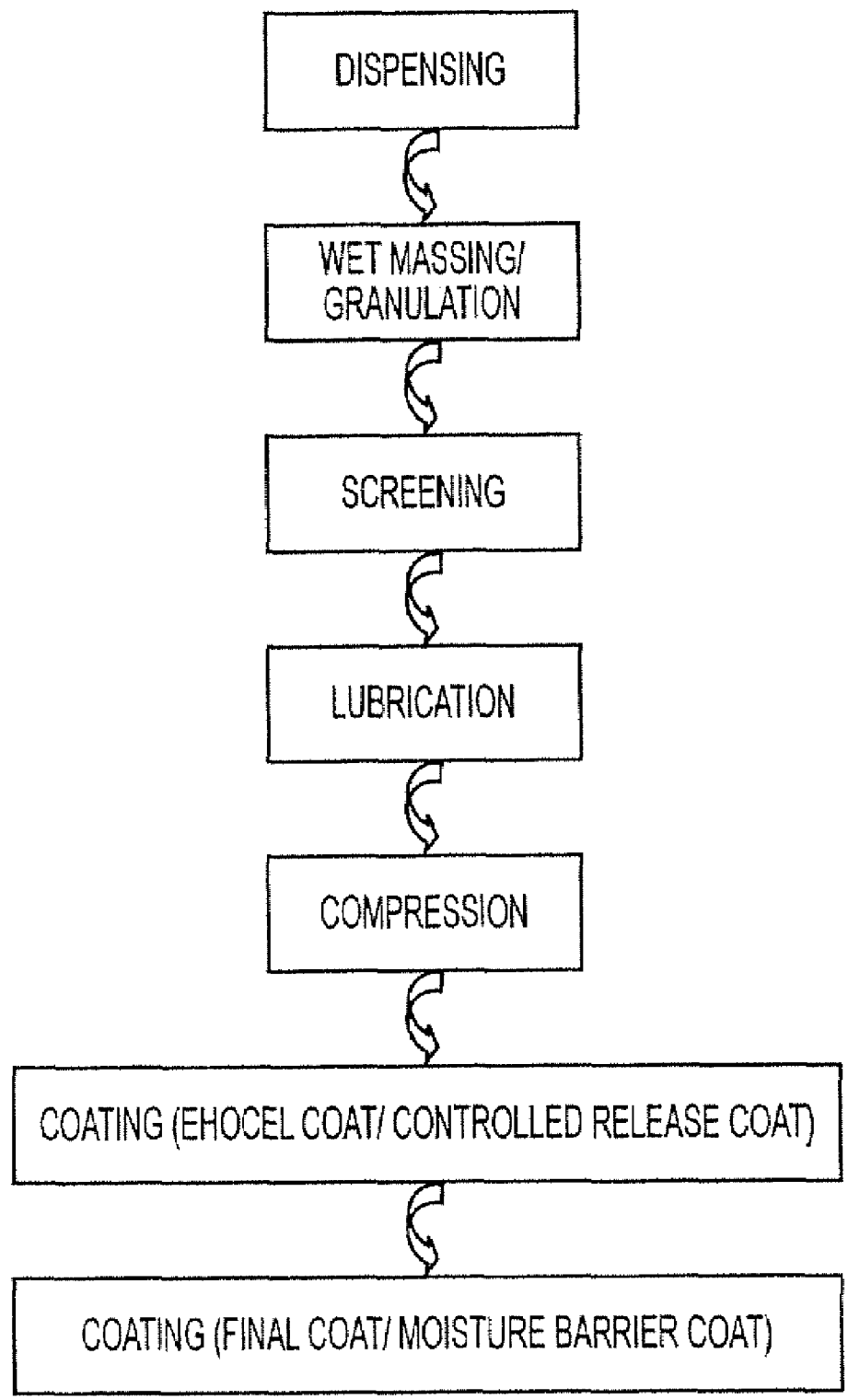
FIG. 11 is a flow chart showing the overall process for the development of bupropion HBr XL tablets.

A summary of the manufacturing process used for the preparation of bupropion HBr XL tablets is shown in FIG. 11.

The following materials were used in the granulation of the immediate release core of the bupropion HBr EA tablets: bupropion HBr, polyvinyl alcohol (PVA) and purified water. Once granulated, lubricant (COMPRITOL® 888) was added to complete the formulation. Each Trial was divided into 5 parts. The percentage of API in each formulation was 93.75%; the percentage of PVA in each formulation was 3.125%. A summary of the breakdown of each trial per part is described in Table 8.

The PVA was dissolved into the purified water using a magnetic stirrer and a clear colourless solution was made.

Figure 12:
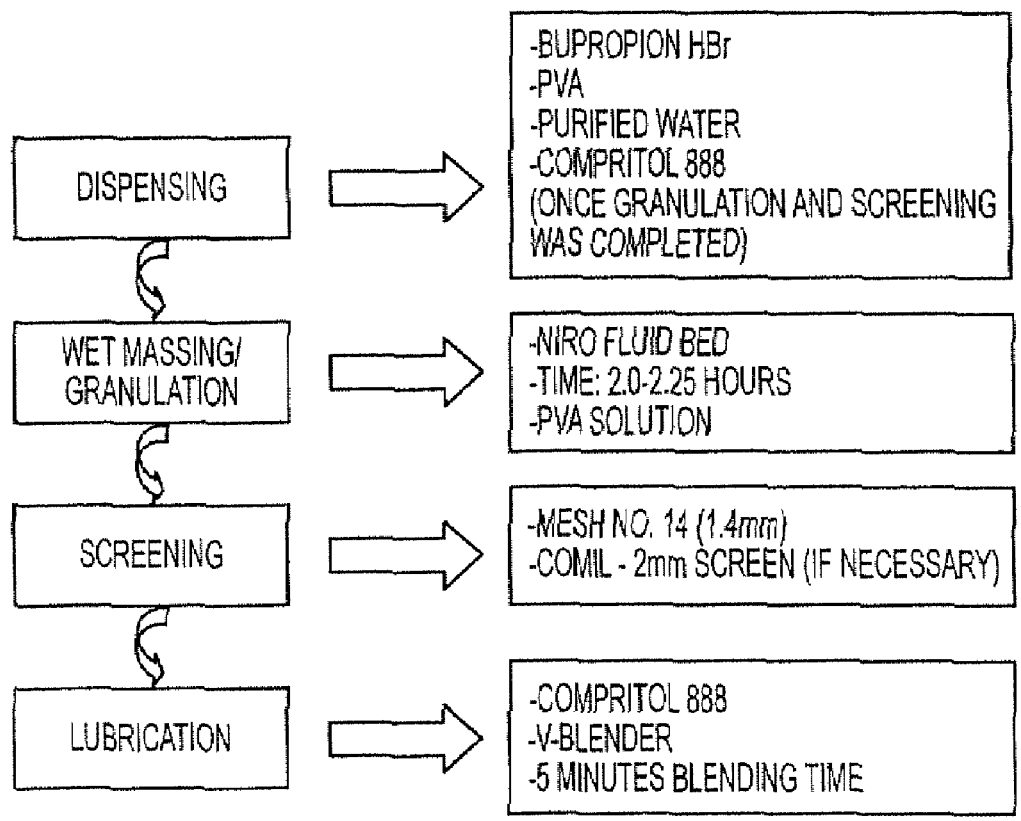
FIG. 12 is a flow chart demonstrating the granulation process of the bupropion HBr XL and EA tablets.

The NIRO Fluid Bed was used to granulate the bupropion HBr Granules with the PVA solution in a process known as wet massing. FIG. 12 shows a summary of the granulation procedure.

The Bupropion HBr was loaded into the fluid bed and granulation was initiated. The specifications that were used as guidelines are listed in Table 9.

Loss on Drying was determined after each granulation using the Moisture Analyzer. A 1 g sample was taken and loaded into the moisture analyzer. The sample ran for 5 minutes at a temperature of 105° C.

Upon completion of each batch part's granulation, the five parts were combined together. They were hand screened using Mesh No. 14 (1.4 mm) and any oversized granulation was passed through the Comil fitted with a 2 mm screen.

COMPRITOL® 888 was used as a lubricant in the formulation. The screened bupropion HBr granules and the COMPRITOL® 888 were loaded into the V-blender and were blended for 5 minutes. The COMPRITOL® 888 made up 3.125% of the formulation. The final granule batch size is described in Table 10.

Bupropion HBr XL—Tabletting Process

The Beta Press was used to compress the Bupropion HBr tablets. Depending on the dose of the tablet, 174 mg or 348 mg, different tooling sets were used. The 7 mm punches were used to compress the 174 mg tablets and 9 mm and 10 mm punches were used to compress the 348 mg tablets. Tooling was polished prior to each run.

The tablet weights were determined as being 185.6 mg for the 174 mg dose tablets and 371.2 mg for the 348 mg dose tablets. These adjustments to tablet weight were made in order to compensate for the fact that bupropion HBr was being used in place of bupropion HCl. The individual tablet weights had a control limit of ±5%, and the average tablet weight had a control limit of ±3% (using ten tablets).

A hardness tester was used to determine the load required to diametrically break the tablets (crushing strength) into two equal halves. A predetermined range set the specifications for hardness, which was 6.0-12.0 SC for both the 174 mg and 348 mg tablets.

Friability was determined using tablets that equaled a weight of 6.5 g in a friability tester for 4 minutes at 25 rpm. Tablets were de-dusted before and after testing. A weight loss of less than 0.8% was used as the criteria in order to accept or reject a batch.

Table 11 summarizes the specifications of the tablet press set-up. All the specifications were kept within the range and at the setting that was assigned, throughout all of the batches.

Table 12 summarizes the specifications that were kept constant throughout the compression of all the batches.

Figure 13:
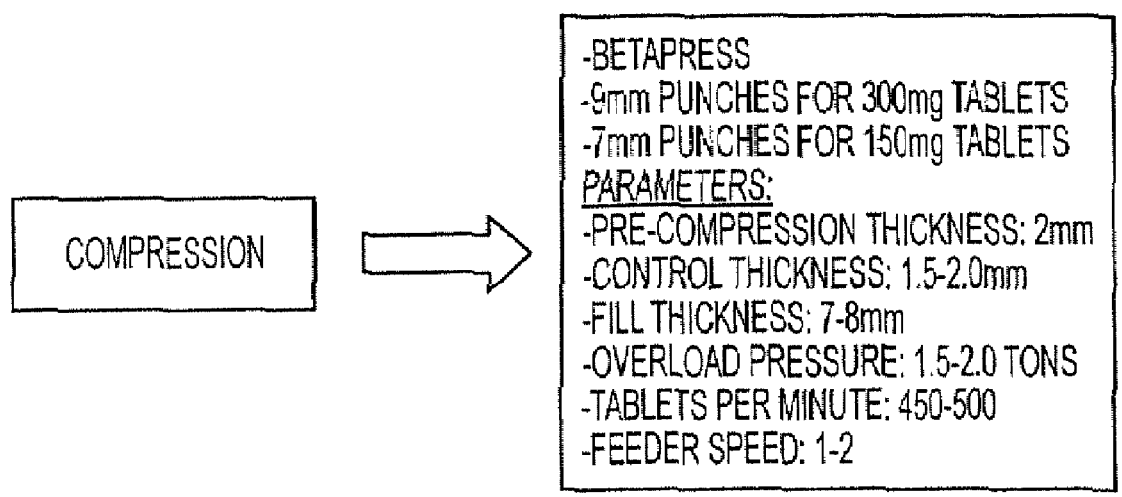
FIG. 13 is a flow chart showing the overall tabletting process of bupropion HBr XL.

The flow chart shown in FIG. 12 describes the steps that led up to and including the tabletting process. FIG. 13 shows a summary of the tabletting procedure.

Bupropion HBr XL—Coating Process

Figure 14:
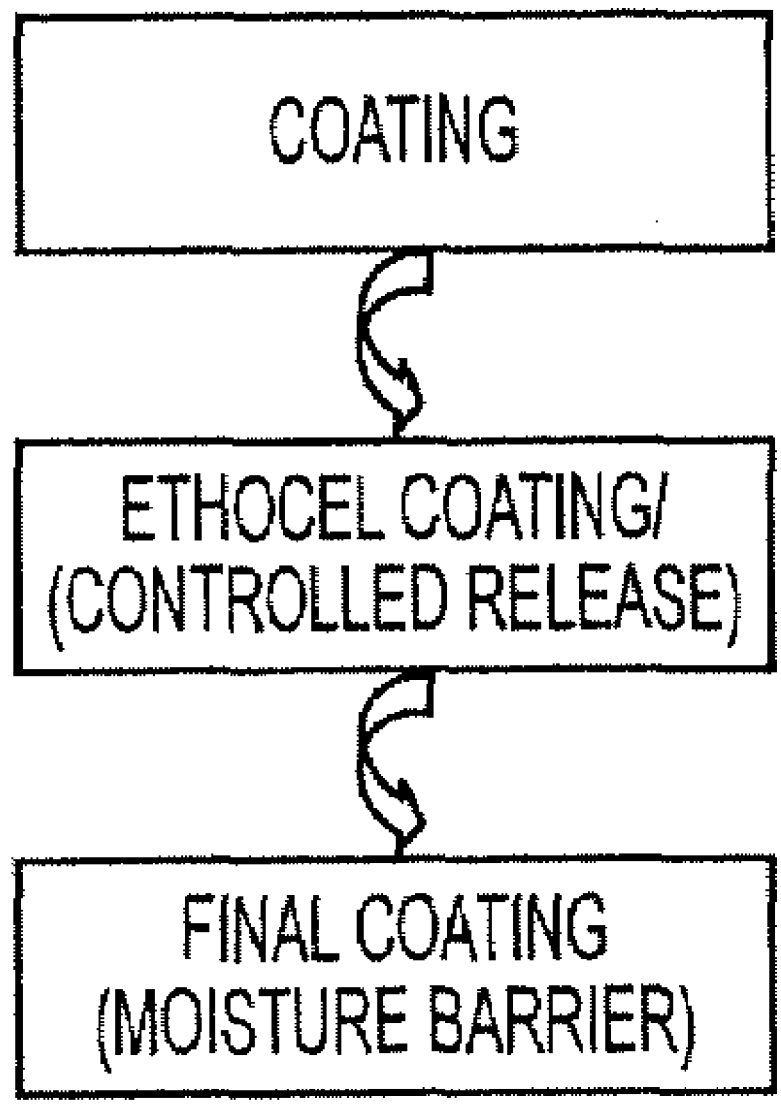
FIG. 14 is a flow chart showing the overall coating process of bupropion HBr XL.

A summary of the coating process used for the coating of the Bupropion HBr XL tablets is shown in FIG. 14. The first coat is an ethylcellulose (e.g. ETHOCEL®) coat that controls the release, which is followed by a final coat that acts as a moisture barrier.

For the ethylcellulose coating and final coating of the Bupropion HBr XL tablets, the 15 inches O'Hara Labcoat II System was used. An attached spraying nozzle and a propeller mixer were also used.

Several ethylcellulose coating solutions were developed and used to coat the Bupropion HBr tablets. The ethylcellulose coating layer was placed on the tablets containing one of the formulations listed in Table 13.

In formulation 1, ethyl Alcohol 95% and IPA 99% were combined together in a stainless steel container. While stirring, PEG 4000 was added and allowed to dissolve. Once dissolved, ethylcellulose (e.g. ETHOCEL®) was added and left to stir for 30 minutes. Then, Povidone was added to the solution and was mixed for an overnight period (15-20 hours).

In formulation 2, PEG4000 was placed into a beaker with the Dibutyl Sebacate and was stirred until it dissolved. Ethyl Alcohol 95% was added accordingly in order to allow the PEG 4000 to completely dissolve. In a separate stainless steel container, the remaining Ethyl Alcohol 95% was placed and, while being stirred, ethylcellulose was added and stirred for 30 minutes. Following that, Povidone was added and allowed to stir for an overnight period (15-20 hours).

In formulation 3, Ethyl Alcohol 95% was placed in a stainless steel container. While stirring, PEG 4000 was added and allowed to dissolve. Once dissolved, ethylcellulose was added and left to stir for 30 minutes. Then, Povidone was added to the solution and was mixed for an overnight period (15-20 hours).

Two Final coating solutions were developed and used to coat the Bupropion HBr tablets after they had been first coated with the ethylcellulose coat.

One of the following formulations shown in Table 14 was used to coat the tablets with a final coat.

In Formulation A, the purified water was placed in a glass beaker and Chroma-Tone DEB 5156-CLE was added and allowed to mix for 15 minutes. The EUDRAGIT® was passed through a Mesh screen (no. 60) prior to use. Following this, the EUDRAGIT® was added to the beaker and was stirred for 15 more minutes.

In Formulation B, part 1 of the Purified Water was placed into a glass beaker and PEG 4000 was added to it and allowed to mix until it was completely dissolved (5 minutes). The Triethyl Citrate was then added and left to mix for another 5 minutes. Once dissolved, the solution was then added to the EUDRAGIT® Suspension and left to stir for 45 minutes. The EUDRAGIT® was passed through a Mesh screen (no. 60) prior to use. In a separate beaker, part 2 of the purified water was added to the SYLOID® 244FP and mixed until it was completely dissolved (10 minutes). Finally the SYLOID® Suspension was added to the EUDRAGIT® Suspension and left to stir for another 10 minutes.

Table 15 summarizes the specifications that were monitored in the ethylcellulose coating process and their ranges.

Table 16 summarizes the specifications that were monitored in the final coating process and their ranges.

In-Vitro Studies on the Bupropion HBr Cores

Dissolution was performed on the Bupropion HBr cores, on the different weight gains of ethylcellulose coated cores and on the different weight gains of final coated tablets. USP-1 method was used to conduct these studies. The dissolution test was performed using 900 mL of 0.1N HCl and at a speed of 75 rpm. Samples were taken at every hour for 16 hours. The dissolution profiles were obtained by plotting the cumulative percent of API dissolved against sampling time points. Sink conditions were maintained throughout all the experiments.

On several trials, USP-3 method was used to conduct the dissolution studies. These dissolution tests were performed for 16 hours total with the following breakdown: 2 hours using 900 mL of Simulated Gastric Fluid (SGF) at pH 1.2 with 0.5% of Sodium Lauryl Sulfate (SLS), followed by 2 hours in 900 mL of Acetate Buffer at a pH of 4.5, followed by 12 hours in 900 mL of Phosphate Buffer Simulated Intestinal Fluid (SIF) at a pH of 6.8. These results were plotted with the in-vivo data and the Bupropion HCl data in order for a comparison to be made.

Study on Batch BUP-HBr-XL-009-5

Figure 15:
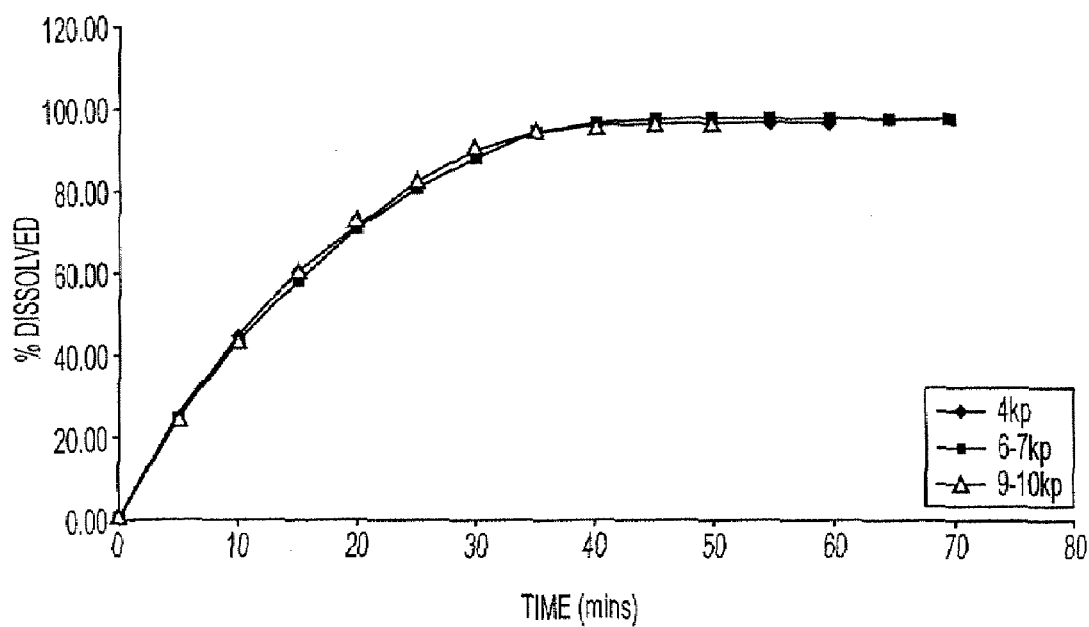
FIG. 15 is a dissolution profile of the 4 kp, 6-7 kp and 9-10 kp tablets, comparing the effects of hardness on dissolution in the study on Batch BUP-HBr-XL-009-5.
Figure 16:
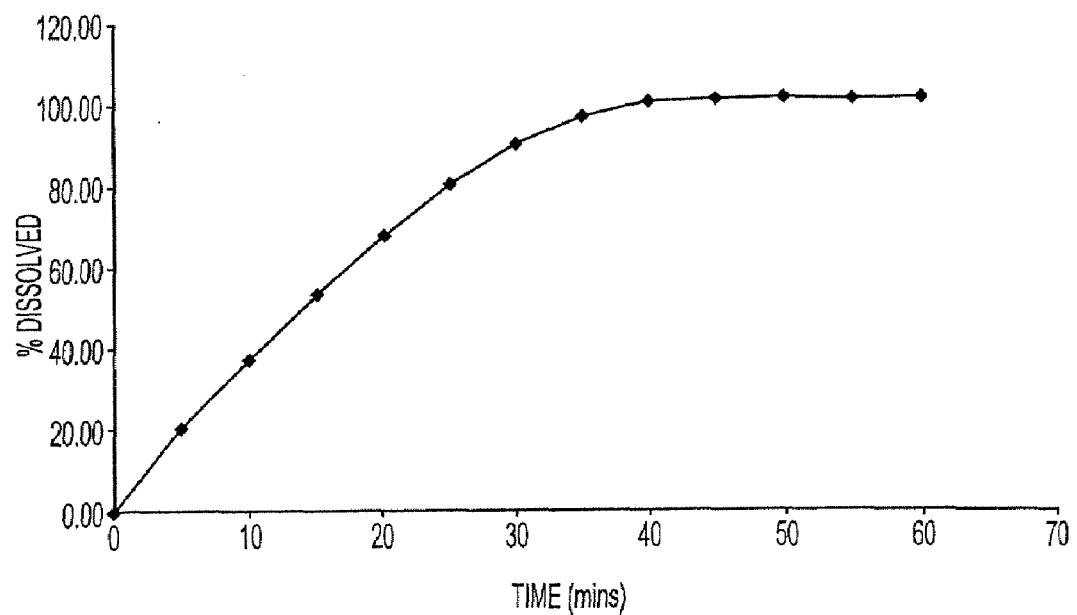
FIG. 16 is a dissolution profile of the 348 mg Bupropion HBr cores which have been compressed using 9 mm tooling in the study on Batch BUP-HBr-XL-009-5.

The formulation was granulated using NIRO Fluid Bed. After granulation was completed, the batch was screened and then prior to compression the lubricant (COMPRITOL® 888) was added. The final blend was compressed into 348 mg tablets using the Beta press with 9 mm and 10 mm standard, round, concave tooling. Table 17 describes the amounts of each material in the granulation of the 348 mg tablets. A first compression run was done to produce tablets with different hardness values so as to determine the effects of hardness, if any, on the dissolution (FIG. 15). Dissolution was conducted on the 348 mg cores in order to determine their release (FIG. 16).

The granulation results show that the average granulation time is 2.0 hours and the average LOD % is 0.345%. Tables 18 and 19 summarize the theoretical and actual values of the parameters that were monitored in the compression process using the 9 mm and 10 mm tooling, respectively.

In order to determine the tablet hardness for this study, tablets of different hardness values were compressed and dissolution was conducted on them to see the difference.

Tablets with a hardness of 4 kp, 6-7 kp and 9-10 kp were compressed and the dissolution profiles of each were shown in FIG. 15. It was observed that there was no significant difference between the three different hardness ranges.

The dissolution profiles of the 348 mg (FIG. 16) and 174 mg cores (FIG. 17) showed that the cores were releasing approximately 100 percent of API in an hour.

Figure 17:
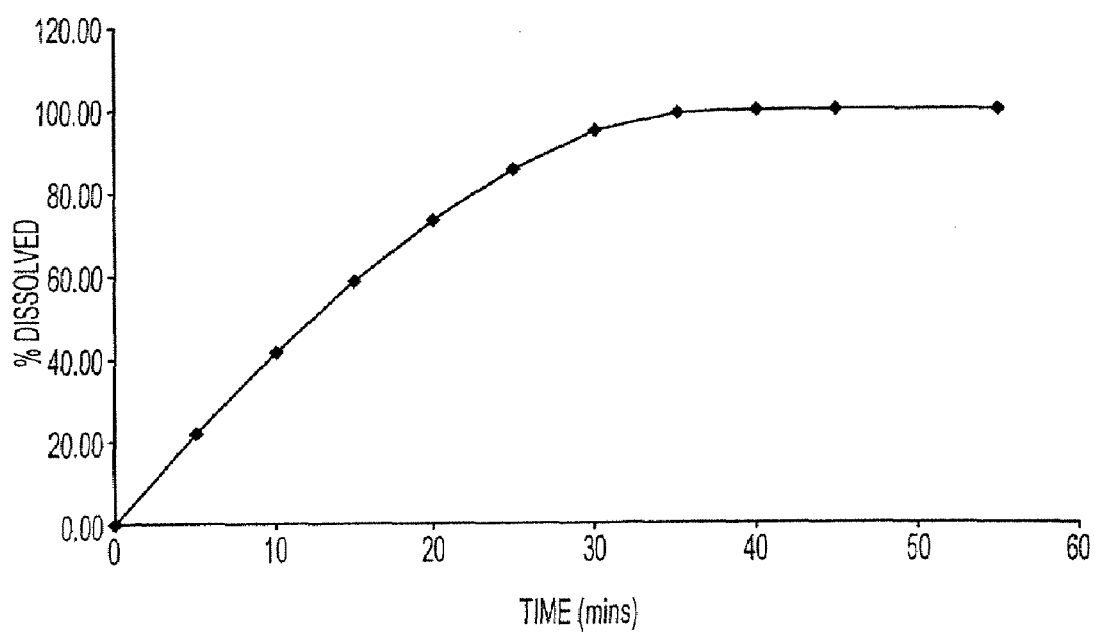
FIG. 17 is a dissolution profile of the 348 mg Bupropion HBr cores which have been compressed using 10 mm tooling in the study on Batch BUP-HBr-XL-009-5.

Dissolution of the 10 mm, 348 mg cores was done also in order to see if these tablets released faster when compared to the 9 mm cores due to their larger surface area (FIG. 17).

Figure 18:
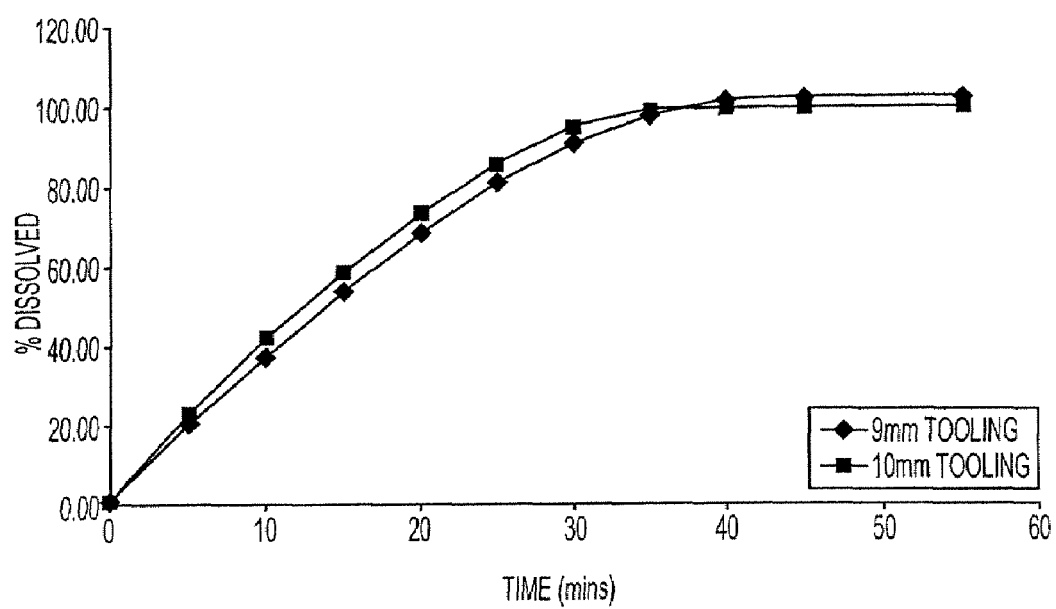
FIG. 18 is a dissolution profile comparison of the 9 mm and 10 mm diameter 348 mg Bupropion HBr cores in the study on Batch BUP-HBr-XL-009-5.

When the dissolution results of the 9 mm and 10 mm cores were compared (FIG. 18), the 10 mm cores showed no difference from the 9 mm cores. Thus, the 10 mm cores were no longer manufactured or used in this study.

Study on Batch BUP-HBr-XL-021-5

Figure 19:
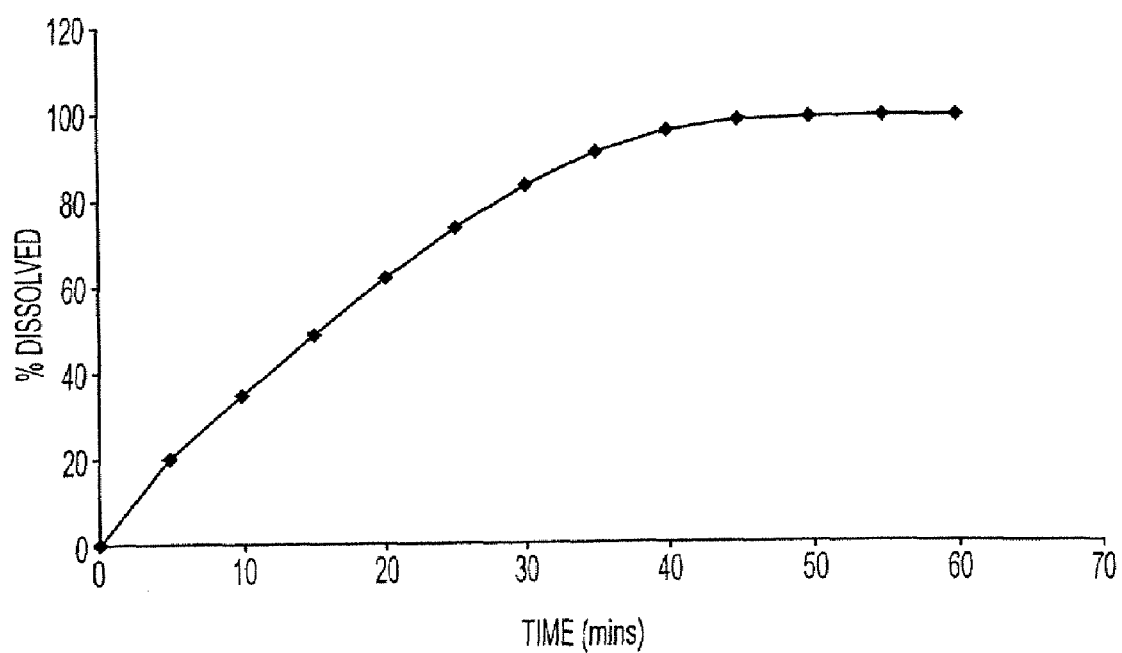
FIG. 19 is a dissolution profile of the 174 mg in the study on Batch BUP-HBr-XL-021-5.

The Formulation was granulated using NIRO Fluid Bed. The final blend was compressed into 174 mg tablets using the Beta press with 7 mm standard, round, concave, stainless steel tooling. Table 20 describes the amounts of each material in the granulation of the 174 mg tablets. It was noted that the 348 and the 174 mg tablets had the same composition and amounts of each material; the only variation was the tablet weight, which was adjusted at the compression stage. Dissolution was conducted on the 174 mg cores in order to see their release (FIG. 19).

The granulation results show that the granulation time is 2 hours 6 minutes and the average LOD % is 0.26%. Table 21 summarizes the theoretical and actual values of the parameters that were monitored in the compression process using the 7 mm tooling.

The dissolution profile of the 174 mg (FIG. 19) showed that the cores were releasing approximately 100 percent of API in an hour.

Study on Batch BUP-HBr-XL-348 mg-013-5

Using 348 mg tablets, an ethylcellulose (e.g. ETHOCEL® or "EC") coating followed by a Final coating, were sprayed onto the tablets using the O'Hara Labcoat II Coating Equipment. The materials used in the ethylcellulose coating, their percent contribution to the total solution, the amounts of each in the batch and the percentage of the solids in the solution were all listed in Table 22.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 2 hours and 25 minutes to coat the tablets with a weight gain of 32 mg. Tablet weights were taken and recorded in Table 23 at 28 mg, 30 mg, 32 mg, and 34 mg weight gains.

Figure 20:
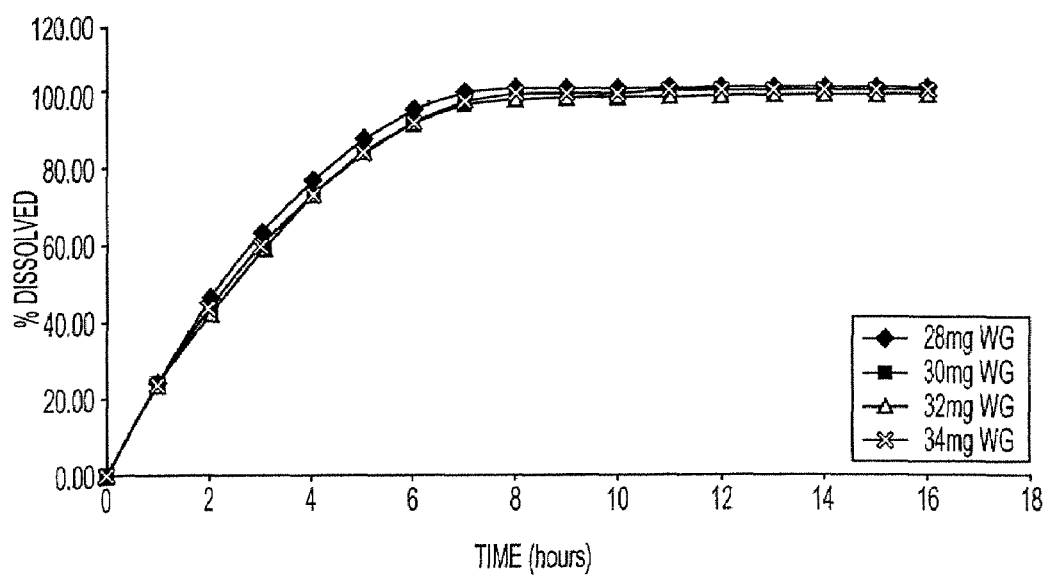
FIG. 20 is a dissolution profile of BUP-HBr-XL-348 mg-013-5 (28 mg, 30 mg, 32 mg and 34 mg weight gains).

The dissolution profile (FIG. 20) shows that the tablets with the 34 mg weight gain of ethylcellulose coating released Bupropion HBr the slowest when compared to the others and that the tablets with the 28 mg weight gain released Bupropion HBr the fastest when compared to the other weight gains.

The materials used in the final coating, their percent contribution to the total solution, the amounts of each in the batch, the amount of solid contribution in grams and the percentage of the solids in the solution were all listed in Table 24.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

After this trial run, Chroma-Tone was no longer used due to the formulation problems it caused. First, it limited the composition of the formulation due to its inflexibility, as SYLOID®, PEG and Triethyl Citrate ratios could not be varied. Second, the solution foamed and coagulated, which in turn caused the process for making the coating solution to be changed from the original so that it did not re-coagulate. Chroma-Tone can, however, still be considered an option for the formulation but different grades and mixtures would need to be used and made in order to accommodate the Bupropion HBr XL tablets.

It took 31 minutes to add a 7 mg weight gain of the final coating solution to the tablets. Tablet weights were taken and recorded in Table 25 at 4 mg, 5 mg, 6 mg and 7 mg weight gains.

Figure 21:
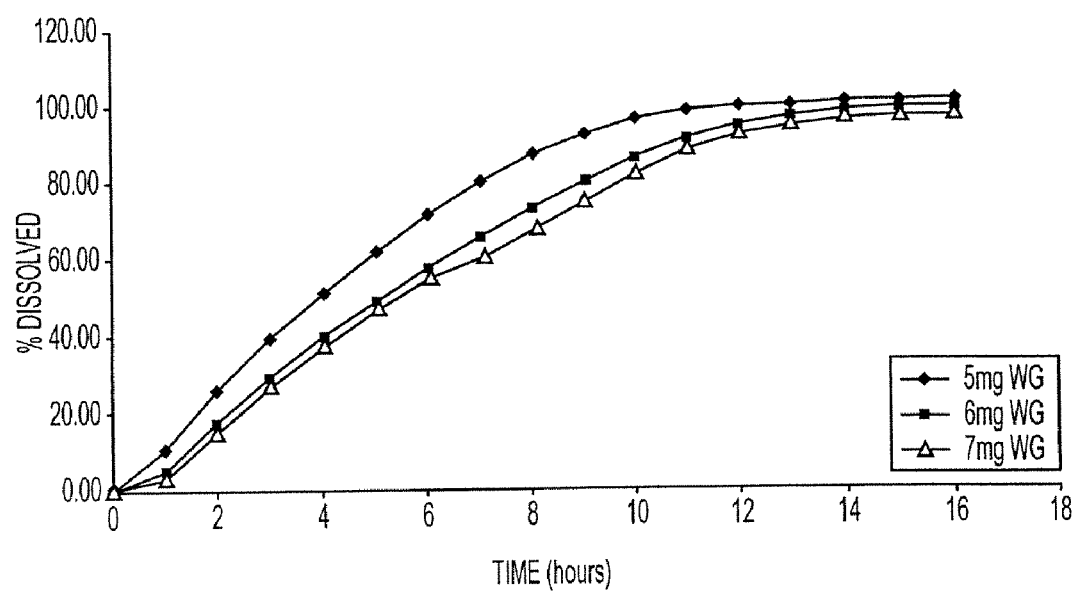
FIG. 21 is a dissolution profile of BUP-HBr-XL-348 mg-013-5 (5 mg, 6 mg, and 7 mg weight gains).

The dissolution profile (FIG. 21) shows that the tablets with the 7 mg weight gain of Final coating released the slowest when compared to the other two weight gains (5 mg and 6 mg weight gains).

Study on Batch BUP-HBr-XL-348 mg-018-5

Using 348 mg tablets, an ethylcellulose coating followed by a final coating, were sprayed onto the tablets using the O'Hara Labcoat II Coating Equipment.

The materials used in the ethylcellulose (e.g. ETHOCEL®) coating, their percent contribution to the total solution, the amounts of each in the batch and the percentage of the solids in the solution were all listed in Table 26.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

The coating process of this trial took 2 hours and 13 minutes to obtain a 32 mg weight gain. Tablet weights were taken and recorded in Table 27 at 26 mg, 28 mg, 30 mg, and 32 mg weight gains.

Figure 22:
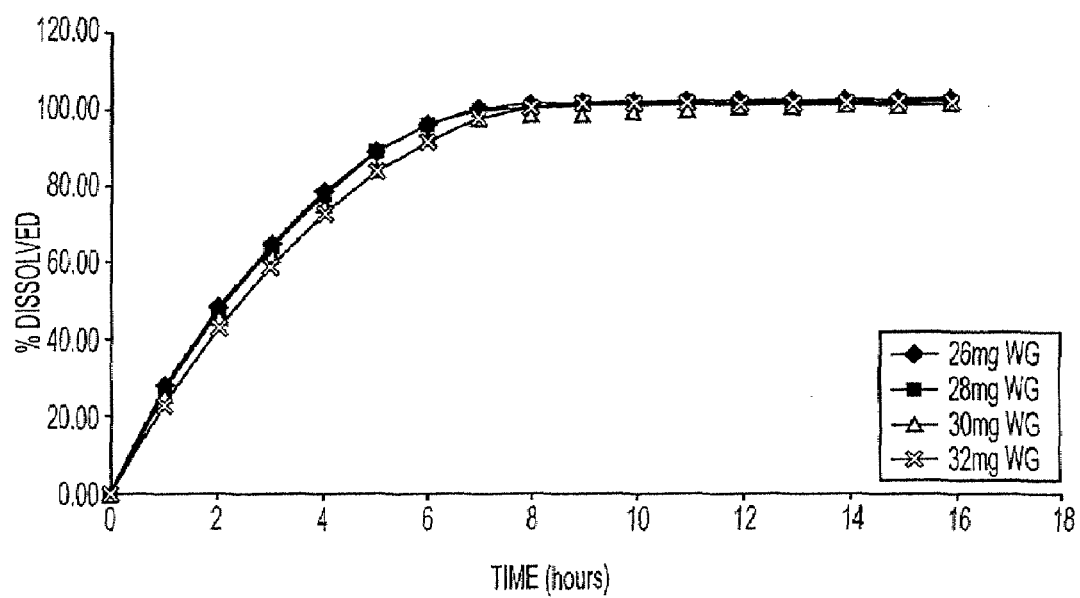
FIG. 22 is a dissolution profile of BUP-HBr-XL-348 mg-018-5 (26 mg, 28 mg, 30 mg and 32 mg weight gains).

FIG. 22 shows that the tablets with the 30 mg and 32 mg weight gain of ethylcellulose coating solution released at almost the same rate. The tablets with the 32 mg weight gain released slower than the tablets with the 30 mg weight gain in the first 5 hours of dissolution. After 6 hours, the tablets with the 32 mg weight gain released slightly faster than those with a 30 mg weight gain. The f2 similarity factor confirmed that the release rate of both weight gains was similar (91.32%).

The materials used in the final coating, their percent contribution to the total solution, the amounts of each in the batch, the amount of solid contribution in grams and the percentage of the solids in the solution were all listed in Table 28.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

It took 41 minutes to add a 7 mg weight gain of the final coating solution to the tablets. Tablet weights were taken and recorded in Table 29 at 4 mg, 5 mg, 6 mg, and 7 mg weight gains.

Figure 23:
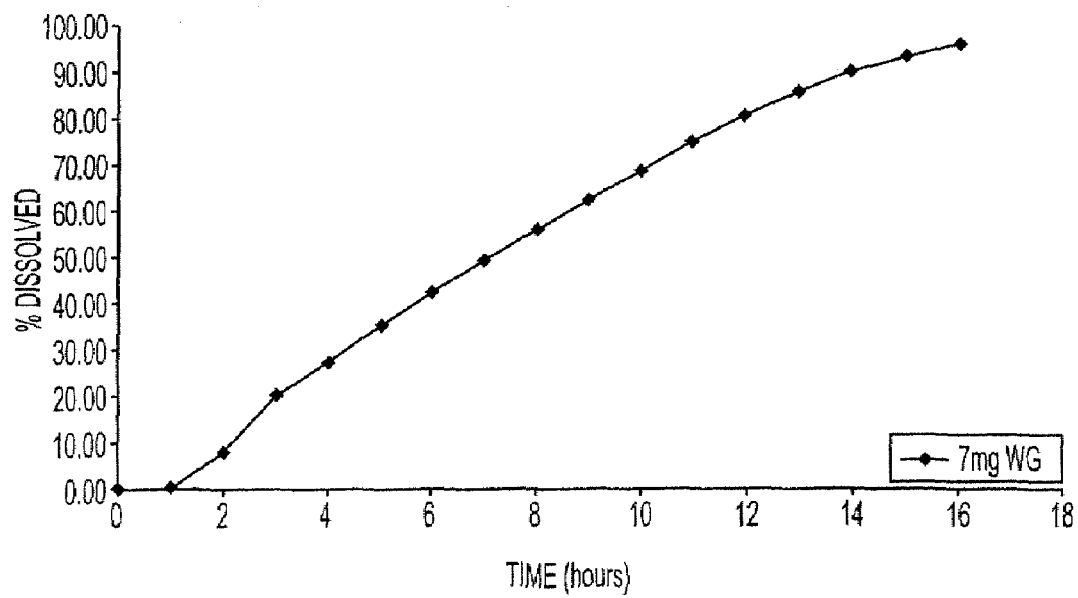
FIG. 23 is a dissolution profile of BUP-HBr-XL-348 mg-018-5 (7 mg weight gain).

FIG. 23 shows the release profile of the tablets with the 7 mg weight gain of Final coating.

Study on Batch BUP-HBr-XL-174 mg-022-5

Using 174 mg tablets, an ethylcellulose coating followed by a final coating, were sprayed onto the tablets using the O'Hara Labcoat II Coating Equipment.

The materials used in the ethylcellulose (e.g. ETHOCEL®) coating, their percent contribution to the total solution, the amounts of each in the batch and the percentage of the solids in the solution were all listed in Table 30.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 4 hours and 30 minutes to add a 30 mg weight gain of the ethylcellulose coating solution to the tablets. Tablet weights were taken at 20 mg, 22 mg, 24 mg, 26 mg, 28 mg, 29 mg, and 30 mg weight gains and were recorded in Table 31.

Figure 24:
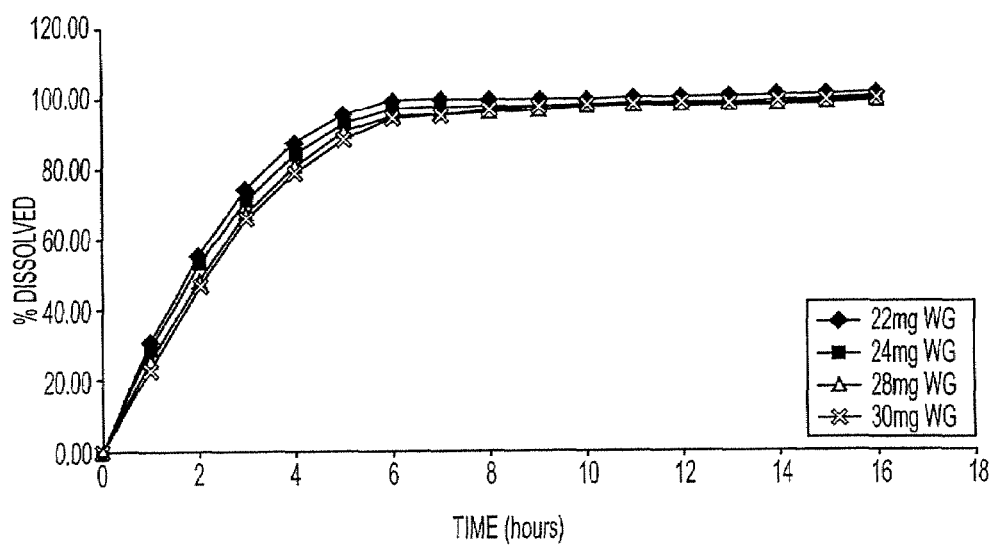
FIG. 24 is a dissolution profile of BUP-HBr-XL-174 mg-022-5 (22 mg, 24 mg, 28 mg and 30 mg weight gains).

FIG. 24 shows the % dissolved of each of the samples with different weight gains of ethylcellulose coating (22 mg, 24 mg, 28 mg and 30 mg weight gains). From the graph, it was evident that the tablets with the 30 mg weight gain of ethylcellulose coating released slower than the other weight gains. When the release rates of the tablets with the 30 mg and the 28 mg weight gains were compared, there was only a slight difference noticed in the release. The f2 similarity factor confirmed the similarity of the two releases (92.34%).

The materials used in the final coating, their percent contribution to the total solution, the amounts of each in the batch, the amount of solid contribution in grams and the percentage of the solids in the solution were all listed in Table 32.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

It took 1 hour and 26 minutes to add a 7 mg weight gain of the final coating solution to the tablets. Tablet weights were taken and recorded in Table 33 at 4 mg, 5 mg, 6 mg, and 7 mg weight gains.

Figure 25:
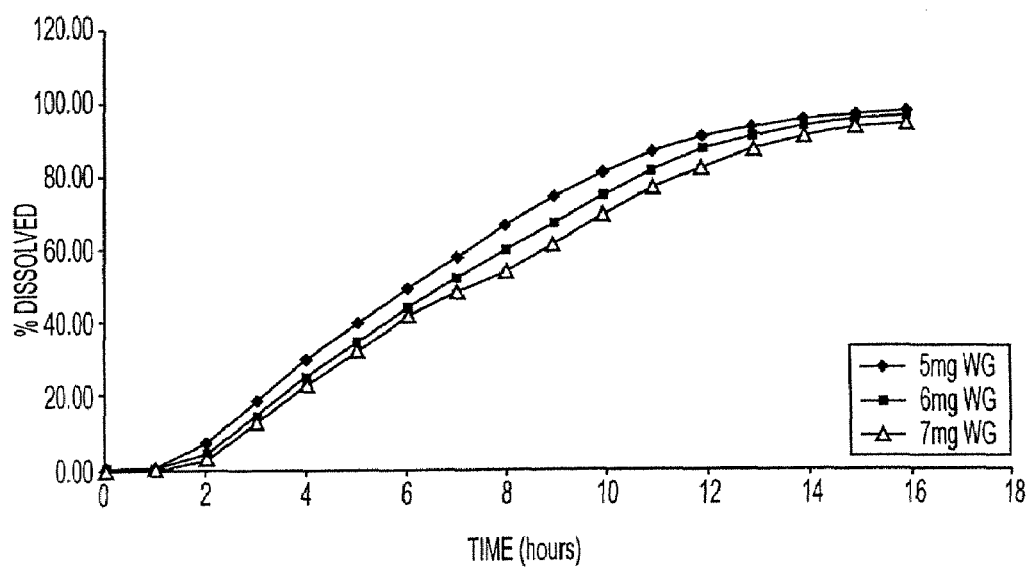
FIG. 25 is a dissolution profile of BUP-HBr-XL-174 mg-022-5 (5 mg, 6 mg, and 7 mg weight gains).

The dissolution profile (FIG. 25) shows that the tablets with the 7 mg weight gain of final coating released the slowest, in comparison to the 5 mg and the 6 mg weight gains.

Study on Batch BUP-HBr-XL-348 mg-023-5

Using 348 mg tablets, an ethylcellulose coating was sprayed onto the tablets using the O'Hara Labcoat II Coating Equipment.

The materials used in the ethylcellulose (e.g. ETHOCEL®) coating, their percent contribution to the total solution, the amounts of each in the batch and the percentage of the solids in the solution were all listed in Table 34.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 2 hours and 16 minutes to add a 32 mg weight gain of the ethylcellulose coating solution to the tablets. Tablet weights were taken at 26 mg, 28 mg, 30 mg, and 32 mg weight gains and were recorded in Table 35.

Figure 26:
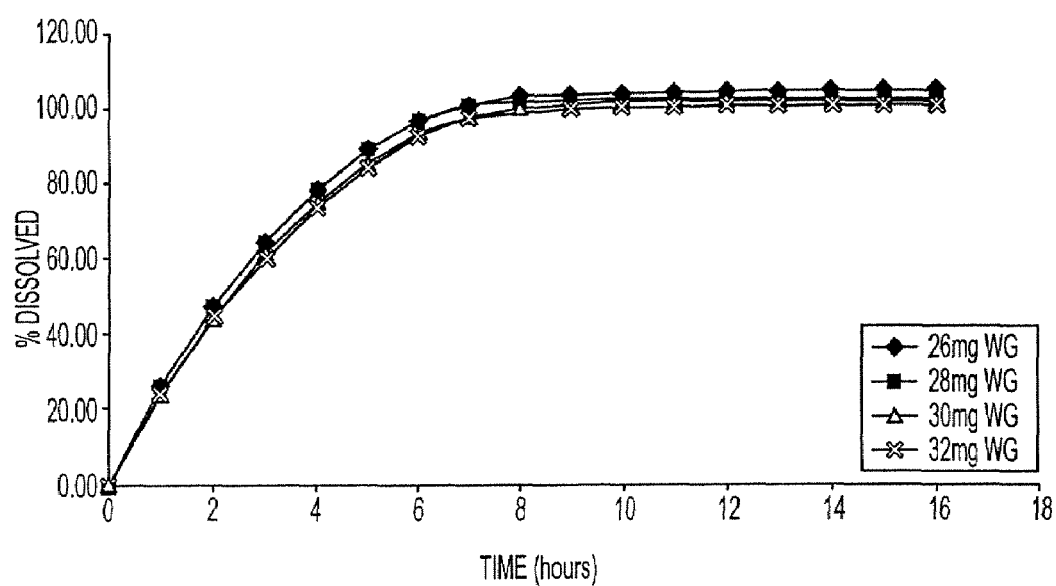
FIG. 26 is a dissolution profile of BUP-HBr-XL-348 mg-023-5 (26 mg, 28 mg, 30 mg and 32 mg weight gains).

The dissolution profile (FIG. 26) shows that the tablets with the 32 mg weight gain of ethylcellulose coating, when compared to the tablets with the 26 mg, 28 mg and the 30 mg weight gain of ethylcellulose coating, released at the slowest rate.

Study on Batch BUP-HBr-XL-348 mg-025-5

Using 348 mg tablets, an ethylcellulose coating followed by a final coating, were sprayed onto the tablets using the O'Hara Labcoat II Coating Equipment.

The materials used in the ethylcellulose (e.g. ETHOCEL® or EC) coating, their percent contribution to the total solution, the amounts of each in the batch and the percentage of the solids in the solution were all listed in Table 36.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 2 hours and 13 minutes to add a 32 mg weight gain of the ethylcellulose coating solution to the tablets. Tablet weights were taken at 26 mg, 28 mg, 30 mg, and 32 mg weight gains and were recorded in Table 37.

Figure 27:
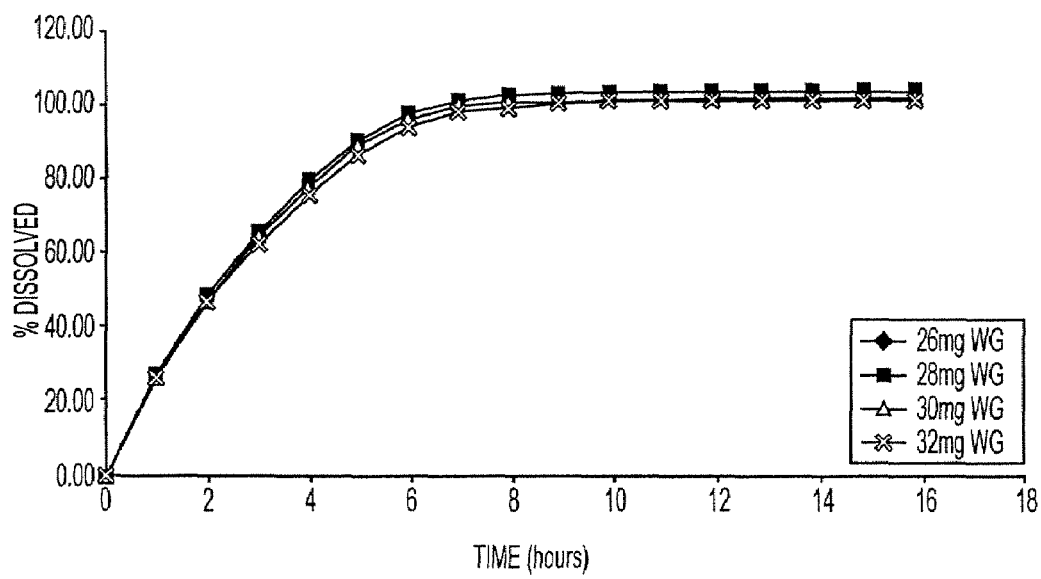
FIG. 27 is a dissolution profile of BUP-HBr-XL-348 mg-025-5 (26 mg, 28 mg, 30 mg, and 32 mg weight gains).

The dissolution profile (FIG. 27) shows that the tablets with the 32 mg weight gain of ethylcellulose coating when compared to those with 26 mg weight gain released slower in the beginning and then faster after 7 hours. When comparing the tablets with 32 mg weight gain of ethylcellulose coating to those with 30 mg weight gain of ethylcellulose coating, the tablets with the 32 mg weight gain released slower up until 10 hours. The f2 similarity factor showed that the release of the tablets with the 30 mg and 32 mg weight gains were in fact similar (93.72%).

The materials used in the final coating, their percent contribution to the total solution, the amounts of each in the batch, the amount of solid contribution in grams and the percentage of the solids in the solution were all listed in Table 38.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

The coating solution was altered for this batch by changing the percentage of solid from each of the solid components in the solution. The percentage of EUDRAGIT® solid contribution was decreased from 65% to 56.5%. The percentage of SYLOID®, CARBOWAX® and Triethyl Citrate were increased from 25%, 6.65% and 3.39% to 30%, 9% and 4.5%, respectively.

Figure 28:
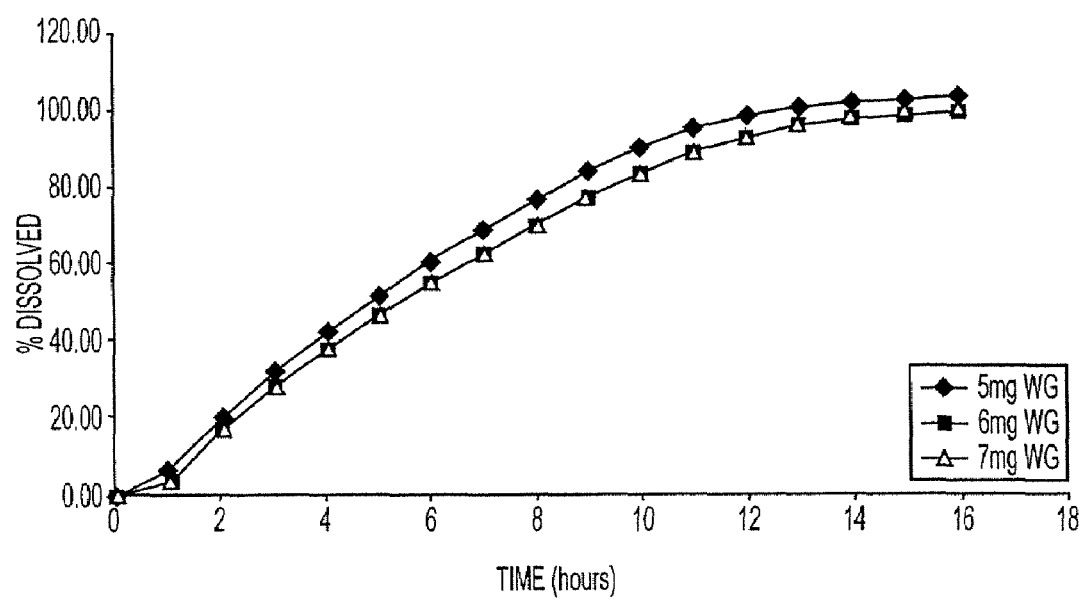
FIG. 28 is a dissolution profile of BUP-HBr-XL-348 mg-025-5 (5 mg, 6 mg, and 7 mg weight gains).

It took 40 minutes to add a 7 mg weight gain of the final coating solution to the tablets. Tablet weights were taken and recorded (Table 39) at 4 mg, 5 mg, 6 mg, and 7 mg weight gains. The dissolution profile (FIG. 28) shows that the tablets with the 7 mg weight gains released the slowest of the three samples tested. However, f2 calculation showed that the tablets with the 6 mg weight gain released similarly to those with the 7 mg weight gain of Final coating (93.33%).

Study on Batch BUP-HBr-XL-348 mg-026-5

Using 348 mg tablets, an ethylcellulose coating was sprayed onto the tablets using the O'Hara Labcoat II Coating Equipment.

The materials used in the ethylcellulose (e.g. ETHOCEL® or EC) coating, their percent contribution to the total solution, the amounts of each in the batch and the percentage of the solids in the solution were all listed in Table 40.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 2 hours and 11 minutes to add a 32 mg weight gain of the ethylcellulose coating solution to the tablets. Tablet weights were taken at 26 mg, 28 mg, 30 mg, and 32 mg weight gains and were recorded in Table 41.

Figure 29:
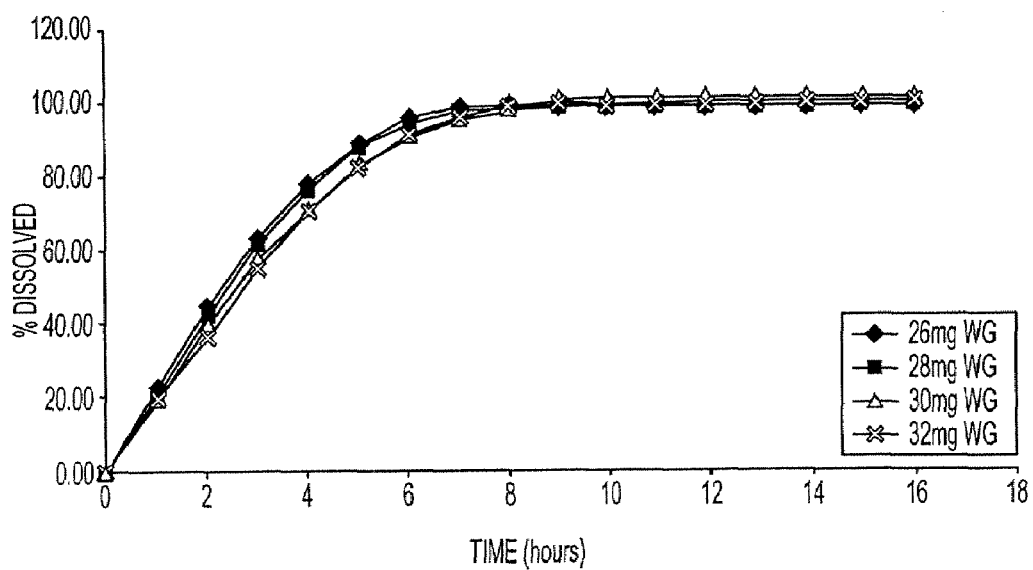
FIG. 29 is a dissolution profile of BUP-HBr-XL-348 mg-026-5 (26 mg, 28 mg, 30 mg, and 32 mg weight gains).

The dissolution profile (FIG. 29) shows that the tablets with the 32 mg weight gain of ethylcellulose coating released the slowest when compared to the other three samples with lower weight gains of ethylcellulose coating (26 mg, 28 mg and 30 mg).

Study on Batch BUP-HBr-XL-174 mg-027-5

Using 174 mg tablets, an ethylcellulose coating followed by a final coating, were sprayed onto the tablets using the O'Hara Labcoat II Coating Equipment.

The materials used in the ethylcellulose (e.g. ETHOCEL® or EC) coating, their percent contribution to the total solution, the amounts of each in the batch and the percentage of the solids in the solution were all listed in Table 42.

The parameters are as follows: Spray Rate: 13 g/min; Pan Speed: 12.0 rpm; Inlet Air: 50° C.; Product Temperature: 35° C.±5° C.; and Supply Air Flow: 200 CFW.

It took 3 hours and 29 minutes to add a 32 mg weight gain of the ethylcellulose coating solution to the tablets. Tablet weights were taken at 22 mg, 24 mg, and 26 mg weight gains and were recorded in Table 43.

Figure 30:
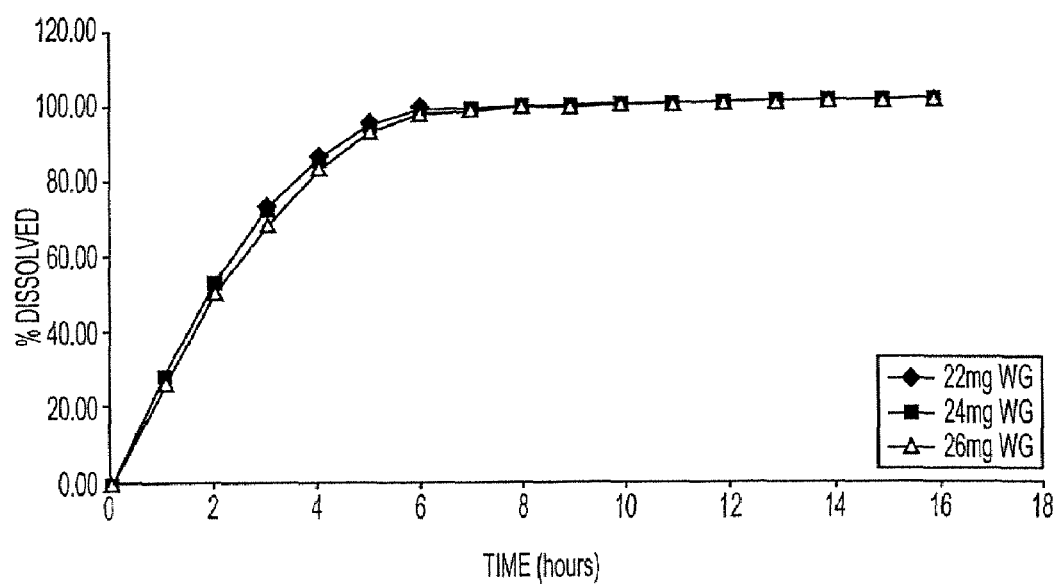
FIG. 30 is a dissolution profile of BUP-HBr-XL-174 mg-027-5 (22 mg, 24 mg, and 26 mg weight gains).

The dissolution profile (FIG. 30) shows that the tablets with the 26 mg weight gain of ethylcellulose coating released the slowest of the three samples tested.

The materials used in the final coating, their percent contribution to the total solution, the amounts in each in the batch, the amount of solid contribution in grams and the percentage of the solids in the solution were all listed in Table 44.

The parameters are as follows: Spray Rate: 6 g/min; Pan Speed: 12.0 rpm; Inlet Air: 40° C.; Product Temperature: 35° C.±5° C.; and Supply Air Flow: 200 CFW.

It took 1 hour and 17 minutes to add a 7 mg weight gain of the final coating solution to the tablets. Tablet weights were taken and recorded in Table 45 at 4 mg, 5 mg, 6 mg, and 7 mg weight gains.

Figure 31:
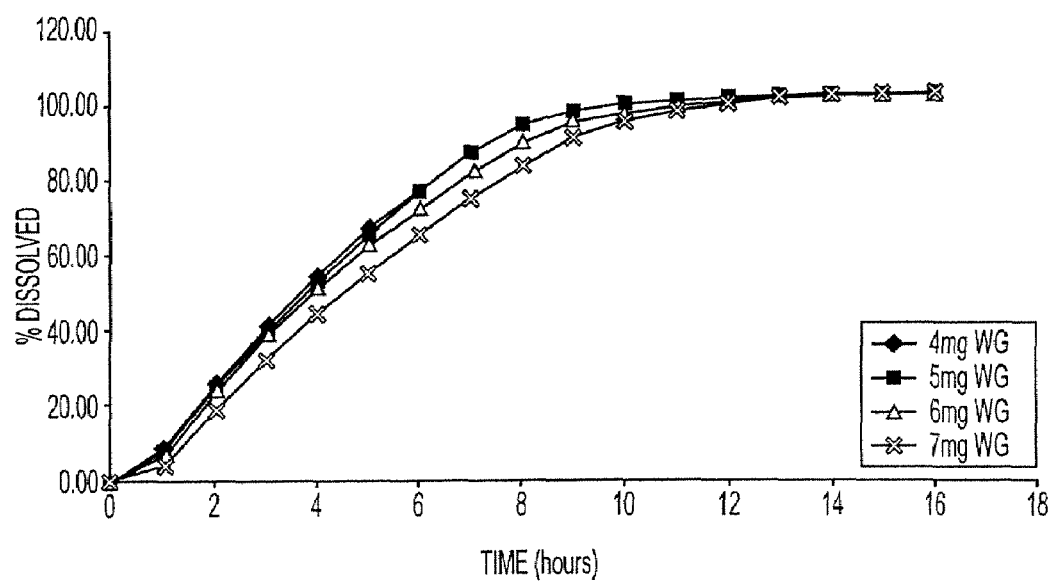
FIG. 31 is a dissolution profile of BUP-HBr-XL-174 mg-027-5 (4 mg, 5 mg, 6 mg, and 7 mg weight gains).

The dissolution profile (FIG. 31) shows that the tablets with the 7 mg weight gain of final coating initially released slower that the tablets with 4 mg, 5 mg and 6 mg weight gains. However, at approximately 12 hours, all 4 samples were releasing similarly.

Example 6

Buproprpion HBr Enhanced Absorption (EA) Tablets

This example describes the development of bupropion EA "Enhanced Absorption" tablets (150 mg and 300 mg). Granulation, tabletting and coating procedures are all described thoroughly in this example. In-vitro testing was conducted on the ethylcellulose coated cores in order to determine which formulation gave the desired results.

Bupropion HBr was used in this study and its only difference to Bupropion HCl is the salt. A major advantage of an enhanced absorption composition can be lessening the amount of drug in the composition, which in turn can lead to a reduction of side effects.

Figure 32:
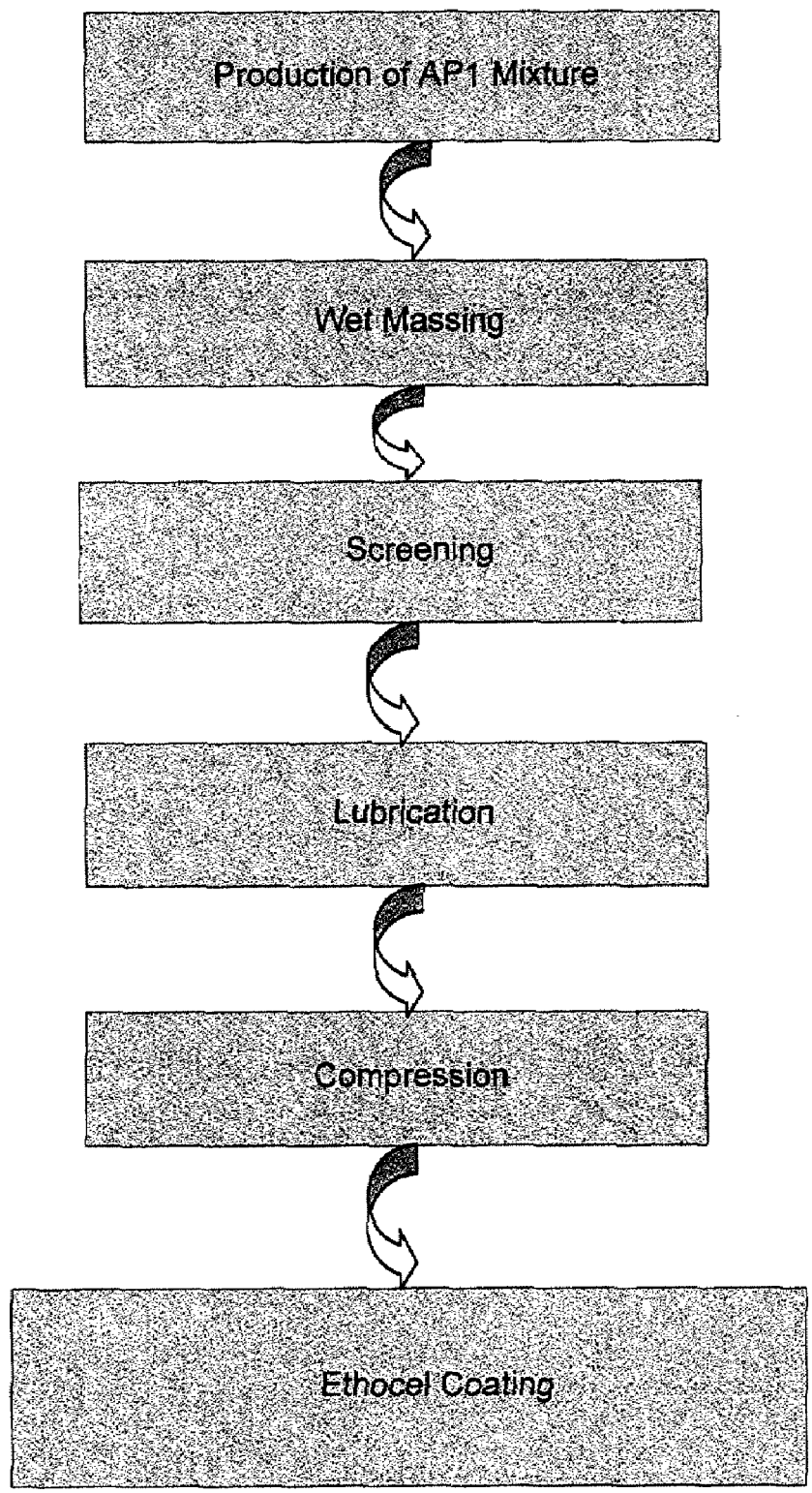
FIG. 32 is a flow chart showing the overall process for the development of bupropion HBr EA tablets.

The overall process for the development of bupropion HBr EA tablets is shown in FIG. 32.

Bupropion HBr EA—Granulation Process

Figure 33:
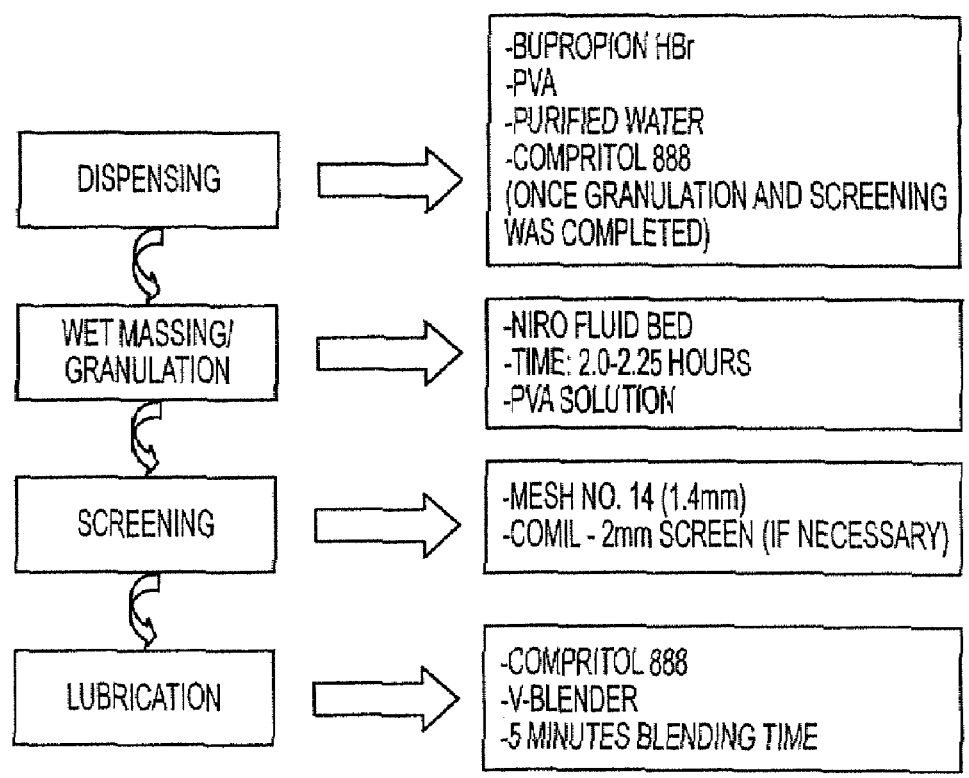
FIG. 33 is a flow chart demonstrating the granulation process of the bupropion HBr EA tablets.
Figure 34:
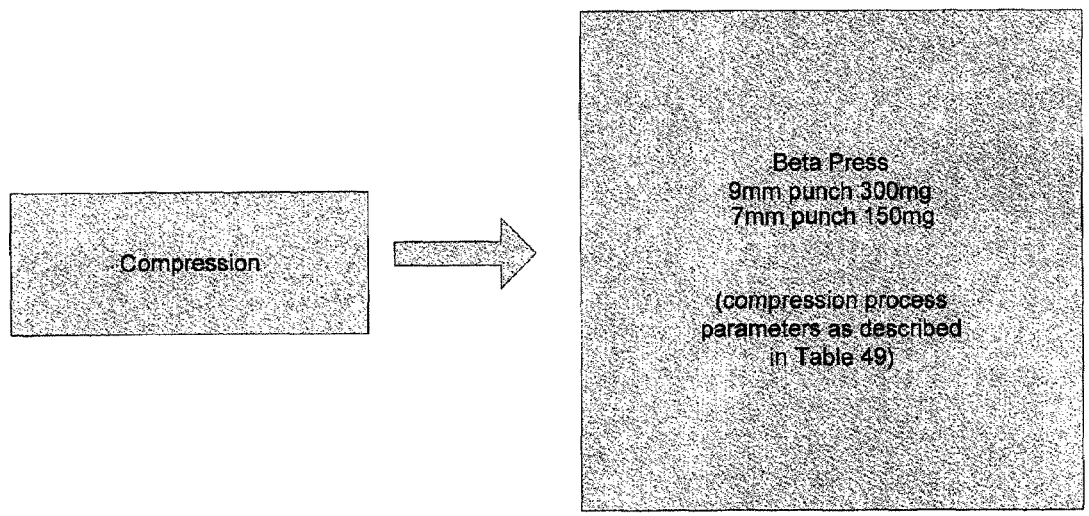
FIG. 34 is a flow chart showing the compression process of the 300 mg and 150 mg bupropion HBr EA Tablets.

A summary of the granulation process of the bupropion HBr EA tablets is shown in FIG. 33.

The following materials were used in the granulation of the immediate release core of the bupropion HBr EA tablets: bupropion HBr, polyvinyl alcohol and purified water. Once granulated, lubricant (COMPRITOL® 888) was added to complete the formulation. The granulation procedure for the bupropion HBr XL and Bupropion HBr EA can be, and preferably are, the same.

Each trial was divided into 5 parts. The percentage of API in each formulation was 93.75% and the percentage of PVA in each formulation was 3.125%. A summary of the breakdown of each trial per part was described in Table 46.

The Polyvinyl Alcohol was dissolved into the purified water using a magnetic stirrer and a clear colourless solution was made.

The NIRO Fluid Bed was used to granulate the Bupropion HBr Granules with the PVA solution in a process known as wet massing.

The Bupropion HBr was loaded into the fluid bed and granulation was initiated. The specifications that were used as guidelines were listed in Table 47.

Loss on Drying was determined after each granulation using the Moisture Analyzer. A 1 g sample was taken and loaded into the moisture analyzer. The sample ran for 5 minutes at a temperature of 105° C.

Upon completion of each batch part's granulation, the five parts were combined together. They were hand screened using Mesh No. 14 (1.4 mm) and any oversized granulation was passed through the Comil fitted with a 2 mm screen.

COMPRITOL® 888 was used as a lubricant in the formulation. The screened Bupropion HBr granules and the COMPRITOL® 888 were loaded into the V-blender and were blended for 5 minutes. The COMPRITOL® 888 made up 3.125% of the formulation. The final granule batch size was described in Table 48.

Bupropion HBr EA—Tabletting Process

The Beta Press was used to compress the Bupropion HBr tablets. Depending on the dose of the tablet, 150 mg or 300 mg, different tooling sets were used. The 7 mm punches were used to compress the 150 mg tablets and 9 mm punches were used to compress the 300 mg tablets. Tooling was polished prior to each run.

The tablet weights were determined as being 160.0 mg for the 150 mg dose tablets and 320.0 mg for the 300 mg dose tablets. These adjustments to tablet weight were made in order to compensate for the fact that bupropion HBr was being used in place of bupropion HCl. Prior investigations showed that bupropion HBr tablets with the above stated weights gave in-vitro results similar to those of the 150 mg and 300 mg bupropion HCl tablets. The individual tablet weights had a control limit of ±5%, and the average tablet weight had a control limit of ±3% (using ten tablets).

A hardness tester was used to determine the load required to diametrically break the tablets (crushing strength) into two equal halves. A predetermined range set the specifications for hardness, which was 6.0-12.0 SC for both the 174 mg and 348 mg tablets.

Friability was determined using tablets that equaled a weight of 6.5 g in a friability tester for 4 minutes at 25 rpm. Tablets were de-dusted before and after testing. A weight loss of less than 0.8% was used as the criteria in order to accept or reject a batch.

Table 49 summarizes the specifications of the tablet press set-up. All the specifications were kept within the range and at the setting that was assigned, throughout all of the batches. Table 50 summarizes the specifications that were kept constant throughout the compression of all the batches.

Bupropion HBr EA—Coating Process

Figure 35:
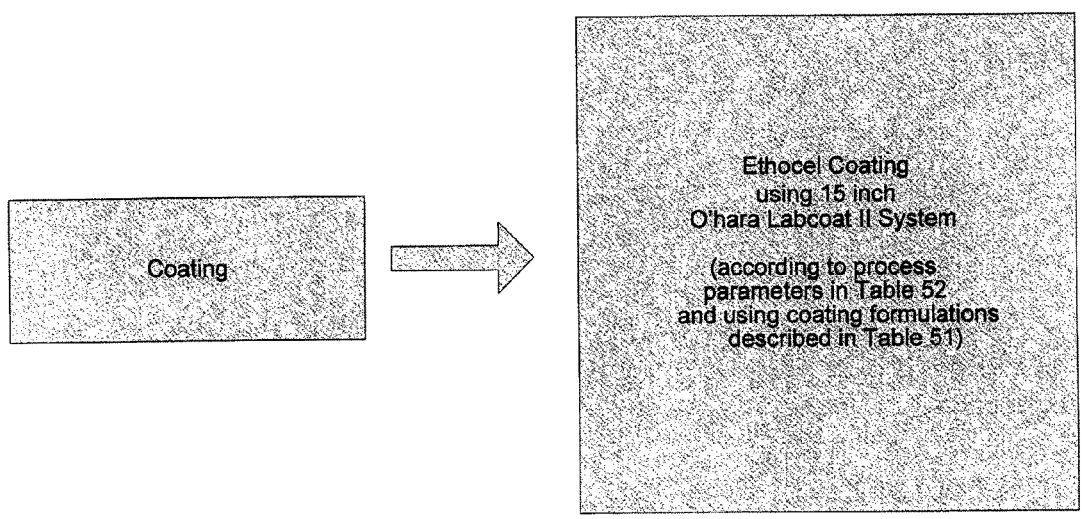
FIG. 35 is a flow chart showing the coating process of 150 mg and 300 mg bupropion HBr EA Tablets with an ETHOCEL™ Coating.

A summary of the coating process of the 150 mg and 300 mg bupropion HBr EA tablets with an ethylcellulose (e.g. ETHOCEL® or EC) Coating is shown in FIG. 35.

For the ethylcellulose coating of the Bupropion HBr EA tablets, the 15 inches O'Hara Labcoat II System was used. An attached spraying nozzle and a propeller mixer were also used.

Several ethylcellulose coating solutions were developed and used to coat the Bupropion HBr tablets. An ethylcellulose coating layer was placed on the tablets containing one of the formulations listed in Table 51.

In formulation 1, Ethyl Alcohol 200 proof was weighed out in a stainless steel container. While stirring, PEG 4000 was added and allowed to dissolve. Once dissolved, ethylcellulose was added and left to stir for 30 minutes. Then, Povidone was added to the solution and was mixed for an overnight period (15-20 hours).

In formulation 2, PEG4000 was placed into a beaker with the Dibutyl Sebacate and was stirred until it dissolved. This was added to the Ethyl Alcohol 200 proof that had already been weighed out in a stainless steel container. Following this, ethylcellulose was added and stirred for 30 minutes. Thereafter, Povidone was added and allowed to stir for an overnight period (15-20 hours).

In formulation 3, Ethyl Alcohol 200 proof was placed in a stainless steel container. While stirring, Dibutyl Sebacate was added and allowed to dissolve. Once dissolved, ethylcellulose was added and left to stir for 30 minutes. Then, Povidone was added to the solution and was mixed for an overnight period (15-20 hours).

In formulation 4, Ethyl Alcohol 95% USP was weighed out in a stainless steel container. While stirring, PEG 4000 was added and allowed to dissolve. Once dissolved, ethylcellulose was added and left to stir for 30 minutes. Then, Povidone was added to the solution and was mixed for an overnight period (15-20 hours).

Table 52 summarizes the specifications that were monitored in the coating process and their ranges.

In-Vitro Studies on the Bupropion HBr cores

Dissolution was performed on the Bupropion HBr cores and on the different weight gains of ethylcellulose coated cores. USP-1 method was used to conduct these studies. The dissolution test was performed using 900 mL of 0.1N HCl and at a speed of 75 rpm. Samples were taken at every hour for 16 hours. The dissolution profiles were obtained by plotting the cumulative percent of API dissolved against sampling time points. Sink conditions were maintained throughout all the experiments.

On several trials, USP-3 method was used to conduct the dissolution studies. These dissolution tests were performed for 16 hours total with the following breakdown: 2 hours using 900 mL of Simulated Gastric Fluid (SGF) at pH 1.2 with 0.5% of Sodium Lauryl Sulfate (SLS), followed by 2 hours in 900 mL of Acetate Buffer at a pH of 4.5, followed by 12 hours in 900 mL of Phosphate Buffer Simulated Intestinal Fluid (SIF) at a pH of 6.8. These results were plotted with the in-vitro data and the Bupropion HCl data in order for a comparison to be made.

Study on Batch BUP-HBr-XL-016-5

Figure 36:
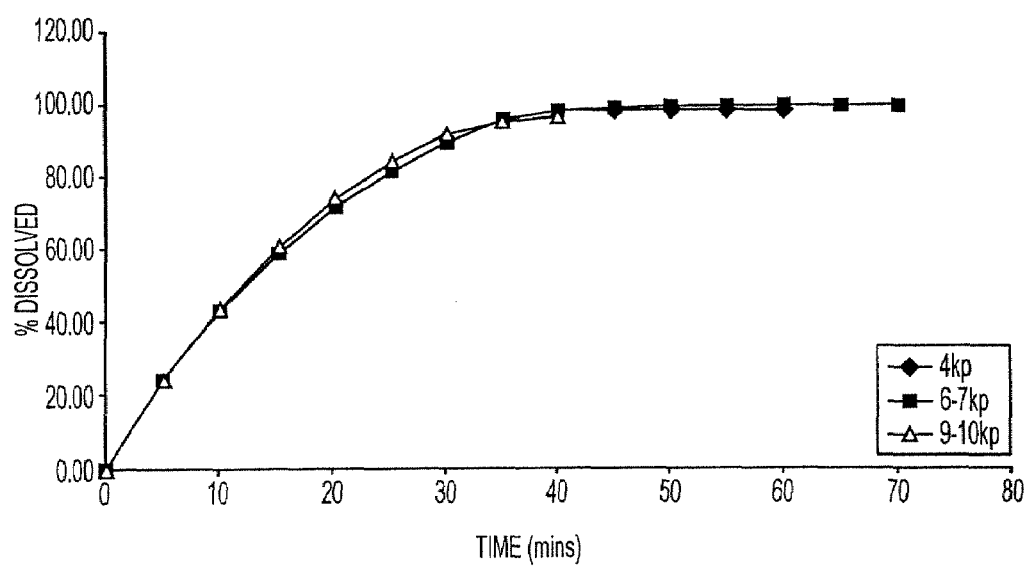
FIG. 36 is a dissolution profile of the of tablet cores at different hardness levels (4 kp, 6-7 kp and 9 kp) in the study on Batch BUP-HBr-XL-016-5.
Figure 37:
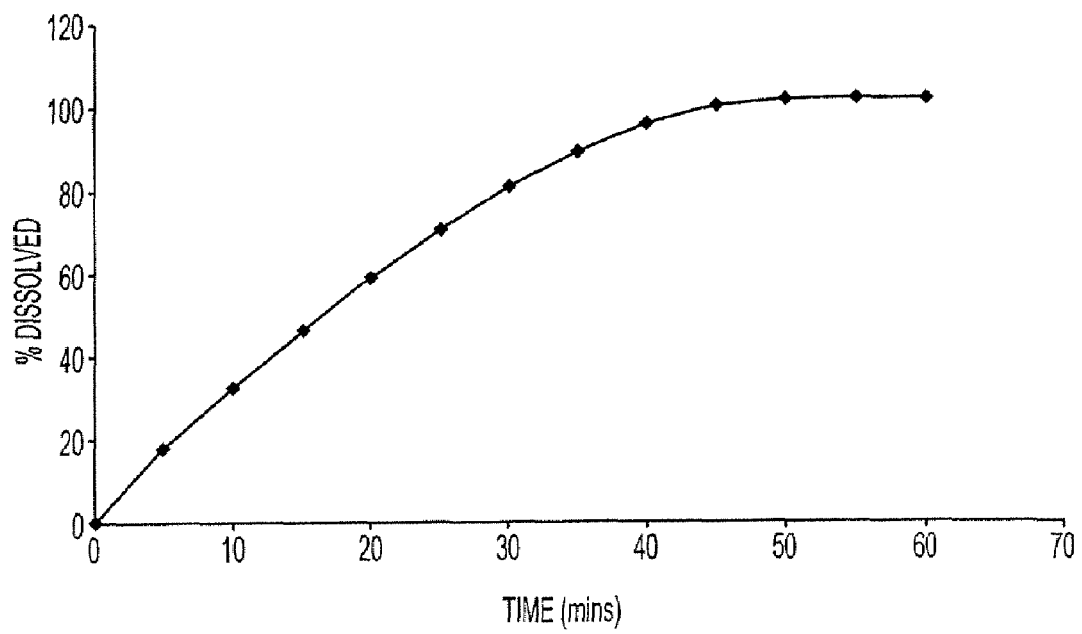
FIG. 37 is a dissolution profile of the 300 mg Bupropion HBr EACores in the study on Batch BUP-HBr-XL-016-5.
Figure 38:
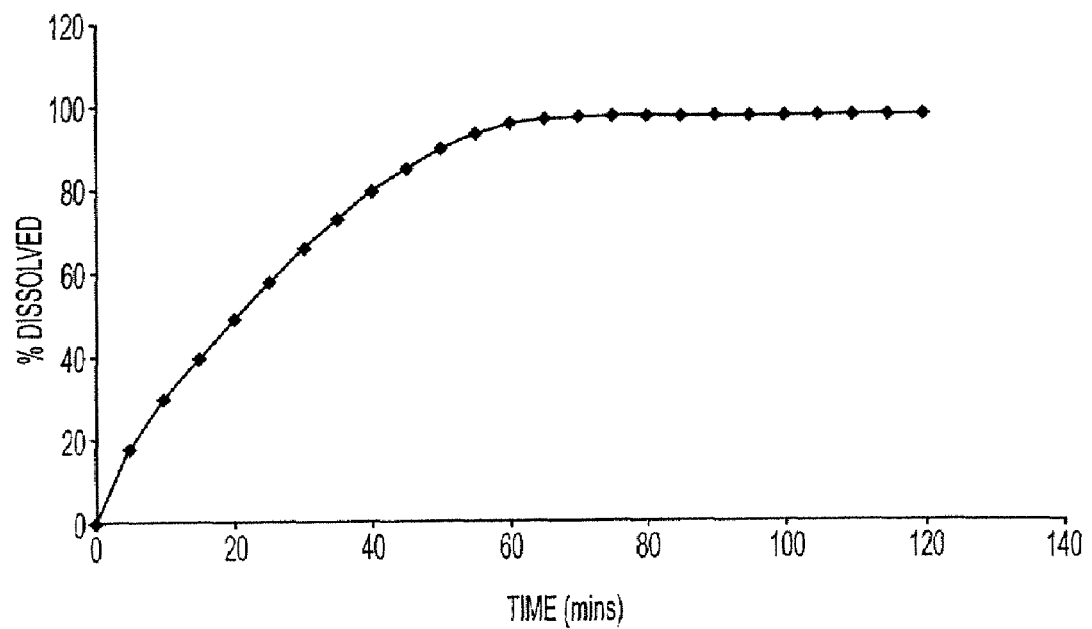
FIG. 38 is a dissolution profile of the 150 mg Bupropion HBr Cores in the study on Batch BUP-HBr-XL-016-5.

The formulation was granulated using NIRO Fluid Bed. The final blend was compressed into 300 mg tablets using the Beta press with 9 mm round, concave tooling and into 150 mg tablets with 7 mm round, concave tooling. Table 53 describes the amounts of each material in the granulation of the 300 mg tablets and Table 54 describes the amounts for the 150 mg tablets. It was noted that they were the same; the only variation was the tablet weight, which was adjusted at the compression stage. A first compression run was done to produce tablets with different hardness values so as to determine the effects of hardness, if any, on the dissolution (FIG. 36). Dissolution was conducted on the 300 mg and 150 mg cores in order to determine their release (FIGS. 37 and 38, respectively). After granulation was completed, the batch was screened and then prior to compression, the lubricant (COMPRITOL® 888) was added. The granulation results show that the average granulation time is 2.0 hours and the average LOD % is 0.342%. Table 55 and Table 56 summarize the theoretical and actual values of the parameters that were monitored in the compression process using the 9 mm and 7 mm tooling respectively.

FIG. 36 shows that the different hardness ranges did not drastically affect the dissolution profiles. The dissolution profiles of the 300 mg (FIG. 37) and 150 mg cores (FIG. 38) show that the cores were releasing approximately 100 percent of API in an hour.

Study on Batch BUP-HBr-EA-300 mg-001-5

Using 300 mg Bupropion HBr core tablets, an ethylcellulose coating was sprayed onto the tablets using the O'Hara Labcoat II Coating Equipment.

The materials used in the ethylcellulose (e.g. ETHOCEL® or EC) coating, their percent contribution to the total solution, the amounts of each in the batch and the percentage of the solids in the solution were all listed in Table 57.

The parameters are as follows: Spray Rate: 14 g/min; Pan Speed: 12.0 rpm; Inlet Air: 50° C.; Product Temperature: 35° C.±2° C.; and Supply Air Flow: 200 CFW.

It took 4 hours and 4 minutes to coat the tablets with a weight gain of 54 mg. Tablet weights were taken and recorded in Table 58 at 44 mg, 46 mg, 48 mg, 50 mg 52 mg, and 54 mg weight gains.

Figure 39:
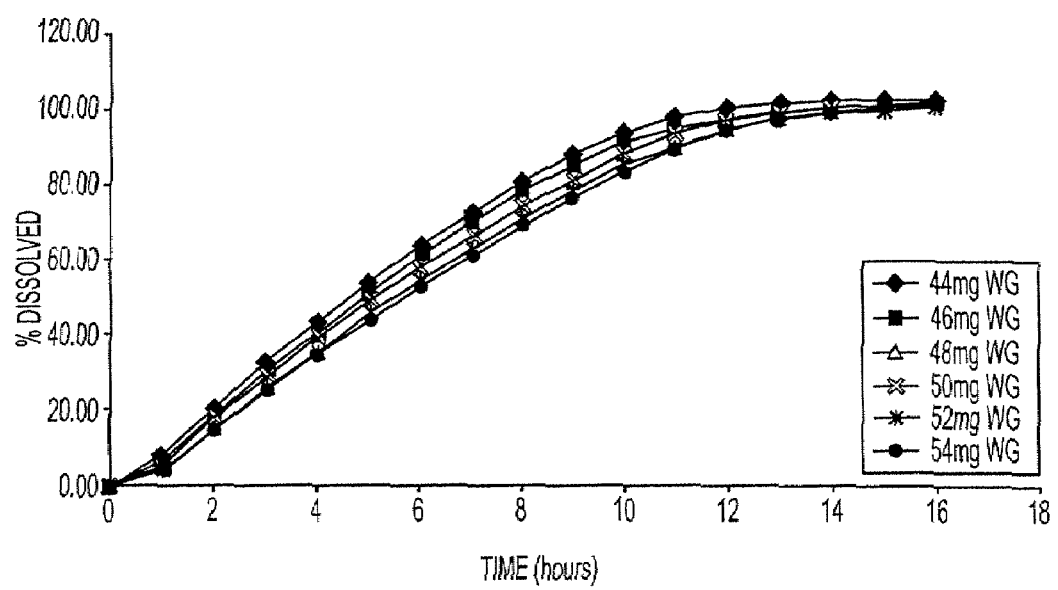
FIG. 39 is a dissolution profile of BUP-HBr-EA-300 mg-001-5 (44 mg, 46 mg, 48 mg, 50 mg 52 mg, and 54 mg weight gains).

The dissolution profile (FIG. 39) shows that the tablets with the 44 mg weight gain released the fastest and the tablets with the 54 mg weight gain released the slowest from the 6 different weight gains that were tested.

Figure 40:
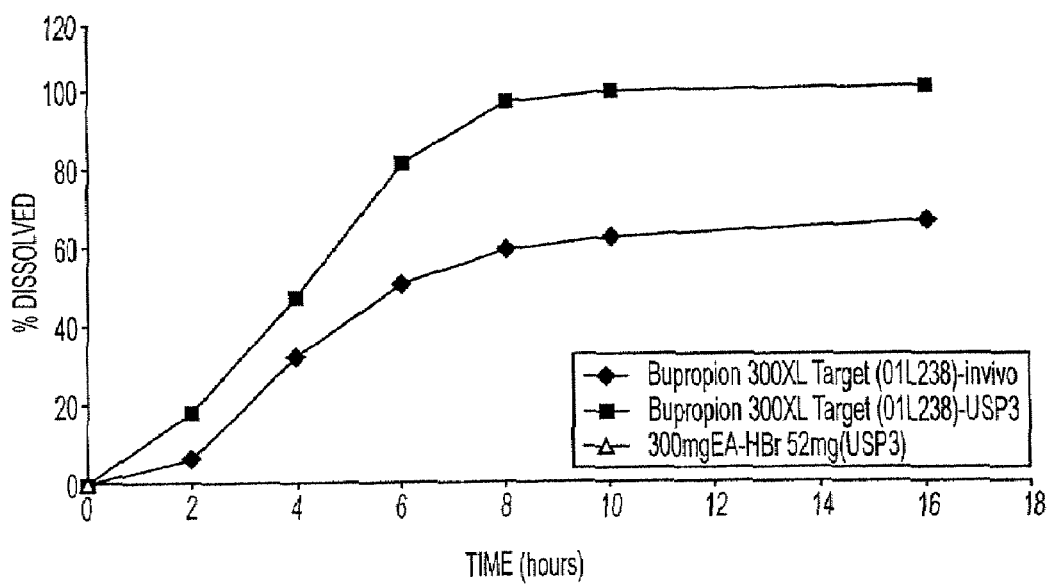
FIG. 40 is a comparative USP3 dissolution profile of Bupropion HBr 300 mg EA Tablets with 52 mg weight gain to the in-vivo and the in-vitro profiles of the target (Bupropion HCl 300 mg).

Dissolution using USP3 was also conducted on this trial, using the tablet with the 52 mg weight gain. The dissolution profile was plotted as time in hours versus % Dissolved, and was plotted alongside the in-vivo data and the Bupropion HCl data in order for a comparison to be made. The results (FIG. 40) showed that the trial did not match the in-vivo data, nor did it match the Bupropion HCl data.

Study on Batch BUP-HBr-EA-150 mg-002-5

Using 150 mg tablets, an ethylcellulose coating was sprayed onto the tablets using the O'Hara Labcoat II Coating Equipment.

The materials used in the ethylcellulose coating, their percent contribution to the total solution, the amounts of each in the batch and the percentage of the solids in the solution were all listed in Table 59.

The parameters are as follows: Spray Rate: 14 g/min; Pan Speed: 12.0 rpm; Inlet Air: 50° C.; Product Temperature: 35° C.±2° C.; and Supply Air Flow: 200 CFW.

The coating process of this trial took 4 hours and 38 minutes to obtain a 36 mg weight gain. Tablet weights were taken and recorded in Table 60 at 18 mg, 20 mg, 22 mg, 24 mg, 26 mg, 28 mg, 30 mg, 32 mg, 34 mg and 36 mg weight gains.

Figure 41:
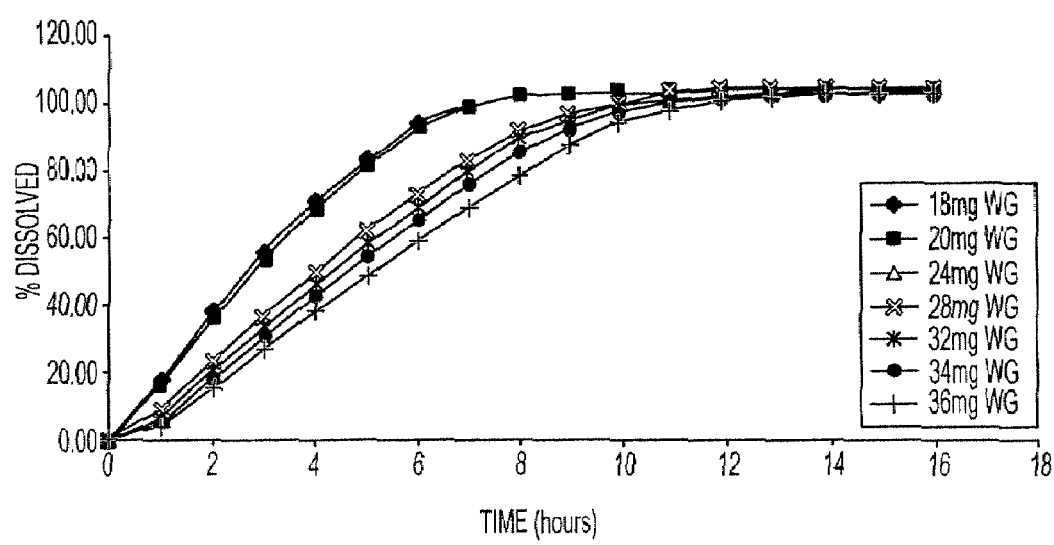
FIG. 41 is a dissolution profile of BUP-HBr-EA-150 mg-002-5 (18 mg, 20 mg, 22 mg, 24 mg, 26 mg, 28 mg, 30 mg, 32 mg, 34 mg and 36 mg weight gains).

The dissolution profile (FIG. 41) shows that the tablets with the 18 mg and 20 mg weight gains of ethylcellulose coating released the fastest of all the weight gains tested. It was the tablets with the 36 mg weight gain that released the slowest when compared to all the other weight gains.

Study on Batch BUP-HBr-EA-300 mg-003-5

Using 300 mg tablets, an ethylcellulose coating was sprayed onto the tablets using the O'Hara Labcoat II Coating Equipment.

The materials used in the ethylcellulose (e.g. ETHOCEL® or EC) coating, their percent contribution to the total solution, the amounts of each in the batch and the percentage of the solids in the solution were all listed in Table 61.

The parameters are as follows: Spray Rate: 14 g/min; Pan Speed: 12.0 rpm; Inlet Air: 50° C.; Product Temperature: 35° C.±2° C.; and Supply Air Flow: 200 CFW.

It took 4 hours and 13 minutes to add a 54 mg weight gain of the ethylcellulose coating solution to the tablets. Tablet weights were taken at 44 mg, 46 mg, 48 mg, 50 mg, 52 mg, and 54 mg weight gains and were recorded in Table 62.

Figure 42:
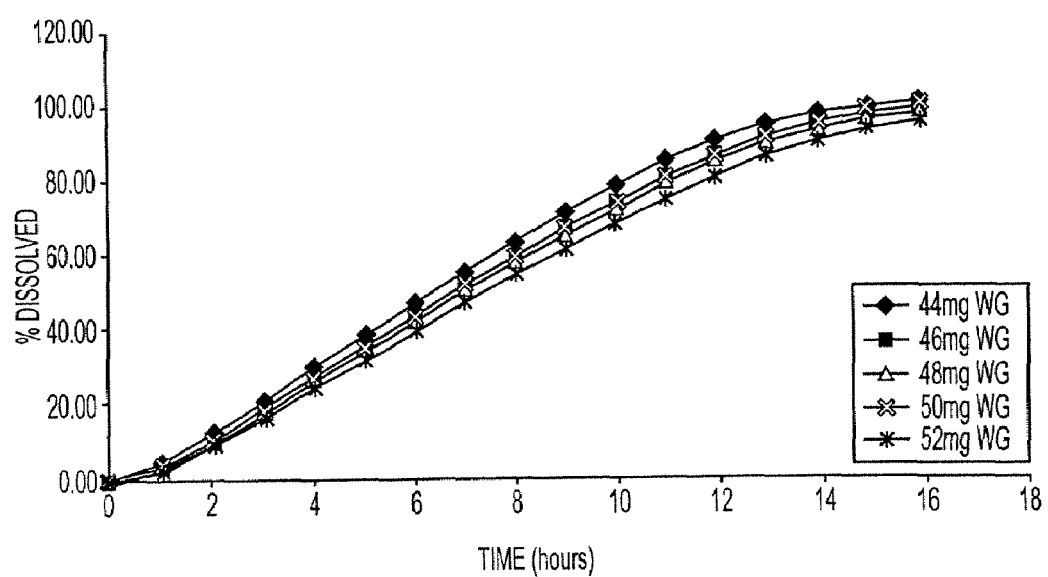
FIG. 42 is a dissolution profile of BUP-HBr-EA-300 mg-003-5 (44 mg, 46 mg, 48 mg, 50 mg, 52 mg, and 54 mg weight gains).

The dissolution profile (FIG. 42) shows that the tablets with the 52 mg weight gain of ethylcellulose coating released the slowest when compared to the other profiles with different weight gains.

Study on Batch BUP-HBr-EA-300 mg-004-5

Using 300 mg tablets, an ethylcellulose coating was sprayed onto the tablets using the O'Hara Labcoat II Coating Equipment.

The materials used in the ethylcellulose (e.g. ETHOCEL® or EC) coating, their percent contribution to the total solution, the amounts of each in the batch and the percentage of the solids in the solution were all listed in Table 63.

The parameters are as follows: Spray Rate: 14 g/min; Pan Speed: 12.0 rpm; Inlet Air: 50° C.; Product Temperature: 35° C.±2° C.; and Supply Air Flow: 200 CFW.

It took 4 hours and 13 minutes to add a 54 mg weight gain of the ethylcellulose coating solution to the tablets. Tablet weights were taken at 44 mg, 46 mg, 48 mg, 50 mg, 52 mg, and 54 mg weight gains and were recorded in Table 64.

Figure 43:
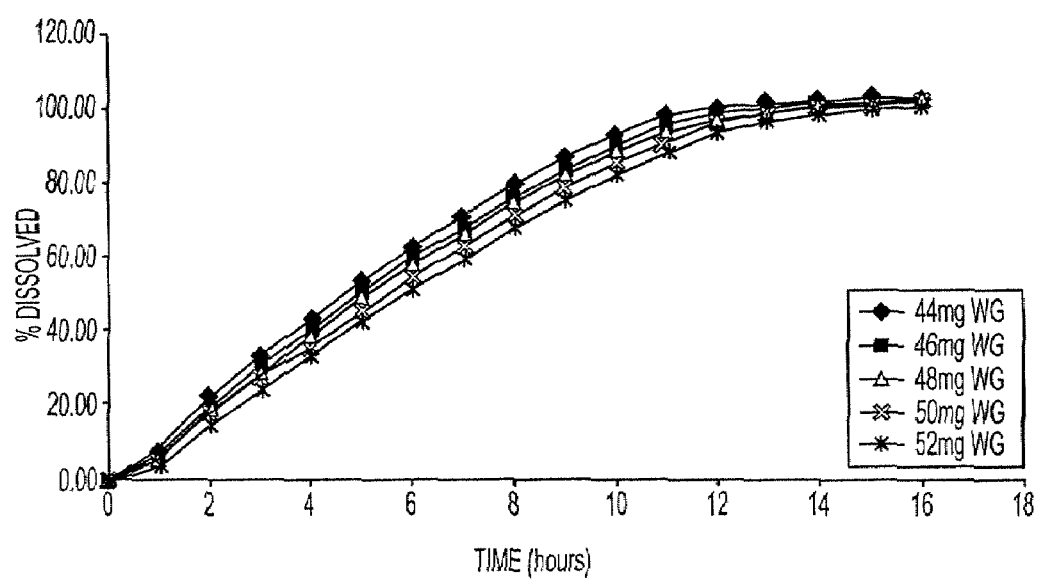
FIG. 43 is a dissolution profile of BUP-HBr-EA-300 mg-004-5 (44 mg, 46 mg, 48 mg, 50 mg, 52 mg, and 54 mg weight gains).

The dissolution profile (FIG. 43) shows that the tablets with the 52 mg weight gain released the slowest when compared to the other profile and the tablets with the 44 mg weight gain of ethylcellulose coating released the fastest.

Study on Batch BUP-HBr-EA-300 mg-005-5

Using 300 mg tablets, an ethylcellulose coating was sprayed onto the tablets using the O'Hara Labcoat II Coating Equipment.

The materials used in the ethylcellulose (e.g. ETHOCEL® or EC) coating, their percent contribution to the total solution, the amounts of each in the batch and the percentage of the solids in the solution were all listed in Table 65.

The parameters are as follows: Spray Rate: 14 g/min; Pan Speed: 12.0 rpm; Inlet Air: 50° C.; Product Temperature: 35° C.±2° C.; and Supply Air Flow: 200 CFW.

It took 4 hours and 14 minutes to add a 54 mg weight gain of the ethylcellulose coating solution to the tablets. Tablet weights were taken at 44 mg, 46 mg, 48 mg, 50 mg, 52 mg, and 54 mg weight gains and were recorded in Table 66.

Figure 44:
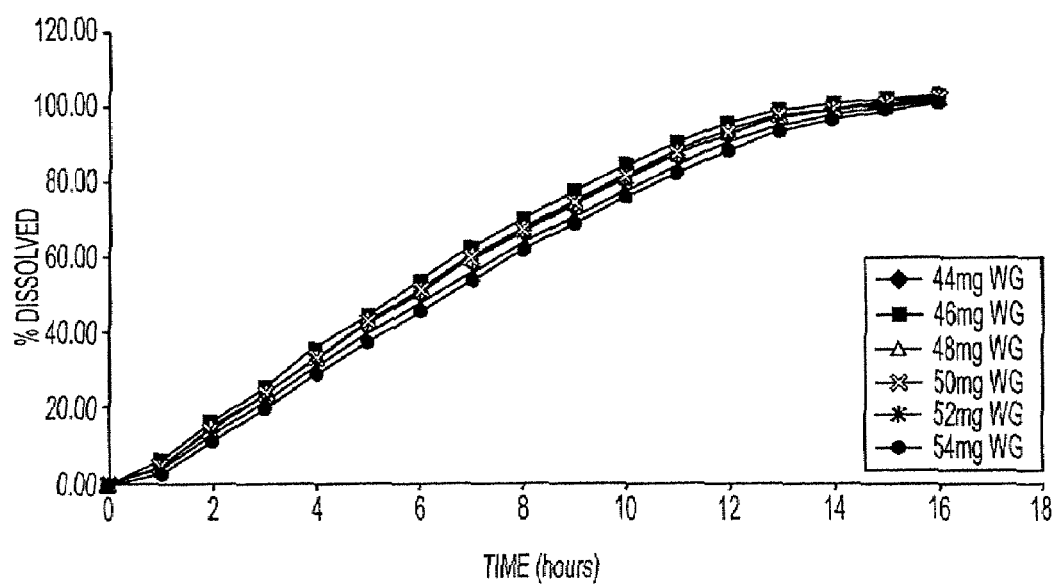
FIG. 44 is a dissolution profile of BUP-HBr-EA-300 mg-005-5 (44 mg, 46 mg, 48 mg, 50 mg, 52 mg, and 54 mg weight gains).

FIG. 44 shows that the tablets with the 54 mg weight gain released the slowest when compared to the other profiles and that the tablets with the 44 mg weight gain of ethylcellulose coating released the fastest of the six profiles.

Study on Batch BUP-HBr-EA-150 mg-006-5

Using 150 mg tablets, an ethylcellulose coating was sprayed onto the tablets using the O'Hara Labcoat II Coating Equipment.

The materials used in the ethylcellulose (e.g. ETHOCEL® or EC) coating, their percent contribution to the total solution, the amounts of each in the batch and the percentage of the solids in the solution were all listed in Table 67.

The parameters are as follows: Spray Rate: 14 g/min; Pan Speed: 12.0 rpm; Inlet Air: 50° C.; Product Temperature: 35° C.±2° C.; and Supply Air Flow: 200 CFW.

The coating process of this trial took 4 hours and 36 minutes to obtain a 36 mg weight gain. Tablet weights were taken and recorded in Table 68 at 18 mg, 20 mg, 22 mg, 24 mg, 26 mg, 28 mg, 30 mg, 32 mg, 34 mg and 36 mg weight gains.

Figure 45:
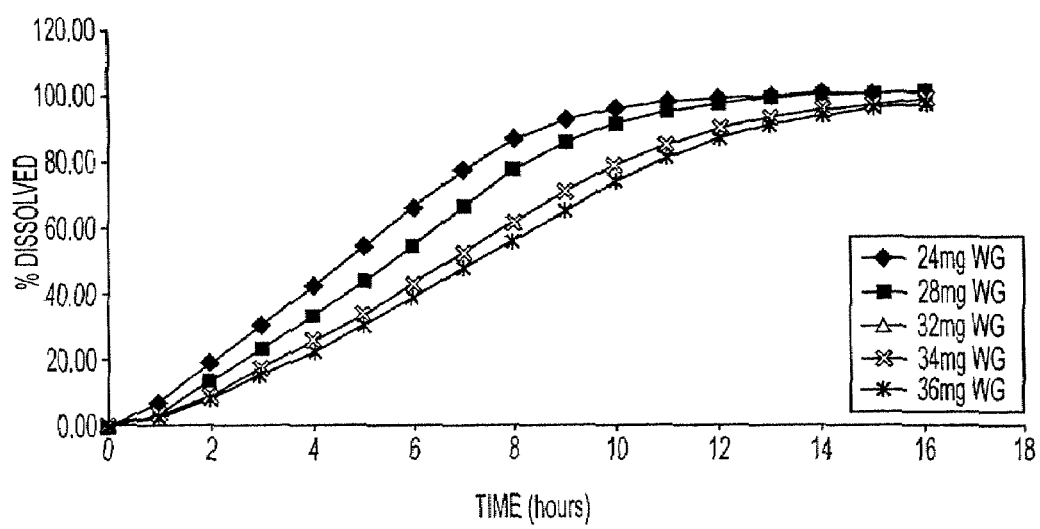
FIG. 45 is a dissolution profile of BUP-HBr-EA-150 mg-006-5 (24 mg, 28 mg, 32 mg, 34 mg and 36 mg weight gains).

The dissolution profile (FIG. 45) shows that the tablets with the 36 mg weight gain of ethylcellulose coating released the slowest when compared to the other four profiles (24 mg, 28 mg, 32 mg and 34 mg weight gains).

Figure 46:
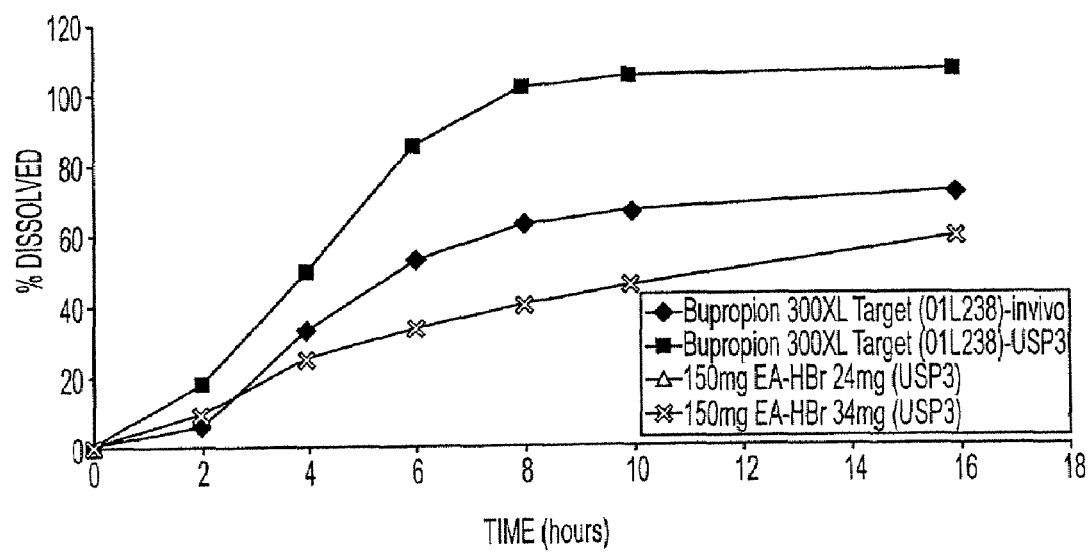
FIG. 46 is a comparative USP3 dissolution profile of bupropion HBr 150 mg EA Tablets with 24 and 34 mg weight gains to the in-vivo and the in-vitro profiles of the target (bupropion HCl 300 mg).

Dissolution using USP3 was also conducted with this trial, in order to see if the results were close to the in-vivo data and the in-vitro data of the Bupropion HCl 300 mg target. The dissolution profile (FIG. 46) shows that the 150 mg Bupropion HBr EA tablets with 24 mg weight gain was close to the in-vivo profile.

Study on Batch BUP-HBr-EA-150 mg-007-5

Using 150 mg tablets, an ethylcellulose coating was sprayed onto the tablets using the O'Hara Labcoat II Coating Equipment.

The materials used in the ethylcellulose (e.g. ETHOCEL® or EC) coating, their percent contribution to the total solution, the amounts of each in the batch and the percentage of the solids in the solution were all listed in Table 69.

Example 7

Comparative Forced Degradation Studies on Bupropion HCl and Bupropion HBr Drug Products The Bupropion HCl and HBr tablets (ethylcellulose coated tablet, and the ethylcellulose coated and moisture barrier coated tablet) were placed individually on an open dish, and exposed to the accelerated conditions of 40° C./75% RH in the stability chamber. After 13 and 20 days, the samples were assayed and impurity analysis was performed as per the method HPLC P05.901.10.

Figure 47:
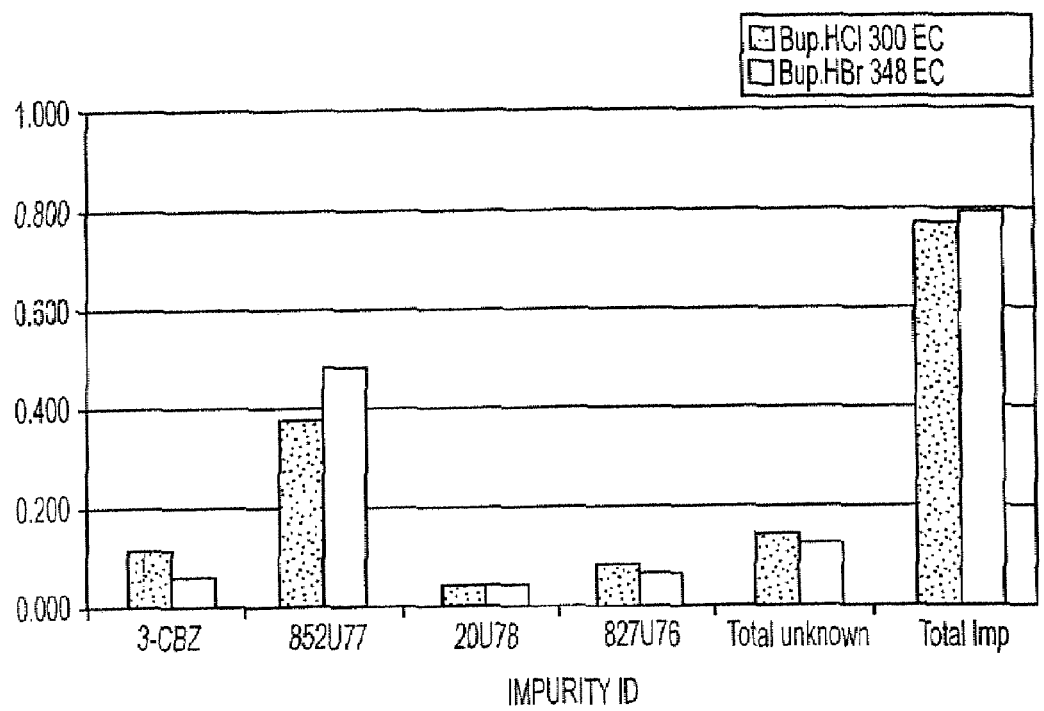
FIG. 47 is a bar graph showing the % impurities for the bupropion HCl XL 300 mg and bupropion HBr 348 mg EC coated tablets at 40 degrees C. and 75% relative humidity.
Figure 48:
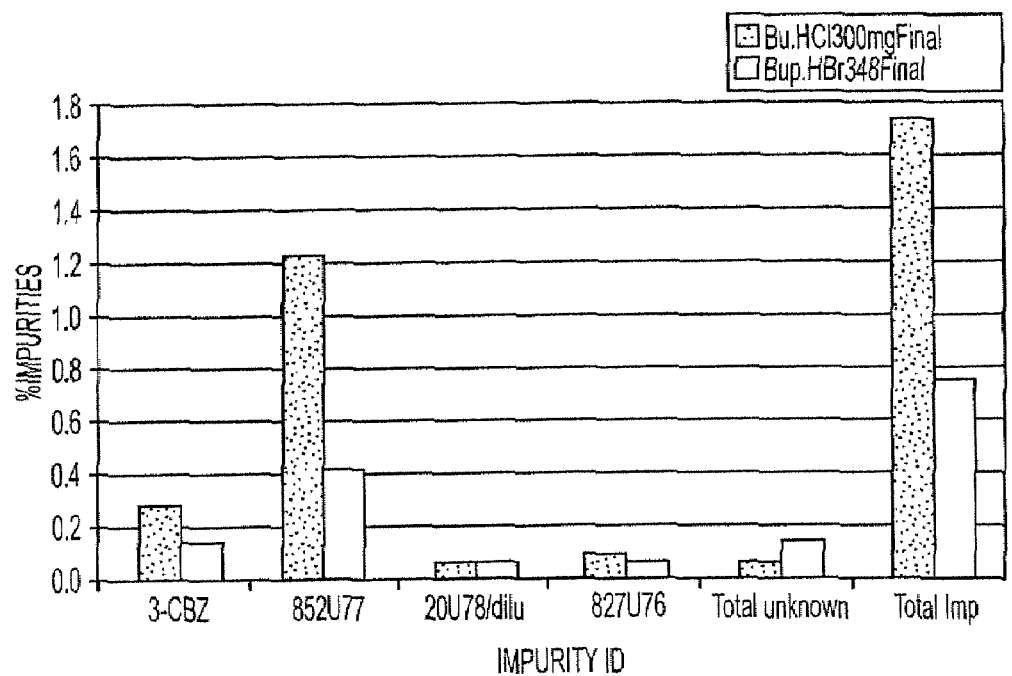
FIG. 48 is a bar graph showing the % impurities for the bupropion HCl 300 mg (Wellbutrin XL) and bupropion HBr 348 mg XL final tablets at 40 degrees C. and 75% relative humidity.

Table 70 and FIG. 47 show the 13 and 20 days results of the forced degradation study on both Bupropion HCl and HBr ethylcellulose coated tablets. For the Bupropion HCl product, the main bupropion degradation impurities 3-CBZ and 852U77 were 0.12% and 0.38% respectively, whereas, for the Bupropion HBr, these values were 0.07% and 0.49% respectively. The other degradation impurities and the total unknowns were very similar for both products; however, the assay value for the HBr product was higher than the HCl. The difference in the assay and the impurity levels were more significant in the final drug products. As shown in the Table 71 and FIG. 48, for the same period of the study the assay of the Bupropion HCl was lower (95.5%) and the level of the degradation and total unknowns were higher (3-CBZ: 0.28%, 852U77:1.23%, 827U76:0.10% and total 1.73%) than the Bupropion HBr (3-CBZ: 0.12%, 852U77:0.41%, 827U76: 0.05% and total 0.75%).

Example 8

Figure 50:
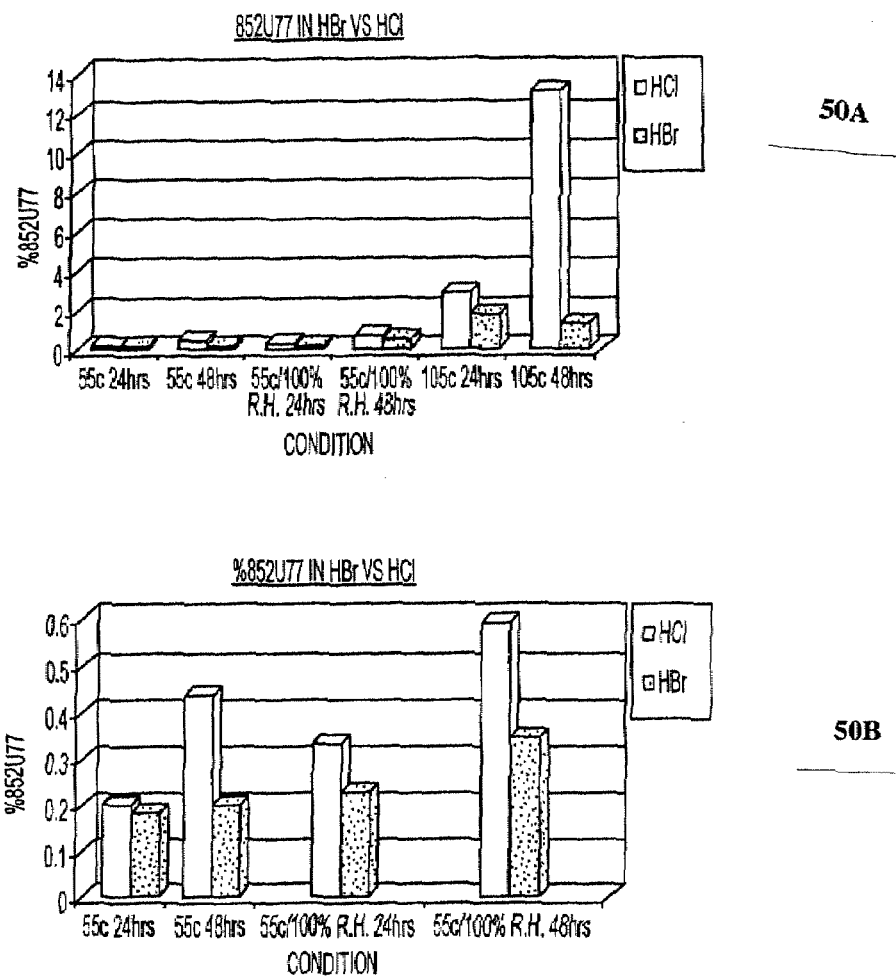
FIGS. 50A and 50B contain bar graphs showing the % of 852U77 formed in forced degradation studies of bupropion HCl vs. bupropion HBr in the presence of excipients.
Figure 51:
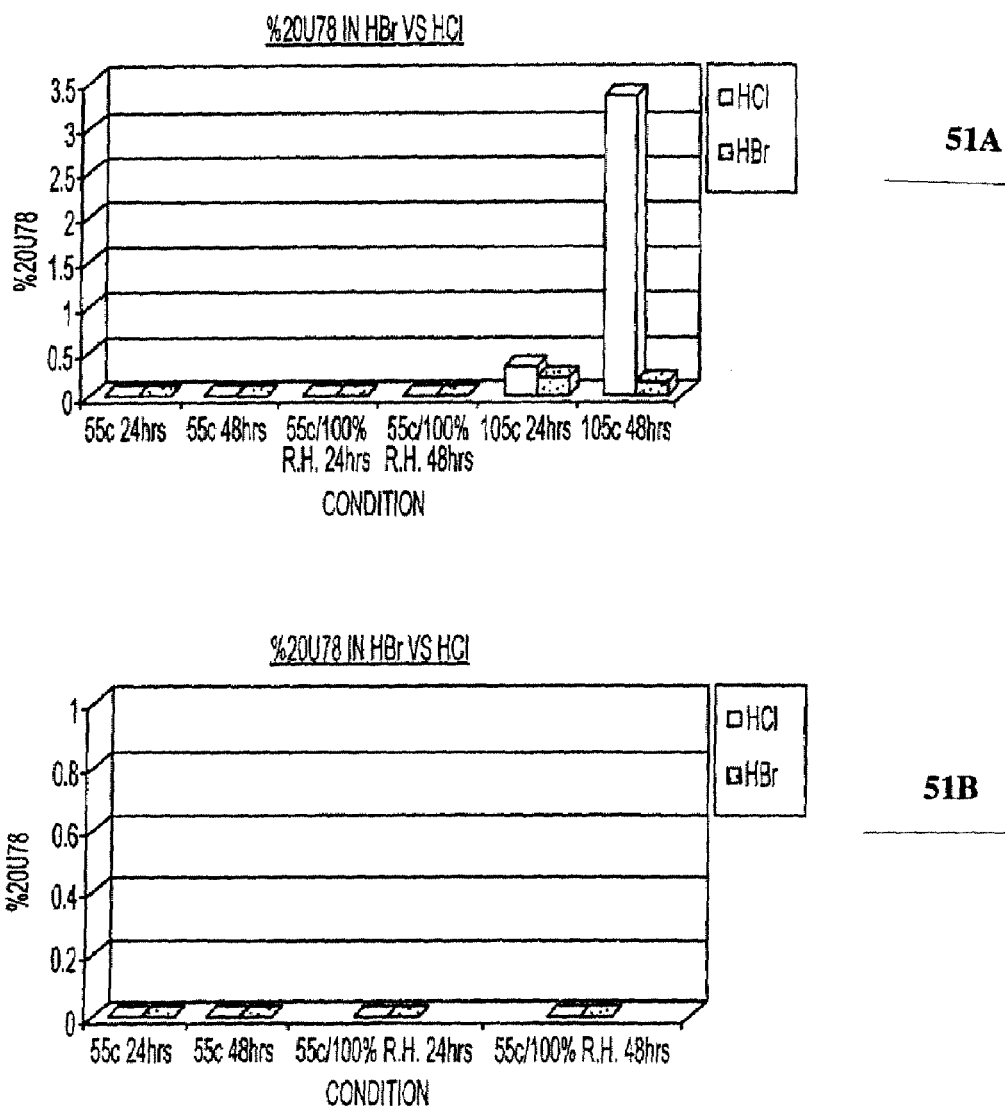
FIGS. 51A and 51B contain bar graphs showing the % of 20U78 formed in forced degradation studies of bupropion HCl vs. bupropion HBr in the presence of excipients.
Figure 53:
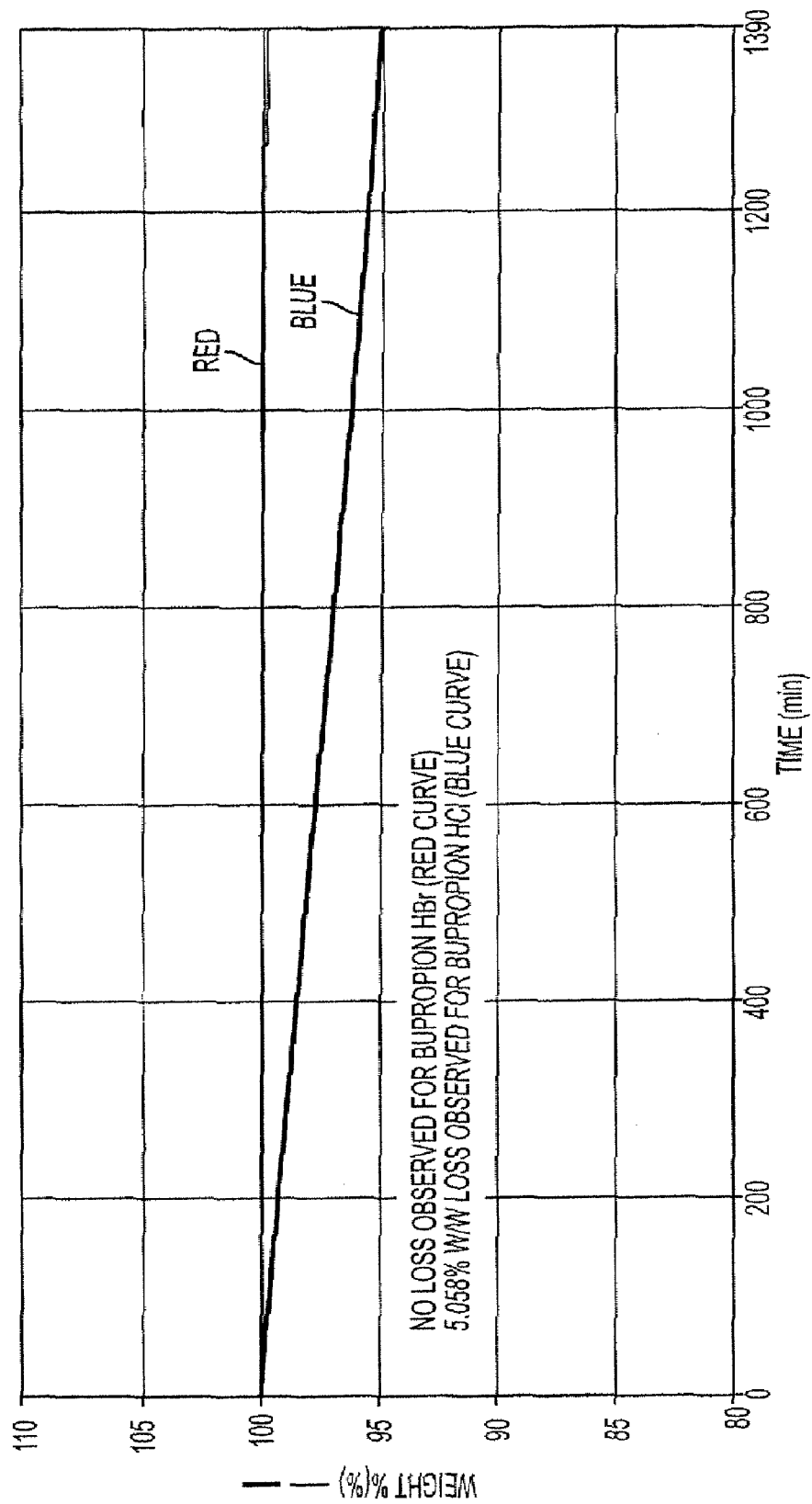
FIG. 53 is a graph showing the loss of API in a thermal gravimetric analysis (TGA) experiment at 100 degrees C. of bupropion HCl vs. bupropion HBr.

Further Forced Degradation Studies on Bupropion HBr and Bupropion HCl in the Presence of Excipients Further forced degradation studies were carried out at 55° C., at 55° C. and 100% relative humidity, at 100° C., and at 105° C. on both the HCl and HBr Bupropion salts in the presence of excipients. The average weight of the excipients and the weight of the active pharmaceutical ingredient (API) present in the samples are presented in Table 72. The results from this study are presented in FIGS. 49-53. FIG. 49 shows the amount of 3-CBA bupropion degradation impurity in the various samples. FIG. 50 shows the amount of 852U77 bupropion degradation impurity in the various samples. FIG. 51 shows the amount of 20U78 bupropion degradation impurity in the various samples. FIG. 52 shows the amount of 827U76 bupropion degradation impurity in the various samples. FIG. 53 is a graph showing the loss of each salt over time in a TGA experiment at 100° C. These results indicate that at elevated temperatures, a disproportionation of the HCl salt occurs with concomitant loss of gaseous HCl. This disproportionation did not occur with the HBr salt.

It is clear from the results that bupropion HBr shows significant improvements in stability compared to bupropion HCl. The degradation of bupropion HBr was slower as indicated by the formation of less amounts of bupropion degradation impurities compared to bupropion HCl.

Example 9

Preparation of Further Bupropion HBr EA Tablets

Using procedures as described in Example 6, further bupropion EA tablets were prepared using the quantities listed in Table 73.

Example 10

Accelerated Stability Study of Bupropion HBr

The stability of bupropion HBr was evaluated under the accelerated conditions of 40° C. 12° C. and 75%±5% R.H. in a stability chamber. The samples were prepared in closed bottles and placed in the stability chamber. HPLC analysis was conducted on the samples prior to placing them in the stability chamber (time 0), and after 3 months and 6 months. The amounts of the main degradation products present at time 0 were compared with those amounts present after 3 months and 6 months. As shown in Table 74-76 three different batches of bupropion HBr were tested. For each sample tested, at each time period, two different HPLC assays were run. The first assay labeled chromatographic purity A, measured the percentage of three impurities 3'-chloropropiophenone, 3'-Chloro-2-bromopropiophenone and 3'-Chlorobenzoic acid. The second assay, labelled chromatographic purity B, measured the percentage of 2-N-(tert-Butyl)-aminopropiophenone, a single unknown impurity and the total unknown impurities. Finally a total percentage of impurities (known and unknown) was reported for each sample. From the data presented it can be seen that there is a slight increase in the impurity 3'-chloropropiophenone. While slight fluctuations were seen in the percentage of other impurities there was no trend showing an increase of these impurities at the 3- and 6-month time periods as measured. The total percentage of impurities for each of the HBr samples did not change at either the 3-month or the 6-month time periods. These results indicate that the HBr salt of bupropion was highly stable under the accelerated stability test conditions.

Example 11

Shelf Life Stability Program

The stability of bupropion HBr was studied over a longer term under conditions meant to approximate standard storage or shelf conditions. Samples were prepared in closed containers and subjected to long-term storage at 25° C.±2° C. and 60%±5% RH in a stability chamber. The samples were analyzed by HPLC prior to being placed in the stability chamber (time 0) and after 3 months and 6 months. The amounts of the main degradation products present at time 0 were compared with the amounts present at 3 months and 6 months. As shown in Table 77-79 three different batches of bupropion HBr were tested. As in Example 10 each sample was tested under two HPLC assay conditions to identify 6 impurities or groups of impurities as described in Example 10. From the results shown in tables 77-79 it can be seen that the percentage of the impurity 3'-chloropropiophenone increased slightly over time. While the other impurities fluctuated slightly they did not show an increasing trend over time. These results demonstrate the stability of bupropion HBr under standard shelf conditions over an extended period of time.

Example 12

Preparation and Stability Study of Bupropion HBr Polymorphic Forms I, II and III Bupropion hydrobromide polymorphic forms I, II and III were prepared in the following manner and their stability was studied under the conditions described below:

Form I:

A 250 ml flask equipped with overhead stirrer and gas inlet was charged with 34 g of bupropion base and 138 ml of isopropanol. The solution was maintained under stirring while 13 g of gaseous HBr was introduced through the gas inlet in a time of 20' while the internal temperature of the mixture raises from 25° C. to 40° C. During the gas addition a heavy white precipitate formed. At the end of the gas addition the temperature of the mixture was raised to reflux (80° C.), to get complete solution of the suspended solid. The temperature was then lowered to 25° C. in 1 hour and further lowered to 0-5° C. in 1 additional hour. The precipitate obtained was filtered and washed with 20 ml of cold isopropanol. The discharged wet solid was dried under vacuum (30 mmHg) in a static drier at 50° C. for 16 hours. 34 g of bupropion hydrobromide form I were obtained.

Figure 60:
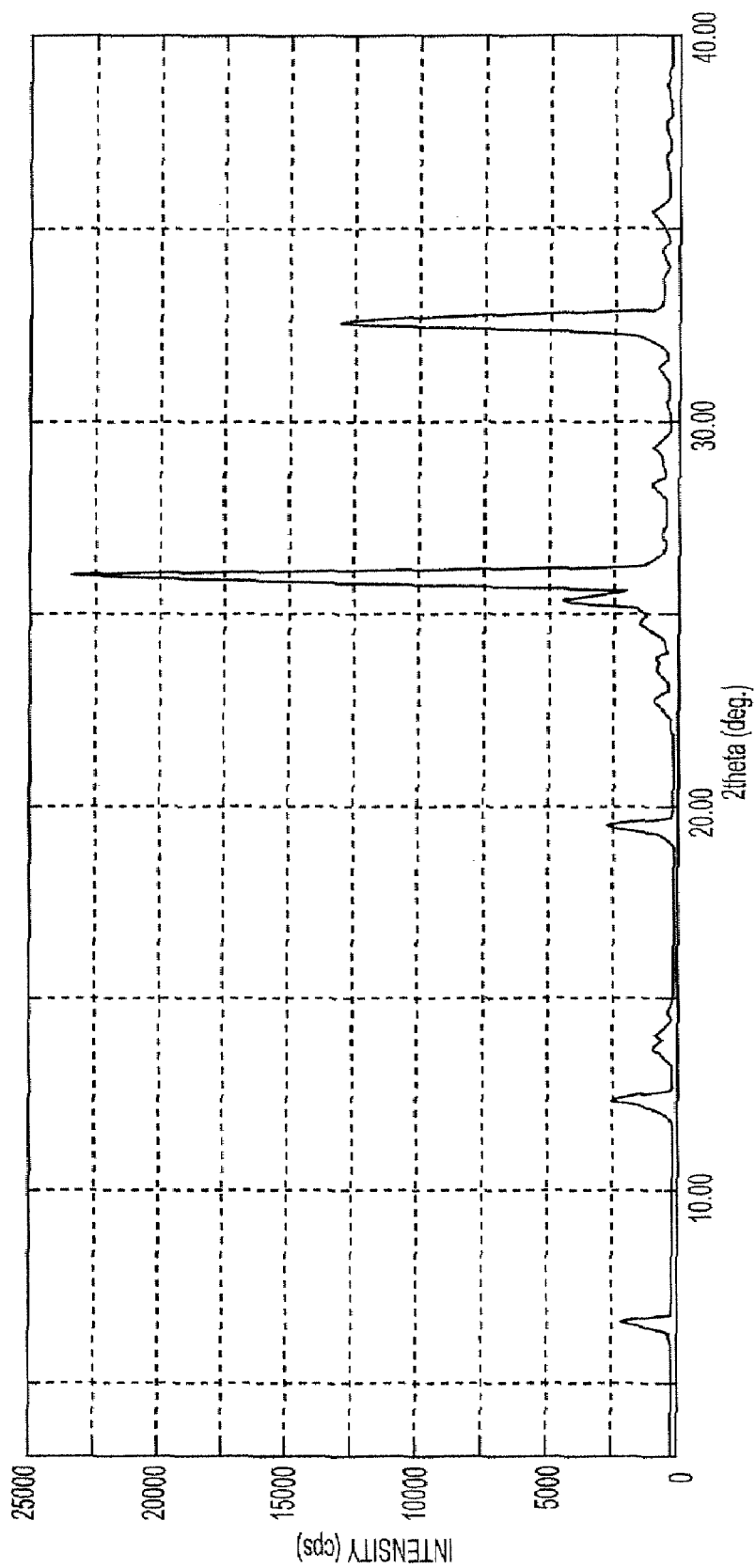
FIG. 60 is a graph of the relative PXRD of a sample of bupropion hydrobromide polymorphic form I after 6 months under the ICH (International Conference on Harmonisation of Technical Requirements for Registration of Pharmaceuticals for Human Use) conditions (40 degrees C., 75% R.H.).

Samples of bupropion HBr form I were subjected to the conditions for the accelerated stability study as described in Example 10 and the shelf life stability study as described in Example 11. PXRD studies carried out after 3 months and 6 months for each sample gave the same results. The PXRD profile of one of the samples after 6 months in the accelerated stability condition is provided in FIG. 60.

Figure 61:
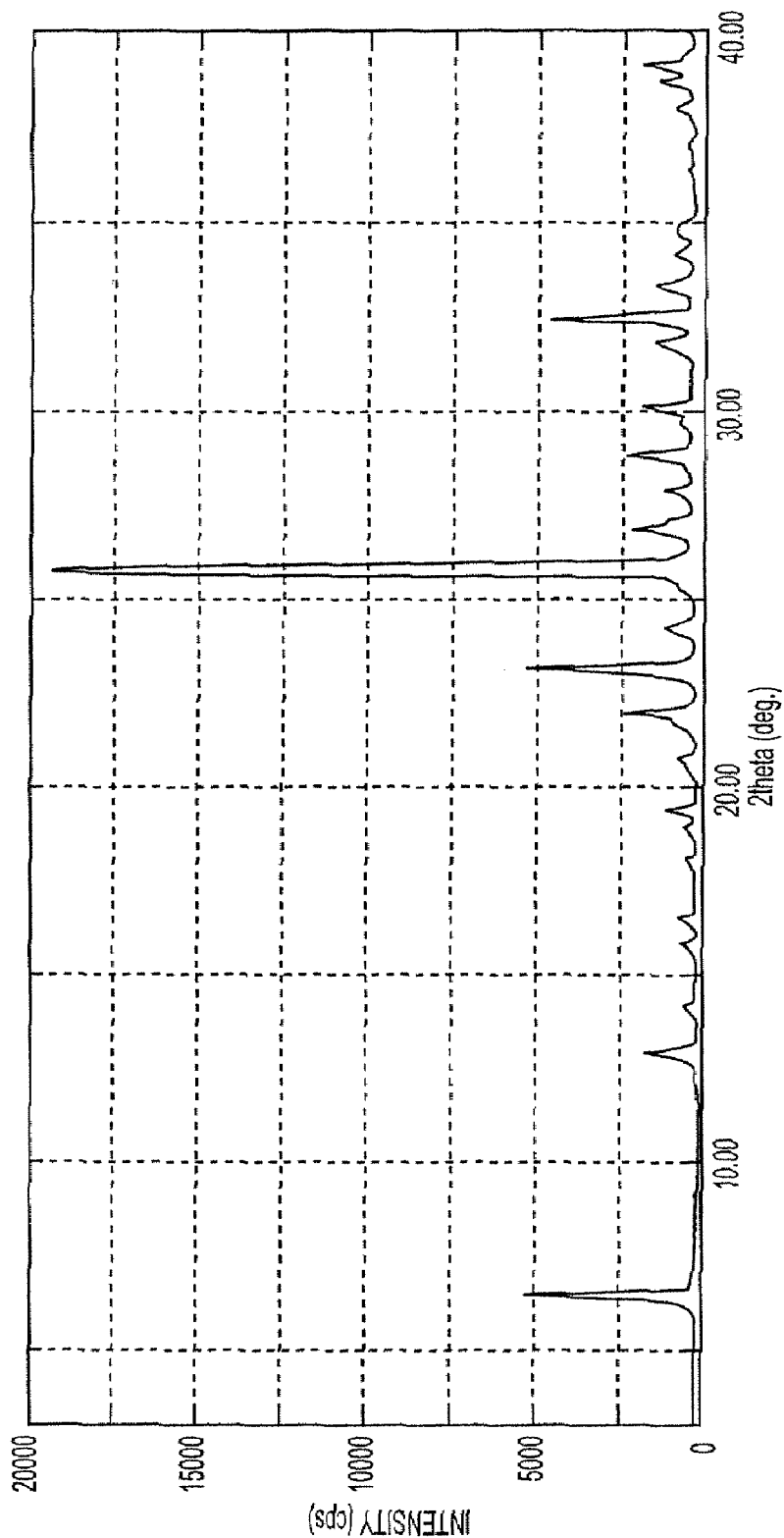
FIG. 61 is a graph of the PXRD of a sample of bupropion hydrobromide polymorphic form II after 1 month under ICH conditions (40 degrees C., 75% R.H.).

Form II:

10 g of bupropion HBr form I were dissolved in a mixture of 170 ml of acetone and 7 ml of water. The mixture was brought to reflux with dissolution of the solid. The solution was then cooled to room temperature. After one night the precipitate formed was filtered and dried at 40° C. under vacuum (30 mmHg) for 12 hours. 2.4 g of bupropion HBr form II were obtained. A sample of the product was prepared for an accelerated stability test, in ICH (International Conference on Harmonisation of Technical Requirements for Registration of Pharmaceuticals for Human Use) conditions (40° C./75% R.H.), by sealing the product in polyethylene bags, which in turn were placed in aluminium bags containing silica and sealed and placed in the stability chamber in ICH conditions (40° C./75% R.H.). The crystalline form was checked after maintaining the product under these conditions for 1 month. The PXRD profile shown in FIG. 61 shows that the compound is still in form II. This demonstrates the stability of crystal form II under these conditions.

Figure 62:
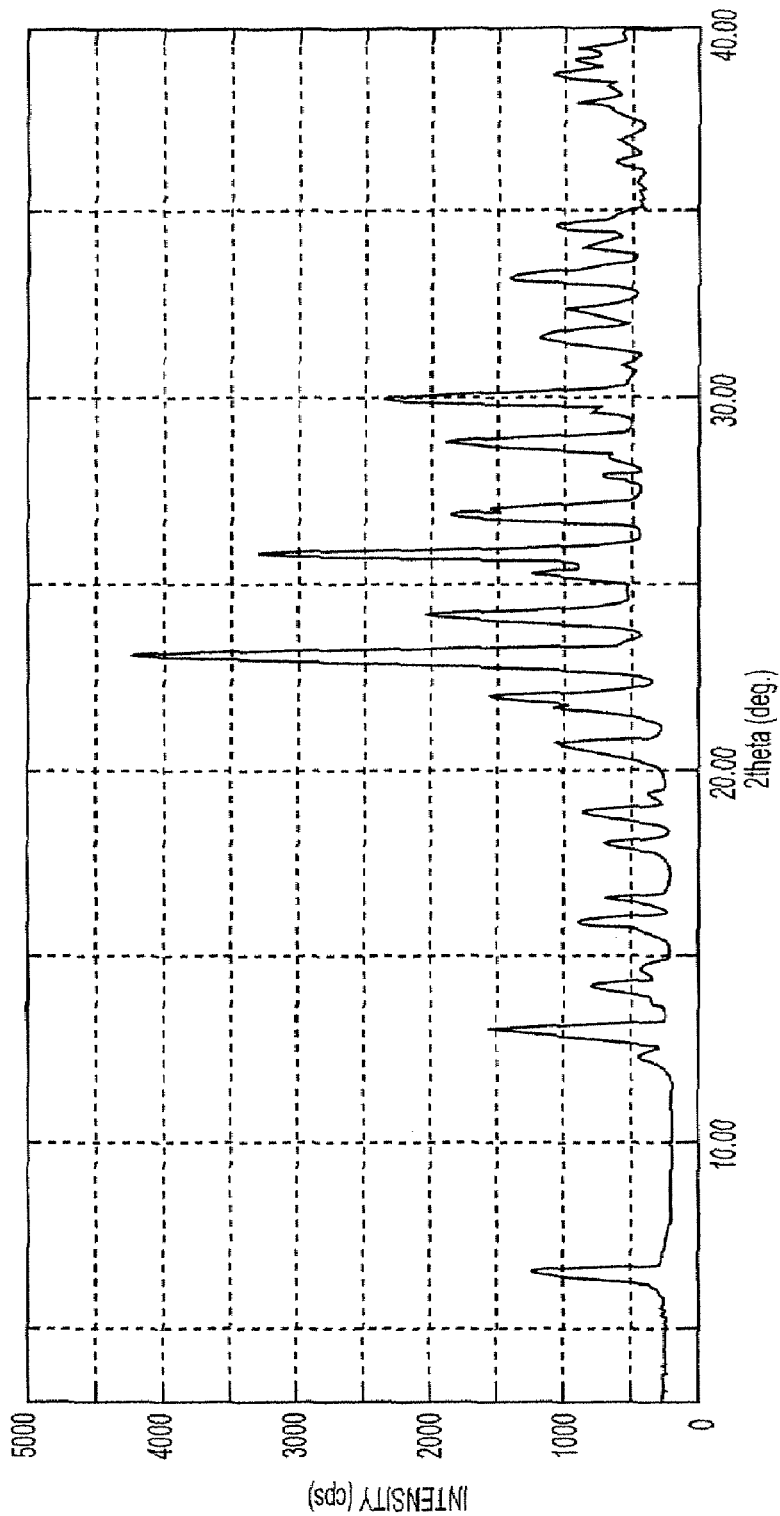
FIG. 62 is a graph of the PXRD of a sample of bupropion hydrobromide polymorphic form III after 1 month under ICH conditions (40 degrees C., 75% R.H.).

Form III:

20 g of bupropion hydrobromide form I and 96 ml of absolute ethanol were placed in a 250 ml flask. The mixture was brought to reflux obtaining complete dissolution of the solid. The solution was then cooled to room temperature without stirring and left in these conditions for 18 hours. The resulting crystalline solid was then filtered and dried under vacuum (30 mmHg) at 50° C. for 4 hours. 11.2 g of bupropion HBr form III were obtained. A sample of the product was prepared for stability testing by sealing the product in polyethylene bags, which in turn were placed in aluminium bags containing silica and sealed, and placed in the stability chamber in ICH conditions (40° C./75% R.H.). The crystalline form was checked after maintaining the product in these conditions for 1 month. The PXRD profile shown in FIG. 62 demonstrates that the product is not stable in this form under these conditions, as the majority of the product changed to form II.

Example 13

HBr-SR Tablets for 100 and 150 Mg Strength as Alternate to HCl-SR

Formulation to be based on options used during the development of the Wellbutrin HCl SR 100 and 150 mg.

Bupropion HCl was replaced with HBr and adjusted to obtain same amount Bupropion base. Filler materials adjusted accordingly in order to obtain the same tablet core weights.

e.g.

150 mg HCl=130 mg base=174 mg HBr 100 mg=86.7=116

HBr Granulation Process:

Bupropion HBr is granulated with an aqueous solution containing Polyvinyl Alcohol and Stabilizing agent such as Oxalic acid or Succinic acid or Aspartic acid or other suitable acid compounds, in a Fluid bed granulator.

The dry granules are than mixed with water soluble polymer or mixtures of hydrophobic/hydrophilic polymers at various viscosity grades. In trials used Hypromellose (Hydroxypropyl methylcellulose K4M CR grade) as well as Hydroxypropyl Cellulose ("HPC") at quantities to obtain target release.

Microcrystalline Cellulose ("MCC") was used as filler and binding material. Could be replaced with Lactose. For final lubrication Glyceryl Behenate (COMPRITOL® 888 ATO) was used. Other suitable lubricant such as Stearic Acid, Sodium Fumarate are suitable.

The compressed tablets are then coated with a non-functional colored film coating solution. Formulation example: mg/unit (Target weight 400 mg) for 174 mg strength (equivalent to 150 mg HCl)

| | |
|---|---|
| Bupropion HBr | 174 mg |
| Polyvinyl Alcohol | 16 |
| Stabilizer | 20 |
| HPMC (HPC) | 40 |
| MCC | 144 |
| Glyceryl Behenate | 6 |

Coating: Opadry provided by Colorcon, approximately 3-4% weight gain

Above formulation(s) are evaluated without use of stabilizers.

Example 14

Further Stability Studies

Stability of Bupropion HBr 348 mg Tablets

In these studies, the stability of bupropion HBr tablets (Lot #Bup-HBr-XL-348-025-5 (7, 30 and 90 counts) were tested after storage at 40 degrees C. and 75% relative humidity as described previously for 348 mg tablets prepared as described above and having the tablet composition shown in Table 99. These experiments evaluated the results of accelerated stability of the bupropion HBr XL 348 mg tablets packaged in 7, 30 and 90 counts based on a comparison of the changes in physical appearance, assay, the level of the known degradation impurities and the dissolution profiles of the 1, 2, 3 and 6M time points within the initial data. No significant changes were observed in physical appearance, and the assay values of the tablets for all counts, however, as expected, there were gradual increase in the levels of two major known degradation impurities (3-CBZ and 852U77) and going from 7 to 90 counts, the percentages of the latter two impurities were varied. The dissolution profiles of the drug product for all counts were lower at the first month for all time points in comparison with the initial profile, however, other stability time points varied, for example:

7 Counts: the 2M and 3M were similar to the initial and 6M similar to the 1M.

30 Counts: The 6M was similar to the 1M and lower than the initial, the 2 & 4 hours time points for 2M and 3M were similar to the initial, however, the 8 & 16 hours time points were lower than the corresponding values.

90 Counts: Essentially lower dissolution profiles were observed for 2M, 3M, and 6M in comparison with the initial profiles These results are contained in FIG. 63.

Example 15

Additional Stability Testing of 150 mg, 300 mg Bupropion HBr

Tablets (Lot #Bup-HBr-EA-150-002-5 and Bup-HBr-300-001-5)

The same criteria were used to evaluate the stability of Bupropion HBr EA 150 and 300 mg drug products for the 90 counts. Similar results were obtained for the two drug products as compared with the bupropion HBr XL 348 mg tablet-90 counts, however, better dissolution stability data were observed, i.e., no significant differences of the dissolution profiles for 1M, 2M, 3M, & 6M were observed for the two EA products in comparison with their corresponding initials, except the 6M dissolution data for the 300 mg which showed slightly lower values. These results are in FIG. 64.

Example 16

Additional Open Dish-Closed Bottle Stability Studies

Experiments were conducted comparing the stability of bupropion HBr XL 174 mg core, Bupropion HBr XL 348 core, Bupropion HCl XL 150 mg core and Bupropion HCl XL 300 mg core over 10 and 20 days under open bottle and closed bottle conditions. These studies were again effected at 40 degrees C. and 75% relative humidity. Degradation was again assessed by assaying for known bupropion degradation impurities 3-CBZ and 852U77. As before the bupropion HBr cores were less subject to degradation than the bupropion HCl cores under open and closed bottle conditions. These results are contained in FIG. 65.

Example 17

Figure 67:
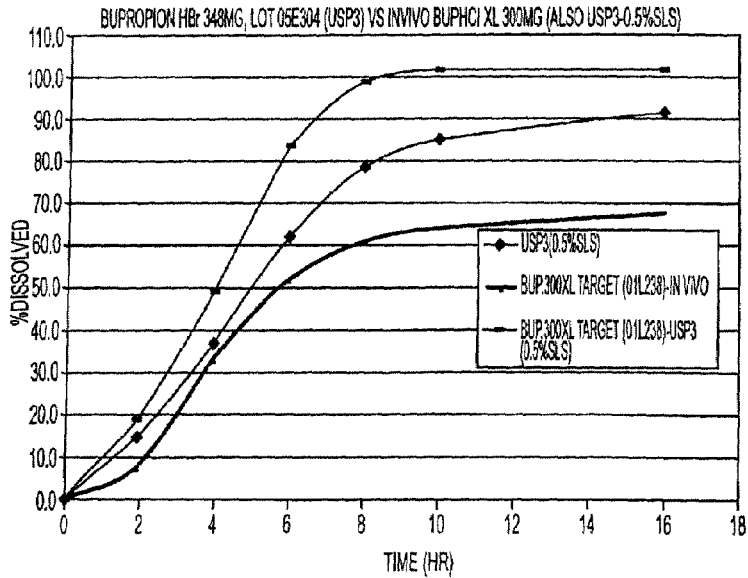
FIGS. 67A, 67B and 67C compare the dissolution profiles and drug release for Bupropion HBr 348 mg Lot #05E304 in different USP-3 media (SGF pH 1.2, Acetate Buffer pH 4.5, Phosphate Buffer SIF pH 6.8) over a period of 16 hours and further compares this release profile against the release profile for Bup 300 XL Target (01L238) in-vivo and BUP 300 XL Target (01L238) in-vitro in USP-3 media.

Dissolution of Bupropion Formulations According to the Invention in Different USP-3 Media The dissolution of bupropion HBr formulations according to the invention were assessed in three USP-3 media, i.e., SGF pH 1.2, Acetate Buffer pH 4.5 and Phosphate Buffer pH 6.8 over a period of 16 hours. These results are contained in FIG. 66. Particularly Bupropion HBr XL 348 mg tablets (final), Lot #Bup-HBr-XL-012-5; Wellbutrin XL 300 mg tablets (final), Lot #05A116; Bupropion HBr XL 348 mg tablets EC1 Lot #Bup-HBr-XL-012-5 (EC 32 mg wg) and Wellbutrin XL 300 mg tablets (EC10-Lot #05D047 were assessed in SGF media pH 1.2 for 2 hours, Acetate Buffer pH 4.5 for 2 hours, and Phosphate Buffer SIF pH 6.8 for a total of 10 hours. The results are contained in the FIG. 66-68.

Additionally, FIG. 66 contains the results of dissolution testing of a bupropion HBr formulation according to the invention, i.e., bupropion HBr 348 mg, lot #05E304, versus bupropion HCl 300 mg (Bup 300XL Target) lot #01L238 in-vivo and Bup 300XL Target in USP3-0.5% SLS media over times ranging from 0 to 16 hours.

Additionally the same Figure tabulates the results of these dissolution experiments comparing % drug release over time for bupropion HBr 348 mg Lot #05E304 in USP-3 media (SGF pH 1.2 and 0.5% SLS after 2 hours, Acetate Buffer pH 4.5 after 2 hours and Phosphate Buffer pH 6.8 after a total of 16 hrs.

Figure 68:
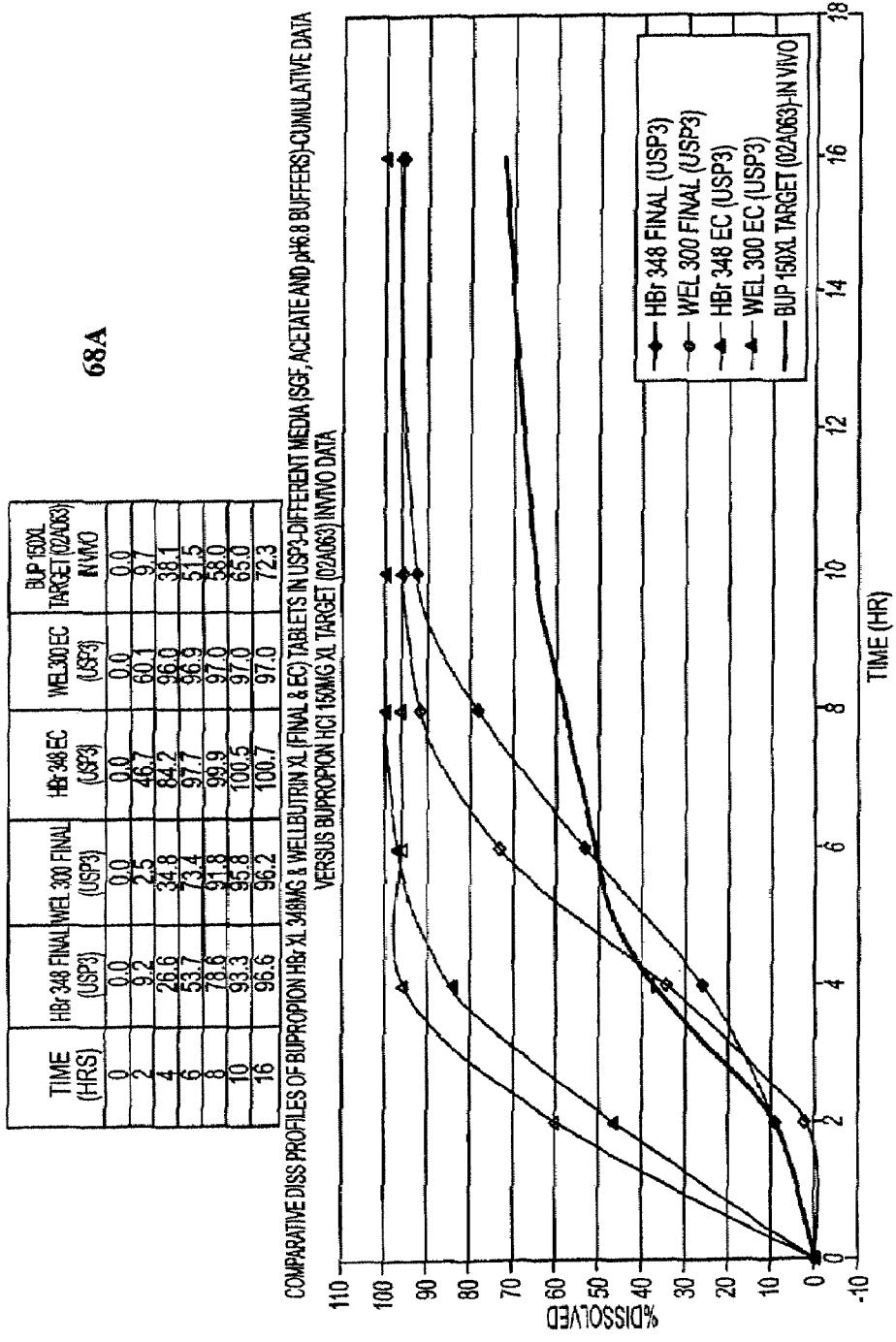
FIGS. 68A and 68B contain comparative dissolution profiles for Bupropion HBr XL 348 mg and Wellbutrin XL (final and EC) in USP-3 media (pH 1.2 SGF, pH 4.5 acetate buffer and pH 6.8 phosphate buffer over a period of 16 hours.
Figure 69:
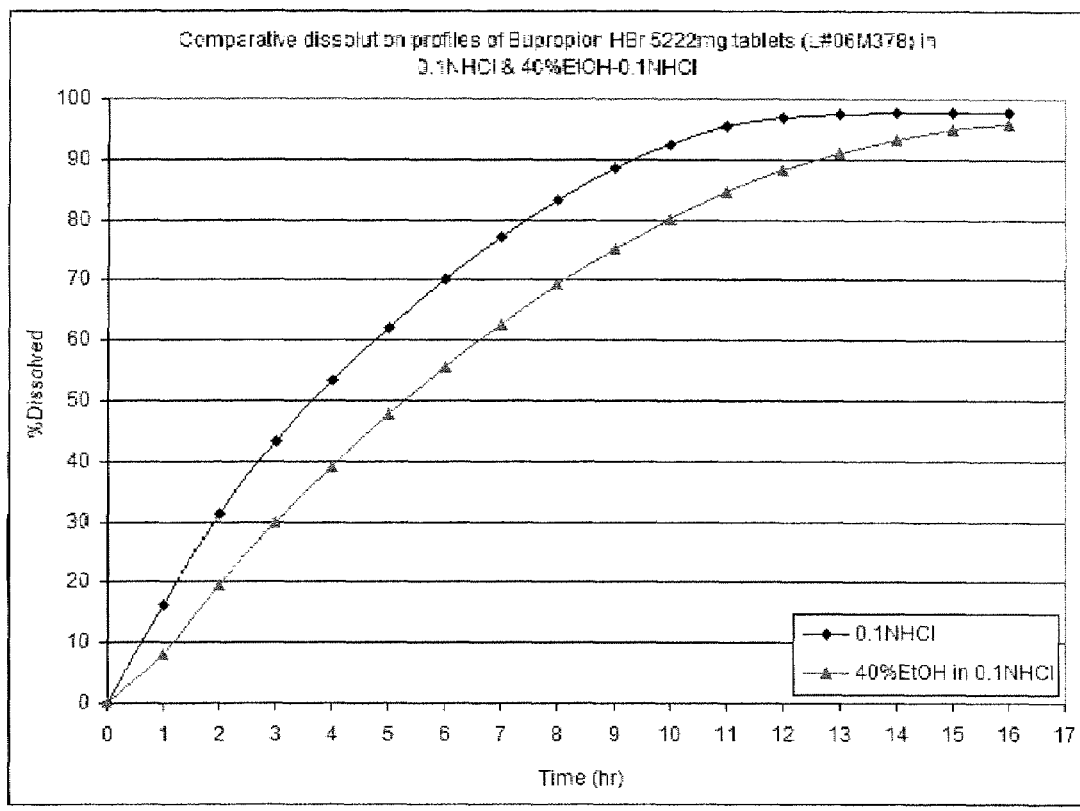
FIGS. 69-74 show comparative dissolution profiles of Bupropion HBr XL tablets in various media.
Figure 70:
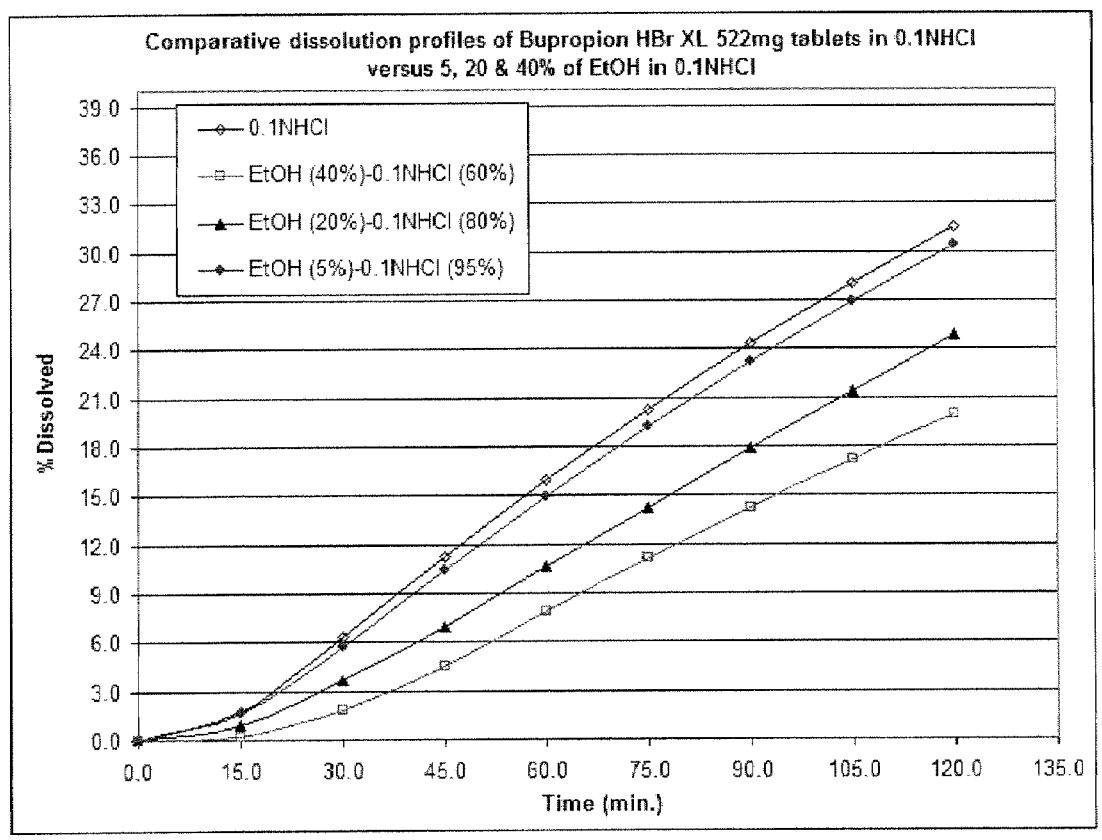
Figure 71:
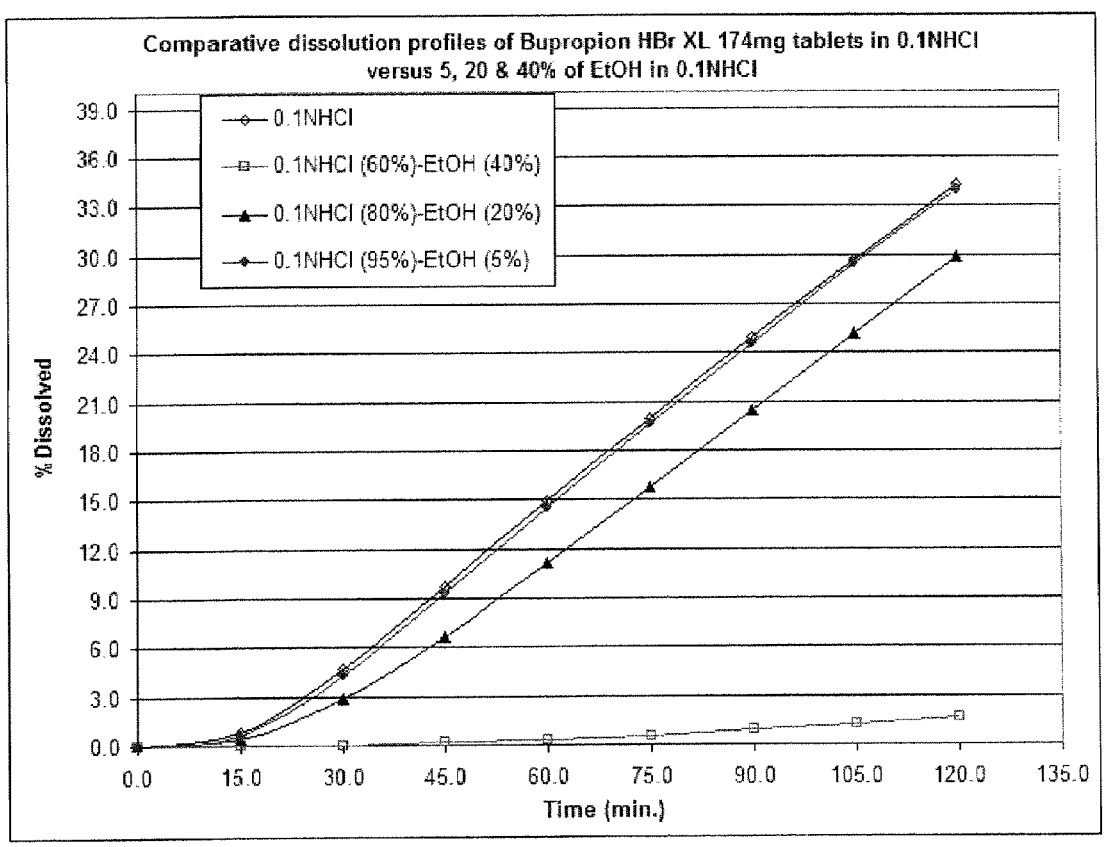
Figure 72:
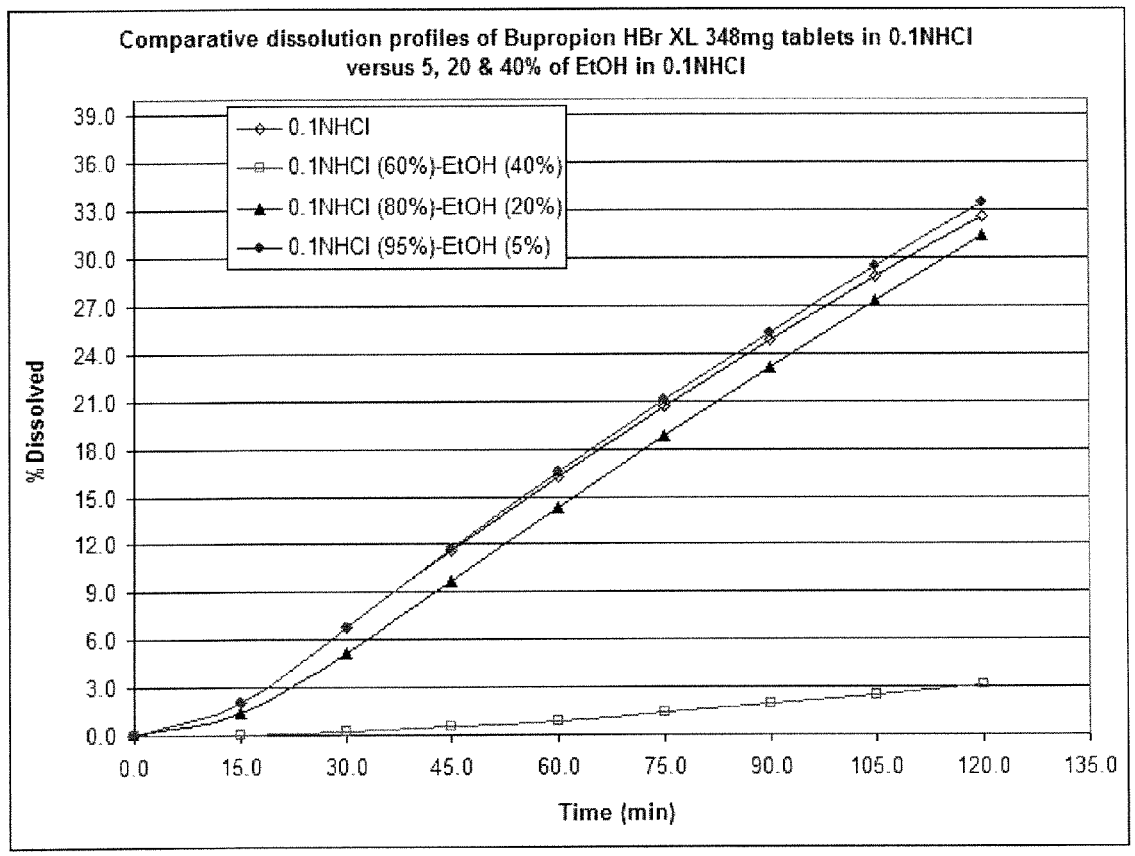
Figure 73:
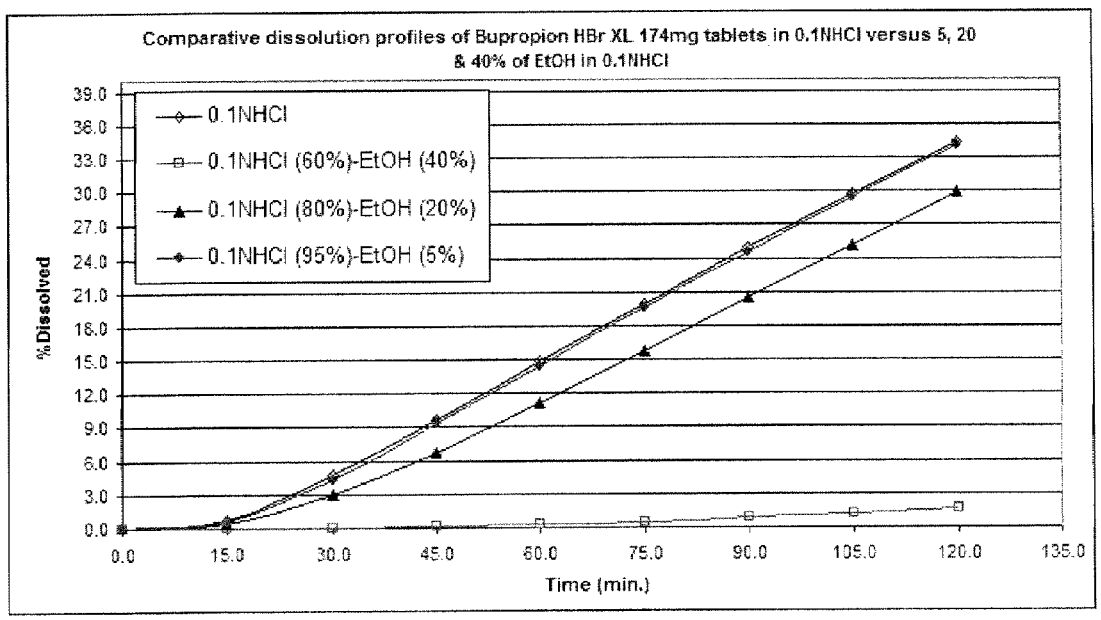
Figure 74:
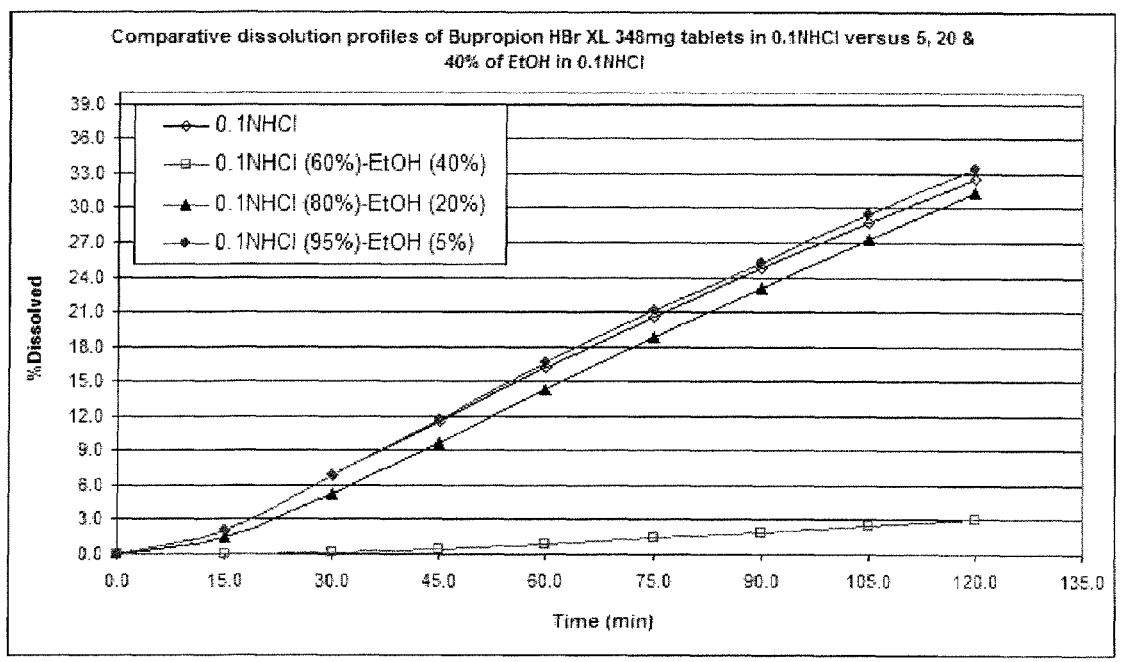
Figure 75:
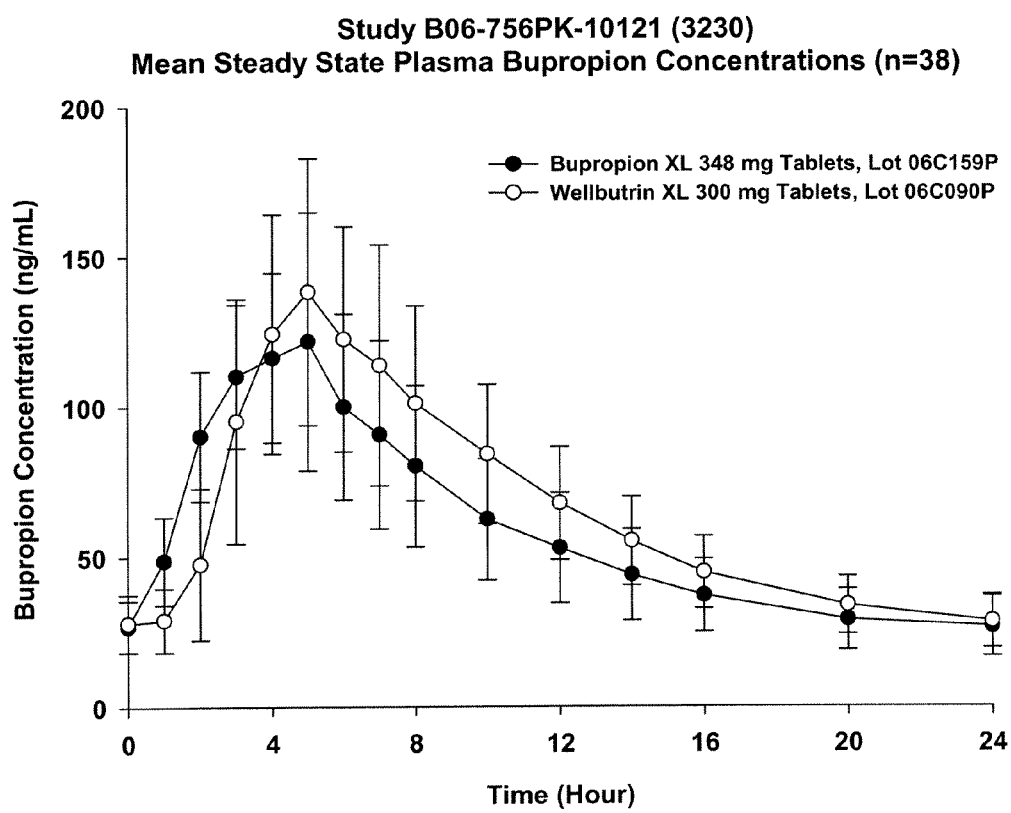
FIG. 75: Mean Plasma Bupropion Concentration-Time Plot for Study B06-756PK-10121 (3230)
Figure 76:
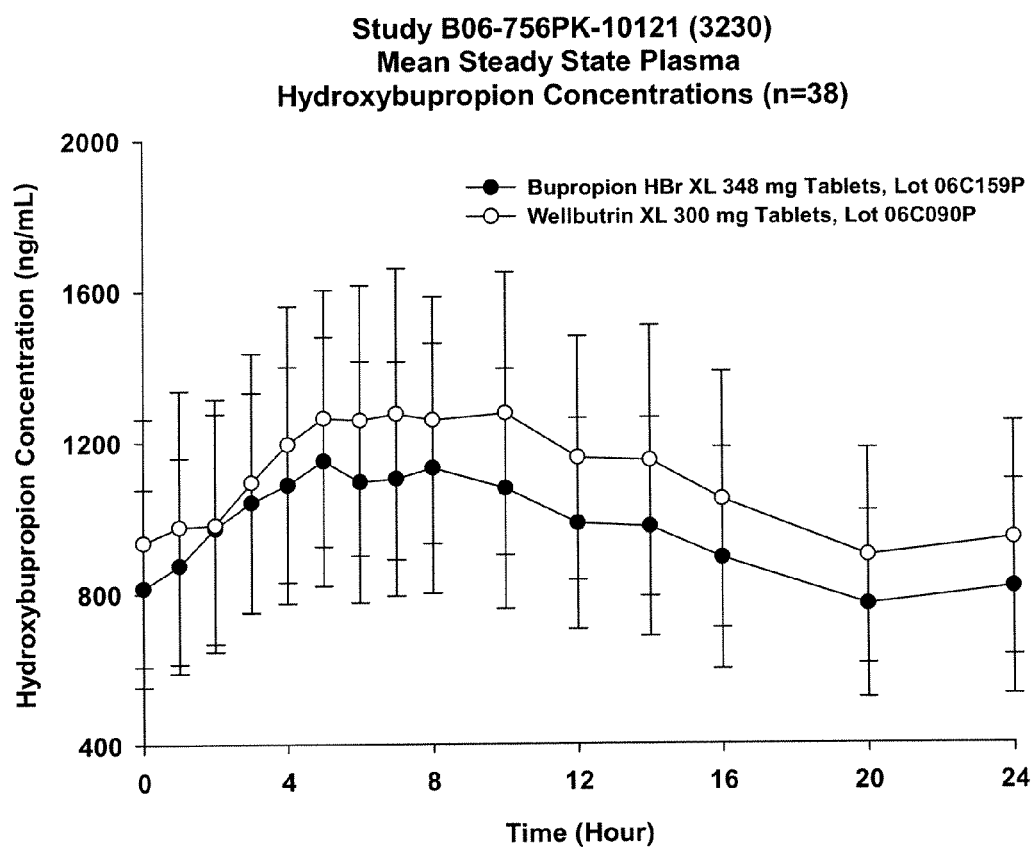
FIG. 76: Mean Plasma Hydroxybupropion Concentration-Time Plot for Study B06-756PK-10121(3230)
Figure 77:
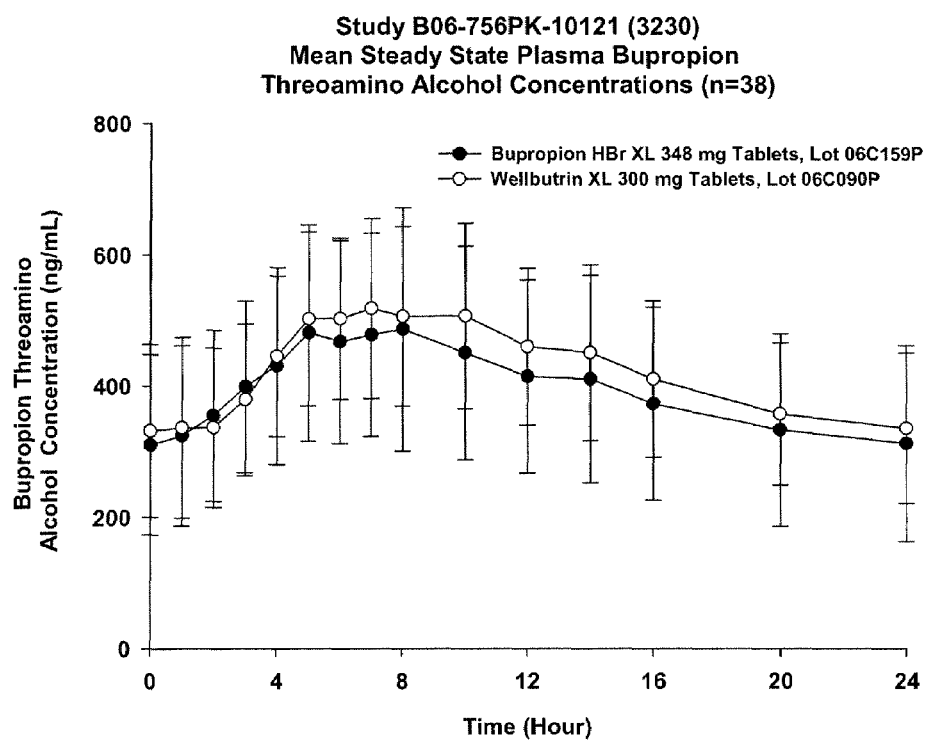
FIG. 77: Mean Plasma Bupropion Threoamino Alcohol Concentration-Time Plot for Study B06-756PK-10121 (3230)
Figure 78:
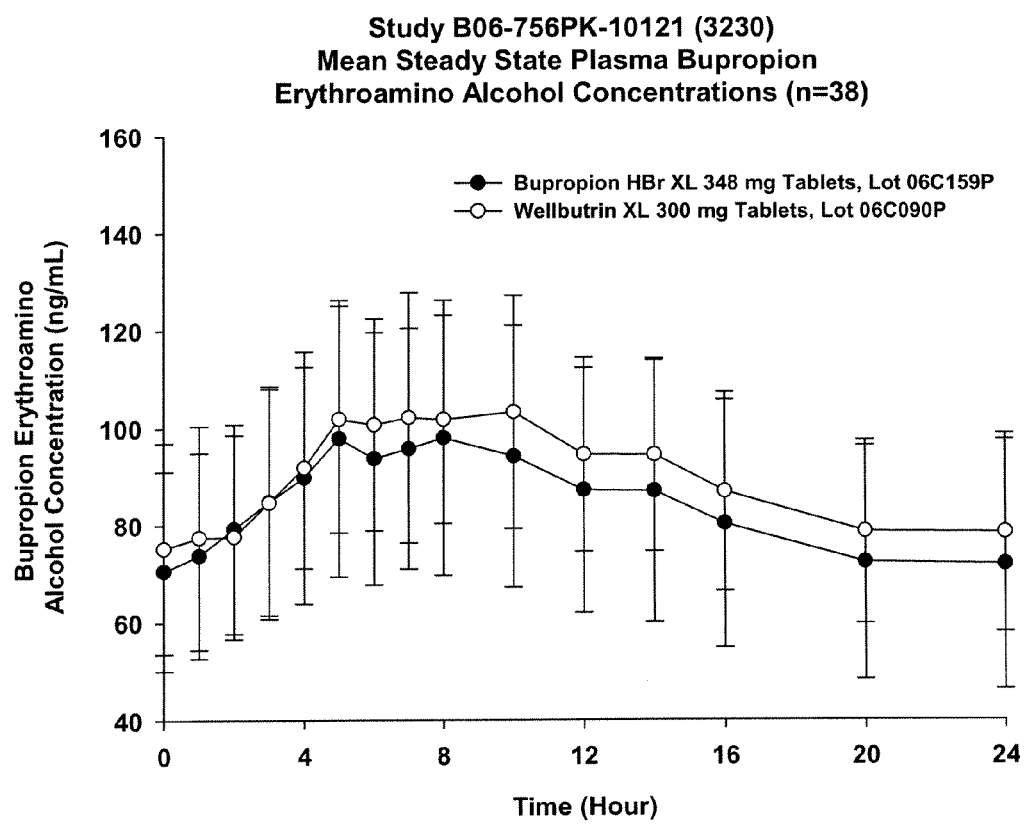
FIG. 78: Mean Plasma Bupropion Erythroamino Alcohol Concentration-Time Plot for Study B06-756PK-10121 (3230)
Figure 79:
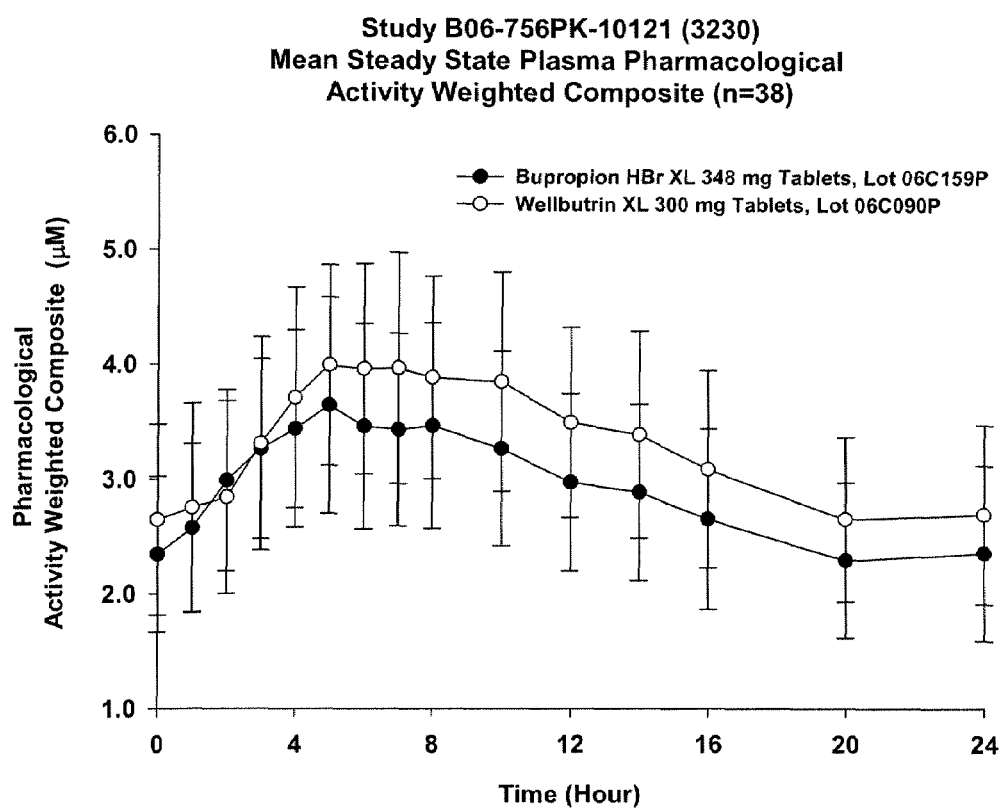
FIG. 79: Mean Plasma Pharmacological Activity Weighted Composite (PAWC)-Time Plot for Study B06-756PK-10121 (3230)
Figure 80:
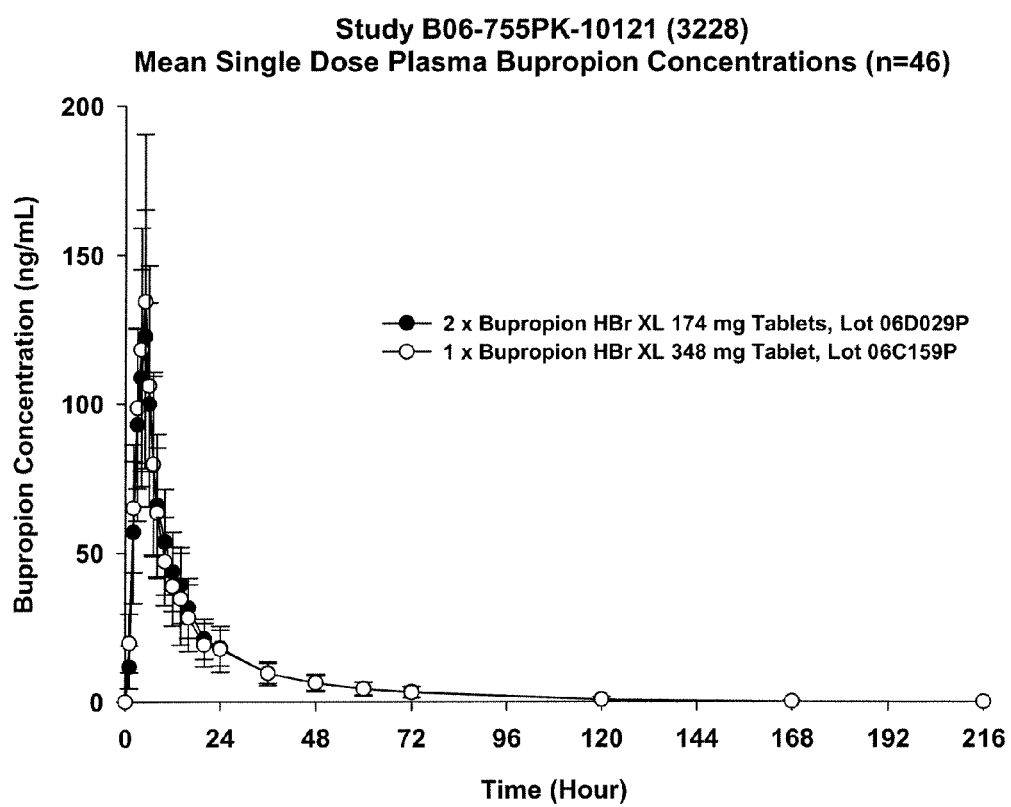
FIG. 80: Mean Plasma Bupropion Concentration-Time Plot for Study B06-755PK-10121 (3228)
Figure 81:
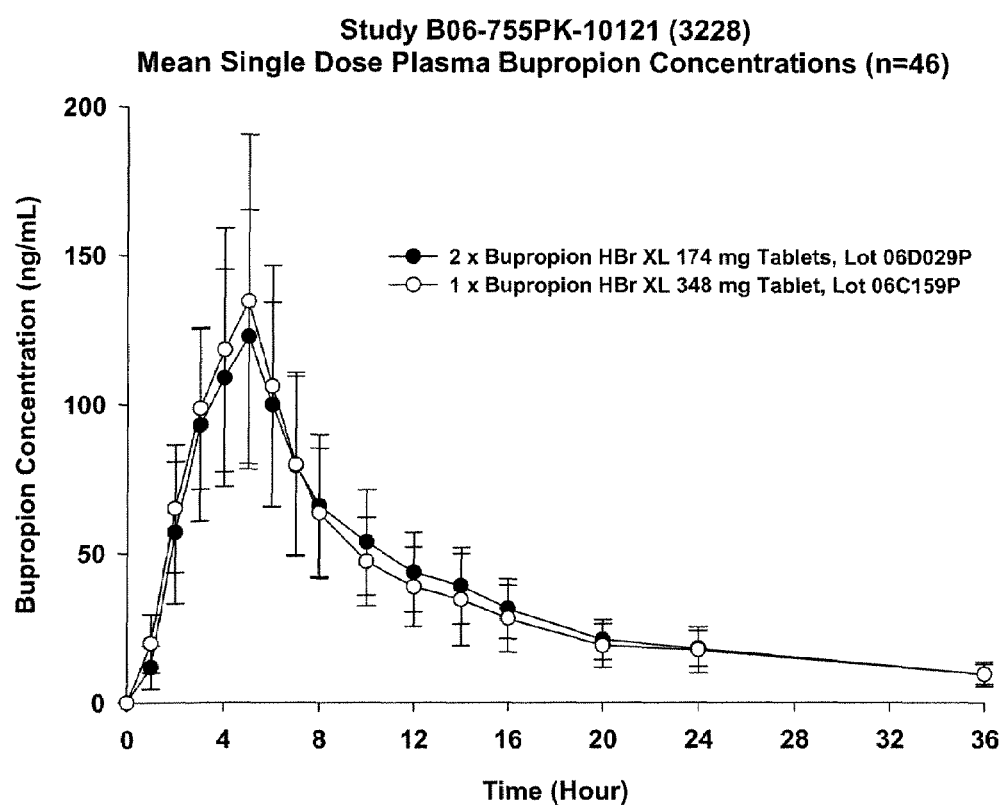
FIG. 81: Mean Plasma Bupropion Concentration-Time Plot for Study B06-755PK-10121 (3228)—Magnified Showing Only Datapoints From 0-36 Hours
Figure 82:
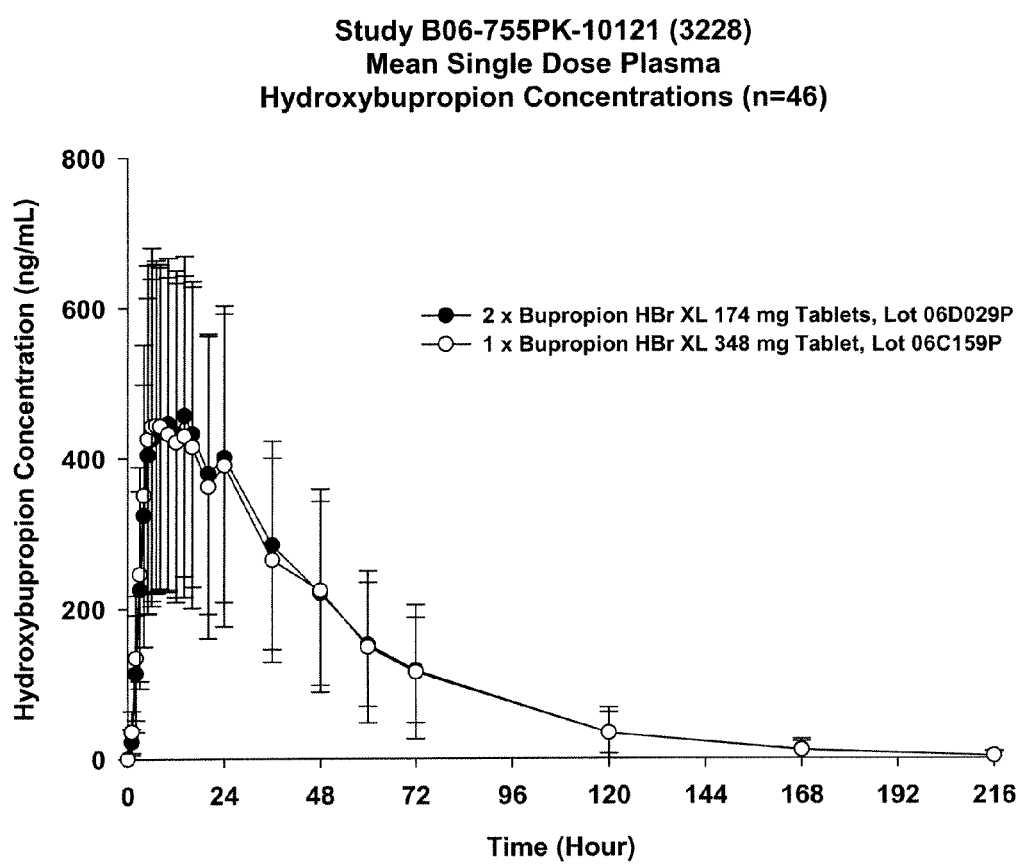
FIG. 82: Mean Plasma Hydroxybupropion Concentration-Time Plot for Study B06-755PK-10121 (3228)
Figure 83:
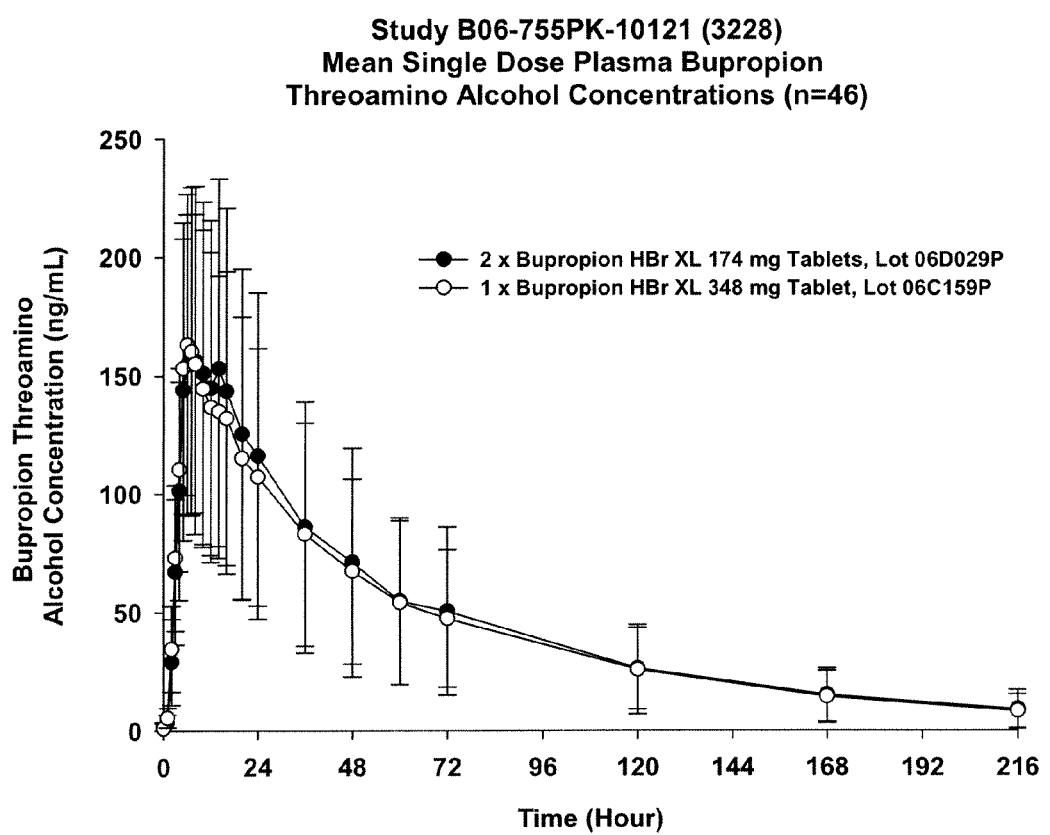
FIG. 83: Mean Plasma Bupropion Threoamino Alcohol Concentration-Time Plot for Study B06-755PK-10121 (3228)
Figure 84:
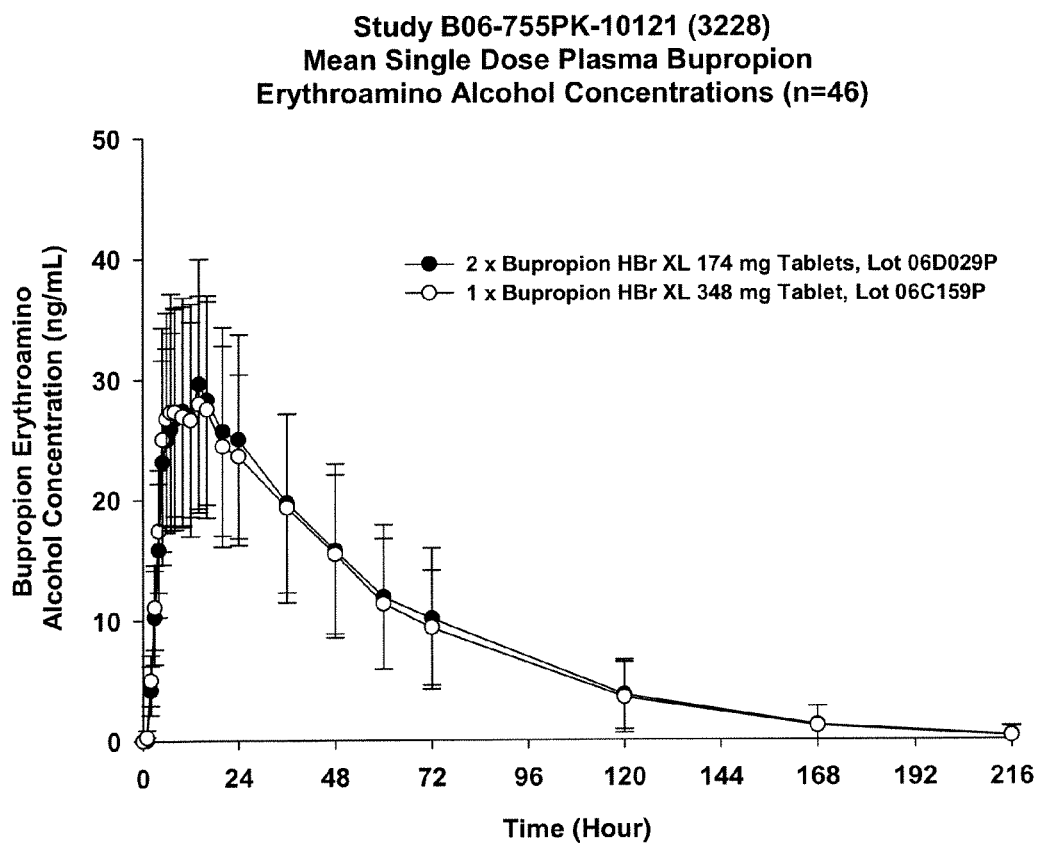
FIG. 84: Mean Plasma Bupropion Erythroamino Alcohol Concentration-Time Plot for Study B06-755PK-10121 (3228)
Figure 85:
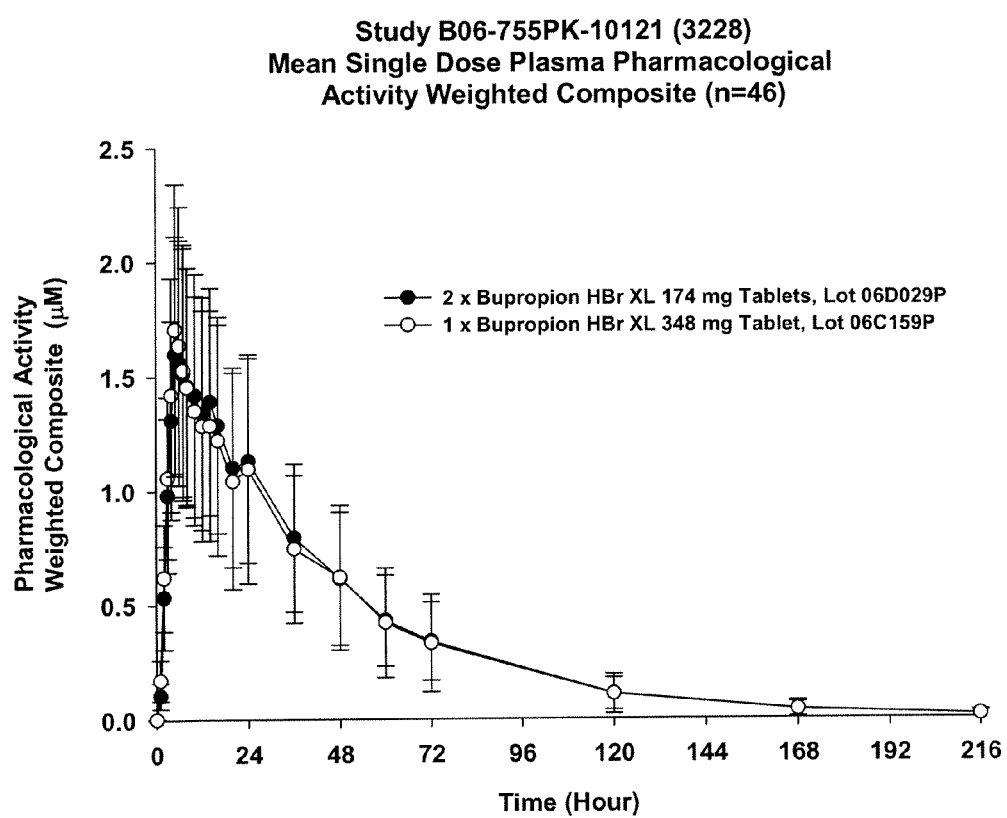
FIG. 85: Mean Plasma Pharmacological Activity Weighted Composite (PAWC)-Time Plot for Study B06-755PK-10121 (3228)
Figure 86:
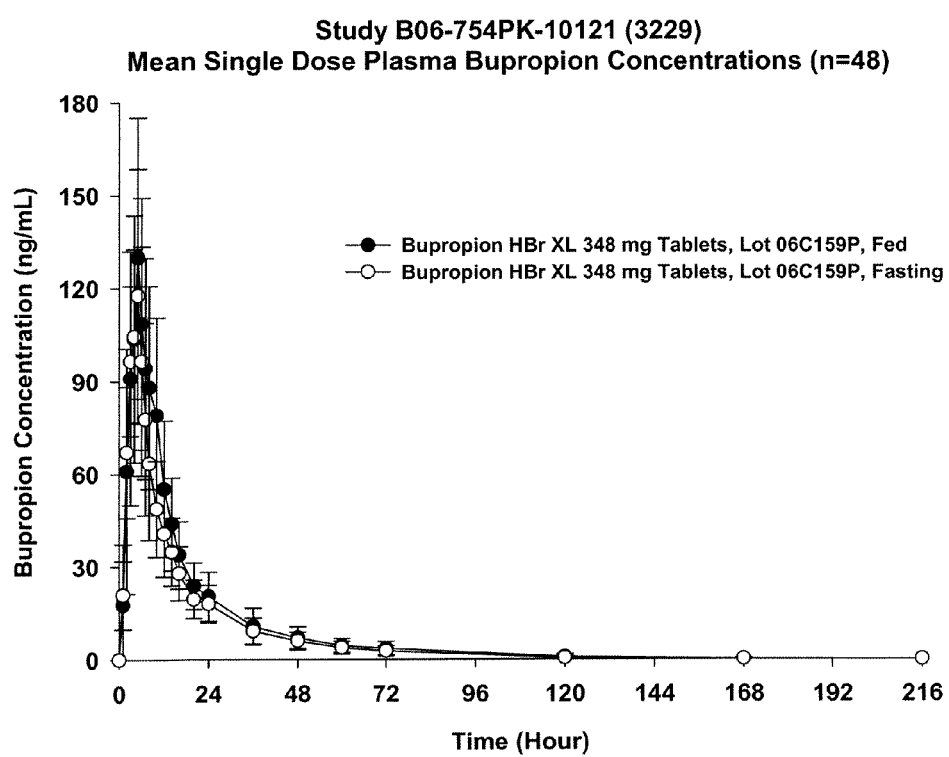
FIG. 86: Mean Plasma Bupropion Concentration-Time Plot for Study B06-754PK-10121 (3229)
Figure 87:
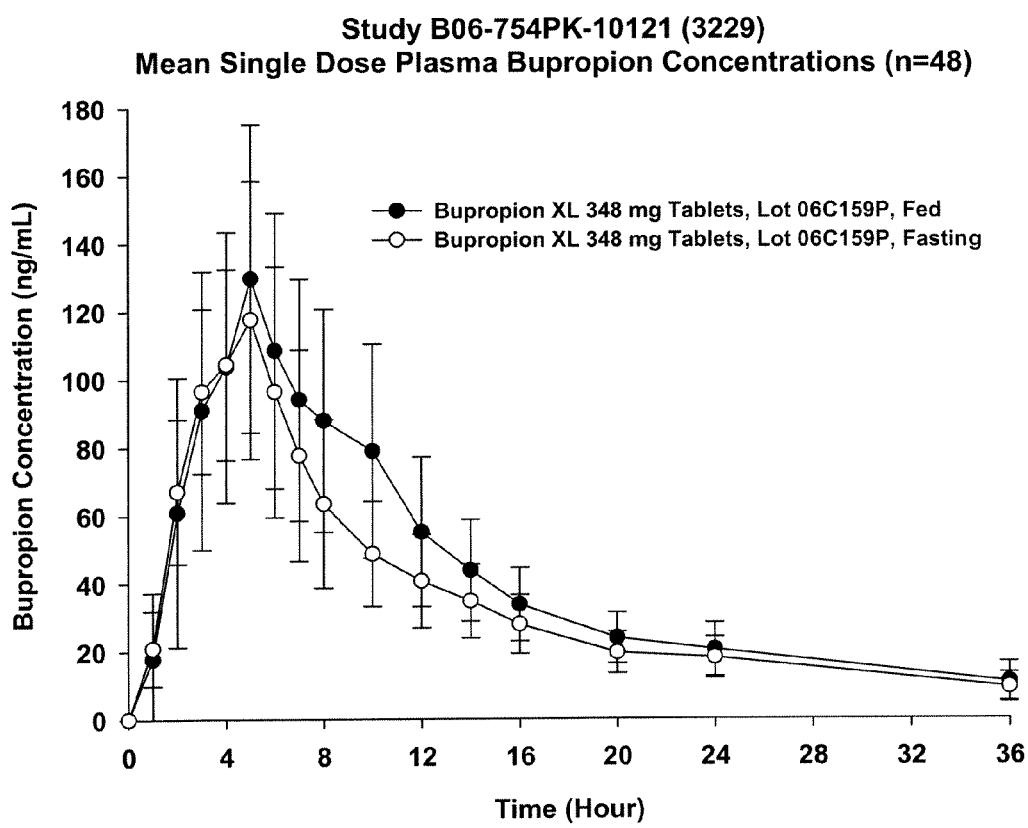
FIG. 87: Mean Plasma Bupropion Concentration-Time Plot for Study B06-754PK-10121 (3229)—Magnified Showing Only Datapoints From 0-36 Hours
Figure 88:
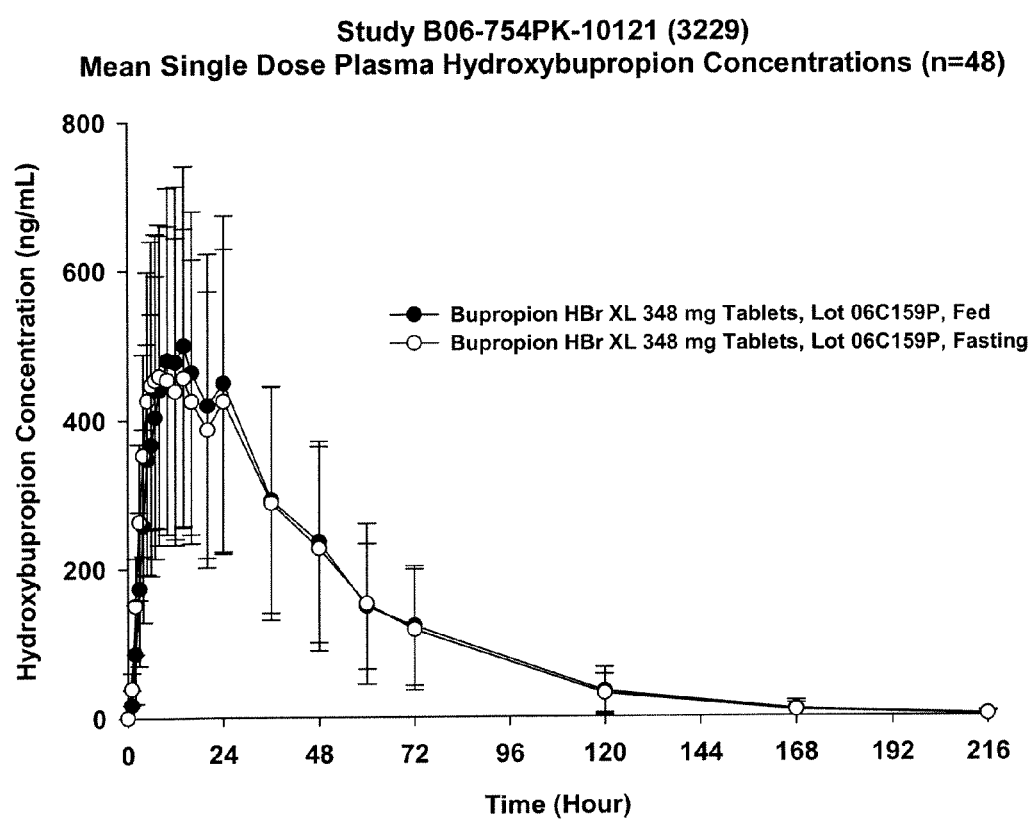
FIG. 88: Mean Plasma Hydroxybupropion Concentration-Time Plot for Study B06-754PK-10121 (3229)
Figure 89:
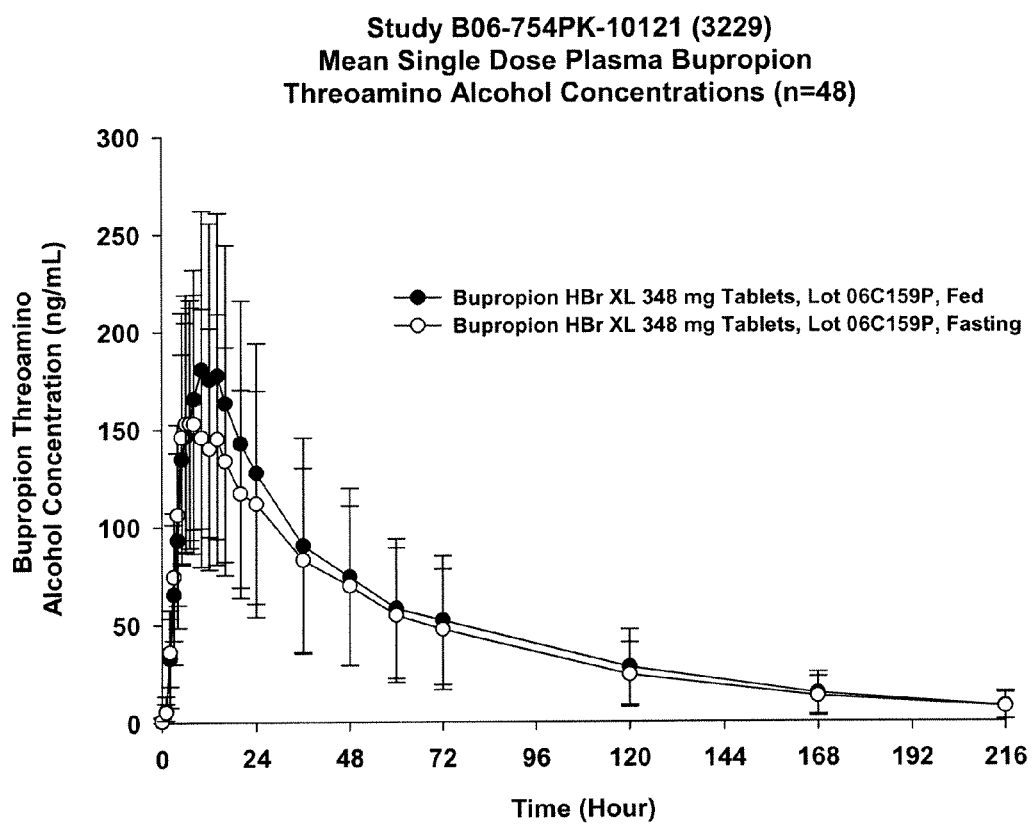
FIG. 89: Mean Plasma Bupropion Threoamino Alcohol Concentration-Time Plot for Study B06-754PK-10121 (3229)
Figure 90:
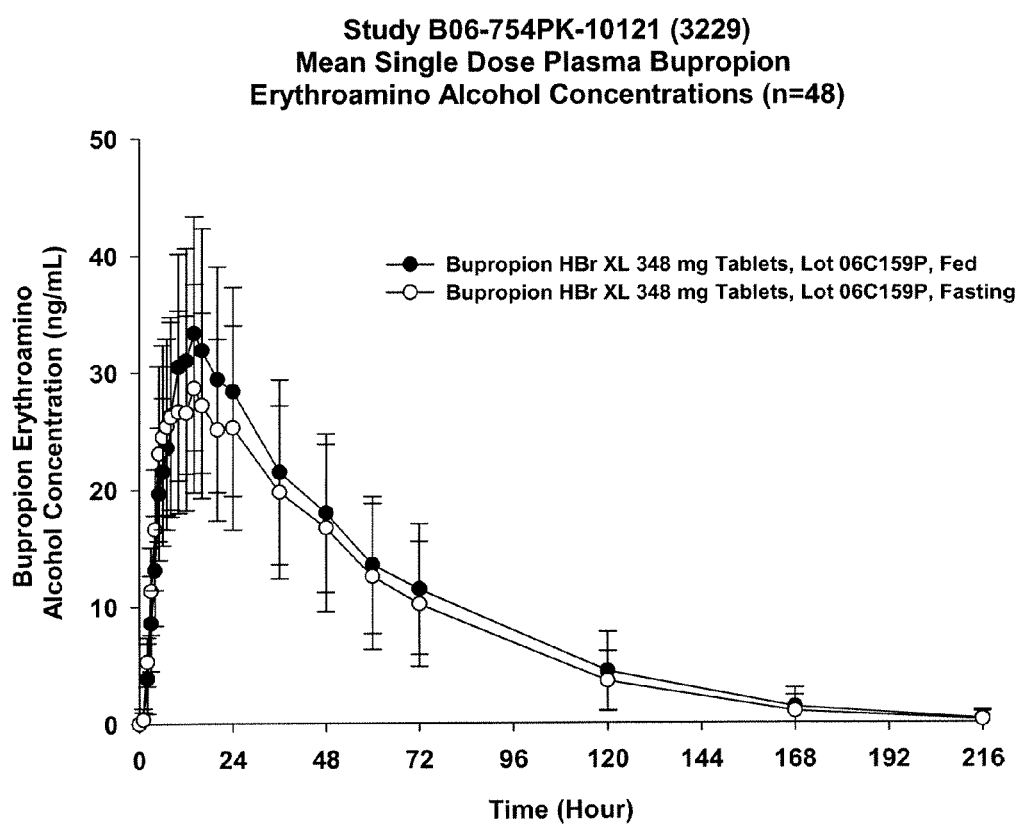
FIG. 90: Mean Plasma Bupropion Erythroamino Alcohol Concentration-Time Plot for Study B06-754PK-10121 (3229)
Figure 91:
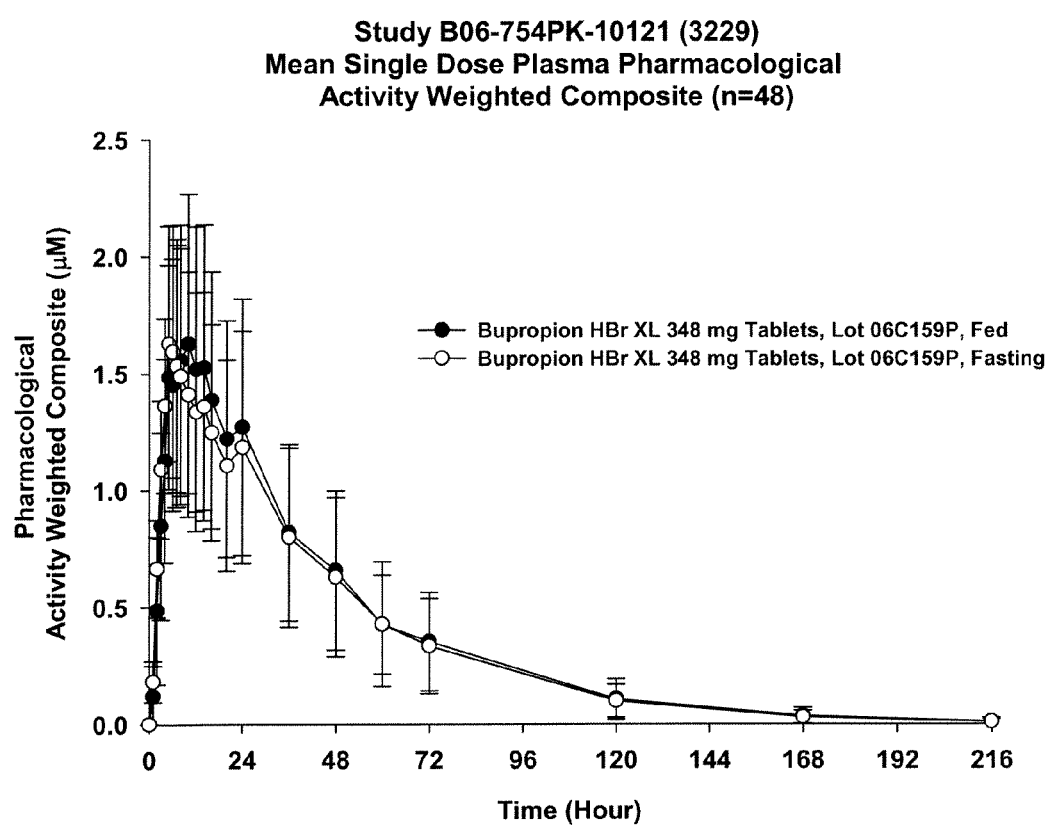
FIG. 91: Mean Plasma Pharmacological Activity Weighted Composite (PAWC)-Time Plot for Study B06-754PK-10121 (3229)
Figure 92:
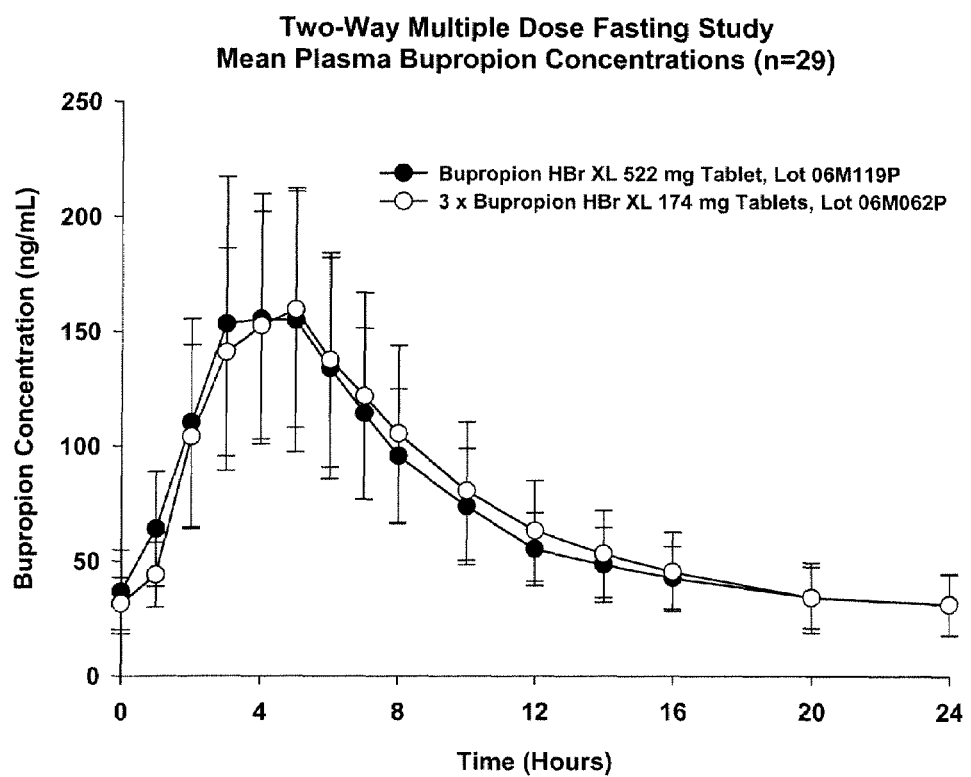
FIG. 92: Mean Plasma Bupropion Concentration-Time Plot For Study B06-802PK-10121 (AA40055)
Figure 93:
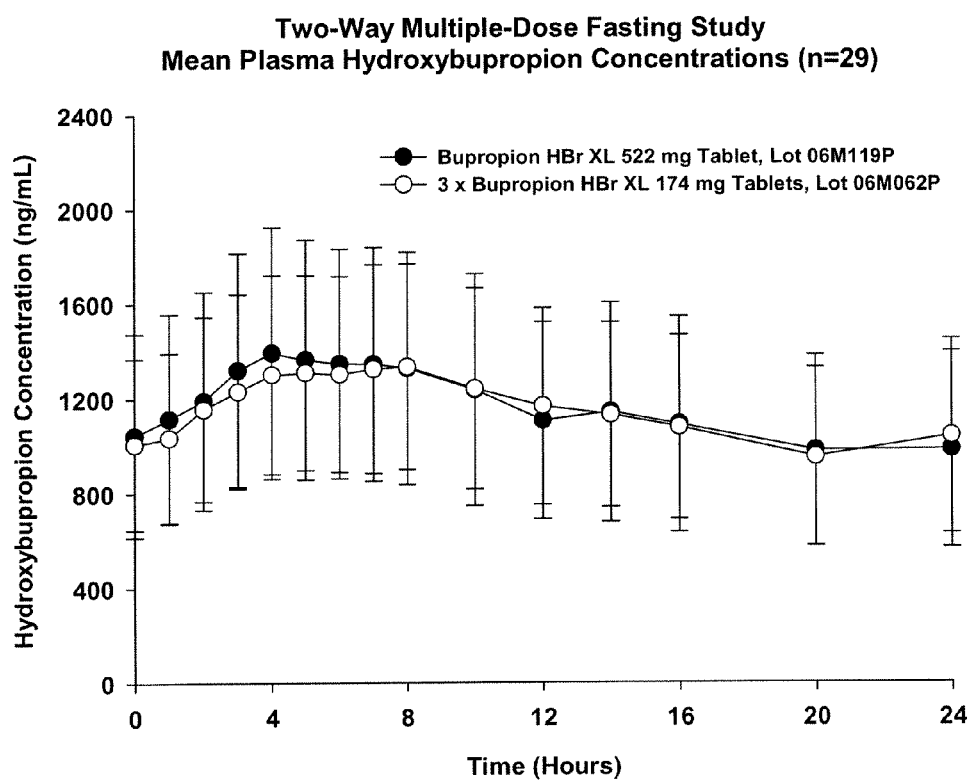
FIG. 93: Mean Plasma Hydroxybupropion Concentration-Time Plot For Study B06-802PK-10121 (AA40055)
Figure 94:
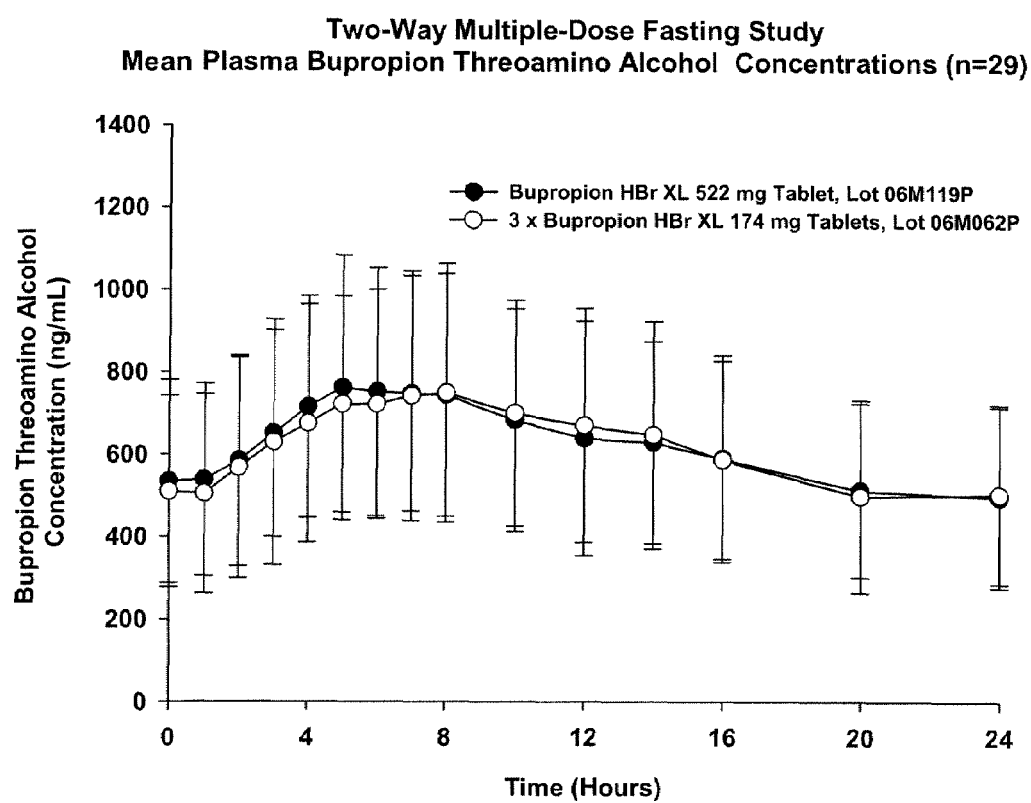
FIG. 94: Mean Plasma Bupropion Threoamino Alcohol Concentration-Time Plot For Study B06-802PK-10121 (AA40055)
Figure 95:
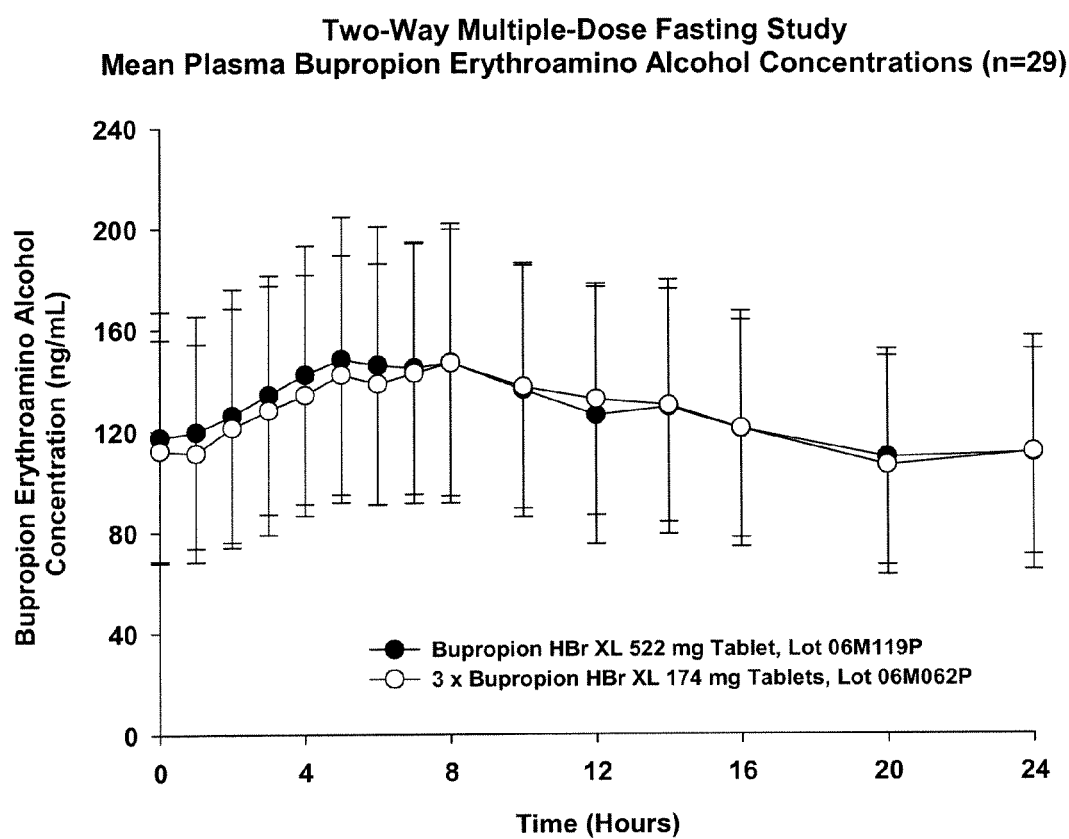
FIG. 95: Mean Plasma Bupropion Erythroamino Alcohol Concentration-Time Plot
Figure 96:
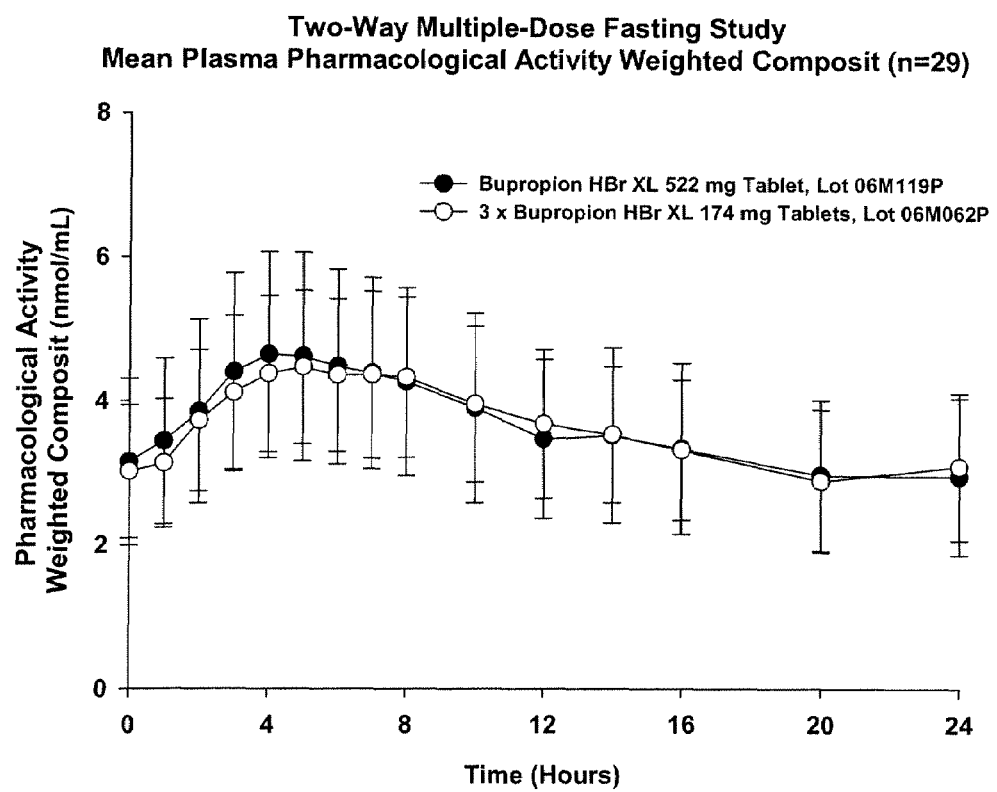
FIG. 96: Mean Plasma Pharmacological Activity Weighted Composite (PAWC)-Time Plot

Also, FIG. 68 contains comparative dissolution profiles for Bupropion HBr XL 348 mg final, Wellbutrin XL EC, tablets in different USP-3 media (SGF pH 1.2, acetate buffer pH 4.5 and phosphate buffer pH 6.8) compared against in-vivo data for Bupropion HCl 150 mg XL target (Lot 02A063) over a period of 16 hours.

Example 18

Assessment of Bupropion Hydrochloride and Bupropion Hydrobromide at Convulsive and Non-Convulsive Doses on Cortical EEG in Mice Initially a behavioral study was conducted to evaluate proconvulsant activities in CD-1 mice comparing bupropion hydrochloride and bupropion hydrobromide. The studies showed that the seizure activity in mice was more severe with bupropion hydrochloride than with bupropion hydrobromide. These studies, however, were limited to observable behavioral differences between the two salt forms of bupropion, and did not measure nonobservable differences (e.g. electroencephalographic activity). Therefore, EEG was employed to study the seizure inducing effects of these drugs and quantify the EEG effects of bupropion hydrochloride and bupropion hydrobromide at a range of doses.

The study evaluated the cortical mouse electroencephalogram (EEG) effects of bupropion hydrochloride and bupropion hydrobromide at five doses over the range of 100-150 mg/kg. A comparison of the effects of equimolar doses of bupropion hydrochloride and bupropion hydrobromide salts by EEG monitoring in the mouse was conducted.

Test system: 30 healthy female mice, of strain CD-1, having a bodyweight of 25-29 g, were acclimatized for a minimum period of 4 days and used for this study. Each animal, after allocation to groups, was identified by markings on the dorsal surface of the tail. Environmental conditions included a temperature of 22±3° C., and artificial lighting of 12 hours light/dark cycle. Routine activities such as cleaning, feeding and watering were performed according to the RCSI's current SOPS.

The diluent used was 0.9% sodium chloride solution. Storage temperature was at about 25° C. The appropriate amount of bupropion salt (bupropion hydrochloride or bupropion hydrobromide) was added to 0.9% sodium chloride solution to give the desired concentration.

| Test Item | Dose Level (mg/kg body wt) | Quantity of Salt (g) | Volume of Saline (mL) | Dose Volume (mL/kg) |
|---|---|---|---|---|
| Bupropion Hydrochloride | 100 | 0.05 | 5 | 10 |
| Bupropion Hydrochloride | 125 | 0.0625 | 5 | 10 |
| Bupropion Hydrochloride | 150 | 0.075 | 5 | 10 |

| Test Item | Dose Level (equivalent to mg of the HCl salt/kg body wt) | Quantity of Salt (g) | Volume of Saline (mL) | Dose Volume (mL/kg) |
|---|---|---|---|---|
| Bupropion Hydrobromide | 100 | 0.058 | 5 | 10 |
| Bupropion Hydrobromide | 125 | 0.0725 | 5 | 10 |
| Bupropion Hydrobromide | 150 | 0.087 | 5 | 10 |

Test Item Administration: The test item was administered intraperitoneally using a disposable syringe with a 1 ml syringe and 26 g needle. The route of administration was intraperitoneal. Animals were dosed once with the exception of those that received 100 mg/kg of each salt, which were re-tested with a higher dose (115 mg/kg) the following week. Bupropion hydrochloride and bupropion hydrobromide were initially tested at 150 mg/kg in side-by-side comparison. Subsequently they were tested at 125 mg/kg, 100 mg/kg and then (n 2 each) at 135 mg/kg and 115 mg/kg.

Protocol: Habituated mice were anesthetized with isoflurane, placed in a stereotaxic frame and maintained normothermic (36-37° C.) by means of a feedback-controlled mouse-designed homeothermic blanket (Harvard Apparatus). Under isoflurane anaesthesia, a midline skill incision was made over the skull and the skull exposed. Three partial craniectomies were performed: one overlying each temporal lobe and a third across the region overlying frontal cortex. Mouse-sized cranial EEG (E363/20, electrode with mounting screw and socket, Plastics One Inc) were affixed at each point. The electrode assembly was affixed to the skull with dental cement and then anaesthesia discontinued and the animal placed in the recording chamber for 30-60 minutes after recovery. Electrodes were then connected to a multichannel 363 Connector Cable system with SL6C 6 channel swivel commutator and baseline EEG recordings commenced using a Grass model Comet Portable 40-channel Digital EEG & Review System with Twin digital EEG in tandem with continuous digital video. After a baseline video-EEG recording for 10 minutes, mice were injected with bupropion hydrochloride or bupropion hydrobromide (100, 115, 125, 135 or 150 mg/kg, i.p.). Mice were run in parallel so that a hydrochloride mouse was injected within minutes of a hydrobromide mouse and recordings made simultaneously. Video-EEG was recorded for a period of one (1) hour. Afterwards, mice were returned to cages and then euthanized at 24 h and brains harvested.

Analysis: The duration of type IV polyspike high frequency (>1 Hz) high amplitude (>2×baseline) was determined for each mouse over the 1 h recording period.

Results: Generally, 150 mg/kg triggered strong seizure-like behavior within 5 minutes of injection with either salt. This was most pronounced during the early recording time (first 15-20 minutes) but episodic events continued through the hour of recording. However, for study pairs 1, 2 and 3 the convulsive behavior of the hydrobromide-treated mouse lasted longer than the hydrochloride-treated mouse (in some cases up to 30 min more). For, example the second hydrochloride-treated mouse ceased any seizure-like behavioural activity in about 30 mins after injection while we were still observing rearing and falling, forepaw running and turning in the hydrobromide-treated mouse at 60 minutes.

EEG: At 150 mg/kg (n=4 per salt) essentially no seizure EEG was detected. Very brief (2-3 s) bursts were detected within the first 5 minutes after injection that coincided with the onset of seizure-like behavior. No other EEG seizures were detected in any mice with either salt after that time despite ongoing "behavioural" seizures (e.g. convulsions).

Set 1HCl: EEG—no seizure EEG; HBr—single, very brief seizure

Set 2HCl: EEG—two very brief EEG bursts; HBr, no seizure EEG

Set 3HCl: EEG—brief burst of seizure; HBr, brief burst of seizure EEG

At 125 mg/kg (n=4 per salt) some significant seizure EEG was recorded. In this case there was a tendency for more seizure bursts in the bupropion hydrochloride animals. The quantitation of this is shown below.

| Total Duration (seconds) - Bupropion Hydrochloride | Total Duration (seconds) - Bupropion Hydrobromide |
|---|---|
| 290 | 30 |
| 130 | 25 |
| 115 | 0 |
| 0 | 0 |
| MEAN = 133.8 | MEAN = 13.8 |
| SD = 119.3 | SD = 16.0 |

P value t-test 0.093

| Number of Events - Bupropion Hydrochloride | Number of Events - Bupropion Hydrobromide |
|---|---|
| 12 | 2 |
| 8 | 1 |
| 10 | 0 |

-continued

| Number of Events - Bupropion Hydrochloride | Number of Events - Bupropion Hydrobromide |
|---|---|
| 0 | 0 |
| MEAN = 7.5 | MEAN = 0.75 |
| SD = 5.259911 | SD = 0.957427 |

P value t-test 0.045

No type IV seizure bursts of any significance were captured in any mouse with either salt at 100 mg/kg (n=2); 135 mg/kg (n=2); or 115 mg/kg (n=2).

There appears to be a small difference between the two salts in the number of seizure EEG bursts elicited at one dose: 125 mg/kg. The magnitude of this difference was compromised by the fourth pairing test because neither animal expressed seizure EEG. Cortical EEG recordings picked up very brief events at the 150 mg/kg dose but these occurred equally between the salts. No significant seizure EEG events were detected at the other doses tested. The explanation for why no seizure EEG was detected at the higher 150 mg/kg dose which caused profound convulsive behavior is not known. It may reside with subcortical pathway activation and inhibition. Depth electrode recordings might yield explanations for this lack of EEG result at the 150 mg/kg dose. An additional point is that even at the 125 mg/kg dose there appears to be a variable effect of the salts on EEG. The reason for this is not clear but we suggest the following: (i) Simple and inherent in-vivo biological variability; (ii) A CD1 mouse-specific genotype effect; (iii) The use of female mice (introducing, perhaps, oestrous cycle events); (iv) Higher than previous mouse study weight. All the CD1 mice we used were 25 g and above, which may be higher than was previously used for behavioural testing.

There may be a small difference in seizure EEG between the two salts of bupropion at one dose (125 mg/kg). However, the data reveal the convulsions triggered by this drug in mice do not commonly manifest as epileptiform seizure EEG as detected by cortically-mounted electrodes.

Example 19

Evaluation of Bupropion Hydrochloride and Bupropion Hydrobromide for Effects on the EEG Trace in the Rat A further comparison of the effects of equimolar doses of bupropion hydrochloride and bupropion hydrobromide salts by EEG trace monitoring in the rat was conducted.

The effects of the two bupropion salt forms hydrochloride and hydrobromide on central nervous system activity after intraperitoneal administration were evaluated by means of EEG trace monitoring in conscious rats. The method which detects electroencephalographic activity in conscious rats follows that described by Dürmüller et al., (2000) Vigilance-Controlled Quantified EEG in Safety Pharmacology, Current Protocols in Pharmacology Unit 10.6. The study was conducted at Porsolt & Partners Pharmacology, Research Laboratory, Z. A. des Suhards—B.P. 9, 53940 Le Genest-Saint-Isle, France.

Materials and General Methods:

Substances: The formulation excipient used was physiological saline (Laboratoire Aguettant). The bupropion hydrochloride salt and bupropion hydrobromide used were from Biovail Technologies (Ireland) Ltd., and provided as white powders and dissolved in physiological saline. All substances were stored in a dry, dark, controlled access area and maintained at a controlled ambient temperature of about 20±3° C. The vehicle solutions were stored at about +4° C. The substances were administered in a volume of 5 ml/kg body weight. The doses of bupropion hydrochloride are expressed in mg/kg of salt. The doses of bupropion hydrobromide are expressed in mg/kg of the bupropion hydrochloride molar equivalent (correction factor=1.16). The substances were dissolved in physiological saline and prepared freshly at each day of experimentation.

Test systems: The rats used were male Rj: Wistar (Han) rats, weighing from about 280 g to 324 g at the time of implantation. They were supplied by Elevage Janvier, 53940 Le Genest-Saint-Isle, France. The characteristics of the animals used (age, species and strain) are comparable with those described in the scientific literature. Upon delivery to the laboratory, the animals were housed in groups of 5 animals maximum, in macrolon cages (44×28×19 cm) containing wood litter (Litalabo—SPPS, 95100 Argenteuil, France). The animals had free access to food (Code 113—SAFE, 89290 Augy, France) and tap water. The animal house was maintained under artificial lighting (12 hrs) from 7:00 to 19:00 in a controlled ambient temperature of about 21±3° C. and relative humidity maintained at from about 30% to about 80%. After implantation, the animals were kept individually in macrolon cages (30×18×19 cm) in a separate room for implanted animals under the same environmental conditions as before. Except during the test sessions, the animals had free access to food (Code 113) and tap water. The animals were identified by marking the connector fixed on the animal's head with an indelible pen. Rats were sacrificed at the end of the experiments by lethal injection of pentobarbital (>100 mg/kg i.p.). Animals were not submitted to necropsy. There is no reason to expect that contaminants were present in the feed, water or bedding at levels capable of interfering with the results of the tests. No checks were performed for this particular study.

For the EEG signal acquisition, the software IOX2 and for the visual off-line analysis, the software ECG_auto (both from EMKA Technologies, France) were used.

Experimental Procedure:

Electrode implantation procedure: Implantation surgery was carried out under aseptic conditions. Rats, anesthetized with sodium pentobarbital (60 mg/kg i.p., plus supplementary doses of from about 5 mg/kg to about 10 mg/kg to maintain anesthesia until surgery completion) were implanted with 2 surface EEG electrodes, comprised of miniature titanium screws, placed bilaterally over the frontal-parietal cortex and 2 depth electrodes, comprised of twisted platinum-iridium wires, placed stereotaxically into the hippocampus CA3 area (Paxinos and Watson coordinates interaural: AP +5.0 mm, L ±2.5 mm, V +7.0 mm). An additional screw, placed over the right occipital cortex, served as ground electrode. The electrodes were connected to small plugs and the whole assembly was secured on the skull with dental acrylate. Following surgery, implanted animals were kept in individual macrolon cages (30×18×19 cm and were allowed at least 10 days to recover. A total of 27 rats were implanted.

Apparatus: For the EEG recording, the animals were placed in rectangular Plexiglas cubicles (30×10×25 cm) mounted on treadmills. Five recording units were run in parallel. A turning commutator was attached above the centre of each cubicle, about 30 cm above walking level. On one side, it was connected via an electrically shielded multicore cable to the animal and on the other side to the signal conditioning system (Coulbourn Model V75-01). The system filters were set for all channels to high pass 1 Hz and low pass 150 Hz, respectively. The amplification levels were kept at from 1000× to 10000×. The EEG signals were acquired and processed on a PC (DELL GX620-2800) installed with a 16 channel 200 kHz/12-bit AD acquisition card (NI PCI-6023E). This PC was integrated in a local network (Ethernet), which also included a PC for the data analysis, and a CD writer for data storage.

Testing procedure: Before beginning of the testing procedure, the rats were habituated in a 1 hour training session connecting to the recording cable and treadmill walking. A few minutes before launching the first recording, the animals were transferred from the holding to the testing room, connected to the recording cable, and placed into the recording cubicle. The EEG signals were briefly inspected for their quality and amplification levels adjusted as necessary. The animals were then given a 1 hour recording session without any treatment (baseline control) with intervals of 10 minutes with the treadmill alternatively turned on (walking speed: 1.8 m/min) and off. Immediately after the end of the baseline control recording, animals were administered (i.p.) bupropion hydrochloride or bupropion hydrobromide and recorded for another 2-hour session. 23 hours after the injection, the animals were given a 1 hour recording session under the same experimental conditions as the day before. Then the same recording procedure as on the previous day was followed. The same animal was always run on the same treadmill, and was connected to the same unit of the signal conditioning system. The treadmills were always operated with the same recording cables.

Data acquisition and analysis: The EEG signal was digitized at a sampling rate of 500 Hz/recording-channel and the data stored in raw data files. The analysis was performed off-line by visual inspection of the traces. The cortical and hippocampal traces were displayed individually for each rat on the computer screen at a time resolution of 10 sec/window. The windows then were scrolled and halted when a signal showed irregularity and the sequence was noted. Representative samples of pathologic signals were saved in pdf-format files for presentation in the report. Spike trains or spike-and-wave activity clearly exceeding baseline amplitudes and lasting at least one second were defined as seizure activity.

EEG Observations:

As shown in Tables 106 and 107: Isolated and infrequent atypical EEG events of probably non-pathologic character were observed on various occasions at all doses. Some events were observed before and after substance administration and do not appear directly to be linked to or predispose to seizure activity. In 3 rats, however, short seizure activity was observed in the hippocampus, in all cases before bupropion hydrochloride administration which may indicate that those rats were epilepsy prone. On the other hand, all 3 rats were administered substance the day before (10, 30 and 60 mg/kg respectively).

At 10 mg/kg, no seizure activity was observed in either cortex or hippocampus in any rat administered bupropion hydrochloride or bupropion hydrobromide.

At 30 mg/kg, apart from one rat with a short seizure activity in the hippocampus during the pre-administration phase (FIG. 97, rat Q0343, HCl group), no seizure activity was observed in either cortex or hippocampus in any rat administered bupropion hydrochloride or bupropion hydrobromide.

At 60 mg/kg, apart from one rat with a short seizure activity in the hippocampus during the pre-administration phase (FIG. 98, rat Q0337, HCl group), no seizure activity was observed in either cortex or hippocampus in any rat administered bupropion hydrochloride or bupropion hydrobromide.

Figure 99A:
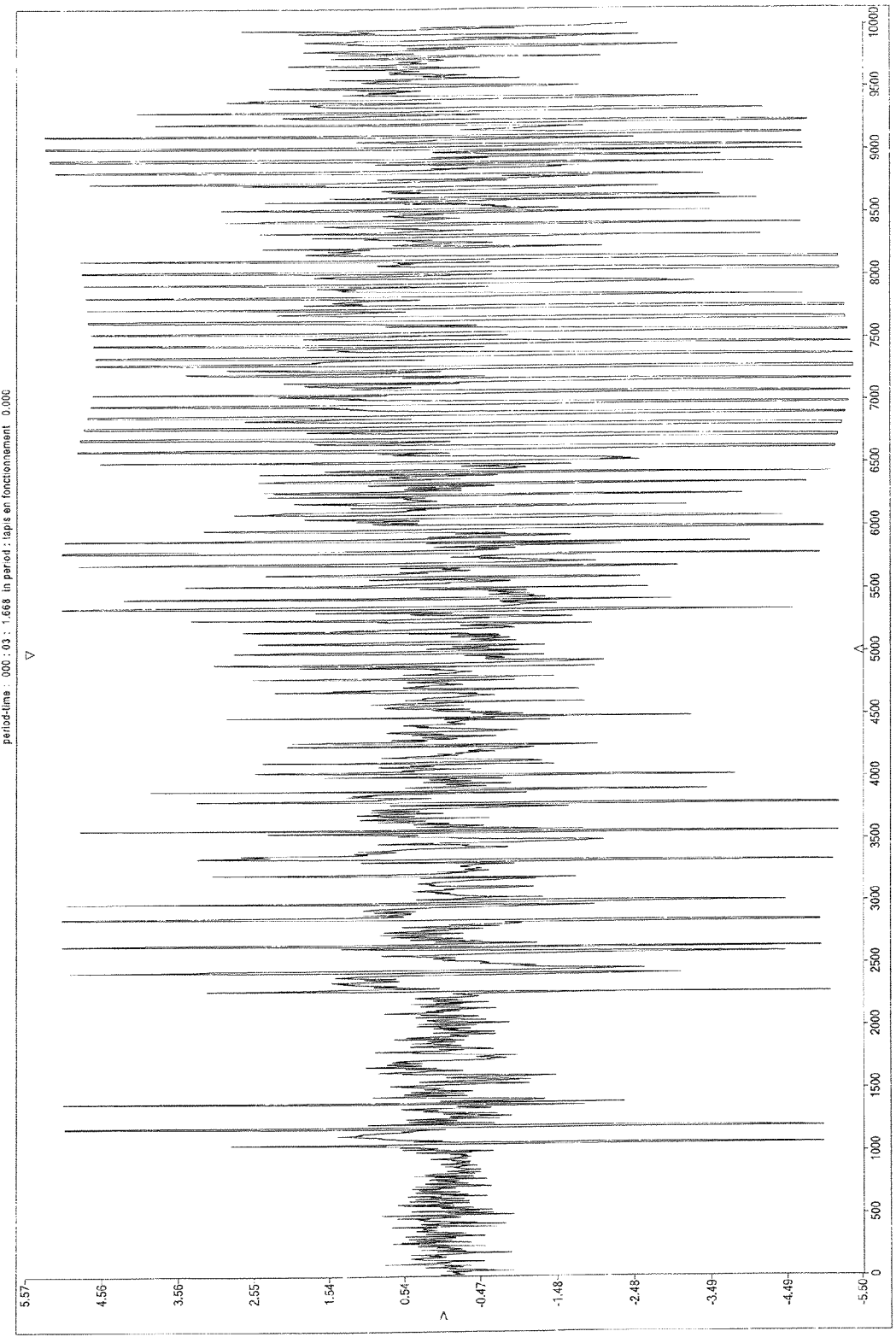
FIGS. 99 A and B: Seizure activity in the hippocampus during the pre-administration phase of 100 mg/kg dose of bupropion hydrochloride test.
Figure 99B:
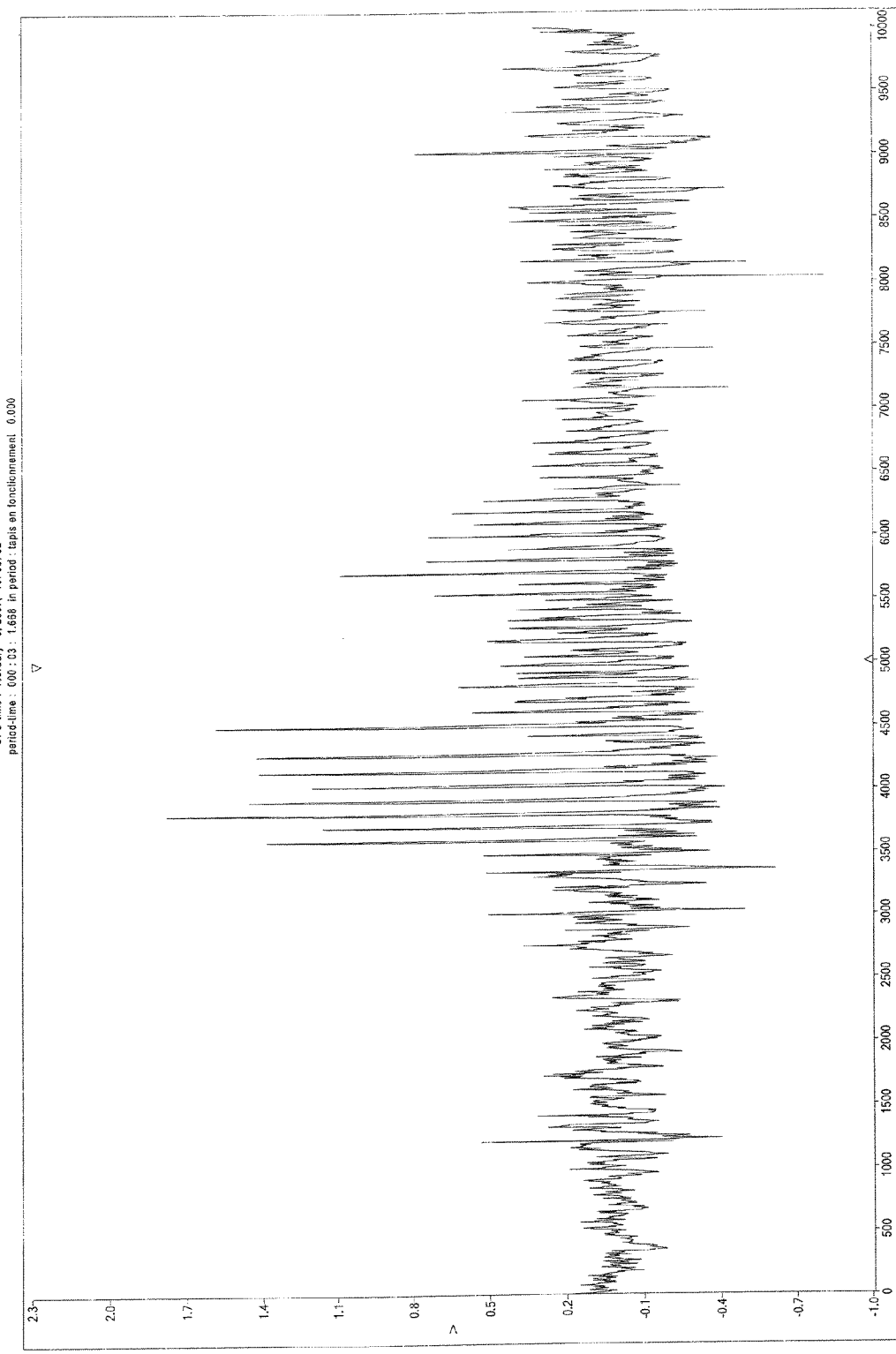
Figure 100A:
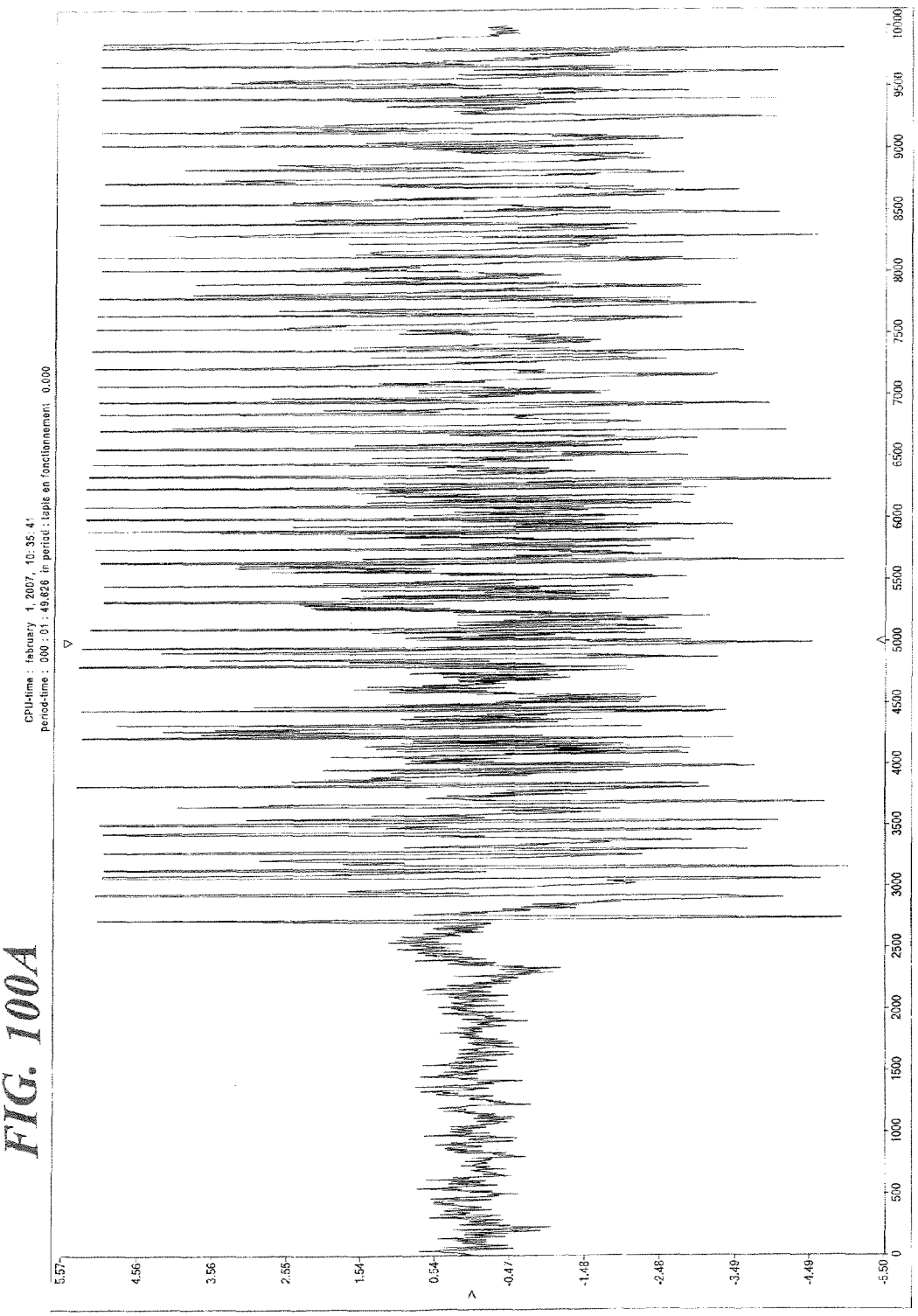
FIGS. 100 A and B: Seizure activity in the hippocampus during the pre-administration phase of 100 mg/kg dose of bupropion hydrobromide test.
Figure 100B:
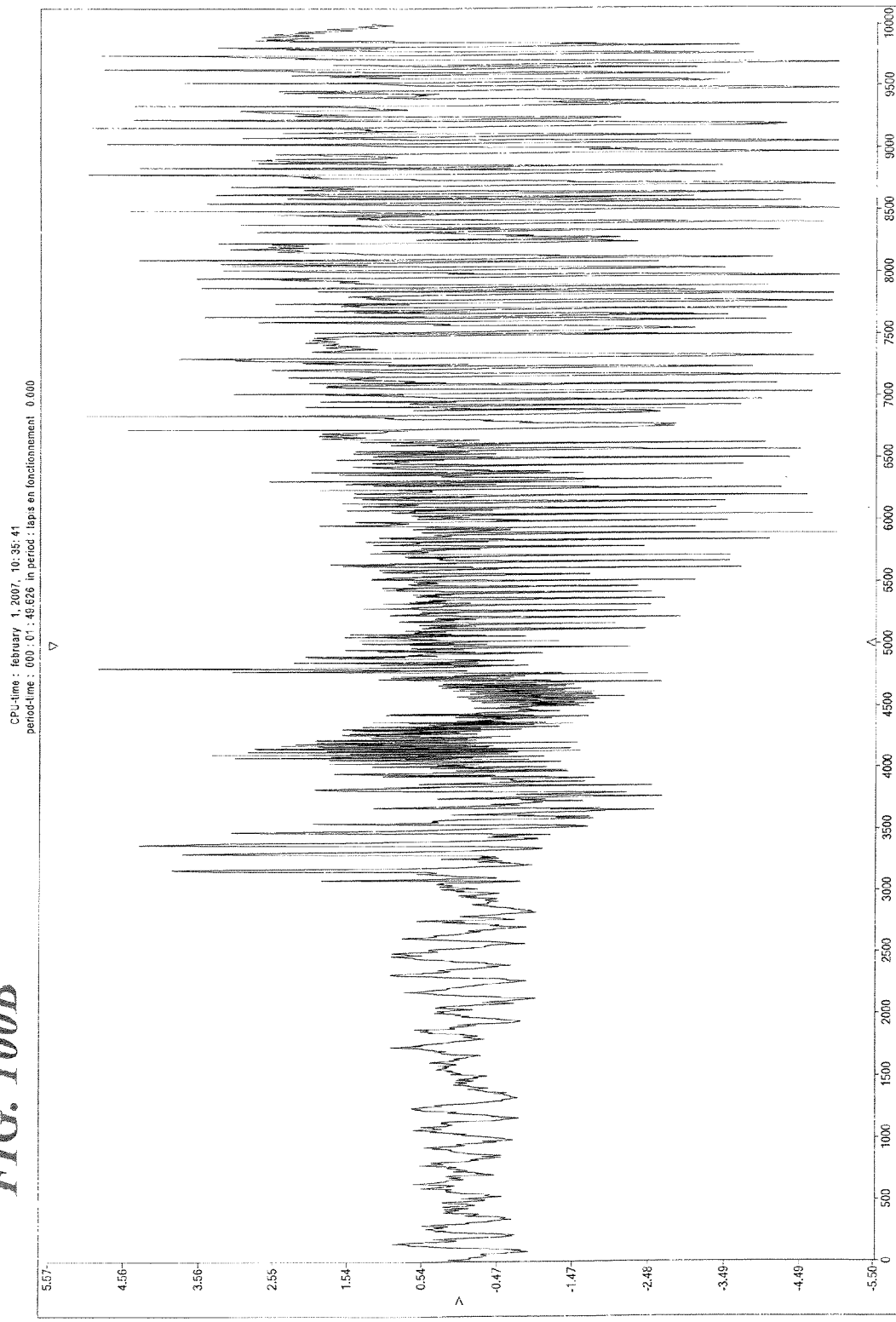

At 100 mg/kg, one rat was observed with a short seizure activity in the hippocampus during the pre-administration phase. In addition, all 10 rats administered bupropion hydrochloride had from 1 to 4 seizures, and 4/9 rats administered bupropion hydrobromide had 1 seizure (FIGS. 99 A and B rat Q0348, bupropion hydrochloride group; FIGS. 100 A and B rat Q0352, bupropion hydrobromide group).

Seizures generally started in the cortex and were shorter in the hippocampus than in the cortex with both salt forms. Seizure onset delay was very short for both salt forms, approximately 3 minutes on the average for the hydrochloride salt and approximately 2 minutes for the hydrobromide salt. Seizure duration was from 15 to 50 seconds in the cortex. Comparing to the first seizure phase, there was no clear difference in the mean seizure duration between the two salt forms in both the cortex and the hippocampus (Tables 108 and 109). Taking the multiple occurrences of seizures into account, the overall seizure duration of the bupropion hydrochloride group was longer than that of the bupropion hydrobromide group.

Figure 97:
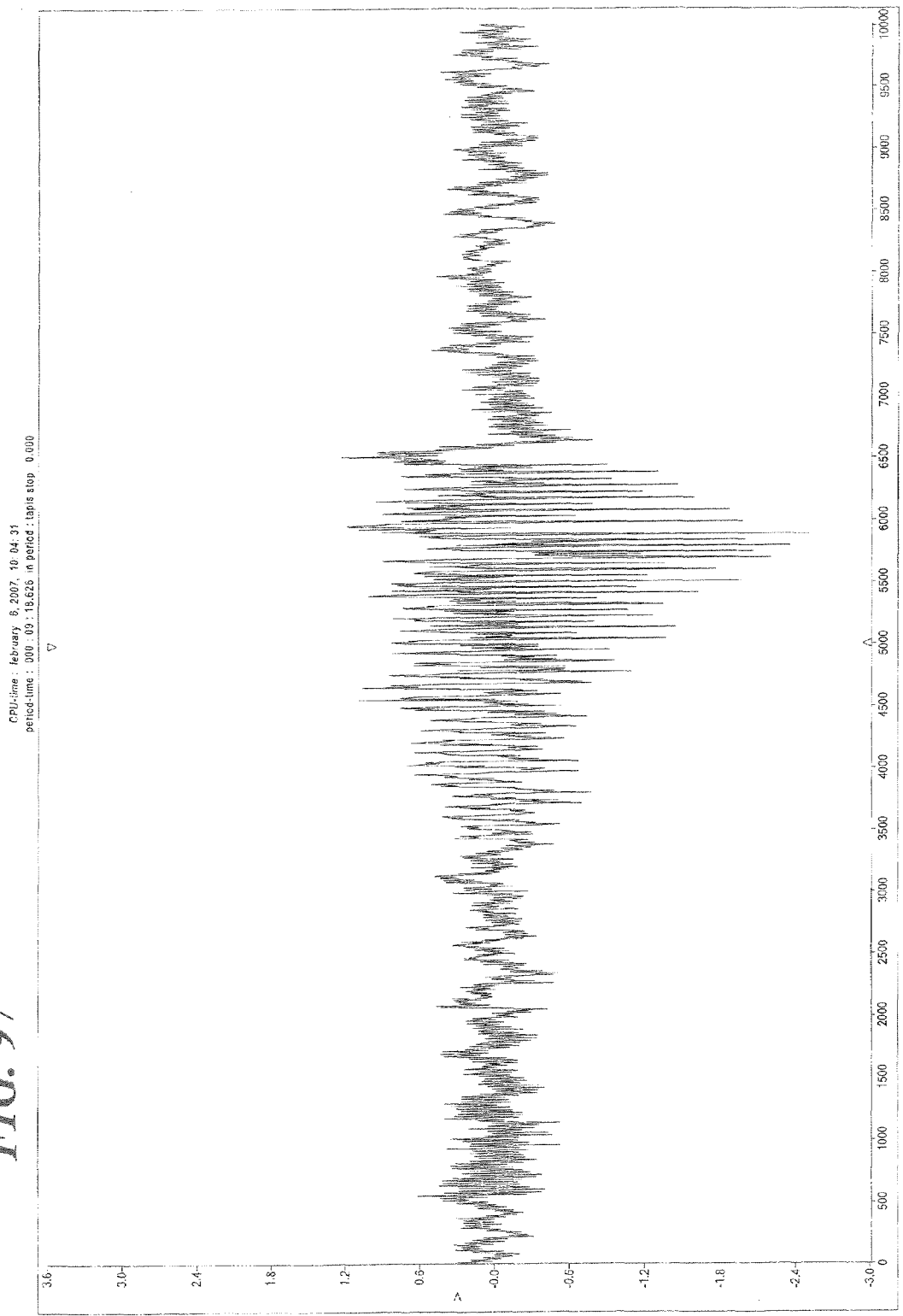
FIG. 97: Seizure activity in the hippocampus during the pre-administration phase of 30 mg/kg dose test.
Figure 98:
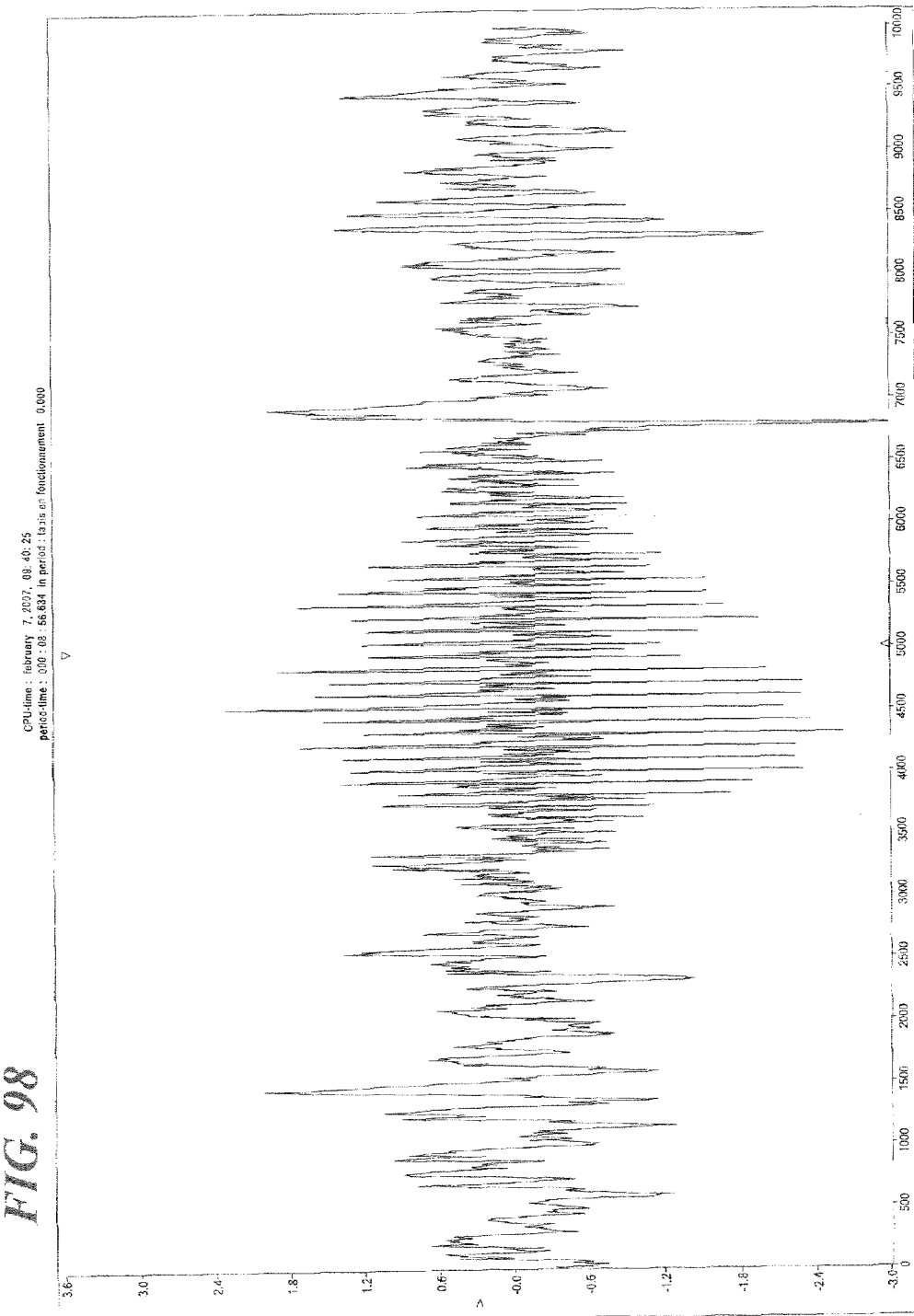
FIG. 98: Seizure activity in the hippocampus during the pre-administration phase of 60 mg/kg dose test.

EEG Trace monitoring in the rat: FIGS. 97 and 98 show traces of 10 seconds of hippocampal activity. The amplitude scales are expressed in volts [V]. In FIG. 97, hippocampal seizure activity of about 3 seconds duration in rat Q0343 is shown and in FIG. 98, a similar activity in rat Q0337. FIGS. 99 A and B show traces of 10 seconds of cortical (FIG. 99A) and hippocampal (FIG. 99B) activity. The amplitude scales are expressed in volts [V]. The initial phase of seizure activity in both the cortex and hippocampus in rat Q0348 is shown. The rat was administered bupropion hydrochloride at 100 mg/kg. FIGS. 100 A and 100B show traces of 10 seconds of cortical (FIG. 100 A) and hippocampal (FIG. 100 B) activity. The amplitude scales are expressed in volts [V]. The initial phase of seizure activity in both the cortex and hippocampus in rat Q0352 is shown. The rat was administered bupropion hydrobromide at 100 mg/kg.

Behavioural Observations:

As shown in Tables 106 and 107: At 10 mg/kg, no abnormal behavior was observed apart from one rat in the bupropion hydrobromide group which had a short lasting facial clonus while being connected to the recording system. Since it happened before launching the data acquisition, that event was not captured by the EEG.

At 30 mg/kg, all rats administered the bupropion hydrochloride salt, but none the bupropion hydrobromide salt, showed stereotypes/hyperactivity.

At 60 mg/kg, all rats administered either the bupropion hydrochloride or bupropion hydrobromide salt showed stereotypies/hyperactivity. One rat in the bupropion hydrobromide group had a fatal whole body clonus immediately after administration before being connected to the recording system. Since it happened before launching the data acquisition, that event was not captured by the EEG.

At 100 mg/kg, all rats administered either the bupropion hydrochloride or bupropion hydrobromide salt showed stereotypies/hyperactivity. The convulsions expressed by either form of bupropion appeared as facial clonus with or without additional rearing and forelimb clonus. The difference in the number of rats having seizures was statistically significant ($p<0.05$) (Table 108).

The results of this study show that bupropion hydrobromide has a lower potency for inducing convulsions compared with bupropion hydrochloride. In contrast to bupropion hydrochloride, the bupropion hydrobromide salt form induced fewer convulsions in fewer animals. The behavioral convulsions were mild, and were accompanied by electrical seizures activity. The short seizure activities observed in the hippocampi of 3 rats are most likely incidental findings, since they occurred in an apparent random fashion. There were, however unexpected immediate reactions observed in one rat administered 10 mg/kg and one rat administered 60 mg/kg bupropion hydrobromide which may ask for further testing.

Example 20

Convulsant Activity of Hydrochloride and Hydrobromide Salts of Bupropion

I.

Two studies were performed to investigate the relative proconvulsant properties of the two bupropion salts. In the first instance a range finding study was performed to establish the appropriate dose range for the main study. In each study the mice were divided into two dose groups and injected intraperitoneally with either bupropion HCl or bupropion HBr.

Post-treatment, mice were continuously observed for a period of 120 minutes followed by periodic observation at 135 minutes, 150 minutes, 165 minutes, 180 minutes, 210 minutes, 240 minutes, 300 minutes and 24 hours for incidence and intensity of clonic convulsions. A clonic convulsion was defined as a stiffening of the animal followed by jerking movements. The convulsions were classified as mild, moderate and severe according to the following descriptions.

Mild: Head and tail slightly extended and little jerking

Moderate: Head and tail fully extended with some jerking

Severe: Head and tail fully extended with strong jerking

Range Finding Study

The CD-1 mice were divided into dose groups (N=3/dose group) and injected intraperitoneally with the following doses of Bupropion HCl 75, 100, 125 or 150 mg/kg with a parallel series of dose groups administered with an equimolar dose range of Bupropion HBr. Post-treatment findings recorded included continuous observation for 120 minutes for evidence of clonic convulsions, and intermittent (fixed) observations for 24 hours for other signs, including tonic convulsions, movement, activity, paralysis, gait and evidence of recovery.

Main Study

The CD-1 mice were divided into dose groups (N=10/dose group) and injected intraperitoneally with the following doses of Bupropion HCl 100, 125 or 150 mg/kg with a parallel series of dose groups administered with an equimolar dose range of Bupropion HBr. Post-treatment, mice were continuously observed for a period of 120 minutes for incidence and intensity of clonic convulsions.

Results

Range Finding Study

The Bupropion HBr had an apparently higher threshold (125 mg/kg) for tonic convulsions than Bupropion HCl group (100 mg/kg) and a tendency to recover more quickly from other treatment-related signs. It was found that the incidence and intensity of clonic convulsions provided a quantal basis for comparison of the two treatments and are summarized in the Table below.

Incidence and Intensity of Clonic Convulsions in CD-1 Mice Dosed Intraperitoneally with Bupropion HCl or Bupropion HBr (Range-Finding Study, N=3/Dose Group).

| Dose (mg/kg)§ | Mean Number of Convulsions/Mouse | |
|---|---|---|
| | Bupropion HCl | Bupropion HBr |
| 75 | 0 | 0 |
| 100 | 1.0 (2/3)* | 0 |
| 125 | 6.0 (3/3)* | 8.0 (3/3)* |
| 150 | 32.0 (3/3) | 11.0 (3/3)* |

§Dose level is quoted as Bupropion HCl. Bupropion HBr is dosed at equimolar levels
*Numbers in parentheses are numbers of mice that had convulsions in each dose group.

Main Study

Post-treatment, mice were continuously observed for a period of 120 minutes for incidence of clonic convulsions, as shown in the Table below Incidence and Intensity of Clonic Convulsions in CD-1 Mice Dosed Intraperitoneally with Bupropion HCl or Bupropion HBr (Second Study, N=10/Dose Group).

| Dose (mg/kg)§ | Mean Number of Convulsions/Mouse | |
|---|---|---|
| | Bupropion HCl | Bupropion HBr |
| 100 | 0 | 1.0 (3/10)* |
| 125 | 16.0 (10/10)* | 14.3 (8/10)* |
| 150 | 82.7 (10/10)* | 57.3 (10/10)* |

§Dose level is quoted as Bupropion HCl. Bupropion HBr is administered at equimolar levels
*Numbers in parentheses are numbers of mice that had convulsions in each dose group.

Combined Studies

The pooled data for the two studies for the incidence of clonic convulsions is shown in the table below:

Incidence and Intensity of Clonic Convulsions in CD-1 Mice Dosed Intraperitoneally with Bupropion HCl or Bupropion HBr (Pooled Data N=13/Dose Group).

| Dose (mg/kg)§ | Mean Number of Convulsions/Mouse | |
|---|---|---|
| | Bupropion HCl | Bupropion HBr |
| 100 | 0.2 (2/13)* | 0.8 (3/13)* |
| 125 | 13.7 (13/13)* | 12.8 (11/13)* |
| 150 | 71.0 (13/13)* | 46.6 (13/13)* |

§Dose level is quoted as Bupropion HCl. Bupropion HBr is administered at equimolar levels
*Numbers in parentheses are numbers of mice that had convulsions in each dose group.

The Table below shows the pooled data for severity of clonic convulsions.

Intensity of Clonic Convulsions in CD-1 Mice Dosed Intraperitoneally with Bupropion HCl or Bupropion HBr (Pooled Data N=13/Dose Group).

| | Mean Intensity of Convulsions/Mouse % of Total | |
|---|---|---|
| Dose (mg/kg)[§] | Bupropion HCl | Bupropion HBr |
| 100 | | |
| Severe | 66.7 | 0.0 |
| Moderate | 33.3 | 10.0 |
| Mild | 0.0 | 90.0 |
| 125 | | |
| Severe | 71.9 | 47.3 |
| Moderate | 10.1 | 31.7 |
| Mild | 18.0 | 21.0 |
| 150 | | |
| Severe | 79.0 | 53.0 |
| Moderate | 12.2 | 25.7 |
| Mild | 8.8 | 21.3 |

[§]Dose level is quoted as Bupropion HCl. Bupropion HBr is administered at equimolar levels From the above results it is clear that the threshold dose for induction of clonic convulsions for both salts is approximately 100 mg/kg (as bupropion HCl). At this level due to the low number of convulsions observed per mouse it is difficult to discern meaningful differences between the two salt forms although we do observe attenuation of the severity of the convulsions with the HBr salt.

At the 125 mg/kg dose level a 6.6% reduction in the mean number of convulsions per mouse and a 15.4% reduction in the number of convulsant mice is observed. Furthermore it would seem that at this level the HCl salt has reached the top of its dose response curve whereas this is not the case for the HBr salt. As observed at the 100 mg/kg dose level the severity of the convulsions is also attenuated with a 34.2% reduction in the % of severe convulsions observed.

At the 150 mg/kg dose level both salt forms are at the top of their dose response curves. However the reduction in the mean number of convulsions per mouse is even more marked than at the 125 mg/kg dose level with a 34.4% reduction in the number of convulsions observed. Again the severity of the convulsions is attenuated with a 32.9% reduction in the % of severe convulsions observed.

II.

A statistical analysis was also conducted to investigate the relative proconvulsant properties of the two bupropion salts: bupropion hydrochloride and bupropion hydrobromide. Post-treatment, mice were continuously observed for a period of 120 minutes for incidence and intensity of clonic convulsions. Number of convulsions and the intensity of the convulsions were recorded. The data is presented below.

Number of Convulsions Per Mouse by Severity (Pooled Data N=13/Dose Group).

| | | Mean Number of Convulsions/Mouse (Total Number) | |
|---|---|---|---|
| Dose (mg/kg)* | Intensity of Convulsions | Bupropion HCl (N = 13) | Bupropion HBr (N = 13) |
| 100 | Severe | 0.15 (2) | 0.0 (0) |
| 100 | Moderate | 0.08 (1) | 0.08 (1) |
| 100 | Mild | 0.0 (0) | 0.69 (9) |
| 125 | Severe | 9.85 (128) | 6.08 (79) |
| 125 | Moderate | 1.38 (18) | 4.08 (53) |
| 125 | Mild | 2.46 (32) | 2.69 (35) |
| 150 | Severe | 56.08 (729) | 24.69 (321) |
| 150 | Moderate | 8.69 (113) | 12.00 (156) |
| 150 | Mild | 6.23 (81) | 9.92 (129) |

*Dose level is quoted as Bupropion HCl. Bupropion HBr is administered at equimolar levels Mild: Head and tail slightly extended and little jerking;

Moderate: Head and tail fully extended with some jerking;

Severe: Head and tail fully extended with strong jerking.

Statistical Analysis: Step 1: To detect general difference in the patterns of convulsion occurrence in terms of intensity between the bupropion hydrochloride and bupropion hydrobromide salts. The Cochran-Mantel-Haenszel test was performed and showed that the association between the salts (bupropion hydrochloride or bupropion hydrobromide) and severity of convulsions, controlling for dose level, was statistically significant ($p<0.0001$). The results indicated that, given any dose level, there was statistical evidence that the two salts had different patterns in terms of convulsion intensities.

Figure 101:
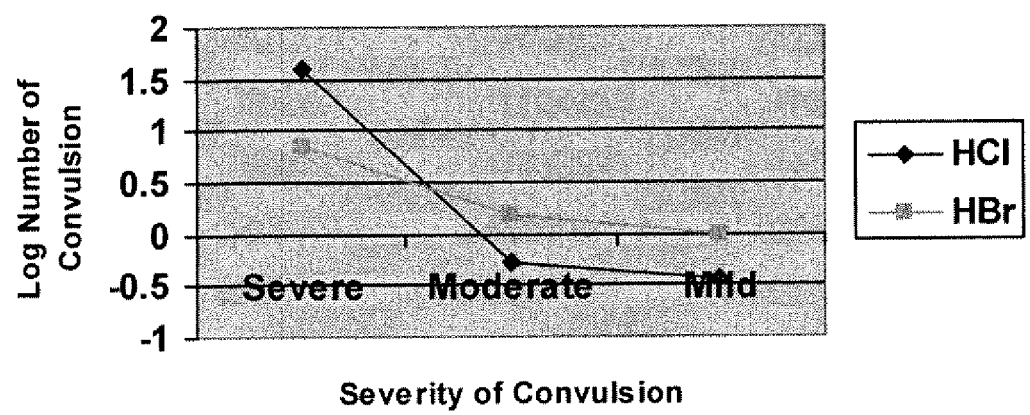
FIG. 101: Relative log number of convulsions, severe, moderate, or mild, in rats administered bupropion hydrobromide or bupropion hydrochloride is displayed

Step 2: To further investigate the patterns of convulsion occurrence using loglinear Poisson regression models. The number of convulsions was analyzed using the loglinear Poisson regression models with formulation, dose, and severity as predictors. With the main effects model (the model with formulation, dose and severity main effects only), it showed that, adjusted for dose and severity, the odds of number of convulsions of the bupropion hydrochloride group vs the bupropion hydrobromide group is $\exp(0.3436)=1.41$, or a 41% increase. This increase was statistically significant ($p<0.001$). Further investigations revealed that there is a significant interaction term between formulation and severity ($p<0.001$). While the bupropion hydrochloride group had more severe convulsions, the bupropion hydrobromide group had more mild and moderate convulsions. The relative log number of convulsions is displayed in FIG. 101.

In addition, the data can also be presented as the cumulative table. In all but one case (0.23 vs. 0.77, all in 100 mg/kg), the bupropion hydrochloride group had higher cumulative incidence rate of convulsions compared to the bupropion hydrobromide group. This is seen most clearly at the highest dose tested (150 mg/kg)

Number of Convulsions Per Mouse by Severity—Cumulative (Pooled Data N=13/Dose Group)

| | | Mean Number of Convulsions/Mouse | |
|---|---|---|---|
| Dose (mg/kg)* | Intensity of Convulsions | Bupropion HCl (N = 13) | Bupropion HBr (N = 13) |
| 100 | Severe | 0.15 | 0.0 |
| 100 | Severe + Moderate | 0.23 | 0.08 |
| 100 | All | 0.23 | 0.77 |
| 125 | Severe | 9.85 | 6.08 |

-continued

| Dose (mg/kg)* | Intensity of Convulsions | Mean Number of Convulsions/Mouse | |
|---|---|---|---|
| | | Bupropion HCl (N = 13) | Bupropion HBr (N = 13) |
| 125 | Severe + Moderate | 11.23 | 10.16 |
| 125 | All | 13.69 | 12.85 |
| 150 | Severe | 56.08 | 24.69 |
| 150 | Severe + Moderate | 64.77 | 36.69 |
| 150 | All | 71.00 | 46.61 |

*Dose level is quoted as Bupropion HCl. Bupropion HBr is administered at equimolar levels The main study showed that higher incidence of convulsions was observed in the bupropion hydrochloride group compared to the bupropion hydrobromide group. The increase was around 41% on average and was statistically significant ($p<0.001$). Furthermore, the bupropion hydrochloride group appeared to have much more severe convulsions in proportions compared to the bupropion hydrobromide group.

In terms of the cumulative incidence, the raw data showed very clear trends that the bupropion hydrochloride salt was consistently higher compared to the bupropion hydrobromide salt.

Example 21

Stability and Comparative Dissolution Studies

The stability of Bupropion HBr under various conditions and in certain embodiments of the invention was investigated and compared with Bupropion HCl. In addition, the dissolution profiles of Bupropion HBr XL tablets in various media were investigated. For example, the dissolution profiles of the 174 mg and 348 mg Bupropion HBr XL tablets were measured in the following media: 0.1 NHCl, water, acetate buffer (pH 4.5), phosphate buffer (pH 6.2), 5% ethanol in 0.1N HCl, 20% ethanol in 0.1N HCl, and 40% ethanol in 0.1NHCl. In addition, the dissolution profiles of the 522 mg Bupropion HBr XL tablets were measured in the following media: 0.1N HCl, 5% ethanol in 0.1N HCl, 20% ethanol in 0.1N HCl, and 40% ethanol in 0.1NHCl.

In the following stability studies, Bupropion HBr in the form of XL tablets were tested as per ICH guidelines under conditions of constant temperature and humidity for periods of 0, 3, 6, 9 and 12 months at 25 degrees C+/−2 degrees C. and 60+/−5% relative humidity (RH) and under accelerated conditions of 40 degrees C+/−2 degrees C. and 75+/−5% RH which allowed for the calculation/estimation of stability data at 18 months. The Bupropion HBr XL tablets were stored in bulk containers (LDPE bags and fiber drums) and in 7, 30 and 90-count HDPE bottles. The samples were exposed to controlled conditions of humidity and temperature in a stability chamber.

After exposure, the tablets were tested for physical description, moisture content by Karl Fischer, assay and impurities by HPLC, and dissolution properties after 3, 6, 9 and 12 months. The dissolution test was performed by placing the test sample in 900 ml of 0.1N HCl at 37 degrees C+/−0.5 degrees C. in an automated USP Dissolution Apparatus Type 1 (Basket) with stirring at 75 rpm. Samples and standard bupropion hydrobromide active were analyzed with a UV spectrophotometer at a wavelength of 252 nm.

The Bupropion HBr XL tablets used in both the stability and dissolution studies were prepared by granulating Bupropion HBr in a fluid bed using an aqueous solution of polyvinyl alcohol using top spray technology with a 0.8 mm nozzle. After granulation and drying the granules are screened through a 1.4 mm sieve and blended with glyceryl behenate lubricant (e.g. Compritol 888 ATO) in a blender to produce a bulk blend. The bulk blend is then pressed into tablets using a Fette 2200 tablet press.

The tablets were then coated in a tablet coater with a coating solution prepared by mixing a homogenized (DeBee homogenizer) mixture of dibutyl sebacate and polyethylene glycol 4000 in 190-200 proof ethyl alcohol in which has been incorporated ethylcellulose and polyvinylpyrrolidone (e.g. povidone) using a powder dispersion unit, and coated with carnuba wax.

In-vitro dissolution experiments were performed on 174 mg, 348 mg and 522 mg Bupropion HBr XL tablets using USP Type 1 apparatus with a rotational speed of 75 rpm, temperature of 37 degrees C.±0.5° C., 900 ml of dissolution media, and detection at UV wavelength of 252 nm. Dissolution media included 0.1N HCl (100%); Ethanol (5%) with 0.1N HCl (95%); Ethanol (20%) with 0.1N HCl (80%); and Ethanol (40%) with 0.1N HCl (60%). The dissolution experiments investigated the risks of alcohol-induced dose dumping on the noted dosage forms. Dissolution data was provided: after 2 hours for all dosage forms for 12 tablets in 0.1N HCl, 5% ethanol in 0.1 N HCl, 20% ethanol in 0.1 N HCl, and 40% ethanol in 0.1NHCl; after 16 hours for 6 of the 522 mg Bupropion HBr XL tablets in 0.1NHCl, and 40% ethanol in 0.1N HCl; and after 20 hours for 6 of the 174 mg and 348 mg Bupropion HBr XL tablets in 0.1 N HCl, and 40% ethanol in 0.1N HCl. In all cases, the dissolution profiles showed that the release rate profile of the Bupropion HBr drug product was slower in the presence of alcohol (e.g. 40% ethanol) when compared with the release rate profile of the same dosage form in 100% 0.1N HCl.

Results are shown below and in FIGS. 69-74, where Compound C is the intermediate bupropion degradation product 20U78, Compound E is the intermediate bupropion degradation product 827U76, and Compound F is the intermediate bupropion degradation product 852U77:

Bupropion HBr 174 mg/348 mg—Stability Data Evaluation

| Condition: | 25 degrees C./60% RH; |
|---|---|
| Time Points: | 0, 3, 6, 9, 12 months |

| | 174 mg | |
|---|---|---|
| Test Item | % Change/month | Total changes (%) in 18 months (as calculated) |
| Dissolution | | |
| 2 hours | +0.17% | +3.1% |
| 4 hours | +0.13% | +2.3% |
| 8 hours | −0.09% | −1.6% |
| 16 hours | — | — |
| Assay | | |
| 3-Chlorobenzoic Acid | +0.003% | +0.05% |
| Compound C | +0.0008% | +0.01% |
| Compound E | — | — |
| Compound F | +0.003% | +0.05% |
| Total Impurities | +0.007% | +0.13% |

| | 348 mg | |
|---|---|---|
| Test Item | % Change/month | Total changes (%) in 18 months (as calculated) |
| Dissolution | | |
| 2 hours | +0.12% | +2.2% |
| 4 hours | — | — |
| 8 hours | — | — |
| 16 hours | +0.06% | +1.1% |
| Assay | | |
| 3-Chlorobenzoic Acid | +0.003% | +0.05% |
| Compound C | +0.001% | +0.02% |
| Compound E | — | — |
| Compound F | +0.003% | +0.05% |
| Total Impurities | +0.007% | +0.13% |

Stability Data Comparison—Bupropion HCl vs. Bupropion HBr

The Bupropion HBr tablets (174, 348 & 522 mg dosages) were in the form of XL tablets as described above. The Bupropion HCl tablets (150 & 300 mg dosages) were made in the same manner as the Bupropion HBr tablets. The Bupropion HCl tablets had the same formulation as the Bupropion HBr tablets with the exception that the Bupropion HCl tablets had a moisture barrier coating surrounding the controlled release coating, and a different plasticizer in the coatings. The ingredients of the 2nd coat (i.e. moisture barrier coat) in the Bupropion HCl tablets were: Eudragit L30D 55 (film forming polymer, 2.4% total in 150 mg tablet; 1.9% total in 300 mg tablet) PEG 1450 (0.3% in 150 mg, 0.25% in 300 mg), silicon dioxide (0.9% in 150 mg; 0.7% in 300 mg), Triethyl citrate (0.12% in 150 mg; 0.097% in 300 mg) The plasticizer used in the coatings of the Bupropion HCl tablet was PEG1450 in the following amounts: Bupropion HCl 150 mg tablet: PEG1450 1.8% total (1.5% in 1st coat; 0.3% in 2nd coat); Bupropion HCl 300 mg tablet: PEG1450=1.2% total (0.95% in 1st coat; 0.25% in 2nd coat). The controlled release coating of the Bupropion HBr tablet had a plasticizer mix of dibutyl sebacate and PEG4000.

| Experimental specification limits 12 months results comparison (25 degrees C./60% RH) | |
|---|---|
| Assay: | 90%-110% of LC |
| 3-Chlorobenzoic Acid | NMT 0.7% |
| Related Compound C | NMT 0.3% |
| Related Compound E | NMT 0.4% |
| Related Compound F | NMT 1.0% |
| Total Impurities | NMT 2.5% |

| Stability Data Comparison at 12 months (25 degrees C./60% RH) | | | | |
|---|---|---|---|---|
| | Bupropion HCl | | Bupropion HBr | |
| Test | 150 mg | 300 mg | 174 mg | 348 mg |
| Assay | 94.7% | 97.5% | 98.3% | 97.9% |
| 3-Chlorobenzoic Acid | 0.14% | 0.13% | 0.04% | 0.04% |
| Compound C | 0.00% | 0.01% | 0.04% | 0.03% |
| Compound E | 0.01% | 0.01% | 0.01% | 0.01% |
| Compound F | 0.12% | 0.09% | 0.05% | 0.05% |
| Total Impurities | 0.38% | 0.35% | 0.21% | 0.21% |
| Dissolution | | | | |
| 2 hours | 2.3% | 3.2% | 32.5% | 33.7% |
| 4 hours | 24.8% | 26.6% | 61.8% | 59.2% |
| 8 hours | 72.5% | 67.0% | 95.6% | 90.4% |
| 16 hours | 95.5% | 94.1% | 99.8% | 98.6% |

| Experimental specification limits Prophetic 18 months results comparison (25 degrees C./60% RH) | |
|---|---|
| Assay: | 90%-110% of LC |
| 3-Chlorobenzoic Acid | NMT 0.7% |
| Related Compound C | NMT 0.3% |
| Related Compound E | NMT 0.4% |
| Related Compound F | NMT 1.0% |
| Total Impurities | NMT 2.5% |

| Prophetic Stability Data Comparison as calculated at 18 months (25 degrees C./60% RH) | | | | |
|---|---|---|---|---|
| | Bupropion HCl (Actual Testing) | | Bupropion HBr (Predicted Results) | |
| Test | 150 mg | 300 mg | 174 mg | 348 mg |
| Assay | 95.7% | 98.0% | 97.3% | 97.9% |
| 3-Chlorobenzoic Acid | 0.18% | 0.16% | 0.06% | 0.06% |
| Compound C | 0.01% | 0.02% | 0.04% | 0.04% |
| Compound E | 0.01% | 0.02% | 0.01% | 0.01% |
| Compound F | 0.12% | 0.11% | 0.06% | 0.06% |
| Total Impurities | 0.41% | 0.36% | 0.26% | 0.26% |
| Dissolution | | | | |
| 2 hours | 2.5% | 3.4% | 33.4% | 34.6% |
| 4 hours | 26.6% | 27.1% | 62.2% | 59.0% |
| 8 hours | 72.1% | 65.5% | 94.9% | 91.0% |
| 16 hours | 95.4% | 93.4% | 100.3% | 98.6% |

| Experimental specification limits 6 months results comparison (25 degrees C./60% RH) | |
|---|---|
| Assay: | 90%-110% of LC |
| 3-Chlorobenzoic Acid | NMT 0.7% |
| Related Compound C | NMT 0.3% |
| Related Compound E | NMT 0.4% |
| Related Compound F | NMT 1.0% |
| Total Impurities | NMT 2.5% |

Stability Data Comparison at 6 months
(25 degrees C./60% RH)

| Test | Bupropion HCl | | Bupropion HBr | | |
|---|---|---|---|---|---|
| | 150 mg | 300 mg | 174 mg | 348 mg | 522 mg |
| Assay | 96.6 | 98.3 | 98.03 | 97.21 | 98.08 |
| 3-Chlorobenzoic | 0.10 | 0.09 | 0.03 | 0.03 | 0.03 |
| Related Compound C | 0.02 | 0.02 | 0.02 | 0.02 | 0.04 |
| Related Compound E | 0.02 | 0.01 | 0.01 | 0.01 | 0.01 |
| Related Compound F | 0.12 | 0.10 | 0.05 | 0.05 | 0.04 |
| Total Impurities | 0.35 | 0.33 | 0.16 | 0.17 | 0.18 |
| Dissolution | | | | | |
| 2 hours | 2.40 | 3.50 | 32.28 | 33.87 | 32.26 |
| 4 hours | 25.79 | 28.77 | 61.96 | 59.96 | 55.30 |
| 8 hours | 73.88 | 69.47 | 95.87 | 91.72 | 85.09 |
| 16 hours | 96.02 | 94.60 | 99.93 | 98.44 | 98.96 |

Dissolution data was also obtained for Bupropion HCl tablets as above (150 mg and 300 mg) but with the Bupropion HCl tablets having only one controlled release coating (i.e. without the moisture barrier coating), as follows:

1 hour: 28-32%

2 hours: 50-55%

3 hours: 70-75%

4 hours: >85%

5 hours: approximately 100% in 0.1 N HCl using USP Apparatus I at 75 rpm and 37±0.5° C.

Example 22

Bioavailability/Pharmacokinetic (PK) Studies

Two-Way Crossover, Open-Label, Multiple-Dose, Fasting, Comparative Bioavailability Study of Bupropion HBr XL 348 mg Tablets Versus Wellbutrin XL® 300 mg Tablets in Normal, Healthy, Non-Smoking Male and Female Subjects. Study B06-756PK-10121 (3230)

In this study the rate and extent of absorption of Bupropion HBr XL 348 mg tablets was studied relative to Wellbutrin XL® 300 mg tablets under multiple-dose fasting conditions. The study showed that Bupropion HBr XL 348 mg tablets were equivalent to Wellbutrin XL® 300 mg tablets under multiple-dose fasting conditions.

Results are shown below and in FIGS. 75-79.

Study Design and Phase of Development:

Two-way crossover, randomized, steady-state, open-label, multiple-dose, fasting, relative bioavailability study.

Objectives:

The objective of this study was to compare the rate and extent of absorption of bupropion from a novel formulation of Bupropion HBr XL 348 mg Tablets versus the reference Wellbutrin XL® 300 mg Tablets at steady-state (SS) under fasting conditions.

Main Criteria for Inclusion:

Normal, healthy, non-smoking male and female subjects at ages of from 18 to 55 years.

Titration Product, Lot Number and Mode of Administration:

Following an overnight fast of at least 10 hours, 1 Wellbutrin XL® 150 mg Tablet, Lot #: 05K077P, administered orally with 240 mL of ambient temperature water on Days 1 to 3 of each study period.

Test Product/Investigational Product, Batch or Lot Number and Mode of Administration:

Following an overnight fast of at least 10 hours, 1 Bupropion HBr XL 348 mg Tablet, Lot #: 06C159P (potency value=97.0% of label claim), administered orally with 240 mL of ambient temperature water on Days 4 to 13 of the study period.

Reference Product, Batch or Lot Number and Mode of Administration:

Following an overnight fast of at least 10 hours, 1 Wellbutrin XL® 300 mg Tablet, Lot #: 06C090P (potency value=99.3% of label claim), administered orally with 240 mL of ambient temperature water on Days 4 to 13 of the study period.

Number of Subjects (Planned and Analyzed):

There were 48 subjects dosed in Period I, 40 of whom completed the study. The final pharmacokinetic and statistical analyses were performed on 38 of the 40 subjects who completed the study.

Blood Draw Timepoints:

During each study period, 19 blood samples were collected from each subject at the following timepoints:

Days 1, 10, 11, and 12:0.00 hour (pre-dose)

Day 13: 0.00 (pre-dose), 1.00, 2.00, 3.00, 4.00, 5.00, 6.00, 7.00, 8.00, 10.00, 12.00, 14.00, 16.00, 20.00, and 24.00 hours post-dose.

There were no blood samples taken on Days 2, 3, 4, 5, 6, 7, 8, and 9.

All pre-dose blood samples were drawn within 10 minutes before dosing.

Bioanalytical Procedure:

Bupropion and its metabolites, bupropion erythroamino alcohol, bupropion threoamino alcohol, hydroxybupropion, and the internal standard, 1-(3-chlorophenyl)-piperazine, were extracted by solid phase extraction into an organic media from 0.50 mL of human plasma. An aliquot of this extract was injected into a High Performance Liquid Chromatography system and detected using a tandem mass spectrometer. The analytes were separated by reverse phase chromatography. Evaluation of the assay was carried out by the construction of an 8 point calibration curve (excluding zero concentration) covering the range of 1.000 ng/mL to 1023.900 ng/mL for bupropion, 1.000 ng/mL to 1023.900 ng/mL for bupropion erythroamino alcohol, 1.000 ng/mL to 1023.900 ng/mL for bupropion threoamino alcohol, and 3.906 ng/mL to 3999.600 ng/mL for hydroxybupropion in human plasma. The slope and intercept of the calibration curves were determined through weighted linear regression analysis (1/peak area2). Two calibration curves and duplicate QC samples (at three concentration levels) were analyzed along with each batch of the study samples. Peak area ratios were used to determine the concentration of the standards, quality control samples, and the unknown study samples from the calibration curves.

Criteria for Evaluation:

The pharmacokinetic analysis was performed on 38 subjects who completed the 2 study periods. The safety assessment was performed on all subjects who received at least 1 dose during the course of the study.

Pharmacokinetics (PK):

The following pharmacokinetic parameters for bupropion and its metabolites hydroxybupropion, bupropion threoamino alcohol, and bupropion erythroamino alcohol were calculated by standard non-compartmental methods: AUCτ, Cmax, Cmin, Cavg, MRT, M/P ratio, % Fluctuation, % Swing, and Tmax. These parameters were also computed for pharmacologic activity-weighted composite (PAWC).

Statistical Methods:

Using General Linear Model (GLM) procedures in Statistical Analysis System (SAS), analysis of variance (ANOVA) was performed on ln transformed AUCτ, Cmax, Cmin, Cavg, and on untransformed MRT, M/P ratio, % Fluctuation and % Swing at the significance level of 0.05. The intra-subject coefficient of variation (CV) was calculated using the Mean Square Error (MSE) from the ANOVA table. The ratio of geometric means and the 90% geometric confidence interval (90% C.I.) were calculated based on the difference in the Least Squares Means of the ln transformed AUCτ, Cmax, Cmin, between the test and reference formulations. Tmax was analyzed using nonparametric methods.

Pharmacokinetic Parameters for Bupropion:

| Pharmacokinetic Parameters | Geometric Mean (% CV) Arithmetic Mean ± SD | |
|---|---|---|
| | Bupropion HBr XL 348 mg Tablets (A) (n = 38) | Wellbutrin XL ® 300 mg Tablets (B) (n = 38) |
| AUCt (ng · hr/mL) | 1362.44 (24.53) | 1541.27 (20.43) |
| | 1409.24 ± 345.72 | 1575.03 ± 321.80 |
| Cmax (ng/mL) | (28.44) | 151.03 (27.15) |
| | 134.33 ± 38.20 | 156.83 ± 42.57 |
| Cmin (ng/mL) | 24.72 (37.50) | 26.95 (31.48) |
| | 26.60 ± 9.98 | 28.32 ± 8.92 |
| Cavg (ng/mL) | 56.77 (24.53) | 64.22 (20.43) |
| | 58.72 ± 14.41 | 65.63 ± 13.41 |
| Tmax (hr)* | 4.01 (2.00-7.00) | 4.50 (3.00-7.00) |
| Degree of Fluctuation (%) | 187.51 ± 53.50 | 195.47 ± 47.80 |
| Degree of Swing (%) | 475.44 ± 280.21 | 499.74 ± 228.53 |
| MRT (hr) | 9.12 ± 0.72 | 9.76 ± 0.69 |

*median (min-max)

Relative Bioavailability Assessments for Bupropion:

| | Potency Uncorrected Data | | |
|---|---|---|---|
| Parameter | 90% C.I. | Ratio of Means | Intra-Subject CV |
| AUCt | 84.19% to 93.95% | 88.93% | 14.16% |
| Cmax | 80.20% to 92.15% | 85.97% | 17.97% |
| Cmin | 86.56% to 100.00% | 93.04% | 18.68% |

| | Potency Corrected Data | |
|---|---|---|
| Parameter | 90% C.I. | Ratio of Means |
| AUC0-t | 86.18% to 96.18% | 91.04% |
| AUC0-inf | 82.10% to 94.33% | 88.00% |
| Cmax | 88.61% to 102.37% | 95.24% |

Pharmacokinetic Parameters for Hydroxybupropion:

| Pharmacokinetic Parameters | Geometric Mean (% CV) Arithmetic Mean ± SD | |
|---|---|---|
| | Bupropion HBr XL 348 mg Tablets (A) (n = 38) | Wellbutrin XL ® 300 mg Tablets (B) (n = 38) |
| AUCt (ng · hr/mL) | 21815.79 (29.60) | 25099.08 (29.19) |
| | 22879.88 ± 6771.48 | 26180.58 ± 7642.05 |
| Cmax (ng/mL) | 1158.54 (28.08) | 1344.33 (29.42) |
| | 1208.14 ± 339.24 | 1403.10 ± 412.83 |
| Cmin (ng/mL) | 762.55 (34.99) | 895.28 (32.81) |
| | 814.63 ± 285.05 | 944.00 ± 309.69 |
| Cavg (ng/mL) | 908.99 (26.0) | 1045.80 (29.19) |
| | 953.33 ± 282.14 | 1090.86 ± 318.42 |
| Tmax (hr)* | 6.00 (3.00-10.00) | 7.00 (4.00-10.02) |
| Degree of Fluctuation (%) | 43.46 ± 16.88 | 43.12 ± 17.82 |
| Degree of Swing (%) | 53.97 ± 25.74 | 52.19 ± 26.83 |
| MRT (hr) | 11.32 ± 0.31 | 11.51 ± 0.29 |
| M/P Ratio | 15.57 ± 4.20 | 15.97 ± 4.84 |

*median (min-max)

Relative Bioavailability Assessments for Hydroxybupropion:

| | Potency Uncorrected Data | | |
|---|---|---|---|
| Parameter | 90% C.I. | Ratio of Means | Intra-Subject CV |
| AUCt | 82.96% to 92.04% | 87.39% | 13.39% |
| Cmax | 81.93% to 91.10% | 86.39% | 13.68% |
| Cmin | 81.45% to 90.94% | 86.06% | 14.22% |

Pharmacokinetic Parameters for Bupropion Threoamino Alcohol:

| Pharmacokinetic Parameters | Geometric Mean (% CV) Arithmetic Mean ± SD | |
|---|---|---|
| | Bupropion HBr XL 348 mg Tablets (A) (n = 38) | Wellbutrin XL ® 300 mg Tablets (B) (n = 38) |
| AUCt (ng · hr/mL) | 8842.06 (37.35) | 9768.54 (27.53) |
| | 9446.28 ± 3528.05 | 10112.95 ± 2783.98 |
| Cmax (ng/mL) | 486.58 (34.68) | 541.95 (26.73) |
| | 514.82 ± 178.53 | 560.74 ± 149.88 |
| Cmin (ng/mL) | 282.78 (47.91) | 318.60 (34.19) |
| | 312.46 ± 149.70 | 335.65 ± 114.75 |
| Cavg (ng/mL) | 368.42 (37.35) | 407.02 (27.53) |
| | 393.60 ± 147.00 | 421.37 ± 116.00 |
| Tmax (hr)* | 6.00 (3.00-10.00) | 7.00 (5.00-14.00) |
| Degree of Fluctuation (%) | 55.17 ± 18.45 | 55.08 ± 19.06 |
| Degree of Swing (%) | 74.98 ± 32.28 | 72.78 ± 31.30 |
| MRT (hr) | 11.39 ± 0.37 | 11.60 ± 0.28 |
| M/P Ratio | 6.76 ± 2.29 | 6.60 ± 2.34 |

*median (min-max)

Relative Bioavailability Assessments for Bupropion Threoamino Alcohol:

| | Potency Uncorrected Data | | |
|---|---|---|---|
| Parameter | 90% C.I. | Ratio of Means | Intra-Subject CV |
| AUCt | 85.78% to 96.23% | 90.86% | 14.83% |
| Cmax | 84.49% to 95.91% | 90.02% | 16.38% |
| Cmin | 83.54% to 95.43% | 89.29% | 17.21% |

Pharmacokinetic Parameters for Bupropion Erythroamino Alcohol:

| | Geometric Mean (% CV) Arithmetic Mean ± SD | |
|---|---|---|
| Pharmacokinetic Parameters | Bupropion HBr XL 348 mg Tablets (A) (n = 38) | Wellbutrin XL ® 300 mg Tablets (B) (n = 38) |
| AUCt (ng · hr/mL) | 1922.76 (29.01)<br>2009.09 ± 582.74 | 2091.51 (22.07)<br>2143.79 ± 473.12 |
| Cmax (ng/mL) | 99.98 (27.31)<br>103.93 ± 28.38 | 108.26 (23.57)<br>111.35 ± 26.25 |
| Cmin (ng/mL) | 67.46 (35.71)<br>72.00 ± 25.71 | 76.01 (25.97)<br>78.52 ± 20.39 |
| Cavg (ng/mL) | 80.11 (29.01)<br>83.71 ± 24.28 | 87.15 (22.07)<br>89.32 ± 19.71 |
| Tmax (hr)* | 7.00 (5.00-14.00) | 7.00 (5.00-12.00) |
| Degree of Fluctuation (%) | 40.46 ± 16.49 | 37.10 ± 14.22 |
| Degree of Swing (%) | 50.16 ± 24.94 | 43.65 ± 19.18 |
| MRT (hr) | 11.54 ± 0.32 | 11.72 ± 0.25 |
| M/P Ratio | 1.47 ± 0.45 | 1.40 ± 0.42 |

*median (min-max)

Relative Bioavailability Assessments for Bupropion Erythroamino Alcohol:

| | Potency Uncorrected Data | | |
|---|---|---|---|
| Parameter | 90% C.I. | Ratio of Means | Intra-Subject CV |
| AUCt | 87.32% to 97.69% | 92.36% | 14.48% |
| Cmax | 87.66% to 97.91% | 92.64% | 14.27% |
| Cmin | 83.81% to 95.28% | 89.36% | 16.57% |

Pharmacokinetic Parameters for Total Bupropion (PAWC):

| | Geometric Mean (% CV) Arithmetic Mean ± SD | |
|---|---|---|
| Pharmacokinetic Parameters | Bupropion HBr XL 348 mg Tablets (A) (n = 38) | Wellbutrin XL ® 300 mg Tablets (B) (n = 38) |
| AUCt (µM · hr) | 66.48 (26.44)<br>69.03 ± 18.25 | 75.89 (24.59)<br>78.13 ± 19.21 |
| Cmax (µM) | 3.70 (24.37)<br>3.81 ± 0.93 | 4.26 (25.37)<br>4.39 ± 1.11 |
| Cmin (µM) | 2.21 (32.88)<br>2.34 ± 0.77 | 2.57 (29.67)<br>2.68 ± 0.79 |
| Cavg (µM) | 2.77 (26.44)<br>2.88 ± 0.76 | 3.16 (24.59)<br>3.26 ± 0.80 |
| Tmax (hr)* | 5.00 (2.00-10.00) | 6.00 (4.00-10.02) |
| Degree of Fluctuation (%) | 53.54 ± 17.61 | 53.73 ± 18.91 |
| Degree of Swing (%) | 69.50 ± 29.41 | 68.34 ± 30.09 |
| MRT (hr) | 11.15 ± 0.32 | 11.38 ± 0.31 |

*median (min-max)

Relative Bioavailability Assessments for Total Bupropion (PAWC):

| | Potency Uncorrected Data | | |
|---|---|---|---|
| Parameter | 90% C.I. | Ratio of Means | Intra-Subject CV |
| AUCt | 83.72% to 92.62% | 88.06% | 13.02% |
| Cmax | 82.39% to 92.05% | 87.09% | 14.31% |
| Cmin | 82.48% to 91.87% | 87.05% | 13.91% |

Conclusion:

The pharmacokinetics of bupropion were assessed, after multiple oral doses of Bupropion HBr XL 348 mg Tablets (Treatment A), and Wellbutrin XL® 300 mg Tablets (Treatment B) under fasting conditions.

The comparative bioavailability of bupropion, its metabolites and the pharmacologic activity-weighted composite (PAWC) data were assessed by measuring and comparing the peak and total systemic exposure from the two treatments at steady state.

The statistical results indicated that steady state was achieved by Day 13. The test/reference geometric mean ratios and the corresponding 90% confidence intervals for AUCt, Cmax, and Cmin were within the range of 80.00%-125.00% for bupropion, its metabolites and the PAWC under steady-state fasting conditions. There was no significant difference in the bupropion Tmax values between the two treatments (p value>0.05).

In conclusion, Bupropion HBr XL 348 mg Tablets demonstrated equivalent peak concentration, minimum concentration and systemic exposure relative to Wellbutrin XL® 300 mg Tablets under steady-state fasting conditions.

Overall, Bupropion HBr XL 348 mg Tablets were well tolerated when administered under multiple-dose, fasting conditions, and no significant safety issues emerged.

This study was performed in compliance with GCP.

TABLE

| Mean (±SD) Pharmacokinetic Parameters for Bupropion (n = 38) | | |
|---|---|---|
| | Bupropion HBr XL 348 mg Tablets (06C159) (n = 38) | Wellbutrin XL ® 300 mg Tablets (06C090P) (n = 38) |
| AUC0-τ (ng * hr/mL) | 1409 ± 346 | 1575 ± 322 |
| Cmax (ng/mL) | 134 ± 38 | 156.8 ± 43 |
| Cmin (ng/mL) | 26.6 ± 10.0 | 28.3 ± 8.9 |
| Cavg (ng/mL) | 58.7 ± 14.4 | 65.6 ± 13.4 |

TABLE-continued

Mean (±SD) Pharmacokinetic Parameters for Bupropion (n = 38)

|  | Bupropion HBr XL 348 mg Tablets (06C159) (n = 38) | Wellbutrin XL ® 300 mg Tablets (06C090P) (n = 38) |
|---|---|---|
| Tmax (hr)* | 4.0 (2.0-7.0) | 4.5 (3.0-7.0) |
| Degree of Fluctuation (%) | 187.5 ± 53.5 | 195.5 ± 47.8 |

*Median (Range)

TABLE

Summary Statistics for Bupropion (n = 38)

| | Bupropion HBr XL 348 mg Tablets Versus Wellbutrin ® XL 300 mg Tablets | |
|---|---|---|
| | Ratio of Geometric Means | 90% Geometric Confidence Interval |
| AUC0-τ | 88.93% | 84.19 to 93.95% |
| Cmax | 85.97% | 80.20 to 92.15% |
| Cmin | 93.04% | 86.56 to 100.00% |

TABLE

Mean (±SD) Pharmacokinetic Parameters for Hydroxybupropion (n = 38)

|  | Bupropion HBr XL 348 mg Tablets (06C159) (n = 38) | Wellbutrin XL ® 300 mg Tablets (06C090P) (n = 38) |
|---|---|---|
| AUC0-τ (ng * hr/mL) | 22880 ± 6771 | 26181 ± 7642 |
| Cmax (ng/mL) | 1208.1 ± 339.2 | 1403.1 ± 412.8 |
| Cmin (ng/mL) | 814.6 ± 285.1 | 944.0 ± 309.7 |
| Cavg (ng/mL) | 953.3 ± 282.1 | 1090.9 ± 318.4 |
| Tmax (hr)* | 6.0 (3.0-10.0) | 7.0 (4.0-10.0) |
| Degree of Fluctuation (%) | 43.5 ± 16.9 | 43.1 ± 17.8 |
| Metabolite/Parent Ratio | 15.6 ± 4.2 | 16.0 ± 4.8 |

*Median (Range)

TABLE

Summary Statistics for Hydroxybupropion (n = 38)

| | Bupropion HBr XL 348 mg Tablets Versus Wellbutrin ® XL 300 mg Tablets | |
|---|---|---|
| | Ratio of Geometric Means | 90% Geometric Confidence Interval |
| AUC0-τ | 87.39% | 82.96 to 92.04% |
| Cmax | 86.39% | 81.93 to 91.10% |
| Cmin | 86.06% | 81.45 to 90.94% |

TABLE

Mean (±SD) Pharmacokinetic Parameters for Bupropion Threoamino Alcohol (n = 38)

|  | Bupropion HBr XL 348 mg Tablets (06C159) (n = 38) | Wellbutrin XL ® 300 mg Tablets (06C090P) (n = 38) |
|---|---|---|
| AUC0-τ (ng * hr/mL) | 9446 ± 3528 | 10113 ± 2784 |
| Cmax (ng/mL) | 514.8 ± 178.5 | 560.7 ± 149.9 |
| Cmin (ng/mL) | 312.5 ± 149.7 | 335.7 ± 114.8 |
| Cavg (ng/mL) | 393.6 ± 147.0 | 421.4 ± 116.0 |
| Tmax (hr)* | 6.0 (3.0-10.0) | 7.0 (5.0-14.0) |
| Degree of Fluctuation (%) | 55.2 ± 18.5 | 55.1 ± 19.1 |
| Metabolite/Parent Ratio | 6.8 ± 2.3 | 6.6 ± 2.3 |

*Median (Range)

TABLE

Summary Statistics for Bupropion Threoamino Alcohol (n = 38)

| | Bupropion HBr XL 348 mg Tablets Versus Wellbutrin ® XL 300 mg Tablets | |
|---|---|---|
| | Ratio of Geometric Means | 90% Geometric Confidence Interval |
| AUC0-τ | 90.86% | 85.78 to 96.23% |
| Cmax | 90.02% | 84.49 to 95.91% |
| Cmin | 89.29% | 83.54 to 95.43% |

TABLE

Mean (±SD) Pharmacokinetic Parameters for Bupropion Erythroamino Alcohol (n = 38)

|  | Bupropion HBr XL 348 mg Tablets (06C159) (n = 38) | Wellbutrin XL ® 300 mg Tablets (06C090P) (n = 38) |
|---|---|---|
| AUC0-τ (ng * hr/mL) | 2009 ± 583 | 2144 ± 473 |
| Cmax (ng/mL) | 103.9 ± 28.4 | 111.4 ± 26.3 |
| Cmin (ng/mL) | 72.0 ± 25.7 | 78.5 ± 20.4 |
| Cavg (ng/mL) | 83.7 ± 24.3 | 89.3 ± 19.7 |
| Tmax (hr)* | 7.0 (5.0-14.0) | 7.0 (5.0-12.0) |
| Degree of Fluctuation (%) | 40.5 ± 16.5 | 37.1 ± 14.2 |
| Metabolite/Parent Ratio | 1.5 ± 0.5 | 1.4 ± 0.4 |

*Median (Range)

TABLE

Summary Statistics for Bupropion Erythroamino Alcohol (n = 38)

| | Bupropion HBr XL 348 mg Tablets Versus Wellbutrin ® XL 300 mg Tablets | |
|---|---|---|
| | Ratio of Geometric Means | 90% Geometric Confidence Interval |
| AUC0-τ | 92.36% | 87.32 to 97.69% |
| Cmax | 92.64% | 87.66 to 97.91% |
| Cmin | 89.36% | 83.81 to 95.28% |

TABLE

Mean (±SD) Pharmacokinetic Parameters for PAWC (n = 38)

| Pharmacokinetic Parameters | Bupropion HBr XL 348 mg Tablets (06C159) (n = 38) | Wellbutrin XL ® 300 mg Tablets (06C090P) (n = 38) |
|---|---|---|
| AUC0-τ (µM * hr) | 69.0 ± 18.3 | 78.1 ± 19.2 |
| Cmax (µM) | 3.8 ± 0.9 | 4.4 ± 1.1 |
| Cmin (µM) | 2.3 ± 0.8 | 2.7 ± 0.8 |
| Cavg (µM) | 2.9 ± 0.8 | 3.3 ± 0.8 |
| Tmax (hr)* | 5.0 (2.0-10.0) | 6.0 (4.0-10.0) |
| Degree of Fluctuation (%) | 53.5 ± 17.6 | 53.7 ± 18.9 |

*Median (Range)

TABLE

Summary Statistics for PAWC (n = 38)

Bupropion HBr XL 348 mg Tablets Versus Wellbutrin ® XL 300 mg Tablets

| | Ratio of Geometric Means | 90% Geometric Confidence Interval |
|---|---|---|
| AUC0-τ | 88.06% | 83.72% to 92.62% |
| Cmax | 87.09% | 82.39% to 92.05% |
| Cmin | 87.05% | 82.48% to 91.87% |

Two-Way Crossover, Open-Label, Single-Dose, Fasting, Dosage Strength Proportionality Study of Two Strengths of Bupropion HBr XL Tablets (2×174 mg Versus 1×348 mg) In Normal, Healthy, Non Smoking Male And Female Subjects. Study B06-755PK-10121 (3228)

In this study the dosage strength proportionality between the 174 mg and 348 mg strengths of Bupropion HBr XL tablets were evaluated under single dose fasting conditions. Bupropion HBr XL 174 mg tablets when given as 2×174 mg were equivalent to Bupropion HBr XL 348 mg tablets given as 1×348 mg.

Results are shown below and in FIGS. 80-85.

Study Design and Phase of Development:

Two-way crossover, randomized, open-label, single-dose, fasting, dosage strength proportionality study Main Criteria for Inclusion:

Normal, healthy, non-smoking male and female subjects at ages of from 18 to 55 years.

Treatment A: Test Product/Investigational Product, Lot Number and Mode of Administration:

Following an overnight fast of at least 10 hours, 2 Bupropion HBr XL 174 mg Tablets, Lot #: 06D029P (potency value=97.1% of label claim), administered orally with 240 mL of ambient temperature water.

Treatment B: Test Product, Lot Number and Mode of Administration:

Following an overnight fast of at least 10 hours, 1 Bupropion HBr XL 348 mg Tablet, Lot #: 06C159P (potency value=97.0% of label claim), administered orally with 240 mL of ambient temperature water.

Number of Subjects (Planned and Analyzed):

There were 48 subjects dosed in Period I, 46 of whom completed the study. Pharmacokinetic and statistical analyses were performed on 46 subjects who completed the study.

Blood Draw Timepoints:

During each study period, 22 blood samples were collected from each subject at the following timepoints: 0.00 (pre-dose), 1.00, 2.00, 3.00, 4.00, 5.00, 6.00, 7.00, 8.00, 10.00, 12.00, 14.00, 16.00, 20.00, 24.00, 36.00, 48.00, 60.00, 72.00, 120.00, 168.00, and 216.00 hours post-dose.

Bioanalytical Procedure:

Bupropion, bupropion erythroamino alcohol, bupropion threoamino alcohol, hydroxybupropion, and the internal standard, 1-(3-chlorophenyl)-piperazine, were extracted by solid phase extraction into organic media from 0.50 mL of human plasma. An aliquot of this extract was injected into a High Performance Liquid Chromatography system and detected using a tandem mass spectrometer. The analytes were separated by reverse phase chromatography. Evaluation of the assay was carried out by the construction of an eight (8) point calibration curve (excluding zero concentration) covering the range of 1.000 ng/mL to 1023.900 ng/mL (in human plasma) for bupropion, 1.000 ng/mL to 1023.900 ng/mL (in human plasma) for bupropion erythroamino alcohol, 1.000 ng/mL to 1023.900 ng/mL (in human plasma) for bupropion threoamino alcohol, and 3.906 ng/mL to 3999.600 ng/mL (in human plasma) for hydroxybupropion. The slope and intercept of the calibration curves were determined through weighted linear regression analysis (1/peak area2). Two calibration curves and duplicate QC samples (at three concentration levels) were analyzed along with each batch of the study samples. Peak area ratios were used to determine the concentration of the standards, quality control samples, and the unknown study samples from the calibration curves.

Criteria for Evaluation:

The pharmacokinetic analysis was performed on 46 subjects who completed the 2 study periods. The safety assessment was performed on all subjects who received at least 1 dose during the course of the study.

Pharmacokinetics (PK):

The following pharmacokinetic parameters for bupropion and its metabolites hydroxybupropion, bupropion threoamino alcohol, bupropion erythroamino alcohol and pharmacologic activity-weighted composite (PAWC) were calculated by standard non-compartmental methods: AUC0-t, AUC0-inf, Cmax, Tmax, Kel, t½, mean residence time (MRT), and Metabolite/Parent (M/P) ratio.

Safety:

The incidences of all adverse events (AEs) were tabulated by treatment and subject number. Absolute values for vital signs, electrocardiogram (ECG) parameters, laboratory parameters and physical examinations were also documented and values outside the normal range were flagged. Shifts from baseline values were tabulated. AEs were documented using investigator and Medical Dictionary for Regulatory Activities (MedDRA) terms.

Statistical Methods:

Using General Linear Model (GLM) procedures in Statistical Analysis System (SAS), analysis of variance (ANOVA) was performed on ln-transformed AUC0-t, AUC0-inf, and Cmax and on untransformed Kel, t½, MRT, and M/P ratio at the significance level of 0.05. The intra-subject coefficient of variation (CV) was calculated using the Mean Square Error (MSE) from the ANOVA table. The ratio of geometric means and the 90% geometric confidence interval (90% C.I.) were calculated based on the difference in the Least Squares Means of the ln-transformed AUC0-t, AUC0-inf, and Cmax between the test and reference formulations. Tmax was analyzed using nonparametric methods.

Pharmacokinetic Parameters for Bupropion:

|  | Geometric Mean (% CV) Arithmetic Mean ± SD | |
| --- | --- | --- |
| Pharmacokinetic Parameters | 2 × Bupropion HBr XL 174 mg Tablets (A) (n = 46) | 1 × Bupropion HBr XL 348 mg Tablet (B) (n = 46) |
| AUC0-τ (ng · hr/mL) | 1523.91 (30.65) 1596.96 ± 489.42 | 1493.80 (34.76) 1581.85 ± 549.92 |
| AUC0-inf (ng · hr/mL) | 1585.29 (30.09) 1658.90 ± 499.09 | 1556.42 (34.03) 1644.75 ± 559.69 |
| Cmax (ng/mL) | 122.81 (32.48) 128.54 ± 41.75 | 132.51 (37.22) 141.16 ± 52.54 |
| Tmax (hr)* | 5.00 (3.00-6.07) | 5.00 (3.00-7.00) |
| t½ (hr) | 23.65 ± 7.36 | 23.84 ± 6.90 |
| Kel (hr−1) | 3.29E−02 ± 1.28E−02 | 3.17E−02 ± 9.78E−03 |
| MRT (hr) | 23.02 ± 5.21 | 22.52 ± 5.12 |

*median (min-max)

Relative Bioavailability Assessments for Bupropion:

| | Potency Uncorrected Data | | |
| --- | --- | --- | --- |
| Parameter | 90% C.I. | Ratio of Means | Intra-Subject CV |
| AUC0-t | 96.48% to 107.86% | 102.02% | 16.01% |
| AUC0-inf | 96.59% to 107.41% | 101.85% | 15.24% |
| Cmax | 86.68% to 99.10% | 92.68% | 19.29% |

| | Potency Corrected Data | |
| --- | --- | --- |
| Parameter | 90% C.I. | Ratio of Means |
| AUC0-t | 96.39% to 107.75% | 101.91% |
| AUC0-inf | 96.49% to 107.30% | 101.75% |
| Cmax | 86.59% to 98.99% | 92.58% |

Summary of Pharmacokinetic Results (Cont'd):

Pharmacokinetic Parameters for Hydroxybupropion:

|  | Geometric Mean (% CV) Arithmetic Mean ± SD | |
| --- | --- | --- |
| Pharmacokinetic Parameters | 2 × Bupropion HBr XL 174 mg Tablets (A) (n = 46) | 1 × Bupropion HBr XL 348 mg Tablet (B) (n = 46) |
| AUC0-t (ng · hr/mL) | 21175.12 (50.57) 24691.89 ± 12487.03 | 20088.61 (60.27) 24435.37 ± 14728.10 |
| AUC0-inf (ng · hr/mL) | 21601.69 (50.27) 25050.12 ± 12593.05 | 20505.06 (59.96) 24779.61 ± 14857.90 |
| Cmax (ng/mL) | 421.40 (46.88) 480.18 ± 225.10 | 411.57 (50.75) 478.90 ± 243.02 |
| Tmax (hr)* | 14.00 (5.00-24.00) | 8.00 (5.00-24.00) |
| t½ (hr) | 26.51 ± 5.77 | 26.05 ± 6.24 |
| Kel (hr−1) | 2.75E−02 ± 6.70E−03 | 2.83E−02 ± 7.62E−03 |
| MRT (hr) | 43.58 ± 8.67 | 42.84 ± 9.32 |
| M/P Ratio | 15.02 ± 9.00 | 15.08 ± 11.14 |

*median (min-max)

Relative Bioavailability Assessments for Hydroxybupropion:

| Parameter | 90% C.I. | Ratio of Means | Intra-Subject CV |
| --- | --- | --- | --- |
| AUC0-t | 98.60% to 112.69% | 105.41% | 19.23% |
| AUC0-inf | 98.62% to 112.54% | 105.35% | 19.01% |
| Cmax | 97.00% to 108.08% | 102.39% | 15.53% |

Summary of Pharmacokinetic Results (Cont'd):

Pharmacokinetic Parameters for Bupropion Threoamino Alcohol:

|  | Geometric Mean (% CV) Arithmetic Mean ± SD | |
| --- | --- | --- |
| Pharmacokinetic Parameters | 2 × Bupropion HBr XL 174 mg Tablets (A) (n = 46) | 1 × Bupropion HBr XL 348 mg Tablet (B) (n = 46) |
| AUC0-t (ng · hr/mL) | 8720.28 (58.03) 9894.97 ± 5741.81 | 8399.01 (53.61) 9441.77 ± 5061.45 |
| AUC0-inf (ng · hr/mL) | 9433.66 (59.13) 10815.80 ± 6395.02 | 9012.38 (54.93) 10252.40 ± 5631.37 |
| Cmax (ng/mL) | 157.76 (45.91) 171.83 ± 78.89 | 161.36 (40.12) 173.35 ± 69.55 |
| Tmax (hr)* | 8.00 (5.00-24.00) | 6.00 (5.00-24.00) |
| t½ (hr) | 56.77 ± 20.15 | 53.97 ± 17.31 |
| Kel (hr−1) | 1.35E−02 ± 4.44E−03 | 1.41E−02 ± 4.58E−03 |
| MRT (hr) | 76.90 ± 28.13 | 73.60 ± 23.99 |
| M/P Ratio | 6.65 ± 4.37 | 6.43 ± 3.94 |

*median (min-max)

Relative Bioavailability Assessments for Bupropion Threoamino Alcohol:

| Parameter | 90% C.I. | Ratio of Means | Intra-Subject CV |
| --- | --- | --- | --- |
| AUC0-t | 98.45% to 109.49% | 103.83% | 15.26% |
| AUC0-inf | 99.20% to 110.45% | 104.67% | 15.42% |
| Cmax | 91.39% to 104.59% | 97.77% | 19.42% |

Summary of Pharmacokinetic Results (Cont'd):

Pharmacokinetic Parameters for Bupropion Erythroamino Alcohol:

| Pharmacokinetic Parameters | Geometric Mean (% CV) Arithmetic Mean ± SD | |
|---|---|---|
| | 2 × Bupropion HBr XL 174 mg Tablets (A) (n = 46) | 1 × Bupropion HBr XL 348 mg Tablet (B) (n = 46) |
| AUC0-t (ng · hr/mL) | 1624.49 (47.41) | 1556.84 (45.13) |
| | 1774.20 ± 841.09 | 1699.49 ± 767.04 |
| AUC0-inf (ng · hr/mL) | 1713.80 (46.12) | 1663.28 (43.67) |
| | 1864.11 ± 859.71 | 1804.53 ± 788.09 |
| Cmax (ng/mL) | 29.54 (33.12) | 29.01 (33.02) |
| | 30.79 ± 10.20 | 30.40 ± 10.04 |
| Tmax (hr)* | 14.00 (5.00-24.00) | 13.00 (5.00-24.00) |
| t½ (hr) | 32.71 ± 7.84 | 32.51 ± 8.78 |
| Kel (hr−1) | 2.24E−02 ± 5.24E−03 | 2.27E−02 ± 5.72E−03 |
| MRT (hr) | 52.66 ± 11.42 | 52.28 ± 12.78 |
| M/P Ratio | 1.16 ± 0.68 | 1.13 ± 0.50 |

*median (min-max)

Relative Bioavailability Assessments for Bupropion Erythroamino Alcohol:

| Parameter | 90% C.I. | Ratio of Means | Intra-Subject CV |
|---|---|---|---|
| AUC0-t | 98.39% to 110.66% | 104.35% | 16.89% |
| AUC0-inf | 97.25% to 109.16% | 103.04% | 16.60% |
| Cmax | 96.15% to 107.82% | 101.82% | 16.46% |

Summary of Pharmacokinetic Results (Cont'd):

Pharmacokinetic Parameters for PAWC:

| Pharmacokinetic Parameters | Geometric Mean (% CV) Arithmetic Mean ± SD | |
|---|---|---|
| | 2 × Bupropion HBr XL 174 mg Tablets (A) (n = 46) | 1 × Bupropion HBr XL 348 mg Tablet (B) (n = 46) |
| AUC0-t (µM · hr) | 68.99 (39.40) | 66.21 (47.37) |
| | 74.85 ± 29.49 | 73.65 ± 34.89 |
| AUC0-inf (µM · hr) | 69.68 (39.62) | 66.93 (47.56) |
| | 75.63 ± 29.96 | 74.47 ± 35.42 |
| Cmax (µM) | 1.60 (32.21) | 1.64 (36.18) |
| | 1.68 ± 0.54 | 1.76 ± 0.64 |
| Tmax (hr)* | 5.03 (4.00-14.00) | 5.00 (4.00-24.00) |
| t½ (hr) | 29.45 ± 7.47 | 29.25 ± 8.04 |
| Kel (hr−1) | 2.55E−02 ± 8.61E−03 | 2.56E−02 ± 7.53E−03 |
| MRT (hr) | 44.38 ± 8.96 | 43.99 ± 9.89 |

*median (min-max)

Relative Bioavailability Assessments for PAWC:

| Parameter | 90% C.I. | Ratio of Means | Intra-Subject CV |
|---|---|---|---|
| AUC0-t | 98.43% to 110.30% | 104.20% | 16.36% |
| AUC0-inf | 98.32% to 110.25% | 104.12% | 16.45% |
| Cmax | 91.74% to 102.73% | 97.08% | 16.26% |

Conclusion:

The objective of this study was to evaluate the dosage strength proportionality of the two strengths of Bupropion HBr XL Tablets (2×174 mg versus 1×348 mg) in normal healthy non-smoking male and female subjects. The relative bioavailability of bupropion, its metabolites and the PAWC data were assessed by measuring and comparing the peak and total systemic exposure from the 2 treatments (using AUC0-t, AUC0-inf, and Cmax). The statistical results indicated that test/reference geometric mean ratios and the values of 90% confidence intervals for AUC0-t, AUC0-inf and Cmax of bupropion, its metabolites and PAWC data were within the criteria range of 80.00%-125.00%. Based on these results, Bupropion HBr XL Tablets (2×174 mg) and Bupropion HBr XL Tablets (1×348 mg) were found to demonstrate equivalent peak and systemic exposure of bupropion and its metabolites when both formulations were administered under fasting condition. In conclusion, Bupropion XL 174 mg Tablets (given as 2×174 mg) were found to be dosage strength proportional to Bupropion HBr XL 348 mg Tablets. Overall, Bupropion HBr XL 174 mg Tablets (2×174 mg) and Bupropion HBr XL 348 mg Tablets were well tolerated as a single-dose of 348 mg, administered under fasting conditions, and no significant safety issues emerged.

This study was performed in compliance with GCP.

TABLE

Mean (±SD) Pharmacokinetic Parameters for Bupropion (n = 46)

| | 2 × Bupropion HBr XL 174 mg Tablets (06D029P) (n = 46) | 1 × Bupropion HBr XL 348 mg Tablet (06C159P) (n = 46) |
|---|---|---|
| AUC0-t (ng * hr/mL) | 1597 ± 489 | 1582 ± 550 |
| AUC0-∞ (ng * hr/mL) | 1659 ± 499 | 1645 ± 560 |
| Cmax (ng/mL) | 128.5 ± 41.8 | 141.2 ± 52.5 |
| Tmax (hr)* | 5.0 (3.0-6.1) | 5.0 (3.0-7.0) |
| t½ (hr) | 23.7 ± 7.4 | 23.8 ± 6.9 |
| MRT (hr) | 23.0 ± 5.2 | 22.5 ± 5.1 |

*Median (Range)

TABLE

Summary Statistics for Bupropion (n = 46)

2 × Bupropion HBr XL 174 mg Tablets Versus 1 × Bupropion HBr XL 348 mg Tablet

| | Ratio of Geometric Means | 90% Geometric Confidence Interval |
|---|---|---|
| AUC0-t | 102.02% | 96.48 to 107.86% |
| AUC0-∞ | 101.85% | 96.59 to 107.41% |
| Cmax | 92.68% | 86.68 to 99.10% |

TABLE

Mean (±SD) Pharmacokinetic Parameters for Hydroxybupropion (n = 46)

| | 2 × Bupropion HBr XL 174 mg Tablets (06D029P) (n = 46) | 1 × Bupropion HBr XL 348 mg Tablet (06C159P) (n = 46) |
|---|---|---|
| AUC0-t (ng * hr/mL) | 24692 ± 12487 | 24435 ± 14728 |
| AUC0-∞ (ng * hr/mL) | 25050 ± 12593 | 24780 ± 14858 |
| Cmax (ng/mL) | 480.2 ± 225.1 | 478.9 ± 243.0 |
| Tmax (hr)* | 14.0 (5.0-24.0) | 8.0 (5.0-24.0) |
| t½ (hr) | 26.5 ± 5.8 | 26.1 ± 6.2 |
| MRT (hr) | 43.6 ± 8.7 | 42.8 ± 9.3 |
| Metabolite/Parent Ratio | 15.0 ± 9.0 | 15.1 ± 11.1 |

*Median (Range)

TABLE

Summary Statistics for Hydroxybupropion (n = 46)

2 × Bupropion HBr XL 174 mg Tablets Versus 1 × Bupropion HBr XL 348 mg Tablet

| | Ratio of Geometric Means | 90% Geometric Confidence Interval |
|---|---|---|
| AUC0-t | 105.41% | 98.60 to 112.69% |
| AUC0-∞ | 105.35% | 98.62 to 112.54% |
| Cmax | 102.39% | 97.00 to 108.08% |

TABLE

Mean (±SD) Pharmacokinetic Parameters for Bupropion Threoamino Alcohol (n = 46)

| | 2 × Bupropion HBr XL 174 mg Tablets (06D029P) (n = 46) | 1 × Bupropion HBr XL 348 mg Tablet (06C159P) (n = 46) |
|---|---|---|
| AUC0-t (ng * hr/mL) | 9895 ± 5742 | 9442 ± 5061 |
| AUC0-∞ (ng * hr/mL) | 10816 ± 6395 | 10252 ± 5631 |
| Cmax (ng/mL) | 171.8 ± 78.9 | 173.4 ± 69.6 |
| Tmax (hr)* | 8.0 (5.0-24.0) | 6.0 (5.0-24.0) |
| t½ (hr) | 56.8 ± 20.2 | 54.0 ± 17.3 |
| MRT (hr) | 76.9 ± 28.1 | 73.6 ± 24.0 |
| Metabolite/Parent Ratio | 6.7 ± 4.4 | 6.4 ± 3.9 |

*Median (Range)

TABLE

Summary Statistics for Bupropion Threoamino Alcohol (n = 46)

2 × Bupropion HBr XL 174 mg Tablets Versus 1 × Bupropion HBr XL 348 mg Tablet

| | Ratio of Geometric Means | 90% Geometric Confidence Interval |
|---|---|---|
| AUC0-t | 103.83% | 98.45 to 109.49% |
| AUC0-∞ | 104.67% | 99.20 to 110.45% |
| Cmax | 97.77% | 91.39 to 104.59% |

TABLE

Mean (±SD) Pharmacokinetic Parameters for Bupropion Erythroamino Alcohol (n = 46)

| | 2 × Bupropion HBr XL 174 mg Tablets (06D029P) (n = 46) | 1 × Bupropion HBr XL 348 mg Tablet (06C159P) (n = 46) |
|---|---|---|
| AUC0-t (ng * hr/mL) | 1774 ± 841 | 1699 ± 767 |
| AUC0-∞ (ng * hr/mL) | 1864 ± 860 | 1805 ± 788 |
| Cmax (ng/mL) | 30.8 ± 10.2 | 30.4 ± 10.0 |
| Tmax (hr)* | 14.0 (5.0-24.0) | 13.0 (5.0-24.0) |
| t½ (hr) | 32.7 ± 7.8 | 32.5 ± 8.8 |
| MRT (hr) | 52.7 ± 11.4 | 52.3 ± 12.8 |
| Metabolite/Parent Ratio | 1.2 ± 0.7 | 1.1 ± 0.5 |

*Median (Range)

TABLE

Summary Statistics for Bupropion Erythroamino Alcohol (n = 46)

2 × Bupropion HBr XL 174 mg Tablets Versus 1 × Bupropion HBr XL 348 mg Tablet

| | Ratio of Geometric Means | 90% Geometric Confidence Interval |
|---|---|---|
| AUC0-t | 104.35% | 98.39 to 110.66% |
| AUC0-∞ | 103.04% | 97.25 to 109.16% |
| Cmax | 101.82% | 96.15 to 107.82% |

TABLE

Mean (±SD) Pharmacokinetic Parameters for PAWC (n = 46)

| Pharmacokinetic Parameters | 2 × Bupropion HBr XL 174 mg Tablets (06D029P) (n = 46) | 1 × Bupropion HBr XL 348 mg Tablet (06C159P) (n = 46) |
|---|---|---|
| AUC0-t (µM * hr) | 74.9 ± 29.5 | 73.7 ± 34.9 |
| AUC0-∞ (µM * hr) | 75.6 ± 30.0 | 74.5 ± 35.4 |
| Cmax (µM) | 1.7 ± 0.5 | 1.8 ± 0.6 |
| Tmax (hr)* | 5.0 (4.0-14.0) | 5.0 (4.0-24.0) |
| t½ (hr) | 29.5 ± 7.5 | 29.3 ± 8.0 |
| MRT (hr) | 44.4 ± 9.0 | 44.0 ± 9.9 |

*Median (Range)

TABLE

Summary Statistics for PAWC (n = 46)

2 × Bupropion HBr XL 174 mg Tablets Versus 1 × Bupropion HBr XL 348 mg Tablet

| | Ratio of Geometric Means | 90% Geometric Confidence Interval |
|---|---|---|
| AUC0-t | 104.20% | 98.43 to 110.30% |
| AUC0-∞ | 104.12% | 98.32 to 110.25% |
| Cmax | 97.08% | 91.74 to 102.73% |

Two-Way Crossover, Open-Label, Single-Dose, Food-Effect Study of Bupropion HBr XL 348 mg Tablets In Normal, Healthy, Non-Smoking Male And Female Subjects. Study B06-754PK-10121 (3229)

The effect of food on Bupropion HBr XL 348 mg tablets was studied. Administration of Bupropion HBr XL 348 mg tablets with food resulted in an increase in the peak (Cmax) and systemic exposure (AUC0-t, AUC0-∞) of bupropion by 7% and 19%, respectively. The presence of food did not change lead to a significant change in Tmax. The increase in Cmax was found not to be significant since the 90% geometric confidence interval (CI) fell within the 80 to 125% range. The 90% geometric CIs for AUC0-t and AUC0-∞ were found to fall slightly outside the 80 to 125% range (90% CIs for AUC0-t=113.23 to 126.06%, for AUC0-∞=112.96 to 125.52%). This marginal increase in bupropion AUC with food relative to fasting will not pose any clinical safety concerns since the percentage increase was within ±20% and the upper limit of the 90% geometric CI was approximately 1% above the acceptance range.

Results are shown below and in FIGS. 86-91.

Study Design and Phase of Development:

Two-way crossover, randomized, open-label, single-dose, food-effect, Phase I study Main Criteria for Inclusion:

Normal, healthy, non-smoking male and female subjects within the age range of 18 to 55 years.

Test Product/Investigational Product, Batch or Lot Number and Mode of Administration:

Following an overnight fast of at least 10 hours, and 30 minutes after the start of a high fat content meal, 1 Bupropion HBr XL 348 mg Tablet, Lot #: 06C159P, administered orally with 240 mL of ambient temperature water.

Reference Product, Batch or Lot Number and Mode of Administration:

Following an overnight fast of at least 10 hours, 1 Bupropion HBr XL 348 mg Tablet, Lot #: 06C159P, administered orally with 240 mL of ambient temperature water.

Number of Subjects (Planned and Analyzed):

There were 48 subjects dosed in Period I. All subjects completed the study, and their data were used for the pharmacokinetic and statistical analyses.

Blood Draw Timepoints:

During each study period, 22 blood samples were collected from each subject at the following timepoints: 0.00 (pre-dose), 1.00, 2.00, 3.00, 4.00, 5.00, 6.00, 7.00, 8.00, 10.00, 12.00, 14.00, 16.00, 20.00, 24.00, 36.00, 48.00, 60.00, 72.00, 120.00, 168.00, and 216.00 hours post-dose.

Bioanalytical Procedure:

Bupropion, bupropion erythroamino alcohol, bupropion threoamino alcohol, hydroxybupropion, and the internal standard, 1-(3-chlorophenyl)-piperazine, were extracted by solid phase extraction into organic media from 0.50 mL of human plasma. An aliquot of this extract was injected into a High Performance Liquid Chromatography system and detected using a tandem mass spectrometer. The analytes were separated by reverse phase chromatography. Evaluation of the assay was carried out by the construction of an eight (8) point calibration curve (excluding zero concentration) covering the range of 1.000 ng/mL to 1023.900 ng/mL (in human plasma) for bupropion, 1.000 ng/mL to 1023.900 ng/mL (in human plasma) for bupropion erythroamino alcohol, 1.000 ng/mL to 1023.900 ng/mL (in human plasma) for bupropion threoamino alcohol, and 3.906 ng/mL to 3999.600 ng/mL (in human plasma) for hydroxybupropion. The slope and intercept of the calibration curves were determined through weighted linear regression analysis (1/peak area2). Two calibration curves and duplicate QC samples (at three concentration levels) were analyzed along with each batch of the study samples. Peak area ratios were used to determine the concentration of the standards, quality control samples, and the unknown study samples from the calibration curves.

Criteria for Evaluation:

The pharmacokinetic analysis was performed on 48 subjects who completed the 2 study periods. The safety assessment was performed on all subjects who received at least 1 dose during the course of the study.

Pharmacokinetics (PK):

The following pharmacokinetic parameters for bupropion and its metabolites hydroxybupropion, bupropion threoamino alcohol, bupropion erythroamino alcohol and PAWC were calculated by standard non-compartmental methods: AUC0-t, AUC0-inf, Cmax, Tmax, Kel, t½, MRT, and M/P ratio.

Statistical Methods:

Using General Linear Model (GLM) procedures in Statistical Analysis System (SAS), analysis of variance (ANOVA) was performed on ln transformed AUC0-t, AUC0-inf, and Cmax and on untransformed Kel, t½, MRT, and M/P ratio at the significance level of 0.05. The intra-subject coefficient of variation (CV) was calculated using the Mean Square Error (MSE) from the ANOVA table. The ratio of geometric means and the 90% geometric confidence interval (90% C.I.) were calculated based on the difference in the Least Squares Means of the ln transformed AUC0-t, AUC0-inf, and Cmax between the test and reference formulations. Tmax was analyzed using nonparametric methods.

Summary of Pharmacokinetic Results:

Pharmacokinetic Parameters for Bupropion:

|  | Geometric Mean (% CV) Arithmetic Mean ± SD | |
|---|---|---|
| Pharmacokinetic Parameters | Bupropion HBr XL 348 mg Tablets (A) (Fed) (n = 48) | Bupropion HBr XL 348 mg Tablets (B) (Fasted) (n = 48) |
| AUC0-t (ng · hr/mL) | 1743.38 (29.91) 1813.67 ± 542.56 | 1459.22 (27.36) 1514.68 ± 414.40 |
| AUC0-inf (ng · hr/mL) | 1806.08 (29.34) 1876.44 ± 550.60 | 1516.77 (26.77) 1572.10 ± 420.91 |
| Cmax (ng/mL) | 130.36 (31.47) 136.80 ± 43.05 | 121.28 (27.41) 125.91 ± 34.52 |
| Tmax (hr)* | 5.00 (2.00-10.00) | 5.00 (3.00-7.00) |
| t½ (hr) | 23.19 ± 6.45 | 21.29 ± 6.65 |
| Kel (hr−1) | 3.27E−02 ± 1.10E−02 | 3.60E−02 ± 1.17E−02 |
| MRT (hr) | 22.36 ± 5.92 | 21.20 ± 5.56 |

*median (min-max)

(FED/Fasting) Relative Bioavailability Assessments for Bupropion:

| Parameter | 90% C.I. | Ratio of Means | Intra-Subject CV |
|---|---|---|---|
| AUC0-t | 113.23% to 126.06% | 119.47% | 15.75% |
| AUC0-inf | 112.96% to 125.52% | 119.07% | 15.47% |
| Cmax | 98.20% to 117.64% | 107.48% | 26.83% |

Summary of Pharmacokinetic Results:

Pharmacokinetic Parameters for Hydroxybupropion:

|  | Geometric Mean (% CV) Arithmetic Mean ± SD | |
|---|---|---|
| Pharmacokinetic Parameters | Bupropion HBr XL 348 mg Tablets (A) (Fed) (n = 48) | Bupropion HBr XL 348 mg Tablets (B) (Fasted) (n = 48) |
| AUC0-t (ng · hr/mL) | 21556.18 (54.71) 25505.66 ± 13953.00 | 21143.44 (53.45) 24948.49 ± 13334.10 |
| AUC0-inf (ng · hr/mL) | 22061.74 (54.24) 25870.62 ± 14032.96 | 21628.02 (52.78) 25284.90 ± 13346.59 |
| Cmax (ng/mL) | 457.15 (45.58) 525.08 ± 239.34 | 445.93 (43.57) 507.42 ± 221.07 |
| Tmax (hr)* | 14.00 (7.00-36.00) | 8.00 (5.00-24.02) |
| t½ (hr) | 24.77 ± 4.81 | 24.28 ± 4.92 |
| Kel (hr−1) | 2.90E−02 ± 5.59E−03 | 2.97E−02 ± 5.93E−03 |
| MRT (hr) | 42.65 ± 7.61 | 41.13 ± 7.37 |
| M/P Ratio | 13.17 ± 5.96 | 15.48 ± 7.32 |

*median (min-max)

(FED/Fasting) Relative Bioavailability Assessments for Hydroxybupropion:

| Parameter | 90% C.I. | Ratio of Means | Intra-Subject CV |
|---|---|---|---|
| AUC0-t | 95.40% to 108.96% | 101.95% | 19.58% |
| AUC0-inf | 95.50% to 108.95% | 102.01% | 19.41% |
| Cmax | 96.75% to 108.62% | 102.52% | 17.00% |

Summary of Pharmacokinetic Results:

Pharmacokinetic Parameters for Bupropion Threoamino Alcohol:

|  | Geometric Mean (% CV) Arithmetic Mean ± SD | |
|---|---|---|
| Pharmacokinetic Parameters | Bupropion HBr XL 348 mg Tablets (A) (Fed) (n = 48) | Bupropion HBr XL 348 mg Tablets (B) (Fasted) (n = 48) |
| AUC0-t (ng · hr/mL) | 9430.21 (53.90) 10454.75 ± 5635.07 | 8355.97 (53.13) 9356.36 ± 4971.39 |
| AUC0-inf (ng · hr/mL) | 9970.03 (54.94) 11148.70 ± 6124.76 | 8875.08 (55.60) 10081.16 ± 5604.76 |
| Cmax (ng/mL) | 179.62 (43.15) 193.84 ± 83.63 | 154.88 (41.45) 168.36 ± 69.79 |
| Tmax (hr)* | 11.00 (5.00-36.00) | 7.00 (5.00-24.00) |
| t½ (hr) | 50.49 ± 15.20 | 50.82 ± 18.50 |
| Kel (hr−1) | 1.49E−02 ± 4.29E−03 | 1.51E−02 ± 4.44E−03 |
| MRT (hr) | 69.31 ± 20.00 | 70.03 ± 23.78 |
| M/P Ratio | 5.94 ± 2.85 | 6.35 ± 3.21 |

*median (min-max)

(FED/Fasting) Relative Bioavailability Assessments for Bupropion Threoamino Alcohol:

| Parameter | 90% C.I. | Ratio of Means | Intra-Subject CV |
|---|---|---|---|
| AUC0-t | 106.31% to 119.80% | 112.86% | 17.56% |
| AUC0-inf | 105.67% to 119.42% | 112.34% | 17.99% |
| Cmax | 107.44% to 125.18% | 115.97% | 22.58% |

Summary of Pharmacokinetic Results:

Pharmacokinetic Parameters for Bupropion Erythroamino Alcohol:

|  | Geometric Mean (% CV) Arithmetic Mean ± SD | |
|---|---|---|
| Pharmacokinetic Parameters | Bupropion HBr XL 348 mg Tablets (A) (Fed) (n = 48) | Bupropion HBr XL 348 mg Tablets (B) (Fasted) (n = 48) |
| AUC0-t (ng · hr/mL) | 1827.80 (41.59) 1976.58 ± 822.09 | 1602.42 (43.32) 1762.94 ± 763.75 |
| AUC0-inf (ng · hr/mL) | 1922.92 (40.33) 2069.29 ± 834.50 | 1701.69 (41.91) 1860.34 ± 779.59 |
| Cmax (ng/mL) | 33.52 (29.90) 34.90 ± 10.44 | 28.94 (29.09) 30.18 ± 8.78 |
| Tmax (hr)* | 14.00 (8.00-36.00) | 14.00 (5.00-36.00) |
| t½ (hr) | 31.81 ± 7.32 | 31.09 ± 7.84 |
| Kel (hr−1) | 2.28E−02 ± 4.82E−03 | 2.36E−02 ± 5.60E−03 |
| MRT (hr) | 53.31 ± 11.39 | 51.58 ± 11.29 |
| M/P Ratio | 1.11 ± 0.38 | 1.18 ± 0.42 |

*median (min-max)

(FED/Fasting) Relative Bioavailability Assessments for Bupropion Erythroamino Alcohol:

| Parameter | 90% C.I. | Ratio of Means | Intra-Subject CV |
|---|---|---|---|
| AUC0-t | 106.29% to 122.40% | 114.07% | 20.81% |
| AUC0-inf | 105.83% to 120.66% | 113.00% | 19.32% |
| Cmax | 108.36% to 123.83% | 115.84% | 19.66% |

Summary of Pharmacokinetic Results:

Pharmacokinetic Parameters for PAWC:

| Pharmaco-kinetic Parameters | Geometric Mean (% CV) Arithmetic Mean ± SD | |
|---|---|---|
| | Bupropion HBr XL 348 mg Tablets (A) (Fed) (n = 48) | Bupropion HBr XL 348 mg Tablets (B) (Fasted) (n = 48) |
| AUC0-t (µM · hr) | 71.68 (45.24) 78.53 ± 35.52 | 68.31 (44.26) 74.80 ± 33.11 |
| AUC0-inf (µM · hr) | 72.09 (45.62) 79.05 ± 36.07 | 68.78 (44.28) 75.31 ± 33.34 |
| Cmax (µM) | 1.65 (34.28) 1.75 ± 0.60 | 1.67 (31.70) 1.75 ± 0.55 |
| Tmax (hr)* | 10.00 (2.00-24.00) | 5.51 (4.00-24.00) |
| t½ (hr) | 26.39 ± 6.17 | 26.33 ± 7.38 |
| Kel (hr−1) | 2.78E−02 ± 6.83E−03 | 2.81E−02 ± 6.72E−03 |
| MRT (hr) | 42.31 ± 7.70 | 41.45 ± 8.44 |

*median (min-max)

(FED/Fasting) Relative Bioavailability Assessments for PAWC:

| Parameter | 90% C.I. | Ratio of Means | Intra-Subject CV |
|---|---|---|---|
| AUC0-t | 98.67% to 111.60% | 104.94% | 18.11% |
| AUC0-inf | 98.47% to 111.56% | 104.81% | 18.36% |
| Cmax | 92.74% to 105.44% | 98.89% | 18.89% |

Conclusion:

The objective of this study was to evaluate the effect of food on the rate and extent of absorption of bupropion from a novel formulation of Bupropion HBr XL (extended release) 348 mg Tablets.

The relative bioavailability of bupropion, its metabolites and the pharmacologic activity-weighted composite (PAWC) data were assessed by measuring and comparing the peak and total systemic exposure from the 2 treatments (using AUC0-t, AUC0-inf, and Cmax).

Relative to drug administration under fasting conditions, the peak and systemic exposure for bupropion following a single oral dose of Bupropion HBr XL 348 mg Tablet with food was increased by 7% and 19%, respectively. The increase in Cmax as found not to be significant since the 90% geometric confidence interval fell within the 80.00-125.00% range. The 90% CI for AUC0-t and AUC0-inf however were found to fall slightly outside the 80.00-125.00% range (90% CI for AUC0-t=113.23-126.06%; 90% CI for AUC0-inf=112.96-125.52%). This marginal failure of not being within the 80.00%-125.00% was concluded not to be clinically significant. Lastly, the presence of food did not lead to a change in the Tmax of bupropion.

Similar outcome were observed with hydroxybupropion, bupropion erythroamino alcohol and bupropion threoamino alcohol.

For PAWC, food had no significant influence on the Cmax and AUCs with the 90% CI falling within the 80.00-125.00% range %.

In conclusion it was surmised that Bupropion HBr XL 348 mg Tablets does not exhibit a significant food effect when given as a single oral dose.

Overall, Bupropion HBr XL 348 mg Tablets were well tolerated as a single-dose of 348 mg, administered under fed and fasted conditions, and no significant safety issues emerged.

This study was performed in compliance with GCP.

TABLE

Mean (±SD) Pharmacokinetic Parameters for Bupropion (n = 48)

| | Fed Bupropion HBr XL 348 mg Tablets (06C159P) (n = 48) | Fasting Bupropion HBr XL 348 mg Tablets (06C159P) (n = 48) |
|---|---|---|
| AUC0-t (ng * hr/mL) | 1814 ± 543 | 1515 ± 414 |
| AUC0-∞ (ng * hr/mL) | 1876 ± 551 | 1572 ± 421 |
| Cmax (ng/mL) | 136.8 ± 43.1 | 125.9 ± 34.5 |
| Tmax (hr)* | 5.0 (2.0-10.0) | 5.0 (3.0-7.0) |
| t½ (hr) | 23.2 ± 6.5 | 21.3 ± 6.7 |
| MRT (hr) | 22.4 ± 5.9 | 21.2 ± 5.6 |

*Median (Range)

TABLE

Summary Statistics for Bupropion (n = 48)

| | Bupropion HBr XL 348 mg Tablets: Fed Versus Fasting | |
|---|---|---|
| | Ratio of Geometric Means | 90% Geometric Confidence Interval |
| AUC0-t | 119.47% | 113.23 to 126.06% |
| AUC0-∞ | 119.07% | 112.96 to 125.52% |
| Cmax | 107.48% | 98.20 to 117.64% |

TABLE

Mean (±SD) Pharmacokinetic Parameters for Hydroxybupropion (n = 48)

| | Fed Bupropion HBr XL 348 mg Tablets (06C159P) (n = 48) | Fasting Bupropion HBr XL 348 mg Tablets (06C159P) (n = 48) |
|---|---|---|
| AUC0-t (ng * hr/mL) | 25506 ± 13953 | 24948 ± 13334 |
| AUC0-∞ (ng * hr/mL) | 25871 ± 14033 | 25285 ± 13347 |
| Cmax (ng/mL) | 525.1 ± 239.3 | 507.4 ± 221.1 |
| Tmax (hr)* | 14.0 (7.0-36.0) | 8.0 (5.0-24.0) |
| t½ (hr) | 24.8 ± 4.8 | 24.3 ± 4.9 |
| MRT (hr) | 42.7 ± 7.6 | 41.1 ± 7.4 |
| Metabolite/Parent Ratio | 13.2 ± 6.0 | 15.5 ± 7.3 |

*Median (Range)

TABLE

Summary Statistics for Hydroxybupropion (n = 48)

| | Bupropion HBr XL 348 mg Tablets: Fed Versus Fasting | |
|---|---|---|
| | Ratio of Geometric Means | 90% Geometric Confidence Interval |
| AUC0-t | 101.95% | 95.40 to 108.96% |
| AUC0-∞ | 102.01% | 95.50 to 108.95% |
| Cmax | 102.52% | 96.75 to 108.62% |

TABLE

Mean (±SD) Pharmacokinetic Parameters for Bupropion Threoamino Alcohol (n = 48)

|  | Fed Bupropion HBr XL 348 mg Tablets (06C159P) (n = 48) | Fasting Bupropion HBr XL 348 mg Tablets (06C159P) (n = 48) |
| --- | --- | --- |
| AUC0-t (ng * hr/mL) | 10455 ± 5635 | 9356 ± 4971 |
| AUC0-∞ (ng * hr/mL) | 11149 ± 6125 | 10081 ± 5605 |
| Cmax (ng/mL) | 193.8 ± 83.6 | 168.4 ± 69.8 |
| Tmax (hr)* | 11.0 (5.0-36.0) | 7.0 (5.0-24.0) |
| t½ (hr) | 50.5 ± 15.2 | 50.8 ± 18.5 |
| MRT (hr) | 69.3 ± 20.0 | 70.0 ± 23.8 |
| Metabolite/Parent Ratio | 5.9 ± 2.9 | 6.4 ± 3.2 |

*Median (Range)

TABLE

Summary Statistics for Bupropion Threoamino Alcohol (n = 48)

|  | Bupropion HBr XL 348 mg Tablets: Fed Versus Fasting | |
| --- | --- | --- |
|  | Ratio of Geometric Means | 90% Geometric Confidence Interval |
| AUC0-t | 112.86% | 106.31 to 119.80% |
| AUC0-∞ | 112.34% | 105.67 to 119.42% |
| Cmax | 115.97% | 107.44 to 125.18% |

TABLE

Mean (±SD) Pharmacokinetic Parameters for Bupropion Erythroamino Alcohol (n = 48)

|  | Fed Bupropion HBr XL 348 mg Tablets (06C159P) (n = 48) | Fasting Bupropion HBr XL 348 mg Tablets (06C159P) (n = 48) |
| --- | --- | --- |
| AUC0-t (ng * hr/mL) | 1977 ± 822 | 1763 ± 764 |
| AUC0-∞ (ng * hr/mL) | 2069 ± 835 | 1860 ± 780 |
| Cmax (ng/mL) | 34.9 ± 10.4 | 30.2 ± 8.8 |
| Tmax (hr)* | 14.0 (8.0-36.0) | 14.0 (5.0-36.0) |
| t½ (hr) | 31.8 ± 7.3 | 31.1 ± 7.8 |
| MRT (hr) | 53.3 ± 11.4 | 51.6 ± 11.3 |
| Metabolite/Parent Ratio | 1.1 ± 0.4 | 1.2 ± 0.4 |

*Median (Range)

TABLE

Summary Statistics for Bupropion Erythroamino Alcohol (n = 48)

|  | Bupropion HBr XL 348 mg Tablets: Fed Versus Fasting | |
| --- | --- | --- |
|  | Ratio of Geometric Means | 90% Geometric Confidence Interval |
| AUC0-t | 114.07% | 106.29 to 122.40% |
| AUC0-∞ | 113.00% | 105.83 to 120.66% |
| Cmax | 115.84% | 108.36 to 123.83% |

TABLE

Mean (±SD) Pharmacokinetic Parameters for PAWC (n = 48)

| Pharmacokinetic Parameters | Fed Bupropion HBr XL 348 mg Tablets (06C159P) (n = 48) | Fasting Bupropion HBr XL 348 mg Tablets (06C159P) (n = 48) |
| --- | --- | --- |
| AUC0-t (μM * hr)) | 78.5 ± 35.5 | 74.8 ± 33.1 |
| AUC0-∞ (μM * hr)) | 79.1 ± 36.1 | 75.3 ± 33.3 |
| Cmax (μM) | 1.8 ± 0.6 | 1.8 ± 0.6 |
| Tmax (hr)* | 10.0 (2.0-24.0) | 5.5 (4.0-24.0) |
| t½ (hr) | 26.4 ± 6.2 | 26.3 ± 7.4 |
| MRT (hr) | 42.3 ± 7.7 | 41.5 ± 8.4 |

*Median (Range)

TABLE

Summary Statistics for PAWC (n = 48)

|  | Bupropion HBr XL 348 mg Tablets: Fed Versus Fasting | |
| --- | --- | --- |
|  | Ratio of Geometric Means | 90% Geometric Confidence Interval |
| AUC0-t | 104.94% | 98.67 to 111.60% |
| AUC0-∞ | 104.81% | 98.47 to 111.56% |
| Cmax | 98.89% | 92.74 to 105.44% |

Two-Way Crossover Fasting Steady State Dosage Strength Proportionality Study of Bupropion Hydrobromide XL Tablets (522 mg vs 3×174 mg) in Healthy Non-Smoking Adult Volunteers. Study B06-802PK-10121 (AA40055)

The rate and extent of absorption of a Bupropion HBr XL 522 mg Tablet was studied relative to 3× Bupropion HBr XL 174 mg Tablets under multiple-dose fasting conditions. The 522 mg tablet was equivalent to 174 mg tablets given as 3×174 mg.

Results are shown below and in FIGS. 92-96.

Methodology:

This was an open-label, randomized, 2-way crossover, 2-sequence, multiple-dose, dosage strength proportionality study under fasting conditions.

Number of Subjects (Planned and Analysed):

A total of 40 healthy adult non-smoking subjects (29 males and 11 females) were dosed, and 29 subjects (21 males and 8 females) completed the study. Pharmacokinetic parameters were calculated for subjects who completed the study. Safety assessment was performed for all subjects who received at least one dose.

Main Criteria for Inclusion and Exclusion:

Forty (40) healthy adult non-smoking (for at least 3 months) male or female volunteers at the ages of from 18 to 55 years were to be selected for inclusion in the study.

Test and Reference Products, Dose, Mode of Administration, and Batch Number:

Bupropion HBr XL 522 mg tablets (test product), Manufactured by Biovail Corporation; Lot No.: 06M119P; Bulk Lot No.: 06M303.

Bupropion HBr XL 174 mg tablets (product for titration and reference product), Manufactured by Biovail Corporation; Lot No.: 06M062P; Bulk Lot No.: 06D117.

Duration of Treatment:

This study involved an up-titration period of 8 days prior to the treatment period. In the mornings of Days 1 to 3, all subjects were administered a one tablet dose (1×174 mg; reference product) with 240 mL of water at room temperature, under fasting conditions. In the mornings of Days 4 to 8, all subjects were administered a 2 tablet dose (2×174 mg; reference product for a total dose of 348 mg) with 240 mL of water at room temperature, under fasting conditions.

For 14 consecutive days (Days 9 to 22), subjects received either one 522 mg bupropion hydrobromide tablet (test product) or three 174 mg bupropion hydrobromide tablets (reference product for a total dose of 522 mg). In the mornings of Days 23 to 36, subjects received the alternate treatment. There was no washout between the treatments. Subjects were dosed under fasting conditions.

Criteria for Evaluation:

Study endpoints were the 90% confidence intervals of the ratios of least-squares means (LSM) for the pharmacokinetic parameters AUC0-τ, Cmax,ss and Cmin,ss of the test to reference formulation under fasting conditions.

Safety assessment included laboratory evaluations, sedation tests, neurological tests, physical examinations, adverse events, ECG monitoring and vital signs assessments.

Pharmacokinetics:

Pharmacokinetic analysis was conducted using non-compartmental analysis. The following parameters: AUC0-τ, Cmax,ss, Tmax,ss, Cpd, Cmin,ss, Cssav, % Fluctuation and % Swing were calculated for bupropion, hydroxybupropion, bupropion threoamino alcohol and bupropion erythroamino alcohol.

All pharmacokinetic parameters were also calculated for the pharmacologic activity-weighted composite (PAWC).

In addition, the metabolite/parent (M/P) ratios based on AUC0-τ corrected for molecular weight were calculated for all metabolites.

Safety:

Safety data, including laboratory evaluations, physical examinations, adverse events, ECG monitoring and vital signs assessments were summarized by collection time and by treatment group, when appropriate. Descriptive statistics (arithmetic mean, standard deviation, median, minimum and maximum) were calculated for quantitative safety data as well as for the difference from baseline, if applicable. Frequency counts were compiled for classification of qualitative safety data. In addition, a shift table describing out of normal range shifts was provided for clinical laboratory results. A normal-abnormal shift table was also presented for physical examination and EEG results.

Adverse events were coded using the latest version of MedDRA dictionary and summarized by treatment for the number of subjects reporting the adverse event and the number of adverse events reported. A by-subject adverse event data listing including investigator term, coded term, treatment group, severity, and relationship to treatment were provided. Concomitant medications were listed by subject and coded using the latest version of the WHO drug dictionary. Medical history was listed by subject and coded using the latest version of MedDRA dictionary.

Statistical Methods:

Descriptive statistics were performed for plasma concentrations and for all pharmacokinetic parameters. Using GLM procedure in SAS), an analysis of variance (ANOVA) was performed on ln-transformed pharmacokinetic parameters AUC0-τ, Cmax,ss and Cmin,ss. The intra-subject coefficient of variation (CV) was calculated using the mean square error (MSE) from the ANOVA. The ratios of LSM and the 90% confidence intervals were calculated based on the difference in the LSM of the ln-transformed AUC0-τ, Cmax,ss and Cmin,ss between the test and the reference formulation. Steady state was assessed using pre-dose concentrations on Days 19, 20, 21 and 22 as well as on Days 33, 34, 35 and 36 based on Helmert's contrasts. Bioavailability was evaluated on the basis of the 90% confidence intervals of the ratios of LSM of the test to reference formulation for the parent drug, metabolites and PAWC. Confidence interval percentages were within the 80.0-125.0% acceptance criteria.

The parameter Tmax,ss was analyzed using the nonparametric methods of Koch and Hauschke. The equality of treatment effect in both sequences was evaluated using Wilcoxon rank-sum tests. The shift between the two treatments was estimated by the median unbiased Hodges-Lehmann estimate and its 90% confidence interval. The Hodges-Lehmann procedure extends the Wilcoxon rank-sum test to provide a median unbiased point estimate and a confidence interval for the magnitude of the shift between two populations.

Summary/Results:

Bupropion

The pharmacokinetic parameters of bupropion in plasma following oral administrations of Bupropion HBr XL 522 mg tablets and Bupropion HBr XL 174 mg tablets (total dose of 522 mg) are listed below:

| Parameter | Bupropion HBr XL 1 × 522 mg tablet | Bupropion HBr XL 3 × 174 mg tablets |
|---|---|---|
| Geometric Mean (% CV) | | |
| AUC0-τ (ng · h/mL) | 1655 (32.4%) | 1677 (33.0%) |
| Cmax, ss (ng/mL) | 165 (37.2%) | 159 (32.0%) |
| Cmin, ss (ng/mL) | 28.8 (44.6%) | 28.9 (41.4%) |
| Median Tmax (Min-Max) | | |
| Tmax, ss (h) | 4.00 (2.00-7.00) | 5.00 (3.00-6.06) |
| Arithmetic Mean (±SD) | | |
| AUC0-τ (ng · h/mL) | 1730 ± 494 | 1763 ± 574 |
| Cmax, ss (ng/mL) | 176 ± 63.6 | 167 ± 53.0 |
| Cmin, ss (ng/mL) | 31.4 ± 13.4 | 31.3 ± 13.2 |
| Cssav (ng/mL) | 72.1 ± 20.6 | 73.5 ± 23.9 |
| Fluctuation (%) | 200 ± 48.6 | 187 ± 24.9 |
| Swing (%) | 522 ± 251 | 468 ± 143 |

At steady state, the mean rate and extent of systemic exposure of bupropion within the 24 hours dosing interval (Cmax, ss, AUC0-τ) were similar between Bupropion HBr XL 1×522 mg tablet and Bupropion HBr XL 3×174 mg tablets. The mean % fluctuation and the mean % swing values were 7% and 12%, respectively greater for Bupropion HBr XL 1×522 mg tablet compared to Bupropion HBr XL 3×174 mg tablets.

The median Tmax,ss value of bupropion was 4.0 hours and 5.0 hours for Bupropion HBr XL 1×522 mg and Bupropion HBr XL 3×174 mg tablets, respectively. The non-parametric 90% confidence interval for the median Tmax,ss of the test-reference difference (formulation effect), was [−1.00; 0.50] for bupropion.

Results of the ANOVA for bupropion in plasma following oral administrations of Bupropion HBr XL 1×522 mg tablet and Bupropion HBr XL 3×174 mg tablets (total dose of 522 mg) are presented as follows:

Ratios of LSM (90% Confidence Intervals)

| Parameter | Biovail Bupropion HBr XL 1 × 522 mg tablet (A) vs. Biovail Bupropion HBr XL 3 × 174 mg tablets (B) |
|---|---|
| AUC0-τ | 97.8% (91.4%-104.5%) |
| Cmax, ss | 103.2% (96.0%-111.0%) |
| Cmin, ss | 99.0% (90.7%-108.0%) |

The 90% confidence intervals of the ratio of LSM derived from the analyses of the ln-transformed pharmacokinetic parameters AUC0-τ, Cmax,ss and Cmin,ss for bupropion in plasma were within 80.0-125.0%

Helmert's contrasts results demonstrated that the relative bioavailability for bupropion for both dosage strength tablets (1×522 mg and 3×174 mg) was assessed under steady state conditions on Days 22 and 36.

Bupropion Metabolites

The pharmacokinetic parameters of bupropion metabolites in plasma following oral administrations of Bupropion HBr XL 1×522 mg tablet and Bupropion HBr XL 3×174 mg tablets (total dose of 522 mg) are listed below.

At steady state, the metabolic ratios based on the AUC0-τ of hydroxybupropion, bupropion threoamino alcohol and bupropion erythroamino alcohol over bupropion were 15.7, 8.65, and 1.81, respectively, for the Biovail Bupropion HBr XL 1×522 mg tablet. Metabolic ratios were similar when compared to Biovail Bupropion HBr XL 3×174 mg tablets.

The mean % fluctuation and the mean % swing values of all bupropion metabolites were comparable following both dosage strength tablets (1×522 mg and 3×174 mg tablets).

The median Tmax,ss value of hydroxybupropion and bupropion erythroamino alcohol was observed 2 hours earlier for Bupropion HBr XL 1×522 mg tablet than for Bupropion HBr XL 3×174 mg tablets. The median Tmax,ss value of bupropion threoamino alcohol was observed 1 hour earlier for Bupropion HBr XL 1×522 mg tablet than for Bupropion HBr XL 3×174 mg tablets. The nonparametric 90% confidence intervals for the median Tmax,ss of the test-reference difference (formulation effect), were [−2.00; 0.00] for hydroxybupropion, [−2.00; −0.50] for bupropion threoamino alcohol and [−2.00; 0.00] for bupropion erythroamino alcohol.

The pharmacokinetic results of bupropion metabolites in plasma following oral administrations of Bupropion HBr XL 1×522 mg and Bupropion HBr XL 3×174 mg tablets (total dose of 522 mg) are listed below.

| Parameter | Hydroxybupropion | | Bupropion Threoamino Alcohol | | Bupropion Erythroamino Alcohol | |
|---|---|---|---|---|---|---|
| | Bupropion HBr XL 1 × 522 mg | Bupropion HBr XL 3 × 174 mg | Bupropion HBr XL 1 × 522 mg | Bupropion HBr XL 3 × 174 mg | Bupropion HBr XL 1 × 522 mg | Bupropion HBr XL 3 × 174 mg |
| Geometric Mean (% CV) | | | | | | |
| AUC0-τ (ng · h/mL) | 25158 (53.4%) | 25271 (48.5%) | 13802 (40.2%) | 13658 (40.7%) | 2857 (38.0%) | 2831 (36.5%) |
| Cmax, ss (ng/mL) | 1338 (48.5%) | 1311 (42.9%) | 753 (38.3%) | 731 (39.6%) | 146 (35.8%) | 144 (36.9%) |
| Cmin, ss (ng/mL) | 880 (57.7%) | 943 (54.5%) | 450 (48.7%) | 466 (40.8%) | 101 (48.2%) | 105 (36.7%) |
| Median Tmax, (Min-Max) | | | | | | |
| Tmax, ss (h) | 5.04 (2.00-8.00) | 7.00 (3.00-12.00) | 6.00 (2.03-10.00) | 7.00 (3.00-14.00) | 6.00 (2.00-10.00) | 8.00 (3.00-16.00) |
| Arithmetic Mean (±SD) | | | | | | |
| AUC0-τ (ng · h/mL) | 27738 ± 10583 | 27389 ± 9385 | 14840 ± 5929 | 14730 ± 6138 | 3048 ± 1135 | 3006 ± 1075 |
| Cmax, ss (ng/mL) | 1457 ± 530 | 1402 ± 446 | 805 ± 309 | 785 ± 311 | 155 ± 55.4 | 154 ± 54.9 |
| Cmin, ss (ng/mL) | 986 ± 415 | 1042 ± 410 | 496 ± 220 | 504 ± 218 | 111 ± 46.5 | 112 ± 40.8 |
| Cssav (ng/mL) | 1156 ± 441 | 1141 ± 391 | 618 ± 247 | 614 ± 256 | 127 ± 47.3 | 125 ± 44.8 |
| Fluctuation (%) | 43.0 ± 17.3 | 34.9 ± 15.4 | 52.1 ± 19.0 | 46.7 ± 13.3 | 37.1 ± 17.0 | 33.5 ± 12.6 |
| Swing (%) | 55.1 ± 32.8 | 40.5 ± 20.8 | 71.9 ± 45.3 | 58.3 ± 20.3 | 47.3 ± 32.9 | 38.6 ± 16.9 |
| M/P ratio | 15.7 ± 6.82 | 16.0 ± 8.35 | 8.65 ± 2.70 | 8.47 ± 2.83 | 1.81 ± 0.599 | 1.77 ± 0.610 |

Ratios of LSM (90% Confidence Intervals)

| Parameter | Hydroxybupropion Biovail Bupropion HBr XL 1 × 522 mg (A) vs. Biovail Bupropion HBr XL 3 × 174 mg tablets (B) | Bupropion Threoamino Alcohol Biovail Bupropion HBr XL 1 × 522 mg (A) vs. Biovail Bupropion HBr XL 3 × 174 mg tablets (B) | Bupropion Erythroamino Alcohol Biovail Bupropion HBr XL 1 × 522 mg (A) vs. Biovail Bupropion HBr XL 3 × 174 mg tablets (B) |
|---|---|---|---|
| AUC0-τ | 99.5% (95.3%-104.0%) | 100.9% (94.1%-108.1%) | 100.7% (94.6%-107.2%) |
| Cmax, ss | 102.2% (98.0%-106.6%) | 102.6% (95.4%-110.3%) | 101.0% (94.8%-107.6%) |
| Cmin, ss | 93.7% (87.7%-100.2%) | 96.6% (88.2%-105.7%) | 96.4% (88.2%-105.4%) |

The 90% confidence intervals of the ratio of LSM derived from the analyses of the ln-transformed pharmacokinetic parameters AUC0-τ, Cmax,ss and Cmin,ss for all bupropion metabolites were within 80.0-125.0%.

PAWC (Pharmacological Activity Weighted Composite)

The pharmacokinetic parameters of PAWC following oral administrations of Bupropion HBr XL 1×522 mg tablet and Bupropion HBr XL 3×174 mg tablets (total dose of 522 mg) are listed below.

| Parameter | PAWC Bupropion HBr XL 1 × 522 mg tablet | Bupropion HBr XL 3 × 174 mg tablets |
|---|---|---|
| Geometric Mean (% CV) | | |
| AUC0-τ (nmol · h/mL) | 82.2 (39.1%) | 82.9 (32.4%) |
| Cmax, ss (nmol/mL) | 4.64 (34.7%) | 4.51 (27.0%) |
| Cmin, ss (nmol/mL) | 2.73 (45.5%) | 2.91 (39.3%) |
| Median Tmax (Min-Max) | | |
| Tmax, ss (h) | 5.00 (2.00-7.00) | 5.00 (3.00-12.00) |
| Arithmetic Mean (± SD) | | |
| AUC0-τ (nmol · h/mL) | 87.4 ± 27.8 | 86.5 ± 23.6 |
| Cmax, ss (nmol/mL) | 4.88 ± 1.45 | 4.65 ± 1.12 |
| Cmin, ss (nmol/mL) | 2.96 ± 1.09 | 3.09 ± 1.03 |
| Cssav (nmol/mL) | 3.64 ± 1.16 | 3.61 ± 0.983 |
| Fluctuation (%) | 55.2 ± 18.6 | 46.3 ± 16.9 |
| Swing (%) | 73.8 ± 38.4 | 57.0 ± 26.2 |

The nonparametric 90% confidence intervals for the median Tmax,ss of the test-reference difference (formulation effect) was [−1.50; −0.50] for PAWC.

The pharmacokinetic results for the PAWC dataset following oral administration of Bupropion HBr XL 1×522 mg tablet and Bupropion HBr XL 3×174 mg tablets (total dose of 522 mg) are listed below.

Ratios of LSM (90% Confidence Intervals)

| Parameter | PAWC Biovail Bupropion HBr XL 1 × 522 mg tablet (A) vs. Biovail Bupropion HBr XL 3 × 174 mg tablets (B) |
|---|---|
| AUC0-τ | 99.1% (94.6%-103.8%) |
| Cmax, ss | 102.9% (98.2%-107.7%) |
| Cmin, ss | 94.2% (87.9%-100.9%) |

The 90% confidence intervals of the ratio of LSM derived from the analyses of the ln-transformed pharmacokinetic parameters AUC0-τ, Cmax,ss and Cmin,ss for PAWC were within 80.0-125.0%.

Conclusion:

Following repeated oral administrations of bupropion Hydrobromide XL Tablets (522 mg vs. 3×174 mg) in healthy volunteers, the 90% confidence intervals of the ratios of LSM derived from the analyses of the ln-transformed pharmacokinetic parameters AUC0-τ, Cmax,ss and Cmin,ss for bupropion, hydroxybupropion, bupropion threoamino alcohol, bupropion erythroamino alcohol and PAWC in plasma were within 80.0-125.0%.

In conclusion, results from the current dosage strength proportionality study demonstrated that repeated oral administrations of Biovail bupropion hydrobromide XL tablets as a single 522 mg tablet and three 174 mg tablets are equivalent under multiple dose fasting conditions.

TABLE

Mean (±SD) Pharmacokinetic Parameters for Bupropion (n = 29)

| | 1 × Bupropion HBr XL 522 mg Tablet (06M119P) (n = 29) | 3 × Bupropion HBr XL 174 mg Tablets (06M062P) (n = 29) |
|---|---|---|
| AUC0-τ (ng * hr/mL) | 1730 ± 494 | 1763 ± 574 |
| Cmax (ng/mL) | 176.1 ± 63.6 | 166.9 ± 53.0 |
| Cmin (ng/mL) | 31.4 ± 13.4 | 31.3 ± 13.2 |
| Cavg (ng/mL) | 72.1 ± 20.6 | 73.5 ± 23.9 |
| Tmax (hr)* | 4.0 (2.0, 7.0) | 5.0 (3.0, 6.1) |
| Degree of Fluctuation (%) | 199.9 ± 48.6 | 186.7 ± 24.9 |

*Median (Range)

TABLE

Summary Statistics for Bupropion (n = 29)

| | 1 × Bupropion HBr XL 522 mg Tablet Versus 3 × Bupropion HBr XL 174 mg Tablets | |
|---|---|---|
| | Ratio of Geometric Means | 90% Geometric Confidence Interval |
| AUC0-τ | 97.8% | 91.4-104.5% |
| Cmax | 103.2% | 96.0-111.0% |
| Cmin | 99.0% | 90.7-108.0% |

TABLE

Mean (±SD) Pharmacokinetic Parameters for Hydroxybupropion (n = 29)

| | 1 × Bupropion HBr XL 522 mg Tablet (06M119P) (n = 29) | 3 × Bupropion HBr XL 174 mg Tablets (06M062P) (n = 29) |
|---|---|---|
| AUC0-τ (ng * hr/mL) | 27738 ± 10583 | 27389 ± 9385 |
| Cmax (ng/mL) | 1457.0 ± 530.3 | 1401.9 ± 445.8 |
| Cmin (ng/mL) | 985.9 ± 414.8 | 1042.4 ± 410.4 |
| Cavg (ng/mL) | 1155.7 ± 441.0 | 1141.2 ± 391.0 |
| Tmax (hr)* | 5.0 (2.0, 8.0) | 7.0 (3.0, 12.0) |
| Degree of Fluctuation (%) | 43.0 ± 17.3 | 34.9 ± 15.4 |
| Metabolite/Parent Ratio | 15.7 ± 6.8 | 16.0 ± 8.3 |

TABLE-continued

Mean (±SD) Pharmacokinetic Parameters for Hydroxybupropion (n = 29)

|  | 1 × Bupropion HBr XL 522 mg Tablet (06M119P) (n = 29) | 3 × Bupropion HBr XL 174 mg Tablets (06M062P) (n = 29) |
|---|---|---|

*Median (Range)

TABLE

Summary Statistics for Hydroxybupropion (n = 29)

1 × Bupropion HBr XL 522 mg Tablet Versus 3 × Bupropion HBr XL 174 mg Tablets

|  | Ratio of Geometric Means | 90% Geometric Confidence Interval |
|---|---|---|
| AUC0-τ | 99.5% | 95.3-104.0% |
| Cmax | 102.2% | 98.0-106.6% |
| Cmin | 93.7% | 87.7-100.2% |

TABLE

Mean (±SD) Pharmacokinetic Parameters for Bupropion Threoamino Alcohol (n = 29)

|  | 1 × Bupropion HBr XL 522 mg Tablet (06M119P) (n = 29) | 3 × Bupropion HBr XL 174 mg Tablets (06M062P) (n = 29) |
|---|---|---|
| AUC0-τ (ng * hr/mL) | 14840 ± 5929 | 14730 ± 6138 |
| Cmax (ng/mL) | 805.2 ± 3008.7 | 784.9 ± 310.9 |
| Cmin (ng/mL) | 496.2 ± 219.5 | 503.6 ± 217.9 |
| Cavg (ng/mL) | 618.4 ± 247.1 | 613.8 ± 255.8 |
| Tmax (hr)* | 6.0 (2.0, 10.0) | 7.0 (3.0, 14.0) |
| Degree of Fluctuation (%) | 51.2 ± 19.0 | 46.7 ± 13.3 |
| Metabolite/Parent Ratio | 8.7 ± 2.7 | 8.5 ± 2.8 |

*Median (Range)

TABLE

Summary Statistics for Bupropion Threoamino Alcohol (n = 29)

1 × Bupropion HBr XL 522 mg Tablet Versus 3 × Bupropion HBr XL 174 mg Tablets

|  | Ratio of Geometric Means | 90% Geometric Confidence Interval |
|---|---|---|
| AUC0-τ | 100.9% | 94.2-108.1% |
| Cmax | 102.6% | 95.4-110.3% |
| Cmin | 96.6% | 88.2-105.7% |

TABLE

Mean (±SD) Pharmacokinetic Parameters for Bupropion Erythroamino Alcohol (n = 29)

|  | 1 × Bupropion HBr XL 522 mg Tablet (06M119P) (n = 29) | 3 × Bupropion HBr XL 174 mg Tablets (06M062P) (n = 29) |
|---|---|---|
| AUC0-τ (ng * hr/mL) | 3048 ± 1135 | 3006 ± 1074 |
| Cmax (ng/mL) | 155.3 ± 55.4 | 153.6 ± 54.9 |
| Cmin (ng/mL) | 111.3 ± 46.5 | 111.6 ± 40.8 |
| Cavg (ng/mL) | 127.0 ± 47.3 | 125.3 ± 44.8 |
| Tmax (hr)* | 6.0 (2.0, 10.0) | 8.0 (3.0, 16.0) |
| Degree of luctuation (%) | 37.1 ± 17.0 | 33.5 ± 12.6 |
| Metabolite/Parent Ratio | 1.8 ± 0.6 | 1.8 ± 0.6 |

*Median (Range)

TABLE

Summary Statistics for Bupropion Erythroamino Alcohol (n = 29)

1 × Bupropion HBr XL 522 mg Tablet Versus 3 × Bupropion HBr XL 174 mg Tablets

|  | Ratio of Geometric Means | 90% Geometric Confidence Interval |
|---|---|---|
| AUC0-τ | 100.7% | 94.6-107.2% |
| Cmax | 101.0% | 94.8-107.6% |
| Cmin | 96.4% | 88.2-105.4% |

TABLE

Mean (±SD) Pharmacokinetic Parameters for PAWC (n = 29)

| Pharmacokinetic Parameters | 1 × Bupropion HBr XL 522 mg Tablet (06M119P) (n = 29) | 3 × Bupropion HBr XL 174 mg Tablets (06M062P) (n = 29) |
|---|---|---|
| AUC0-τ (nmol * hr/mL) | 87.4 ± 27.8 | 86.5 ± 23.6 |
| Cmax (nmol/mL) | 4.9 ± 1.5 | 4.7 ± 1.1 |
| Cmin (nmol/mL) | 3.0 ± 1.1 | 3.1 ± 1.0 |
| Cavg (nmol/mL) | 3.6 ± 1.2 | 3.6 ± 1.0 |
| Tmax (hr)* | 5.0 (2.0, 7.0) | 5.0 (3.0, 12.0) |
| Degree of Fluctuation (%) | 55.2 ± 18.6 | 46.3 ± 16.9 |

*Median (Range)

TABLE

Summary Statistics for PAWC (n = 29)

1 × Bupropion HBr XL 522 mg Tablet Versus 3 × Bupropion HBr XL 174 mg Tablets

|  | Ratio of Geometric Means | 90% Geometric Confidence Interval |
|---|---|---|
| AUC0-τ | 99.1% | 94.6-103.8% |
| Cmax | 102.9% | 98.2-107.7% |
| Cmin | 94.2% | 87.9-100.9% |

Example 23

The analysis of 3'-Chloro-2-bromopropiophenone impurity in Bupropion HBr samples in this example is based on a HPLC LIMIT TEST. The impurity peak, eventually present in the sample chromatogram, should not exceed in area the peak of the analyte in the "reference solution" chromatogram corresponding to a concentration of 3 ppm of impurity in the sample. The method uses a C18 column with UV detection at 255 nm and an isocratic mobile phase.

| | Operating conditions |
|---|---|
| Instrument: | Shimadzu HPLC pump LC-10AD, system controller SCL-10A, autoinjector SIL-10A (or equivalent) |
| Column: | phase: Waters XBridge C18<br>particle size: 5 mm<br>column length: 250 mm<br>column ID: 4.6 mm |
| Injection volume: | 50 ml |
| Detector: | Shimadzu UV detector model SPD-10A (or equivalent) |
| Wavelength: | UV, 255 nm |
| Mobile phase: | see preparation below |
| Column T: | 40° C. |
| Flow: | 1.2 ml/min. |

Mobile phase: mix 1100 ml of acetonitrile and 1000 ml of $Na_2HPO_4$ 20 mM solution in HPLC water. Adjust the pH to pH 7.2 with phosphoric acid 85%.

Sample solution: weigh accurately 500 mg of sample and transfer into a 50 ml volumetric flask. Dissolve and dilute to volume with HPLC water (10 mg/ml).

Reference solution (3'-Chloro-2-bromopropiophenone 3 ppm spiked solution): weigh accurately 15 mg (±1 mg) of 3'-Chloro-2-bromopropiophenone WSTD into a 100 ml volumetric flask. Dissolve and dilute to volume with acetonitrile (0.15 mg/ml, sol.A). Pipet accurately 1.0 ml of "sol.A" into another 100 ml volumetric flask and dilute to volume with HPLC water (0.0015 mg/ml, sol. B). Into a 50 ml volumetric flask weigh about 500 mg of Bupropion.HBr WSTD and add accurately 1.0 ml of "sol.B". Dissolve and dilute to volume with HPLC water (Bupropion.HBr 10 mg/ml and analyte 0.03 µg/ml, which corresponds to 0.0003% (3 ppm) of the sample concentration 10,000 µg/ml).

System suitability test: condition the HPLC system with the prescribed "operating conditions" until a stable, flat baseline is obtained then inject 50 ml of "reference solution". Allow the analysis to carry on. The system suitability test is complied if:

1) Specificity and sensitivity: The peak of 3'-Chloro-2-bromopropiophenone is resolved from the Bupropion and other eventual impurity peaks and has an RT of 13 min.±2 min. The peak area of the analyte is NLT 5000.
2) Precision: the RSD % of all analyte peak areas obtained in the "reference solution" chromatograms is NMT 20%.

Procedure: on system suitability compliance separately inject 50 µl of reference and sample solutions. Record the chromatograms and measure the peak area responses of the 3'-Chloro-2-bromopropiophenone impurity peaks.

Evaluation:

Identification: identify the 3'-Chloro-2-bromopropiophenone impurity in the sample runs, if present, by comparing the peak RTs with the "reference solution" runs. The expected RT is tabulated below:

| RT/RRT TABULATION | |
|---|---|
| Compound | RT min. |
| 3'-chloro-2-bromopropiophenone | 13 min. ± 2 min |

Limit evaluation: any peak, eventually present on the sample chromatogram identified as 3'-Chloro-2-bromopropiophenone should have a peak area NMT the mean peak area of the 3'-Chloro-2-bromopropiophenone in the "reference solution" replicates corresponding to a content of 3 ppm (0.0003%) impurity in the sample. For the result report consider the following tabulation:

| RESULT REPORTING TABULATION | |
|---|---|
| Impurity | Report |
| the 3'-chloro-2-bromopropiophenone peak area is lower than the 3 ppm reference area | <3 ppm |
| the 3'-chloro-2-bromopropiophenone peak area is higher than the 3 ppm reference area | >3 ppm |

| METHOD SENSITIVITY | | |
|---|---|---|
| Impurity | LOQ | LOD |
| 3'-chloro-2-bromopropiophenone | not applicable to limit test | 1 ppm*<br>(0.01 µg/ml) |

*1 ppm or 0.0001% in regards to the sample concentration 10,000 µg/ml.

Results:

This example describes a HPLC/UV method specifically for detecting the 3'-chloro-2-bromopropiophenone impurity. To increase sensitivity the UV wavelength of the detector was set at the maximum absorbance for the analyte corresponding to 255 nm and the mobile phase was adjusted to sharpen the analyte peak as much as possible. The method operating conditions as a "3 ppm LIMIT TEST" are reported herein. The tabulated batches of API were tested. Results show that 3'-Chloro-2-bromo-propiophenone is well below the practical detection limit of 1 ppm in each batch tested.

| BATCH ANALYSIS RESULTS<br>3 PPM LIMIT TEST FOR 3'-CHLORO-2-BROMO-PROPIOPHENONE<br>IN BUPROPION HYDROBROMIDE | |
|---|---|
| BATCH | RESULT |
| D00894 | NOT DETECTABLE |
| D00895 | NOT DETECTABLE |
| D00896 | NOT DETECTABLE |
| 06PK0970 | NOT DETECTABLE |
| 06PK0971 | NOT DETECTABLE |

LIMIT OF DETECTION: 1 ppm

TABLE 1

Assay of bupropion salts by HPLC

| Test | Maleate | Tosylate | Fumarate | HBr | Succinate | Tartrate acid | Tartrate neutral | Citrate |
|---|---|---|---|---|---|---|---|---|
| Assay | 99.7% | 97.4% | 89.8% | 99.7% | 97.6 | 84.9% | 51.7%* | 85.0% |

TABLE 2 moisture content and pH of aqueous solutions:

| | Original (Initial APIs) | | After recrystallization (R & D) | | |
|---|---|---|---|---|---|
| | | | Tested after 1 day | | |
| Sample ID | KF | pH (aq. 0.5%) | KF | pH (aq. 0.5%) | Tested after 2 Months KF |
| Bup-HCl | 0.0 | 5.90 | | | |
| Bup-Maleate | 0.10 | 4.29 | | | |
| Bup-Tosylate | 1.71* | 5.56 | 023 | 5.88 | 0.18 |
| Bup-Fumarate | 0.09 | 3.84 | | | |
| Bup-HBr | 0.00 | 5.92 | | | |
| Bup-Succinate | 0.13 | 4.82 | | | |
| Bup-Tartrate | 0.18 | 3.62 | | | |
| Bup-Tartrate neutral | 0.14 | 3.62 | | | |
| Bup-Citrate (I) | 0.23 | 3.89 | | | |

*KF after 3M = 1.80%
Bup = bupropion

TABLE 3

Solubility & other physical properties: Bupropion HBr vs Bupropion HCl.

| | Solubility (mg/ml) | | |
|---|---|---|---|
| Sample ID | Water | EtOH | IPA |
| Bupropion HCl | 270 | 80 | 10 |
| Bupropion HBr | 143 | 92 | 12 |

| Sample ID | PS (Malvern) | | Moisture Content (KF) | pH (aq. 0.5%) | MP (DSC) |
|---|---|---|---|---|---|
| Bupropion HCl (Erregierre) | 10% | 32 μm | 0.01% | 5.90 | 243.6 C. |
| | 50% | 102 μm | | | |
| | 90% | 276 μm | | | |
| Bupropion HBr (Chemi) | 10% | 72 μm | 0.00% | 5.92 | 234.1 C. |
| | 50% | 245 μm | | | |
| | 90% | 657 μm | | | |

TABLE 4

40° C./75% RH Close Vial

| (DS + Placebo)1 | (DS + Placebo)1 + Water2 | (DS + Placebo)1 + (Water + EtOH + IPA)3 | (DS + Placebo)1 + (IPA + EtOH)4 |
|---|---|---|---|

1 300 mg of the drug substance was placed in a 2 mL vial, then 100 mg placebo (almost double of the required amount) was added, and mixed well.
2 Two drops of water was added to the spiked placebo and mixed well with a spatula, then closed with a cup.
3 A mixture of equal volume of water, EtOH and IPA was prepared. Two drops of the latter mixture was added to the spiked placebo, and mixed well with a spatula, then closed with a cup.

TABLE 4-continued

40° C./75% RH Close Vial

4 A mixture of equal volume of EtOH and IPA was prepared. Two drops of the latter mixture was added to the spiked placebo, and mixed well with a spatula, then closed with a cup.

TABLE 5

| API ID | Lot# | Quantity/bottle | # of glass bottle 40° C./75% RH | Stability pulling time (Day) |
|---|---|---|---|---|
| Bupropion HBr | STN07492 | 348 mg | 2 | 14 & 24 |
| Bupropion HCl | STN06973 | 300 mg | 2 | 14 & 24 |
| Bupropion HBr | STN07491 | 348 mg | 1 | 10 |
| | STN07492 | 348 mg | 1 | 10 |
| Bupropion HCl | STN06973 | 300 mg | 1 | 10 |
| | STN06978 | 300 mg | 1 | 10 |

TABLE 6

Closed glass bottle stability studies (40° C./75% RH) on Bupropion-HBr & HCl APIs.

| | Bupropion HBr, Lot# STN07492 | | | Bupropion HCl, L# STN06973 | | |
|---|---|---|---|---|---|---|
| Tests | Initial | 14-Days | 24 Days | Initial | 14-Days | 24 Days |
| % Assay | 99.6 | 98.8 | 99.5 | 100.4 | 98.5 | 98.5 |
| % Impurities | | | | | | |
| 3-CBZ | 0.007 | 0.015 | 0.022 | 0.002 | 0.019 | 0.082 |
| 852U77 | 0.009 | 0.058 | 0.052 | 0.003 | 0.010 | 0.023 |
| 20U78/dilu | 0.044 | 0.048 | 0.038 | 0.043 | 0.038 | 0.040 |
| 827U76 | ND | 0.012 | 0.016 | ND | ND | 0.102 |
| Total unknown | 0.098 | 0.105 | 0.104 | 0.044 | 0.038 | 0.049 |
| Total (%) | 0.16 | 0.23 | 0.23 | 0.09 | 0.11 | 0.30 |

TABLE 7

Closed glass bottle stability studies (40 C/75% RH) on Bupropion HCl & Bupropion HBr APIs.

| | Bupropion HBr, Lot# STN07491 | | Bupropion HBr, Lot# STN07492 | |
|---|---|---|---|---|
| Tests | Initial | 10-Days | Initial | 10 Days |
| % Assay | 99.5 | 98.2 | 99.6 | 99.2 |
| % Impurities | | | | |
| 3-CBZ | 0.011 | 0.070 | 0.007 | 0.031 |
| 852U77 | ND | 0.125 | ND | 0.055 |
| 20U78/dilu | 0.041 | 0.051 | 0.041 | 0.044 |
| 827U76 | ND | 0.039 | ND | ND |
| Total unknown | 0.129 | 0.129 | 0.194 | 0.15 |
| Total (%) | 0.17 | 0.42 | 0.23 | 0.24 |

TABLE 7-continued

Closed glass bottle stability studies (40 C/75% RH) on Bupropion HCl & Bupropion HBr APIs.

| Tests | Bupropion HCl, Lot# STN06973 Initial | 10-Days | Bupropion HCl, Lot# STN06978 Initial | 10 Days |
|---|---|---|---|---|
| % Assay | 99.4 | 96.3 | 99.1 | 96.5 |
| % Impurities | | | | |
| 3-CBZ | 0.003 | 0.110 | 0.002 | 0.278 |
| 852U77 | ND | 0.047 | ND | 0.124 |
| 20U78/dilu | 0.040 | 0.047 | 0.04 | 0.057 |
| 827U76 | ND | 0.045 | ND | 0.141 |
| Total unknown | 0.053 | 0.187 | 0.165 | 0.137 |
| Total (%) | 0.10 | 0.44 | 0.21 | 0.74 |

TABLE 8

Each trial's contents and amounts of each material per part

| | Amount (g) | | | | |
|---|---|---|---|---|---|
| Materials | Part 1 | Part 2 | Part 3 | Part 4 | Part 5 |
| Bupropion HBr | 2062.5 | 2062.5 | 2062.5 | 2062.5 | 2062.5 |
| PVA | 68.75 | 68.75 | 68.75 | 68.75 | 68.75 |
| Purified Water | 1452.5 | 1452.5 | 1452.5 | 1452.5 | 1452.5 |

TABLE 9

Summary of specifications for granulation procedure.

| Specification | Range | Target |
|---|---|---|
| Fan Speed | Slow | Slow |
| Air Volume (CMH) | 60-65 | 65 |
| Exhaust Temperature (° C.) | 35-45 | 40 |
| Supply Temperature (° C.) | 60-65 | 65 |
| Product Temperature (° C.) | 35-55 | 45 |
| Atomizing Air Pressure (Bar/psi) | 35 | 35 |
| Pump Speed (rpm) | 18 | 18 |
| Liquid Flow Rate (g/min) | 13 | 13 |
| Bed Dew Point (MMWC) | 0 | 0 |
| Filter Dew Point (MMWC | 100-300 | 200 |

TABLE 10

The amount of lubricant in the final formulation was 343.75 g, which was 3.125% of the total.

| Materials | Amount (g) |
|---|---|
| Part 1 | 2131.25 |
| Part 2 | 2131.25 |
| Part 3 | 2131.25 |
| Part 4 | 2131.25 |
| Part 5 | 2131.25 |
| COMPRITOL ® 888 | 343.75 |
| Total | 11000.0 |

TABLE 11

Summary of Specifications for Tablet Press Set-up.

| Parameters | Settings/Ranges |
|---|---|
| Pre-Compression Thickness (mm) | 2 |
| Control Thickness (mm) | 1.5 |
| Fill Thickness (mm) | 7-8 |
| Overload Pressure (Tons) | 1.5-2.0 |
| Tablets per minute | 450-500 |
| Feeder Speed | 1-2 |
| Feeder Control | Auto |

TABLE 12

Summary of specifications for compression

| Parameters | Specification for 174 mg Tablet | Specification for 348 mg Tablet |
|---|---|---|
| Individual Tablet Weight (mg) | 185.6 ± 5% (176.3 mg-194.9 mg) | 371.2 ± 5% (352.6 mg-389.8 mg) |
| Average Tablet Weight (mg) | 185.6 ± 3% (180.0 mg-191.2 mg) | 371.2 ± 3% (360.1 mg-382.3 mg) |
| Tablet Hardness (SC) | 6.0-12.0 | 6.0-12.0 |
| Tablet Thickness (mm) | 5.0-6.0 | 4.5-5.0 |
| Friability (%) | <0.8 | <0.8 |

TABLE 13

Formulations used as the ethylcellulose (e.g. ETHOCEL ® or EC) coating on the 174 mg and 348 mg Bupropion HBr cores.

| FORMULATION 1 | FORMULATION 2 | FORMULATION 3 |
|---|---|---|
| ETHOCEL ® (Ethyl Cellulose) Standard 100 Premium | ETHOCEL ® (Ethyl Cellulose) Standard 100 Premium | ETHOCEL ® (Ethyl Cellulose) Standard 100 Premium |
| Povidone USP (KOLLIDON ® 90F) | Povidone USP (KOLLIDON ® 90F) | Povidone USP (KOLLIDON ® 90F) |
| Polyethylene Glycol 4000 | Polyethylene Glycol 4000 | Polyethylene Glycol 4000 |
| Ethyl Alcohol 95% USP | Dibutyl Sebacate | Ethyl Alcohol 95% USP |
| Isopropyl Alcohol (IPA) | Ethyl Alcohol 95% USP | |

TABLE 14

Formulations used as the Final Coats on the 174 mg and 348 mg Bupropion HBr tablets.

| FORMULATION A | FORMULATION B |
|---|---|
| EUDRAGIT ® L30D-55 | EUDRAGIT ® L30D-55 |
| Chroma-Tone DEB 5156-CLE | SYLOID ® 244FP |
| Purified Water | Polyethylene Glycol 4000 |
|  | Triethyl Citrate |
|  | Purified Water |

TABLE 15

Summary of Specifications that were kept constant in the ethylcellulose coating Process.

| Process Parameters | Operational Ranges | Target |
|---|---|---|
| Inlet Temperature for coating (° C.) | SV: 40 ± 5  PV: 40 ± 5 | 40 |
| Inlet Temperature for Drying (° C.) | 30-35 | 35 |
| Exhaust Temperature | 30 ± 10 | 30 |
| Product Temperature | 25-35 | 28 |
| ΔP Differential Pressure (W.C) | (−0.1)-(−0.12) | −0.10 |
| Supply Air Flow (CFM) | 200 ± 50 | 200 |
| Pan Speed (rpm) | 2.5-12 | 5.0 |
| Atomizing Air (psi) | 35-40 | 35 |
| Pattern Air (psi) | 20-30 | 25 |
| Spray Rate (g/min) | 5-15 | 6.0 |

TABLE 16

Summary of Specifications that were kept constant in the Final coating Process.

| Process Parameters | Operational Ranges | Target |
|---|---|---|
| Inlet Temperature for coating (° C.) | SV: 50 ± 5  PV: 50 ± 5 | 50 |
| Inlet Temperature for Drying (° C.) | 40 ± 5 | 40 |
| Exhaust Temperature | 35 ± 5 | 38 |
| Product Temperature | 35 ± 2 | 35 |
| ΔP Differential Pressure (W.C) | (−0.1)-(−0.12) | −0.10 |
| Supply Air Flow (CFM) | 200 ± 50 | 200 |
| Pan Speed (rpm) | 2.5-15 | 12.0 |
| Atomizing Air (psi) | 25-35 | 35 |
| Pattern Air (psi) | 20-30 | 25 |
| Spray Rate (g/min) | 5-15 | 13.0 |

TABLE 17

Materials used in one part of the batch, the percentage of each constituent, the amount per tablet and the amount per batch, for BUP-HBr-XL-009-5

| Materials | % | mg/tablet | Batch Quantity (g) |
|---|---|---|---|
| Bupropion HBr | 93.75 | 348.00 | 1993.75 |
| PVA | 3.125 | 11.60 | 68.75 |
| COMPRITOL ® 888 | 3.125 | 11.60 | 68.75 |
| Total | 100.00 | 371.2 mg | 2131.25 |

TABLE 18

Results obtained using 9 mm tooling for batch BUP-HBr-XL-009-5.

| Parameters | Theoretical | Actual |
|---|---|---|
| Average Individual Tablet Weight | 371.2 mg | 371.5 mg |
| Average Hardness | 6.0-12.0 SC | 10.77 SC |
| Average Thickness | 5.0-6.0 mm | 5.60 mm |
| Friability | <0.8% | 0% |

TABLE 19

Results obtained using 10 mm tooling for batch BUP-HBr-XL-009-5.

| Parameters | Theoretical | Actual |
|---|---|---|
| Average Individual Tablet Weight | 371.2 mg | 366.5 mg |
| Average Hardness | 6.0-12.0 SC | 7.50 SC |
| Average Thickness | 5.0-6.0 mm | 4.97 mm |
| Friability | <0.8% | 0% |

TABLE 20

Materials used in one part of the batch, the percentage of each constituent, the amount per tablet and the amount per batch for batch BUP-HBr-XL-021-5.

| Materials | % | mg/tablet | Batch Quantity (g) |
|---|---|---|---|
| Bupropion HBr | 93.75 | 174.00 | 1993.75 |
| PVA | 3.125 | 5.80 | 68.75 |
| COMPRITOL ® 888 | 3.125 | 5.80 | 68.75 |
| Total | 100.00 | 185.60 | 2131.25 |

TABLE 21

Results obtained using 7 mm tooling for batch BUP-HBr-XL-021-5.

| Parameters | Theoretical | Actual |
|---|---|---|
| Average Individual Tablet Weight | 185.6 mg | 186.8 mg |
| Average Hardness | 6.0-12.0 SC | 9.23SC |
| Average Thickness | 4.5-5.0 mm | 4.70 mm |
| Friability | <0.8% | 0% |

TABLE 22

Materials used in the ethylcellulose coating and their quantities for batch BUP-HBr-XL-348-013-5.

| Materials | % Contribution to Total Solution | Batch Quantity (g) | % of Solids in Solution |
|---|---|---|---|
| ETHOCEL ® (Ethyl Cellulose) Standard 100 Premium | 3.60 | 77.44* | 38.74 |
| Povidone USP (KOLLIDON ® 90F) | 4.600 | 99.22* | 49.64 |
| PEG 4000 | 1.07 | 23.23* | 11.62 |
| Ethyl Alcohol 95% USP | 86.44 | 1859.50 | N/A |
| Isopropyl Alcohol 99% USP | 4.54 | 97.87 | N/A |
| Total | 100.00 | 2151.00 | 100.00 |

*Total solid component of the formulation included 77.44 g of ethylcellulose (e.g. ETHOCEL ®), 99.22 g of Povidone and 23.23 g of PEG 4000, which gave a total solid amount of 199.89 g. The solid component of the formulation made up 9% of the total solution and the remaining 91% was made up of liquid.

TABLE 23

Theoretical and Actual Tablet weights at 28 mg, 30 mg, 32 mg and 34 mg weight gains for batch BUP-HBr-XL-348-013-5.

| Weight Gain (mg) | Theoretical Weight (mg) | Actual Weight (mg) |
|---|---|---|
| 28.0 | 400.0 | 401.3 |
| 30.0 | 402.0 | 402.6 |
| 32.0 | 404.0 | 404.5 |
| 34.0 | 406.0 | 406.8 |

TABLE 24

Materials used in the Final coating and their quantities for batch BUP-HBr-XL-348-013-5.

| Materials | % Contribution to Total Solution | Batch Quantity (g) | Amount of Solid (g) | % of Solids in Solution |
|---|---|---|---|---|
| EUDRAGIT ® L30 D-55 | 22.73 | 104.8 | 31.44 | 65.00* |
| Chroma-Tone DEB 5156-CLE | 3.66 | 16.90 | 16.90 | 35.00** |
| Purified Water (1) | 21.78 | 100.40 | N/A | N/A |
| Purified Water (2) | 51.89 | 239.20 | N/A | N/A |
| Total | 100.00 | 460.95 | 48.34*** | 100.00 |

*The percentage of EUDRAGIT ®, solid, that contributed to the total amount of solid was 65%.
**The percentage of Chroma-Tone, solid, that contributed to the total amount of solid was 35%.
***The Total amount of solid (48.34 g) was 10.5% of the total solution.

TABLE 25

Theoretical and Actual Tablet weights at 4 mg, 5 mg, 6 mg and 7 mg weight gains.

| Weight Gain (mg) | Theoretical Weight (mg) | Actual Weight (mg) |
|---|---|---|
| 4.0 | 410.0 | 410.5 |
| 5.0 | 411.0 | 410.8 |
| 6.0 | 412.0 | 412.4 |
| 7.0 | 413.0 | 413.9 |

TABLE 26

Materials used in the ethylcellulose coating and their quantities for batch BUP-HBr-XL-348 mg-018-5.

| Materials | % Contribution to Total Solution | Batch Quantity (g) | % of Solids in Solution* |
|---|---|---|---|
| ETHOCEL ® (ethylcellulose) Standard 100 Premium | 3.42 | 73.57 | 38.00 |
| Povidone USP (KOLLIDON ® 90F) | 4.41 | 94.86 | 49.00 |
| PEG 4000 | 1.17 | 25.17 | 13.00 |
| Ethyl Alcohol 95% USP | 86.45 | 1859.53 | N/A |
| Isopropyl Alcohol 99% USP | 4.55 | 97.87 | N/A |
| Total | 100.00 | 2151.00 | 100.00 |

*Total solid included 73.57 g of ethylcellulose 94.86 g of Povidone and 25.17 g of PEG 4000. This gave a total of 193.6 g total solid amount.

TABLE 27

Theoretical and Actual Tablet weights at 26 mg, 28 mg, 30 mg, and 32 mg weight gains for batch BUP-HBr-XL-348 mg-018-5.

| Weight Gain (mg) | Theoretical Weight (mg) | Actual Weight (mg) |
|---|---|---|
| 26.0 | 398.0 | 397.7 |
| 28.0 | 400.0 | 399.5 |
| 30.0 | 402.0 | 401.5 |
| 32.0 | 404.0 | 404.0 |

TABLE 28

Materials used in the Final coating and their quantities for batch BUP-HBr-XL-348 mg-018-5.

| Materials | % Contribution to Total Solution | Batch Quantity (g) | Amount of Solid (g) | % of Solids in Solution |
|---|---|---|---|---|
| EUDRAGIT ® L30D D-55 | 22.75 | 104.86 | 31.46 | 65.00* |
| SYLOID ® 244FP | 2.62 | 12.08 | 12.08 | 25.00** |
| CARBOWAX ® 4000 | 0.70 | 3.22 | 3.22 | 6.65** |
| Triethyl Citrate | 0.36 | 1.64 | 1.64 | 3.39** |
| Purified Water (1) | 33.84 | 156.00 | N/A | N/A |
| Purified Water (2) | 39.73 | 183.15 | N/A | N/A |
| Total | 100.00 | 460.95 | 48.40*** | 100.00 |

*The percentage of EUDRAGIT ®, solid, that contributed to the total amount of solid was 65%.
**The percentage of SYLOID ®, CARBOWAX ® 4000 and Triethyl Citrate that contributed to the total amount of solid was 25%, 6.65% and 3.39%, respectively. This gave a total of 35%.
***The total amount of solid (48.4 g) was 10.5% of the total solution.

TABLE 29

Theoretical and Actual Tablet weights at 4 mg, 5 mg, 6 mg, and 7 mg weight gains for batch BUP-HBr-XL-348 mg-018-5.

| Weight Gain (mg) | Theoretical Weight (mg) | Actual Weight (mg) |
|---|---|---|
| 4.0 | 408.0 | 408.5 |
| 5.0 | 409.0 | 409.3 |
| 6.0 | 410.0 | 410.7 |
| 7.0 | 411.0 | 411.1 |

TABLE 30

Materials used in the ethylcellulose coating and their quantities for batch BUP-HBr-XL-174 mg-022-5.

| Materials | % Contribution to Total Solution | Batch Quantity (g) | % of Solids in Solution* |
|---|---|---|---|
| ETHOCEL ® (ethylcellulose) Standard 100 Premium | 3.60 | 116.12 | 40.00 |
| Povidone USP (KOLLIDON ® 90F) | 4.32 | 139.34 | 48.00 |
| PEG 4000 | 1.08 | 34.84 | 12.00 |
| Ethyl Alcohol 95% USP | 86.45 | 2788.54 | N/A |
| Isopropyl Alcohol 99% USP | 4.55 | 146.76 | N/A |
| Total | 100.00 | 3225.60 | 100.00 |

*Total Solid included 116.12 g of ETHOCEL ®, 139.34 g of Povidone and 34.84 g of PEG 4000. This gave a total solid amount of 290.3 g.

TABLE 31

Theoretical and Actual Tablet weights at 20 mg, 22 mg, 24 mg, 26 mg, 28 mg, 29 mg, and 30 mg weight gains for batch BUP-HBr-XL-174 mg-022-5.

| Weight Gain (mg) | Theoretical Weight (mg) | Actual Weight (mg) |
|---|---|---|
| 20.0 | 206.0 | 206.1 |
| 22.0 | 208.0 | 207.8 |
| 24.0 | 210.0 | 210.2 |
| 26.0 | 212.0 | 211.5 |
| 28.0 | 214.0 | 213.7 |
| 29.0 | 215.0 | 214.9 |
| 30.0 | 216.0 | 216.5 |

TABLE 32

Materials used in the Final coating and their quantities for batch BUP-HBr-XL-174 mg-022-5.

| Materials | % Contribution to Total Solution | Batch Quantity (g) | Amount of Solid (g) | % of Solids in Solution |
|---|---|---|---|---|
| EUDRAGIT ® L30D D-55 | 22.75 | 104.86 | 31.46 | 65.0* |
| SYLOID ® 244FP | 2.62 | 12.08 | 12.08 | 25.0** |
| CARBOWAX ® 4000 | 0.70 | 3.22 | 3.22 | 6.65** |
| Triethyl Citrate | 0.36 | 1.64 | 1.64 | 3.39** |
| Purified Water (1) | 33.84 | 156.00 | N/A | N/A |
| Purified Water (2) | 39.73 | 183.15 | N/A | N/A |
| Total | 100.00 | 460.95 | 48.40*** | 100.00 |

*The percentage of EUDRAGIT ®, solid, that contributed to the total amount of solid was 65%.
**The percentage of SYLOID ®, CARBOWAX ® 4000 and Triethyl Citrate that contributed to the total amount of solid was 25%, 6.65% and 3.39%, respectively. This gave a total of 35%.
***The Total amount of solid (48.4 g) was 10.5% of the total solution.

TABLE 33

Theoretical and Actual Tablet weights at 4 mg, 5 mg, 6 mg, and 7 mg weight gains for batch BUP-HBr-XL-174 mg-022-5.

| Weight Gain (mg) | Theoretical Weight (mg) | Actual Weight (mg) |
|---|---|---|
| 4.0 | 219.0 | 219.4 |
| 5.0 | 220.0 | 220.2 |
| 6.0 | 221.0 | 221.2 |
| 7.0 | 222.0 | 223.0 |

TABLE 34

Materials used in the ethylcellulose coating and their quantities for batch BUP-HBr-XL-348 mg-023-5.

| Materials | % Contribution to Total Solution | Batch Quantity (g) | % of Solids in Solution* |
|---|---|---|---|
| ETHOCEL ® (ethylcellulose) Standard 100 Premium | 3.69 | 79.37 | 42.71 |
| Povidone USP (KOLLIDON ® 90F) | 3.69 | 79.37 | 42.71 |
| PEG 4000 | 1.26 | 27.11 | 14.58 |
| Dibutyl Sebacate, NF | 0.36 | 7.75 | N/A |
| Ethyl Alcohol 95% USP | 91.00 | 1957.4 | N/A |
| Total | 100.00 | 2151.00 | 100.00 |

*Total Solid includes 79.37 g of ETHOCEL ®, 79.37 g of Povidone, 27.11 g of PEG 4000 and 7.75 g of Dibutyl Sebacate. This gave a total solid amount of 193.6 g.

TABLE 35

Theoretical and Actual Tablet weights at 26 mg, 28 mg, 30 mg, and 32 mg weight gains for batch BUP-HBr-XL-348 mg-023-5.

| Weight Gain (mg) | Theoretical Weight (mg) | Actual Weight (mg) |
|---|---|---|
| 26.0 | 398.0 | 399.3 |
| 28.0 | 400.0 | 401.0 |
| 30.0 | 402.0 | 401.7 |
| 32.0 | 404.0 | 402.7 |

TABLE 36

Materials used in the ethylcellulose coating and their quantities for batch BUP-HBr-XL-348 mg-025-5.

| Materials | % Contribution to Total Solution | Batch Quantity (g) | % of Solids in Solution* |
|---|---|---|---|
| ETHOCEL ® (ethylcellulose) Standard 100 Premium | 3.69 | 79.40 | 41.00 |
| Povidone USP (KOLLIDON ® 90F) | 3.78 | 81.30 | 42.00 |
| PEG 4000 | 1.53 | 32.90 | 17.00 |
| Ethyl Alcohol 95% USP | 91.00 | 1957.40 | N/A |
| Total | 100.00 | 2151.00 | 100.00 |

*Total Solid included 79.40 g of ETHOCEL ®, 81.30 g of Povidone and 32.90 g of PEG 4000. This gave a total solid amount of 193.6 g.

TABLE 37

Theoretical and Actual Tablet weights at 26 mg, 28 mg, 30 mg, and 32 mg weight gains for batch BUP-HBr-XL-348 mg-025-5.

| Weight Gain (mg) | Theoretical Weight (mg) | Actual Weight (mg) |
|---|---|---|
| 26.0 | 398.0 | 397.8 |
| 28.0 | 400.0 | 400.6 |
| 30.0 | 402.0 | 401.4 |
| 32.0 | 404.0 | 402.2 |

TABLE 38

Materials used in the Final coating and their quantities for batch BUP-HBr-XL-348 mg-025-5.

| Materials | % Contribution to Total Solution | Batch Quantity (g) | Amount of Solid (g) | % of Solids in Solution |
|---|---|---|---|---|
| EUDRAGIT ® L30D D-55 | 19.77 | 91.13 | 27.34 | 56.50* |
| SYLOID ® 244FP | 3.15 | 14.52 | 14.52 | 30.00** |
| CARBOWAX ® 4000 | 0.95 | 4.36 | 4.36 | 9.00** |
| Triethyl Citrate | 0.47 | 2.17 | 2.17 | 4.50** |
| Purified Water (1) | 21.70 | 100.00 | N/A | N/A |
| Purified Water (2) | 53.96 | 248.77 | N/A | N/A |
| Total | 100.00 | 460.95 | 48.39*** | 100.00 |

*The percentage of EUDRAGIT ®, solid, that contributed to the total amount of solid was 65%.
**The percentage of SYLOID ®, CARBOWAX ® 4000 and Triethyl Citrate that contributed to the total amount of solid was 30%, 9% and 4.5%, respectively. This gave a total of 43.5%.
***The Total amount of solid (48.39 g) was 10.5% of the total solution.

TABLE 39

Theoretical and Actual Tablet weights at 4 mg, 5 mg, 6 mg, and 7 mg weight gains for batch BUP-HBr-XL-348 mg-025-5.

| Weight Gain (mg) | Theoretical Weight (mg) | Actual Weight (mg) |
|---|---|---|
| 4.0 | 408.0 | 408.3 |
| 5.0 | 409.0 | 408.8 |
| 6.0 | 410.0 | 409.5 |
| 7.0 | 411.0 | 411.1 |

TABLE 40

Materials used in the ethylcellulose coating and their quantities for batch BUP-HBr-XL-348 mg-026-5.

| Materials | % Contribution to Total Solution | Batch Quantity (g) | % of Solids Solution* |
|---|---|---|---|
| ETHOCEL ® (ethylcellulose) Standard 100 Premium | 3.69 | 79.37 | 41.00 |
| Povidone USP (KOLLIDON ® 90F) | 3.69 | 79.37 | 41.00 |
| PEG 4000 | 0.36 | 7.75 | 4.00 |
| Dibutyl Sebacate, NF | 1.26 | 27.11 | 14.00 |
| Ethyl Alcohol 95% USP | 91.00 | 1957.4 | N/A |
| Total | 100.00 | 2151.00 | 100.00 |

*Total Solid included 79.37 g of ETHOCEL ®, 79.37 g of Povidone, 7.75 g of PEG 4000 and 27.11 g of Dibutyl Sebacate. This gave a total solid amount of 193.6 g.

TABLE 41

Theoretical and Actual Tablet weights at 26 mg, 28 mg, 30 mg, and 32 mg weight gains for batch BUP-HBr-XL-348 mg-026-5.

| Weight Gain (mg) | Theoretical Weight (mg) | Actual Weight (mg) |
|---|---|---|
| 26.0 | 398.0 | 398.8 |
| 28.0 | 400.0 | 400.5 |
| 30.0 | 402.0 | 402.5 |
| 32.0 | 404.0 | 403.6 |

TABLE 42

Materials used in the ethylcellulose coating and their quantities for batch BUP-HBr-XL-174 mg-027-5.

| Materials | % Contribution to Total Solution | Batch Quantity (g) | % of Solid in Solution* |
|---|---|---|---|
| ETHOCEL ® (ethylcellulose) Standard 100 Premium | 3.69 | 138.87 | 41.00 |
| Povidone USP (KOLLIDON ® 90F) | 3.78 | 142.25 | 42.00 |
| PEG 4000 | 1.53 | 57.58 | 17.00 |
| Ethyl Alcohol 95% USP | 91.00 | 3424.63 | N/A |
| Total | 100.00 | 3763.33 | 100.00 |

*Total Solid included 138.87 g of ETHOCEL ®, 142.25 g of Povidone and 57.58 g of PEG 4000. This gave a total solid amount of 338.7 g.

TABLE 43

Theoretical and Actual Tablet weights at 22 mg, 24 mg, and 26 mg weight gains for batch BUP-HBr-XL-174 mg-027-5.

| Weight Gain (mg) | Theoretical Weight (mg) | Actual Weight (mg) |
|---|---|---|
| 22.0 | 208.0 | 207.7 |
| 24.0 | 210.0 | 210.8 |
| 26.0 | 212.0 | 212.4 |

TABLE 44

Materials used in the Final coating and their quantities for batch BUP-HBr-XL-174 mg-027-5.

| Materials | % Contribution to Total Solution | Batch Quantity (g) | Amount of Solid (g) | % of Solids in Solution |
|---|---|---|---|---|
| EUDRAGIT ® L30D D-55 | 19.77 | 182.27 | 54.68 | 56.5* |
| SYLOID ® 244FP | 3.15 | 29.03 | 29.03 | 30.0** |
| CARBOWAX ® 4000 | 0.95 | 8.71 | 8.71 | 9.0** |
| Triethyl Citrate | 0.47 | 4.35 | 4.35 | 4.5** |
| Purified Water (1) | 21.70 | 200.00 | N/A | N/A |
| Purified Water (2) | 53.98 | 497.26 | N/A | N/A |
| Total | 100.00 | 921.62 | 96.77*** | 100.00 |

*The percentage of EUDRAGIT ®, solid, that contributed to the total amount of solid was 56.5%.
**The percentage of SYLOID ®, CARBOWAX ® 4000 and Triethyl Citrate that contributed to the total amount of solid was 30.0%, 9.0% and 4.5%, respectively. This gave a total of 43.5%.
***The Total amount of solid (9.77 g) was 10.5% of the total solution.

TABLE 45

Theoretical and Actual Tablet weights at 4 mg, 5 mg, 6 mg, and 7 mg weight gains for batch BUP-HBr-XL-174 mg-027-5.

| Weight Gain (mg) | Theoretical Weight (mg) | Actual Weight (mg) |
|---|---|---|
| 4.0 | 216.0 | 216.6 |
| 5.0 | 217.0 | 217.6 |
| 6.0 | 218.0 | 217.8 |
| 7.0 | 219.0 | 219.8 |

TABLE 46

Each trial's contents and amounts of each material per part for EA formulation.

| Materials | Amount (g) | | | | |
|---|---|---|---|---|---|
| | Part 1 | Part 2 | Part 3 | Part 4 | Part 5 |
| Bupropion HBr | 2062.5 | 2062.5 | 2062.5 | 2062.5 | 2062.5 |
| PVA | 68.75 | 68.75 | 68.75 | 68.75 | 68.75 |
| Purified Water | 1452.5 | 1452.5 | 1452.5 | 1452.5 | 1452.5 |

TABLE 47

Summary of specifications for granulation procedure for EA formulations.

| Specification | Setting/Range | Target |
|---|---|---|
| Fan Speed | Slow | Slow |
| Air Volume (CMH) | 60-65 | 65 |
| Exhaust Temperature (° C.) | 35-45 | 40 |
| Supply Temperature (° C.) | 60-65 | 65 |
| Product Temperature (° C.) | 35-55 | 45 |
| Atomizing Air Pressure (Bar/psi) | 35 | 35 |
| Pump Speed (rpm) | 18 | 18 |
| Liquid Flow Rate (g/min) | 13 | 13 |
| Bed Dew Point (MMWC) | 0 | 0 |
| Filter Dew Point (MMWC | 100-300 | 200 |

TABLE 48

The amount of lubricant in the final EA formulation was 343.75 g, which was 3.125% of the total.

| Materials | Amount (g) |
|---|---|
| Bupropion HBr Granules | 10656.25 |
| COMPRITOL ® 888 | 343.75 |
| Total | 11000 |

TABLE 49

Summary of Specifications for Tablet Press Set-up for the EA formulation.

| Parameters | Settings/Ranges |
|---|---|
| Pre-Compression Thickness (mm) | 2 |
| Control Thickness (mm) | 1.5 |
| Fill Thickness (mm) | 7-8 |
| Overload Pressure (Tons) | 1.5-2.0 |
| Tablets per minute | 450-500 |
| Feeder Speed | 1-2 |
| Feeder Control | Auto |

TABLE 50

Summary of specifications for compression for the EA formulation.

| Parameters | Specification for 150 mg Tablet | Specification for 300 mg Tablet |
|---|---|---|
| Individual Tablet Weight (mg) | 160.0 ± 5% (152.0 mg-168.0 mg) | 320.0 ± 5% (304.0 mg-336.0 mg) |
| Average Tablet Weight (mg) | 160.0 ± 3% (155.2 mg-164.8 mg) | 320.0 ± 3% (310.4 mg-329.6 mg) |
| Tablet Hardness (SC) | 6.0-12.0 | 6.0-12.0 |
| Tablet Thickness (mm) | 5.0-6.0 | 4.5-5.0 |
| Friability (%) | <0.8 | <0.8 |

TABLE 51

Formulations used as the ETHOCEL ® coating on the 150 mg and 300 mg Bupropion HBr EA cores.

| FORMULATION 1 | FORMULATION 2 | FORMULATION 3 | FORMULATION 4 |
|---|---|---|---|
| ETHOCEL ® (Ethyl Cellulose) Standard 100 Premium | ETHOCEL ® (Ethyl Cellulose) Standard 100 Premium | ETHOCEL ® (Ethyl Cellulose) Standard 100 Premium | ETHOCEL ® (Ethyl Cellulose) Standard 100 Premium |
| Povidone USP (KOLLIDON ® 90F) | Povidone USP (KOLLIDON ® 90F) | Povidone USP (KOLLIDON ® 90F) | Povidone USP (KOLLIDON ® 90F) |
| Polyethylene Glycol 4000 | Polyethylene Glycol 4000 | Dibutyl Sebacate | Polyethylene Glycol 4000 |
| Ethyl Alcohol 200 proof | Dibutyl Sebacate | Ethyl Alcohol 200 proof | Ethyl Alcohol 95% USP |
| | Ethyl Alcohol 200 proof | | |

TABLE 52

Summary of Specifications that were kept constant in the Coating Process for the EA formulations.

| Process Parameters | Ranges | Target |
|---|---|---|
| Inlet Temperature for coating (° C.) | SV: 50 ± 5<br>PV: 50 ± 5 | 50 |
| Inlet Temperature for Drying (° C.) | 40 ± 5 | 40 |
| Exhaust Temperature | 35 ± 5 | 35 |
| Product Temperature | 35 ± 2 | 35 |
| ΔP Differential Pressure (W.C) | (−0.1)-(−0.12) | −0.10 |
| Supply Air Flow (CFM) | 200 ± 50 | 200 |
| Pan Speed (rpm) | 2.5-15 | 12.0 |
| Atomizing Air (psi) | 25-35 | 35 |
| Pattern Air (psi) | 20-30 | 25 |
| Spray Rate (g/min) | 5-15 | 13 |

TABLE 53

Materials used in the batch, the percentage of each constituent, the amount per 300 mg EA tablet and the amount per batch.

| Materials | % | mg/tablet | Batch Quantity (g) |
|---|---|---|---|
| Bupropion HBr | 93.75 | 300.00 | 1993.75 |
| PVA | 3.125 | 10.00 | 68.75 |
| COMPRITOL ® 888 | 3.125 | 10.00 | 68.75 |
| Total | 100.00 | 320.0 mg | 2131.25 |

TABLE 54

Materials used in the batch, the percentage of each constituent, the amount per 150 mg EA tablet and the amount per batch.

| Materials | % | mg/tablet | Batch Quantity (g) |
|---|---|---|---|
| Bupropion HBr | 93.75 | 150.00 | 1993.75 |
| PVA | 3.125 | 5.00 | 68.75 |
| COMPRITOL ® 888 | 3.125 | 5.00 | 68.75 |
| Total | 100.00 | 160.0 mg | 2131.25 |

TABLE 55

Results obtained using 9 mm tooling (EA formulations).

| Parameters | Theoretical | Actual |
|---|---|---|
| Average Individual Tablet Weight | 372.0 mg | 371.5 mg |
| Average Hardness | 6.0-12.0 SC | 10.77 SC |
| Average Thickness | 5.0-6.0 mm | 5.60 mm |
| Friability | <0.8% | 0% |

TABLE 56

Results obtained using 7 mm tooling (EA formulations).

| Parameters | Theoretical | Actual |
|---|---|---|
| Average Individual Tablet Weight | 372.0 mg | 366.5 mg |
| Average Hardness | 6.0-12.0 SC | 7.50 SC |
| Average Thickness | 5.0-6.0 mm | 4.97 mm |
| Friability | <0.8% | 0% |

TABLE 57

Materials used in the ethylcellulose coating and their quantities for batch BUP-HBr-EA-300 mg-001-5.

| Materials | % Contribution to Total Solution | Batch Quantity (g) | % of Solids in Solution |
|---|---|---|---|
| ETHOCEL ® (ethylcellulose) Standard 100 Premium | 4.94 | 185.62* | 55.00 |
| Povidone USP (KOLLIDON ® 90F) | 2.52 | 94.50* | 28.00 |
| PEG 4000 | 0.77 | 28.69* | 8.50 |
| Dibutyl Sebacate | 0.77 | 28.69* | 8.50 |
| Ethyl Alcohol Anhydrous (200 Proof) | 91.0 | 3412.5 | N/A |
| Total | 100.00 | 3750.00 | 100.00 |

*Total solid component of the formulation included all the material except for the Ethyl Alcohol. This formulation comprised a total solid amount of 337.5 g, which made up 9% of the total solution. The remaining 91% was made up of the Ethyl Alcohol 200 proof (liquid).

TABLE 58

Theoretical and Actual EA Tablet weights at 44 mg, 46 mg, 48 mg, 50 mg, 52 mg and 54 mg weight gains for batch BUP-HBr-EA-300 mg-001-5.

| Weight Gain (mg) | Theoretical Weight (mg) | Actual Weight (mg) |
|---|---|---|
| 44.0 | 364.0 | 362.9 |
| 46.0 | 366.0 | 365.6 |
| 48.0 | 368.0 | 366.6 |
| 50.0 | 370.0 | 369.3 |
| 52.0 | 372.0 | 371.7 |
| 54.0 | 374.0 | 374.8 |

TABLE 59

Materials used in the ethylcellulose coating and their quantities for batch BUP-HBr-EA-150 mg-002-5.

| Materials | % Contribution to Total Solution | Batch Quantity (g) | % of Solids in Solution |
|---|---|---|---|
| ETHOCEL ® (ethylcellulose) Standard 100 Premium | 4.94 | 232.03* | 55.0 |
| Povidone USP (KOLLIDON ® 90F) | 2.52 | 118.12* | 28.0 |
| PEG 4000 | 0.77 | 35.86* | 8.5 |
| Dibutyl Sebacate | 0.77 | 35.86* | 8.5 |
| Ethyl Alcohol Anhydrous (200 Proof) | 91.0 | 4265.63 | N/A |
| Total | 100.00 | 4687.50 | 100.00 |

*Total solid included 232.03 g of ETHOCEL ®, 118.12 g of Povidone, 35.86 g of PEG 4000 and 35.86 g of Dibutyl Sebacate. This gave a total solid amount of 421.87 g.

TABLE 60

Theoretical and Actual Tablet weights at 18 mg, 20 mg, 22 mg, 24 mg, 26 mg, 28 mg, 30 mg, 32 mg, 34 mg, and 36 mg weight gains for batch BUP-HBr-EA-150 mg-002-5.

| Weight Gain (mg) | Theoretical Weight (mg) | Actual Weight (mg) |
|---|---|---|
| 18.0 | 178.0 | 178.2 |
| 20.0 | 180.0 | 181.0 |

TABLE 60-continued

Theoretical and Actual Tablet weights at 18 mg, 20 mg, 22 mg, 24 mg, 26 mg, 28 mg, 30 mg, 32 mg, 34 mg, and 36 mg weight gains for batch BUP-HBr-EA-150 mg-002-5.

| Weight Gain (mg) | Theoretical Weight (mg) | Actual Weight (mg) |
|---|---|---|
| 22.0 | 182.0 | 181.8 |
| 24.0 | 184.0 | 184.3 |
| 26.0 | 186.0 | 185.8 |
| 28.0 | 188.0 | 188.1 |
| 30.0 | 190.0 | 190.7 |
| 32.0 | 192.0 | 192.5 |
| 34.0 | 194.0 | 193.7 |
| 36.0 | 196.0 | 195.5 |

TABLE 61

Materials used in the ethylcellulose coating and their quantities for batch BUP-HBr-EA-300 mg-003-5.

| Materials | % Contribution to Total Solution | Batch Quantity (g) | % of Solids in Solution |
|---|---|---|---|
| ETHOCEL ® (ethylcellulose) Standard 100 Premium | 4.94 | 185.62* | 55.00 |
| Povidone USP (KOLLIDON ® 90F) | 2.52 | 94.50* | 28.00 |
| Dibutyl Sebacate | 1.54 | 57.38* | 17.00 |
| Ethyl Alcohol Anhydrous (200 Proof) | 91.0 | 3412.5 | N/A |
| Total | 100.00 | 3750.0 | 100.00 |

*Total Solid included 185.62 g of ETHOCEL ®, 94.50 g of Povidone and 57.38 g of Dibutyl Sebacate. This gave a total solid amount of 337.5 g.

TABLE 62

Theoretical and Actual Tablet weights at 44 mg, 46 mg, 48 mg, 50 mg, 52 mg, and 54 mg weight gains for batch BUP-HBr-EA-300 mg-003-5.

| Weight Gain (mg) | Theoretical Weight (mg) | Actual Weight (mg) |
|---|---|---|
| 44.0 | 364.0 | 364.7 |
| 46.0 | 366.0 | 365.8 |
| 48.0 | 368.0 | 367.7 |
| 50.0 | 370.0 | 369.7 |
| 52.0 | 372.0 | 371.9 |
| 54.0 | 374.0 | 372.9 |

TABLE 63

Materials used in the ethylcellulose coating and their quantities for batch BUP-HBr-EA-300 mg-004-5.

| Materials | % Contribution to Total Solution | Batch Quantity (g) | % of Solids in Solution |
|---|---|---|---|
| ETHOCEL ® (ethylcellulose) Standard 100 Premium | 4.94 | 185.62* | 55.00 |
| Povidone USP (KOLLIDON ® 90F) | 2.52 | 94.50* | 28.00 |
| PEG 4000 | 1.54 | 57.38* | 17.00 |
| Ethyl Alcohol Anhydrous (200 Proof) | 91.00 | 3412.50 | N/A |
| Total | 100.00 | 3750.00 | 100.00 |

*Total Solid amount included 185.62 g of ETHOCEL ®, 94.50 g of Povidone and 57.38 g of PEG 4000. This gave a total solid amount of 337.5 g.

TABLE 64

Theoretical and Actual Tablet weights at 44 mg, 46 mg, 48 mg, 50 mg, 52 mg, and 54 mg weight gains for batch BUP-HBr-EA-300 mg-004-5.

| Weight Gain (mg) | Theoretical Weight (mg) | Actual Weight (mg) |
|---|---|---|
| 44.0 | 364.0 | 363.6 |
| 46.0 | 366.0 | 365.5 |
| 48.0 | 368.0 | 368.5 |
| 50.0 | 370.0 | 370.2 |
| 52.0 | 372.0 | 372.6 |
| 54.0 | 374.0 | 374.3 |

TABLE 65

Materials used in the ethylcellulose coating and their quantities for batch BUP-HBr-EA-300 mg-005-5.

| Materials | % Contribution to Total Solution | Batch Quantity (g) | % of Solids in Solution |
|---|---|---|---|
| ETHOCEL ® (ethylcellulose) Standard 100 Premium | 4.94 | 185.62* | 55.00 |
| Povidone USP (KOLLIDON ® 90F) | 2.52 | 94.50* | 28.00 |
| PEG 4000 | 0.77 | 28.69* | 8.50 |
| Dibutyl Sebacate | 0.77 | 28.69* | 8.50 |
| Ethyl Alcohol Anhydrous (200 Proof) | 91.00 | 3412.50 | N/A |
| Total | 100.00 | 3750.0 | 100.00 |

*Total Solids included 185.62 g of ETHOCEL ®, 94.50 g of Povidone, 28.69 g of PEG 4000 and 28.69 g of Dibutyl Sebacate. This gave a total solid amount of 337.50 g. Therefore, solids made 9% contribution to the Total solution, and the remaining 91% was made up by the liquid component (Ethyl Alcohol Anhydrous).

TABLE 66

Theoretical and Actual Tablet weights at 44 mg, 46 mg, 48 mg, 50 mg, 52 mg, and 54 mg weight gains for batch BUP-HBr-EA-300 mg-005-5.

| Weight Gain (mg) | Theoretical Weight (mg) | Actual Weight (mg) |
|---|---|---|
| 44.0 | 364.0 | 364.9 |
| 46.0 | 366.0 | 366.3 |
| 48.0 | 368.0 | 368.5 |
| 50.0 | 370.0 | 371.7 |
| 52.0 | 372.0 | 372.9 |
| 54.0 | 374.0 | 373.7 |

TABLE 67

Materials used in the ethylcellulose coating and their quantities for batch BUP-HBr-EA-300 mg-006-5.

| Materials | % Contribution to Total Solution | Batch Quantity (g) | % of Solids in Solution |
|---|---|---|---|
| ETHOCEL (ethylcellulose) Standard 100 Premium | 4.94 | 232.03* | 55.00 |

TABLE 67-continued

Materials used in the ethylcellulose coating and their quantities for batch BUP-HBr-EA-300 mg-006-5.

| Materials | % Contribution to Total Solution | Batch Quantity (g) | % of Solids in Solution |
|---|---|---|---|
| Povidone USP (KOLLIDON ® 90F) | 2.52 | 118.12* | 28.00 |
| Dibutyl Sebacate | 1.54 | 71.72* | 17.00 |
| Ethyl Alcohol Anhydrous (200 Proof) | 91.0 | 4265.63 | N/A |
| Total | 100.00 | 4687.50 | 100.00 |

*Total solid included 232.03 g of ETHOCEL ®, 118.12 g of Povidone and 71.72 g of Dibutyl Sebacate. This gave a total solid amount of 421.87 g. The Solid component of the coating solution made up 9% of the total solution. The remaining 91% of the solution was made up by the Ethyl Alcohol Anhydrous (liquid component).

TABLE 68

Theoretical and Actual Tablet weights at 18 mg, 20 mg, 22 mg, 24 mg, 26 mg, 28 mg, 30 mg, 32 mg, 34 mg, and 36 mg weight gains for batch BUP-HBr-EA-150 mg-006-5.

| Weight Gain (mg) | Theoretical Weight (mg) | Actual Weight (mg) |
|---|---|---|
| 18.0 | 178.0 | 178.2 |
| 20.0 | 180.0 | 180.3 |
| 22.0 | 182.0 | 181.8 |
| 24.0 | 184.0 | 184.6 |
| 26.0 | 186.0 | 185.8 |
| 28.0 | 188.0 | 188.8 |
| 30.0 | 190.0 | 190.9 |
| 32.0 | 192.0 | 191.6 |
| 34.0 | 194.0 | 194.1 |
| 36.0 | 196.0 | 196.7 |

TABLE 69

Materials used in the ethylcellulose coating and their quantities for batch BUP-HBr-EA-150 mg-007-5.

| Materials | % Contribution to Total Solution | Batch Quantity (g) | % of Solids Solution* |
|---|---|---|---|
| ETHOCEL ® (ethylcellulose) Standard 100 Premium | 4.94 | 232.03 | 55.00 |
| Povidone USP (KOLLIDON ® 90F) | 2.52 | 118.12 | 28.00 |
| PEG 4000 | 1.54 | 71.72 | 17.00 |
| Ethyl Alcohol 95% USP | 91.00 | 4265.63 | N/A |
| Total | 100.00 | 4687.50 | 100.00 |

*Total Solid included 232.03 g of ETHOCEL ®, 118.12 g of Povidone and 71.72 g of PEG 4000. This gave a total solid amount of 421.87 g.

TABLE 70

Open-dish stability studies (40 C./75% RH) on Bupropion HCl & Bupropion HBr Ethylcellulose ("EC") Coated Tablets

| Tests | Initial | Open dish stability (40 C./75% RH) 13 Days | 20 Days |
|---|---|---|---|
| Bupropion HBr XL 348 mg coated EC tablets (EC-32 mg WG.), Lot# Bup-HBr-XL-012-5 (EC-32 mg wg.) | | | |
| % Assay | 101.2 | 99.6 | 99.9 |
| % Impurities | | | |
| 3-CBZ | 0.021 | 0.056 | 0.067 |
| 852U77 | 0.029 | 0.350 | 0.486 |
| 20U78/dilu | 0.054 | 0.046 | 0.047 |
| 827U76 | ND | 0.056 | 0.062 |
| Total unknown | 0.356 | 0.059 | 0.123 |
| Total | 0.46 | 0.57 | 0.79 |
| Bupropion HCl XL 300 mg coated EC tablets (EC, Lot# 05D047) | | | |
| % Assay | 100.4 | 100.2 | 96.2 |
| % Impurities | | | |
| 3-CBZ | 0.015 | 0.089 | 0.117 |
| 852U77 | 0.041 | 0.337 | 0.378 |
| 20U78/dilu | 0.038 | 0.046 | 0.045 |
| 827U76 | 0.023 | 0.071 | 0.080 |
| Total unknown | 0.118 | 0.112 | 0.145 |
| Total | 0.24 | 0.66 | 0.77 |

TABLE 71

Open dish-stability studies (40 C./75% RH) on Bupropion HCl & HBr Final Coated Tablets

| Tests | Bupropion HBr XL 348 mg coated tablets (final 8 mg wg), Lot# Bup-HBr-XL-012-5 (EC32 mg wg-final 8 mg wg.) Initial | 13-Days | 20 Days | Wellbutrin (Bupropion HCl) XL 300 mg tablets Lot# 05A116 Initial | 13 Days | 20 Days |
|---|---|---|---|---|---|---|
| % Assay | 97.7 | 103.0 | 98.6 | 98.1 | 95.6 | 95.5 |
| % Impurities | | | | | | |
| 3-CBZ | 0.021 | 0.091 | 0.119 | 0.032 | 0.171 | 0.279 |
| 852U77 | 0.039 | 0.505 | 0.412 | 0.193 | 0.974 | 1.228 |
| 20U78/dilu | 0.051 | 0.055 | 0.048 | 0.042 | 0.055 | 0.062 |
| 827U76 | ND | 0.046 | 0.054 | 0.028 | 0.082 | 0.096 |
| Total unknown | 0.476 | 0.110 | 0.112 | 0.083 | 0.033 | 0.06 |
| Total (%) | 0.58 | 0.80 | 0.75 | 0.38 | 1.32 | 1.73 |

TABLE 72

Average weight of excipients and weight of the API present in the forced degradation samples for Example 8

| Component | Average weight in mgs present in samples used for Forced deg study | |
|---|---|---|
| | 348 - HBr | 350 - HCl |
| API | 162 | |
| Precirol | 413 | |
| Mannitol | 154 | |
| AVICEL ® pH101 | | |

TABLE 72-continued

Average weight of excipients and weight of the API present in the forced degradation samples for Example 8

| Component | Average weight in mgs present in samples used for Forced deg study |
|---|---|
| L-HPC | 20 |
| KOLLIDON ® | 20 |
| Citric acid | 31 |
| Ethylcellulose E45 | 54 |
| ATBC | 16 |

TABLE 73

BUPROPION HBr EA COATING SOLUTION FORMULATION/mg/TABLET

| Item # | Material | Qty. Required (kg) | % of Batch | Mg/tablet |
|---|---|---|---|---|
| 150 mg EA Coated Tablets - Pivotal Coating Formulation/Batch Size | | | | |
| RE0233 | Ethylcellulose 100, NF | 4.210 | 4.95% | 19.80 |
| RE0067 | Povidone, USP | 2.140 | 2.52% | 10.06 |
| RE0331 | Polyethylene Glycol 4000, NF | 0.435 | 0.51% | 2.05 |
| RE0103 | Dibutyl Sebacate, NF | 0.870 | 1.02% | 4.09 |
| RS0010 | Dehydrated Alcohol, 200 proof, USP | 73.475 | 86.44% | N/A |
| RS0006 | Ethyl Alcohol, 95%, USP | 3.870 | 4.56% | N/A |
| | COOATING SOLUTION TOTAL (kg) | 85 kg | 100% | 36 mg Range: (38-40 mg) |
| *RE0223 | Carnauba Wax, NF | 0.010 kg | N/A | 0.05 mg/tablet |
| 300 mg EA Coated Tablets - Pivotal Coating Formulation/Batch Size | | | | |
| RE0233 | Ethylcellulose 100, NF | 5.450 | 4.95% | 23.12 |
| RE0067 | Povidone, USP | 2.770 | 2.52% | 11.75 |
| RE0331 | Polyethylene Glycol 4000, NF | 0.560 | 0.51% | 2.38 |
| RE0103 | Dibutyl Sebacate, NF | 1.120 | 1.02% | 4.75 |
| RS0010 | Dehydrated Alcohol, 200 proof, USP | 95.070 | 86.43% | N/A |
| RS0006 | Ethyl Alcohol, 95%, USP | 5.030 | 4.57% | N/A |
| | COATING SOLUTION TOTAL (kg) | 110 kg | 100% | 42 mg/tablet Range: (40-44 mg) |
| *RE0223 | Carnauba Wax, NF | 0.010 kg | N/A | 0.05 mg/tablet |

Note:
Where applicable, percentages and mg/tablet totals have been rounded to two decimal places.
*Carnauba Wax not included as part of coating solution formulation. Trace amounts applied after completion of the coating process.

TABLE 74

ACCELERATED STABILITY PROGRAM

| Product: Bupropion.HBr FV0092 | Batch No.: D00894 | Start date: 20/12/04 | Temperature: 40° C. ± 2° C. R.H.: 75% ± 5% | | |
|---|---|---|---|---|---|
| Analysis | Specification | | time 0 | 3 month | 6 months |
| Description | white or almost white crystalline powder | | conform | conform | conform |
| Identification | IR, HPLC (positive) | | positive | positive | positive |
| Water content (K.F.) | NMT 0.5% | | 0.05 | 0.07 | 0.08 |
| Chromatographic purity A) (HPLC) | 1) NMT 0.1% 2) NMT 0.1% 3) NMT 0.1% | | 1) n.d. 2) n.d. 3) n.q. | 1) n.q. 2) n.d. 3) n.q. | 1) 0.05 2) n.d. 3) n.q. |
| Chromatographic purity B) (HPLC) | 4) NMT 0.1% 5) NMT 0.1% 6) NMT 0.3% | | 4) 0.04 5) 0.04 6) 0.04 | 4) 0.03 5) 0.04 6) 0.06 | 4) 0.04 5) n.q. 6) 0.02 |
| Chromatographic purity (HPLC: A + B) | Total impurities NMT 0.5% | | 0.1 | 0.1 | 0.1 |
| Assay (HPLC) | 98.0-102.0% on d.b. | | 99.6 | 99.6 | 99.7 |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).

Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 75

ACCELERATED STABILITY PROGRAM

| Product: Bupropion.HBr FV0092 | Batch No.: D00895 | Start date: 20/12/04 | Temperature: 40° C. ± 2° C. R.H.: 75% ± 5% | | |
|---|---|---|---|---|---|
| Analysis | Specification | | time 0 | 3 month | 6 months |
| Description | white or almost white crystalline powder | | conform | conform | conform |
| Identification | IR, HPLC (positive) | | positive | positive | positive |
| Water content (K.F.) | NMT 0.5% | | 0.04 | 0.07 | 0.07 |
| Chromatographic purity A) (HPLC) | 1) NMT 0.1% 2) NMT 0.1% 3) NMT 0.1% | | 1) n.d. 2) n.d. 3) n.q. | 1) n.q. 2) n.d. 3) 0.05 | 1) 0.05 2) n.d. 3) n.q. |
| Chromatographic purity B) (HPLC) | 4) NMT 0.1% 5) NMT 0.1% 6) NMT 0.3% | | 4) 0.04 5) 0.04 6) 0.04 | 4) 0.03 5) 0.04 6) 0.05 | 4) 0.04 5) n.q. 6) 0.02 |
| Chromatographic purity (HPLC: A + B) | Total impurities NMT 0.5% | | 0.1 | 0.1 | 0.1 |
| Assay (HPLC) | 98.0-102.0% on d.b. | | 99.2 | 100.7 | 99.7 |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).

Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 76

ACCELERATED STABILITY PROGRAM

| Product: Bupropion.HBr FV0092 | Batch No.: D00896 | Start date: 20/12/04 | Temperature: 40° C. ± 2° C. R.H.: 75% ± 5% | | |
|---|---|---|---|---|---|
| Analysis | Specification | | time 0 | 3 month | 6 months |
| Description | white or almost white crystalline powder | | conform | conform | conform |
| Identification | IR, HPLC (positive) | | positive | positive | positive |
| Water content (K.F.) | NMT 0.5% | | 0.06 | 0.11 | 0.04 |
| Chromatographic purity A) (HPLC) | 1) NMT 0.1% 2) NMT 0.1% 3) NMT 0.1% | | 1) n.d. 2) n.d. 3) n.q. | 1) n.q. 2) n.d. 3) n.q. | 1) 0.05 2) n.d. 3) n.q. |
| Chromatographic purity B) (HPLC) | 4) NMT 0.1% 5) NMT 0.1% 6) NMT 0.3% | | 4) 0.04 5) 0.05 6) 0.05 | 4) 0.03 5) 0.04 6) 0.05 | 4) 0.04 5) n.q. 6) n.q. |
| Chromatographic purity (HPLC: A + B) | Total impurities NMT 0.5% | | 0.1 | 0.1 | 0.1 |
| Assay (HPLC) | 98.0-102.0% on d.b. | | 99.3 | 100.0 | 100.4 |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).

Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 77

SHELF LIFE STABILITY PROGRAM

| Product: Bupropion.HBr FV0092 | Batch No.: D00894 | | Start date: 20/12/04 | | Temperature: 25° C. ± 2° C.; Relative Humidity: 60% ± 5% | | | |
|---|---|---|---|---|---|---|---|---|
| Analysis | Specification | time 0 | 3 months | 6 months | 9 months | 12 months | 18 months | 24 months | 36 months |
| Description | white or almost white crystalline powder | conform | conform | conform | conform | conform | | | |
| Identification | IR, HPLC (positive) | positive | positive | positive | positive | positive | | | |
| Water content (K.F.) | NMT 0.5% | 0.05 | 0.05 | 0.06 | 0.05 | 0.05 | | | |
| Chromatographic purity A) (HPLC) | 1) NMT 0.1% | 1) n.d. | 1) n.q. | 1) 0.05 | 1) n.q. | 1) n.d. | 1) | 1) | 1) |
| | 2) NMT 0.1% | 2) n.d. | 2) n.d. | 2) n.d. | 2) n.d. | 2) n.d. | 2) | 2) | 2) |
| | 3) NMT 0.1% | 3) n.q. | 3) n.q. | 3) n.q. | 3) n.q. | 3) 0.05 | 3) | 3) | 3) |
| Chromatographic purity B) (HPLC) | 4) NMT 0.1% | 4) 0.04 | 4) 0.03 | 4) 0.05 | 4) n.d. | 4) 0.05 | 4) | 4) | 4) |
| | 5) NMT 0.1% | 5) 0.04 | 5) 0.04 | 5) n.q. | 5) n.q. | 5) 0.05 | 5) | 5) | 5) |
| | 6) NMT 0.3% | 6) 0.04 | 6) 0.05 | 6) 0.02 | 6) n.q. | 6) 0.07 | 6) | 6) | 6) |
| Chromatographic purity (HPLC: A + B) | Total impurities NMT 0.5% | 0.1 | 0.1 | 0.1 | n.q. | 0.2 | | | |
| Assay (HPLC) | 98.0-102.0% on d.b. | 99.6 | 99.4 | 100.2 | 99.5 | 99.6 | | | |
| Microbial cont. | total microbial count <1000 cfu/g moulds and yeast <100 cfu/g | not applied | not applied | not applied | not applied | <100 ufc/g <100 ufc/g | not applied | | |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).

Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 78

SHELF LIFE STABILITY PROGRAM

| Product: Bupropion.HBr FV0092 | Batch No.: D00895 | | Start date: 20/12/04 | | Temperature: 25° C. ± 2° C.; Relative Humidity: 60% ± 5% | | | |
|---|---|---|---|---|---|---|---|---|
| Analysis | Specification | time 0 | 3 months | 6 months | 9 months | 12 months | 18 months | 24 months | 36 months |
| Description | white or almost white crystalline powder | conform | conform | conform | conform | conform | | | |
| Identification | IR, HPLC (positive) | positive | positive | positive | positive | positive | | | |
| Water content (K.F.) | NMT 0.5% | 0.04 | 0.04 | 0.05 | 0.05 | 0.04 | | | |
| Chromatographic purity A) (HPLC) | 1) NMT 0.1% | 1) n.d. | 1) n.q. | 1) 0.05 | 1) n.q. | 1) n.d. | 1) | 1) | 1) |
| | 2) NMT 0.1% | 2) n.d. | 2) n.d. | 2) n.d. | 2) n.d. | 2) n.d. | 2) | 2) | 2) |
| | 3) NMT 0.1% | 3) n.q. | 3) n.q. | 3) n.q. | 3) n.q. | 3) 0.05 | 3) | 3) | 3) |
| Chromatographic purity B) (HPLC) | 4) NMT 0.1% | 4) 0.04 | 4) 0.03 | 4) 0.05 | 4) n.d. | 4) 0.05 | 4) | 4) | 4) |
| | 5) NMT 0.1% | 5) 0.04 | 5) 0.04 | 5) n.q. | 5) n.q. | 5) 0.07 | 5) | 5) | 5) |
| | 6) NMT 0.3% | 6) 0.04 | 6) 0.05 | 6) 0.02 | 6) n.q. | 6) 0.07 | 6) | 6) | 6) |
| Chromatographic purity (HPLC: A + B) | Total impurities NMT 0.5% | 0.1 | 0.1 | 0.1 | n.q. | 0.2 | | | |
| Assay (HPLC) | 98.0-102.0% on d.b. | 99.2 | 99.5 | 100.1 | 99.4 | 99.4 | | | |
| Microbial cont. | total microbial count <1000 cfu/g moulds and yeast <100 cfu/g | not applied | not applied | not applied | not applied | <100 ufc/g <100 ufc/g | not applied | | |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).

Notes:

TABLE 78-continued

SHELF LIFE STABILITY PROGRAM n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 79

SHELF LIFE STABILITY PROGRAM

Product: Bupropion.HBr FV0092  Batch No.: D00896  Start date: 20/12/04  Temperature: 25° C. ± 2° C.; Relative Humidity: 60% ± 5%

| Analysis | Specification | time 0 | 3 months | 6 months | 9 months | 12 months | 18 months | 24 months | 36 months |
|---|---|---|---|---|---|---|---|---|---|
| Description | white or almost white crystalline powder | conform | conform | conform | conform | conform | | | |
| Identification | IR, HPLC (positive) | positive | positive | positive | positive | positive | | | |
| Water content (K.F.) | NMT 0.5% | 0.06 | 0.04 | 0.04 | 0.04 | 0.03 | | | |
| Chromatographic purity A) (HPLC) | 1) NMT 0.1% | 1) n.d. | 1) n.q. | 1) 0.05 | 1) n.q. | 1) n.d. | 1) | 1) | 1) |
| | 2) NMT 0.1% | 2) n.d. | 2) n.d. | 2) n.d. | 2) n.d. | 2) n.d. | 2) | 2) | 2) |
| | 3) NMT 0.1% | 3) n.q. | 3) n.q. | 3) n.q. | 3) n.q. | 3) n.q. | 3) | 3) | 3) |
| Chromatographic purity B) (HPLC) | 4) NMT 0.1% | 4) 0.04 | 4) 0.03 | 4) 0.04 | 4) n.d. | 4) 0.05 | 4) | 4) | 4) |
| | 5) NMT 0.1% | 5) 0.05 | 5) 0.04 | 5) n.q. | 5) n.q. | 5) 0.07 | 5) | 5) | 5) |
| | 6) NMT 0.3% | 6) 0.05 | 6) 0.05 | 6) n.q. | 6) n.q. | 6) 0.07 | 6) | 6) | 6) |
| Chromatographic purity (HPLC: A + B) | Total impurities NMT 0.5% | 0.1 | 0.1 | 0.1 | n.q. | 0.1 | | | |
| Assay (HPLC) | 98.0-102.0% on d.b. | 99.3 | 99.4 | 100.5 | 99.4 | 100.3 | | | |
| Microbial cont. | total microbial count <1000 cfu/g moulds and yeast <100 cfu/g | not applied | not applied | not applied | not applied | <100 ufc/g <100 ufc/g | not applied | | |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).
Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 80

Bupropion Hydrobromide Polymorphs Table

| Trial | Solvent (voll.) | Cosolvent (voll.) | Yield (%) | Form | K.F. (%) | Notes |
|---|---|---|---|---|---|---|
| 085 | IPA + HBr gas | | | I | 0.07 | Standard procedure |
| 097 | Water 2 | / | 72 | I | 0.06 | |
| 098A | Methanol 2.4 | / | | II | 0.13 | |
| 098B | Acetone 17 | water 0.7 | 24 | II | 0.16 | |
| 099 | Ethanol abs. 4.8 | / | 56 | III | 0.12 | |
| 100 | IPA 15.1 | / | 77 | I | 0.11 | |
| 102 | AcOi-Pr 20 | MeOH 3.6 | 26 | I | 0.25 | |
| 108 | Acetonitrile 20 | / | 70 | I | 0.14 | |
| 109 | Dichloromethane 30 | / | 25 | II | 0.21 | |
| 110 | Water 2 | HBr 48% 1 | 83 | I | 0.12 | |
| 111 | IPA 6 | HBr 48% 1 | 69 | I | 0.32 | |
| 112 | MTBE 10 | MeOH 3 | 67 | I | 0.18 | |
| 113 | Toluene 10 | MeOH 1.25 | 40 | II | 0.39 | |
| 114 | DMC 10 | MeOH 1.75 | 67 | II | 0.17 | |
| 115 | t-BuOH 20 | Water 0.55 | 74 | I | 0.15 | |
| 116 | Form I in rotavapor 100° C. 24 h | | | I | 0.45 | |
| 117 | IPA 10 | Water 0.125 | 88 | I | 0.32 | |
| 118 | Toluene 10 | MeOH 1.15 | 99 | I | 0.16 | |
| 119 | IPA 8 | MeOH 1.32 | 83 | I | 0.47 | |
| 120 | Sec-BuOH 25 | / | 89 | I | 0.13 | |
| 122 | Water 8 | / | | I | 1.3 | Spray dried |

TABLE 81

Polyethoxylated Fatty Acids
Although polyethylene glycol (PEG) itself does not function as a surfactant, a variety of PEG-fatty acid esters have useful surfactant properties. Examples of polyethoxylated fatty acid monoester surfactants commercially available are shown here in Table 81.
PEG-Fatty Acid Monoester Surfactants

| Compound | Commercial Product (Supplier) | HLB |
|---|---|---|
| PEG 4-100 monolaurate | Crodet L series (Croda) | >9 |
| PEG 4-100 monooleate | Crodet O series (Croda) | >8 |
| PEG 4-100 monostearate | Crodet S series (Croda), Myrj Series (Atlas/ICI) | >6 |
| PEG 400 distearate | Cithrol 4DS series (Croda) | >10 |
| PEG 100, 200, 300 monolaurate | Cithrol ML series (Croda) | >10 |
| PEG 100, 200, 300 monooleate | Cithrol MO series (Croda) | >10 |
| PEG 400 dioleate | Cithrol 4DO series (Croda) | >10 |
| PEG 400-1000 monostearate | Cithrol MS series (Croda) | >10 |
| PEG-1 stearate | Nikkol MYS-IEX (Nikko), Coster KI (Condea) | 2 |
| PEG-2 stearate | Nikkol MYS-2 (Nikko) | 4 |
| PEG-2 oleate | Nikkol MYO-2 (Nikko) | 4.5 |
| PEG-4 laurate | Mapeg ® 200 ML (PPG), Kessco ® PEG 200ML (Stepan), LIPOPEG 2L (LIPO Chem.) | 9.3 |
| PEG-4 oleate | Mapeg ® 200 MO (PPG), Kessco ® PEG200 MO (Stepan), | 8.3 |
| PEG-4 stearate | Kessco ® PEG 200 MS (Stepan), Hodag 20 S (Calgene), Nikkol MYS-4 (Nikko) | 6.5 |
| PEG-5 stearate | Nikkol TMGS-5 (Nikko) | 9.5 |
| PEG-5 oleate | Nikkol TMGO-5 (Nikko) | 9.5 |
| PEG-6 oleate | Algon OL 60 (Auschem SpA), Kessco ® PEG 300 MO (Stepan), Nikkol MYO-6 (Nikko), Emulgante A6 (Condea) | 8.5 |
| PEG-7 oleate | Algon OL 70 (Auschem SpA) | 10.4 |
| PEG-6 laurate | Kessco ® PEG300 ML (Stepan) | 11.4 |
| PEG-7 laurate | Lauridac 7 (Condea) | 13 |
| PEG-6 stearate | Kessco ® PEG300 MS (Stepan) | 9.7 |
| PEG-8 laurate | Mapeg ® 400 ML (PPG), LIPOPEG 4DL(Lipo Chem.) | 13 |
| PEG-8 oleate | Mapeg ® 400 MO (PPG), Emulgante A8 (Condea); Kessco PEG 400 MO (Stepan) | 12 |
| PEG-8 stearate | Mapeg ® 400 MS (PPG), Myrj 45 | 12 |
| PEG-9 oleate | Emulgante A9 (Condea) | >10 |
| PEG-9 stearate | Cremophor 59 (BASF) | >10 |
| PEG-10 laurate | Nikkol MYL-10 (Nikko), Lauridac 10 (Croda) | 13 |
| PEG-10 oleate | Nikkol MYO-10 (Nikko) | 11 |
| PEG-10 stearate | Nikkol MYS-10 (Nikko), Coster K100 (Condea) | 11 |
| PEG-12 laurate | Kessco ® PEG 600ML (Stepan) | 15 |
| PEG-12 oleate | Kessco ® PEG 600MO (Stepan) | 14 |
| PEG-12 ricinoleate | (CAS #9004-97-1) | >10 |
| PEG-12 stearate | Mapeg ® 600 MS (PPG), Kessco ® PEG 600MS (Stepan) | 14 |
| PEG-15 stearate | Nikkol TMGS-15 (Nikko), Koster K15 (Condea) | 14 |
| PEG-15 oleate | Nikkol TMGO-15 (Nikko) | 15 |
| PEG-20 laurate | Kessco ® PEG 1000 ML (Stepan) | 17 |
| PEG-20 oleate | Kessco ® PEG 1000 MO (Stepan) | 15 |
| PEG-20 stearate | Mapeg ® 1000 MS (PPG), Kessco ® PEG 1000 MS (Stepan), Myrj 49 | 16 |
| PEG-25 stearate | Nikkol MYS-25 (Nikko) | 15 |
| PEG-32 laurate | Kessco ® PEG 1540 ML (Stepan) | 16 |
| PEG-32 oleate | Kessco ® PEG 1540 MO (Stepan) | 17 |
| PEG-32 stearate | Kessco ® PEG 1540 MS (Stepan) | 17 |
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-40 stearate | Myrj 52, Emerest ® 2715 (Henkel), Nikkol MYS-40 (Nikko) | >10 |
| PEG-45 stearate | Nikkol MYS-45 (Nikko) | 18 |
| PEG-50 stearate | Myrj 53 | >10 |
| PEG-55 stearate | Nikkol MYS-55 (Nikko) | 18 |
| PEG-100 oleate | Crodet 0-100 (Croda) | 18.8 |
| PEG-100 stearate | Myrj 59, Arlacel 165 (ICI) | 19 |
| PEG-200 oleate | Albunol 200 MO (Taiwan Surf.) | >10 |
| PEG-400 oleate | LACTOMUL (Henkel), Albunol 400 MO (Taiwan Surf.) | >10 |
| PEG-600 oleate | Albunol 600 MO (Taiwan Surf) | >10 |

TABLE 82

PEG-Fatty Acid Diesters
Polyethylene glycol (PEG) fatty acid diesters are also suitable for use as surfactants in the compositions of the present invention. Representative PEG-fatty acid diesters are shown here in Table 82.
PEG-Fatty Acid Diester Surfactants

| Compound | Commercial Product (Supplier) | HLB |
|---|---|---|
| PEG-4 dilaurate | Mapeg ® 200 DL (PPG), Kessco ® PEG 200 DL (Stepan), LIPOPEG 2-DL (Lipo Chem.) | 7 / 6 |
| PEG-4 dioleate | Mapeg ® 200 DO (PPG), | 6 |
| PEG-4 distearate | Kessco ® 200 DS (Stepan) | 5 |
| PEG-6 dilaurate | Kessco ® PEG 300 DL (Stepan) | 9.8 |
| PEG-6 dioleate | Kessco ® PEG 300 DO (Stepan) | 7.2 |
| PEG-6 distearate | Kessco ® PEG 300 DS (Stepan) | 6.5 |
| PEG-8 dilaurate | Mapeg ® 400 DL (PPG), Kessco ® PEG 400 DL (Stepan), LIPOPEG 4 DL (Lipo Chem.) | 11 |
| PEG-8 dioleate | Mapeg ® 400 DO (PPG), Kessco ® PEG 400 DO (Stepan), LIPOPEG 4 DO (Lipo Chem.) | 8.8 |
| PEG-8 distearate | Mapeg ® 400 DS (PPG), CDS 400 (Nikkol) | 11 |
| PEG-10 dipalmitate | Polyaldo 2PKFG | >10 |
| PEG-12 dilaurate | Kessco ® PEG 600 DL (Stepan) | 11.7 |
| PEG-12 distearate | Kessco ® PEG 600 DS (Stepan) | 10.7 |
| PEG-12 dioleate | Mapeg ® 600 DO (PPG), Kessco ® 600 DO(Stepan) | 10 |
| PEG-20 dilaurate | Kessco ® PEG 1000 DL (Stepan) | 15 |
| PEG-20 dioleate | Kessco ® PEG 1000 DO (Stepan) | 13 |
| PEG-20 distearate | Kessco ® PEG 1000 DS (Stepan) | 12 |
| PEG-32 dilaurate | Kessco ® PEG 1540 DL (Stepan) | 16 |
| PEG-32 dioleate | Kessco ® PEG 1540 DO (Stepan) | 15 |
| PEG-32 distearate | Kessco ® PEG 1540 DS (Stepan) | 15 |
| PEG-400 dioleate | Cithrol 4DO series (Croda) | >10 |
| PEG-400 distearate | Cithrol 4DS series (Croda) | >10 |

TABLE 83

PEG-Fatty Acid Mono- and Di-ester Mixtures
In general, mixtures of surfactants are also useful in the present invention, including mixtures of two or more commercial surfactant products. Several PEG-fatty acid esters are marketed commercially as mixtures or mono- and diesters. Representative surfactant mixtures are shown here in Table 83.
PEG-Fatty Acid Mono-and Diester Mixtures

| Compound | Commercial Product (Supplier) |
|---|---|
| PEG 4-150 mono, dilaurate | Kessco ® PEG 200-6000 mono, dilaurate (Stepan) |

TABLE 83-continued

PEG-Fatty Acid Mono- and Di-ester Mixtures
In general, mixtures of surfactants are also useful in the present invention, including mixtures of two or more commercial surfactant products. Several PEG-fatty acid esters are marketed commercially as mixtures or mono- and diesters. Representative surfactant mixtures are shown here in Table 83.

PEG-Fatty Acid Mono-and Diester Mixtures

| Compound | Commercial Product (Supplier) |
|---|---|
| PEG 4-150 mono, dioleate | Kessco ® PEG 200-6000 mono, dioteate (Stepan) |
| PEG 4-150 mono, distearate | Kessco ® 200-6000 mono, distearate (Stepan) |

TABLE 84

Polyethylene Glycol Glycerol Fatty Acid Esters
Suitable PEG glycerol fatty acid esters are shown here in Table 84.

PEG Glycerol Fatty Acid Esters

| Compound | Commercial Product (Supplier) | HLB |
|---|---|---|
| PEG-20 glyceryl laurate | Tagat ® L (Goldschmidt) | 16 |
| PEG-30 glyceryl laurate | Tagat ® L2 (Goldschmidt) | 16 |
| PEG-15 glyceryl laurate | Glycerox L series (Croda) | 15 |
| PEG-40 glyceryl laurate | Glycerox L series (Croda) | 15 |
| PEG-20 glyceryl stearate | Capmul ® EMG (ABITEC), Aldo ® MS-20 KFG (Lonza) | 13 |
| PEG-20 glyceryl oleate | Tagat ® O (Goldschmidt) | >10 |
| PEG-30 glyceryl oleate | Tagat ® O2 (Goldschmidt) | >10 |

TABLE 85

Alcohol--Oil Transesterification Products
A large number of surfactants of different degrees of lipophilicity or hydrophilicity can be prepared by reaction of alcohols or polyalcohols with a variety of natural and/or hydrogenated oils. In certain embodiments, the oils used are castor oil or hydrogenated castor oil or an edible vegetable oil such as corn oil, olive oil, peanut oil, palm kernel oil, apricot kernel oil, or almond oil. Examples of alcohols include glycerol, propylene glycol, ethylene glycol, polyethylene glycol, sorbitol, and pentaerythritol. Representative surfactants of this class suitable for use in the present invention are shown here in Table 85.

Transesterification Products of Oils and Alcohols

| Compound | Commercial Product (Supplier) | HLB |
|---|---|---|
| PEG-3 castor oil | Nikkol CO-3 (Nikko) | 3 |
| PEG-5, 9, and 16 castor oil | ACCONON CA series (ABITEC) | 6-7 |
| PEG-20 castor oil | Emalex C-20 (Nihon Emulsion), Nikkol CO-20 TX (Nikko) | 11 |
| PEG-23 castor oil | Emulgante EL23 | >10 |
| PEG-30 castor oil | Emalex C-30 (Nihon Emulsion), Alkamuls ® EL 620 (Rhone-Poulenc), Incrocas 30 (Croda) | 11 |
| PEG-35 castor oil | Cremophor EL and EL-P (BASF), Emulphor EL, Incrocas-35 (Croda), Emulgin RO 35 (Henkel) | |
| PEG-38 castor oil | Emulgante EL 65 (Condea) | |
| PEG-40 castor oil | Emalex C-40 (Nihon Emulsion), Alkamuls ® EL 719 (Rhone-Poulenc) | 13 |
| PEG-50 castor oil | Emalex C-50 (Nihon Emulsion) | 14 |
| PEG-56 castor oil | Eumulgin ® PRT 56 (Pulcra SA) | >10 |
| PEG-60 castor oil | Nikkol CO-60TX (Nikko) | 14 |
| PEG-100 castor oil | Thornley | >10 |
| PEG-200 castor oil | Eumulgin ® PRT 200 (Pulcra SA) | >10 |
| PEG-5 hydrogenated castor oil | Nikkol HCO-5 (Nikko) | 6 |
| PEG-7 hydrogenated castor oil | Simusol ® 989 (Seppic), Cremophor WO7 (BASF) | 6 |
| PEG-10 hydrogenated castor oil | Nikkol HCO-10 (Nikko) | 6.5 |
| PEG-20 hydrogenated castor oil | Nikkol HCO-20 (Nikko) | 11 |
| PEG-25 hydrogenated castor oil | Simulsol ® 1292 (Seppic), Cerex ELS 250 (Auschem SpA) | 11 |
| PEG-30 hydrogenated castor oil | Nikkol HCO-30 (Nikko) | 11 |
| PEG-40 hydrogenated castor oil | Cremophor RH 40 (BASF), Croduret (Croda), Emulgin HRE 40 (Henkel) | 13 |
| PEG-45 hydrogenated castor oil | Cerex ELS 450 (Auschem Spa) | 14 |
| PEG-50 hydrogenated castor oil | Emalex HC-50 (Nihon Emulsion) | 14 |
| PEG-60 hydrogenated castor oil | Nikkol HCO-60 (Nikko), Cremophor RH 60 (BASF) | 15 |
| PEG-80 hydrogenated castor oil | Nikkol HCO-80 (Nikko) | 15 |
| PEG-100 hydrogenated castor oil | Nikkol HCO-100 (Nikko) | 17 |
| PEG-6 corn oil | Labrafil ® M 2125 CS (Gattefosse) | 4 |
| PEG-6 almond oil | Labrafil ® M 1966 CS (Gattefosse) | 4 |
| PEG-6 apricot kernel oil | Labrafil ® M 1944 CS (Gattefosse) | 4 |
| PEG-6 olive oil | Labrafil ® M 1980 CS (Gattefosse) | 4 |
| PEG-6 peanut oil | Labrafil ® M 1969 CS (Gattefosse) | 4 |
| PEG-6 hydrogenated palm kernel oil | Labrafil ® M 2130 BS (Gattefosse) | 4 |
| PEG-6 palm kernel oil | Labrafil ® M 2130 CS (Gattefosse) | 4 |
| PEG-6 triolein | Labrafil ® M 2735 CS (Gattefosse) | 4 |
| PEG-8 corn oil | Labrafil ® WL 2609 BS (Gattefosse) | 6-7 |
| PEG-20 corn glycerides | Crovol M40 (Croda) | 10 |
| PEG-20 almond glycerides | Crovol A40 (Croda) | 10 |
| PEG-25 trioleate | TAGAT ® TO (Goldschmidt) | 11 |
| PEG-40 palm kernel oil | Crovol PK-70 | >10 |
| PEG-60 corn glycerides | Crovol M70(Croda) | 15 |
| PEG-60 almond glycerides | Crovol A70 (Croda) | 15 |
| PEG-4 caprylic/capric triglyceride | Labrafac ® Hydro (Gattefosse), | 4-5 |
| PEG-8 caprylic/capric glycerides | Labrasol (Gattefosse), Labrafac CM 10 (Gattefosse) | >10 |
| PEG-6 caprylic/capric glycerides | SOFTIGEN ® 767 (Huls), Glycerox 767 (Croda) | 19 |
| Lauroyl macrogol-32 glyceride | GELUCIRE 44/14 (Gattefosse) | 14 |
| Stearoyl macrogol glyceride | GELUCIRE 50/13 (Gattefosse) | 13 |
| Mono, di, tri, tetraesters of vegetable oils and sorbitol | SorbitoGlyceride (Gattefosse) | <10 |
| Pentaerythrityl tetraisostearate | Crodamol PTIS (Croda) | <10 |

TABLE 85-continued

Alcohol--Oil Transesterification Products
A large number of surfactants of different degrees of lipophilicity or hydrophilicity can be prepared by reaction of alcohols or polyalcohols with a variety of natural and/or hydrogenated oils. In certain embodiments, the oils used are castor oil or hydrogenated castor oil or an edible vegetable oil such as corn oil, olive oil, peanut oil, palm kernel oil, apricot kernel oil, or almond oil. Examples of alcohols include glycerol, propylene glycol, ethylene glycol, polyethylene glycol, sorbitol, and pentaerythritol. Representative surfactants of this class suitable for use in the present invention are shown here in Table 85.
Transesterification Products of Oils and Alcohols

| Compound | Commercial Product (Supplier) | HLB |
|---|---|---|
| Pentaerythrityl distearate | Albunol DS (Taiwan Surf.) | <10 |
| Pentaerythrityl tetraoleate | Liponate PO-4 (Lipo Chem.) | <10 |
| Pentaerythrityl tetrastearate | Liponate PS-4 (Lipo Chem.) | <10 |
| Pentaerythrityl tetracaprylate/ tetracaprate | Liponate PE-810 (Lipo Chem.), Crodamol PTC (Croda) | <10 |
| Pentaerythrityl tetraoctanoate | Nikkol Pentarate 408 (Nikko) | |

TABLE 86

Polyglycerized Fatty Acids
Polyglycerol esters of fatty acids are also suitable surfactants for the present invention. Examples of suitable polyglyceryl esters are shown here in Table 86.
Polyglycerized Fatty Acids

| Compound | Commercial Product (Supplier) | HLB |
|---|---|---|
| Polyglyceryl-2 stearate | Nikkol DGMS (Nikko) | 5-7 |
| Polyglyceryl-2 oleate | Nikkol DGMO (Nikko) | 5-7 |
| Polyglyceryl-2 isostearate | Nikkol DGMIS (Nikko) | 5-7 |
| Polyglyceryl-3 oleate | Caprol ® 3G0 (ABITEC), Drewpol 3-1-O (Stepan) | 6.5 |
| Polyglyceryl-4 oleate | Nikkol Tetraglyn 1-O (Nikko) | 5-7 |
| Polyglyceryl-4 stearate | Nikkol Tetraglyn 1-S (Nikko) | 5-6 |
| Polyglyceryl-6 oleate | Drewpol 6-1-O (Stepan), Nikkol Hexaglyn 1-O (Nikko) | 9 |
| Polyglyceryl-10 laurate | Nikkol Decaglyn 1-L (Nikko) | 15 |
| Polyglyceryl-10 oleate | Nikkol Decaglyn 1-O (Nikko) | 14 |
| Polyglyceryl-10 stearate | Nikkol Decaglyn 1-S (Nikko) | 12 |
| Polyglyceryl-6 ricinoleate | Nikkol Hexaglyn PR-15 (Nikko) | |
| Polyglyceryl-10 linoleate | Nikkol Decaglyn I-LN (Nikko) | 12 |
| Polyglyceryl-6 pentaoleate | Nikkol Hexaglyn S-O (Nikko) | <10 |
| Polyglyceryl-3 dioleate | Cremophor GO32 (BASF) | <10 |
| Polyglyceryl-3 distearate | Cremophor GS32 (BASF) | <10 |
| Polyglyceryl-4 pentaoleate | Nikkol Tetraglyn 5-O (Nikko) | <10 |
| Polyglyceryl-6 dioleate | Caprol ® 6G20 (ABITEC); Hodag PGO-62 (Calgene), PLUROL OLEIQUE CC 497 (Gattefosse) | 8.5 |
| Polyglyceryl-2 dioleate | Nikkol DGDO (Nikko) | 7 |
| Polyglyceryl-10 trioleate | Nikkol Decaglyn 3-O (Nikko) | 7 |
| Polyglyceryl-10 pentaoleate | Nikkol Decaglyn 5-O (Nikko) | 3.5 |
| Polyglyceryl-10 septaoleate | Nikkol Decagtyn 7-O (Nikko) | 3 |
| Polyglyceryl-10 tetraoleate | Caprol ® 10G40 (ABITEC); Hodag PGO-62 (CALGENE), Drewpol 10-4-O (Stepan) | 6.2 |
| Polyglyceryl-10 decaisostearate | Nikkol Decaglyn 10-IS (Nikko) | <10 |
| Polyglyceryl-10 decaoleate | Drewpol 10-10-O (Stepan), Caprol 10G10O (ABITEC), Nikkol Decaglyn 10-O | 3.5 |
| Polyglyceryl-10 mono, dioleate | Caprol ® PGE 860 (ABITEC) | 11 |
| Polyglyceryl polyricinoleate | Polymuls (Henkel) | 3-20 |

TABLE 87

Propylene Glycol Fatty Acid Esters
Esters of propylene glycol and fatty acids are suitable surfactants for use in the present invention. Examples of surfactants of this class are given here in Table 87.
Propylene Glycol Fatty Acid Esters

| Compound | Commercial Product (Supplier) | HLB |
|---|---|---|
| Propylene glycol monocaprylate | Capryol 90 (Gattefosse), Nikkol Sefsol 218 (Nikko) | <10 |
| Propylene glycol monolaurate | Lauroglycol 90 (Gattefosse), Lauroglycol FCC (Gattefosse) | <10 |
| Propylene glycol oleate | Lutrol OP2000 (BASF) | <10 |
| Propylene glycol myristate | Mirpyl | <10 |
| Propylene glycol monostearate | ADM PGME-03 (ADM), LIPO PGMS (Lipo Chem.), Aldo ® PGHMS (Lonza) | 3-4 |
| Propylene glycol hydroxy stearate | | <10 |
| Propylene glycol ricinoleate | PROPYMULS (Henkel) | <10 |
| Propylene glycol isostearate | | <10 |
| Propylene glycol monooleate | Myverol P-06 (Eastman) | <10 |
| Propylene glycol dicaprylate/dicaprate | Captex ® 200 (ABITEC), Miglyol ® 840 (Huls), Neobee ® M-20 (Stepan) | >6 |
| Propylene glycol dioctanoate | Captex ® 800 (ABITEC) | |
| Propylene glycol caprylate/caprate | LABRAFAC PG (Gattefosse) | >6 |
| Propylene glycol dilaurate | | >6 |
| Propylene glycol distearate | Kessco ® PGDS (Stepan) | >6 |
| Propylene glycol dicaprylate | Nikkol Sefsol 228 (Nikko) | >6 |
| Propylene glycol dicaprate | Nikkol PDD (Nikko) | >6 |

TABLE 88

Mixtures of Propylene Glycol Esters-Glycerol Esters
In general, mixtures of surfactants are also suitable for use in the present invention. In particular, mixtures of propylene glycol fatty acid esters and glycerol fatty acid esters are suitable and are commercially available. Examples of these surfactants are shown here in Table 88.
Glycerol/Propylene Glycol Fatty Acid Esters

| Compound | Commercial Product (Supplier) | HLB |
|---|---|---|
| Oleic | ATMOS 300, ARLACEL 186 (ICI) | 3-4 |
| Stearic | ATMOS 150 | 3-4 |

TABLE 89

Mono- and Diglycerides
Another class of surfactants is the class of mono- and diglycerides. These surfactants are generally lipophilic. Examples of these surfactants are given here in Table 89.
Mono- and Diglyceride Surfactants

| Compound | Commercial Product (Supplier) | HLB |
|---|---|---|
| Monopalmitolein (C16:1) | (Larodan) | <10 |
| Monoelaidin (C18:1) | (Larodan) | <10 |
| Monocaproin (C6) | (Larodan) | <10 |
| Monocaprylin | (Larodan) | <10 |
| Monocaprin | (Larodan) | <10 |
| Monolaurin | (Larodan) | <10 |
| Glyceryl monomyristate (C14) | Nikkol MGM (Nikko) | 3-4 |
| Glyceryl monooleate (C18:1) | PECEOL (Gattefosse), Hodag GMO-D, Nikkol MGO (Nikko) | 3-4 |
| Glyceryl monooleate | RYLO series (Danisco), DIMODAN series (Danisco), EMULDAN (Danisco), ALDO ® MO FG (Lonza), Kessco GMO (Stepan), MONOMULS ® series (Henkel), TEGIN O, DREWMULSE GMO (Stepan), Atlas G-695 (ICI), GMOrphic 80 (Eastman), ADM DMG-40, 70, and 100 (ADM), Myverol (Eastman) | 3-4 |
| Glycerol monooleate/linoleate | OLICINE (Gattefosse) | 3-4 |
| Glycerol monolinoleate | Maisine (Gattefosse), MYVEROL 18-92, Myverol 18-06 (Eastman) | 3-4 |
| Glyceryl ricinoleate | Softigen ® 701 (Huls), HODAG GMR-D (Calgene), ALDO ® MR (Lonza) | 6 |
| Glyceryl monolaurate | ALDO ® MLD (Lonza), Hodag GML (Calgene) | 6.8 |
| Glycerol monopalmitate | Emalex GMS-P (Nihon) | 4 |
| Glycerol monostearate | Capmul ® GMS. (ABITEC), Myvaplex (Eastman), IMWITOR ® 191 (Huls), CUTINA GMS, Aldo ® MS (Lonza), Nikkol MGS series (Nikko) | 5-9 |
| Glyceryl mono-, dioleate | Capmul ® GMO-K (ABITEC) | <10 |
| Glyceryl palmitic/stearic | CUTINA MD-A, ESTAGEL-G18 | <10 |
| Glyceryl acetate | Lamegin ® EE (Grunau GmbH) | <10 |
| Glyceryl laurate | Inwitor ® 312 (Huls), Monomuls ® 90-45 (Grunau GmbH), Aldo ® MLD (Lonza) | 4 |
| Glyceryl citrate/lactate/oleate/linoieate | Imwitor ® 375 (Huls) | <10 |
| Glyceryl caprylate | Imwitor ® 308 (Huls), Capmul ® MCMC8 (ABITEC) | 5-6 |
| Glyceryl caprylate/caprate | Capmul ® MCM (ABITEC) | 5-6 |
| Caprylic acid mono, diglycerides | Imwitor ® 988 (Huls) | 5-6 |
| Caprylic/capric glycerides | Imwitor ® 742 (Huls) | <10 |
| Mono-and diacetylated monoglycerides | Myvacet ® 9-45, Myvacet ® 9-40, Myvacet ® 9-08 (Eastman), Lamegin ® (Grunau) | 3.8-4 |
| Glyceryl monostearate | Aldo ® MS, Arlacel 129 (ICI), LIPO GMS (Lipo Chem.), Imwitor ® 191 (Huls), Myvaplex (Eastman) | 4.4 |
| Lactic acid esters of mono, diglycerides | LAMEGIN GLP (Henkel) | <10 |
| Dicaproin (C6) | (Larodan) | <10 |
| Dicaprin (C10) | (Larodan) | <10 |
| Dioctanoin (C8) | (Larodan) | <10 |
| Dimyristin (C14) | (Larodan) | <10 |
| Dipalmitin (C16) | (Larodan) | |
| Distearin | (Larodan) | <10 |
| Glyceryl dilaurate (C12) | Capmul ® GDL (ABITEC) | 3-4 |
| Glyceryl dioleate | Capmul ® GDO (ABITEC) | 3-4 |
| Glycerol esters of fatty acids | GELUCIRE 39/01 (Gattefosse), GELUCIRE 43/01 (Gattefosse) GELUCIRE 37/06 (Gattefosse) | 1<br>6 |
| Dipalmitolein (C16:1) 1,2 and 1,3-diolein (C18:1) | (Larodan) | <10 |
| Dielaidin (C18:1) | (Larodan) | <10 |
| Dilinolein (C18:2) | (Larodan) | <10 |

TABLE 90

Sterol and Sterol Derivatives
Sterols and derivatives of sterols are suitable surfactants for use in the present invention. These surfactants can be hydrophilic or lipophilic. Examples of surfactants of this class are shown here in Table 90.
Sterol and Sterol Derivative Surfactants

| Compound | Commercial Product (Supplier) | HLB |
|---|---|---|
| Cholesterol, sitosterol, lanosterol | | <10 |
| PEG-24 cholesterol ether | Solulan C-24 (Amerchol) | >10 |
| PEG-30 cholestanol | Nikkol DHC (Nikko) | >10 |
| Phytosterol | GENEROL series (Henkel) | <10 |
| PEG-25 phyto sterol | Nikkol BPSH-25 (Nikko) | >10 |
| PEG-5 soya sterol | Nikkol BPS-S (Nikko) | <10 |
| PEG-10 soya sterol | Nikkol BPS-10 (Nikko) | <10 |
| PEG-20 soya sterol | Nikkol BPS-20 (Nikko) | <10 |
| PEG-30 soya sterol | Nikkol BPS-30 (Nikko) | >10 |

TABLE 91

Polyethylene Glycol Sorbitan Fatty Acid Esters
A variety of PEG-sorbitan fatty acid esters are available
and are suitable for use as surfactants in the present invention.
In general, these surfactants are hydrophilic, although several
lipophilic surfactants of this class can be used.
Examples of these surfactants are shown here in Table 91.
PEG-Sorbitan Fatty Acid Esters

| Compound | Commercial Product (Supplier) | HLB |
|---|---|---|
| PEG-10 sorbitan laurate | Liposorb L-10 (Lipo Chem.) | >10 |
| PEG-20 sorbitan monolaurate | Tween-20 (Atlas/ICI), Crillet 1 (Croda), DACOL MLS 20 (Condea) | 17 |
| PEG-4 sorbitan monolaurate | Tween-21 (Atlas/ICI), Crillet 11 (Croda) | 13 |
| PEG-80 sorbitan monolaurate | Hodag PSML-80 (Calgene); T-Maz 28 | >10 |
| PEG-6 sorbitan monolaurate | Nikkol GL-1 (Nikko) | 16 |
| PEG-20 sorbitan monopalmitate | Tween-40 (Atlas/ICI), Crillet 2 (Croda) | 16 |
| PEG-20 sorbitan monostearate | Tween-60 (Atlas/ICI), Crillet 3 (Croda) | 15 |
| PEG-4 sorbitan monostearate | Tween-61 (Atlas/ICI), Crillet 31 (Croda) | 9.6 |
| PEG-8 sorbitan monostearate | DACOL MSS (Condea) | >10 |
| PBG-6 sorbitan monostearate | Nikkol TS106 (Nikko) | 11 |
| PEG-20 sorbitan tristearate | Tween-65 (Atlas/ICI), Crillet 35 (Croda) | 11 |
| PEG-6 sorbitan tetrastearate | Nikkol GS-6 (Nikko) | 3 |
| PEG-60 sorbitan tetrastearate | Nikkol GS-460 (Nikko) | 13 |
| PEG-5 sorbitan monooleate | Tween-81 (Atlas/ICI), Crillet 41 (Croda) | 10 |
| PEG-6 sorbitan monooleate | Nikkol TO-106 (Nikko) | 10 |
| PEG-20 sorbitan monooleate | Tween-80 (Atlas/ICI), Crillet 4 (Croda) | 15 |
| PEG-40 sorbitan oleate | Emalex ET 8040, (Nihon Emulsion) | 18 |
| PEG-20 sorbitan trioleate | Tween-85 (Atlas/ICI), Crillet 45 (Croda) | 11 |
| PEG-6 sorbitan tetraoleate | Nikkol GO-4 (Nikko) | 8.5 |
| PEG-30 sorbitan tetraoleate | Nikkol GO-430 (Nikko) | 12 |
| PEG-40 sorbitan tetraoleate | Nikkol GO-440 (Nikko) | 13 |
| PEG-20 sorbitan monoisostearate | Tween-120 (Atlas/ICI), Crillet 6 (Croda) | >10 |
| PEG sorbitol hexaoleate | Atlas G-1086 (ICI) | 10 |
| PEG-6 sorbitol hexastearate | Nikkol GS-6 (Nikko) | 3 |

TABLE 92

Polyethylene Glycol Alkyl Ethers
Ethers of polyethylene glycol and alkyl alcohols are suitable
surfactants for use in the present invention.
Examples of these surfactants are shown here in Table 92.
Polyethylene Glycol Alkyl Ethers

| Compound | Commercial Product (Supplier) | HLB |
|---|---|---|
| PEG-2 oleyl ether, oleth-2 | Brij 92/93 (Atlas/ICI) | 4.9 |
| PEG-3 oleyl ether, oleth-3 | Volpo 3 (Croda) | <10 |
| PEG-5 oleyl ether, oleth-5 | Volpo 5 (Croda) | <10 |
| PEG-10 oleyl ether, oleth-10 | Volpo 10 (Croda), Brij 96/97 (Atlas/ICI) | 12 |
| PEG-20 oleyl ether, oleth-20 | Volpo 20 (Croda), Brij 98/99 (Atlas/ICI) | 15 |
| PEG-4 lauryl ether, laureth-4 | Brij 30 (Atlas/ICI) | 9.7 |
| PEG-9 lauryl ether | | >10 |
| PEG-23 lauryl ether, laureth-23 | Brij 35 (Atlas/ICI) | 17 |
| PEG-2 cetyl ether | Brij 52 (ICI) | 5.3 |
| PEG-10 cetyl ether | Brij 56 (ICI) | 13 |
| PEG-20 cetyl ether | Brij 58 (ICI) | 16 |
| PEG-2 stearyl ether | Brij 72 (ICI) | 4.9 |
| PEG-10 stearyl ether | Brij 76 (ICI) | 12 |
| PEG-20 stearyl ether | Brij 78 (ICI) | 15 |
| PEG-100 stearyl ether | Brij 700 (ICI) | >10 |

TABLE 93

Sugar Esters
Esters of sugars are suitable surfactants for use in the present invention.
Examples of such surfactants are shown here in Table 93.
Sugar Ester Surfactants

| Compound | Commercial Product (Supplier) | HLB |
|---|---|---|
| Sucrose distearate | SUCRO ESTER 7 (Gattefosse), Crodesta F-10 (Croda) | 3 |
| Sucrose distearate/ monostearate | SUCRO ESTER 11 (Gattefosse), Crodesta F-110 (Croda) | 12 |
| Sucrose dipalmitate | | 7.4 |
| Sucrose monostearate | Crodesta F-160 (Croda) | 15 |
| Sucrose monopalmitate | SUCRO ESTER 15 (Gattefosse) | >10 |
| Sucrose monolaurate | Saccharose monolaurate 1695 (Mitsubishi-Kasei) | 15 |

TABLE 94

Polyethylene Glycol Alkyl Phenols
Several hydrophilic PEG-alkyl phenol surfactants are available,
and are suitable for use in the present invention.
Examples of these surfactants are shown here in Table 94.
Polyethylene Glycol Alkyl Phenol Surfactants

| Compound | Commercial Product (Supplier) | HLB |
|---|---|---|
| PEG-10-100 nonyl phenol | Triton X series (Rohm & Haas), Igepal CA series (GAF, USA), Antarox CA series (GAF, UK) | >10 |
| PEG-15-100 octyl phenol ether | Triton N-series (Rohm & Haas), Igepal CO series (GAF, USA), Antarox CO series (GAF, UK) | >10 |

TABLE 95

Polyoxyethylene-Polyoxypropylene Block Copolymers
The POE-POP block copolymers are a unique class of polymeric surfactants. The unique structure of the surfactants, with hydrophilic POE and lipophilic POP moieties in well-defined ratios and positions, provides a wide variety of surfactants suitable for use in the present invention. These surfactants are available under various trade names, including Synperonic PE series (ICI); Pluronic ® series (BASF), Emkalyx, Lutrol (BASF), Supronic, Monolan, Pluracare, and Plurodac. The generic term for these polymers is "poloxamer" (CAS 9003-11-6). These polymers have the formula: $HO(C_2H_4O)_a(C_3H_6O)_b(C_2H_4O)_aH$ where "a" and "b" denote the number of polyoxyethylene and polyoxypropylene units, respectively.
Examples of suitable surfactants of this class are shown here in Table 95. Since the compounds are widely available, commercial sources are not listed in the Table. The compounds are listed by generic name, with the corresponding "a" and "b" values.

POE-POP Block Copolymers

| Compound | a, b values in $HO(C_2H_4O)_a(C_3H_6O)_b(C_2H_4O)_aH$ | | HLB |
|---|---|---|---|
| Poloxamer 105 | a = 11 | b = 16 | 8 |
| Poloxamer 108 | a = 46 | b = 16 | >10 |
| Poloxamer 122 | a = 5 | b = 21 | 3 |
| Poloxamer 123 | a = 7 | b = 21 | 7 |
| Poloxamer 124 | a = 11 | b = 21 | >7 |
| Poloxamer 181 | a = 3 | b = 30 | |
| Poloxamer 182 | a = 8 | b = 30 | 2 |
| Poloxamer 183 | a = 10 | b = 30 | |
| Poloxamer 184 | a = 13 | b = 30 | |
| Poloxamer 185 | a = 19 | b = 30 | |
| Poloxamer 188 | a = 75 | b = 30 | 29 |
| Poloxamer 212 | a = 8 | b = 35 | |
| Poloxamer 215 | a = 24 | b = 35 | |
| Poloxamer 217 | a = 52 | b = 35 | |
| Poloxamer 231 | a = 16 | b = 39 | |
| Poloxamer 234 | a = 22 | b = 39 | |
| Poloxamer 235 | a = 27 | b = 39 | |
| Poloxamer 237 | a = 62 | b = 39 | 24 |
| Poloxamer 238 | a = 97 | b = 39 | |
| Poloxamer 282 | a = 10 | b = 47 | |
| Poloxamer 284 | a = 21 | b = 47 | |
| Poloxamer 288 | a = 122 | b = 47 | >10 |
| Poloxamer 331 | a = 7 | b = 54 | 0.5 |
| Poloxamer 333 | a = 20 | b = 54 | |
| Poloxamer 334 | a = 31 | b = 54 | |
| Poloxamer 335 | a = 38 | b = 54 | |
| Poloxamer 338 | a = 128 | b = 54 | |
| Poloxamer 401 | a = 6 | b = 67 | |
| Poloxamer 402 | a = 13 | b = 67 | |
| Poloxamer 403 | a = 21 | b = 67 | |
| Poloxamer 407 | a = 98 | b = 67 | |

TABLE 96

Sorbitan Fatty Acid Esters
Sorbitan esters of fatty acids are suitable surfactants for use in the present invention.
Examples of these surfactants are shown here in Table 96.

Sorbitan Fatty Acid Ester Surfactants

| Compound | Commercial Product (Supplier) | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |
| Sorbitan trioleate | Span-85 (Atlas/ICI), Crill 45 (Croda), Nikkol SO-30 (Nikko) | 4.3 |
| Sorbitan sesquioleate | Arlacel-C (ICI), Crill 43 (Croda), Nikkol SO-15 (Nikko) | 3.7 |
| Sorbitan tristearate | Span-65 (Atlas/ICI) Crill 35 (Croda), Nikkol SS-30 (Nikko) | 2.1 |
| Sorbitan monoisostearate | Crill 6 (Croda), Nikkol SI-10 (Nikko) | 4.7 |
| Sorbitan sesquistearate | Nikkol SS-15 (Nikko) | 4.2 |

TABLE 97

Lower Alcohol Fatty Acid Esters
Esters of lower alcohols ($C_2$ to $C_4$) and fatty acids ($C_8$ to $C_{18}$) are suitable surfactants for use in the present invention.
Examples of these surfactants are shown here in Table 97.

Lower Alcohol Fatty Acid Ester Surfactants

| Compound | Commercial Product (Supplier) | HLB |
|---|---|---|
| Ethyl oleate | Crodamol EO (Croda), Nikkol EOO (Nikko) | <10 |
| Isopropyl myristate | Crodamol IPM (Croda) | <10 |
| Isopropyl palmitate | Crodamol IPP (Croda) | <10 |
| Ethyl linoleate | Nikkol VF-E (Nikko) | <10 |
| Isopropyl linoleate | Nikkol VF-IP (Nikko) | <10 |

TABLE 98

Ionic Surfactants
Ionic surfactants, including cationic, anionic and zwitterionic surfactants, are suitable hydrophilic surfactants for use in the present invention. Examples of anionic surfactants include fatty acid salts and bile salts. Examples of cationic surfactants include carnitines. Specifically, examples of ionic surfactants include sodium oleate, sodium lauryl sulfate, sodium lauryl sarcosinate, sodium dioctyl sulfosuccinate, sodium cholate, sodium taurocholate; lauroyl carnitine; palmitoyl carnitine; and myristoyl carnitine. Examples of such surfactants are shown here in Table 98. For simplicity, typical counterions are shown in the entries in the Table. It will be appreciated by one skilled in the art, however, that any bioacceptable counterion can be used. For example, although the fatty acids are shown as sodium salts, other cation counterions can also be used, such as alkali metal cations or ammonium. Unlike typical non-ionic surfactants, these ionic surfactants are generally available as pure compounds, rather than commercial (proprietary) mixtures. Because these compounds are readily available from a variety of commercial suppliers, such as Aldrich, Sigma, and the like, commercial sources are not generally listed in the Table.

Ionic Surfactants

| Compound | HLB |
|---|---|
| FATTY ACID SALTS | >10 |
| Sodium caproate | |
| Sodium caprylate | |
| Sodium caprate | |
| Sodium laurate | |
| Sodium myristate | |
| Sodium myristolate | |
| Sodium palmitate | |
| Sodium palmitoleate | |
| Sodium oleate | 18 |
| Sodium ricinoleate | |
| Sodium linoleate | |
| Sodium linolenate | |
| Sodium stearate | |
| Sodium lauryl sulfate (dodecyl) | 40 |
| Sodium tetradecyl sulfate | |
| Sodium lauryl sarcosinate | |
| Sodium dioctyl sulfosuccinate [sodium docusate (Cytec)] | |

TABLE 98-continued

Ionic Surfactants

Ionic surfactants, including cationic, anionic and zwitterionic surfactants, are suitable hydrophilic surfactants for use in the present invention. Examples of anionic surfactants include fatty acid salts and bile salts. Examples of cationic surfactants include carnitines. Specifically, examples of ionic surfactants include sodium oleate, sodium lauryl sulfate, sodium lauryl sarcosinate, sodium dioctyl sulfosuccinate, sodium cholate, sodium taurocholate; lauroyl carnitine; palmitoyl carnitine; and myristoyl carnitine. Examples of such surfactants are shown here in Table 98. For simplicity, typical counterions are shown in the entries in the Table. It will be appreciated by one skilled in the art, however, that any bioacceptable counterion can be used. For example, although the fatty acids are shown as sodium salts, other cation counterions can also be used, such as alkali metal cations or ammonium. Unlike typical non-ionic surfactants, these ionic surfactants are generally available as pure compounds, rather than commercial (proprietary) mixtures. Because these compounds are readily available from a variety of commercial suppliers, such as Aldrich, Sigma, and the like, commercial sources are not generally listed in the Table.

Ionic Surfactants

| Compound | HLB |
|---|---|
| BILE SALTS | >10 |
| Sodium cholate | |
| Sodium taurocholate | |
| Sodium glycocholate | |
| Sodium deoxycholate | |
| Sodium taurodeoxycholate | |
| Sodium glycodeoxycholate | |
| Sodium ursodeoxycholate | |
| Sodium chenodeoxycholate | |
| Sodium taurochenodeoxycholate | |
| Sodium glycol cheno deoxycholate | |
| Sodium cholylsarcosinate | |
| Sodium N-methyl taurocholate | |
| Sodium lithocholate | |
| PHOSPHOLIPIDS | |
| Egg/Soy lecithin [Epikuron ™ (Lucas Meyer), Ovothin ™ (Lucas Meyer)] | |
| Lyso egg/soy lecithin | |
| Hydroxylated lecithin | |
| Lysophosphatidylcholine | |
| Cardiolipin | |
| Sphingomyelin | |
| Phosphatidylcholine | |
| Phosphatidyl ethanolamine | |
| Phosphatidic acid | |
| Phosphatidyl glycerol | |
| Phosphatidyl serine | |
| PHOSPHORIC ACID ESTERS | |
| Diethanolammonium polyoxyethylene-10 oleyl ether phosphate | |
| Esterification products of fatty alcohols or fatty alcohol ethoxylates with phosphoric acid or anhydride | |
| CARBOXYLATES | |
| Ether carboxylates (by oxidation of terminal OH group of fatty alcohol ethoxylates) | |
| Succinylated monoglycerides [LAMEGIN ZE (Henkel)] | |
| Sodium stearyl fumarate | |
| Stearoyl propylene glycol hydrogen succinate | |
| Mono/diacetylated tartaric acid esters of mono- and diglycerides | |
| Citric acid esters of mono-, diglycerides | |
| Glyceryl-lacto esters of fatty acids (CFR ref. 172.852) | |
| Acyl lactylates: | |
| lactylic esters of fatty acids calcium/sodium stearoyl-2-lactylate | |
| calcium/sodium stearoyl lactylate | |
| Alginate salts | |
| Propylene glycol alginate | |
| SULFATES AND SULFONATES | |
| Ethoxylated alkyl sulfates | |
| Alkyl benzene sulfones | |
| α-olefin sulfonates | |
| Acyl isethionates | |
| Acyl taurates | |
| Alkyl glyceryl ether sulfonates | |
| Octyl sulfosuccinate disodium | |
| Disodium undecylenamideo-MEA-sulfosuccinate | |
| CATIONIC Surfactants | >10 |
| Lauroyl carnitine | |
| Palmitoyl carnitine | |
| Myristoyl carnitine | |
| Hexadecyl triammonium bromide | |
| Decyl trimethyl ammonium bromide | |
| Cetyl trimethyl ammonium bromide | |
| Dodecyl ammonium chloride | |
| Alkyl benzyldimethylammonium salts | |
| Diisobutyl phenoxyethoxydimethyl benzylammonium salts | |
| Alkylpyridinium salts | |
| Betaines (trialkylglycine): | |
| Lauryl betaine (N-lauryl,N,N-dimethylglycine) | |
| Ethoxylated amines: | |
| Polyoxyethylene-15 coconut amine | |

TABLE 99

BUPROPION HBr XL TABLETS, 348 mg
TABLET COMPOSITION (mg/tablet)
Table 1: Core Tablets

| Item # | Material | Qty. Required (kg) | % of Tablet Tablet Core Formulation | 348 mg Strength Target Weight: 371.2 mg/tablet |
|---|---|---|---|---|
| RS0009 | Polyvinyl Alcohol | 2.25 kg dispensed 2.00 kg used | 3.125% | 11.6 mg/tablet |
| RA0057 | Bupropion HBr | 60.00 | 93.750% | 348 mg/tablet |
| RE0200 | Glyceryl Behenate, NF | 2.00 | 3.125% | 11.6 mg/tablet |
| RS0003 | *Purified Water, USP | 47.75 | 0 | 0 |
| | Theoretical Batch Size: kg | 64.00 | 100% | 371.2 mg/tablet |

*Evaporated during granulating process and not included in tablet core composition.

TABLE 101

Coated/Printed Tablets
348 mg XL Coated/Printed Tablets - Pivotal Coating Formulation/Batch Size

| Item # | Material | Qty. Required (kg) | % of Batch | Applied Solids Mg/tablet Target Weight Gain: 32 mg (Range: 30-34 mg/tablet) |
|---|---|---|---|---|
| RE0233 | Ethylcellulose 100, NF | 3.230 | 4.61% | 16.406 mg |
| RE0067 | Povidone, USP | 2.000 | 2.86% | 10.159 mg |
| RE0331 | Polyethylene Glycol 4000, NF | 0.720 | 1.03% | 3.657 mg |
| RE0103 | Dibutyl Sebacate, NF | 0.350 | 0.50% | 1.778 mg |
| *RS0010 | *Dehydrated Alcohol, 200 proof, USP | 57.300 | 81.86% | 0 |
| *RS0006 | *Ethyl Alcohol, 95%, USP | 6.400 | 9.14% | 0 |
| | COATING SOLUTION TOTAL (kg) | 70 kg | 100% | 32 mg/tablet |
| **RE0223 | **Carnauba Wax, NF | 0.010 kg | N/A | Trance Amounts |
| RE0234 | Opacode Black Ink S-1-8090 or S-1-17823 | 1.00 | 50% | Trace Amounts to brand tablets with logo on one side BR 348 |
| ***RS0001 | ***Isopropyl Alcohol | 1.00 | 50% | Used for cleaning design and transfer rolls only |

Note:
Where applicable, percentages and mg/tablet totals have been rounded to two decimal places.
*Evaporated during coating process.
**Carnauba Wax not included as part of coating solution formulation, trace amounts applied after completion of the coating process.
***Isopropyl Alcohol used for cleaning only. Only trace amounts of black ink to brand tablets with specific logo is applied to one side of tablet. Weight of this material applied to tablet cannot be measured.

TABLE 102

BUPROPION HBr XL TABLETS, 348 mg:
OVERALL FINAL PRINTED TABLET COMPOSITION/WEIGHT

| Material | 348 mg (+32 mg Coating)/ Overall % of Final Tablet Composition |
|---|---|
| Polyvinyl Alcohol | 11.6 mg (2.88%) |
| Bupropion HBr (API) | 348 mg (86.29%) |
| Purified Water, USP | 0 |
| Glyceryl Behenate, NF | 11.6 mg (2.88%) |
| Ethylcellulose 100, NF | 16.406 mg (4.07%) |
| Povidone, USP | 10.159 mg (2.52%) |
| Polyethylene Glycol 4000, NF | 3.657 mg (0.91%) |
| Dibutyl Sebacate, NF | 1.778 mg (0.44%) |
| Dehydrated Alcohol, 200 proof, USP | 0 |
| Ethyl Alcohol, 95%, USP | 0 |
| Carnauba Wax, NF | 0.058 mg/tablet (0.01%) (based on 172,413 tablets for coating pan-load) |
| Opacode Black Ink S-1-8090 or S-1-17823 | Trace Amounts |
| Isopropyl Alcohol | 0 |
| Final Printed Tablet Weight (mg) | 403.258 mg/tablet (100%) |

NOTE:
Bupropion HBr XL Tablets, 174 mg and 348 mg have the same tablet core formulation and coating formulation (composition). The only difference in percentage of material per tablet is due to the differences in core tablet weight and coating weight gain. Total quantity of Carnauba Wax applied to tablets will vary based on coating pan-load. The percent (%) Composition of each ingredient in final tablet formulation, is based on final target coating weight gain and target amount of Carnauba Wax for calculation.

TABLE 102

BUPROPION HBr XL TABLETS, 174 mg
TABLET COMPOSITION (mg/tablet)
Table 1: Core Tablets

| Item # | Material | Qty. Required (kg) | % of Tablet Tablet Core Formulation | 174 mg Strength Target Weight: 185.6 mg/tablet |
|---|---|---|---|---|
| RS0009 | Polyvinyl Alcohol | 2.25 kg dispensed 2.00 kg used | 3.125% | 5.8 mg/tablet |
| RA0057 | Bupropion HBr | 60.00 | 93.750% | 174 mg/tablet |
| RE0200 | Glyceryl Behenate, NF | 2.00 | 3.125% | 5.8 mg/tablet |
| RS0003 | *Purified Water, USP | 47.75 | 0 | 0 |
| | Theoretical Batch Size: kg | 64.00 | 100% | 185.6 mg/tablet |

*Evaporated during granulating process and not included in tablet core composition.

TABLE 103

Coated/Printed Tablets
174 mg XL Coated/Printed Tablets - Pivotal Coating Formulation/Batch Size

| Item # | Material | Qty. Required (kg) | % of Batch | Applied Solids Mg/tablet Target Weight Gain: 30 mg (Range: 28-32 mg/tablet) |
|---|---|---|---|---|
| RE0233 | Ethylcellulose 100, NF | 3.230 | 4.61% | 15.381 mg |
| RE0067 | Povidone, USP | 2.000 | 2.86% | 9.524 mg |
| RE0331 | Polyethylene Glycol 4000, NF | 0.720 | 1.03% | 3.428 mg |
| RE0103 | Dibutyl Sebacate, NF | 0.350 | 0.50% | 1.667 mg |
| *RS0010 | *Dehydrated Alcohol, 200 proof, USP | 57.300 | 81.86% | 0 |
| *RS0006 | *Ethyl Alcohol, 95%, USP | 6.400 | 9.14% | 0 |
| | COATING SOLUTION TOTAL (kg) | 70 kg | 100% | 30 mg/tablet |
| **RE0223 | **Carnauba Wax, NF | 0.010 kg | N/A | Trance Amounts |
| RE0234 | Opacode Black Ink S-1-8090 or S-1-17823 | 1.00 | 50% | Trace Amounts to brand tablets with logo on one side BR 174 |
| ***RS0001 | ***Isopropyl Alcohol | 1.00 | 50% | Used for cleaning design and transfer rolls only |

Note:
Where applicable, percentages and mg/tablet totals have been rounded to two decimal places.
*Evaporated during coating process.
**Carnauba Wax not included as part of coating solution formulation, trace amounts applied after completion of the coating process.
***Isopropyl Alcohol used for cleaning only. Only trace amounts of black ink to brand tablets with specific logo is applied to one side of tablet. Weight of this material applied to tablet cannot be measured.

TABLE 104

BUPROPION HBr XL TABLETS, 174 mg:
OVERALL FINAL PRINTED TABLET COMPOSITION/WEIGHT

| Material | 174 mg (+30 mg Coating)/ Overall % of Final Tablet Composition |
|---|---|
| Polyvinyl Alcohol | 5.8 mg (2.69%) |
| Bupropion HBr (API) | 174 mg (80.68%) |
| Purified Water, USP | 0 |
| Glyceryl Behenate, NF | 5.8 mg (2.69%) |
| Ethylcellulose 100, NF | 15.381 mg (7.13%) |
| Povidone, USP | 9.524 mg (4.42%) |
| Polyethylene Glycol 4000, NF | 3.428 mg (1.59%) |
| Dibutyl Sebacate, NF | 1.667 mg (0.77%) |
| Dehydrated Alcohol, 200 proof, USP | 0 |

TABLE 104-continued

BUPROPION HBr XL TABLETS, 174 mg: OVERALL FINAL PRINTED TABLET COMPOSITION/WEIGHT

| Material | 174 mg (+30 mg Coating)/ Overall % of Final Tablet Composition |
|---|---|
| Ethyl Alcohol, 95%, USP | 0 |
| Carnauba Wax, NF | 0.058 mg/tablet (0.03%) (based on 172,413 tablets for coating pan-load) |
| Opacode Black Ink S-1-8090 or S-1-17823 | Trace Amounts |
| Isopropyl Alcohol | 0 |
| Final Printed Tablet Weight (mg) | 215.658 mg/tablet (100%) |

NOTE:
Bupropion HBr XL Tablets, 174 mg and 348 mg have the same tablet core formulation and coating formulation (composition). The only difference in percentage of material per tablet is due to the differences in core tablet weight and coating weight gain. Total quantity of Carnauba Wax applied to tablets will vary based on coating pan-load. The percent (%) Composition of each ingredient in final tablet formulation, is based on final target coating weight gain and target amount of Carnauba Wax for calculation.

TABLE 105

(1): ACCELERATED STABILITY ACCELERATED STABILITY PROGRAM

Product: Bupropion.HBr FV0092  Batch No.: D00894  Start date: 20/12/04  Temperature: 40° C. ± 2° C.  R.H.: 75% ± 5%

| Analysis | Specification | time 0 | 3 month | 6 months |
|---|---|---|---|---|
| Description | white or almost white crystalline powder | conform | conform | conform |
| Identification | IR, HPLC (positive) | positive | positive | positive |
| Water content (K.F.) | NMT 0.5% | 0.05 | 0.07 | 0.08 |
| Chromatographic purity A) (HPLC) | 1) NMT 0.1% | 1) n.d. | 1) n.q. | 1) 0.05 |
|  | 2) NMT 0.1% | 2) n.d. | 2) n.d. | 2) n.d. |
|  | 3) NMT 0.1% | 3) n.q. | 3) n.q. | 3) n.q. |
| Chromatographic purity B) (HPLC) | 4) NMT 0.1% | 4) 0.04 | 4) 0.03 | 4) 0.04 |
|  | 5) NMT 0.1% | 5) 0.04 | 5) 0.04 | 5) n.q. |
|  | 6) NMT 0.3% | 6) 0.04 | 6) 0.06 | 6) 0.02 |
| Chromatographic purity (HPLC: A + B) | Total impurities NMT 0.5% | 0.1 | 0.1 | 0.1 |
| Assay (HPLC) | 98.0-102.0% on d.b. | 99.6 | 99.6 | 99.7 |

(2): ACCELERATED STABILITY PROGRAM

Product: Bupropion.HBr FV0092  Batch No.: D00895  Start date: 20/12/04  Temperature: 40° C. ± 2° C.  R.H.: 75% ± 5%

| Analysis | Specification | time 0 | 3 month | 6 months |
|---|---|---|---|---|
| Description | white or almost white crystalline powder | conform | conform | conform |
| Identification | IR, HPLC (positive) | positive | positive | positive |
| Water content (K.F.) | NMT 0.5% | 0.04 | 0.07 | 0.07 |
| Chromatographic purity A) (HPLC) | 1) NMT 0.1% | 1) n.d. | 1) n.q. | 1) 0.05 |
|  | 2) NMT 0.1% | 2) n.d. | 2) n.d. | 2) n.d. |
|  | 3) NMT 0.1% | 3) n.q. | 3) 0.05 | 3) n.q. |
| Chromatographic purity B) (HPLC) | 4) NMT 0.1% | 4) 0.04 | 4) 0.03 | 4) 0.04 |
|  | 5) NMT 0.1% | 5) 0.04 | 5) 0.04 | 5) n.q. |
|  | 6) NMT 0.3% | 6) 0.04 | 6) 0.05 | 6) 0.02 |
| Chromatographic purity (HPLC: A + B) | Total impurities NMT 0.5% | 0.1 | 0.1 | 0.1 |
| Assay (HPLC) | 98.0-102.0% on d.b. | 99.2 | 100.7 | 99.7 |

(3): ACCELERATED STABILITY PROGRAM

Product: Bupropion.HBr FV0092  Batch No.: D00896  Start date: 20/12/04  Temperature: 40° C. ± 2° C.  R.H.: 75% ± 5%

TABLE 105-continued

| Analysis | Specification | time 0 | 3 month | 6 months |
|---|---|---|---|---|
| Description | white or almost white crystalline powder | conform | conform | conform |
| Identification | IR, HPLC (positive) | positive | positive | positive |
| Water content (K.F.) | NMT 0.5% | 0.06 | 0.11 | 0.04 |
| Chromatographic purity A) (HPLC) | 1) NMT 0.1% | 1) n.d. | 1) n.q. | 1) 0.05 |
| | 2) NMT 0.1% | 2) n.d. | 2) n.d. | 2) n.d. |
| | 3) NMT 0.1% | 3) n.q. | 3) n.q. | 3) n.q. |
| Chromatographic purity B) (HPLC) | 4) NMT 0.1% | 4) 0.04 | 4) 0.03 | 4) 0.04 |
| | 5) NMT 0.1% | 5) 0.05 | 5) 0.04 | 5) n.q. |
| | 6) NMT 0.3% | 6) 0.05 | 6) 0.05 | 6) n.q. |
| Chromatographic purity (HPLC: A + B) | Total impurities NMT 0.5% | 0.1 | 0.1 | 0.1 |
| Assay (HPLC) | 98.0-102.0% on d.b. | 99.3 | 100.0 | 100.4 |

(4): SHELF LIFE
SHELF LIFE STABILITY PROGRAM

| Product: Bupropion.HBr FV0092 | Batch No.: D00894 | Start date: 20/12/04 | | Temperature: 25° C. ± 2° C.; Relative Humidity: 60% ± 5% | | | | |
|---|---|---|---|---|---|---|---|---|
| Analysis | Specification | time 0 | 3 months | 6 months | 9 months | 12 months | 18 months | 24 months | 36 months |
| Description | white or almost white crystalline powder | conform | conform | conform | conform | conform | | | |
| Identification | IR, HPLC (positive) | positive | positive | positive | positive | positive | | | |
| Water content (K.F.) | NMT 0.5% | 0.05 | 0.05 | 0.06 | 0.05 | 0.05 | | | |
| Chromatographic purity A) (HPLC) | 1) NMT 0.1% | 1) n.d. | 1) n.q. | 1) 0.05 | 1) n.q. | 1) n.d. | 1) | 1) | 1) |
| | 2) NMT 0.1% | 2) n.d. | 2) n.d. | 2) n.d. | 2) n.d. | 2) n.d. | 2) | 2) | 2) |
| | 3) NMT 0.1% | 3) n.q. | 3) n.q. | 3) n.q. | 3) n.q. | 3) 0.05 | 3) | 3) | 3) |
| Chromatographic purity B) (HPLC) | 4) NMT 0.1% | 4) 0.04 | 4) 0.03 | 4) 0.05 | 4) n.d. | 4) 0.05 | 4) | 4) | 4) |
| | 5) NMT 0.1% | 5) 0.04 | 5) 0.04 | 5) n.q. | 5) n.q. | 5) 0.05 | 5) | 5) | 5) |
| | 6) NMT 0.3% | 6) 0.04 | 6) 0.05 | 6) 0.02 | 6) n.q. | 6) 0.07 | 6) | 6) | 6) |
| Chromatographic purity (HPLC: A + B) | Total impurities NMT 0.5% | 0.1 | 0.1 | 0.1 | n.q. | 0.2 | | | |
| Assay (HPLC) | 98.0-102.0% on d.b. | 99.6 | 99.4 | 100.2 | 99.5 | 99.6 | | | |
| Microbial cont. | total microbial count <1000 cfu/g moulds and yeast <100 cfu/g | not applied | not applied | not applied | not applied | <100 ufc/g <100 ufc/g | not applied | | |

(5): SHELF LIFE STABILITY PROGRAM

| Product: Bupropion.HBr FV0092 | Batch No.: D00895 | Start date: 20/12/04 | | Temperature: 25° C. ± 2° C.; Relative Humidity: 60% ± 5% | | | | |
|---|---|---|---|---|---|---|---|---|
| Analysis | Specification | time 0 | 3 months | 6 months | 9 months | 12 months | 18 months | 24 months | 36 months |
| Description | white or almost white crystalline powder | conform | conform | conform | conform | conform | | | |
| Identification | IR, HPLC (positive) | positive | positive | positive | positive | positive | | | |
| Water content (K.F.) | NMT 0.5% | 0.04 | 0.04 | 0.05 | 0.05 | 0.04 | | | |
| Chromatographic purity A) (HPLC) | 1) NMT 0.1% | 1) n.d. | 1) n.d. | 1) 0.05 | 1) n.q. | 1) n.d. | 1) | 1) | 1) |
| | 2) NMT 0.1% | 2) n.d. | 2) n.d. | 2) n.d. | 2) n.d. | 2) n.d. | 2) | 2) | 2) |
| | 3) NMT 0.1% | 3) n.q. | 3) n.q. | 3) n.q. | 3) n.q. | 3) 0.05 | 3) | 3) | 3) |
| Chromatographic purity B) (HPLC) | 4) NMT 0.1% | 4) 0.04 | 4) 0.03 | 4) 0.05 | 4) n.d. | 4) 0.05 | 4) | 4) | 4) |
| | 5) NMT 0.1% | 5) 0.04 | 5) 0.04 | 5) n.q. | 5) n.q. | 5) 0.07 | 5) | 5) | 5) |
| | 6) NMT 0.3% | 6) 0.04 | 6) 0.05 | 6) 0.02 | 6) n.q. | 6) 0.07 | 6) | 6) | 6) |
| Chromatographic purity (HPLC: A + B) | Total impurities NMT 0.5% | 0.1 | 0.1 | 0.1 | n.q. | 0.2 | | | |
| Assay (HPLC) | 98.0-102.0% on d.b. | 99.2 | 99.5 | 100.1 | 99.4 | 99.4 | | | |
| Microbial cont. | total microbial count <1000 cfu/g moulds and yeast <100 cfu/g | not applied | not applied | not applied | not applied | <100 ufc/g <100 ufc/g | not applied | | |

(6): SHELF LIFE STABILITY PROGRAM

| Product: Bupropion.HBr FV0092 | Batch No.: D00896 | Start date: 20/12/04 | | Temperature: 25° C. ± 2° C.; Relative Humidity: 60% ± 5% | | | | |
|---|---|---|---|---|---|---|---|---|
| Analysis | Specification | time 0 | 3 months | 6 months | 9 months | 12 months | 18 months | 24 months | 36 months |
| Description | white or almost white crystalline powder | conform | conform | conform | conform | conform | | | |
| Identification | IR, HPLC (positive) | positive | positive | positive | positive | positive | | | |
| Water content (K.F.) | NMT 0.5% | 0.06 | 0.04 | 0.04 | 0.04 | 0.03 | | | |

TABLE 105-continued

| | | | | | | | | | |
|---|---|---|---|---|---|---|---|---|---|
| Chromatographic purity A) (HPLC) | 1) NMT 0.1% 2) NMT 0.1% 3) NMT 0.1% | 1) n.d. 2) n.d. 3) n.q. | 1) n.q. 2) n.d. 3) n.q. | 1) 0.05 2) n.d. 3) n.q. | 1) n.q. 2) n.d. 3) n.q. | 1) n.d. 2) n.d. 3) n.q. | 1) 2) 3) | 1) 2) 3) | 1) 2) 3) |
| Chromatographic purity B) (HPLC) | 4) NMT 0.1% 5) NMT 0.1% 6) NMT 0.3% | 4) 0.04 5) 0.05 6) 0.05 | 4) 0.03 5) 0.04 6) 0.05 | 4) 0.04 5) n.q. 6) n.q. | 4) n.d. 5) n.q. 6) n.q. | 4) 0.05 5) 0.07 6) 0.07 | 4) 5) 6) | 4) 5) 6) | 4) 5) 6) |
| Chromatographic purity (HPLC: A + B) | Total impurities NMT 0.5% | 0.1 | 0.1 | 0.1 | n.q. | 0.1 | | | |
| Assay (HPLC) | 98.0-102.0% on d.b. | 99.3 | 99.4 | 100.5 | 99.4 | 100.3 | | | |
| Microbial cont. | total microbial count <1000 cfu/g moulds and yeast <100 cfu/g | not applied | not applied | not applied | not applied | <100 ufc/g <100 ufc/g | not applied | | |

Impurities:
1) 3'-Chloropropiophenone;
2) 3'-Chloro-2-bromopropiophenone;
3) 3'-Chlorobenzoic acid;
4) 2-N-(tert-Butyl)-aminopropiophenone;
5) single unknown impurity (each);
6) total unknown impurities (calculated from the sum of all impurity peak areas, also peaks below LOQ are included).

Notes:
n.d. = not detectable;
n.q. = not quantifiable;
LOQ = 0.05% for imp. 1, 2 and 3;
LOQ = 0.02% for imp. 4 and 5;
LOD = 0.01% for imp. 1 and 3;
LOD = 0.04% for imp. 2;
LOD = 0.002% for imp. 4 and 5.

TABLE 106

EFFECTS OF BUPROPION HYDROCHLORIDE
IN THE EEG TRACE MONITORING
IN THE RAT
(10 RATS PER GROUP)

OBSERVATIONS

| TREATMENT (mg/kg) i.p | NUMBER OF RAT | TIME | BEHAVIOR ||||||| EEG ANALYSIS ||||||||||||||||
|---|---|---|---|---|---|---|---|---|---|---|---|---|---|---|---|---|---|---|---|---|---|---|---|
| | | | Hyper-activity Sterotypies | Head twitches | Rear-ing | Facial clonus | Fore-limb clonus | Whole-body clonus | Spike-and-waves cx | | Sharp waves cx | | High frequency burst activity cx | | Com-plex spike cx | | Repetitive isolated spike cx | | High amplitude fast frequency cx | | Burst cx | | Short seizure activity cx | | Long seizure activity cx | | Post ictal activity cx |
| | | | | | | | | | | hipp | | hipp | | hipp | | hipp | | hipp | | hipp | | hipp | | hipp | | hipp | | hipp |
| BUPROPION HYDRO-CHLORIDE 10 | Q0336 | T-1 to T0 | − | − | − | − | − | − | − | − | − | − | − | − | − | − | − | − | − | − | − | − | − | − | − | − | − |
| | | T0 to T2 | − | − | − | − | − | − | − | − | − | − | − | + | − | + | − | − | − | + | − | − | − | − | − | − | − |
| | Q0337 | T-1 to T0 | − | − | − | − | − | − | − | − | − | − | − | − | − | − | − | − | − | − | − | − | − | − | − | − | − |
| | | T0 to T2 | − | − | − | − | − | − | − | − | − | − | − | + | − | + | − | − | − | − | − | − | − | − | − | − | − |
| | Q0338 | T-1 to T0 | − | − | − | − | − | − | − | − | − | − | − | − | − | − | − | − | − | − | − | − | − | − | − | − | − |
| | | T0 to T2 | + | − | − | − | − | − | − | − | − | − | − | − | − | − | − | − | − | − | − | − | − | − | − | − | − |
| | Q0342 | T-1 to T0 | − | − | − | − | − | − | − | − | − | − | − | − | − | − | − | − | − | − | − | − | − | − | − | − | − |
| | | T0 to T2 | − | − | − | − | − | − | − | − | − | − | − | + | − | − | − | − | − | − | − | − | − | − | − | − | − |
| | Q0343 | T-1 to T0 | − | − | − | − | − | − | − | − | − | − | − | − | − | − | − | − | − | − | − | − | − | − | − | − | − |
| | | T0 to T2 | − | − | − | − | − | − | − | − | − | − | − | − | − | − | − | − | − | − | − | − | − | − | − | − | − |
| | Q0344 | T-1 to T0 | − | − | − | − | − | − | − | − | − | − | − | − | − | − | − | − | − | − | − | − | − | − | − | − | − |
| | | T0 to T2 | − | − | − | − | − | − | − | − | − | − | − | + | − | − | − | − | − | − | − | − | − | − | − | − | − |
| | Q0346 | T-1 to T0 | − | − | − | − | − | − | − | − | − | − | − | − | − | − | − | − | − | − | − | − | − | − | − | − | − |
| | | T0 to T2 | − | − | − | − | − | − | − | − | − | − | − | − | − | − | − | − | − | − | − | − | − | − | − | − | − |
| | Q0348 | T-1 to T0 | − | − | − | − | − | − | − | − | − | − | − | − | − | − | − | − | − | − | − | − | − | − | − | − | − |
| | | T0 to T2 | − | − | − | − | − | − | − | − | − | − | − | + | − | − | − | − | − | − | − | − | − | − | − | − | − |
| | Q0349 | T-1 to T0 | − | − | − | − | − | − | − | − | − | − | − | − | − | − | − | − | − | − | − | − | − | − | − | − | − |
| | | T0 to T2 | − | − | − | − | − | − | − | − | − | − | − | + | − | − | − | − | − | − | − | − | − | − | − | − | − |
| | Q0351 | T-1 to T0 | − | − | − | − | − | − | − | − | − | − | − | − | − | − | − | − | − | − | − | − | − | − | − | − | − |
| | | T0 to T2 | − | − | − | − | − | − | − | − | − | − | − | + | + | − | − | − | − | − | − | − | − | − | − | − | − |
| BUPROPION HYDRO-CHLORIDE 30 | Q0336 | T-1 to T0 | − | − | − | − | − | − | − | − | − | − | − | − | − | − | − | − | − | − | − | − | − | − | − | − | − |
| | | T0 to T2 | + | − | − | − | − | − | − | − | − | − | − | − | − | + | − | − | − | + | − | − | − | − | − | − | − |
| | Q0337 | T-1 to T0 | − | − | − | − | − | − | − | − | − | − | − | − | − | − | − | − | − | − | − | − | − | − | − | − | − |
| | | T0 to T2 | + | − | − | − | − | − | − | − | − | − | − | − | − | + | − | − | − | + | − | − | − | − | − | − | − |
| | Q0338 | T-1 to T0 | − | − | − | − | − | − | − | − | − | − | − | − | − | − | − | − | − | − | − | − | − | − | − | − | − |
| | | T0 to T2 | + | − | − | − | − | − | − | − | − | − | − | − | − | − | − | − | − | − | − | − | − | − | − | − | − |
| | Q0342 | T-1 to T0 | − | − | − | − | − | − | − | − | − | − | − | − | − | − | − | − | − | − | − | − | − | − | − | − | − |
| | | T0 to T2 | + | − | − | − | − | − | − | − | − | − | − | − | − | − | + | − | − | − | − | − | − | − | − | − | − |
| | Q0343 | T-1 to T0 | − | − | − | − | − | − | − | − | − | − | − | − | − | − | − | − | − | − | − | − | − | − | − | − | − |
| | | T0 to T2 | + | − | − | − | − | − | − | − | − | − | − | − | − | − | − | − | − | − | − | − | − | − | − | − | − |
| | Q0344 | T-1 to T0 | − | − | − | − | − | − | − | − | − | − | − | − | − | − | − | − | − | − | − | + | − | − | − | − | − |
| | | T0 to T2 | + | − | − | − | − | − | − | − | − | − | − | − | − | − | − | − | − | − | − | − | − | − | − | − | − |
| | Q0346 | T-1 to T0 | − | − | − | − | − | − | − | − | − | − | − | − | − | − | − | − | − | − | − | − | − | − | − | − | − |

TABLE 106-continued

EFFECTS OF BUPROPION HYDROCHLORIDE IN THE EEG TRACE MONITORING IN THE RAT
(10 RATS PER GROUP)

OBSERVATIONS

| TREATMENT (mg/kg) i.p | NUMBER OF RAT | TIME | BEHAVIOR | | | | | | EEG ANALYSIS | | | | | | | | | | | | | | | | | |
|---|---|---|---|---|---|---|---|---|---|---|---|---|---|---|---|---|---|---|---|---|---|---|---|---|---|---|
| | | | Hyper-activity Sterotypies | Head twitches | Rear-ing | Facial clonus | Fore-limb clonus | Whole-body clonus | Spike-and-waves cx | Spike-and-waves hipp | Sharp waves cx | Sharp waves hipp | High frequency burst activity cx | High frequency burst activity hipp | Com-plex spike cx | Com-plex spike hipp | Repetitive isolated spike cx | Repetitive isolated spike hipp | High amplitude fast frequency cx | High amplitude fast frequency hipp | Burst cx | Burst hipp | Short seizure activity cx | Short seizure activity hipp | Long seizure activity cx | Long seizure activity hipp | Post ictual activity cx | Post ictual activity hipp |
| | Q0348 | T0 to T2 | + | − | − | − | − | − | − | − | − | − | − | − | − | − | − | − | − | − | − | − | − | − | − | − | − | − |
| | Q0349 | T-1 to T0 | + | − | − | − | − | − | − | − | − | − | − | − | − | − | − | − | − | − | − | − | − | − | − | − | − | − |
| | Q0349 | T0 to T2 | + | − | − | − | − | − | − | − | − | − | − | − | − | − | − | − | − | − | − | − | − | − | − | − | − | − |
| | Q0351 | T-1 to T0 | + | − | − | − | − | − | − | − | − | − | − | − | − | − | − | − | − | − | − | − | − | − | − | − | − | − |
| | Q0351 | T0 to T2 | + | − | − | − | − | − | − | − | − | − | − | − | − | − | − | − | − | − | − | − | − | − | − | − | − | − |
| BUPROPION HYDRO-CHLORIDE 60 | Q0336 | T-1 to T0 | + | − | − | − | − | − | + | − | − | − | − | − | − | − | − | − | − | − | − | − | − | − | − | − | − | − |
| | Q0336 | T0 to T2 | + | − | − | − | − | − | − | − | − | − | − | + | − | − | − | + | − | − | − | − | − | − | − | − | − | − |
| | Q0337 | T-1 to T0 | + | − | − | − | − | − | − | − | − | − | − | − | − | − | − | − | − | − | − | − | − | − | − | − | − | − |
| | Q0337 | T0 to T2 | + | − | − | − | − | − | − | − | − | − | + | − | − | − | − | − | − | − | − | − | − | − | − | − | − | − |
| | Q0338 | T-1 to T0 | + | − | − | − | − | − | − | − | − | − | − | − | − | − | − | − | − | − | − | − | − | − | − | − | − | − |
| | Q0338 | T0 to T2 | + | − | − | − | − | − | − | − | − | + | − | − | − | − | + | − | − | − | − | − | − | − | + | − | − | − |
| | Q0342 | T-1 to T0 | + | − | − | − | − | − | − | − | − | − | − | − | − | − | − | − | − | − | − | − | − | − | − | − | − | − |
| | Q0342 | T0 to T2 | + | − | − | − | − | − | − | − | − | − | + | − | − | − | − | − | − | − | − | − | − | − | − | − | − | − |
| | Q0343 | T-1 to T0 | + | − | − | − | − | − | − | − | − | − | − | − | − | − | − | − | − | − | − | − | − | − | − | − | − | − |
| | Q0343 | T0 to T2 | + | − | − | − | − | − | − | − | − | − | − | − | − | − | − | − | − | − | − | − | − | − | − | − | − | − |
| | Q0344 | T-1 to T0 | + | − | − | − | − | − | − | − | − | − | − | − | − | − | − | − | − | − | − | − | − | − | − | − | − | − |
| | Q0344 | T0 to T2 | + | − | − | − | − | − | − | − | − | − | − | − | − | − | − | − | − | − | − | − | − | − | − | − | − | − |
| | Q0346 | T-1 to T0 | + | − | − | − | − | − | − | − | − | − | − | − | − | − | − | − | − | − | − | − | − | − | − | − | − | − |
| | Q0346 | T0 to T2 | + | − | − | − | − | − | − | − | − | − | − | − | − | − | − | − | − | − | − | − | − | − | − | − | − | − |
| | Q0348 | T-1 to T0 | + | − | − | − | − | − | − | − | − | − | − | − | − | − | − | − | − | − | − | − | − | − | − | − | − | − |
| | Q0348 | T0 to T2 | + | − | − | − | − | − | − | − | − | − | − | − | − | − | + | − | − | − | − | − | − | − | − | − | − | − |
| | Q0349 | T-1 to T0 | − | − | + | + | + | − | + | − | + | − | − | − | − | − | − | − | − | − | − | − | − | − | − | − | − | − |
| | Q0349 | T0 to T2 | + | − | − | − | − | − | − | − | − | − | + | − | − | − | − | − | − | − | − | − | − | − | − | − | − | − |
| | Q0351 | T-1 to T0 | − | − | − | + | − | − | − | − | − | − | − | − | − | − | − | − | − | − | − | − | − | − | − | − | − | − |
| | Q0351 | T0 to T2 | + | − | − | − | − | − | − | − | − | − | + | − | − | − | + | − | − | − | − | − | − | − | − | − | − | − |
| BUPROPION HYDRO-CHLORIDE 100 | Q0336 | T-1 to T0 | − | − | − | + | − | − | − | − | − | − | − | − | − | − | − | − | − | − | − | − | − | − | − | − | − | − |
| | Q0336 | T0 to T2 | + | − | − | − | − | − | − | − | − | − | − | − | − | − | − | − | − | − | − | − | + | − | + | − | + | − |
| | Q0337 | T-1 to T0 | − | − | − | − | − | − | − | − | − | − | − | − | − | − | − | − | − | − | − | − | − | − | − | − | − | − |
| | Q0337 | T0 to T2 | + | − | − | − | − | − | − | − | − | − | − | − | − | − | − | − | − | − | − | − | + | − | + | − | + | − |
| | Q0338 | T-1 to T0 | − | − | − | − | − | − | − | − | − | − | − | − | − | − | − | − | − | − | − | − | + | − | + | − | + | − |
| | Q0338 | T0 to T2 | + | − | − | − | − | − | − | − | − | − | − | − | − | − | − | − | − | − | − | − | − | − | − | − | − | − |
| | Q0342 | T-1 to T0 | − | − | − | − | − | − | − | − | − | − | − | − | − | − | − | − | − | − | − | − | − | − | − | − | − | − |

TABLE 106-continued

EFFECTS OF BUPROPION HYDROCHLORIDE
IN THE EEG TRACE MONITORING
IN THE RAT
(10 RATS PER GROUP)

OBSERVATIONS

| TREATMENT (mg/kg) i.p | NUMBER OF RAT | TIME | BEHAVIOR | | | | | | EEG ANALYSIS | | | | | | | | | | | | | | | | |
|---|---|---|---|---|---|---|---|---|---|---|---|---|---|---|---|---|---|---|---|---|---|---|---|---|---|
| | | | Hyper-activity | Head twitches | Rearing | Facial clonus | Fore-limb clonus | Whole-body clonus | Spike-and-waves | | Sharp waves | | High frequency burst activity | | Complex spike | | Repetitive isolated spike | | High amplitude fast frequency | | Burst | | Short seizure activity | | Long seizure activity | | Post ictal activity |
| | | | | | | | | | cx | hipp | cx | hipp | cx | hipp | cx | hipp | cx | hipp | cx | hipp | cx | hipp | cx | hipp | cx | hipp | cx | hipp |
| | | T0 to T2 | + | + | + | + | + | - | - | - | - | - | - | - | - | - | - | - | - | - | - | - | - | - | - | + | + | + | + |
| | Q0343 | T-1 to T0 | - | - | + | + | + | + | - | - | - | - | + | - | - | - | - | - | - | - | - | - | - | - | - | - | - | - | - |
| | | T0 to T2 | - | - | + | + | + | - | - | - | - | - | - | - | - | - | - | - | - | - | - | - | - | - | - | - | + | + | + | + |
| | Q0344 | T-1 to T0 | + | - | - | - | - | - | - | - | - | - | + | - | - | - | - | - | - | - | - | - | - | - | - | - | - | - | - |
| | | T0 to T2 | + | - | - | + | - | - | - | - | - | - | - | - | - | - | - | - | - | - | - | - | - | - | - | - | + | + | + | + |
| | Q0346 | T-1 to T0 | - | - | - | + | - | - | - | - | - | - | + | - | - | - | - | - | - | - | - | - | - | - | - | - | - | - | - |
| | | T0 to T2 | + | - | - | - | - | - | - | - | - | - | - | - | - | - | - | - | - | - | - | - | - | - | - | - | + | + | + | + |
| | Q0348 | T-1 to T0 | + | - | - | + | - | - | - | - | - | - | + | - | - | + | - | - | - | - | - | - | - | - | - | - | - | - | - |
| | | T0 to T2 | + | - | - | - | - | - | - | - | - | - | - | - | - | - | - | - | - | - | - | - | + | - | + | + | + | + | + |
| | Q0349 | T-1 to T0 | - | - | - | + | - | - | - | - | - | - | + | - | - | - | - | - | - | - | - | - | - | - | - | - | - | - | - |
| | | T0 to T2 | + | - | - | - | - | - | - | - | - | - | - | - | - | - | - | - | - | - | - | - | - | - | - | + | + | + | + | + |
| | Q0351 | T-1 to T0 | + | - | - | + | - | - | + | + | + | + | - | - | - | - | - | - | - | - | - | - | - | - | - | - | - | - | - | cx: cortex.
hipp: hippocampus.
Short seizure activity: up to 4 seconds.
Long seizure activity: between 4 and 60 seconds.
T-1 to T0: baseline recording (1 hour before injection).
T0 to T2: recording immediately after injection for 2 hours.
- sign: absence of symptom.
+ sign: presence of symptom.

TABLE 107

EFFECTS OF BUPROPION HYDROBROMIDE
IN THE EEG TRACE MONITORING
IN THE RAT
(10 RATS PER GROUP)

| TREATMENT (mg/kg) i.p | NUMBER OF RAT | TIME | BEHAVIOR | | | | | | OBSERVATIONS | | | | | | | | | | | | | | EEG ANALYSIS | | | | | | | | | | | | |
|---|---|---|---|---|---|---|---|---|---|---|---|---|---|---|---|---|---|---|---|---|---|---|---|---|---|---|---|---|---|---|---|---|---|---|---|
| | | | Hyper-activity Sterotypies | Head twitch-es | Rear-ing | Facial clonus | Fore-limb clonus | Whole-body clonus | Spike-and-waves cx | | hipp | Sharp waves cx | | hipp | High fre-quency burst activity cx | | hipp | Com-plex spike cx | | hipp | Repeti-tive isolated spike cx | | hipp | High ampli-tude fast fre-quency cx | | hipp | Burst cx | | hipp | Short seizure activity cx | | hipp | Long seizure activity cx | | hipp | Post ictual activity cx | | hipp |
| BUPROPION HYDRO-BROMIDE 10 | Q0352 | T-1 to T0 | - | - | - | - | - | - | - | - | - | - | - | - | - | - | - | - | - | - | - | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| | Q0353 | T-1 to T0 | - | - | - | - | - | - | - | - | - | - | - | - | - | - | - | - | - | - | - | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| | Q0354 | T-1 to T0 | - | - | - | - | - | - | - | - | - | - | - | - | - | - | - | - | - | - | - | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| | Q0355 | T-1 to T0 | - | - | - | - | - | - | - | - | - | - | - | - | - | - | - | - | - | - | - | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| | Q0356 | T-1 to T0 | - | - | - | - | - | - | - | - | - | - | - | - | - | - | - | - | - | - | - | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| | Q0357 | T-1 to T0 | - | - | - | - | - | - | + | - | - | + | - | - | + | - | - | - | - | - | - | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| | Q0358 | T-1 to T0 | - | - | - | - | - | - | - | - | - | - | - | - | - | - | - | - | - | - | - | - | - | - | - | - | - | - | - | - | - | - | - | - | - |
| | | T0 to T2 | - | - | - | - | - | - | - | - | - | - | - | - | + | - | - | - | - | - | - | - | - | - | - | - | - | - | - | - | - | - | - | - | - |
| | Q0359 | T-1 to T0 | - | - | - | - | - | - | - | - | - | - | - | - | + | - | - | - | - | - | - | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| | Q0360 | T-1 to T0 | - | - | - | +(*) | - | - | - | - | - | - | - | - | + | - | - | - | - | - | - | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| | Q0361 | T-1 to T0 | - | - | - | - | - | - | - | - | - | - | - | - | - | - | - | - | - | - | - | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| BUPROPION HYDRO-BROMIDE 30 | Q0352 | T-1 to T0 | - | - | - | - | - | - | - | - | - | - | - | - | - | - | - | - | - | - | + | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| | Q0353 | T-1 to T0 | - | - | - | - | - | - | - | - | - | - | - | - | - | - | - | - | - | - | + | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| | Q0354 | T-1 to T0 | - | - | - | - | - | - | - | - | - | - | - | - | - | - | - | - | - | - | + | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| | Q0355 | T-1 to T0 | - | - | - | - | - | - | - | - | - | - | - | - | - | - | - | - | - | - | - | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| | Q0356 | T-1 to T0 | - | - | - | - | - | - | - | - | - | - | - | - | - | - | - | - | - | - | - | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| | Q0357 | T-1 to T0 | - | - | - | - | - | - | - | - | - | - | - | - | - | - | - | - | - | - | - | - | - | - | - | - | - | - | - | - | - | - | - | - | - |
| | | T0 to T2 | - | - | - | - | - | - | - | - | - | - | - | - | - | - | - | - | - | - | - | - | - | - | - | - | - | - | - | - | - | - | - | - | - |
| | Q0358 | T-1 to T0 | - | - | - | - | - | - | - | - | - | - | - | - | - | - | - | - | - | - | - | - | - | - | - | - | - | - | - | - | - | - | - | - | - |

TABLE 107-continued

EFFECTS OF BUPROPION HYDROBROMIDE
IN THE EEG TRACE MONITORING
IN THE RAT
(10 RATS PER GROUP)

OBSERVATIONS

| TREATMENT (mg/kg) i.p | NUMBER OF RAT | TIME | BEHAVIOR | | | | | | EEG ANALYSIS | | | | | | | | | | | | |
|---|---|---|---|---|---|---|---|---|---|---|---|---|---|---|---|---|---|---|---|---|---|
| | | | Hyper-activity Sterotypies | Head twitches | Rear-ing | Facial clonus | Fore-limb clonus | Whole-body clonus | Spike-and-waves cx | hipp | High frequency burst activity cx | hipp | Com-plex spike cx | hipp | Repetitive isolated spike cx | hipp | High amplitude fast frequency cx | hipp | Burst cx | hipp | Short seizure activity cx | hipp | Long seizure activity cx | hipp | Post ictal activity cx | hipp |
| | | T0 to T2 | − | − | − | − | − | − | − | − | − | − | − | − | − | − | − | − | − | − | − | − | − | − | − | − |
| | Q0359 | T-1 to T0 | − | − | − | − | − | − | − | − | − | − | − | − | − | − | − | − | − | − | − | − | − | − | − | − |
| | Q0360 | T0 to T2 | − | − | − | − | − | − | − | − | − | − | − | − | − | − | − | − | − | − | − | − | − | − | − | − |
| | | T-1 to T0 | − | − | − | − | − | − | − | − | − | − | − | − | − | − | − | − | − | − | − | − | − | − | − | − |
| | Q0361 | T0 to T2 | − | − | − | − | − | − | + | − | + | − | − | − | − | − | − | − | − | − | − | − | − | − | − | − |
| | | T-1 to T0 | − | − | − | − | − | − | − | − | − | − | − | − | − | − | − | − | − | − | − | − | − | − | − | − |
| BUPROPION HYDRO-BROMIDE 60 | Q0352 | T0 to T2 | + | − | − | − | − | − | − | − | + | − | − | − | − | − | − | − | − | − | − | − | − | − | − | − |
| | | T-1 to T0 | + | − | − | − | − | − | − | − | − | − | − | − | + | − | − | − | − | − | − | − | − | − | − | − |
| | Q0353 | T0 to T2 | + | − | − | − | − | − | − | − | + | − | − | − | + | − | − | − | − | − | − | − | − | − | − | − |
| | | T-1 to T0 | + | − | − | − | − | − | − | − | + | − | − | − | + | − | − | − | − | − | − | − | − | − | − | − |
| | Q0354 | T0 to T2 | + | − | − | − | − | − | − | − | + | − | − | − | − | − | − | − | − | − | − | − | − | − | − | − |
| | | T-1 to T0 | + | − | − | − | − | − | − | − | − | − | − | − | − | − | − | − | − | − | − | − | − | − | − | − |
| | Q0355 | T0 to T2 | # | # | # | # | # | + | # | # | # | # | # | # | # | # | # | # | # | # | # | # | # | # | # | # |
| | | T-1 to T0 | # | # | # | # | # | # | # | # | # | # | # | # | # | # | # | # | # | # | # | # | # | # | # | # |
| | Q0356 | T0 to T2 | + | − | − | − | − | − | − | − | + | − | − | − | − | − | − | − | − | − | − | − | − | − | − | − |
| | | T-1 to T0 | + | − | − | − | − | − | − | − | − | − | − | − | − | − | − | − | − | − | − | − | − | − | − | − |
| | Q0357 | T0 to T2 | + | − | − | − | − | − | − | − | − | − | − | − | − | − | − | − | − | − | − | − | − | − | − | − |
| | | T-1 to T0 | + | − | − | − | − | − | − | − | − | − | − | − | − | − | − | − | − | − | − | − | − | − | − | − |
| | Q0358 | T0 to T2 | + | − | − | − | − | − | − | − | − | − | − | − | − | − | − | − | − | − | − | − | − | − | − | − |
| | | T-1 to T0 | + | − | − | − | − | − | − | − | − | − | − | − | − | − | − | − | − | − | − | − | − | − | − | − |
| | Q0359 | T0 to T2 | + | − | − | − | − | − | − | − | − | − | − | − | − | − | − | − | − | − | − | − | − | − | − | − |
| | | T-1 to T0 | − | − | − | − | − | − | − | − | − | − | − | − | − | − | − | − | − | − | − | − | − | − | − | − |
| | Q0360 | T0 to T2 | + | − | − | − | − | − | − | − | + | − | − | − | + | − | − | − | + | − | − | − | − | − | − | − |
| | | T-1 to T0 | − | − | − | − | − | − | − | − | − | − | − | − | − | − | − | − | − | − | − | − | − | − | − | − |
| | Q0361 | T0 to T2 | + | − | − | − | + | − | − | − | + | − | − | − | − | − | − | − | − | − | − | − | − | − | − | − |
| BUPROPION HYDRO-BROMIDE 100 | Q0352 | T-1 to T0 | − | − | − | + | − | − | − | + | − | − | − | − | − | − | − | − | − | − | − | − | − | − | − | − |
| | | T0 to T2 | + | − | − | + | − | − | − | + | − | − | − | − | − | − | − | − | − | − | − | − | − | − | − | − |
| | Q0353 | T-1 to T0 | − | − | − | + | − | − | + | − | − | − | − | − | − | − | − | − | − | − | − | − | − | − | − | − |
| | Q0354 | T0 to T2 | + | − | − | − | − | − | − | − | − | − | − | − | − | − | − | − | − | + | − | + | − | + | − | + | − |
| | | T-1 to T0 | − | − | − | − | − | − | − | − | − | − | − | − | − | − | − | − | − | − | − | − | − | − | − | − |
| | Q0356 | T0 to T2 | + | − | − | − | − | − | − | − | + | − | − | − | − | − | − | − | + | − | + | − | + | − | + | − |

TABLE 107-continued

EFFECTS OF BUPROPION HYDROBROMIDE IN THE EEG TRACE MONITORING IN THE RAT
(10 RATS PER GROUP)

| TREATMENT (mg/kg) i.p | NUMBER OF RAT | TIME | BEHAVIOR | | | | | | EEG ANALYSIS OBSERVATIONS | | | | | | | | | | | | | | | | | |
|---|---|---|---|---|---|---|---|---|---|---|---|---|---|---|---|---|---|---|---|---|---|---|---|---|---|---|
| | | | Hyper-activity | Stereo-typies | Head twitches | Rear-ing | Facial clonus | Fore-limb clonus | Whole-body clonus | Spike-and-waves cx | hipp | Sharp waves cx | hipp | High frequency burst activity cx | hipp | Com-plex spike cx | hipp | Repetitive isolated spike cx | hipp | High amplitude fast frequency cx | hipp | Burst cx | hipp | Short seizure activity cx | hipp | Long seizure activity cx | hipp | Post ictal activity cx | hipp |
| | Q0357 | T0 to T2 | + | − | − | − | − | − | − | − | − | − | − | − | − | − | − | − | − | − | − | − | − | − | − | − | − | − | − |
| | | T-1 to T0 | − | − | − | − | − | − | − | − | − | − | − | + | − | − | − | − | − | − | − | − | − | − | − | − | − | − | − |
| | Q0358 | T0 to T2 | + | − | − | − | − | − | − | − | − | − | − | − | − | − | − | − | − | − | − | − | − | − | − | − | − | − | − |
| | | T-1 to T0 | + | − | − | − | − | − | − | − | − | − | − | + | − | − | − | − | − | − | − | − | − | − | − | − | − | − | − |
| | Q0359 | T0 to T2 | + | − | − | − | − | − | − | − | − | − | − | − | − | − | − | − | − | − | − | − | − | − | − | − | − | − | − |
| | | T-1 to T0 | − | − | − | − | − | − | − | − | − | − | − | + | − | − | − | − | − | − | − | − | − | − | − | − | − | − | − |
| | Q0360 | T0 to T2 | + | − | − | + | + | + | − | − | − | − | − | − | − | − | − | − | − | − | − | − | − | − | − | + | − | + | − |
| | | T-1 to T0 | − | − | − | − | − | − | − | − | − | − | − | + | − | − | − | − | − | − | − | − | − | − | − | − | − | − | − |
| | Q0361 | T0 to T2 | + | − | − | − | − | − | − | − | − | − | − | − | − | − | − | − | − | − | − | − | − | − | − | − | − | − | − | cx: cortex.
hipp: hippocampus.
Short seizure activity: up to 4 seconds.
Long seizure activity: between 4 and 60 seconds.
T-1 to T0: baseline recording (1 hour before injection).
T0 to T2: recording immediately after injection for 2 hours.
− sign: absence of symptom.
+ sign: presence of symptom.
*Symptom was not recording (facial clonus during connection).
rat died immediately after administration (no EEG recording).

TABLE 108

EFFECTS OF BUPROPION HYDROCHLORIDE AND
BUPROPION HYDROBROMIDE IN THE EEG TRACE
MONITORING IN THE RAT
(10 RATS PER GROUP)
Long seizure activity

| TREATMENT (mg/kg) i.p. | NUMBER OF ANIMALS WITH SEIZURE ACTIVITY | DURATION OF INITIAL SEIZURE | |
|---|---|---|---|
| | | CORTEX mean ± s.e.m. | HIPPOCAMPUS mean ± s.e.m. |
| Bupropion hydrochloride 100 | 10 | 33 ± 3 | 25 ± 4 |
| Bupropion hydrobromide# 100 | 4* | 31 ± 6 | 23 ± 2 |

Chi-Square test: *= p < 0.05.
dead (1/10).
NB:
Doses of bupropion hydrochloride (HCl) expressed in mg/kg of salt and doses of bupropion hydrobromide (HBr) expressed in mg/kg HCl molar equivalent (correction factor = 1.16).

TABLE 109

EFFECTS OF BUPROPION HYDROCHLORIDE AND BUPROPION
HYDROBROMIDE IN THE EEG TRACE MONITORING
IN THE RAT
(10 RATS PER GROUP)
Long seizure activity

| RAT NUMBER | BRAIN STRUCTURE | ELECTRICAL SEIZURES | | |
|---|---|---|---|---|
| | | Begin | End | Duration |
| BUPROPION HCl (100 mg/kg) | | | | |
| Q0336 | Cortex | 02:26.1 | 02:54.3 | 00:28.2 |
| | Hippocampus | 02:26.8 | 02:51.7 | 00:24.9 |
| Q0337 | Cortex | 00:51.9 | 01:31.4 | 00:39.5 |
| | Hippocampus | 00:51.8 | 01:23.7 | 00:31.9 |
| | Cortex | 06:22.9 | 06:36.4 | |
| | Hippocampus | 06:23.2 | 06:36.3 | |
| Q0338 | Cortex | 01:17.0 | 01:48.1 | 00:31.1 |
| | Hippocampus | 01:20.0 | 01:40.8 | 00:20.8 |
| Q0342 | Cortex | 08:35.3 | 09:10.2 | 00:34.9 |
| | Hippocampus | 08:36.3 | 08:40.4 | 00:04.0 |
| | Cortex | — | — | |
| | Hippocampus | 08:42.3 | 09:10.2 | |
| Q0343 | Cortex | 00:00.0 | 00:14.8 | 00:14.8 |
| | Hippocampus | 00:00.0 | 00:12.6 | 00:12.6 |
| | Cortex | 02:34.5 | 02:50.8 | |
| | Hippocampus | 02:36.0 | 02:50.6 | |
| | Cortex | 04:01.5 | 04:13.8 | |
| | Hippocampus | 04:05.2 | 04:13.5 | |
| | Cortex | 08:10.5 | 08:21.8 | |
| | Hippocampus | 08:12.6 | 08:21.6 | |
| Q0344 | Cortex | 03:27.9 | 04:16.9 | 00:49.0 |
| | Hippocampus | 03:30.5 | 04:12.3 | 00:41.8 |
| | Cortex | 08:35.2 | 08:55.7 | |
| | Hippocampus | 08:35.8 | 08:55.5 | |
| Q0346 | Cortex | 03:35.1 | 04:11.6 | 00:36.5 |
| | Hippocampus | 03:35.1 | 04:11.5 | 00:36.4 |
| | Cortex | 08:38.1 | 08:59.6 | |
| | Hippocampus | 08:39.8 | 09:00.6 | |
| Q0348 | Cortex | 02:58.0 | 03:33.2 | 00:35.2 |
| | Hippocampus | 02:59.9 | 03:30.5 | 00:30.6 |
| Q0349 | Cortex | 04:03.8 | 04:37.0 | 00:33.2 |
| | Hippocampus | 04:06.7 | 04:35.1 | 00:28.4 |
| Q0351 | Cortex | 01:29.2 | 01:56.0 | 00:26.8 |
| | Hippocampus | 01:39.4 | 01:55.8 | 00:16.4 |
| | | | Mean | 00:32.9 00:24.8 |

TABLE 109-continued

EFFECTS OF BUPROPION HYDROCHLORIDE AND BUPROPION
HYDROBROMIDE IN THE EEG TRACE MONITORING
IN THE RAT
(10 RATS PER GROUP)
Long seizure activity

| RAT NUMBER | BRAIN STRUCTURE | ELECTRICAL SEIZURES | | |
|---|---|---|---|---|
| | | Begin | End | Duration |
| BUPROPION HBr (100 mg/kg) | | | | |
| Q0352 | Cortex | 01:47.7 | 02:04.6 | 00:16.9 |
| | Hippocampus | 01:48.1 | 02:04.8 | 00:16.7 |
| Q0353 | Cortex | 00:15.0 | 00:53.7 | 00:38.8 |
| | Hippocampus | 00:24.8 | 00:48.6 | 00:23.8 |
| Q0354 | Cortex | 01:47.5 | 02:14.1 | 00:26.5 |
| | Hippocampus | 01:49.9 | 02:14.6 | 00:24.7 |
| Q0360 | Cortex | 04:11.4 | 04:53.8 | 00:42.3 |
| | Hippocampus | 04:14.2 | 04:39.5 | 00:25.3 |
| | | | Mean | 00:31.1 00:22.6 |

The invention claimed is:

1. A composition comprising bupropion hydrobromide and at least one pharmaceutically acceptable excipient;
    wherein administration of an amount of a bupropion hydrobromide to a first rat results in less incidences of and/or less severe bupropion-induced seizures when compared to incidences of and/or severity of bupropion-induced seizures resulting from administration of an equivalent molar amount of bupropion hydrochloride to a second rat; and
    wherein the incidences of and/or severity of bupropion-induced seizures are measured by an electroencephalogram analysis using a hippocampally implanted depth electrode.

2. The composition of claim 1, which is in tablet form.

3. The composition of claim 1, which is a modified release formulation.

4. The composition of claim 1, which is in tablet form and wherein the bupropion hydrobromide is contained within a core of the tablet further comprising a coating over the core.

5. The composition of claim 4, wherein the coating is a controlled release coating.

6. A composition comprising bupropion hydrobromide and at least one pharmaceutically acceptable excipient;
    wherein administration of about 100 mg/kg of a bupropion hydrobromide to a first rat results in less incidences of and/or severity of bupropion-induced seizures when compared to incidences of and/or severity of bupropion-induced seizures resulting from administration of an equivalent molar amount of bupropion hydrochloride to a second rat; and
    wherein the incidences of and/or severity of bupropion-induced seizures are measured by an electroencephalogram analysis using a hippocampally implanted depth electrode.

7. A method of treating a subject at risk of bupropion-induced seizures in need of bupropion treatment, the method comprising:
    administering a composition comprising bupropion hydrobromide to said subject in an amount sufficient to treat said subject.

8. The method of claim 7, wherein the composition comprises an amount of bupropion hydrobromide chosen from 174 mg, 348 mg and 522 mg.

9. The method of claim 7, wherein the composition is in tablet form and the administering comprises oral administration.

10. The method of claim 7, wherein the composition is a modified release formulation.

11. The method of claim 7, wherein the composition is in tablet form and wherein the bupropion hydrobromide is contained within a core of the tablet further comprising a coating over the core.

12. The method of claim 7, wherein the coating is a controlled release coating.

13. A method of reducing incidences of bupropion-induced seizures comprising: administering a pharmaceutically effective amount of bupropion hydrobromide to a subject in need of bupropion administration;
wherein incidences of bupropion-induced seizures resulting from the administration of bupropion hydrobromide is less than incidences of bupropion-induced seizures resulting from administration of an equivalent molar amount of bupropion hydrochloride.

14. The method of claim 13 wherein bupropion-induced seizures resulting from the administration of bupropion hydrobromide is less severe than bupropion-induced seizures resulting from administration of an equivalent molar amount of bupropion hydrochloride.

15. A method of reducing incidences of bupropion-induced seizures comprising:
administering a pharmaceutically effective amount of bupropion hydrobromide to a subject in need of bupropion administration;
wherein administration of about 100 mg/kg of the bupropion hydrobromide to a first rat results in less incidences of bupropion-induced seizures when compared to incidences of bupropion-induced seizures resulting from administration of an equivalent molar amount of bupropion hydrochloride to a second rat; and
wherein the incidences of bupropion-induced seizures in the first and second rats are measured by an electroencephalogram analysis using a hippocampally implanted depth electrode.

16. A composition comprising bupropion hydrobromide and at least one pharmaceutically acceptable excipient;
wherein administration of about 100 mg/kg of a bupropion hydrobromide used to manufacture the composition to a first rat results in less incidences of and/or severity of bupropion induced seizures when compared to incidences of and/or severity of bupropion-induced seizures resulting from administration of an equivalent molar amount of bupropion hydrochloride to a second rat; and
wherein the incidences of and/or severity of bupropion-induced seizures are measured by an electroencephalogram analysis using a hippocampally implanted depth electrode.

* * * * *